US011492401B2

(12) United States Patent
Burden et al.

(10) Patent No.: US 11,492,401 B2
(45) Date of Patent: Nov. 8, 2022

(54) THERAPEUTIC MUSK ANTIBODIES

(71) Applicants: NEW YORK UNIVERSITY, New York, NY (US); argenx IIP BV, Ghent (BE)

(72) Inventors: Steven J. Burden, New York, NY (US); Shohei Koide, New York, NY (US); Akiko Koide, New York, NY (US); Nadia Leloup, New York, NY (US); Julien Oury, New York, NY (US); Karen Silence, Ghent (BE); Roeland Vanhauwaert, Ghent (BE); Christophe Blanchetot, Ghent (BE)

(73) Assignees: NEW YORK UNIVERSITY, New York, NY (US); ARGENX IIP BV, Ghent (BE)

( * ) Notice: Subject to any disclaimer, the term of this patent is extended or adjusted under 35 U.S.C. 154(b) by 0 days.

(21) Appl. No.: 17/565,994

(22) Filed: Dec. 30, 2021

(65) Prior Publication Data
US 2022/0259304 A1    Aug. 18, 2022

Related U.S. Application Data

(63) Continuation of application No. PCT/US2021/027801, filed on Apr. 16, 2021.

(60) Provisional application No. 63/112,375, filed on Nov. 11, 2020, provisional application No. 63/038,633, filed on Jun. 12, 2020, provisional application No. 63/011,986, filed on Apr. 17, 2020.

(51) Int. Cl.
C07K 16/00       (2006.01)
C07K 16/28       (2006.01)
A61P 21/04       (2006.01)

(52) U.S. Cl.
CPC .............. *C07K 16/28* (2013.01); *A61P 21/04* (2018.01); *C07K 2317/21* (2013.01); *C07K 2317/55* (2013.01); *C07K 2317/622* (2013.01)

(58) Field of Classification Search
CPC combination set(s) only.
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell et al. |
| 5,225,539 A | 7/1993 | Winter |
| 5,530,101 A | 6/1996 | Queen et al. |
| 5,585,089 A | 12/1996 | Queen et al. |
| 5,859,205 A | 1/1999 | Adair et al. |
| 6,407,213 B1 | 6/2002 | Carter et al. |
| 2003/0039649 A1 | 2/2003 | Foote |
| 2004/0008201 A1 | 4/2004 | Vincent et al. |
| 2004/0180061 A1 | 9/2004 | Donovan |
| 2006/0177441 A1 | 8/2006 | Adams et al. |
| 2015/0050289 A1 | 2/2015 | Burden et al. |

FOREIGN PATENT DOCUMENTS

| | | |
|---|---|---|
| JP | 2011-207769 A | 10/2011 |
| WO | WO 1997/021811 A2 | 6/1997 |
| WO | WO 2003/011161 A1 | 2/2003 |
| WO | WO 2013/074636 A1 | 5/2013 |
| WO | WO 2015/039015 A2 | 3/2015 |

OTHER PUBLICATIONS

Arimura et al., "DOK7 gene therapy benefits mouse models of diseases characterized by defects in the neuromuscular junction", Science, Sep. 19, 2014, 345(6203): 1505-0508.
Barderas et al., "Affinity maturation of antibodies assisted by in silico modeling", PNAS, Jul. 2008, 405(26): 9029-9034.
Beeson et al., "Dok-7 mutations underlie a neuromuscular junction synaptopathy", Science, Sep. 29, 2006, 313: 1975-1978.
Bird et al., "Single-Chain Antigen-Binding Proteins", Science, Oct. 21, 1988, 242: 423-426.
Broekman et al., "Adeno-associated virus vectors serotyped with AAV8 capsid are more efficient than AAV-1 or -2 serotypes for widespread gene delivery to the neonatal mouse brain", Journal of Experimental Medicine, Jan. 2006, 138(2): 501-510.
Burden et al., "Fundamental Molecules and Mechanisms for Forming and Maintaining Neuromuscular Synapses", Int J Mol Sci., Feb. 6, 2018,19(2): 490.
Burden et al., "The role of MuSK in synapse formation and neuromuscular disease", Perspect Biol., May 1, 2013, 5(5): a009167.
Cantor et al., "Preserving neuromuscular synapses in ALS by stimulating MuSK with a therapeutic agonist antibody", eLife, Feb. 20, 2018, 7: e34375.
Carter et al., "Humanization of an Anti-P185her2 Antibody for Human Cancer Therapy", PNAS, May 15, 1992, 89(10): 4285-4289.
Co et al., "Humanized Antibodies for Antiviral Therapy", PNAS, Apr. 1991, 88(7): 2869-2873.
Cossins et al., "The spectrum of mutations that underlie the neuromuscular junction synaptopathy in DOK7 congenital myasthenic syndrome", Human Molecular Genetics, Sep. 2012, 21(17): 3765-3775.
De Haard et al., "A large non-immunized human Fab fragment phage library that permits rapid isolation and kinetic analysis of high affinity antibodies", Journ Bio Chem, Jun. 25, 1999, 274(26): 18218-18230.
Dechiara et al., "The Receptor Tyrosine Kinase MuSK Is Required for Neuromuscular Junction Formation In Vivo", Cell, May 1996, 85(4): 501-512.

(Continued)

*Primary Examiner* — Lei Yao
(74) *Attorney, Agent, or Firm* — Dechert LLP; Andrew T. Wilkins; Victoria E. Pedanou

(57) ABSTRACT

The present invention relates to antibody-based molecules, including full-length antibodies, antigen-binding domains thereof, and antibody derivatives that are capable of binding to and activating human muscle-specific tyrosine protein kinase (MuSK). The present invention further discloses methods of treating neuromuscular conditions using the aforementioned MuSK antibodies.

24 Claims, 131 Drawing Sheets

Specification includes a Sequence Listing.

(56) References Cited

OTHER PUBLICATIONS

Deverman et al., "Gene therapy for neurological disorders: progress and prospects", Nature Reviews Drug Discovery, Sep. 2018, 17(9): 641-659.
Engel et al., "Congenital myasthenic syndromes: pathogenesis, diagnosis, and treatment", The Lancet Neurology, Apr. 1, 2015, 14(4): 420-434.
Engel et al., "Current status of the congenital myasthenic syndromes", Neuromuscular Disorders, Oct. 13, 2011, 22(2): 99-111.
Evans et al., "Rapid expression of an anti-human C5 chimeric Fab utilizing a vector that replicates in COS and 293 cells", Journal of Immunological Methods, Jul. 17, 1995, 184(1): 123-138.
Evoli et al., "Clinical correlates with anti-MuSK antibodies in generalized seronegative myasthenia gravis", Brain, Oct. 2003, 126(Pt 10): 2304-2311.
Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions", Journal of Molecular Biology, May 8, 2009, 388(3): 541-558.
Glass et al., "Agrin Acts via a Musk Receptor Complex", Cell, May 17, 1996, 85(4): 513-523.
Gonzales et al., "SDR grafting of a murine antibody using multiple human germline templates to minimize its immunogenicity", Molecular Immunology, Jun. 17, 2004, 41(9): 863-872.
Gorman et al., "Reshaping a Therapeutic CD4 Antibody", PNAS, May 15, 1991, 88(10): 4181-4185.
Gustchina et al., "Affinity maturation by targeted diversification of the CDR-H2 loop of a monoclonal Fab derived from a synthetic naive human antibody library and directed against the internal trimeric coiled-coil of gp41 yields a set of Fabs with improved HIV-1 neutralization potency and breadth", Virology, Oct. 10, 2009, 393(1): 112-119.
Hackel et al., "Stability and CDR Composition Biases Enrich Binder Functionality Landscapes", Journal of Molecular Biology, Aug. 6, 2010, 401(1): 84-96.
Hattori et al., "Multiplex bead binding assays using off-the-shelf components and common flow cytometers", Journ Immuno Meth., Dec. 25, 2020, vol. 490.
Herbst et al., "The juxtamembrane region of MuSK has a crucial role in agrin-mediated signaling", EMBO Journal, Jan. 2000, 19: 67-77.
Hesser et al., "Synapse disassembly and formation of new synapses in postnatal muscle upon conditional inactivation of MuSK", Mol Cell Neurosci., Mar. 2006, 31(3): 470-480.
Hoch et al., "Auto-antibodies to the receptor tyrosine kinase MuSK in patients with myasthenia gravis without acetylcholine receptor antibodies", Nat Med., Mar. 2001, 7(3): 365-368.
Holliger et al., "'Diabodies': small bivalent and bispecific antibody fragments", PNAS, Jul. 15, 1993, 90(14): 6444-6448.
Holt et al., "Domain antibodies: proteins for therapy", Trends on Biotechnology, Nov. 2003, 21(11): 484-490.
Huijbers et al., "IgG4-mediated autoimmune diseases: a niche of antibody-mediated disorders: IgG4-mediated autoimmune diseases", Annals of the New York Academy of Sciences, Jan. 28, 2018, 1413(1): 92-103.
Huijbers et al., "MuSK myasthenia gravis monoclonal antibodies: Valency dictates pathogenicity", Neurology—Neuroimmunology Neuroinflammation, Feb. 21, 2019, 6(3): e547.
Huijbers et al., "Longitudinal epitope mapping in MuSK myasthenia gravis: implications for disease severity", J Neuroimmunol., Feb. 15, 2016, 291: 82-88.
Huijbers et al., "MuSK IgG4 autoantibodies cause myasthenia gravis by inhibiting binding between MuSK and Lrp4", PNAS USA, Dec. 17, 2013, 10(51): 20783-20788.
Huston et al., "Protein Engineering of Antibody Binding Sites: Recovery of Specific Activity in an Anti-Digoxin Single-Chain FV Analogue Produced in *Escherichia coli*", PNAS, Aug. 1988, 85(16): 5879-5883.

International Search Report and Written Opinion for PCT International Patent Application No. PCT/US2021/027801, dated Oct. 12, 2021.
International Search Report and Written Opinion for PCT International Patent Application No. PCT/NL2019/050577, dated Dec. 9, 2019.
International Search Report and Written Opinion for PCT International Patent Application No. PCT/NL2019/050576, dated Jan. 3, 2020.
Ising et al., "AAV-mediated expression of anti-tau scFvs decreases tau accumulation in a mouse model of tauopathy", Journ Exper Med., May 2017, 214(5): 1227-1238.
Jennings et al., "Muscle-Specific Trk-Related Receptor with a Kringle Domain Defines a Distinct Class of Receptor Tyrosine Kinases", PNAS, Apr. 1, 1993, 90(7): 2895-2899.
Kim et al., "Lrp4 is a receptor for agrin and forms a complex wit MuSK", Cell, Jan. 2008, 135(2): 334-342.
Klooster et al., "Muscle-specific kinase myasthenia gravis IgG4 autoantibodies cause severe neuromuscular junction dysfunction in mice", Brain, Apr. 2012, 135(Pt 4): 1081-1101.
Koneczny et al., "IgG4 autoantibodies against muscle-specific kinase undergo Fab-arm exchange in myasthenia gravis patients", J Autoimmun., Feb. 2017, 77:104-115.
Koneczny et al., "MuSK myasthenia gravis IgG4 disrupts the interaction of LRP4 with MuSK but both IgG4 and IgG1-3 can disperse preformed agrin-independent AChR clusters", PLoS One, Nov. 7, 2013, 8(11): e80695.
Koning et al., "Artisan PCR: rapid identification of full-length immunoglobulin rearrangements without primer binding bias", Br J Haematol., Sep. 2017, 178(6): 983-986.
Krause et al., "An Insertion Mutation That Distorts Antibody Binding Site Architecture Enhances Function of a Human Antibody", mBio, Feb. 8, 2011, 2(1): e00345-10.
Lighaam et al., "Phenotypic differences between IgG4+ and IgG1+ B cells point to distinct regulation of the IgG4 response", J Allergy Clin Immunol., Jan. 2014, 133(1): 267-270: e1-6.
Lighaam et al., "The Immunobiology of Immunoglobulin G4", Semin Liver Dis., Aug. 2016, 36(3): 200-215.
Lo et al., "Effector-attenuating Substitutions That Maintain Antibody Stability and Reduce Toxicity in Mice", Journ Bio Chem., Mar. 3, 2017, 292(9): 3900-3908.
Lobuglio et al., "Mouse/human chimeric monoclonal antibody in man: Kinetics and immune response", PNAS, Jun. 1989, 86: 4220-4224.
McConville et al., "Detection and characterization of MuSK antibodies in seronegative myasthenia gravis", Ann Neurol., Apr. 2004, 55(4): 580-584.
Montgomery et al., "Affinity maturation and characterization of a human monoclonal antibody against HIV-1 gp41", mAbs, Sep. 2009, 1(5): 462-474.
Mori et al., "Divalent and monovalent autoantibodies cause dysfunction of MuSK by distinct mechanisms in a rabbit model of myasthenia gravis", Journal of Neuroimmunology, Jan. 1, 2012, 244(1): 1-7.
Nishikori et al., "Broad Ranges of Affinity and Specificity of Anti-Histone Antibodies Revealed by a Quantitative Peptide Immunoprecipitation Assay", Journ Molecular Bio., Dec. 2012, 424(5): 391-399.
Okada et al., "The muscle protein Dok-7 is essential for neuromuscular synaptogenesis", Science, Jun. 23, 2006, 312(5781): 1802-1805.
Otsuka et al., "Collagen Q and anti-MuSK autoantibody competitively suppress agrin/LRP4/MuSK signaling", Sci Rep., Sep. 10, 2015, 5: 13928.
Revets et al., "Nanobodies as Novel Agents for Cancer Therapy", Expert Opinion on Biological Therapy, Jan. 2005, 5(1): 111-124.
Riechmann, "Reshaping Human Antibodies for Therapy", Nature, Mar. 24, 1988, 332(6162): 323-327.
Schier et al., "Isolation of Picomolar Affinity Anti-c-erbB-2 Single-chain Fv by Molecular Evolution of the Complementarity Determining Regions in the Center of the Antibody Binding Site", Journal of Molecular Biology, Nov. 8, 1996, 263(4): 551-567.
Sengupta-Ghosh et al., "Muscle specific kinase (MuSK) activation preserves neuromuscular junctions in the diaphragm but is not

(56) References Cited

OTHER PUBLICATIONS sufficient to provide a functional benefit in the SOD1 G93A mouse model of ALS", Neurobiology of Disease, 2018, 124: 340-352.
Steidl et al., "In vitro affinity maturation of human GM-CSF antibodies by targeted CDR-diversification", Molecular Immunology, Nov. 2008, 46(1): 135-144.
Stiegler et al., "Crystal structure of the agrin-responsive immunoglobulin-like domains 1 and 2 of the receptor tyrosine kinase MuSK", J Mol Biol., Dec. 1, 2006, 364(3): 424-433.
Takamori, "Structure and function of neuromuscular junction, centered on musclespecifictyrosine kinase and related proteins", Clinical and Experimental Neuroimmunology, Aug. 1, 2016, 7(3): 215-225.
Takata et al., "Characterization of pathogenic monoclonal autoantibodies derived from muscle-specific kinase myasthenia gravis patients", JCI Insight, Jun. 20, 2019, 4(12): 1-7.
Tempest et al., "Reshaping a Human Monoclonal Antibody to Inhibit Human Respiratory Syncytial Virus Infection in Vivo", Biotechnology, the International Monthly for Industrial Biology, Mar. 1991, 9(3): 266-271.
Van De Bovenkamp et al., "Adaptive antibody diversification through /V-linked glycosylation of the immunoglobulin variable region", PNAS USA, Feb. 20, 2018, 115(8): 1901-1906.
Van Der Neut Kolfschoten et al., "Anti-inflammatory activity of human IgG4 antibodies by dynamic Fab arm exchange", Science, Sep. 14, 2007, 317(5844): 1554-1557.
Vergoossen et al., "MuSK antibodies, lessons learned from poly- and monoclonality", Journ of Autoimmunity, Jun. 4, 2020, vol. 112.
Verhoeyen et al., "Reshaping Human Antibodies: Grafting an Antilysozyme Activity", Science, Mar. 25, 1988, 239: 1534-1536.
Verschuuren et al., "Passive transfer models of myasthenia gravis with musclespecific kinase antibodies: MuSK MG passive transfer", Annals of the NY Aced of Sciences, Jan. 21, 2018, 1413(1): 111-118.
Zhang et al., "Agrin binds to the N-terminal region of Lrp4 protein and stimulates association between Lrp4 and the first immunoglobulin-like domain in muscle-specific kinase (MuSK)", J Biol Chem., Nov. 25, 2011, 286(47): 40624-40630.
Zhang et al., "LRP4 Serves as a Coreceptor of Agrin", Neuron, Oct. 2008, 60(2): 285-297.
Zhou et al., "Distinct domains of MuSK mediate its abilities to induce and to associate with postsynaptic specializations", The Journal of Cell Biology, Sep. 6, 1999, 146(5): 1133-1146.
U.S. Appl. No. 17/272,791 2022/0002438, filed Mar. 2, 2021 Jan. 6, 2022, Silvère Maria Van Der Maarel.
U.S. Appl. No. 17/272,792, filed Mar. 2, 2021, Silvère Maria Van Der Maarel.
U.S. Appl. No. 17/565,994, filed Mar. 2, 2021, Silvère Maria Van Der Maarel.

Dok7 binding site
MuSK: 541 ELLLDRLHPNPMYQRMPLLL 560
Potential Crk binding site

| Fab Clone | Antigen | | | |
| --- | --- | --- | --- | --- |
| | hFz | hECD | mFz | mECD |
| X1 | 0.39 ± 0.05 | 0.55 ± 0.06 | 1.09 ± 0.07 | 1.34 ± 0.07 |
| X2 | 0.53 ± 0.04 | 0.86 ± 0.11 | 0.45 ± 0.08 | 0.70 ± 0.03 |
| X3 | 0.11 ± 0.01 | 0.16 ± 0.02 | 0.29 ± 0.02 | 0.40 ± 0.03 |
| X6 | 0.90 ± 0.08 | 1.47 ± 0.12 | 0.42 ± 0.02 | 0.59 ± 0.06 |
| X7 | 4.5 ± 0.4 | 6.0 ± 0.4 | 12.0 ± 1.20 | 16.2 ± 1.2 |
| X8 | 1.4 ± 0.2 | 1.69 ± 0.14 | 4.7 ± 0.5 | 44 ± 14 |
| X13 | 1.7 ± 0.2 | 2.39 ± 0.17 | 1.56 ± 0.18 | 2.41 ± 0.19 |
| X14 | 0.31 ± 0.10 | 0.53 ± 0.07 | 8.0 ± 1.9 | 4.1 ± 0.6 |
| X17 | 0.38 ± 0.05 | 0.52 ± 0.07 | 0.47 ± 0.02 | 0.63 ± 0.04 |

$K_D$ values in nM.

*FIG. 4A*

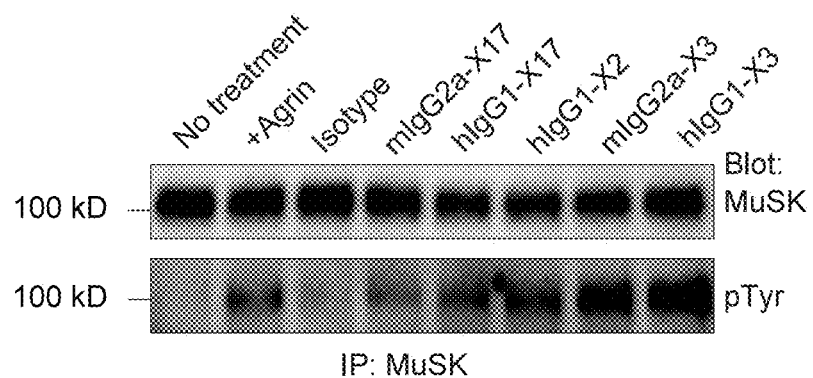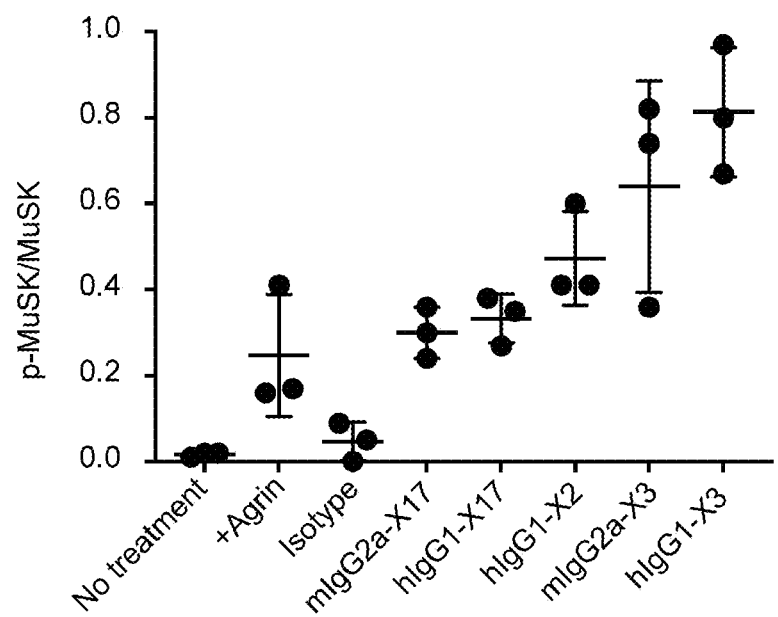
FIG. 4D

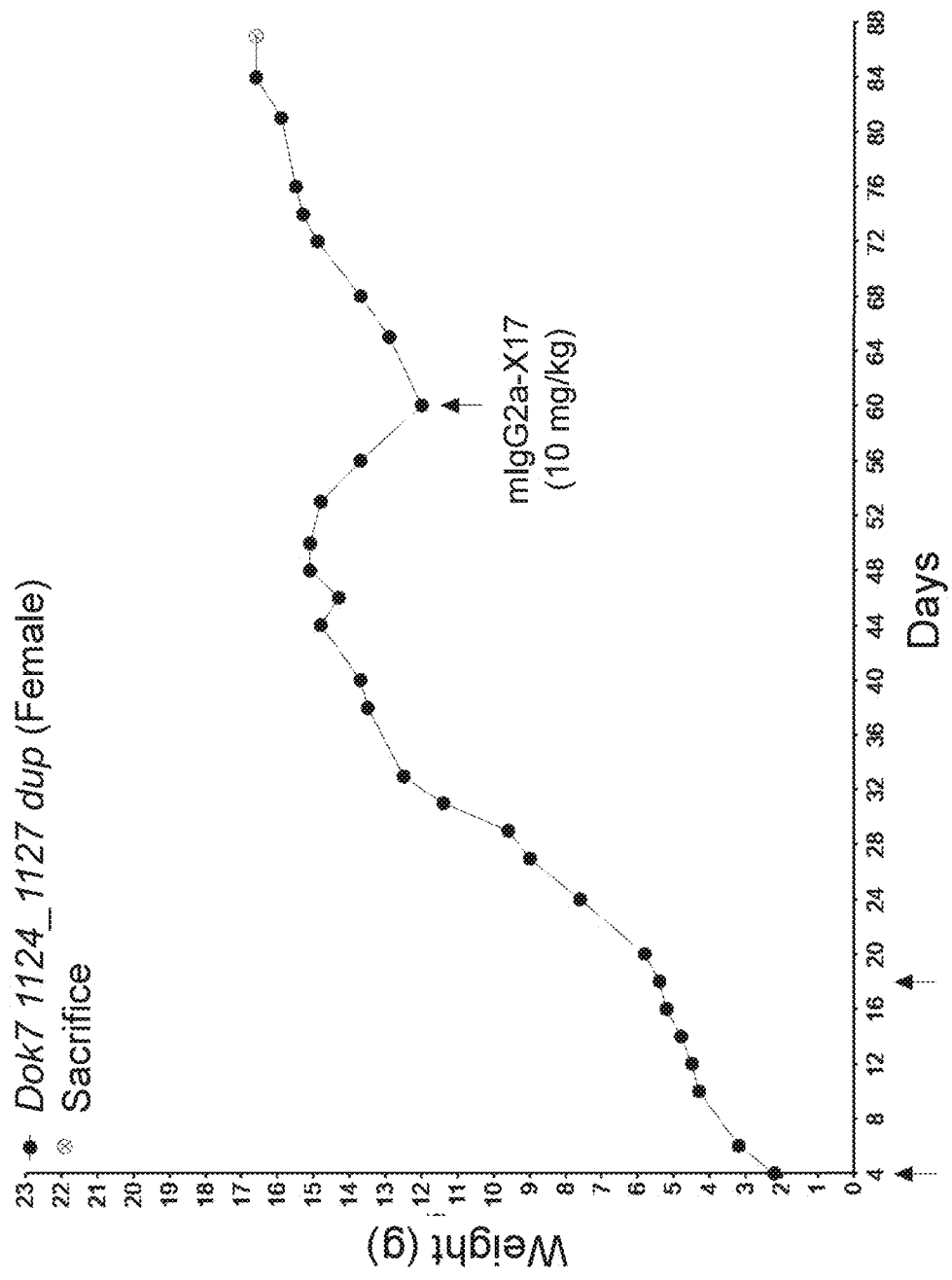

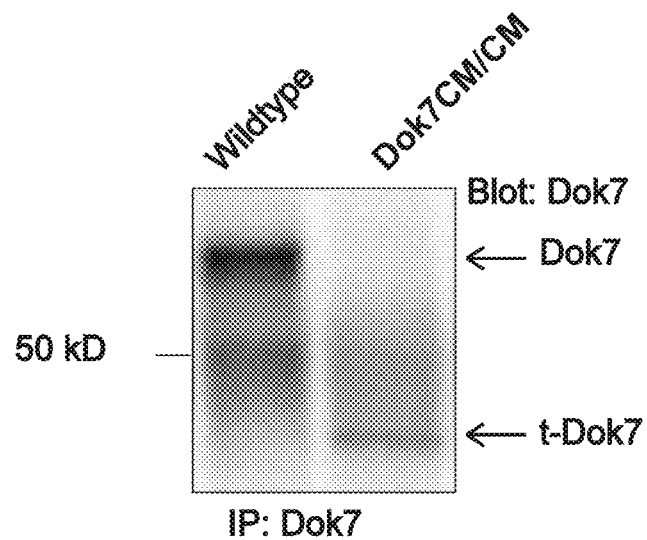
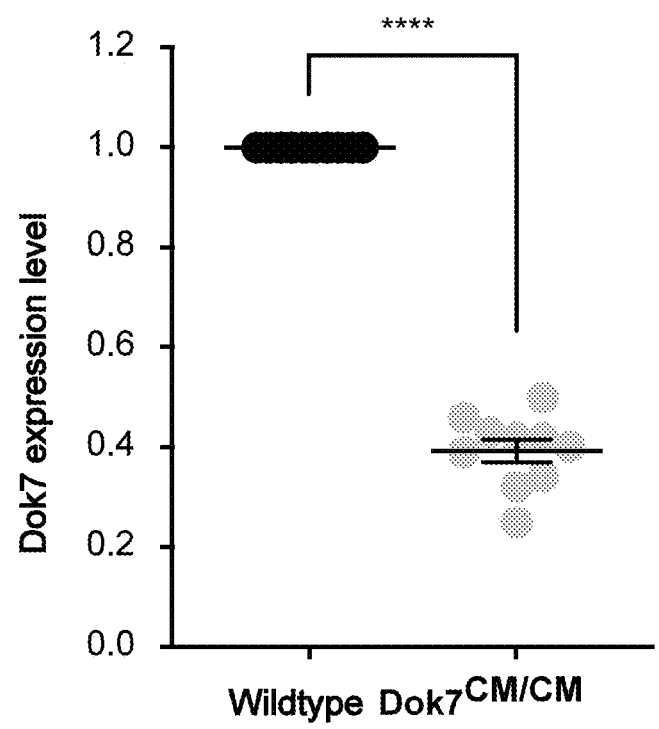
FIG. 10C

A

| C57BL/6-CBA | Observed | Expected | $\chi^2$ |
|---|---|---|---|
| Wildtype | 14 | 15 | 0.04 |
| Dok7$^{CM/+}$ | 36 | 29 | 1.43 |
| Dok7$^{CM/CM}$ | 9 | 15 | 2.24 |
| | | Total $\chi^2$ | 3.71 |
| | | P-value | 0.156 |

| C57BL/6-FVB | Observed | Expected | $\chi^2$ |
|---|---|---|---|
| Wildtype | 23 | 14 | 5.79 |
| Dok7$^{CM/+}$ | 26 | 28 | 0.14 |
| Dok7$^{CM/CM}$ | 7 | 14 | 3.50 |
| | | Total $\chi^2$ | 9.43 |
| | | P-value | 0.008 |

| C57BL/6-129sv1 | Observed | Expected | $\chi^2$ |
|---|---|---|---|
| Wildtype | 10 | 9 | 0.06 |
| Dok7$^{CM/+}$ | 22 | 19 | 0.66 |
| Dok7$^{CM/CM}$ | 5 | 9 | 1.95 |
| | | Total $\chi^2$ | 2.68 |
| | | P-value | 0.262 |

| C57BL/6-BalbC | Observed | Expected | $\chi^2$ |
|---|---|---|---|
| Wildtype | 15 | 10 | 3.18 |
| Dok7$^{CM/+}$ | 20 | 19 | 0.05 |
| Dok7$^{CM/CM}$ | 3 | 9 | 4.45 |
| | | Total $\chi^2$ | 7.68 |
| | | P-value | 0.021 |

B

| Strain | Maximum Survival | Average Survival | SEM | N |
|---|---|---|---|---|
| C57BL/6 | 5 | | 0 | 1 |
| C57BL/6-CBA | 21 | 11.2 | 2.28 | 14 |
| C57BL/6-FVB | 17 | 11.5 | 1.38 | 7 |
| C57BL/6-129sv1 | 17 | 15.2 | 1.32 | 5 |
| C57BL/6-BalbC | 15 | 12.5 | 1.38 | 3 |

FIGs. 14A-14B

A  Potential off-targets in *Dok7 CM* mice

| Off-target | Sequence | Score | Mismatches | Sequence ID | Locus |
|---|---|---|---|---|---|
| 1 | GCCCTGCACAGTCTGCCCCTGG | 2.6 | 3MMs [1:3:8] | AL645994.7 | Chr11:-9049672 |
| 2 | GCACTGCACAGTCTGCCCCTGG | 2.6 | 3MMs [1:3:8] | AC129606.4 | Chr8:+97387576 |
| 3 | TTTATGCTCTGTCTGCCCCAAG | 2.5 | 3MMs [2:4:10] | AC103939.9 | Chr18:+28885886 |
| 4 | GGCCTGCTCAGTCTGCCCCTGG | 2.3 | 3MMs [1:2:3] | AC154126.2 | Chr7:+36061330 |
| 5 | TCAGTCCTCAGTCTGCCCCTGG | 1.4 | 3MMs [3:4:6] | CT033750.18 | Chr17:-15692194 |

B  Potential off-targets in *Dok7 2YF* mice

| Off-target | Sequence | Score | Mismatches | Sequence ID | Locus |
|---|---|---|---|---|---|
| 1 | GAATTCTAGGTGTGTCATAGAGG | 1.7 | 3MMs [2:3:7] | AC113509.14 | Chr1:+183488722 |
| 2 | GGATTCTAGGTGTGTCATCGCGG | 0.7 | 3MMs [3:7:19] | AC120877.15 | Chr6:+16848270 |
| 3 | GGGTTCAATTTGTGTCATAGCAG | 0.5 | 4MMs [3:7:4:10] | AC129777.4 | Chr8:+117950828 |
| 4 | AGCTGCTAGGTATGTCATAGTGG | 0.5 | 4MMs [1:5:7:12] | AL596263.8 | Chr2:+161115283 |
| 5 | CACTTGGAGGGGTGTCATAGAGG | 0.5 | 4MMs [1:2:6:11] | AL772268.6 | Chr11:-5192181 |

*FIGs. 16A-16B*

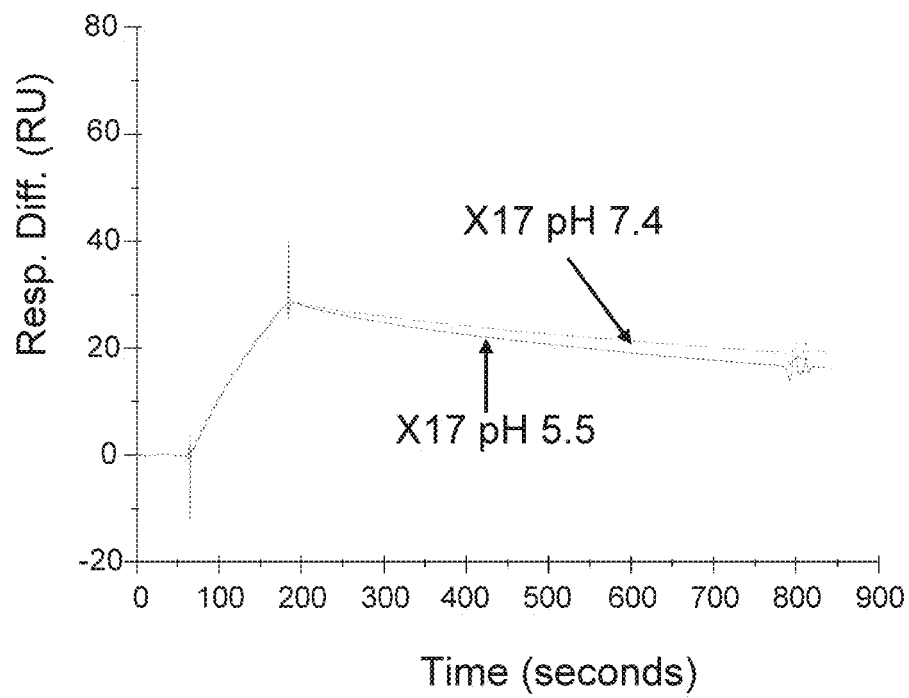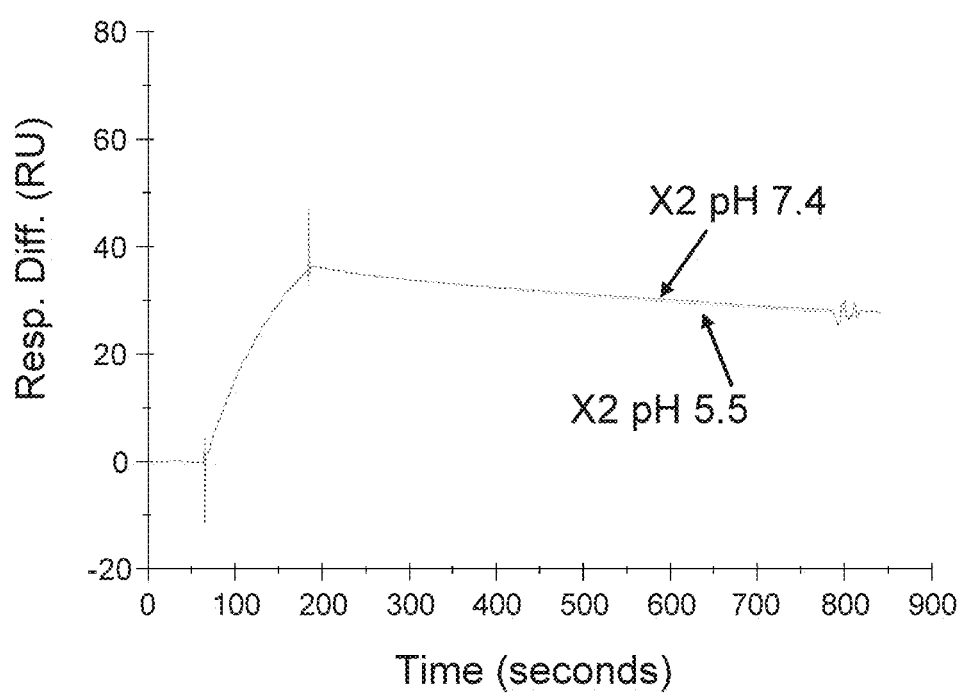
FIG. 23

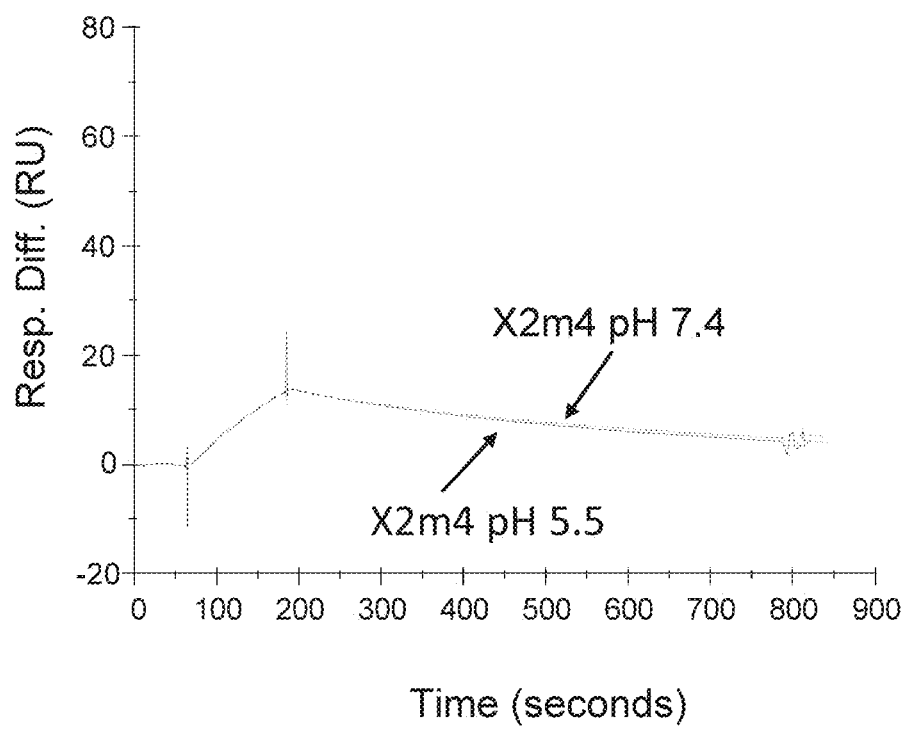
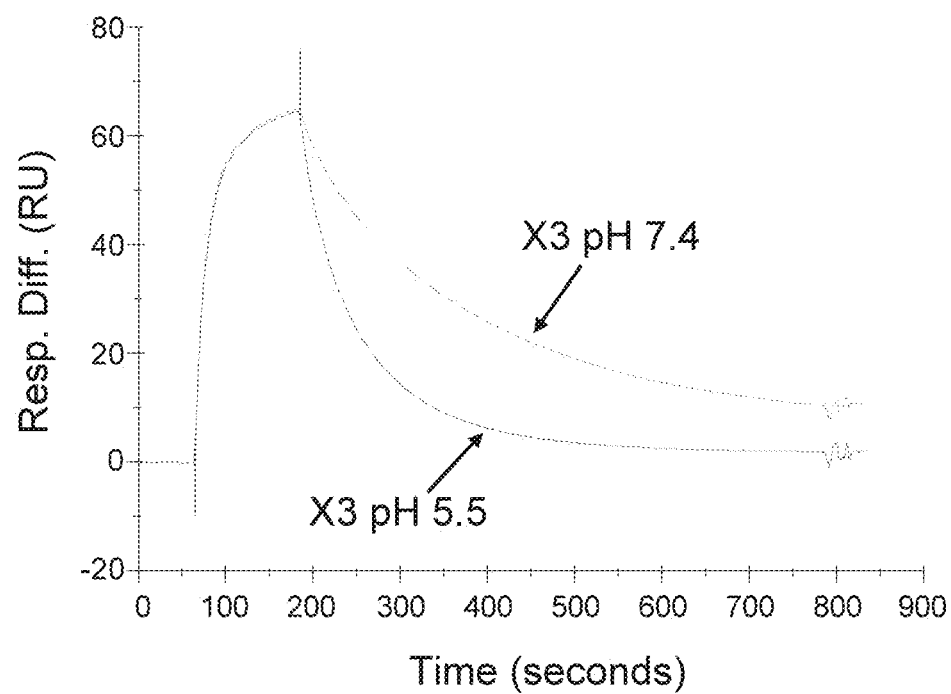
FIG. 23 (continued)

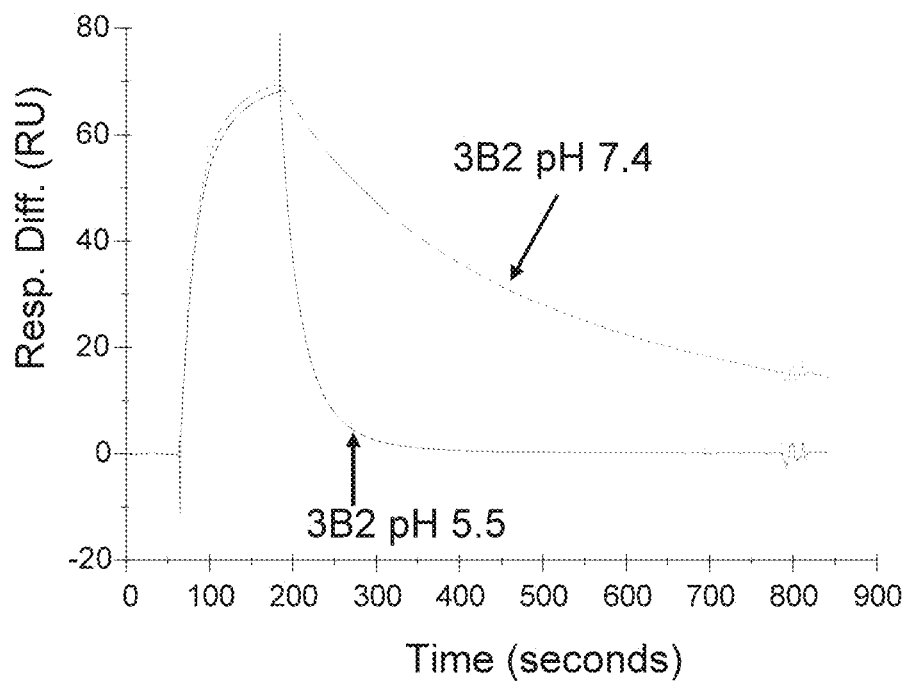
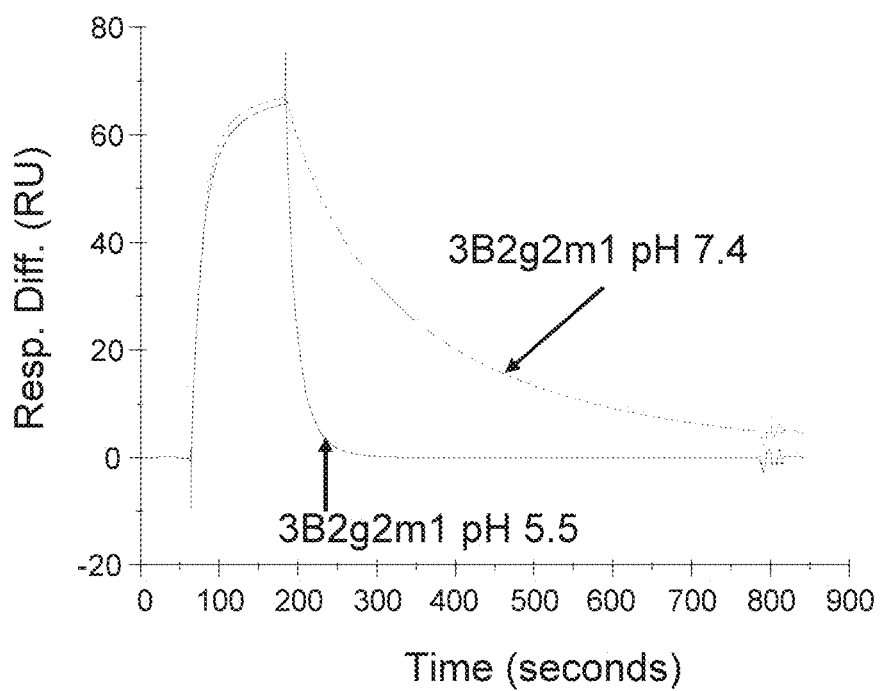
FIG. 23 (continued)

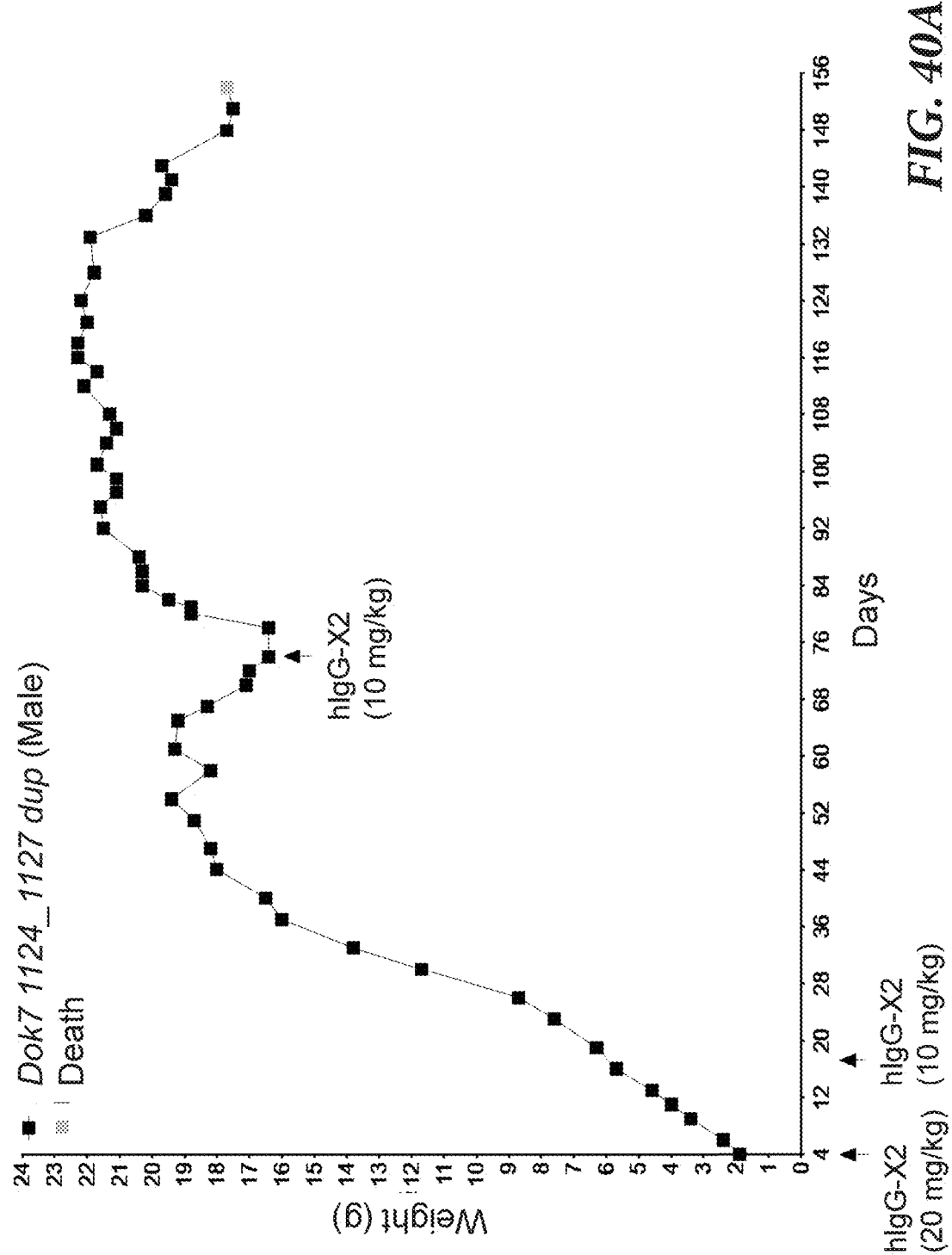

SEQUENCE LISTING

```
<160> NUMBER OF SEQ ID NOS: 289

<210> SEQ ID NO 1
<211> LENGTH: 5
<212> TYPE: PRT
<213> ORGANISM: Artificial Sequence
<220> FEATURE:
<223> OTHER INFORMATION: X1 HCDR1

<400> SEQUENCE: 1

Ser Ser Ser Ile His
1               5

<210> SEQ ID NO 2
<211> LENGTH: 5
<212> TYPE: PRT
<213> ORGANISM: Artificial Sequence
<220> FEATURE:
<223> OTHER INFORMATION: X2 HCDR1

<400> SEQUENCE: 2

Ser Ser Ser Ile His
1               5

<210> SEQ ID NO 3
<211> LENGTH: 5
```

```
<212> TYPE: PRT
<213> ORGANISM: Artificial Sequence
<220> FEATURE:
<223> OTHER INFORMATION: X3 HCDR1

<400> SEQUENCE: 3

Ser Ser Ser Ile His
1               5

<210> SEQ ID NO 4
<211> LENGTH: 5
<212> TYPE: PRT
<213> ORGANISM: Artificial Sequence
<220> FEATURE:
<223> OTHER INFORMATION: X4 HCDR1

<400> SEQUENCE: 4

Ser Ser Ser Ile His
1               5

<210> SEQ ID NO 5
<211> LENGTH: 5
<212> TYPE: PRT
<213> ORGANISM: Artificial Sequence
<220> FEATURE:
<223> OTHER INFORMATION: X5 HCDR1

<400> SEQUENCE: 5

Ser Ser Ser Ile His
1               5

<210> SEQ ID NO 6
<211> LENGTH: 5
<212> TYPE: PRT
<213> ORGANISM: Artificial Sequence
<220> FEATURE:
<223> OTHER INFORMATION: X6 HCDR1

<400> SEQUENCE: 6

Ser Ser Ser Ile His
1               5

<210> SEQ ID NO 7
<211> LENGTH: 5
<212> TYPE: PRT
<213> ORGANISM: Artificial Sequence
<220> FEATURE:
<223> OTHER INFORMATION: X7 HCDR1

<400> SEQUENCE: 7

Ser Ser Ser Ile His
1               5

<210> SEQ ID NO 8
<211> LENGTH: 5
<212> TYPE: PRT
<213> ORGANISM: Artificial Sequence
<220> FEATURE:
<223> OTHER INFORMATION: X8 HCDR1

<400> SEQUENCE: 8

Ser Ser Ser Ile His
1               5

<210> SEQ ID NO 9
<211> LENGTH: 5
<212> TYPE: PRT
```

```
<213> ORGANISM: Artificial Sequence
<220> FEATURE:
<223> OTHER INFORMATION: X9 HCDR1

<400> SEQUENCE: 9

Ser Ser Ser Ile His
1               5

<210> SEQ ID NO 10
<211> LENGTH: 5
<212> TYPE: PRT
<213> ORGANISM: Artificial Sequence
<220> FEATURE:
<223> OTHER INFORMATION: X10 HCDR1

<400> SEQUENCE: 10

Ser Ser Ser Ile His
1               5

<210> SEQ ID NO 11
<211> LENGTH: 5
<212> TYPE: PRT
<213> ORGANISM: Artificial Sequence
<220> FEATURE:
<223> OTHER INFORMATION: X11 HCDR1

<400> SEQUENCE: 11

Ser Ser Ser Ile His
1               5

<210> SEQ ID NO 12
<211> LENGTH: 5
<212> TYPE: PRT
<213> ORGANISM: Artificial Sequence
<220> FEATURE:
<223> OTHER INFORMATION: X12 HCDR1

<400> SEQUENCE: 12

Ser Ser Ser Ile His
1               5

<210> SEQ ID NO 13
<211> LENGTH: 5
<212> TYPE: PRT
<213> ORGANISM: Artificial Sequence
<220> FEATURE:
<223> OTHER INFORMATION: X13 HCDR1

<400> SEQUENCE: 13

Ser Ser Ser Ile His
1               5

<210> SEQ ID NO 14
<211> LENGTH: 5
<212> TYPE: PRT
<213> ORGANISM: Artificial Sequence
<220> FEATURE:
<223> OTHER INFORMATION: X14 HCDR1

<400> SEQUENCE: 14

Ser Ser Ser Ile His
1               5

<210> SEQ ID NO 15
<211> LENGTH: 5
<212> TYPE: PRT
<213> ORGANISM: Artificial Sequence
```

```
<220> FEATURE:
<223> OTHER INFORMATION: X15 HCDR1

<400> SEQUENCE: 15

Ser Ser Ser Ile His
1               5

<210> SEQ ID NO 16
<211> LENGTH: 5
<212> TYPE: PRT
<213> ORGANISM: Artificial Sequence
<220> FEATURE:
<223> OTHER INFORMATION: X16 HCDR1

<400> SEQUENCE: 16

Ser Ser Ser Ile His
1               5

<210> SEQ ID NO 17
<211> LENGTH: 17
<212> TYPE: PRT
<213> ORGANISM: Artificial Sequence
<220> FEATURE:
<223> OTHER INFORMATION: X1 HCDR2

<400> SEQUENCE: 17

Ser Ile Ser Ser Ser Ser Gly Ser Thr Ser Tyr Ala Asp Ser Val Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: X2 HCDR2

<400> SEQUENCE: 18

Ser Ile Ser Ser Ser Tyr Gly Ser Thr Ser Tyr Ala Asp Ser Val Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: X3 HCDR2

<400> SEQUENCE: 19

Ser Ile Ser Ser Ser Ser Gly Tyr Thr Tyr Tyr Ala Asp Ser Val Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: X4 HCDR2

<400> SEQUENCE: 20

Ser Ile Ser Ser Ser Ser Gly Ser Thr Tyr Tyr Ala Asp Ser Val Lys
1               5                   10                  15
```

Gly

```
<210> SEQ ID NO 21
<211> LENGTH: 17
<212> TYPE: PRT
<213> ORGANISM: Artificial Sequence
<220> FEATURE:
<223> OTHER INFORMATION: X5 HCDR2

<400> SEQUENCE: 21

Ser Ile Ser Ser Ser Ser Gly Ser Thr Ser Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: X6 HCDR2

<400> SEQUENCE: 22

Ser Ile Ser Ser Tyr Ser Gly Tyr Thr Tyr Tyr Ala Asp Ser Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: X7 HCDR2

<400> SEQUENCE: 23

Ser Ile Ser Ser Ser Tyr Ser Ser Thr Tyr Tyr Ala Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: X8 HCDR2

<400> SEQUENCE: 24

Ser Ile Ser Ser Ser Ser Gly Ser Thr Ser Tyr Ala Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: X9 HCDR2

<400> SEQUENCE: 25

Ser Ile Tyr Ser Ser Ser Gly Ser Thr Tyr Tyr Ala Asp Ser Val Lys
1               5                   10                  15

Gly

<210> SEQ ID NO 26
```

```
<211> LENGTH: 17
<212> TYPE: PRT
<213> ORGANISM: Artificial Sequence
<220> FEATURE:
<223> OTHER INFORMATION: X10 HCDR2

<400> SEQUENCE: 26

Ser Ile Ser Ser Ser Tyr Ser Ser Thr Ser Tyr Ala Asp Ser Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: X11 HCDR2

<400> SEQUENCE: 27

Ser Ile Ser Ser Tyr Ser Gly Ser Thr Tyr Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: X12 HCDR2

<400> SEQUENCE: 28

Tyr Ile Ser Pro Ser Ser Gly Tyr Thr Ser Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: X13 HCDR2

<400> SEQUENCE: 29

Ser Ile Ser Ser Ser Ser Gly Ser Thr Ser Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: X14 HCDR2

<400> SEQUENCE: 30

Ser Ile Ser Ser Ser Ser Gly Tyr Thr Tyr Tyr Ala Asp Ser Val Lys
1               5                   10                  15

Gly

<210> SEQ ID NO 31
<211> LENGTH: 17
<212> TYPE: PRT
<213> ORGANISM: Artificial Sequence
<220> FEATURE:
```

```
<223> OTHER INFORMATION: X15 HCDR2

<400> SEQUENCE: 31

Ser Ile Ser Ser Ser Tyr Gly Ser Thr Ser Tyr Ala Asp Ser Val Lys
1               5                   10                  15
Gly

<210> SEQ ID NO 32
<211> LENGTH: 17
<212> TYPE: PRT
<213> ORGANISM: Artificial Sequence
<220> FEATURE:
<223> OTHER INFORMATION: X16 HCDR2

<400> SEQUENCE: 32

Ser Ile Tyr Ser Ser Tyr Gly Tyr Thr Ser Tyr Ala Asp Ser Val Lys
1               5                   10                  15
Gly

<210> SEQ ID NO 33
<211> LENGTH: 17
<212> TYPE: PRT
<213> ORGANISM: Artificial Sequence
<220> FEATURE:
<223> OTHER INFORMATION: X1 HCDR3

<400> SEQUENCE: 33

Lys Tyr Trp Ser Gln Tyr Tyr Trp Ala His Tyr Tyr Gly Gly Leu Asp
1               5                   10                  15
Tyr

<210> SEQ ID NO 34
<211> LENGTH: 15
<212> TYPE: PRT
<213> ORGANISM: Artificial Sequence
<220> FEATURE:
<223> OTHER INFORMATION: X2 HCDR3

<400> SEQUENCE: 34

Ser Glu Gly Asp Arg Tyr Val Ser Gly Tyr Met Gly Met Asp Tyr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: X3 HCDR3

<400> SEQUENCE: 35

Ser Trp Tyr Glu Met Trp Met Ser Gly Tyr Phe Gly Phe Asp Tyr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: X4 HCDR3

<400> SEQUENCE: 36

Gly Glu His Asp Tyr Tyr Val Phe Gly Tyr Leu Gly Met Asp Tyr
1               5                   10                  15
```

```
<210> SEQ ID NO 37
<211> LENGTH: 20
<212> TYPE: PRT
<213> ORGANISM: Artificial Sequence
<220> FEATURE:
<223> OTHER INFORMATION: X5 HCDR3

<400> SEQUENCE: 37

Ser Tyr Thr Met Phe Tyr Tyr Gly Gly Trp Tyr Gly Ser Gly Tyr Phe
1               5                   10                  15

Gly Met Asp Tyr
            20

<210> SEQ ID NO 38
<211> LENGTH: 15
<212> TYPE: PRT
<213> ORGANISM: Artificial Sequence
<220> FEATURE:
<223> OTHER INFORMATION: X6 HCDR3

<400> SEQUENCE: 38

Thr Tyr Gly Ser Tyr Tyr Val Ser Ser Tyr Thr Gly Met Asp Tyr
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: X7 HCDR3

<400> SEQUENCE: 39

Leu Ala Gly Leu Tyr His Tyr Pro Gly Tyr Leu Gly Leu Asp Tyr
1               5                   10                  15

<210> SEQ ID NO 40
<211> LENGTH: 19
<212> TYPE: PRT
<213> ORGANISM: Artificial Sequence
<220> FEATURE:
<223> OTHER INFORMATION: X8 HCDR3

<400> SEQUENCE: 40

Ser Trp Ser Tyr His Pro Trp Tyr Tyr His Val Gly Trp Tyr Thr Gly
1               5                   10                  15

Leu Asp Tyr

<210> SEQ ID NO 41
<211> LENGTH: 15
<212> TYPE: PRT
<213> ORGANISM: Artificial Sequence
<220> FEATURE:
<223> OTHER INFORMATION: X9 HCDR3

<400> SEQUENCE: 41

Ser Gly Gly Glu Phe Tyr Ile Thr Ser Tyr Tyr Gly Met Asp Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: X10 HCDR3

<400> SEQUENCE: 42
```

Lys Tyr Tyr Arg Trp Arg His Asn Lys Tyr Gln Gly Phe Asp Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: X11 HCDR3

<400> SEQUENCE: 43

Ser Trp Gly Ser Tyr Tyr Val Ser Gly Phe Val Gly Phe Asp Tyr
1               5                   10                  15

<210> SEQ ID NO 44
<211> LENGTH: 17
<212> TYPE: PRT
<213> ORGANISM: Artificial Sequence
<220> FEATURE:
<223> OTHER INFORMATION: X12 HCDR3

<400> SEQUENCE: 44

Gln Tyr Trp Val Pro Gln Trp Trp Ile Thr Gln Tyr Phe Gly Met Asp
1               5                   10                  15

Tyr

<210> SEQ ID NO 45
<211> LENGTH: 15
<212> TYPE: PRT
<213> ORGANISM: Artificial Sequence
<220> FEATURE:
<223> OTHER INFORMATION: X13 HCDR3

<400> SEQUENCE: 45

Ser Ser Glu His Trp Tyr Thr Ile Gly Tyr Tyr Gly Ile Asp Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: X14 HCDR3

<400> SEQUENCE: 46

Gly Ser His His Trp Phe Leu Trp Ile Tyr Ser Gly Leu Asp Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: X15 HCDR3

<400> SEQUENCE: 47

Ser Glu Gly Asp Arg Tyr Val Ser Gly Tyr Met Gly Met Asp Tyr
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: X16 HCDR3

<400> SEQUENCE: 48

Asn Trp Gly Tyr Tyr Met Tyr Trp Gly Trp Tyr Tyr Ala Leu Asp Tyr
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: X1 LCDR1

<400> SEQUENCE: 49

Arg Ala Ser Gln Ser Val Ser Ser Ala Val Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: X2 LCDR1

<400> SEQUENCE: 50

Arg Ala Ser Gln Ser Val Ser Ser Ala Val Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: X3 LCDR1

<400> SEQUENCE: 51

Arg Ala Ser Gln Ser Val Ser Ser Ala Val Ala
1               5                   10

<210> SEQ ID NO 52
<211> LENGTH: 11
<212> TYPE: PRT
<213> ORGANISM: Artificial Sequence
<220> FEATURE:
<223> OTHER INFORMATION: X4 LCDR1

<400> SEQUENCE: 52

Arg Ala Ser Gln Ser Val Ser Ser Ala Val Ala
1               5                   10

<210> SEQ ID NO 53
<211> LENGTH: 11
<212> TYPE: PRT
<213> ORGANISM: Artificial Sequence
<220> FEATURE:
<223> OTHER INFORMATION: X5 LCDR1

<400> SEQUENCE: 53

Arg Ala Ser Gln Ser Val Ser Ser Ala Val Ala
1               5                   10

<210> SEQ ID NO 54
<211> LENGTH: 11
<212> TYPE: PRT
<213> ORGANISM: Artificial Sequence
<220> FEATURE:
<223> OTHER INFORMATION: X6 LCDR1

<400> SEQUENCE: 54

Arg Ala Ser Gln Ser Val Ser Ser Ala Val Ala
1               5                   10

<210> SEQ ID NO 55
<211> LENGTH: 11
<212> TYPE: PRT
<213> ORGANISM: Artificial Sequence
<220> FEATURE:
<223> OTHER INFORMATION: X7 LCDR1

<400> SEQUENCE: 55

Arg Ala Ser Gln Ser Val Ser Ser Ala Val Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: X8 LCDR1

<400> SEQUENCE: 56

Arg Ala Ser Gln Ser Val Ser Ser Ala Val Ala
1               5                   10

<210> SEQ ID NO 57
<211> LENGTH: 11
<212> TYPE: PRT
<213> ORGANISM: Artificial Sequence
<220> FEATURE:
<223> OTHER INFORMATION: X9 LCDR1

<400> SEQUENCE: 57

Arg Ala Ser Gln Ser Val Ser Ser Ala Val Ala
1               5                   10

<210> SEQ ID NO 58
<211> LENGTH: 11
<212> TYPE: PRT
<213> ORGANISM: Artificial Sequence
<220> FEATURE:
<223> OTHER INFORMATION: X10 LCDR1

<400> SEQUENCE: 58

Arg Ala Ser Gln Ser Val Ser Ser Ala Val Ala
1               5                   10

<210> SEQ ID NO 59
<211> LENGTH: 11
<212> TYPE: PRT
<213> ORGANISM: Artificial Sequence
<220> FEATURE:
<223> OTHER INFORMATION: X11 LCDR1

<400> SEQUENCE: 59

Arg Ala Ser Gln Ser Val Ser Ser Ala Val Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: X12 LCDR1

<400> SEQUENCE: 60

Arg Ala Ser Gln Ser Val Ser Ser Ala Val Ala

<210> SEQ ID NO 61
<211> LENGTH: 11
<212> TYPE: PRT
<213> ORGANISM: Artificial Sequence
<220> FEATURE:
<223> OTHER INFORMATION: X13 LCDR1

<400> SEQUENCE: 61

Arg Ala Ser Gln Ser Val Ser Ser Ala Val Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: X14 LCDR1

<400> SEQUENCE: 62

Arg Ala Ser Gln Ser Val Ser Ser Ala Val Ala
1               5                   10

<210> SEQ ID NO 63
<211> LENGTH: 11
<212> TYPE: PRT
<213> ORGANISM: Artificial Sequence
<220> FEATURE:
<223> OTHER INFORMATION: X15 LCDR1

<400> SEQUENCE: 63

Arg Ala Ser Gln Ser Val Ser Ser Ala Val Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: X16 LCDR1

<400> SEQUENCE: 64

Arg Ala Ser Gln Ser Val Ser Ser Ala Val Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: X1 LCDR2

<400> SEQUENCE: 65

Ser Ala Ser Ser Leu Tyr Ser
1               5

<210> SEQ ID NO 66
<211> LENGTH: 7
<212> TYPE: PRT
<213> ORGANISM: Artificial Sequence
<220> FEATURE:
<223> OTHER INFORMATION: X2 LCDR2

<400> SEQUENCE: 66

Ser Ala Ser Ser Leu Tyr Ser
1               5

<210> SEQ ID NO 67
<211> LENGTH: 7
<212> TYPE: PRT
<213> ORGANISM: Artificial Sequence
<220> FEATURE:
<223> OTHER INFORMATION: X3 LCDR2

<400> SEQUENCE: 67

Ser Ala Ser Ser Leu Tyr Ser
1               5

<210> SEQ ID NO 68
<211> LENGTH: 7
<212> TYPE: PRT
<213> ORGANISM: Artificial Sequence
<220> FEATURE:
<223> OTHER INFORMATION: X4 LCDR2

<400> SEQUENCE: 68

Ser Ala Ser Ser Leu Tyr Ser
1               5

<210> SEQ ID NO 69
<211> LENGTH: 7
<212> TYPE: PRT
<213> ORGANISM: Artificial Sequence
<220> FEATURE:
<223> OTHER INFORMATION: X5 LCDR2

<400> SEQUENCE: 69

Ser Ala Ser Ser Leu Tyr Ser
1               5

<210> SEQ ID NO 70
<211> LENGTH: 7
<212> TYPE: PRT
<213> ORGANISM: Artificial Sequence
<220> FEATURE:
<223> OTHER INFORMATION: X6 LCDR2

<400> SEQUENCE: 70

Ser Ala Ser Ser Leu Tyr Ser
1               5

<210> SEQ ID NO 71
<211> LENGTH: 7
<212> TYPE: PRT
<213> ORGANISM: Artificial Sequence
<220> FEATURE:
<223> OTHER INFORMATION: X7 LCDR2

<400> SEQUENCE: 71

Ser Ala Ser Ser Leu Tyr Ser
1               5

<210> SEQ ID NO 72
<211> LENGTH: 7
<212> TYPE: PRT
<213> ORGANISM: Artificial Sequence
<220> FEATURE:
<223> OTHER INFORMATION: X8 LCDR2

<400> SEQUENCE: 72

Ser Ala Ser Ser Leu Tyr Ser
1               5

<210> SEQ ID NO 73
<211> LENGTH: 7
<212> TYPE: PRT
<213> ORGANISM: Artificial Sequence
<220> FEATURE:
<223> OTHER INFORMATION: X9 LCDR2

<400> SEQUENCE: 73

Ser Ala Ser Ser Leu Tyr Ser
1               5

<210> SEQ ID NO 74
<211> LENGTH: 7
<212> TYPE: PRT
<213> ORGANISM: Artificial Sequence
<220> FEATURE:
<223> OTHER INFORMATION: X10 LCDR2

<400> SEQUENCE: 74

Ser Ala Ser Ser Leu Tyr Ser
1               5

<210> SEQ ID NO 75
<211> LENGTH: 7
<212> TYPE: PRT
<213> ORGANISM: Artificial Sequence
<220> FEATURE:
<223> OTHER INFORMATION: X11 LCDR2

<400> SEQUENCE: 75

Ser Ala Ser Ser Leu Tyr Ser
1               5

<210> SEQ ID NO 76
<211> LENGTH: 7
<212> TYPE: PRT
<213> ORGANISM: Artificial Sequence
<220> FEATURE:
<223> OTHER INFORMATION: X12 LCDR2

<400> SEQUENCE: 76

Ser Ala Ser Ser Leu Tyr Ser
1               5

<210> SEQ ID NO 77
<211> LENGTH: 7
<212> TYPE: PRT
<213> ORGANISM: Artificial Sequence
<220> FEATURE:
<223> OTHER INFORMATION: X13 LCDR2

<400> SEQUENCE: 77

Ser Ala Ser Ser Leu Tyr Ser
1               5

<210> SEQ ID NO 78
<211> LENGTH: 7
<212> TYPE: PRT
<213> ORGANISM: Artificial Sequence
<220> FEATURE:
<223> OTHER INFORMATION: X14 LCDR2

<400> SEQUENCE: 78

Ser Ala Ser Ser Leu Tyr Ser
1               5

```
<210> SEQ ID NO 79
<211> LENGTH: 7
<212> TYPE: PRT
<213> ORGANISM: Artificial Sequence
<220> FEATURE:
<223> OTHER INFORMATION: X15 LCDR2

<400> SEQUENCE: 79

Ser Ala Ser Ser Leu Tyr Ser
1               5

<210> SEQ ID NO 80
<211> LENGTH: 7
<212> TYPE: PRT
<213> ORGANISM: Artificial Sequence
<220> FEATURE:
<223> OTHER INFORMATION: X16 LCDR2

<400> SEQUENCE: 80

Ser Ala Ser Ser Leu Tyr Ser
1               5

<210> SEQ ID NO 81
<211> LENGTH: 9
<212> TYPE: PRT
<213> ORGANISM: Artificial Sequence
<220> FEATURE:
<223> OTHER INFORMATION: X1 LCDR3

<400> SEQUENCE: 81

Gln Gln Ser Ser Ser Ser Leu Ile Thr
1               5

<210> SEQ ID NO 82
<211> LENGTH: 9
<212> TYPE: PRT
<213> ORGANISM: Artificial Sequence
<220> FEATURE:
<223> OTHER INFORMATION: X2 LCDR3

<400> SEQUENCE: 82

Gln Gln Ser Gly Val Trp Leu Ile Thr
1               5

<210> SEQ ID NO 83
<211> LENGTH: 9
<212> TYPE: PRT
<213> ORGANISM: Artificial Sequence
<220> FEATURE:
<223> OTHER INFORMATION: X3 LCDR3

<400> SEQUENCE: 83

Gln Gln Ser Ser Ser Ser Leu Ile Thr
1               5

<210> SEQ ID NO 84
<211> LENGTH: 11
<212> TYPE: PRT
<213> ORGANISM: Artificial Sequence
<220> FEATURE:
<223> OTHER INFORMATION: X4 LCDR3

<400> SEQUENCE: 84

Gln Gln Ser Tyr Lys Pro Gly Ala Leu Ile Thr
1               5                   10

<210> SEQ ID NO 85
```

```
<211> LENGTH: 9
<212> TYPE: PRT
<213> ORGANISM: Artificial Sequence
<220> FEATURE:
<223> OTHER INFORMATION: X5 LCDR3

<400> SEQUENCE: 85

Gln Gln Ser Ser Ser Ser Leu Ile Thr
1               5

<210> SEQ ID NO 86
<211> LENGTH: 9
<212> TYPE: PRT
<213> ORGANISM: Artificial Sequence
<220> FEATURE:
<223> OTHER INFORMATION: X6 LCDR3

<400> SEQUENCE: 86

Gln Gln Ser Ser Ser Ser Leu Ile Thr
1               5

<210> SEQ ID NO 87
<211> LENGTH: 10
<212> TYPE: PRT
<213> ORGANISM: Artificial Sequence
<220> FEATURE:
<223> OTHER INFORMATION: X7 LCDR3

<400> SEQUENCE: 87

Gln Gln Ser Ser Arg Ser Ser Leu Leu Thr
1               5                   10

<210> SEQ ID NO 88
<211> LENGTH: 9
<212> TYPE: PRT
<213> ORGANISM: Artificial Sequence
<220> FEATURE:
<223> OTHER INFORMATION: X8 LCDR3

<400> SEQUENCE: 88

Gln Gln Ser Ser Ser Ser Leu Ile Thr
1               5

<210> SEQ ID NO 89
<211> LENGTH: 9
<212> TYPE: PRT
<213> ORGANISM: Artificial Sequence
<220> FEATURE:
<223> OTHER INFORMATION: X9 LCDR3

<400> SEQUENCE: 89

Gln Gln Ser Ser Ser Ser Leu Ile Thr
1               5

<210> SEQ ID NO 90
<211> LENGTH: 9
<212> TYPE: PRT
<213> ORGANISM: Artificial Sequence
<220> FEATURE:
<223> OTHER INFORMATION: X10 LCDR3

<400> SEQUENCE: 90

Gln Gln Ser Leu Trp Tyr Pro Val Thr
1               5

<210> SEQ ID NO 91
<211> LENGTH: 9
```

```
<212> TYPE: PRT
<213> ORGANISM: Artificial Sequence
<220> FEATURE:
<223> OTHER INFORMATION: X11 LCDR3

<400> SEQUENCE: 91

Gln Gln Asn Ser Tyr Tyr Leu Ile Thr
1               5

<210> SEQ ID NO 92
<211> LENGTH: 9
<212> TYPE: PRT
<213> ORGANISM: Artificial Sequence
<220> FEATURE:
<223> OTHER INFORMATION: X12 LCDR3

<400> SEQUENCE: 92

Gln Gln Ser Ser Ser Ser Leu Ile Thr
1               5

<210> SEQ ID NO 93
<211> LENGTH: 11
<212> TYPE: PRT
<213> ORGANISM: Artificial Sequence
<220> FEATURE:
<223> OTHER INFORMATION: X13 LCDR3

<400> SEQUENCE: 93

Gln Gln Ser Tyr Gly Ser Phe Ser Leu Ile Thr
1               5                   10

<210> SEQ ID NO 94
<211> LENGTH: 9
<212> TYPE: PRT
<213> ORGANISM: Artificial Sequence
<220> FEATURE:
<223> OTHER INFORMATION: X14 LCDR3

<400> SEQUENCE: 94

Gln Gln Gly Ser Tyr His Leu Ile Thr
1               5

<210> SEQ ID NO 95
<211> LENGTH: 9
<212> TYPE: PRT
<213> ORGANISM: Artificial Sequence
<220> FEATURE:
<223> OTHER INFORMATION: X15 LCDR3

<400> SEQUENCE: 95

Gln Gln Ser Gly Val Trp Leu Ile Thr
1               5

<210> SEQ ID NO 96
<211> LENGTH: 11
<212> TYPE: PRT
<213> ORGANISM: Artificial Sequence
<220> FEATURE:
<223> OTHER INFORMATION: X16 LCDR3

<400> SEQUENCE: 96

Gln Gln Trp Ser Ser Ala Gln Ala Leu Ile Thr
1               5                   10

<210> SEQ ID NO 97
<211> LENGTH: 126
<212> TYPE: PRT
```

-continued

<213> ORGANISM: Artificial Sequence
<220> FEATURE:
<223> OTHER INFORMATION: X1 VH

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Lys Tyr Trp Ser Gln Tyr Tyr Trp Ala His Tyr Tyr Gly Gly
            100                 105                 110

Leu Asp Tyr Trp Gly Gln Gly Thr Leu Val Thr Val Ser Ser
        115                 120                 125

<210> SEQ ID NO 98
<211> LENGTH: 107
<212> TYPE: PRT
<213> ORGANISM: Artificial Sequence
<220> FEATURE:
<223> OTHER INFORMATION: VL

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Leu Ile
                85                  90                  95

Thr Phe Gly Gln Gly Thr Lys Val Glu Ile Lys
            100                 105

<210> SEQ ID NO 99
<211> LENGTH: 124
<212> TYPE: PRT
<213> ORGANISM: Artificial Sequence
<220> FEATURE:
<223> OTHER INFORMATION: X2 VH

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Ser Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Gly Asp Arg Tyr Val Ser Gly Tyr Met Gly Met Asp
            100                 105                 110

Tyr Trp Gly Gln Gly Thr Leu Val Thr Val Ser Ser
            115                 120

<210> SEQ ID NO 100
<211> LENGTH: 107
<212> TYPE: PRT
<213> ORGANISM: Artificial Sequence
<220> FEATURE:
<223> OTHER INFORMATION: X2 VL

<400> SEQUENCE: 100

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gly Val Trp Leu Ile
                 85                  90                  95

Thr Phe Gly Gln Gly Thr Lys Val Glu Ile Lys
            100                 105

<210> SEQ ID NO 101
<211> LENGTH: 124
<212> TYPE: PRT
<213> ORGANISM: Artificial Sequence
<220> FEATURE:
<223> OTHER INFORMATION: X3 VH

<400> SEQUENCE: 101

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Ser Ser
             20                  25                  30

Ser Ile His Trp Val Arg Gln Ala Pro Gly Lys Gly Leu Glu Trp Val
         35                  40                  45

Ala Ser Ile Ser Ser Ser Gly Tyr Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Trp Tyr Glu Met Trp Met Ser Gly Tyr Phe Gly Phe Asp
            100                 105                 110

Tyr Trp Gly Gln Gly Thr Leu Val Thr Val Ser Ser

```
                115                 120

<210> SEQ ID NO 102
<211> LENGTH: 107
<212> TYPE: PRT
<213> ORGANISM: Artificial Sequence
<220> FEATURE:
<223> OTHER INFORMATION: VL

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ser Leu Ile
                85                  90                  95

Thr Phe Gly Gln Gly Thr Lys Val Glu Ile Lys
            100                 105

<210> SEQ ID NO 103
<211> LENGTH: 124
<212> TYPE: PRT
<213> ORGANISM: Artificial Sequence
<220> FEATURE:
<223> OTHER INFORMATION: X4 VH

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu His Asp Tyr Tyr Val Phe Gly Tyr Leu Gly Met Asp
            100                 105                 110

Tyr Trp Gly Gln Gly Thr Leu Val Thr Val Ser Ser
        115                 120

<210> SEQ ID NO 104
<211> LENGTH: 109
<212> TYPE: PRT
<213> ORGANISM: Artificial Sequence
<220> FEATURE:
<223> OTHER INFORMATION: VL

<400> SEQUENCE: 104

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Pro Gly Ala
                85                  90                  95

Leu Ile Thr Phe Gly Gln Gly Thr Lys Val Glu Ile Lys
            100                 105

<210> SEQ ID NO 105
<211> LENGTH: 129
<212> TYPE: PRT
<213> ORGANISM: Artificial Sequence
<220> FEATURE:
<223> OTHER INFORMATION: X5 VH

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Ser
            20                  25                  30

Ser Ile His Trp Val Arg Gln Ala Pro Gly Lys Gly Leu Glu Trp Val
        35                  40                  45

Ala Ser Ile Ser Ser Ser Ser Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Thr Met Phe Tyr Tyr Gly Gly Trp Tyr Gly Ser Gly
            100                 105                 110

Tyr Phe Gly Met Asp Tyr Trp Gly Gln Gly Thr Leu Val Thr Val Ser
        115                 120                 125

Ser

<210> SEQ ID NO 106
<211> LENGTH: 107
<212> TYPE: PRT
<213> ORGANISM: Artificial Sequence
<220> FEATURE:
<223> OTHER INFORMATION: VL

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Ser Ser Leu Ile
                85                  90                  95

Thr Phe Gly Gln Gly Thr Lys Val Glu Ile Lys
            100                 105

<210> SEQ ID NO 107
<211> LENGTH: 124
<212> TYPE: PRT
<213> ORGANISM: Artificial Sequence
<220> FEATURE:
<223> OTHER INFORMATION: X6 VH

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ser Tyr Tyr Val Ser Ser Tyr Thr Gly Met Asp
            100                 105                 110

Tyr Trp Gly Gln Gly Thr Leu Val Thr Val Ser Ser
        115                 120

<210> SEQ ID NO 108
<211> LENGTH: 107
<212> TYPE: PRT
<213> ORGANISM: Artificial Sequence
<220> FEATURE:
<223> OTHER INFORMATION: VL

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Leu Ile
                85                  90                  95

Thr Phe Gly Gln Gly Thr Lys Val Glu Ile Lys
            100                 105

<210> SEQ ID NO 109
<211> LENGTH: 124
<212> TYPE: PRT
<213> ORGANISM: Artificial Sequence
<220> FEATURE:
<223> OTHER INFORMATION: X7 VH
```

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Ala Gly Leu Tyr His Tyr Pro Gly Tyr Leu Gly Leu Asp
            100                 105                 110

Tyr Trp Gly Gln Gly Thr Leu Val Thr Val Ser Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: VL

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Arg Ser Ser Leu
                85                  90                  95

Leu Thr Phe Gly Gln Gly Thr Lys Val Glu Ile Lys
            100                 105

<210> SEQ ID NO 111
<211> LENGTH: 128
<212> TYPE: PRT
<213> ORGANISM: Artificial Sequence
<220> FEATURE:
<223> OTHER INFORMATION: X8 VH

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Ser Gly Ser Thr Ser Tyr Ala Asp Ser Val
    50                  55                  60

-continued

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Ser Tyr His Pro Trp Tyr Tyr His Val Gly Trp Tyr
            100                 105                 110

Thr Gly Leu Asp Tyr Trp Gly Gln Gly Thr Leu Val Thr Val Ser Ser
        115                 120                 125

<210> SEQ ID NO 112
<211> LENGTH: 107
<212> TYPE: PRT
<213> ORGANISM: Artificial Sequence
<220> FEATURE:
<223> OTHER INFORMATION: VL

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ser Leu Ile
                85                  90                  95

Thr Phe Gly Gln Gly Thr Lys Val Glu Ile Lys
            100                 105

<210> SEQ ID NO 113
<211> LENGTH: 124
<212> TYPE: PRT
<213> ORGANISM: Artificial Sequence
<220> FEATURE:
<223> OTHER INFORMATION: X9 VH

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Tyr Ser Ser Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Glu Phe Tyr Ile Thr Ser Tyr Tyr Gly Met Asp
            100                 105                 110

Tyr Trp Gly Gln Gly Thr Leu Val Thr Val Ser Ser
        115                 120

<210> SEQ ID NO 114
<211> LENGTH: 107
<212> TYPE: PRT
<213> ORGANISM: Artificial Sequence
<220> FEATURE:
<223> OTHER INFORMATION: VL

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ser Leu Ile
                85                  90                  95

Thr Phe Gly Gln Gly Thr Lys Val Glu Ile Lys
            100                 105

<210> SEQ ID NO 115
<211> LENGTH: 124
<212> TYPE: PRT
<213> ORGANISM: Artificial Sequence
<220> FEATURE:
<223> OTHER INFORMATION: X10 VH

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Ser Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Lys Tyr Tyr Arg Trp Arg His Asn Lys Tyr Gln Gly Phe Asp
            100                 105                 110

Tyr Trp Gly Gln Gly Thr Leu Val Thr Val Ser Ser
        115                 120

<210> SEQ ID NO 116
<211> LENGTH: 107
<212> TYPE: PRT
<213> ORGANISM: Artificial Sequence
<220> FEATURE:
<223> OTHER INFORMATION: VL

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

```
Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Trp Tyr Pro Val
                85                  90                  95

Thr Phe Gly Gln Gly Thr Lys Val Glu Ile Lys
            100                 105
```

<210> SEQ ID NO 117
<211> LENGTH: 124
<212> TYPE: PRT
<213> ORGANISM: Artificial Sequence
<220> FEATURE:
<223> OTHER INFORMATION: X11 VH

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Ser Ile Ser Ser Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Ser Tyr Tyr Val Ser Gly Phe Val Gly Phe Asp
            100                 105                 110

Tyr Trp Gly Gln Gly Thr Leu Val Thr Val Ser Ser
        115                 120
```

<210> SEQ ID NO 118
<211> LENGTH: 107
<212> TYPE: PRT
<213> ORGANISM: Artificial Sequence
<220> FEATURE:
<223> OTHER INFORMATION: VL

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ser Tyr Tyr Leu Ile
                85                  90                  95

Thr Phe Gly Gln Gly Thr Lys Val Glu Ile Lys
```

<210> SEQ ID NO 119
<211> LENGTH: 126
<212> TYPE: PRT
<213> ORGANISM: Artificial Sequence
<220> FEATURE:
<223> OTHER INFORMATION: X12 VH

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Tyr Ile Ser Pro Ser Ser Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Tyr Trp Val Pro Gln Trp Trp Ile Thr Gln Tyr Phe Gly
            100                 105                 110

Met Asp Tyr Trp Gly Gln Gly Thr Leu Val Thr Val Ser Ser
        115                 120                 125

<210> SEQ ID NO 120
<211> LENGTH: 107
<212> TYPE: PRT
<213> ORGANISM: Artificial Sequence
<220> FEATURE:
<223> OTHER INFORMATION: VL

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ser Leu Ile
                85                  90                  95

Thr Phe Gly Gln Gly Thr Lys Val Glu Ile Lys
            100                 105

<210> SEQ ID NO 121
<211> LENGTH: 124
<212> TYPE: PRT
<213> ORGANISM: Artificial Sequence
<220> FEATURE:
<223> OTHER INFORMATION: X13 VH

<400> SEQUENCE: 121

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Ser Gly Ser Thr Ser Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Glu His Trp Tyr Thr Ile Gly Tyr Tyr Gly Ile Asp
            100                 105                 110

Tyr Trp Gly Gln Gly Thr Leu Val Thr Val Ser Ser
        115                 120
```

<210> SEQ ID NO 122
<211> LENGTH: 109
<212> TYPE: PRT
<213> ORGANISM: Artificial Sequence
<220> FEATURE:
<223> OTHER INFORMATION: VL

<400> SEQUENCE: 122

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Gly Ser Phe Ser
                85                  90                  95

Leu Ile Thr Phe Gly Gln Gly Thr Lys Val Glu Ile Lys
            100                 105
```

<210> SEQ ID NO 123
<211> LENGTH: 124
<212> TYPE: PRT
<213> ORGANISM: Artificial Sequence
<220> FEATURE:
<223> OTHER INFORMATION: X14 VH

<400> SEQUENCE: 123

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

85                  90                  95
Ala Arg Gly Ser His His Trp Phe Leu Trp Ile Tyr Ser Gly Leu Asp
                100                 105                 110
Tyr Trp Gly Gln Gly Thr Leu Val Thr Val Ser Ser
            115                 120

<210> SEQ ID NO 124
<211> LENGTH: 107
<212> TYPE: PRT
<213> ORGANISM: Artificial Sequence
<220> FEATURE:
<223> OTHER INFORMATION: VL

<400> SEQUENCE: 124

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Ser Ser Ala
                20                  25                  30
Val Ala Trp Tyr Gln Gln Lys Pro Gly Lys Ala Pro Lys Leu Leu Ile
            35                  40                  45
Tyr Ser Ala Ser Ser Leu Tyr Ser Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Ser Tyr His Leu Ile
                85                  90                  95
Thr Phe Gly Gln Gly Thr Lys Val Glu Ile Lys
            100                 105

<210> SEQ ID NO 125
<211> LENGTH: 124
<212> TYPE: PRT
<213> ORGANISM: Artificial Sequence
<220> FEATURE:
<223> OTHER INFORMATION: X15 VH

<400> SEQUENCE: 125

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Ser Ser
                20                  25                  30
Ser Ile His Trp Val Arg Gln Ala Pro Gly Lys Gly Leu Glu Trp Val
            35                  40                  45
Ala Ser Ile Ser Ser Ser Tyr Gly Ser Thr Ser Tyr Ala Asp Ser Val
        50                  55                  60
Lys Gly Arg Phe Thr Ile Ser Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Glu Gly Asp Arg Tyr Val Ser Gly Tyr Met Gly Met Asp
                100                 105                 110
Tyr Trp Gly Gln Gly Thr Leu Val Thr Val Ser Ser
            115                 120

<210> SEQ ID NO 126
<211> LENGTH: 107
<212> TYPE: PRT
<213> ORGANISM: Artificial Sequence
<220> FEATURE:

<223> OTHER INFORMATION: VL

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Val Trp Leu Ile
                85                  90                  95

Thr Phe Gly Gln Gly Thr Lys Val Glu Ile Lys
            100                 105

<210> SEQ ID NO 127
<211> LENGTH: 125
<212> TYPE: PRT
<213> ORGANISM: Artificial Sequence
<220> FEATURE:
<223> OTHER INFORMATION: X16 VH

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
        35                  40                  45

Ala Ser Ile Tyr Ser Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Tyr Tyr Met Tyr Trp Gly Trp Tyr Tyr Ala Leu
            100                 105                 110

Asp Tyr Trp Gly Gln Gly Thr Leu Val Thr Val Ser Ser
        115                 120                 125

<210> SEQ ID NO 128
<211> LENGTH: 109
<212> TYPE: PRT
<213> ORGANISM: Artificial Sequence
<220> FEATURE:
<223> OTHER INFORMATION: VL

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly

```
                50              55              60
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Ser Ser Ala Gln Ala
                 85                  90                  95

Leu Ile Thr Phe Gly Gln Gly Thr Lys Val Glu Ile Lys
                100                 105
```

<210> SEQ ID NO 129
<211> LENGTH: 869
<212> TYPE: PRT
<213> ORGANISM: Homo sapiens

<400> SEQUENCE: 129

```
Met Arg Glu Leu Val Asn Ile Pro Leu Val His Ile Leu Thr Leu Val
 1                5                  10                  15

Ala Phe Ser Gly Thr Glu Lys Leu Pro Lys Ala Pro Val Ile Thr Thr
                 20                  25                  30

Pro Leu Glu Thr Val Asp Ala Leu Val Glu Glu Val Ala Thr Phe Met
                 35                  40                  45

Cys Ala Val Glu Ser Tyr Pro Gln Pro Glu Ile Ser Trp Thr Arg Asn
 50                  55                  60

Lys Ile Leu Ile Lys Leu Phe Asp Thr Arg Tyr Ser Ile Arg Glu Asn
 65                  70                  75                  80

Gly Gln Leu Leu Thr Ile Leu Ser Val Glu Asp Ser Asp Asp Gly Ile
                 85                  90                  95

Tyr Cys Cys Thr Ala Asn Asn Gly Val Gly Gly Ala Val Glu Ser Cys
                100                 105                 110

Gly Ala Leu Gln Val Lys Met Lys Pro Lys Ile Thr Arg Pro Pro Ile
                115                 120                 125

Asn Val Lys Ile Ile Glu Gly Leu Lys Ala Val Leu Pro Cys Thr Thr
130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
                180                 185                 190

Lys Asn Ser Leu Gly Thr Ala Tyr Ser Lys Val Val Lys Leu Glu Val
                195                 200                 205

Glu Val Phe Ala Arg Ile Leu Arg Ala Pro Glu Ser His Asn Val Thr
                210                 215                 220

Phe Gly Ser Phe Val Thr Leu His Cys Thr Ala Thr Gly Ile Pro Val
225                 230                 235                 240

Pro Thr Ile Thr Trp Ile Glu Asn Gly Asn Ala Val Ser Ser Gly Ser
                245                 250                 255

Ile Gln Glu Ser Val Lys Asp Arg Val Ile Asp Ser Arg Leu Gln Leu
                260                 265                 270

Phe Ile Thr Lys Pro Gly Leu Tyr Thr Cys Ile Ala Thr Asn Lys His
                275                 280                 285

Gly Glu Lys Phe Ser Thr Ala Lys Ala Ala Thr Ile Ser Ile Ala
                290                 295                 300

Glu Trp Ser Lys Pro Gln Lys Asp Asn Lys Gly Tyr Cys Ala Gln Tyr
305                 310                 315                 320
```

```
Arg Gly Glu Val Cys Asn Ala Val Leu Ala Lys Asp Ala Leu Val Phe
            325                 330                 335

Leu Asn Thr Ser Tyr Ala Asp Pro Glu Ala Gln Glu Leu Leu Val
        340                 345                 350

His Thr Ala Trp Asn Glu Leu Lys Val Val Ser Pro Val Cys Arg Pro
            355                 360                 365

Ala Ala Glu Ala Leu Leu Cys Asn His Ile Phe Gln Glu Cys Ser Pro
370                 375                 380

Gly Val Val Pro Thr Pro Ile Pro Ile Cys Arg Glu Tyr Cys Leu Ala
385                 390                 395                 400

Val Lys Glu Leu Phe Cys Ala Lys Glu Trp Leu Val Met Glu Glu Lys
            405                 410                 415

Thr His Arg Gly Leu Tyr Arg Ser Glu Met His Leu Leu Ser Val Pro
            420                 425                 430

Glu Cys Ser Lys Leu Pro Ser Met His Trp Asp Pro Thr Ala Cys Ala
        435                 440                 445

Arg Leu Pro His Leu Asp Tyr Asn Lys Glu Asn Leu Lys Thr Phe Pro
        450                 455                 460

Pro Met Thr Ser Ser Lys Pro Ser Val Asp Ile Pro Asn Leu Pro Ser
465                 470                 475                 480

Ser Ser Ser Ser Ser Phe Ser Val Ser Pro Thr Tyr Ser Met Thr Val
            485                 490                 495

Ile Ile Ser Ile Met Ser Ser Phe Ala Ile Phe Val Leu Leu Thr Ile
            500                 505                 510

Thr Thr Leu Tyr Cys Cys Arg Arg Arg Lys Gln Trp Lys Asn Lys Lys
            515                 520                 525

Arg Glu Ser Ala Ala Val Thr Leu Thr Thr Leu Pro Ser Glu Leu Leu
530                 535                 540

Leu Asp Arg Leu His Pro Asn Pro Met Tyr Gln Arg Met Pro Leu Leu
545                 550                 555                 560

Leu Asn Pro Lys Leu Leu Ser Leu Glu Tyr Pro Arg Asn Asn Ile Glu
            565                 570                 575

Tyr Val Arg Asp Ile Gly Glu Gly Ala Phe Gly Arg Val Phe Gln Ala
            580                 585                 590

Arg Ala Pro Gly Leu Leu Pro Tyr Glu Pro Phe Thr Met Val Ala Val
            595                 600                 605

Lys Met Leu Lys Glu Glu Ala Ser Ala Asp Met Gln Ala Asp Phe Gln
            610                 615                 620

Arg Glu Ala Ala Leu Met Ala Glu Phe Asp Asn Pro Asn Ile Val Lys
625                 630                 635                 640

Leu Leu Gly Val Cys Ala Val Gly Lys Pro Met Cys Leu Leu Phe Glu
            645                 650                 655

Tyr Met Ala Tyr Gly Asp Leu Asn Glu Phe Leu Arg Ser Met Ser Pro
            660                 665                 670

His Thr Val Cys Ser Leu Ser His Ser Asp Leu Ser Met Arg Ala Gln
            675                 680                 685

Val Ser Ser Pro Gly Pro Pro Pro Leu Ser Cys Ala Glu Gln Leu Cys
        690                 695                 700

Ile Ala Arg Gln Val Ala Gly Met Ala Tyr Leu Ser Glu Arg Lys
705                 710                 715                 720

Phe Val His Arg Asp Leu Ala Thr Arg Asn Cys Leu Val Gly Glu Asn
            725                 730                 735

Met Val Val Lys Ile Ala Asp Phe Gly Leu Ser Arg Asn Ile Tyr Ser
```

```
                   740                 745                 750
Ala Asp Tyr Tyr Lys Ala Asn Glu Asn Asp Ala Ile Pro Ile Arg Trp
            755                 760                 765

Met Pro Pro Glu Ser Ile Phe Tyr Asn Arg Tyr Thr Thr Glu Ser Asp
    770                 775                 780

Val Trp Ala Tyr Gly Val Val Leu Trp Glu Ile Phe Ser Tyr Gly Leu
785                 790                 795                 800

Gln Pro Tyr Tyr Gly Met Ala His Glu Val Ile Tyr Tyr Val Arg
                805                 810                 815

Asp Gly Asn Ile Leu Ser Cys Pro Glu Asn Cys Pro Val Glu Leu Tyr
            820                 825                 830

Asn Leu Met Arg Leu Cys Trp Ser Lys Leu Pro Ala Asp Arg Pro Ser
        835                 840                 845

Phe Thr Ser Ile His Arg Ile Leu Glu Arg Met Cys Glu Arg Ala Glu
    850                 855                 860

Gly Thr Val Ser Val
865

<210> SEQ ID NO 130
<211> LENGTH: 139
<212> TYPE: PRT
<213> ORGANISM: Artificial Sequence
<220> FEATURE:
<223> OTHER INFORMATION: Fz-like domain of MuSK

<400> SEQUENCE: 130

Asp Asn Lys Gly Tyr Cys Ala Gln Tyr Arg Gly Glu Val Cys Asn Ala
1               5                  10                  15

Val Leu Ala Lys Asp Ala Leu Val Phe Leu Asn Thr Ser Tyr Ala Asp
            20                  25                  30

Pro Glu Glu Ala Gln Glu Leu Leu Val His Thr Ala Trp Asn Glu Leu
        35                  40                  45

Lys Val Val Ser Pro Val Cys Arg Pro Ala Ala Glu Ala Leu Leu Cys
    50                  55                  60

Asn His Ile Phe Gln Glu Cys Ser Pro Gly Val Val Pro Thr Pro Ile
65                  70                  75                  80

Pro Ile Cys Arg Glu Tyr Cys Leu Ala Val Lys Glu Leu Phe Cys Ala
                85                  90                  95

Lys Glu Trp Leu Val Met Glu Glu Lys Thr His Arg Gly Leu Tyr Arg
            100                 105                 110

Ser Glu Met His Leu Leu Ser Val Pro Glu Cys Ser Lys Leu Pro Ser
        115                 120                 125

Met His Trp Asp Pro Thr Ala Cys Ala Arg Leu
    130                 135

<210> SEQ ID NO 131
<211> LENGTH: 124
<212> TYPE: PRT
<213> ORGANISM: Artificial Sequence
<220> FEATURE:
<223> OTHER INFORMATION: X17 VH

<400> SEQUENCE: 131

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Ile Ser Tyr Ser
            20                  25                  30
```

```
Ser Ile His Trp Val Arg Gln Ala Pro Gly Lys Gly Leu Glu Trp Val
        35                  40                  45

Ala Ser Ile Tyr Ser Ser Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Asp His Gly Tyr Tyr Val Phe Gly Tyr Leu Gly Met Asp
            100                 105                 110

Tyr Trp Gly Gln Gly Thr Leu Val Thr Val Ser Ser
        115                 120
```

<210> SEQ ID NO 132
<211> LENGTH: 109
<212> TYPE: PRT
<213> ORGANISM: Artificial Sequence
<220> FEATURE:
<223> OTHER INFORMATION: X17 VL

<400> SEQUENCE: 132

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Lys Pro Gly Ala
                 85                  90                  95

Leu Ile Thr Phe Gly Gln Gly Thr Lys Val Glu Ile Lys
            100                 105
```

<210> SEQ ID NO 133
<211> LENGTH: 126
<212> TYPE: PRT
<213> ORGANISM: Artificial Sequence
<220> FEATURE:
<223> OTHER INFORMATION: X18 VH

<400> SEQUENCE: 133

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Ser Gly Tyr Thr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Lys Tyr Ser Lys Arg Ala Tyr Pro Asp Tyr Tyr Trp Arg Gly
            100                 105                 110
```

```
Leu Asp Tyr Trp Gly Gln Gly Thr Leu Val Thr Val Ser Ser
        115                 120                 125

<210> SEQ ID NO 134
<211> LENGTH: 107
<212> TYPE: PRT
<213> ORGANISM: Artificial Sequence
<220> FEATURE:
<223> OTHER INFORMATION: VL

<400> SEQUENCE: 134

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Trp Trp Pro Ile
                85                  90                  95

Thr Phe Gly Gln Gly Thr Lys Val Glu Ile Lys
            100                 105

<210> SEQ ID NO 135
<211> LENGTH: 5
<212> TYPE: PRT
<213> ORGANISM: Artificial Sequence
<220> FEATURE:
<223> OTHER INFORMATION: X17 HCDR1

<400> SEQUENCE: 135

Tyr Ser Ser Ile His
1               5

<210> SEQ ID NO 136
<211> LENGTH: 5
<212> TYPE: PRT
<213> ORGANISM: Artificial Sequence
<220> FEATURE:
<223> OTHER INFORMATION: X18 HCDR1

<400> SEQUENCE: 136

Ser Ser Ser Ile His
1               5

<210> SEQ ID NO 137
<211> LENGTH: 17
<212> TYPE: PRT
<213> ORGANISM: Artificial Sequence
<220> FEATURE:
<223> OTHER INFORMATION: X17 HCDR2

<400> SEQUENCE: 137

Ser Ile Tyr Ser Ser Ser Gly Thr Tyr Tyr Ala Asp Ser Val Lys
1               5                   10                  15

Gly

<210> SEQ ID NO 138
<211> LENGTH: 17
```

```
<212> TYPE: PRT
<213> ORGANISM: Artificial Sequence
<220> FEATURE:
<223> OTHER INFORMATION: X18 HCDR2

<400> SEQUENCE: 138

Ser Ile Ser Ser Ser Ser Gly Tyr Thr Ser Tyr Ala Asp Ser Val Lys
1               5                   10                  15
Gly

<210> SEQ ID NO 139
<211> LENGTH: 15
<212> TYPE: PRT
<213> ORGANISM: Artificial Sequence
<220> FEATURE:
<223> OTHER INFORMATION: X17 HCDR3

<400> SEQUENCE: 139

Gly Asp His Gly Tyr Tyr Val Phe Gly Tyr Leu Gly Met Asp Tyr
1               5                   10                  15

<210> SEQ ID NO 140
<211> LENGTH: 17
<212> TYPE: PRT
<213> ORGANISM: Artificial Sequence
<220> FEATURE:
<223> OTHER INFORMATION: X18 HCDR3

<400> SEQUENCE: 140

Lys Tyr Ser Lys Arg Ala Tyr Pro Asp Tyr Tyr Trp Arg Gly Leu Asp
1               5                   10                  15
Tyr

<210> SEQ ID NO 141
<211> LENGTH: 11
<212> TYPE: PRT
<213> ORGANISM: Artificial Sequence
<220> FEATURE:
<223> OTHER INFORMATION: X17 LCDR1

<400> SEQUENCE: 141

Arg Ala Ser Gln Ser Val Ser Ser Ala Val Ala
1               5                   10

<210> SEQ ID NO 142
<211> LENGTH: 11
<212> TYPE: PRT
<213> ORGANISM: Artificial Sequence
<220> FEATURE:
<223> OTHER INFORMATION: X18 LCDR1

<400> SEQUENCE: 142

Arg Ala Ser Gln Ser Val Ser Ser Ala Val Ala
1               5                   10

<210> SEQ ID NO 143
<211> LENGTH: 7
<212> TYPE: PRT
<213> ORGANISM: Artificial Sequence
<220> FEATURE:
<223> OTHER INFORMATION: X17 LCDR2

<400> SEQUENCE: 143

Ser Ala Ser Ser Leu Tyr Ser
1               5
```

<210> SEQ ID NO 144
<211> LENGTH: 7
<212> TYPE: PRT
<213> ORGANISM: Artificial Sequence
<220> FEATURE:
<223> OTHER INFORMATION: X18 LCDR2

<400> SEQUENCE: 144

Ser Ala Ser Ser Leu Tyr Ser
1               5

<210> SEQ ID NO 145
<211> LENGTH: 11
<212> TYPE: PRT
<213> ORGANISM: Artificial Sequence
<220> FEATURE:
<223> OTHER INFORMATION: X17 LCDR3

<400> SEQUENCE: 145

Gln Gln Ser Tyr Lys Pro Gly Ala Leu Ile Thr
1               5                   10

<210> SEQ ID NO 146
<211> LENGTH: 9
<212> TYPE: PRT
<213> ORGANISM: Artificial Sequence
<220> FEATURE:
<223> OTHER INFORMATION: X18 LCDR3

<400> SEQUENCE: 146

Gln Gln Ser Tyr Trp Trp Pro Ile Thr
1               5

<210> SEQ ID NO 147
<211> LENGTH: 5
<212> TYPE: PRT
<213> ORGANISM: Artificial Sequence
<220> FEATURE:
<223> OTHER INFORMATION: 14D10 HCDR1

<400> SEQUENCE: 147

Asp Tyr Gly Met Ser
1               5

<210> SEQ ID NO 148
<211> LENGTH: 7
<212> TYPE: PRT
<213> ORGANISM: Artificial Sequence
<220> FEATURE:
<223> OTHER INFORMATION: 17H10 HCDR1

<400> SEQUENCE: 148

Ala Arg Tyr Tyr Ser Trp Ser
1               5

<210> SEQ ID NO 149
<211> LENGTH: 5
<212> TYPE: PRT
<213> ORGANISM: Artificial Sequence
<220> FEATURE:
<223> OTHER INFORMATION: 16F11 HCDR1

<400> SEQUENCE: 149

Leu Tyr Tyr Met Asn
1               5

```
<210> SEQ ID NO 150
<211> LENGTH: 17
<212> TYPE: PRT
<213> ORGANISM: Artificial Sequence
<220> FEATURE:
<223> OTHER INFORMATION: 14D10 HCDR2

<400> SEQUENCE: 150

Ala Ile Pro Trp Asn Gly Gly Ser Thr Tyr Tyr Lys Glu Ser Val Lys
1               5                   10                  15
Gly

<210> SEQ ID NO 151
<211> LENGTH: 16
<212> TYPE: PRT
<213> ORGANISM: Artificial Sequence
<220> FEATURE:
<223> OTHER INFORMATION: 17H10 HCDR2

<400> SEQUENCE: 151

Val Ile Ala Tyr Asp Gly Ser Thr Tyr Tyr Ser Pro Ser Leu Lys Ser
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: 16F11 HCDR2

<400> SEQUENCE: 152

Val Ile Asp Thr His Ser Ile Ala Tyr Tyr Ala Asp Ser Val Lys Gly
1               5                   10                  15

<210> SEQ ID NO 153
<211> LENGTH: 17
<212> TYPE: PRT
<213> ORGANISM: Artificial Sequence
<220> FEATURE:
<223> OTHER INFORMATION: 3B2g1m1 HCDR2

<400> SEQUENCE: 153

Ala Ile Pro Trp Ser Gly Gly Ser Thr Tyr Tyr Lys Glu Ser Val Lys
1               5                   10                  15
Gly

<210> SEQ ID NO 154
<211> LENGTH: 17
<212> TYPE: PRT
<213> ORGANISM: Artificial Sequence
<220> FEATURE:
<223> OTHER INFORMATION: 3B2g1m2 HCDR2

<400> SEQUENCE: 154

Ala Ile Pro Gly Ser Gly Gly Ser Thr Tyr Tyr Lys Glu Ser Val Lys
1               5                   10                  15
Gly

<210> SEQ ID NO 155
<211> LENGTH: 17
<212> TYPE: PRT
<213> ORGANISM: Artificial Sequence
<220> FEATURE:
<223> OTHER INFORMATION: 3B2g1m4 HCDR2

<400> SEQUENCE: 155
```

```
Ala Ile Pro Trp Gln Gly Gly Ser Thr Tyr Tyr Lys Glu Ser Val Lys
1               5                   10                  15

Gly

<210> SEQ ID NO 156
<211> LENGTH: 12
<212> TYPE: PRT
<213> ORGANISM: Artificial Sequence
<220> FEATURE:
<223> OTHER INFORMATION: 14D10 HCDR3

<400> SEQUENCE: 156

Arg Ser Gly Arg Ile Ala Phe Gly Ala Leu Asp Ala
1               5                   10

<210> SEQ ID NO 157
<211> LENGTH: 11
<212> TYPE: PRT
<213> ORGANISM: Artificial Sequence
<220> FEATURE:
<223> OTHER INFORMATION: 17H10 HCDR3

<400> SEQUENCE: 157

Gly Ser Ser Arg Val Ala Ala Ala Phe Asp Ser
1               5                   10

<210> SEQ ID NO 158
<211> LENGTH: 7
<212> TYPE: PRT
<213> ORGANISM: Artificial Sequence
<220> FEATURE:
<223> OTHER INFORMATION: 16F11 HCDR3

<400> SEQUENCE: 158

Gly Arg Thr Ala Leu Val Arg
1               5

<210> SEQ ID NO 159
<211> LENGTH: 14
<212> TYPE: PRT
<213> ORGANISM: Artificial Sequence
<220> FEATURE:
<223> OTHER INFORMATION: 14D10  LCDR1

<400> SEQUENCE: 159

Gly Leu Ser Ser Gly Ser Val Thr Ser Ser Asn Tyr Pro Asp
1               5                   10

<210> SEQ ID NO 160
<211> LENGTH: 14
<212> TYPE: PRT
<213> ORGANISM: Artificial Sequence
<220> FEATURE:
<223> OTHER INFORMATION: 3C4 LCDR1

<400> SEQUENCE: 160

Gly Leu Ser Ser Gly Ser Val Thr Ala Ser Asn Tyr Pro Asp
1               5                   10

<210> SEQ ID NO 161
<211> LENGTH: 11
<212> TYPE: PRT
<213> ORGANISM: Artificial Sequence
<220> FEATURE:
<223> OTHER INFORMATION: 17H10  LCDR1
```

```
<400> SEQUENCE: 161

Gly Gly Asn Arg Ile Gly Gly Lys Ser Val Gln
1               5                   10

<210> SEQ ID NO 162
<211> LENGTH: 11
<212> TYPE: PRT
<213> ORGANISM: Artificial Sequence
<220> FEATURE:
<223> OTHER INFORMATION: 23B6  LCDR1

<400> SEQUENCE: 162

Gly Gly Asp Asn Ile Gly Ser Lys Asn Ala Gln
1               5                   10

<210> SEQ ID NO 163
<211> LENGTH: 11
<212> TYPE: PRT
<213> ORGANISM: Artificial Sequence
<220> FEATURE:
<223> OTHER INFORMATION: 30E1  LCDR1

<400> SEQUENCE: 163

Gly Gly Asp Asn Ile Gly Ser Lys Asn Thr Gln
1               5                   10

<210> SEQ ID NO 164
<211> LENGTH: 11
<212> TYPE: PRT
<213> ORGANISM: Artificial Sequence
<220> FEATURE:
<223> OTHER INFORMATION: 30A11   LCDR1

<400> SEQUENCE: 164

Gly Gly Asp Asn Ile Ala Ser Lys Asn Val Gln
1               5                   10

<210> SEQ ID NO 165
<211> LENGTH: 17
<212> TYPE: PRT
<213> ORGANISM: Artificial Sequence
<220> FEATURE:
<223> OTHER INFORMATION: 16F11 LCDR1

<400> SEQUENCE: 165

Lys Ser Ser Gln Ser Val Val Phe Gly Ser Asn Gln Lys Ser Tyr Leu
1               5                   10                  15

Asn

<210> SEQ ID NO 166
<211> LENGTH: 17
<212> TYPE: PRT
<213> ORGANISM: Artificial Sequence
<220> FEATURE:
<223> OTHER INFORMATION: 4C11 LCDR1

<400> SEQUENCE: 166

Arg Ser Ser Gln Ser Val Leu Tyr Ser Ser Asn Gln Lys Asn Tyr Leu
1               5                   10                  15

Asn

<210> SEQ ID NO 167
<211> LENGTH: 15
<212> TYPE: PRT
<213> ORGANISM: Artificial Sequence
```

```
<220> FEATURE:
<223> OTHER INFORMATION: 7A12 LCDR1

<400> SEQUENCE: 167

Glu Ser Ser Gln Ser Val Leu Tyr Asn Gln Lys Asn Tyr Leu Asn
1               5                   10                  15

<210> SEQ ID NO 168
<211> LENGTH: 17
<212> TYPE: PRT
<213> ORGANISM: Artificial Sequence
<220> FEATURE:
<223> OTHER INFORMATION: 7G12 LCDR1

<400> SEQUENCE: 168

Lys Ser Ser Gln Arg Val Gln Leu Gly Ser Asn Gln Lys Ser Tyr Leu
1               5                   10                  15

Asn

<210> SEQ ID NO 169
<211> LENGTH: 15
<212> TYPE: PRT
<213> ORGANISM: Artificial Sequence
<220> FEATURE:
<223> OTHER INFORMATION: 7B8 LCDR1

<400> SEQUENCE: 169

Lys Ser Ser Gln Ser Val Leu Tyr Asn Gln Lys Asn Tyr Leu Ala
1               5                   10                  15

<210> SEQ ID NO 170
<211> LENGTH: 7
<212> TYPE: PRT
<213> ORGANISM: Artificial Sequence
<220> FEATURE:
<223> OTHER INFORMATION: 14D10  LCDR2

<400> SEQUENCE: 170

Thr Thr Asn Ser Arg His Ser
1               5

<210> SEQ ID NO 171
<211> LENGTH: 7
<212> TYPE: PRT
<213> ORGANISM: Artificial Sequence
<220> FEATURE:
<223> OTHER INFORMATION: 7G4  LCDR2

<400> SEQUENCE: 171

Ser Thr Asn Ser Arg His Ser
1               5

<210> SEQ ID NO 172
<211> LENGTH: 7
<212> TYPE: PRT
<213> ORGANISM: Artificial Sequence
<220> FEATURE:
<223> OTHER INFORMATION: 3C4 LCDR2

<400> SEQUENCE: 172

Ser Thr Asp Ser Arg His Ser
1               5

<210> SEQ ID NO 173
<211> LENGTH: 7
<212> TYPE: PRT
```

```
<213> ORGANISM: Artificial Sequence
<220> FEATURE:
<223> OTHER INFORMATION: 31G2  LCDR2

<400> SEQUENCE: 173

Ser Thr Asn Ser Arg Leu Ser
1               5

<210> SEQ ID NO 174
<211> LENGTH: 7
<212> TYPE: PRT
<213> ORGANISM: Artificial Sequence
<220> FEATURE:
<223> OTHER INFORMATION: 17H10  LCDR2

<400> SEQUENCE: 174

Ala Asp Ser Arg Arg Pro Ser
1               5

<210> SEQ ID NO 175
<211> LENGTH: 7
<212> TYPE: PRT
<213> ORGANISM: Artificial Sequence
<220> FEATURE:
<223> OTHER INFORMATION: 16F11 LCDR2

<400> SEQUENCE: 175

Tyr Ala Ser Thr Gln Glu Ser
1               5

<210> SEQ ID NO 176
<211> LENGTH: 7
<212> TYPE: PRT
<213> ORGANISM: Artificial Sequence
<220> FEATURE:
<223> OTHER INFORMATION: 4C11 LCDR2

<400> SEQUENCE: 176

Trp Ala Ser Ala Arg Glu Ser
1               5

<210> SEQ ID NO 177
<211> LENGTH: 7
<212> TYPE: PRT
<213> ORGANISM: Artificial Sequence
<220> FEATURE:
<223> OTHER INFORMATION: 7A12 LCDR2

<400> SEQUENCE: 177

Trp Ala Ser Thr Arg Gln Ser
1               5

<210> SEQ ID NO 178
<211> LENGTH: 7
<212> TYPE: PRT
<213> ORGANISM: Artificial Sequence
<220> FEATURE:
<223> OTHER INFORMATION: 7G12 LCDR2

<400> SEQUENCE: 178

Tyr Ala Ser Thr Gln Gln Ser
1               5

<210> SEQ ID NO 179
<211> LENGTH: 7
<212> TYPE: PRT
<213> ORGANISM: Artificial Sequence
```

-continued

```
<220> FEATURE:
<223> OTHER INFORMATION: 7B8 LCDR2

<400> SEQUENCE: 179

Trp Ala Ser Thr Arg Glu Ser
1               5

<210> SEQ ID NO 180
<211> LENGTH: 12
<212> TYPE: PRT
<213> ORGANISM: Artificial Sequence
<220> FEATURE:
<223> OTHER INFORMATION: 14D10  LCDR3

<400> SEQUENCE: 180

Ala Leu Tyr Met Gly Gly Gly Ser Asn Val Tyr Val
1               5                  10

<210> SEQ ID NO 181
<211> LENGTH: 13
<212> TYPE: PRT
<213> ORGANISM: Artificial Sequence
<220> FEATURE:
<223> OTHER INFORMATION: 7G4  LCDR3

<400> SEQUENCE: 181

Ala Leu Tyr Met Gly Arg Gly Ser Asn Lys Asp Tyr Val
1               5                  10

<210> SEQ ID NO 182
<211> LENGTH: 12
<212> TYPE: PRT
<213> ORGANISM: Artificial Sequence
<220> FEATURE:
<223> OTHER INFORMATION: 3C4 LCDR3

<400> SEQUENCE: 182

Ala Leu Tyr Met Tyr Ser Asp Ser Lys Leu Tyr Val
1               5                  10

<210> SEQ ID NO 183
<211> LENGTH: 12
<212> TYPE: PRT
<213> ORGANISM: Artificial Sequence
<220> FEATURE:
<223> OTHER INFORMATION: 3B2  LCDR3

<400> SEQUENCE: 183

Gly Leu Tyr Met Tyr Ser Gly Ser Lys Asn Tyr Val
1               5                  10

<210> SEQ ID NO 184
<211> LENGTH: 12
<212> TYPE: PRT
<213> ORGANISM: Artificial Sequence
<220> FEATURE:
<223> OTHER INFORMATION: 3G3  LCDR3

<400> SEQUENCE: 184

Ala Leu Tyr Met Gly Ser Asp Ile Arg Asn Tyr Val
1               5                  10

<210> SEQ ID NO 185
<211> LENGTH: 12
<212> TYPE: PRT
<213> ORGANISM: Artificial Sequence
<220> FEATURE:
```

<223> OTHER INFORMATION: 31G2 LCDR3

<400> SEQUENCE: 185

Ala Leu Tyr Met Gly Ser Gly Ser Arg Asn Tyr Val
1               5                   10

<210> SEQ ID NO 186
<211> LENGTH: 12
<212> TYPE: PRT
<213> ORGANISM: Artificial Sequence
<220> FEATURE:
<223> OTHER INFORMATION: 31B7 LCDR3

<400> SEQUENCE: 186

Ala Leu Tyr Met Gly Ser Glu Ser Arg Asn Tyr Val
1               5                   10

<210> SEQ ID NO 187
<211> LENGTH: 10
<212> TYPE: PRT
<213> ORGANISM: Artificial Sequence
<220> FEATURE:
<223> OTHER INFORMATION: 17H10 LCDR3

<400> SEQUENCE: 187

His Val Trp Gly Ser Thr Ala Ser Ala Asp
1               5                   10

<210> SEQ ID NO 188
<211> LENGTH: 10
<212> TYPE: PRT
<213> ORGANISM: Artificial Sequence
<220> FEATURE:
<223> OTHER INFORMATION: 23B6 LCDR3

<400> SEQUENCE: 188

His Val Trp Asp Ser Ser Thr Asn Ala Trp
1               5                   10

<210> SEQ ID NO 189
<211> LENGTH: 11
<212> TYPE: PRT
<213> ORGANISM: Artificial Sequence
<220> FEATURE:
<223> OTHER INFORMATION: 30A11 LCDR3

<400> SEQUENCE: 189

Gln Val Trp Asp Ser Ser Thr Asn Val Ala Val
1               5                   10

<210> SEQ ID NO 190
<211> LENGTH: 8
<212> TYPE: PRT
<213> ORGANISM: Artificial Sequence
<220> FEATURE:
<223> OTHER INFORMATION: 16F11 LCDR3

<400> SEQUENCE: 190

Gln Gln Ala Tyr Ser Ala Pro Thr
1               5

<210> SEQ ID NO 191
<211> LENGTH: 9
<212> TYPE: PRT
<213> ORGANISM: Artificial Sequence
<220> FEATURE:
<223> OTHER INFORMATION: 4C11 LCDR3

<400> SEQUENCE: 191

Gln Gln Ser Tyr Lys Pro Pro Tyr Gly
1               5

<210> SEQ ID NO 192
<211> LENGTH: 9
<212> TYPE: PRT
<213> ORGANISM: Artificial Sequence
<220> FEATURE:
<223> OTHER INFORMATION: 7A12 LCDR3

<400> SEQUENCE: 192

Gln Gln Ala Tyr Asn Ala Pro Leu Thr
1               5

<210> SEQ ID NO 193
<211> LENGTH: 9
<212> TYPE: PRT
<213> ORGANISM: Artificial Sequence
<220> FEATURE:
<223> OTHER INFORMATION: 7G12 LCDR3

<400> SEQUENCE: 193

Gln Gln Gly Tyr Ser Ala Pro Phe Thr
1               5

<210> SEQ ID NO 194
<211> LENGTH: 9
<212> TYPE: PRT
<213> ORGANISM: Artificial Sequence
<220> FEATURE:
<223> OTHER INFORMATION: 7B8 LCDR3

<400> SEQUENCE: 194

Gln Gln Gly Tyr Ser Val Pro Tyr Thr
1               5

<210> SEQ ID NO 195
<211> LENGTH: 12
<212> TYPE: PRT
<213> ORGANISM: Artificial Sequence
<220> FEATURE:
<223> OTHER INFORMATION: 3B2g2m1 LCDR3

<400> SEQUENCE: 195

Gly Leu Tyr Ser Tyr Ser Gly Ser Lys Asn Tyr Val
1               5                   10

<210> SEQ ID NO 196
<211> LENGTH: 121
<212> TYPE: PRT
<213> ORGANISM: Artificial Sequence
<220> FEATURE:
<223> OTHER INFORMATION: 14D10 VH

<400> SEQUENCE: 196

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
    50                  55                  60

Lys Gly Arg Phe Thr Ile Ser Arg Asp Asn Ala Lys Thr Leu Tyr
65                  70                  75                  80

Leu Gln Met Asn Ser Leu Lys Ser Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 197
<211> LENGTH: 112
<212> TYPE: PRT
<213> ORGANISM: Artificial Sequence
<220> FEATURE:
<223> OTHER INFORMATION: VL

<400> SEQUENCE: 197

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Thr Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Gly
                85                  90                  95

Gly Ser Asn Val Tyr Val Phe Gly Gly Gly Thr Lys Leu Thr Val Leu
            100                 105                 110

<210> SEQ ID NO 198
<211> LENGTH: 121
<212> TYPE: PRT
<213> ORGANISM: Artificial Sequence
<220> FEATURE:
<223> OTHER INFORMATION: 7G4 VH

<400> SEQUENCE: 198

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
    50                  55                  60

Lys Gly Arg Phe Thr Ile Ser Arg Asp Asn Ala Lys Thr Leu Tyr
65                  70                  75                  80

Leu Gln Met Asn Ser Leu Lys Ser Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

```
<210> SEQ ID NO 199
<211> LENGTH: 113
<212> TYPE: PRT
<213> ORGANISM: Artificial Sequence
<220> FEATURE:
<223> OTHER INFORMATION: VL

<400> SEQUENCE: 199

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Ala
        35                  40                  45

Leu Ile Tyr Ser Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Arg
                85                  90                  95

Gly Ser Asn Lys Asp Tyr Val Phe Gly Gly Gly Thr Lys Leu Thr Val
            100                 105                 110

Leu

<210> SEQ ID NO 200
<211> LENGTH: 121
<212> TYPE: PRT
<213> ORGANISM: Artificial Sequence
<220> FEATURE:
<223> OTHER INFORMATION: 3C4 VH

<400> SEQUENCE: 200

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Ser Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 201
<211> LENGTH: 112
<212> TYPE: PRT
<213> ORGANISM: Artificial Sequence
<220> FEATURE:
<223> OTHER INFORMATION: VL

<400> SEQUENCE: 201

Gln Ala Val Val Thr Gln Glu Pro Ser Leu Ser Val Ser Pro Gly Gly
1               5                   10                  15
```

```
Thr Val Thr Leu Thr Cys Gly Leu Ser Ser Gly Ser Val Thr Ala Ser
            20                  25                  30

Asn Tyr Pro Asp Trp Tyr Gln Gln Thr Pro Gly Gln Ala Pro Arg Gly
        35                  40                  45

Leu Ile Tyr Ser Thr Asp Ser Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Tyr Met Tyr Ser
                85                  90                  95

Asp Ser Lys Leu Tyr Val Phe Gly Gly Gly Thr Lys Leu Thr Val Leu
            100                 105                 110
```

<210> SEQ ID NO 202
<211> LENGTH: 121
<212> TYPE: PRT
<213> ORGANISM: Artificial Sequence
<220> FEATURE:
<223> OTHER INFORMATION: 3B2 VH

<400> SEQUENCE: 202

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Ser Thr Tyr Tyr Lys Glu Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Ser Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120
```

<210> SEQ ID NO 203
<211> LENGTH: 112
<212> TYPE: PRT
<213> ORGANISM: Artificial Sequence
<220> FEATURE:
<223> OTHER INFORMATION: VL

<400> SEQUENCE: 203

```
Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Gly
        35                  40                  45

Leu Ile Tyr Ser Thr Asp Ser Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Ser Glu Asp Glu Ala Asp Tyr Tyr Cys Gly Leu Tyr Met Tyr Ser
                85                  90                  95
```

```
Gly Ser Lys Asn Tyr Val Phe Gly Gly Gly Thr Lys Leu Thr Val Leu
            100                 105                 110
```

<210> SEQ ID NO 204
<211> LENGTH: 121
<212> TYPE: PRT
<213> ORGANISM: Artificial Sequence
<220> FEATURE:
<223> OTHER INFORMATION: 3G3 VH

<400> SEQUENCE: 204

```
Glu Leu Gln Leu Val Glu Ser Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Gly Arg Ile Ala Phe Gly Ala Leu Asp Ala Trp Gly
            100                 105                 110

Gln Gly Thr Leu Val Thr Val Ser Ser
        115                 120
```

<210> SEQ ID NO 205
<211> LENGTH: 112
<212> TYPE: PRT
<213> ORGANISM: Artificial Sequence
<220> FEATURE:
<223> OTHER INFORMATION: VL

<400> SEQUENCE: 205

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Ala
        35                  40                  45

Leu Ile Tyr Ser Thr Asn Ser Arg His Ser Gly Val Pro Ser Arg Phe
    50                  55                  60

Ser Gly Ser Thr Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Asp Ile Arg Asn Tyr Val Phe Gly Gly Gly Thr Lys Leu Thr Val Leu
            100                 105                 110
```

<210> SEQ ID NO 206
<211> LENGTH: 121
<212> TYPE: PRT
<213> ORGANISM: Artificial Sequence
<220> FEATURE:
<223> OTHER INFORMATION: 31G2 VH

<400> SEQUENCE: 206

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Ser Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
            115                 120
```

<210> SEQ ID NO 207
<211> LENGTH: 112
<212> TYPE: PRT
<213> ORGANISM: Artificial Sequence
<220> FEATURE:
<223> OTHER INFORMATION: VL

<400> SEQUENCE: 207

```
Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Ala
        35                  40                  45

Leu Ile Tyr Ser Thr Asn Ser Arg Leu Ser Gly Val Pro Ser Arg Phe
50                  55                  60

Ser Gly Ser Phe Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Gly Ser Arg Asn Tyr Val Phe Gly Gly Gly Thr Lys Leu Thr Val Leu
            100                 105                 110
```

<210> SEQ ID NO 208
<211> LENGTH: 121
<212> TYPE: PRT
<213> ORGANISM: Artificial Sequence
<220> FEATURE:
<223> OTHER INFORMATION: 31B7 VH

<400> SEQUENCE: 208

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Pro Trp Asn Gly Gly Ser Thr Tyr Tyr Lys Glu Ser Val
50                  55                  60

Lys Gly Arg Phe Thr Ile Ser Arg Asp Asn Ala Lys Lys Thr Leu Tyr
65                  70                  75                  80
```

Leu Gln Met Asn Ser Leu Lys Ser Glu Asp Thr Ala Val Tyr Tyr Cys
                    85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 209
<211> LENGTH: 112
<212> TYPE: PRT
<213> ORGANISM: Artificial Sequence
<220> FEATURE:
<223> OTHER INFORMATION: VL

<400> SEQUENCE: 209

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Ala
        35                  40                  45

Leu Ile Tyr Ser Thr Asn Ser Arg Leu Ser Gly Val Pro Ser Arg Phe
    50                  55                  60

Ser Gly Ser Phe Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Glu Ser Arg Asn Tyr Val Phe Gly Gly Gly Thr Lys Leu Thr Val Leu
            100                 105                 110

<210> SEQ ID NO 210
<211> LENGTH: 121
<212> TYPE: PRT
<213> ORGANISM: Artificial Sequence
<220> FEATURE:
<223> OTHER INFORMATION: 17H10 VH

<400> SEQUENCE: 210

Gln Val Gln Val Gln Glu Ser Gly Pro Gly Leu Val Lys Pro Ser Gln
1               5                   10                  15

Thr Leu Ser Leu Thr Cys Thr Val Ser Gly Gly Ser Ile Thr Ala Arg
            20                  25                  30

Tyr Tyr Ser Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu His Leu Ser Ser Val Thr Pro Asp Asp Thr Ala Val Tyr Tyr
                85                  90                  95

Cys Ala Arg Gly Ser Ser Arg Val Ala Ala Ala Phe Asp Ser Trp Gly
            100                 105                 110

Gln Gly Thr Gln Val Thr Val Ser Ser
        115                 120

<210> SEQ ID NO 211
<211> LENGTH: 107
<212> TYPE: PRT

-continued

```
<213> ORGANISM: Artificial Sequence
<220> FEATURE:
<223> OTHER INFORMATION: VL

<400> SEQUENCE: 211

Ser Tyr Glu Leu Thr Gln Ser Pro Ser Val Ser Val Ala Leu Arg Gln
1               5                   10                  15

Thr Ala Lys Ile Thr Cys Gly Gly Asn Arg Ile Gly Gly Lys Ser Val
            20                  25                  30

Gln Trp Tyr Gln Gln Lys Pro Gly Gln Ala Pro Met Leu Val Ile Tyr
        35                  40                  45

Ala Asp Ser Arg Arg Pro Ser Gly Ile Pro Glu Arg Phe Thr Gly Ser
    50                  55                  60

Asn Ser Gly Asn Thr Ala Thr Leu Thr Ile Thr Gly Ala Gln Ala Glu
65                  70                  75                  80

Asp Glu Ala Asp Tyr Tyr Cys His Val Trp Gly Ser Thr Ala Ser Ala
                85                  90                  95

Asp Phe Gly Gly Gly Thr His Leu Thr Val Leu
            100                 105

<210> SEQ ID NO 212
<211> LENGTH: 121
<212> TYPE: PRT
<213> ORGANISM: Artificial Sequence
<220> FEATURE:
<223> OTHER INFORMATION: 23B6 VH

<400> SEQUENCE: 212

Gln Val Gln Val Gln Glu Ser Gly Pro Gly Leu Val Lys Pro Ser Gln
1               5                   10                  15

Thr Leu Ser Leu Thr Cys Thr Val Ser Gly Gly Ser Ile Thr Ala Arg
            20                  25                  30

Tyr Tyr Ser Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu His Leu Ser Ser Val Thr Pro Asp Asp Thr Ala Val Tyr Tyr
                85                  90                  95

Cys Ala Arg Gly Ser Ser Arg Val Ala Ala Phe Asp Ser Trp Gly
            100                 105                 110

Gln Gly Thr Gln Val Thr Val Ser Ser
        115                 120

<210> SEQ ID NO 213
<211> LENGTH: 107
<212> TYPE: PRT
<213> ORGANISM: Artificial Sequence
<220> FEATURE:
<223> OTHER INFORMATION: VL

<400> SEQUENCE: 213

Ser Tyr Glu Leu Thr Gln Ser Pro Ser Val Ser Val Ala Leu Arg Gln
1               5                   10                  15

Thr Ala Lys Ile Thr Cys Gly Gly Asp Asn Ile Gly Ser Lys Asn Ala
            20                  25                  30

Gln Trp Tyr Gln Gln Lys Pro Gly Gln Ala Pro Val Met Val Leu Tyr
        35                  40                  45
```

```
Ala Asp Ser Arg Arg Pro Ser Gly Ile Pro Glu Arg Phe Ser Gly Ser
    50                  55                  60

Asn Ser Gly Asn Thr Ala Thr Leu Thr Ile Ser Gly Ala Gln Ala Glu
65                  70                  75                  80

Asp Glu Ala Asp Tyr Tyr Cys His Val Trp Asp Ser Ser Thr Asn Ala
                85                  90                  95

Trp Phe Gly Gly Gly Thr His Leu Thr Val Leu
                100                 105

<210> SEQ ID NO 214
<211> LENGTH: 121
<212> TYPE: PRT
<213> ORGANISM: Artificial Sequence
<220> FEATURE:
<223> OTHER INFORMATION: 30E1 VH

<400> SEQUENCE: 214

Gln Val Gln Val Gln Glu Ser Gly Pro Gly Leu Val Lys Pro Ser Gln
1               5                   10                  15

Thr Leu Ser Leu Thr Cys Thr Val Ser Gly Gly Ser Ile Thr Ala Arg
            20                  25                  30

Tyr Tyr Ser Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu His Leu Ser Ser Val Thr Pro Asp Asp Thr Ala Val Tyr Tyr
                85                  90                  95

Cys Ala Arg Gly Ser Ser Arg Val Ala Ala Ala Phe Asp Ser Trp Gly
            100                 105                 110

Gln Gly Thr Gln Val Thr Val Ser Ser
        115                 120

<210> SEQ ID NO 215
<211> LENGTH: 107
<212> TYPE: PRT
<213> ORGANISM: Artificial Sequence
<220> FEATURE:
<223> OTHER INFORMATION: VL

<400> SEQUENCE: 215

Ser Tyr Glu Leu Thr Gln Ser Pro Ser Val Ser Val Ala Leu Arg Arg
1               5                   10                  15

Thr Ala Lys Ile Thr Cys Gly Gly Asp Asn Ile Gly Ser Lys Asn Thr
            20                  25                  30

Gln Trp Tyr Gln Gln Lys Pro Gly Gln Ala Pro Val Leu Val Ile Tyr
        35                  40                  45

Ala Asp Ser Arg Arg Pro Ser Gly Ile Pro Glu Arg Phe Ser Gly Ser
    50                  55                  60

Asn Ser Gly Asn Thr Ala Thr Leu Thr Ile Ser Gly Ala Gln Ala Glu
65                  70                  75                  80

Asp Glu Ala Asp Tyr Tyr Cys His Val Trp Asp Ser Ser Thr Asn Ala
                85                  90                  95

Trp Phe Gly Gly Gly Thr His Leu Thr Val Leu
                100                 105
```

```
<210> SEQ ID NO 216
<211> LENGTH: 121
<212> TYPE: PRT
<213> ORGANISM: Artificial Sequence
<220> FEATURE:
<223> OTHER INFORMATION: 30A11 VH

<400> SEQUENCE: 216

Gln Val Gln Val Gln Glu Ser Gly Pro Gly Leu Val Lys Pro Ser Gln
1               5                   10                  15

Thr Leu Ser Leu Thr Cys Thr Val Ser Gly Ser Ile Thr Ala Arg
            20                  25                  30

Tyr Tyr Ser Trp Ser Trp Ile Arg Gln Pro Pro Gly Lys Gly Leu Glu
        35                  40                  45

Trp Met Gly Val Ile Ala Tyr Asp Gly Ser Tyr Tyr Ser Pro Ser
    50                  55                  60

Leu Lys Ser Arg Thr Ser Ile Ser Arg Asp Thr Ser Lys Asn Gln Phe
65              70                  75                  80

Ser Leu His Leu Ser Ser Val Thr Pro Asp Asp Thr Ala Val Tyr Tyr
                85                  90                  95

Cys Ala Arg Gly Ser Ser Arg Val Ala Ala Ala Phe Asp Ser Trp Gly
            100                 105                 110

Gln Gly Thr Gln Val Thr Val Ser Ser
        115                 120

<210> SEQ ID NO 217
<211> LENGTH: 108
<212> TYPE: PRT
<213> ORGANISM: Artificial Sequence
<220> FEATURE:
<223> OTHER INFORMATION: VL

<400> SEQUENCE: 217

Ser Tyr Glu Leu Thr Gln Ser Pro Ser Val Thr Val Ala Leu Arg Gln
1               5                   10                  15

Thr Ala Lys Ile Thr Cys Gly Gly Asp Asn Ile Ala Ser Lys Asn Val
            20                  25                  30

Gln Trp Tyr Gln Gln Lys Pro Gly Gln Ala Pro Ser Leu Val Ile Trp
        35                  40                  45

Ala Asp Ser Arg Arg Pro Ser Gly Ile Pro Val Arg Phe Ser Gly Ser
    50                  55                  60

Asn Phe Gly Asn Thr Ala Thr Leu Thr Ile Ser Gly Ala Gln Ala Glu
65              70                  75                  80

Asp Glu Ala Asp Tyr Tyr Cys Gln Val Trp Asp Ser Ser Thr Asn Val
                85                  90                  95

Ala Val Phe Gly Gly Gly Thr His Leu Thr Val Leu
            100                 105

<210> SEQ ID NO 218
<211> LENGTH: 115
<212> TYPE: PRT
<213> ORGANISM: Artificial Sequence
<220> FEATURE:
<223> OTHER INFORMATION: 16F11 VH

<400> SEQUENCE: 218

Glu Val Gln Leu Val Glu Ser Gly Gly Gly Leu Val Gln Pro Gly Gly
1               5                   10                  15

Ser Leu Ser Leu Ser Cys Val Ala Ser Gly Phe Thr Phe Ser Leu Tyr
            20                  25                  30
```

Tyr Met Asn Trp Val Arg Gln Ala Pro Gly Lys Gly Leu Glu Trp Leu
            35                  40                  45

Ser Val Ile Asp Thr His Ser Ile Ala Tyr Tyr Ala Asp Ser Val Lys
    50                  55                  60

Gly Arg Phe Thr Ile Ser Arg Asp Asn Val Lys Asn Thr Leu Tyr Leu
65                  70                  75                  80

Gln Leu Asn Asn Leu Lys Pro Glu Asp Thr Ala Leu Tyr Tyr Cys Val
                85                  90                  95

Leu Gly Arg Thr Ala Leu Val Arg Trp Gly Gln Gly Thr Gln Val Thr
            100                 105                 110

Val Ser Ser
    115

<210> SEQ ID NO 219
<211> LENGTH: 112
<212> TYPE: PRT
<213> ORGANISM: Artificial Sequence
<220> FEATURE:
<223> OTHER INFORMATION: VL

<400> SEQUENCE: 219

Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Phe Gly
            20                  25                  30

Ser Asn Gln Lys Ser Tyr Leu Asn Trp Tyr Gln Gln Arg Pro Gly Gln
            35                  40                  45

Ser Pro Arg Leu Leu Ile Tyr Tyr Ala Ser Thr Gln Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Thr Phe Gly Ser Gly Thr Arg Leu Glu Ile Lys
            100                 105                 110

<210> SEQ ID NO 220
<211> LENGTH: 115
<212> TYPE: PRT
<213> ORGANISM: Artificial Sequence
<220> FEATURE:
<223> OTHER INFORMATION: 4C11 VH

<400> SEQUENCE: 220

Glu Val Gln Leu Val Glu Ser Gly Gly Gly Leu Val Gln Pro Gly Gly
1               5                   10                  15

Ser Leu Ser Leu Ser Cys Val Ala Ser Gly Phe Thr Phe Ser Leu Tyr
            20                  25                  30

Tyr Met Asn Trp Val Arg Gln Ala Pro Gly Lys Gly Leu Glu Trp Leu
            35                  40                  45

Ser Val Ile Asp Thr His Ser Ile Ala Tyr Tyr Ala Asp Ser Val Lys
    50                  55                  60

Gly Arg Phe Thr Ile Ser Arg Asp Asn Val Lys Asn Thr Leu Tyr Leu
65                  70                  75                  80

Gln Leu Asn Asn Leu Lys Pro Glu Asp Thr Ala Leu Tyr Tyr Cys Val
                85                  90                  95

Leu Gly Arg Thr Ala Leu Val Arg Trp Gly Gln Gly Thr Gln Val Thr

Val Ser Ser
    115

<210> SEQ ID NO 221
<211> LENGTH: 113
<212> TYPE: PRT
<213> ORGANISM: Artificial Sequence
<220> FEATURE:
<223> OTHER INFORMATION: VL

<400> SEQUENCE: 221

Asp Ile Val Met Thr Gln Ser Pro Ser Ser Val Thr Ala Ser Ala Gly
1               5                   10                  15

Glu Arg Val Thr Ile Asn Cys Arg Ser Ser Gln Ser Val Leu Tyr Ser
                20                  25                  30

Ser Asn Gln Lys Asn Tyr Leu Asn Trp Tyr Gln Gln Arg Leu Gly Gln
            35                  40                  45

Ser Pro Arg Leu Leu Ile Tyr Trp Ala Ser Ala Arg Glu Ser Gly Val
        50                  55                  60

Pro Asp Arg Phe Ser Gly Ser Gly Ser Thr Thr Asn Phe Thr Leu Thr
65                  70                  75                  80

Ile Ser Ser Phe Gln Pro Glu Asp Ala Ala Val Tyr Tyr Cys Gln Gln
                85                  90                  95

Ser Tyr Lys Pro Pro Tyr Gly Phe Gly Ser Gly Thr Arg Leu Glu Ile
                100                 105                 110

Lys

<210> SEQ ID NO 222
<211> LENGTH: 115
<212> TYPE: PRT
<213> ORGANISM: Artificial Sequence
<220> FEATURE:
<223> OTHER INFORMATION: 7A12 VH

<400> SEQUENCE: 222

Glu Val Gln Leu Val Glu Ser Gly Gly Gly Leu Val Gln Pro Gly Gly
1               5                   10                  15

Ser Leu Ser Leu Ser Cys Val Ala Ser Gly Phe Thr Phe Ser Leu Tyr
                20                  25                  30

Tyr Met Asn Trp Val Arg Gln Ala Pro Gly Lys Gly Leu Glu Trp Leu
            35                  40                  45

Ser Val Ile Asp Thr His Ser Ile Ala Tyr Tyr Ala Asp Ser Val Lys
        50                  55                  60

Gly Arg Phe Thr Ile Ser Arg Asp Asn Val Lys Asn Thr Leu Tyr Leu
65                  70                  75                  80

Gln Leu Asn Asn Leu Lys Pro Glu Asp Thr Ala Leu Tyr Tyr Cys Val
                85                  90                  95

Leu Gly Arg Thr Ala Leu Val Arg Trp Gly Gln Gly Thr Gln Val Thr
                100                 105                 110

Val Ser Ser
    115

<210> SEQ ID NO 223
<211> LENGTH: 113
<212> TYPE: PRT
<213> ORGANISM: Artificial Sequence
<220> FEATURE:
<223> OTHER INFORMATION: VL -continued

<400> SEQUENCE: 223

Glu Ile Val Leu Thr Gln Ser Pro Ser Ser Val Thr Ala Ser Ile Gly
1               5                   10                  15

Glu Lys Val Thr Ile Asn Cys Glu Ser Ser Gln Ser Val Leu Tyr Asn
            20                  25                  30

Gln Lys Asn Tyr Leu Asn Trp Tyr Gln Gln Arg Pro Gly Gln Ser Pro
        35                  40                  45

Arg Leu Leu Ile Tyr Trp Ala Ser Thr Arg Gln Ser Gly Val Pro Asp
    50                  55                  60

Arg Phe Ser Gly Ser Gly Ser Gly Ser Thr Thr Asp Phe Thr Leu Thr
65                  70                  75                  80

Ile Ser Ser Phe Gln Pro Glu Asp Val Ala Val Tyr Tyr Cys Gln Gln
                85                  90                  95

Ala Tyr Asn Ala Pro Leu Thr Phe Gly Pro Gly Thr Lys Val Glu Leu
            100                 105                 110

Lys

<210> SEQ ID NO 224
<211> LENGTH: 115
<212> TYPE: PRT
<213> ORGANISM: Artificial Sequence
<220> FEATURE:
<223> OTHER INFORMATION: 7G12 VH

<400> SEQUENCE: 224

Glu Val Gln Leu Val Glu Ser Gly Gly Gly Leu Val Gln Pro Gly Gly
1               5                   10                  15

Ser Leu Ser Leu Ser Cys Val Ala Ser Gly Phe Thr Phe Ser Leu Tyr
            20                  25                  30

Tyr Met Asn Trp Val Arg Gln Ala Pro Gly Lys Gly Leu Glu Trp Leu
        35                  40                  45

Ser Val Ile Asp Thr His Ser Ile Ala Tyr Tyr Ala Asp Ser Val Lys
    50                  55                  60

Gly Arg Phe Thr Ile Ser Arg Asp Asn Val Lys Asn Thr Leu Tyr Leu
65                  70                  75                  80

Gln Leu Asn Asn Leu Lys Pro Glu Asp Thr Ala Leu Tyr Tyr Cys Val
                85                  90                  95

Leu Gly Arg Thr Ala Leu Val Arg Trp Gly Gln Gly Thr Gln Val Thr
            100                 105                 110

Val Ser Ser
        115

<210> SEQ ID NO 225
<211> LENGTH: 113
<212> TYPE: PRT
<213> ORGANISM: Artificial Sequence
<220> FEATURE:
<223> OTHER INFORMATION: VL

<400> SEQUENCE: 225

Glu Ile Val Leu Thr Gln Ser Pro Asn Ser Val Thr Ala Ser Val Gly
1               5                   10                  15

Glu Lys Val Thr Ile Asn Cys Lys Ser Ser Gln Arg Val Gln Leu Gly
            20                  25                  30

Ser Asn Gln Lys Ser Tyr Leu Asn Trp Tyr Gln Gln Arg Pro Gly Gln
        35                  40                  45

Ser Pro Arg Leu Leu Ile Tyr Tyr Ala Ser Thr Gln Gln Ser Gly Ile
                50                  55                  60

Pro Asp Arg Phe Ser Gly Ser Gly Ser Ala Thr Asp Phe Thr Leu Thr
 65                  70                  75                  80

Ile Asn Ser Val Gln Pro Glu Asp Ala Ala Val Tyr Tyr Cys Gln Gln
                85                  90                  95

Gly Tyr Ser Ala Pro Phe Thr Phe Gly Gln Gly Thr Lys Val Glu Leu
                100                 105                 110

Lys

<210> SEQ ID NO 226
<211> LENGTH: 115
<212> TYPE: PRT
<213> ORGANISM: Artificial Sequence
<220> FEATURE:
<223> OTHER INFORMATION: 7B8 VH

<400> SEQUENCE: 226

Glu Val Gln Leu Val Glu Ser Gly Gly Gly Leu Val Gln Pro Gly Gly
 1               5                   10                  15

Ser Leu Ser Leu Ser Cys Val Ala Ser Gly Phe Thr Phe Ser Leu Tyr
                20                  25                  30

Tyr Met Asn Trp Val Arg Gln Ala Pro Gly Lys Gly Leu Glu Trp Leu
                35                  40                  45

Ser Val Ile Asp Thr His Ser Ile Ala Tyr Tyr Ala Asp Ser Val Lys
                50                  55                  60

Gly Arg Phe Thr Ile Ser Arg Asp Asn Val Lys Asn Thr Leu Tyr Leu
 65                  70                  75                  80

Gln Leu Asn Asn Leu Lys Pro Glu Asp Thr Ala Leu Tyr Tyr Cys Val
                85                  90                  95

Leu Gly Arg Thr Ala Leu Val Arg Trp Gly Gln Gly Thr Gln Val Thr
                100                 105                 110

Val Ser Ser
        115

<210> SEQ ID NO 227
<211> LENGTH: 111
<212> TYPE: PRT
<213> ORGANISM: Artificial Sequence
<220> FEATURE:
<223> OTHER INFORMATION: VL

<400> SEQUENCE: 227

Glu Ile Val Leu Thr Gln Ser Pro Ser Ser Val Thr Ala Ser Ala Gly
 1               5                   10                  15

Glu Lys Val Thr Ile Asn Cys Lys Ser Ser Gln Ser Val Leu Tyr Asn
                20                  25                  30

Gln Lys Asn Tyr Leu Ala Trp Tyr Gln Gln Arg Pro Gly Gln Ser Pro
                35                  40                  45

Arg Leu Leu Ile Tyr Trp Ala Ser Thr Arg Glu Ser Gly Val Pro Asp
                50                  55                  60

Arg Phe Ser Gly Ser Gly Ser Thr Thr Asp Phe Thr Leu Thr Ile Ser
 65                  70                  75                  80

Ser Phe Gln Pro Glu Asp Val Ala Val Tyr Tyr Cys Gln Gln Gly Tyr
                85                  90                  95

Ser Val Pro Tyr Thr Phe Gly Ser Gly Thr Arg Leu Glu Ile Lys
                100                 105                 110

<210> SEQ ID NO 228
<211> LENGTH: 121
<212> TYPE: PRT
<213> ORGANISM: Artificial Sequence
<220> FEATURE:
<223> OTHER INFORMATION: 3B2g1m1 VH

<400> SEQUENCE: 228

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Ala Ile Pro Trp Ser Gly Gly Ser Thr Tyr Tyr Lys Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120
```

<210> SEQ ID NO 229
<211> LENGTH: 112
<212> TYPE: PRT
<213> ORGANISM: Artificial Sequence
<220> FEATURE:
<223> OTHER INFORMATION: VL

<400> SEQUENCE: 229

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Ser Thr Asp Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Gly Leu Tyr Met Tyr Ser
                85                  90                  95

Gly Ser Lys Asn Tyr Val Phe Gly Gly Gly Thr Lys Leu Thr Val Leu
            100                 105                 110
```

<210> SEQ ID NO 230
<211> LENGTH: 121
<212> TYPE: PRT
<213> ORGANISM: Artificial Sequence
<220> FEATURE:
<223> OTHER INFORMATION: 3B2g1m2 VH

<400> SEQUENCE: 230

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
```

```
                20                  25                  30
Gly Met Ser Trp Val Arg Gln Ala Pro Gly Lys Gly Leu Glu Trp Val
                35                  40                  45

Ser Ala Ile Pro Gly Ser Gly Gly Ser Thr Tyr Tyr Lys Glu Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Ser Gly Arg Ile Ala Phe Gly Ala Leu Asp Ala Trp Gly
                100                 105                 110

Gln Gly Thr Leu Val Thr Val Ser Ser
                115                 120
```

<210> SEQ ID NO 231
<211> LENGTH: 112
<212> TYPE: PRT
<213> ORGANISM: Artificial Sequence
<220> FEATURE:
<223> OTHER INFORMATION: VL

<400> SEQUENCE: 231

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Thr Ser Ser
                20                  25                  30

Asn Tyr Pro Asp Trp Tyr Gln Gln Thr Pro Gly Gln Ala Pro Arg Thr
                35                  40                  45

Leu Ile Tyr Ser Thr Asp Ser Arg His Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Gly Leu Tyr Met Tyr Ser
                85                  90                  95

Gly Ser Lys Asn Tyr Val Phe Gly Gly Gly Thr Lys Leu Thr Val Leu
                100                 105                 110
```

<210> SEQ ID NO 232
<211> LENGTH: 121
<212> TYPE: PRT
<213> ORGANISM: Artificial Sequence
<220> FEATURE:
<223> OTHER INFORMATION: 3B2g1m4 VH

<400> SEQUENCE: 232

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Gly Met Ser Trp Val Arg Gln Ala Pro Gly Lys Gly Leu Glu Trp Val
                35                  40                  45

Ser Ala Ile Pro Trp Gln Gly Gly Ser Thr Tyr Tyr Lys Glu Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 233
<211> LENGTH: 112
<212> TYPE: PRT
<213> ORGANISM: Artificial Sequence
<220> FEATURE:
<223> OTHER INFORMATION: VL

<400> SEQUENCE: 233

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Ser Thr Asp Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Gly Leu Tyr Met Tyr Ser
                85                  90                  95

Gly Ser Lys Asn Tyr Val Phe Gly Gly Gly Thr Lys Leu Thr Val Leu
            100                 105                 110

<210> SEQ ID NO 234
<211> LENGTH: 121
<212> TYPE: PRT
<213> ORGANISM: Artificial Sequence
<220> FEATURE:
<223> OTHER INFORMATION: 3B2g2m1 VH

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Ala Ile Pro Trp Ser Gly Gly Ser Thr Tyr Tyr Lys Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 235
<211> LENGTH: 112
<212> TYPE: PRT
<213> ORGANISM: Artificial Sequence
<220> FEATURE:
<223> OTHER INFORMATION: VL -continued

<400> SEQUENCE: 235

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Ser Thr Asp Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Gly Leu Tyr Ser Tyr Ser
                85                  90                  95

Gly Ser Lys Asn Tyr Val Phe Gly Gly Gly Thr Lys Leu Thr Val Leu
            100                 105                 110

<210> SEQ ID NO 236
<211> LENGTH: 121
<212> TYPE: PRT
<213> ORGANISM: Artificial Sequence
<220> FEATURE:
<223> OTHER INFORMATION: 3B2g2m2 VH

<400> SEQUENCE: 236

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Ala Ile Pro Gly Ser Gly Gly Ser Thr Tyr Tyr Lys Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 237
<211> LENGTH: 112
<212> TYPE: PRT
<213> ORGANISM: Artificial Sequence
<220> FEATURE:
<223> OTHER INFORMATION: VL

<400> SEQUENCE: 237

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Ser Thr Asp Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Gly Leu Tyr Ser Tyr Ser
                85                  90                  95

Gly Ser Lys Asn Tyr Val Phe Gly Gly Thr Lys Leu Thr Val Leu
            100                 105                 110

<210> SEQ ID NO 238
<211> LENGTH: 121
<212> TYPE: PRT
<213> ORGANISM: Artificial Sequence
<220> FEATURE:
<223> OTHER INFORMATION: 3B2g2m4 VH

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Ala Ile Pro Trp Gln Gly Ser Thr Tyr Tyr Lys Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Gly Arg Ile Ala Phe Gly Ala Leu Asp Ala Trp Gly
            100                 105                 110

Gln Gly Thr Leu Val Thr Val Ser Ser
        115                 120

<210> SEQ ID NO 239
<211> LENGTH: 112
<212> TYPE: PRT
<213> ORGANISM: Artificial Sequence
<220> FEATURE:
<223> OTHER INFORMATION: VL

<400> SEQUENCE: 239

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Thr
        35                  40                  45

Leu Ile Tyr Ser Thr Asp Ser Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Gly Leu Tyr Ser Tyr Ser
                85                  90                  95

Gly Ser Lys Asn Tyr Val Phe Gly Gly Thr Lys Leu Thr Val Leu
            100                 105                 110

<210> SEQ ID NO 240
<211> LENGTH: 15
<212> TYPE: PRT
<213> ORGANISM: Artificial Sequence

```
<220> FEATURE:
<223> OTHER INFORMATION: X2m1 HCDR3

<400> SEQUENCE: 240

Ser Glu Gly Asp Arg Tyr Val Ser Gly Tyr Phe Gly Phe Asp Tyr
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: X2m2 HCDR3

<400> SEQUENCE: 241

Ser Glu Gly Asp Arg Tyr Val Ser Gly Tyr Phe Gly Leu Asp Tyr
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: X2m3 HCDR3

<400> SEQUENCE: 242

Ser Glu Gly Asp Arg Tyr Val Ser Gly Tyr Ser Gly Phe Asp Tyr
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: X2m4 HCDR3

<400> SEQUENCE: 243

Ser Glu Gly Asp Arg Tyr Val Ser Gly Tyr Ser Gly Leu Asp Tyr
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: X2m5 HCDR3

<400> SEQUENCE: 244

Ser Glu Gly Asp Arg Tyr Val Ser Gly Tyr Phe Gly Met Asp Tyr
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: X2m6 HCDR3

<400> SEQUENCE: 245

Ser Glu Gly Asp Arg Tyr Val Ser Gly Tyr Ser Gly Met Asp Tyr
1               5                   10                  15

<210> SEQ ID NO 246
<211> LENGTH: 15
<212> TYPE: PRT
<213> ORGANISM: Artificial Sequence
<220> FEATURE:
```

<223> OTHER INFORMATION: X2m7 HCDR3

<400> SEQUENCE: 246

Ser Glu Gly Asp Arg Tyr Val Ser Gly Tyr Met Gly Phe Asp Tyr
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: X2m8 HCDR3

<400> SEQUENCE: 247

Ser Glu Gly Asp Arg Tyr Val Ser Gly Tyr Met Gly Leu Asp Tyr
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: X17m1 HCDR3

<400> SEQUENCE: 248

Gly Asp His Gly Tyr Tyr Val Ser Gly Tyr Leu Gly Met Asp Tyr
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: X17m2 HCDR3

<400> SEQUENCE: 249

Gly Asp His Gly Tyr Tyr Val Tyr Gly Tyr Leu Gly Met Asp Tyr
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: X17m3 HCDR3

<400> SEQUENCE: 250

Gly Asp His Gly Tyr Tyr Val Ser Gly Tyr Leu Gly Phe Asp Tyr
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: X17m6 HCDR3

<400> SEQUENCE: 251

Gly Glu His Gly Tyr Tyr Val Ser Gly Tyr Leu Gly Phe Asp Tyr
1               5                   10                  15

<210> SEQ ID NO 252
<211> LENGTH: 124
<212> TYPE: PRT
<213> ORGANISM: Artificial Sequence
<220> FEATURE:
<223> OTHER INFORMATION: X2m1 VH

<400> SEQUENCE: 252

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Gly Asp Arg Tyr Val Ser Gly Tyr Phe Gly Phe Asp
            100                 105                 110

Tyr Trp Gly Gln Gly Thr Leu Val Thr Val Ser Ser
        115                 120

<210> SEQ ID NO 253
<211> LENGTH: 124
<212> TYPE: PRT
<213> ORGANISM: Artificial Sequence
<220> FEATURE:
<223> OTHER INFORMATION: X2m2 VH

<400> SEQUENCE: 253

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Gly Asp Arg Tyr Val Ser Gly Tyr Phe Gly Leu Asp
            100                 105                 110

Tyr Trp Gly Gln Gly Thr Leu Val Thr Val Ser Ser
        115                 120

<210> SEQ ID NO 254
<211> LENGTH: 124
<212> TYPE: PRT
<213> ORGANISM: Artificial Sequence
<220> FEATURE:
<223> OTHER INFORMATION: X2m3 VH

<400> SEQUENCE: 254

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

```
Ala Ser Ile Ser Ser Ser Tyr Gly Ser Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Gly Asp Arg Tyr Val Ser Gly Tyr Ser Gly Phe Asp
                100                 105                 110

Tyr Trp Gly Gln Gly Thr Leu Val Thr Val Ser Ser
            115                 120
```

<210> SEQ ID NO 255
<211> LENGTH: 124
<212> TYPE: PRT
<213> ORGANISM: Artificial Sequence
<220> FEATURE:
<223> OTHER INFORMATION: X2m4 VH

<400> SEQUENCE: 255

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Ser
                20                  25                  30

Ser Ile His Trp Val Arg Gln Ala Pro Gly Lys Gly Leu Glu Trp Val
            35                  40                  45

Ala Ser Ile Ser Ser Ser Tyr Gly Ser Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Gly Asp Arg Tyr Val Ser Gly Tyr Ser Gly Leu Asp
                100                 105                 110

Tyr Trp Gly Gln Gly Thr Leu Val Thr Val Ser Ser
            115                 120
```

<210> SEQ ID NO 256
<211> LENGTH: 124
<212> TYPE: PRT
<213> ORGANISM: Artificial Sequence
<220> FEATURE:
<223> OTHER INFORMATION: X2m5 VH

<400> SEQUENCE: 256

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Ser
                20                  25                  30

Ser Ile His Trp Val Arg Gln Ala Pro Gly Lys Gly Leu Glu Trp Val
            35                  40                  45

Ala Ser Ile Ser Ser Ser Tyr Gly Ser Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Gly Asp Arg Tyr Val Ser Gly Tyr Phe Gly Met Asp
```

```
                100                 105                 110
Tyr Trp Gly Gln Gly Thr Leu Val Thr Val Ser Ser
        115                 120

<210> SEQ ID NO 257
<211> LENGTH: 124
<212> TYPE: PRT
<213> ORGANISM: Artificial Sequence
<220> FEATURE:
<223> OTHER INFORMATION: X2m6 VH

<400> SEQUENCE: 257

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Gly Asp Arg Tyr Val Ser Gly Tyr Ser Gly Met Asp
            100                 105                 110

Tyr Trp Gly Gln Gly Thr Leu Val Thr Val Ser Ser
        115                 120

<210> SEQ ID NO 258
<211> LENGTH: 124
<212> TYPE: PRT
<213> ORGANISM: Artificial Sequence
<220> FEATURE:
<223> OTHER INFORMATION: X2m7 VH

<400> SEQUENCE: 258

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Gly Asp Arg Tyr Val Ser Gly Tyr Met Gly Phe Asp
            100                 105                 110

Tyr Trp Gly Gln Gly Thr Leu Val Thr Val Ser Ser
        115                 120

<210> SEQ ID NO 259
<211> LENGTH: 124
<212> TYPE: PRT
<213> ORGANISM: Artificial Sequence
<220> FEATURE:
```

<223> OTHER INFORMATION: X2m8 VH

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Gly Asp Arg Tyr Val Ser Gly Tyr Met Gly Leu Asp
            100                 105                 110

Tyr Trp Gly Gln Gly Thr Leu Val Thr Val Ser Ser
        115                 120

<210> SEQ ID NO 260
<211> LENGTH: 124
<212> TYPE: PRT
<213> ORGANISM: Artificial Sequence
<220> FEATURE:
<223> OTHER INFORMATION: X17m1 VH

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Tyr Ser
            20                  25                  30

Ser Ile His Trp Val Arg Gln Ala Pro Gly Lys Gly Leu Glu Trp Val
        35                  40                  45

Ala Ser Ile Tyr Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Asp His Gly Tyr Tyr Val Ser Gly Tyr Leu Gly Met Asp
            100                 105                 110

Tyr Trp Gly Gln Gly Thr Leu Val Thr Val Ser Ser
        115                 120

<210> SEQ ID NO 261
<211> LENGTH: 124
<212> TYPE: PRT
<213> ORGANISM: Artificial Sequence
<220> FEATURE:
<223> OTHER INFORMATION: X17m2 VH

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Tyr Ser
            20                  25                  30

Ser Ile His Trp Val Arg Gln Ala Pro Gly Lys Gly Leu Glu Trp Val

```
            35                  40                  45

Ala Ser Ile Tyr Ser Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Asp His Gly Tyr Tyr Val Tyr Gly Tyr Leu Gly Met Asp
            100                 105                 110

Tyr Trp Gly Gln Gly Thr Leu Val Thr Val Ser Ser
            115                 120

<210> SEQ ID NO 262
<211> LENGTH: 124
<212> TYPE: PRT
<213> ORGANISM: Artificial Sequence
<220> FEATURE:
<223> OTHER INFORMATION: X17m3 VH

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Tyr Ser
            20                  25                  30

Ser Ile His Trp Val Arg Gln Ala Pro Gly Lys Gly Leu Glu Trp Val
            35                  40                  45

Ala Ser Ile Tyr Ser Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Asp His Gly Tyr Tyr Val Ser Gly Tyr Leu Gly Phe Asp
            100                 105                 110

Tyr Trp Gly Gln Gly Thr Leu Val Thr Val Ser Ser
            115                 120

<210> SEQ ID NO 263
<211> LENGTH: 124
<212> TYPE: PRT
<213> ORGANISM: Artificial Sequence
<220> FEATURE:
<223> OTHER INFORMATION: X17m6 VH

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Tyr Ser
            20                  25                  30

Ser Ile His Trp Val Arg Gln Ala Pro Gly Lys Gly Leu Glu Trp Val
            35                  40                  45

Ala Ser Ile Tyr Ser Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Gly Glu His Gly Tyr Tyr Val Ser Gly Tyr Leu Gly Phe Asp
            100                 105                 110

Tyr Trp Gly Gln Gly Thr Leu Val Thr Val Ser Ser
        115                 120

<210> SEQ ID NO 264
<211> LENGTH: 17
<212> TYPE: DNA
<213> ORGANISM: Artificial Sequence
<220> FEATURE:
<223> OTHER INFORMATION: sgRNA

<400> SEQUENCE: 264
ctgctcagtc tgccccc                                                       17

<210> SEQ ID NO 265
<211> LENGTH: 125
<212> TYPE: DNA
<213> ORGANISM: Artificial Sequence
<220> FEATURE:
<223> OTHER INFORMATION: DNA repair template

<400> SEQUENCE: 265
atgccggcaa tctggacgtc tggcgggccg gtgaggaatt cggttctctg ctcagtctgc        60
ctgccccctg agccagcgc acctgagccc agactgtgtg cctgcccacc tggggcggcc       120
gagta                                                                  125

<210> SEQ ID NO 266
<211> LENGTH: 18
<212> TYPE: DNA
<213> ORGANISM: Artificial Sequence
<220> FEATURE:
<223> OTHER INFORMATION: Primer

<400> SEQUENCE: 266
gcagttacag gaggttgg                                                      18

<210> SEQ ID NO 267
<211> LENGTH: 19
<212> TYPE: DNA
<213> ORGANISM: Artificial Sequence
<220> FEATURE:
<223> OTHER INFORMATION: Forward primer

<400> SEQUENCE: 267
gcggcctcgg cagttacag                                                     19

<210> SEQ ID NO 268
<211> LENGTH: 24
<212> TYPE: DNA
<213> ORGANISM: Artificial Sequence
<220> FEATURE:
<223> OTHER INFORMATION: Reverse primer

<400> SEQUENCE: 268
gctttacctt gagtccgcca caga                                               24

<210> SEQ ID NO 269
<211> LENGTH: 17
<212> TYPE: DNA
<213> ORGANISM: Artificial Sequence
<220> FEATURE:
<223> OTHER INFORMATION: sgRNA

<400> SEQUENCE: 269

```
ttcgaggtgt gtcatag                                                  17

<210> SEQ ID NO 270
<211> LENGTH: 128
<212> TYPE: DNA
<213> ORGANISM: Artificial Sequence
<220> FEATURE:
<223> OTHER INFORMATION: DNA repair template

<400> SEQUENCE: 270
atgccggcag caacctggac gtgtggcggg ccggtgagga attcggttct ctgctcagtc    60
tgcctgcccc ctggagccag cgcacctgag cccagactgt gtgcctgccc acctggggcg   120
gccgagta                                                           128

<210> SEQ ID NO 271
<211> LENGTH: 18
<212> TYPE: DNA
<213> ORGANISM: Artificial Sequence
<220> FEATURE:
<223> OTHER INFORMATION: Primer

<400> SEQUENCE: 271
tggcattgcc acaggcag                                                 18

<210> SEQ ID NO 272
<211> LENGTH: 21
<212> TYPE: PRT
<213> ORGANISM: Artificial Sequence
<220> FEATURE:
<223> OTHER INFORMATION: Peptide

<400> SEQUENCE: 272

Glu Leu Leu Leu Asp Arg Leu His Pro Asn Pro Met Tyr Gln Arg Met
1               5                   10                  15

Pro Leu Leu Leu Asn
            20

<210> SEQ ID NO 273
<211> LENGTH: 21
<212> TYPE: PRT
<213> ORGANISM: Artificial Sequence
<220> FEATURE:
<223> OTHER INFORMATION: MuSK juxtamembrane region peptide
<220> FEATURE:
<221> NAME/KEY: MOD_RES
<222> LOCATION: (13)..(13)
<223> OTHER INFORMATION: PHOSPHORYLATION

<400> SEQUENCE: 273

Glu Leu Leu Leu Asp Arg Leu His Pro Asn Pro Met Tyr Gln Arg Met
1               5                   10                  15

Pro Leu Leu Leu Asn
            20

<210> SEQ ID NO 274
<211> LENGTH: 21
<212> TYPE: PRT
<213> ORGANISM: Artificial Sequence
<220> FEATURE:
<223> OTHER INFORMATION: MuSK juxtamembrane region peptide
<220> FEATURE:
<221> NAME/KEY: MOD_RES
<222> LOCATION: (13)..(13)
<223> OTHER INFORMATION: PHOSPHORYLATION
```

```
<400> SEQUENCE: 274

Glu Leu Leu Leu Asp Arg Leu His Pro Ala Pro Met Tyr Gln Arg Met
1               5                   10                  15

Pro Leu Leu Leu Asn
            20

<210> SEQ ID NO 275
<211> LENGTH: 21
<212> TYPE: PRT
<213> ORGANISM: Artificial Sequence
<220> FEATURE:
<223> OTHER INFORMATION: MuSK juxtamembrane region peptide
<220> FEATURE:
<221> NAME/KEY: MOD_RES
<222> LOCATION: (13)..(13)
<223> OTHER INFORMATION: PHOSPHORYLATION

<400> SEQUENCE: 275

Glu Leu Leu Leu Asp Arg Leu His Pro Asn Pro Met Tyr Ala Ala Ala
1               5                   10                  15

Pro Leu Leu Leu Asn
            20

<210> SEQ ID NO 276
<211> LENGTH: 23
<212> TYPE: DNA
<213> ORGANISM: Artificial Sequence
<220> FEATURE:
<223> OTHER INFORMATION: Hprt primer

<400> SEQUENCE: 276
ctggtgaaaa ggacctctcg aag                                           23

<210> SEQ ID NO 277
<211> LENGTH: 22
<212> TYPE: DNA
<213> ORGANISM: Artificial Sequence
<220> FEATURE:
<223> OTHER INFORMATION: Hprt primer

<400> SEQUENCE: 277
ccagtttcac taatgacaca aa                                            22

<210> SEQ ID NO 278
<211> LENGTH: 22
<212> TYPE: DNA
<213> ORGANISM: Artificial Sequence
<220> FEATURE:
<223> OTHER INFORMATION: Dok7 primer

<400> SEQUENCE: 278
tcagcctcag aagagcgtgt tg                                            22

<210> SEQ ID NO 279
<211> LENGTH: 23
<212> TYPE: DNA
<213> ORGANISM: Artificial Sequence
<220> FEATURE:
<223> OTHER INFORMATION: Dok7 primer

<400> SEQUENCE: 279
gcctcagaag aggaactgga tag                                           23

<210> SEQ ID NO 280
<211> LENGTH: 23
```

```
<212> TYPE: DNA
<213> ORGANISM: Artificial Sequence
<220> FEATURE:
<223> OTHER INFORMATION: Off-target Dok7 CM sequence

<400> SEQUENCE: 280
gccctgcaca gtctgccccc tgg                                              23

<210> SEQ ID NO 281
<211> LENGTH: 23
<212> TYPE: DNA
<213> ORGANISM: Artificial Sequence
<220> FEATURE:
<223> OTHER INFORMATION: Off-target Dok7 CM sequence

<400> SEQUENCE: 281
gcactgcaca gtctgccccc tgg                                              23

<210> SEQ ID NO 282
<211> LENGTH: 23
<212> TYPE: DNA
<213> ORGANISM: Artificial Sequence
<220> FEATURE:
<223> OTHER INFORMATION: Off-target Dok7 CM sequence

<400> SEQUENCE: 282
tttatgctct gtctgccccc aag                                              23

<210> SEQ ID NO 283
<211> LENGTH: 23
<212> TYPE: DNA
<213> ORGANISM: Artificial Sequence
<220> FEATURE:
<223> OTHER INFORMATION: Off-target Dok7 CM sequence

<400> SEQUENCE: 283
ggcctgctca gtctgccccc tgg                                              23

<210> SEQ ID NO 284
<211> LENGTH: 23
<212> TYPE: DNA
<213> ORGANISM: Artificial Sequence
<220> FEATURE:
<223> OTHER INFORMATION: Off-target Dok7 CM sequence

<400> SEQUENCE: 284
tcagtcctca gtctgccccc tgg                                              23

<210> SEQ ID NO 285
<211> LENGTH: 23
<212> TYPE: DNA
<213> ORGANISM: Artificial Sequence
<220> FEATURE:
<223> OTHER INFORMATION: Off-target Dok7 2YF sequence

<400> SEQUENCE: 285
gaattctagg tgtgtcatag agg                                              23

<210> SEQ ID NO 286
<211> LENGTH: 23
<212> TYPE: DNA
<213> ORGANISM: Artificial Sequence
<220> FEATURE:
<223> OTHER INFORMATION: Off-target Dok7 2YF sequence

<400> SEQUENCE: 286
```

```
ggattctagg tgtgtcatcg cgg                                              23

<210> SEQ ID NO 287
<211> LENGTH: 23
<212> TYPE: DNA
<213> ORGANISM: Artificial Sequence
<220> FEATURE:
<223> OTHER INFORMATION: Off-target Dok7 2YF sequence

<400> SEQUENCE: 287
gggttcaatt tgtgtcatag cag                                              23

<210> SEQ ID NO 288
<211> LENGTH: 23
<212> TYPE: DNA
<213> ORGANISM: Artificial Sequence
<220> FEATURE:
<223> OTHER INFORMATION: Off-target Dok7 2YF sequence

<400> SEQUENCE: 288
agctgctagg tatgtcatag tgg                                              23

<210> SEQ ID NO 289
<211> LENGTH: 23
<212> TYPE: DNA
<213> ORGANISM: Artificial Sequence
<220> FEATURE:
<223> OTHER INFORMATION: Off-target Dok7 2YF sequence

<400> SEQUENCE: 289
cacttggagg ggtgtcatag agg                                              23
```

THERAPEUTIC MUSK ANTIBODIES

RELATED APPLICATIONS

This application is a continuation of International Patent Application No. PCT/US2021/027801, filed Apr. 16, 2021, which claims the benefit of U.S. Provisional Patent Application Ser. Nos. 63/011,986, filed Apr. 17, 2020, 63/038,633, filed Jun. 12, 2020, and 63/112,375 filed Nov. 11, 2020, which are hereby incorporated by reference in their entirety.

GOVERNMENT FUNDING CLAUSE

This invention was made with government support under 5R01AG051490 and 5R37NS36193 awarded by National Institutes of Health. The government has certain rights in the invention.

SEQUENCE LISTING

The content of the electronically submitted sequence listing in ASCII text file (Name: 189923_SL.txt; Size 150,741 bytes; and Date of Creation: May 2, 2022) is herein incorporated by reference in its entirety.

FIELD

The present invention relates to antibody-based molecules, including full-length antibodies, antigen-binding domains thereof, and antibody derivatives that are capable of binding to and activating human muscle-specific tyrosine protein kinase (MuSK). The present invention further discloses methods of treating neuromuscular conditions using the aforementioned MuSK antibodies.

BACKGROUND

Muscle-specific kinase (MuSK) is an essential receptor tyrosine kinase for establishment and maintenance of the neuromuscular junction (NMJ). Activation of MuSK by agrin, a neuronally derived heparin sulfate proteoglycan, and LRP4, the agrin receptor, leads to clustering of acetylcholine receptors (AChRs) on the postsynaptic side of the NMJ, enabling neuromuscular transmission and muscle contraction. The ectodomain of MuSK comprises three immunoglobulin-like domains (Ig-like domain 1-3) and a cysteine-rich domain (Fz-CRD) related to those in Frizzled proteins, the receptors for Wnts.

Many neuromuscular disorders are hallmarked by impaired NMJs. Due to the importance of MuSK signaling for establishing and maintaining synapses, it is tempting to speculate that stimulating MuSK might have therapeutic potential for these disorders. Following this hypothesis, it was shown that MuSK overexpression preserved innervation and motor function for more than a month in a mouse model for amyotrophic lateral sclerosis (ALS). In addition, several monoclonal MuSK binding scFvs were identified using phage display. One of these MuSK binders was produced in a (murinized) IgG format and also tested in ALS mice (Cantor et al., "Preserving Neuromuscular Synapses in ALS by Stimulating MuSK with a Therapeutic Agonist Antibody," Elife 7:e34375 (2018) and Sengupta-Ghosh et al., "Muscle Specific Kinase (MuSK) Activation Preserves Neuromuscular Junctions in the Diaphragm but is not Sufficient to Provide a Functional Benefit in the SOD1G93A Mouse Model of ALS," Neurobiol. Dis. 124:340-352 (2019)). Both studies passively transferred antibody #13 in SOD1-G93A mice and demonstrated that treatment with antibody #13 improved innervation of the NMJ and slowed down muscle denervation, compared to mock treated mice. Cantor et al., "Preserving Neuromuscular Synapses in ALS by Stimulating MuSK with a Therapeutic Agonist Antibody," Elife 7:e34375 (2018) further demonstrated improved motor neuron survival and muscle function, resulting in a marginally extended lifespan. These studies demonstrate that MuSK agonists have the ability to at least preserve structural integrity of neuromuscular synapses in ALS mice, more research is needed to confirm improvement of muscle function. Evaluating the therapeutic potential of MuSK agonistic antibodies in other neuromuscular disorders seems an important new line of research (Vergoossen et al., "MuSK Antibodies, Lessons Learned from Poly- and Monoclonality," J. Autoimmun. 112:102488 (2020)).

The present invention is aimed at overcoming this and other deficiencies in the art.

BRIEF DESCRIPTION OF THE DRAWINGS

FIG. 1A is a schematic showing the pleckstrin Homology (PH) and Phosphotyrosine-binding (PTB) domains in Dok7, which mediate Dok7 dimerization and binding to tyrosine phosphorylated MuSK. The C-terminal region contains two tyrosine residues, Y396 and Y406, that are phosphorylated following recruitment of Dok7 to MuSK. Dok7 1124_1127 dup (also referred to herein as Dok7 CM and Dok7$^{CM/CM}$ mice) mice, representing the most common mutation found in humans with Dok7 congenital myasthenia leads to a frame-shift, premature termination, and truncation of Dok7 protein, including a loss of Y396 and Y406. Dok7 Y396F; Y406F (Dok7 2YF) mice carry mutations that replace Y396 and Y406 with phenylalanine. FIG. 1B shows chi-square analysis of progeny derived from intercrossing Dok7$^{CM/+}$ C57BL/6 mice shows that Dok7$^{CM/CM}$ homozygous mice did not survive postnatally. In contrast, Dok7 2YF/2YF mice were present at expected numbers, when genotyped at P5-P10. FIG. 1C shows fluorescence microscopy images of diaphragm muscles from wildtype, Dok7$^{CM/CM}$ and Dok72$^{YF/2YF}$ mice at E18.5, which were stained with Alexa 488-a-BGT to label AChRs (red) and antibodies to Neurofilament/Synapsin to label motor axons/nerve terminals (green). Scale bar=10 µm. FIG. 1D shows graphs showing that, at E18.5, the number of synapses, synaptic size, and the density of synaptic AChRs were reduced by 4.5-, 4- and 5-fold, respectively. In Dok7$^{2YF/2YF}$ mice, synaptic size was normal, but the density of synaptic AChRs was modestly (15%) reduced. The shape of synapses in Dok7$^{2YF/2YF}$ mice often appeared elongated. The graph shows the values for 3 mice of each genotype and the mean±SEM values for these mice (n.s., not significant; p, ****<0.00005).

FIGS. 2A-2B are immunoblots in which Dok7 was immunoprecipitated from muscles of E18.5 wildtype, Dok7$^{CM/+}$, and Dok7$^{2YF/2YF}$ mice. The blots were probed with antibodies to Dok7 (FIGS. 9A-9B).

10C). The scatter plot shows the values for eight mice from each genotype and the mean±SEM values (p, ****<0.00005).

Figures 2A, 2B:
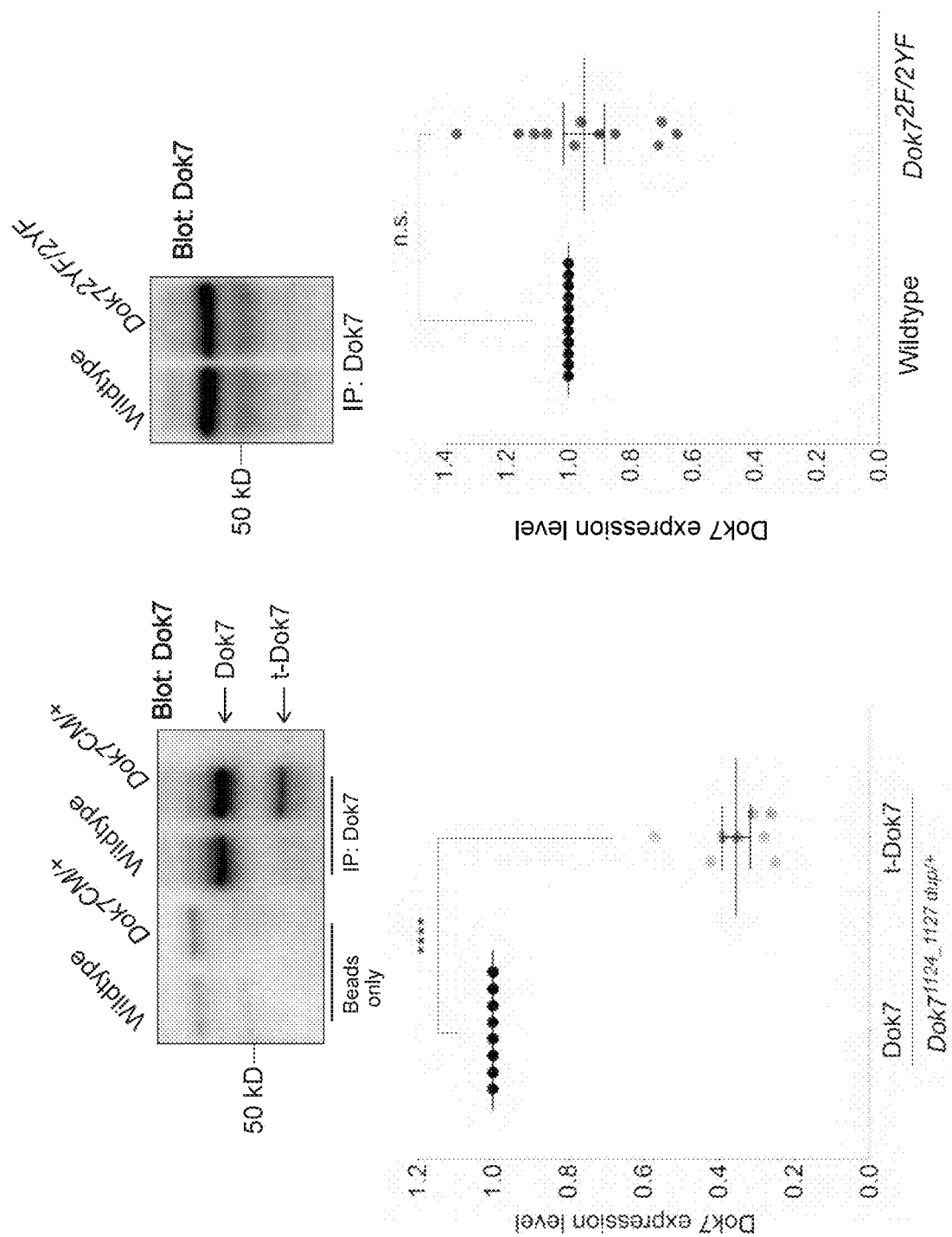
FIGS. 2A-2D demonstrate that truncated Dok7 is poorly expressed and MuSK tyrosine phosphorylation is severely reduced in Dok7$^{CM/CM}$ mice.
Figures 2C, 2D:
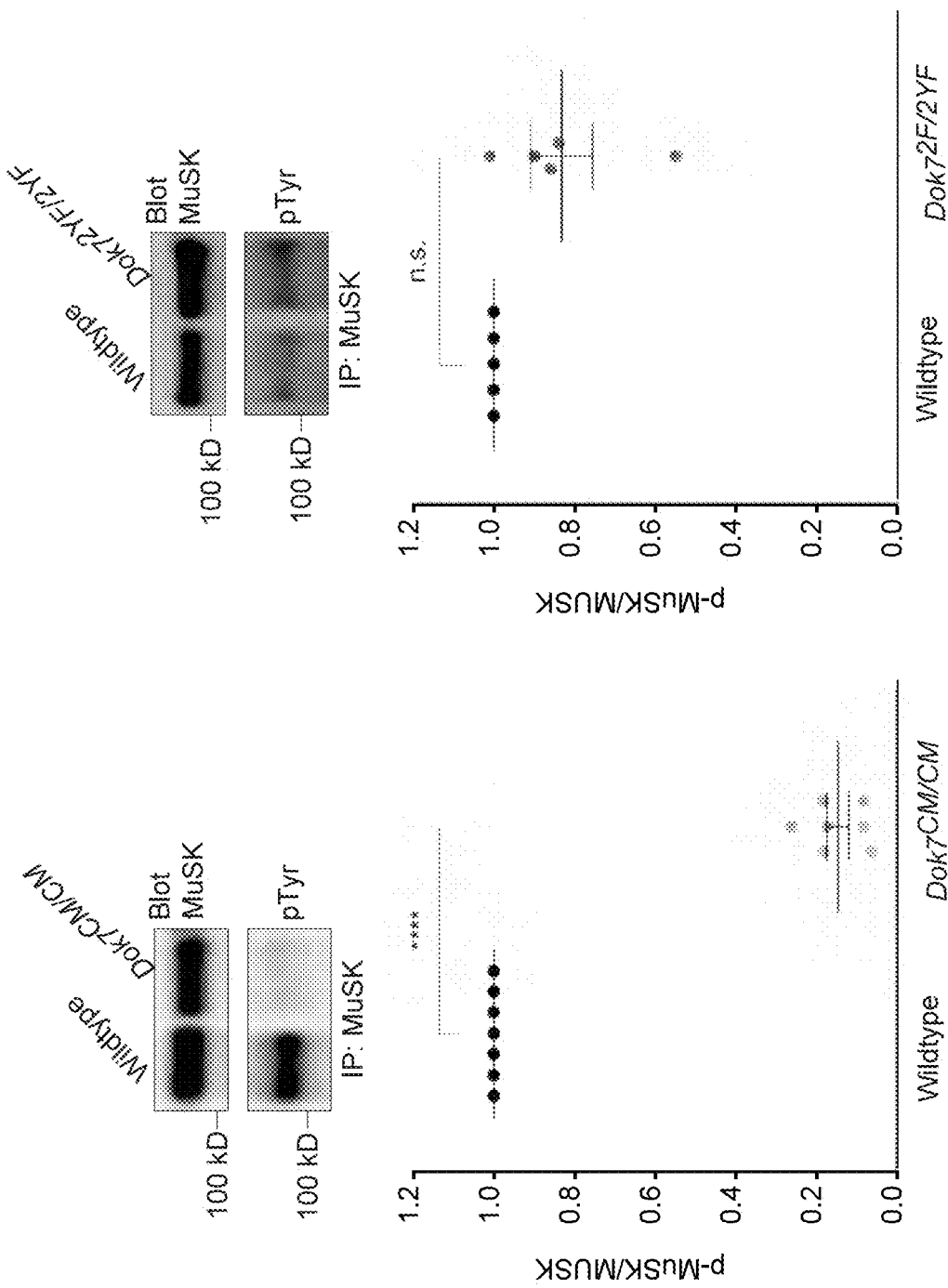

FIG. 2B shows that mutated Dok7 Y396F; Y406F protein migrates at the predicted size, and expression is similar to wildtype Dok7. The scatter plot shows the values for eleven mice of each genotype and the mean±SEM values (n.s., not significant). FIGS. 2C-2D show that MuSK was immunoprecipitated from muscles of E18.5 wildtype, Dok7$^{CM/CM}$, and Dok7$^{2YF/2YF}$ mice and the blots were probed with antibodies to MuSK or phosphotyrosine. MuSK phosphorylation was quantitated and normalized to MuSK expression. FIG. 2C shows that MuSK phosphorylation is 7-fold lower in Dok7$^{CM/CM}$ mice than wildtype mice. The scatter plot shows the values for 7 mice of each genotype and the mean±SEM values (p, ****<0.00005). FIG. 2D shows that MuSK tyrosine phosphorylation is similar in Dok7$^{2YF/2YF}$ and wildtype mice. The scatter plot shows the values for 5 mice of each genotype and the mean±SEM values (n.s., not significant).

Figure 3A:
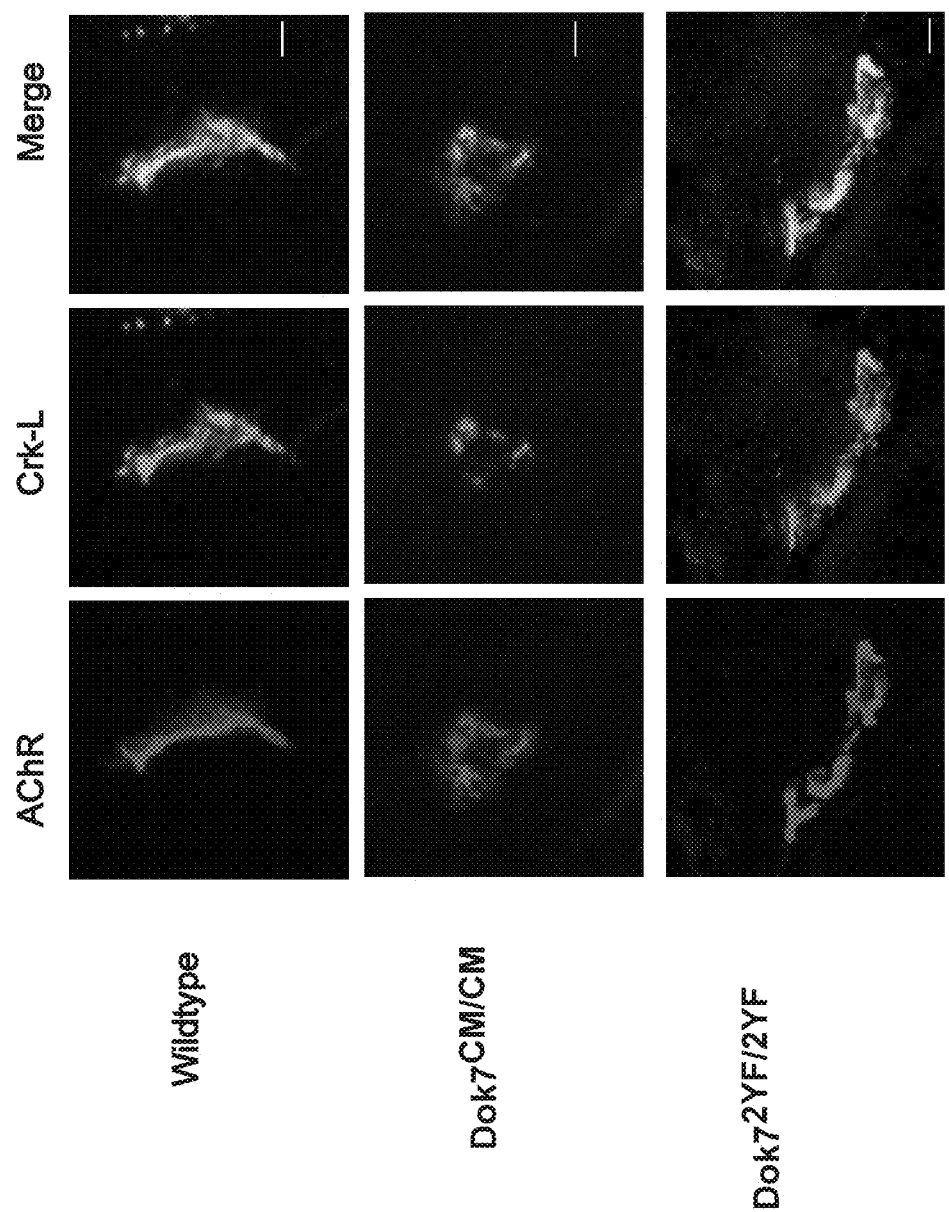
Figure 3C:
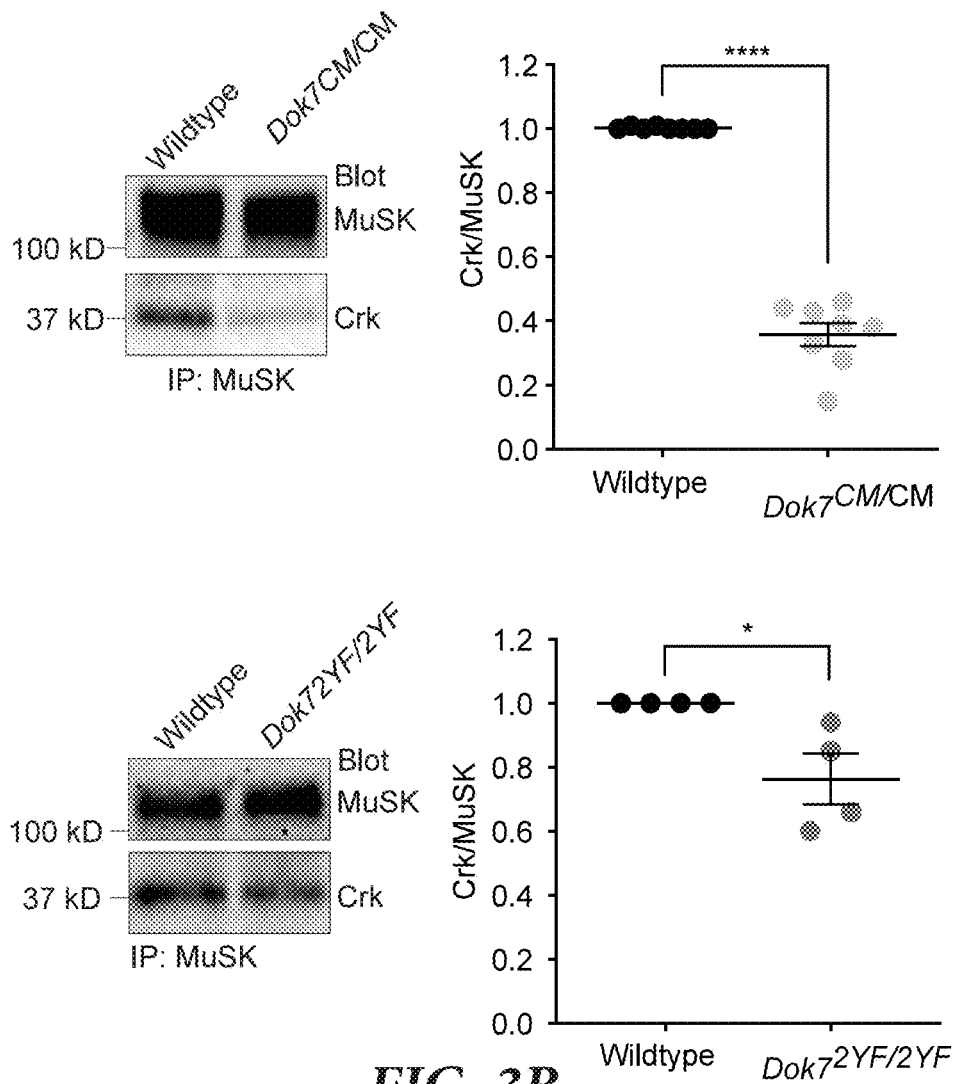
Figure 3D:
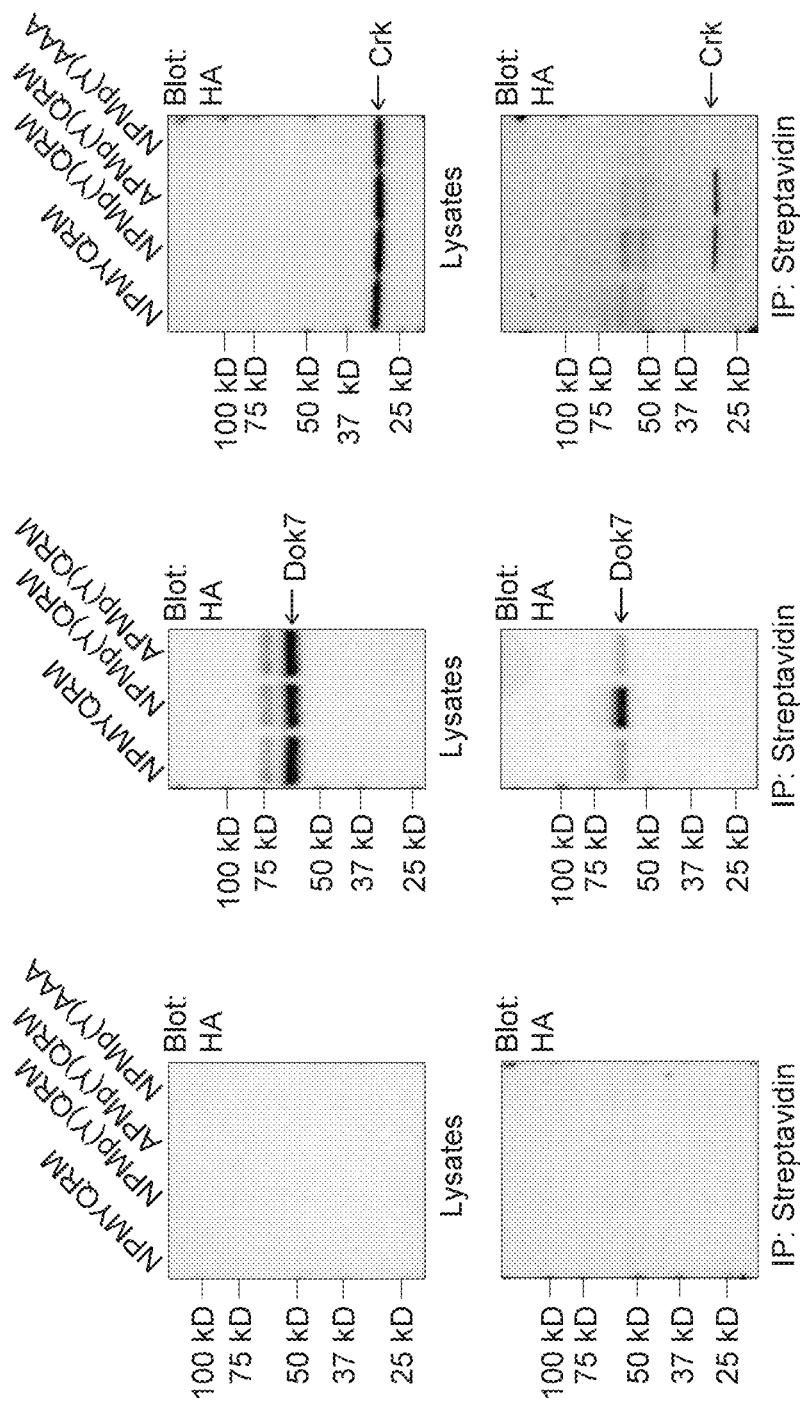

FIGS. 3A-3D demonstrate the recruitment of Crk to the synapse and to the MuSK/Dok7 complex is impaired in Dok7$^{CM/CM}$ mice. FIG. 3A are images showing that Crk-L (green) co-localizes with AChRs at synapses in cross-sections of the tibialis anterior muscle from E18.5 wildtype mice. Crk-L staining persists at synaptic sites in Dok7$^{CM/CM}$ and Dok72YF/2YF mice, but recruitment appears reduced at synapses in Dok7$^{CM/CM}$ mice. Scale bar=5 µm. FIG. 3B shows that MuSK was immunoprecipitated from muscles of E18.5 wildtype, Dok7$^{CM/CM}$ and Dok7$^{2YF/2YF}$ mice, and the blots were probed with antibodies to MuSK or Crk. The level of Crk that co-isolated with the MuSK complex was normalized to MuSK expression. Crk association with the MuSK complex was reduced by 2.8-fold in Dok7$^{CM/CM}$ mice; the scatter plots show the values for 8 mice of each genotype and the mean±SEM values (p, ****<0.00005). Crk association with the MuSK complex was reduced by 24% in Dok7$^{2YF/2YF}$ mice; the mean±SEM values for 4 mice are shown (p, *<0.05, ****<0.00005). FIG. 3C shows that the MuSK juxtamembrane region (JM) contains a binding site for Dok7 (residues 547-554 of SEQ ID NO: 129) and a potential binding site for Crk (residues 554-557 of SEQ ID NO: 129). FIG. 3D shows the results of experiments in which HA-tagged forms of Dok7 or Crk-I were expressed from transfected 293T cells. Biotin-tagged peptides from the MuSK JM (SEQ ID NOs: 272-275) were incubated with lysates from transfected 293T cells. The biotin-tagged peptides were captured with Streptavidin-agarose beads, and blots of the isolated proteins were probed with antibodies to HA and Crk. Both Dok7 and Crk showed greater binding to the phosphopeptide than the non-phosphorylated peptide. Mutation of the critical asparagine at the −3 position in the consensus (NPXY) PTB-binding site in the MuSK JM phosphopeptide prevented binding of Dok7 but not Crk. In contrast, mutation of the consensus SH2 site in the MuSK JM phosphopeptide prevented binding of Crk to the MuSK JM phosphopeptide.

Figures 4B, 4C:
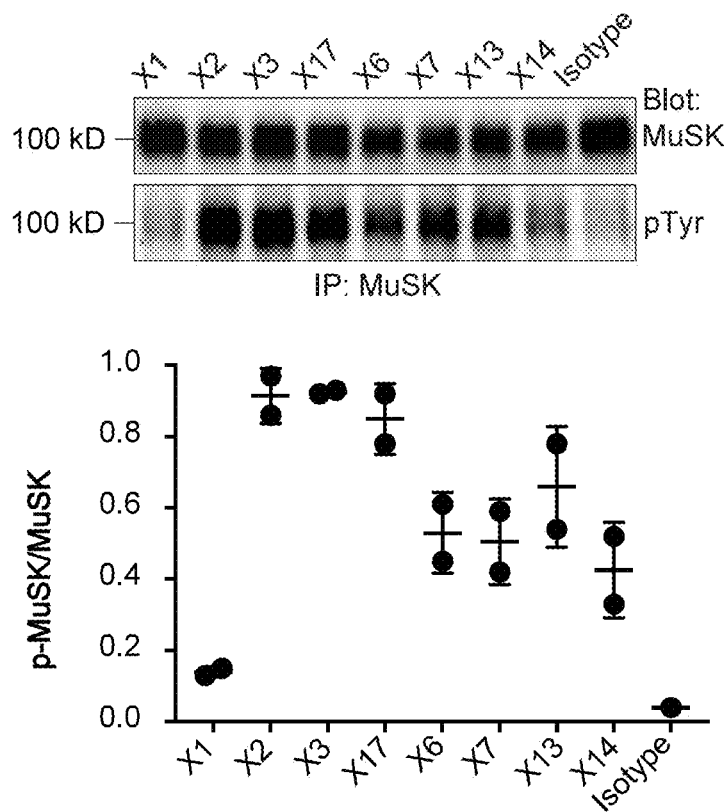
Figure 4E:
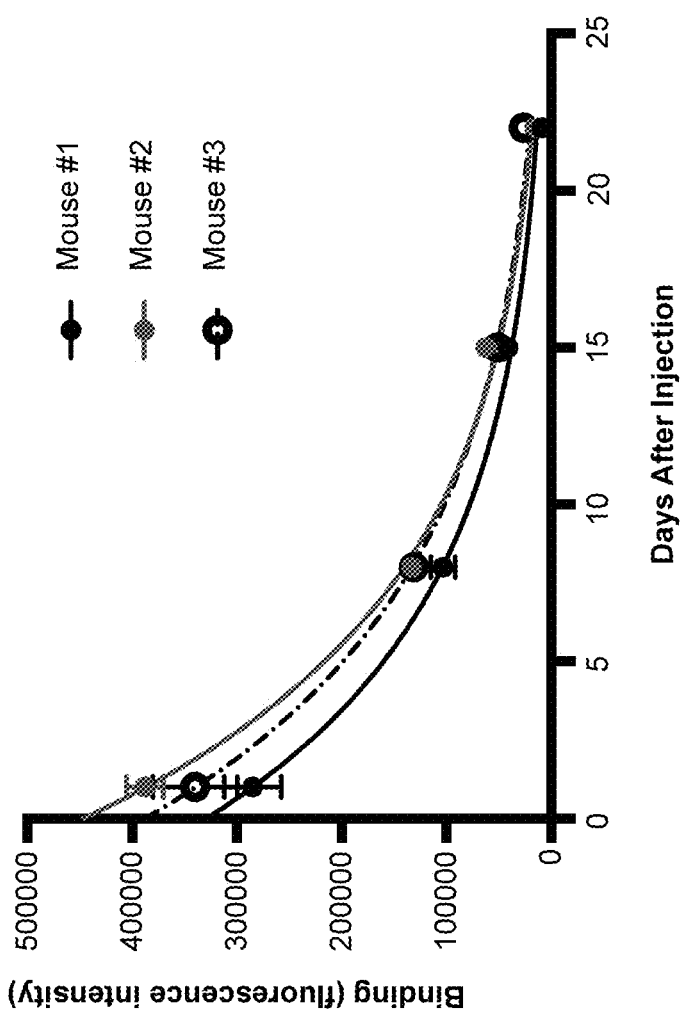
Figure 4F:
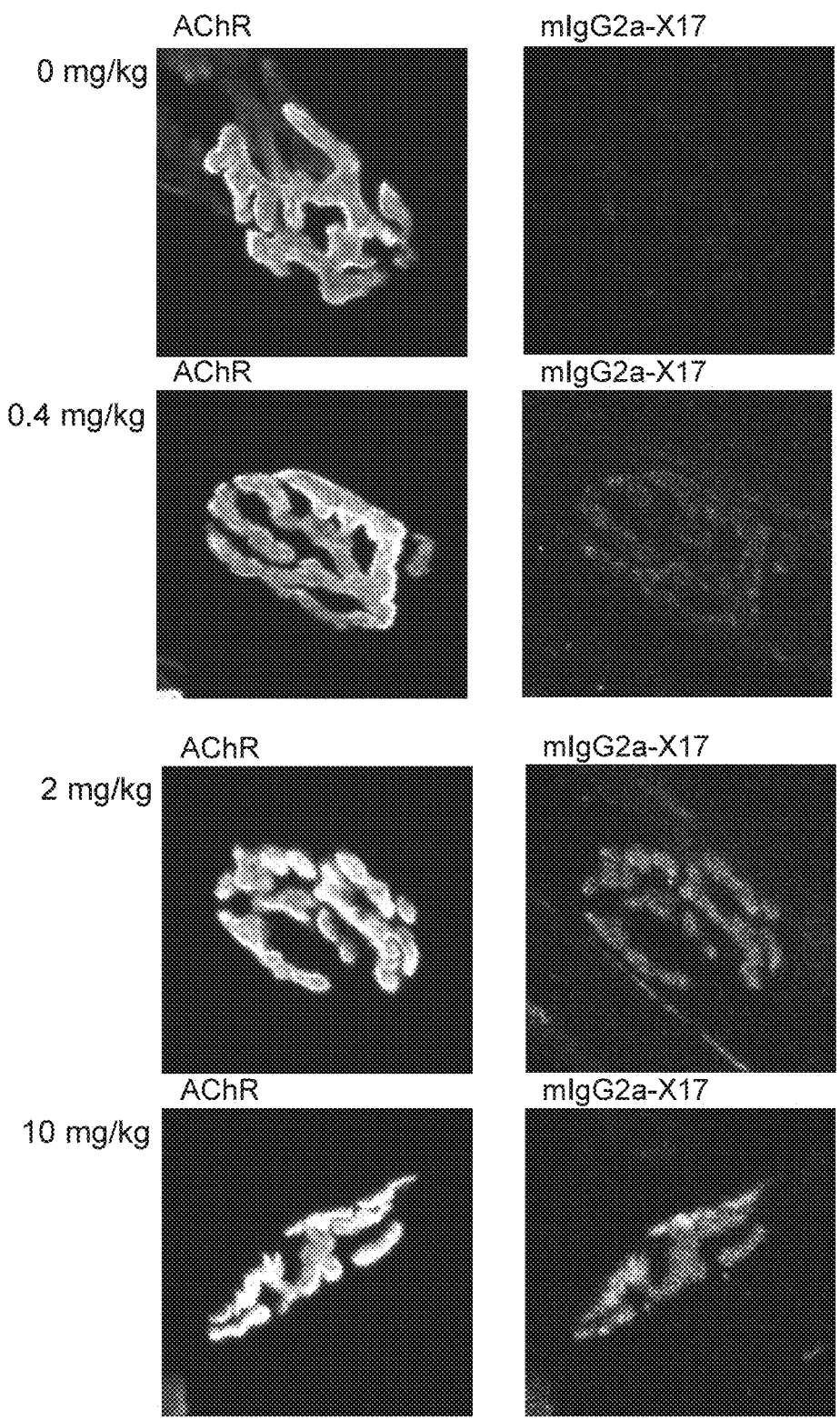
Figure 4F:
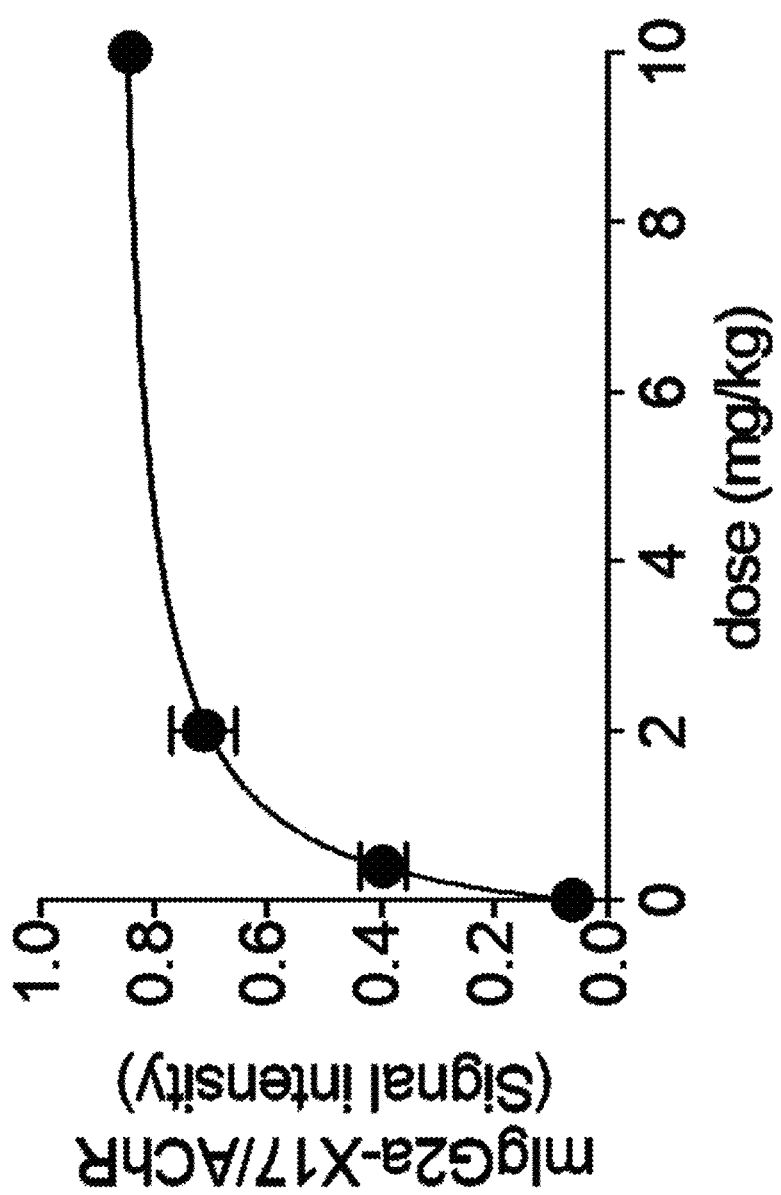

FIGS. 4A-4F demonstrate that antibodies to MuSK bind human and mouse MuSK with high affinity, stimulate MuSK phosphorylation in cultured myotubes and bind MuSK in vivo. FIG. 4A is a table showing the $K_D$ values of antibody clones for different MuSK antigens, tested in the monovalent Fab format using a bead-binding assay. The $K_D$ values are the average and s.d. from n=3. Titrations are given in FIGS. 12A-12C. FIG. 4B shows the results of an experiment in which C2 myotubes were treated for 30 minutes with biotinylated Fabs, including a negative control Fab (Isotype), each tetramerized by preincubation with streptavidin. MuSK was immunoprecipitated, and Western blots were probed with antibodies to MuSK or phosphotyrosine (pTyr). MuSK phosphorylation was normalized to total MuSK expression. The scatter plot shows the values for each Fab and the mean±SEM. FIG. 4C is a table showing the $K_D$ values of IgG antibodies to immobilized hFz, hECD, mFz, and mECD, as tested using a bead-based binding assay. The $K_D$ values are the average and s.d. from n=3. Titrations are given in FIGS. 12A-12C. FIG. 4D shows the results of an experiment in which C2 myotubes were treated with 0.5 nM Agrin, 10 nM antibody X2, X3, or X17, with either mouse IgG2a or human IgG1 Fc regions, or the Isotype control, and MuSK was analyzed as described in FIG. 4B. The scatter plot shows the values of MuSK phosphorylation, normalized to MuSK expression, and the mean±SEM. FIG. 4E is a plot showing blood half-life measurements of X17-mIgG2a-LALAPG. Nonlinear least-squares fitting of the median fluorescence intensities with a single exponential curve for 3 mice are shown. The half-life was determined to be 4.9±0.2 days. FIG. 4F demonstrates that MuSK antibody mIgG2a-X17 engages MuSK at the synapse and saturates MuSK at 10 mg/kg. P30 wildtype mice were injected intraperitoneally with MuSK agonist antibody mIgG2a-X17 (0, 0.4, 2, 10 mg/kg). Two days later, mice were sacrificed and diaphragm muscles were stained with Alexa 488-α-BGT to label AChRs and Alexa 647 Goat Anti-Human IgG, F(ab)$_2$ fragment specific to label X17. Levels of saturation of mIgG2a-X17 at the synapse were measured by the ratio of X17 to AChR signal intensity. The mean±SEM values from 3 mice at each concentration are shown.

Figure 5A:
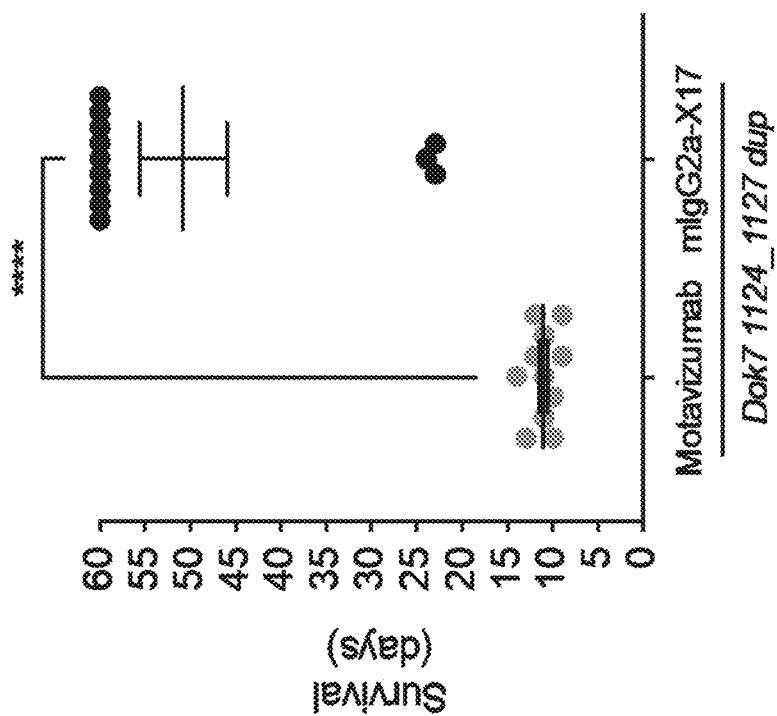

FIGS. 5A-5E demonstrate that an agonist antibody to MuSK, mIgG2a-X17, rescues lethality in young Dok7 1124_1127 dup mice. FIG. 5A shows that Dok7 1124_1127 dup mice in a C57BL/6-CBA mixed background survive for one to two weeks postnatally. Dok7 1124_1127 dup mice in the mixed background were treated at P4 with agonist antibody mIgG2a-X17 or an isotype equivalent negative control. Dok7 1124_1127 dup mice (n=11) injected with the isotype control, like untreated mice, died one to two weeks after birth, whereas Dok7 1124_1127 dup mice injected with mIgG2a-X17 (n=12) at P4, P24, and P44 survived as adults. Six of twelve mutant mice injected with X17 were sacrificed at P60; 3 mutant mice injected with X17 died three weeks after birth, just prior to the second, planned injection, and 3 mutant mice were aged for disease relapse experiments. The scatter plot shows the survival time for each mouse and the mean±SEM values (p, ****<0.00005).

Figure 5B:
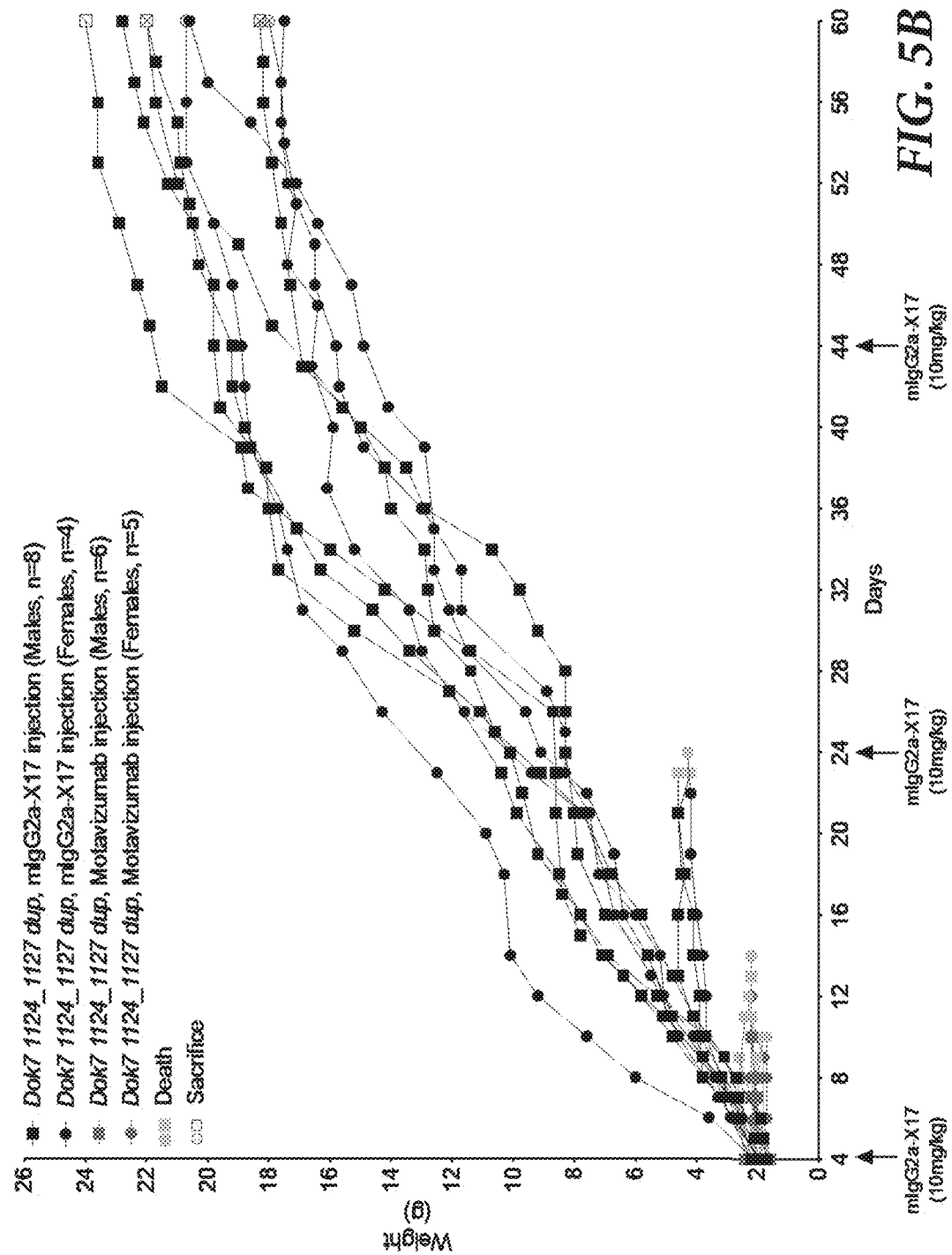
Figure 5C:
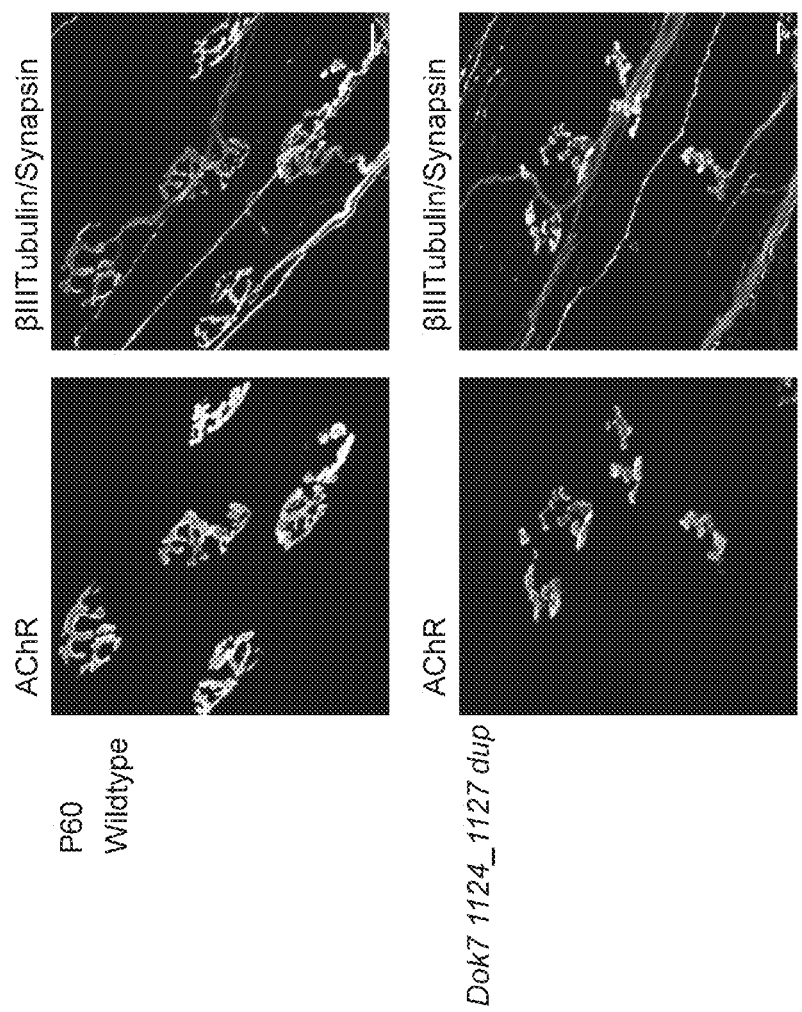
Figure 5C:
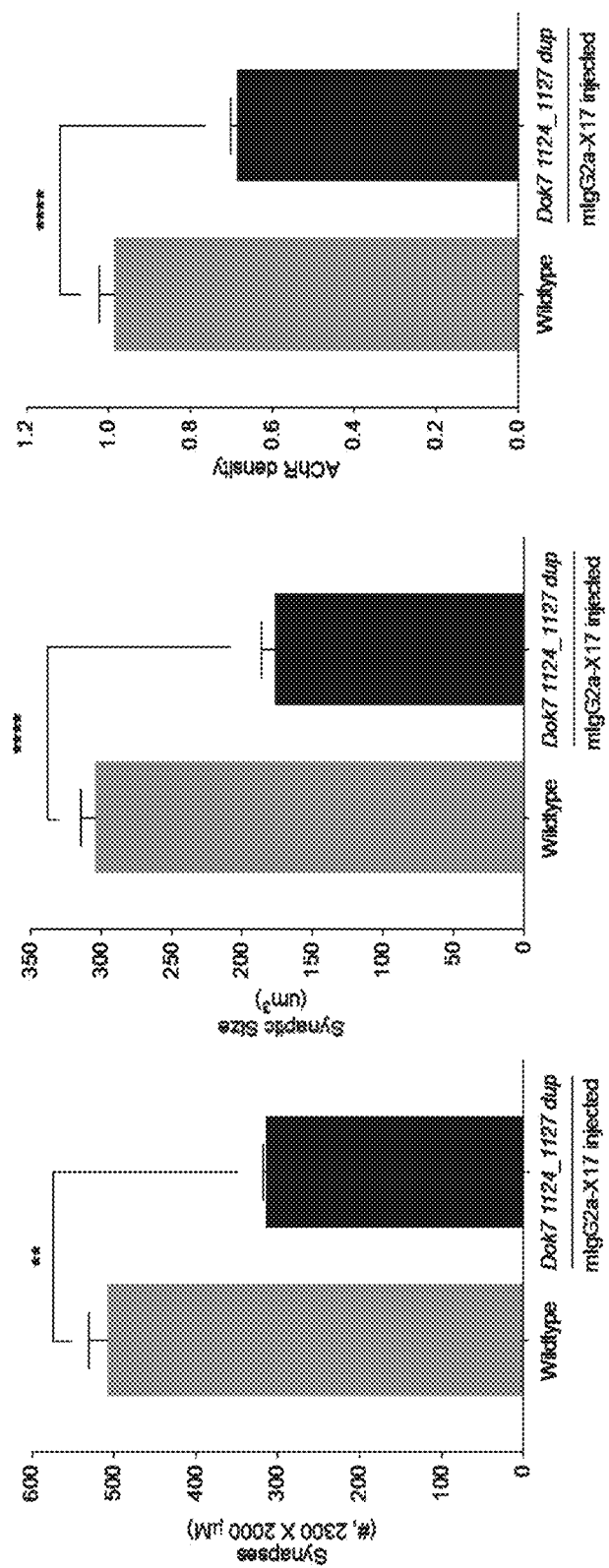
Figure 5D:
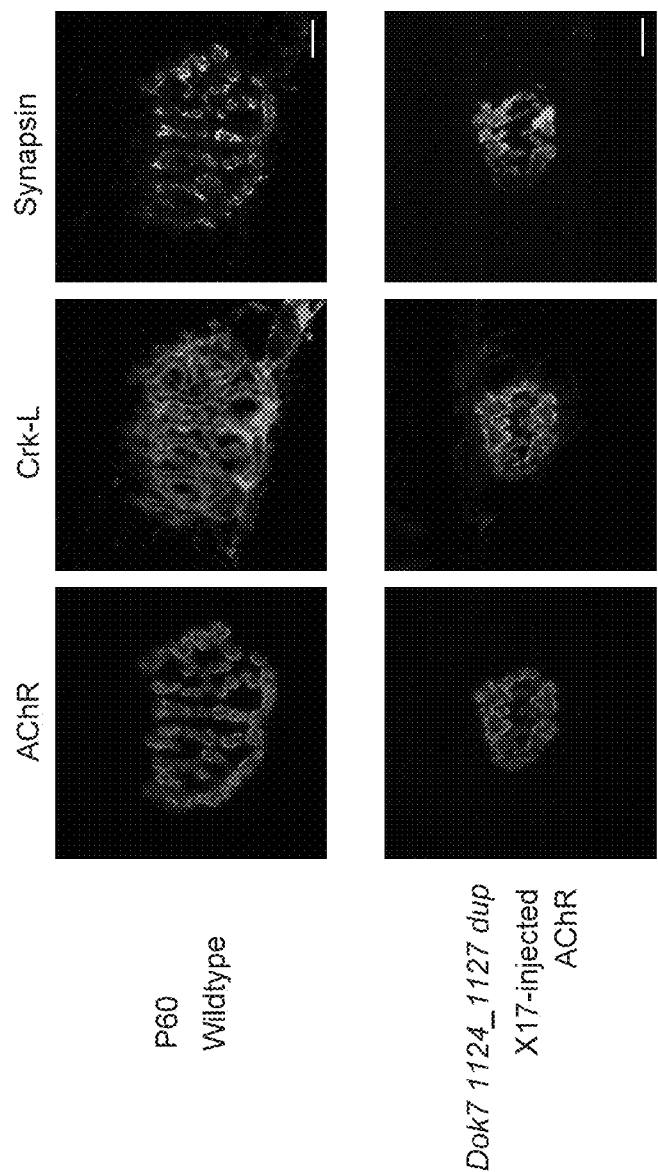
Figure 5E:
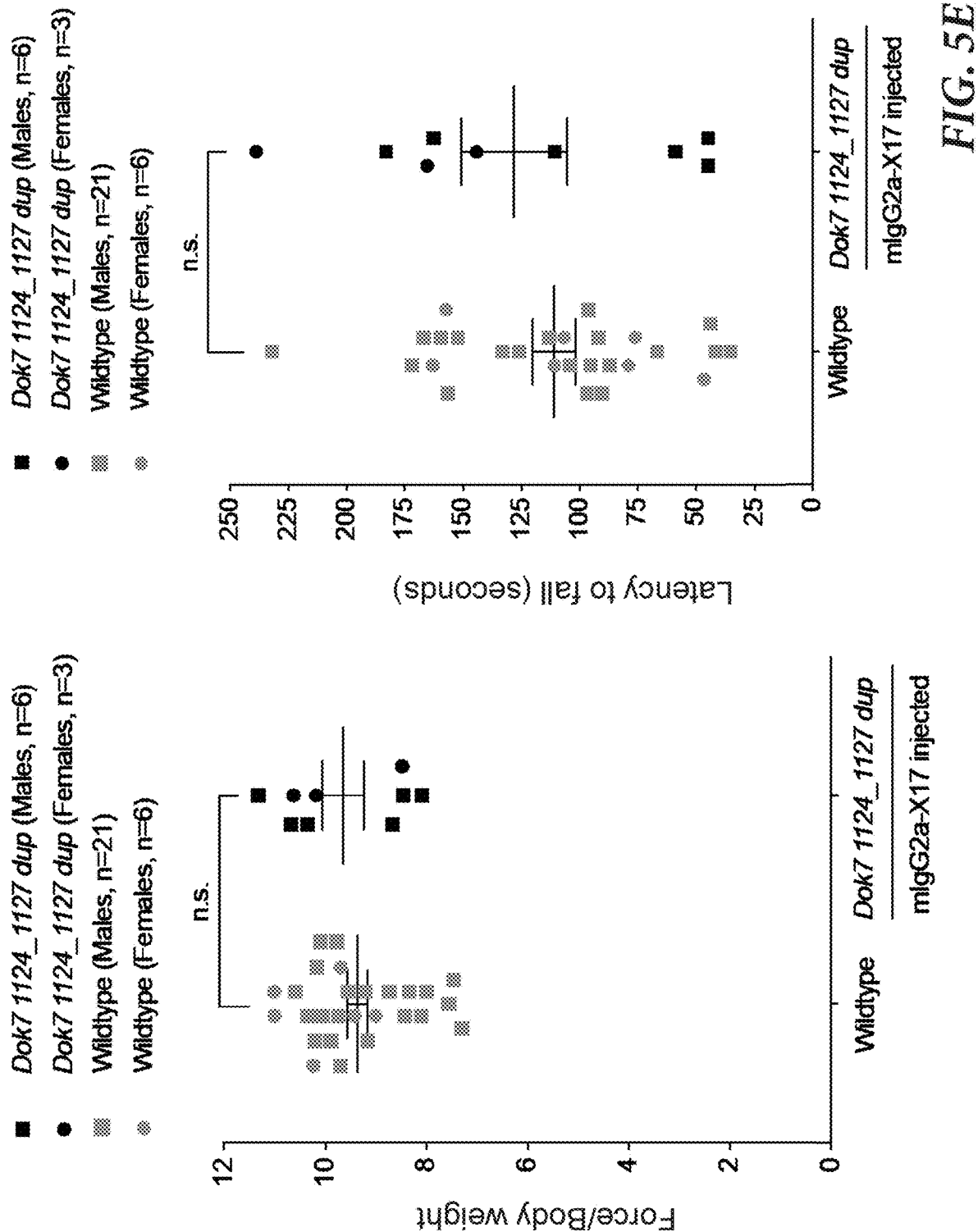

FIG. 5B shows that Dok7 1124_1127 dup mice, injected with mIgG2a-X17 gained weight, unlike Dok7 1124_1127 dup mice treated with the isotype control antibody. Dok7 1124_1127 dup mice were injected with mIgG2a-X17 (10 mg/kg) at P4, P24 and P44. FIG. 5C demonstrates that mIgG2a-X17 restores synapse development in young Dok7 1124_1127 dup mice. Diaphragm muscles from P60 wildtype and Dok7 1124_1127 mice were stained with Alexa 488-α-BGT to label AChRs and antibodies to 0111 Tubulin/ Synapsin to label motor axons/nerve terminals. In Dok7 1124_1127 dup mice treated with mIgG2a-X17, synapses matured from a simple, plaque-like shape to a complex, pretzel-like shape, characteristic of mature murine neuromuscular synapses. Scale bar=10 mm. In Dok7 1124_1127 dup mice treated with mIgG2a-X17, the number of synapses, synaptic size, and density of synaptic AChRs and were restored to 60%, 60%, and 68%, respectively, of normal levels. The mean±SEM values from 3 mice (>50 synapses per mouse) are shown (n.s., **<0.005,

****<0.00005). FIG. 5D are images showing that Crk-L (middle panels) is concentrated at synapses, marked by AChRs (left panels) and nerve terminals (right panels), in single myofibers isolated from tibialis anterior muscles of Dok7 1124_1127 dup mice rescued with X17. The mean±SEM values from 3 mice (10 synapses per mouse; n.s., not significant). Scale bar=5 μm. FIG. 5E are graphs showing that mIgG2a-X17 rescues motor performance of Dok7 1124_1127 dup mice. Motor performance of Dok 1124_1127 dup mice, as assessed by grip strength and the latency to fall from a rotating rotarod, were fully restored by treatment with mIgG2a-X17. The scatter plots show the values for 18 wildtype mice and 9 Dok7 1124_1127 dup mice rescued with X17 and the mean±SEM values (n.s., non significant).

Figure 6A:
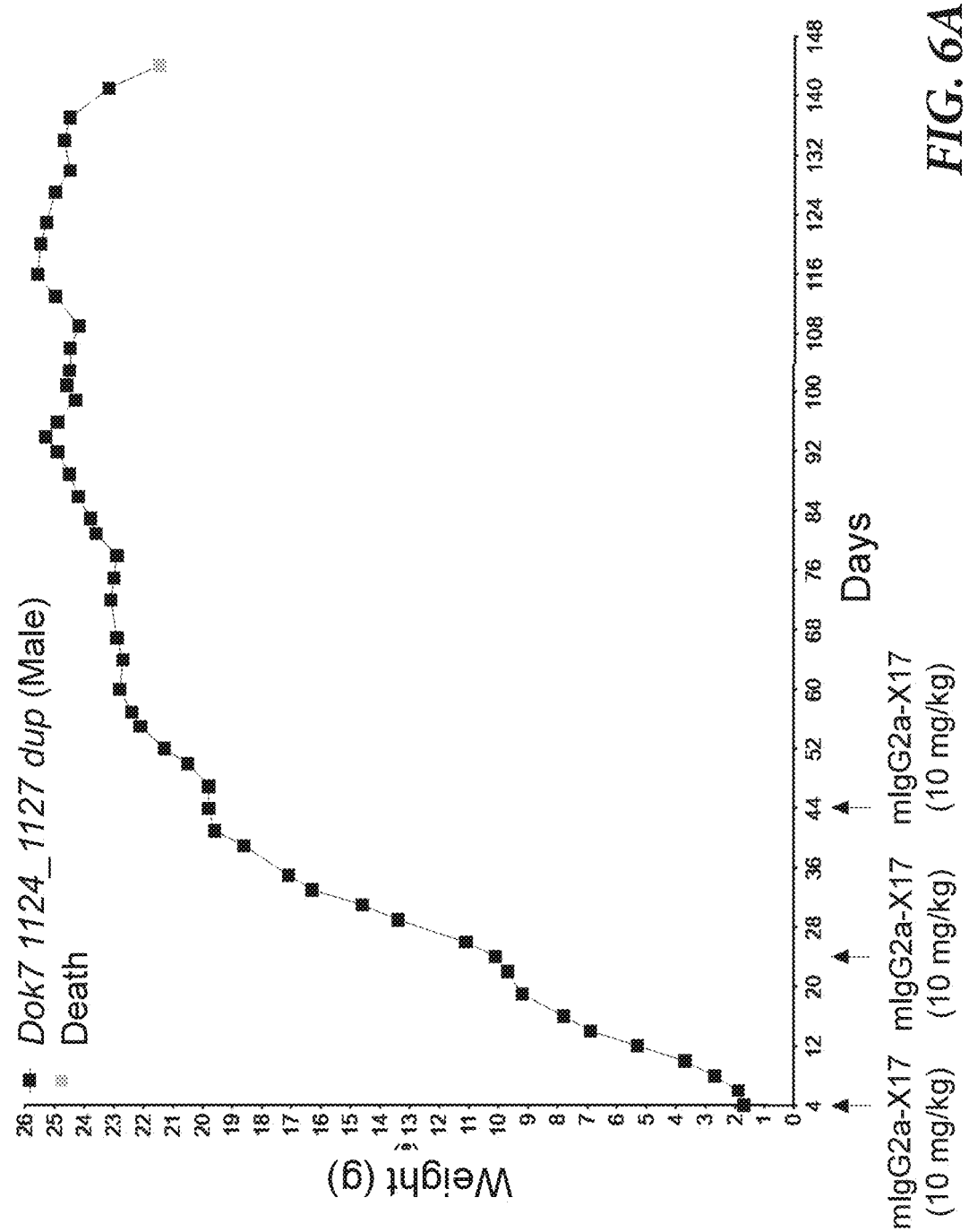
Figure 6B:
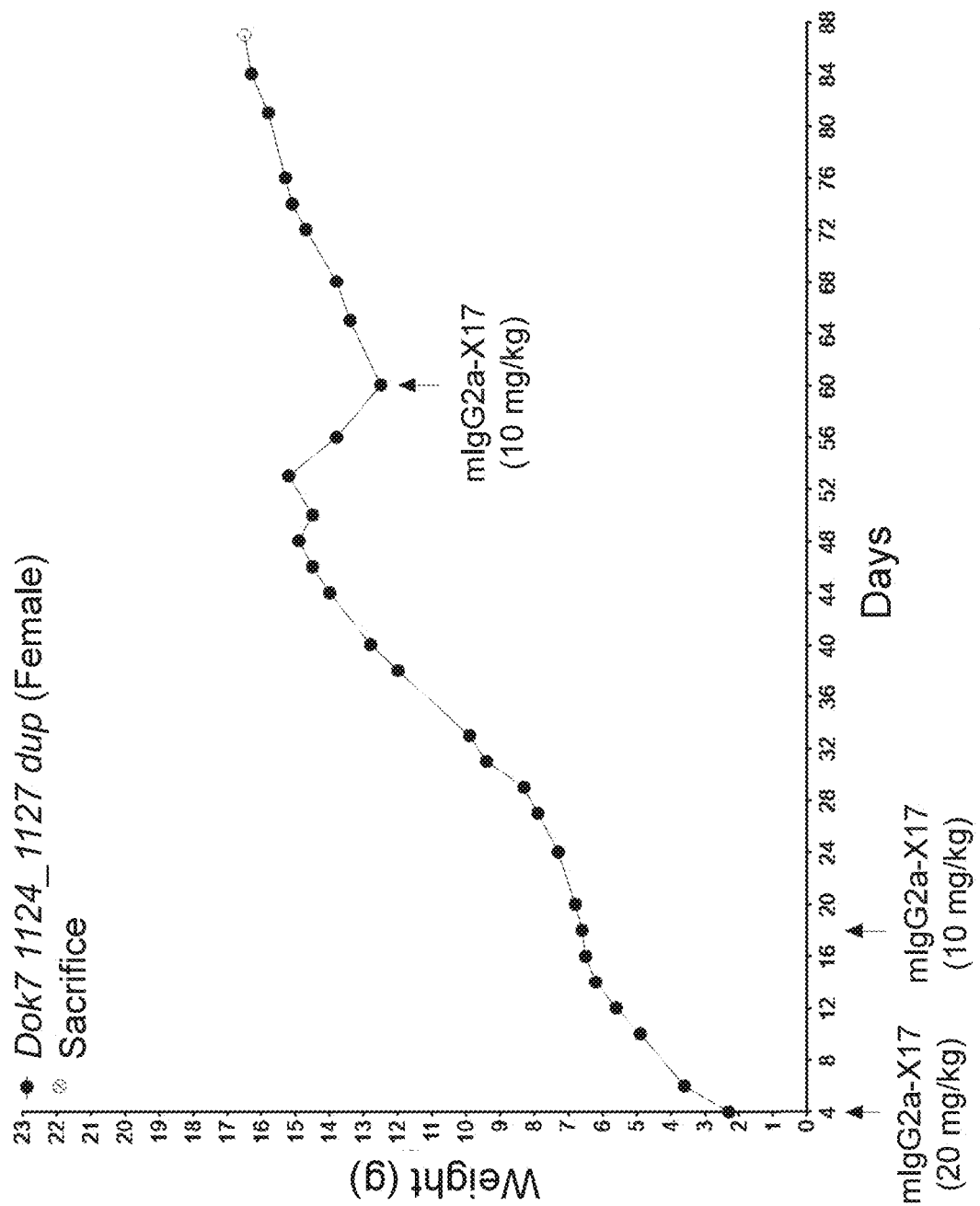
Figure 6C:
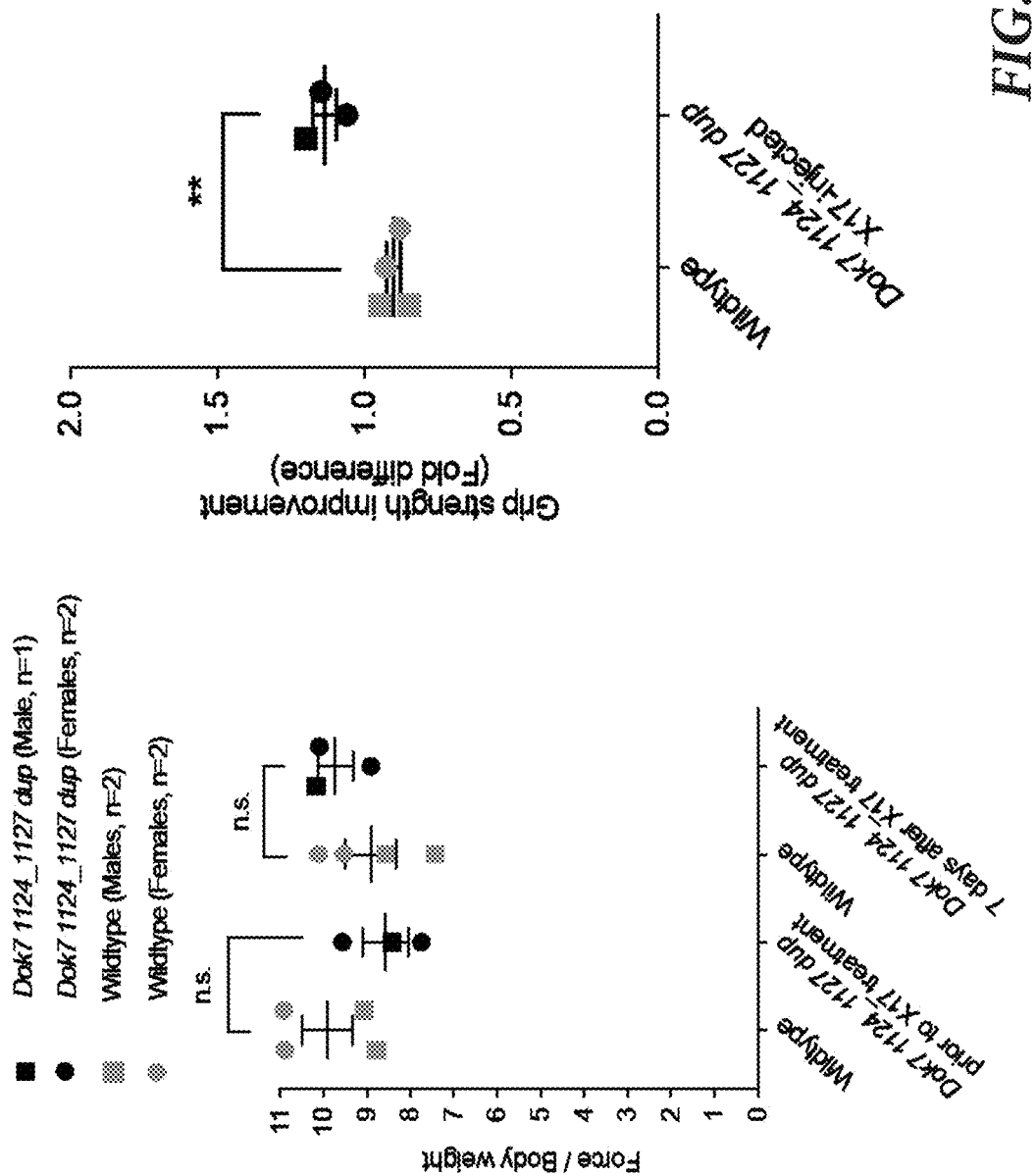
Figure 6C:
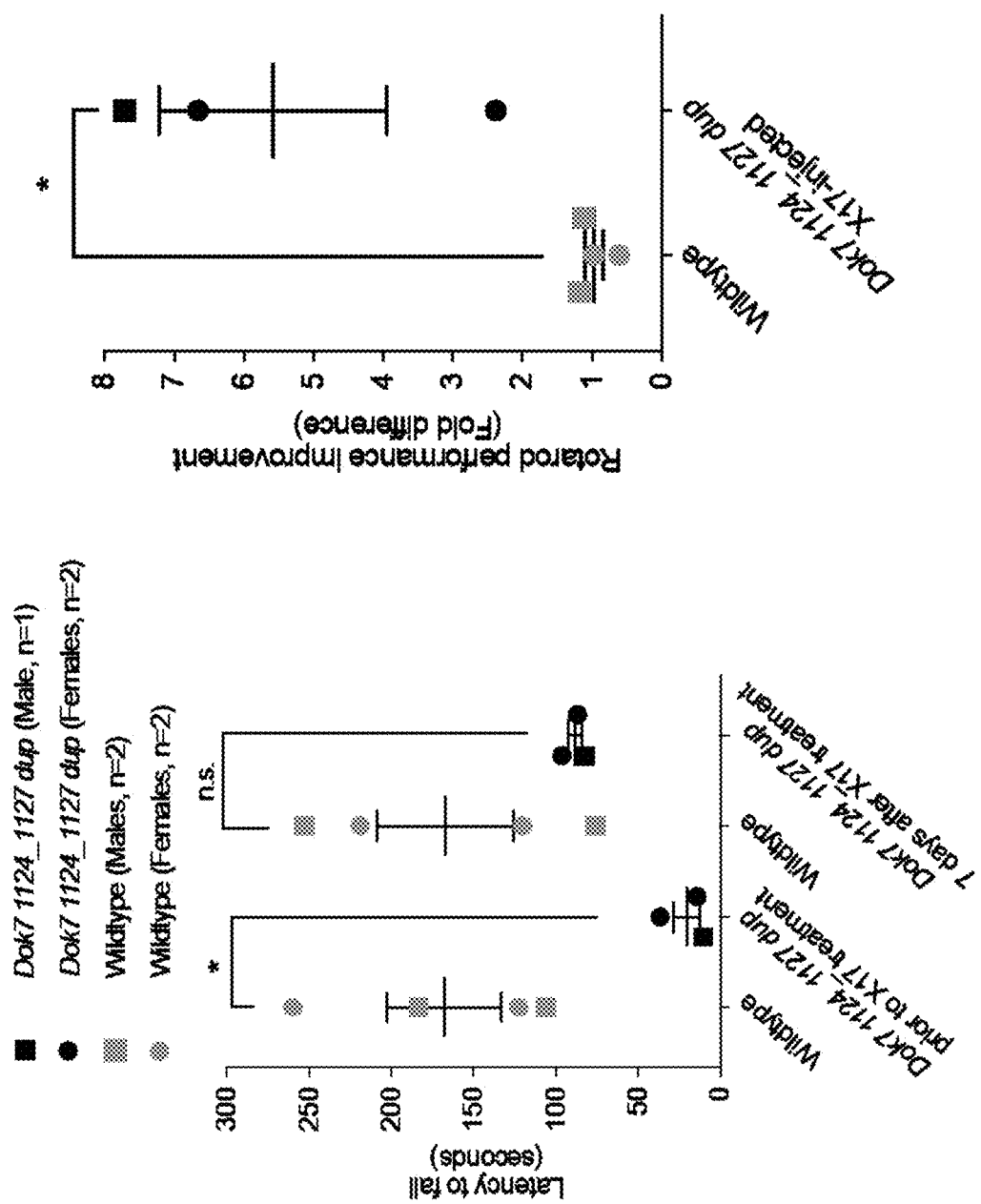

FIGS. 6A-6C demonstrate that mIgG2a-X17 reverses disease relapse in adult Dok7 1124_1127 dup mice. Mice were injected with mIgG2a-X17 (10 mg/kg) either at P4, P24, and P44, or at P4, P18, and then discontinued antibody treatment. These Dok7 1124_1127 dup mice gained weight and maintained their mobility for several months but ultimately began to lose weight (FIGS. 6A-6B) and to display motor deficits, as assessed by grip strength and the latency to fall from a rotating rotarod (FIG. 6C). At this time, mice were either not re-injected with mIgG2a-X17 (FIG. 6A) or re-injected with mIgG2a-X17 (FIG. 6B). Non-reinjected mice die within a few days (FIG. 6A), while after restarting mIgG2a-X17 treatment, the Dok7 1124_1127 dup mice began to gain weight (FIG. 6B), and by one week after restarting treatment their motor deficits were reversed (FIG. 6C). Dok7 1124_1127 dup mice improved their performance on the rotarod by 5.5-fold, and their grip strength by 1.25-fold (p, *<0.05, ***<0.0005 (FIG. 6C).

Figure 7:
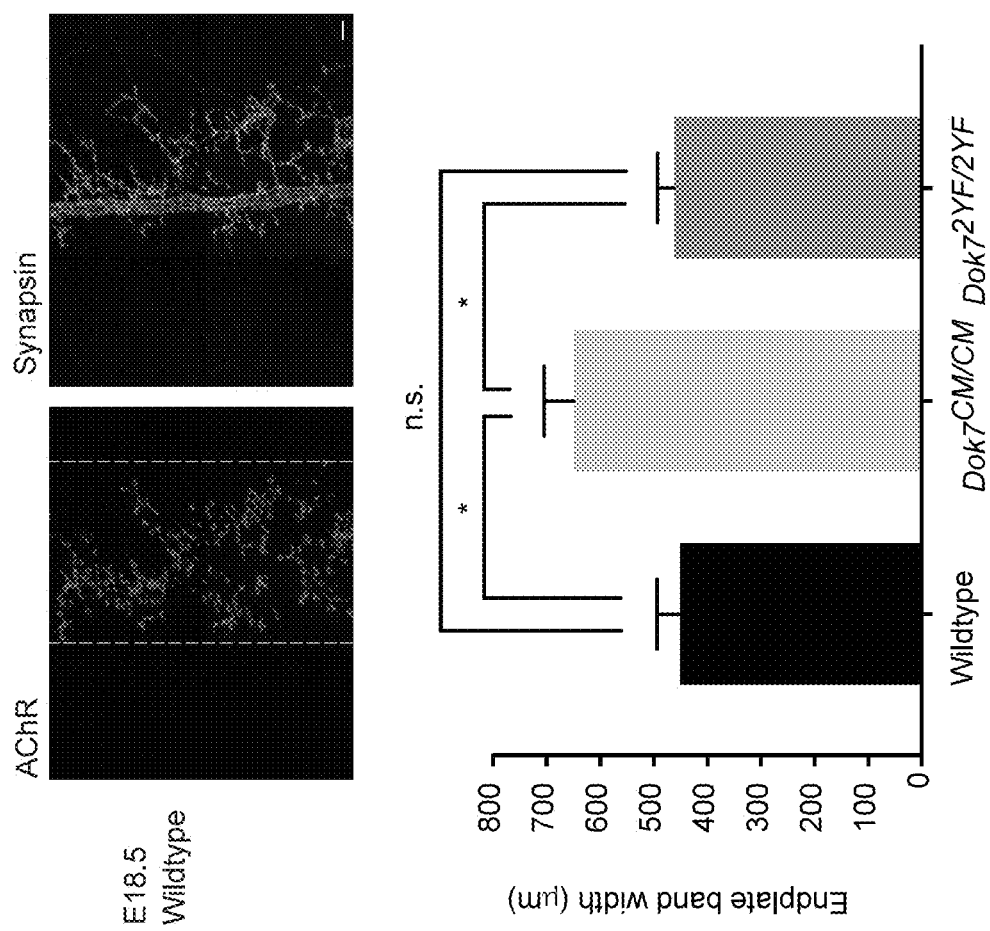
Figure 7:
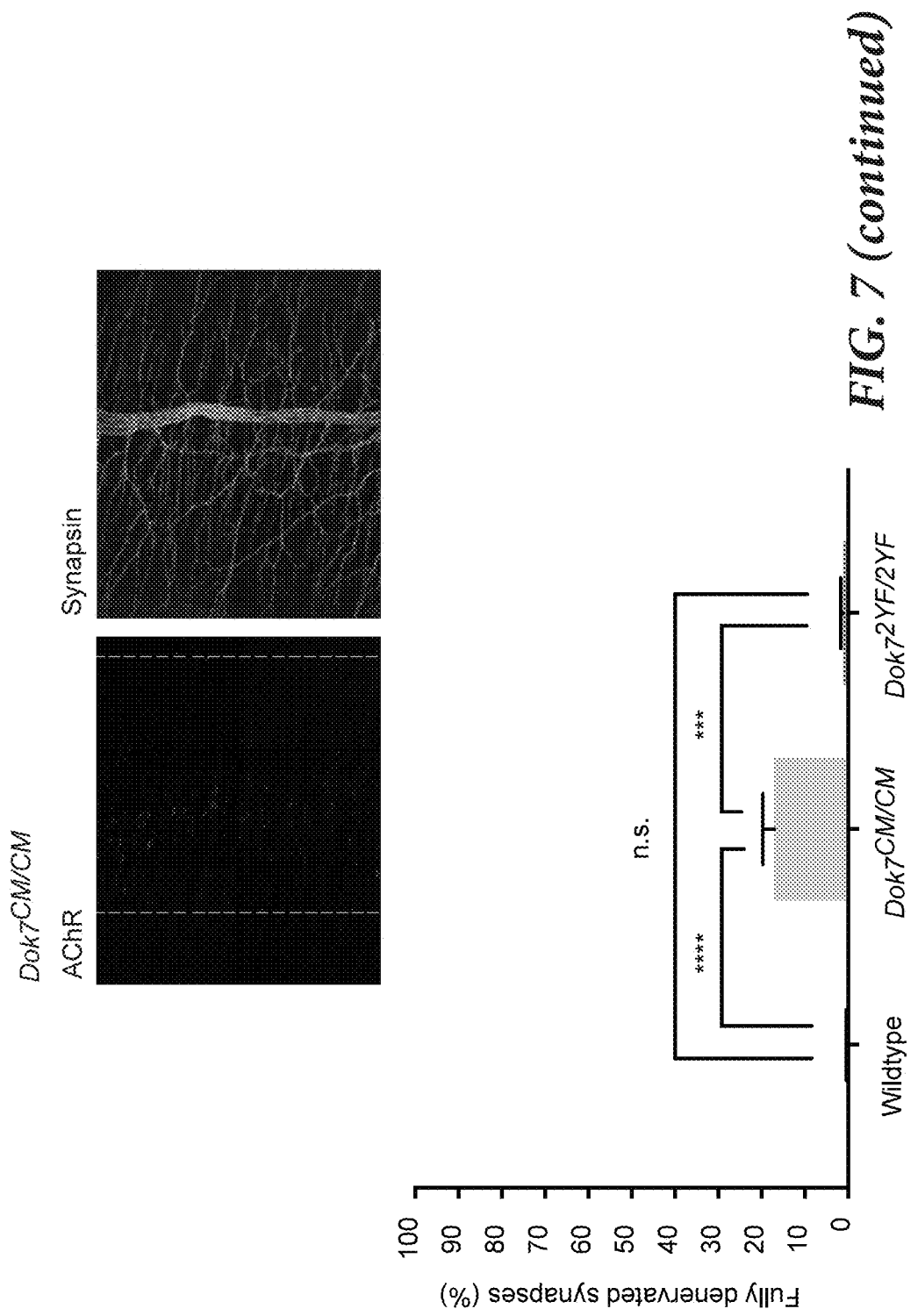
Figure 7:
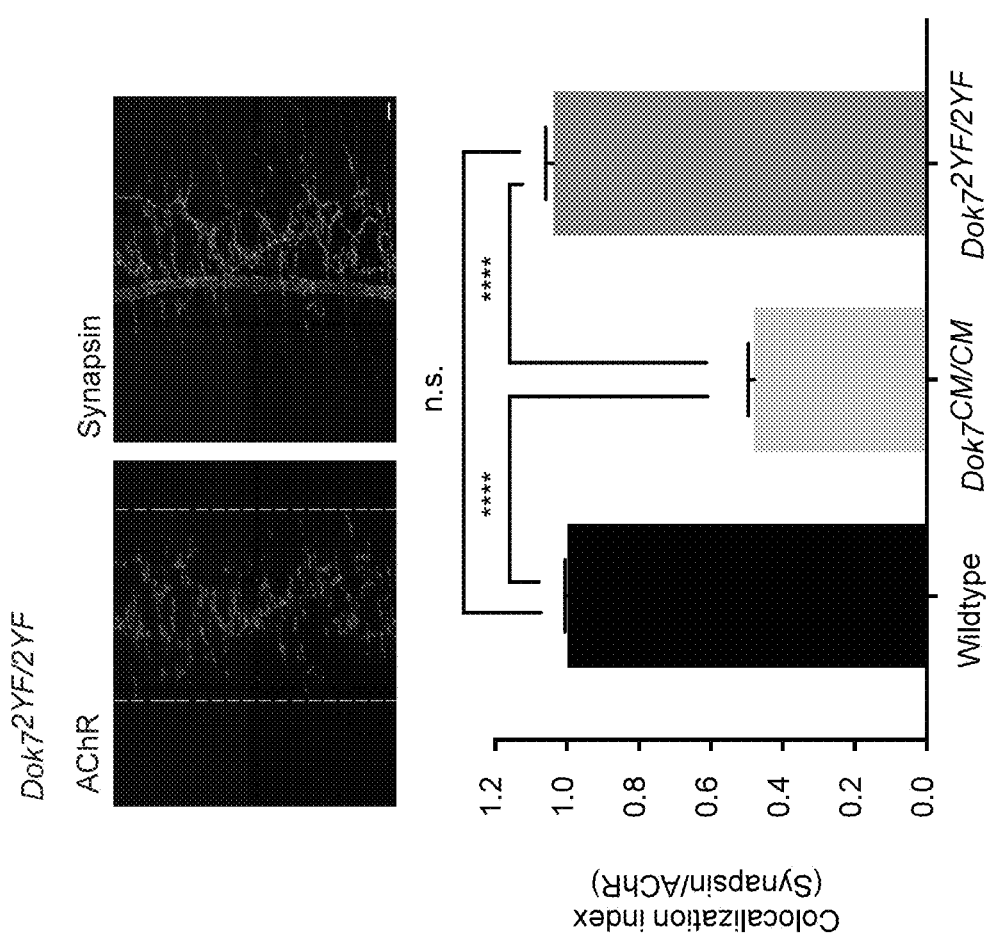

FIG. 7 provides the endplate width, denervation, co-localization of synapses in Dok7 CM (i.e., Dok7 1124_1127 dup) mice. The width of the endplate band (dashed lines) was increased by 45% in Dok7$^{CM/CM}$ mice but normal in Dok7$^{2YF/2YF}$ mice. In Dok7$^{CM/CM}$ mice, 17% of AChR clusters were completely unopposed by nerve terminals, indicative of denervated myofibers. Many synapses in Dok7$^{CM/CM}$ mice were partially innervated, as nearly half of the AChR-rich area at synapses was not juxtaposed by nerve terminals. The mean±SEM values from 3 mice of each genotype (100 synapses per mouse) are shown (p, *<0.05; p, <0.005; p, *<0.0005; p, ****<0.00005; n.s. not significant). Scale bar=50 μm.

Figure 8:
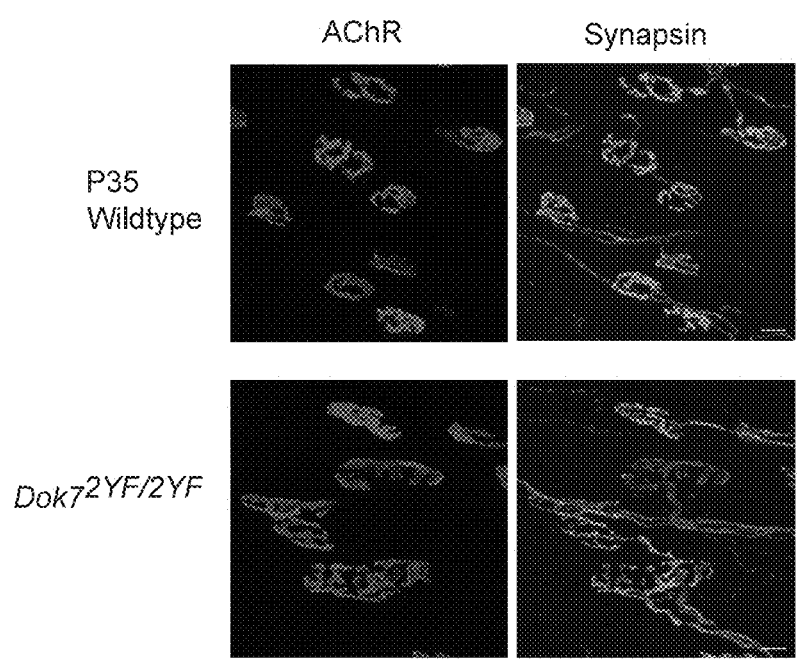
Figure 8:
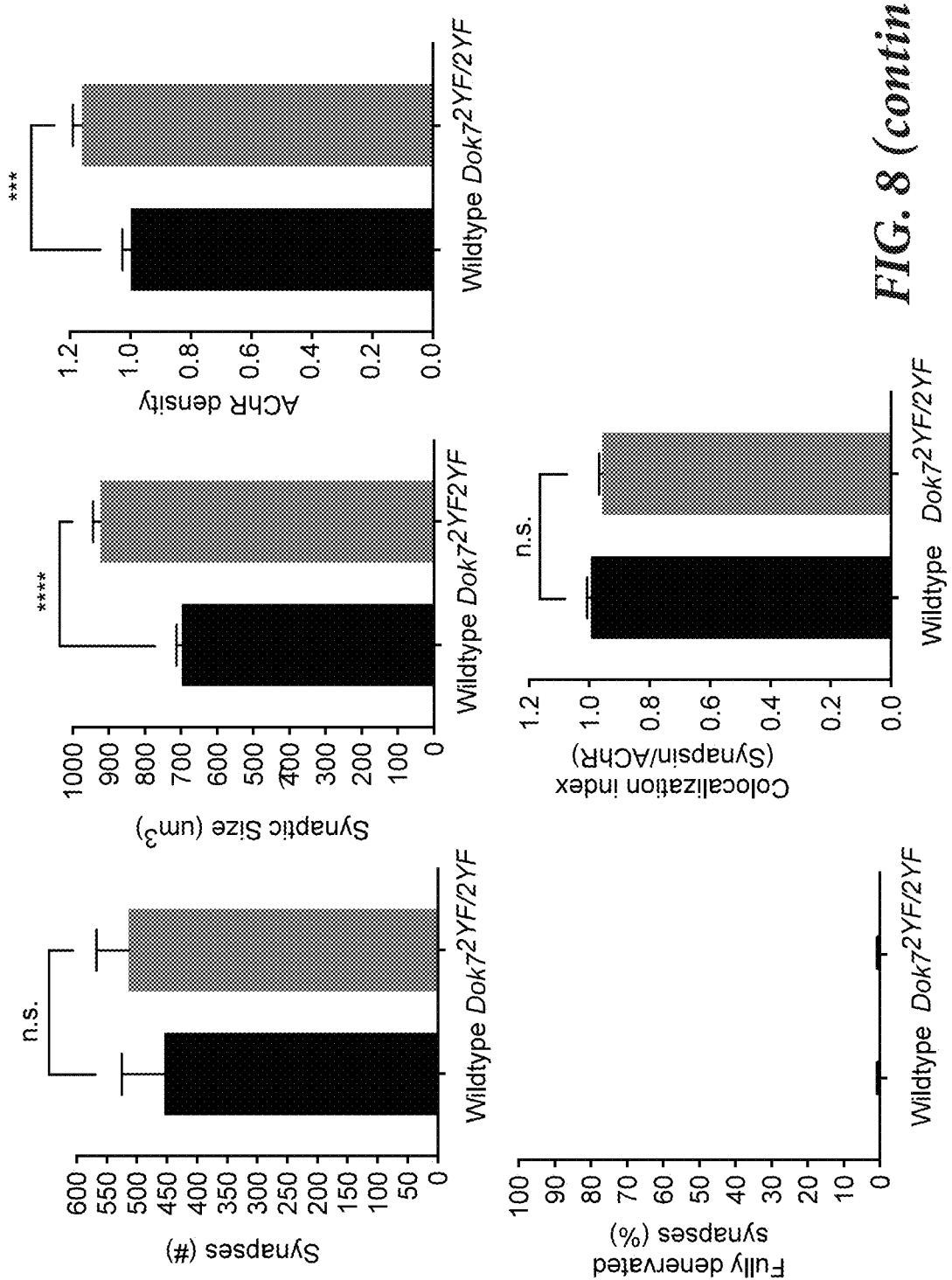

FIG. 8 demonstrates that Y396 and Y406F in the carboxy-terminal region of Dok7 are dispensable for maturation of neuromuscular synapses. Diaphragm muscles from P35 wildtype and Dok7$^{2YF/2YF}$ mice were stained with Alexa 488-a-BGT to label AChRs and antibodies to Neurofilament/Synapsin to label motor axons/nerve terminals. Scale bar=10 μm. In Dok7$^{2YF/2YF}$ mice, synapses mature from a plaque-like to a complex, pretzel-like shape, characteristic of mature murine neuromuscular synapses. The number of synapses were similar in wildtype and Dok7$^{2YF/2YF}$ mice. The density of synaptic AChRs and synaptic size were greater, 15% and 20%, respectively, in Dok7$^{2YF/2YF}$ mice than wildtype mice. The mean±SEM values from 3 mice (100 synapses per mouse) are shown (n.s., not significant; p, *<0.0005, **<0.00005).

Figure 9A:
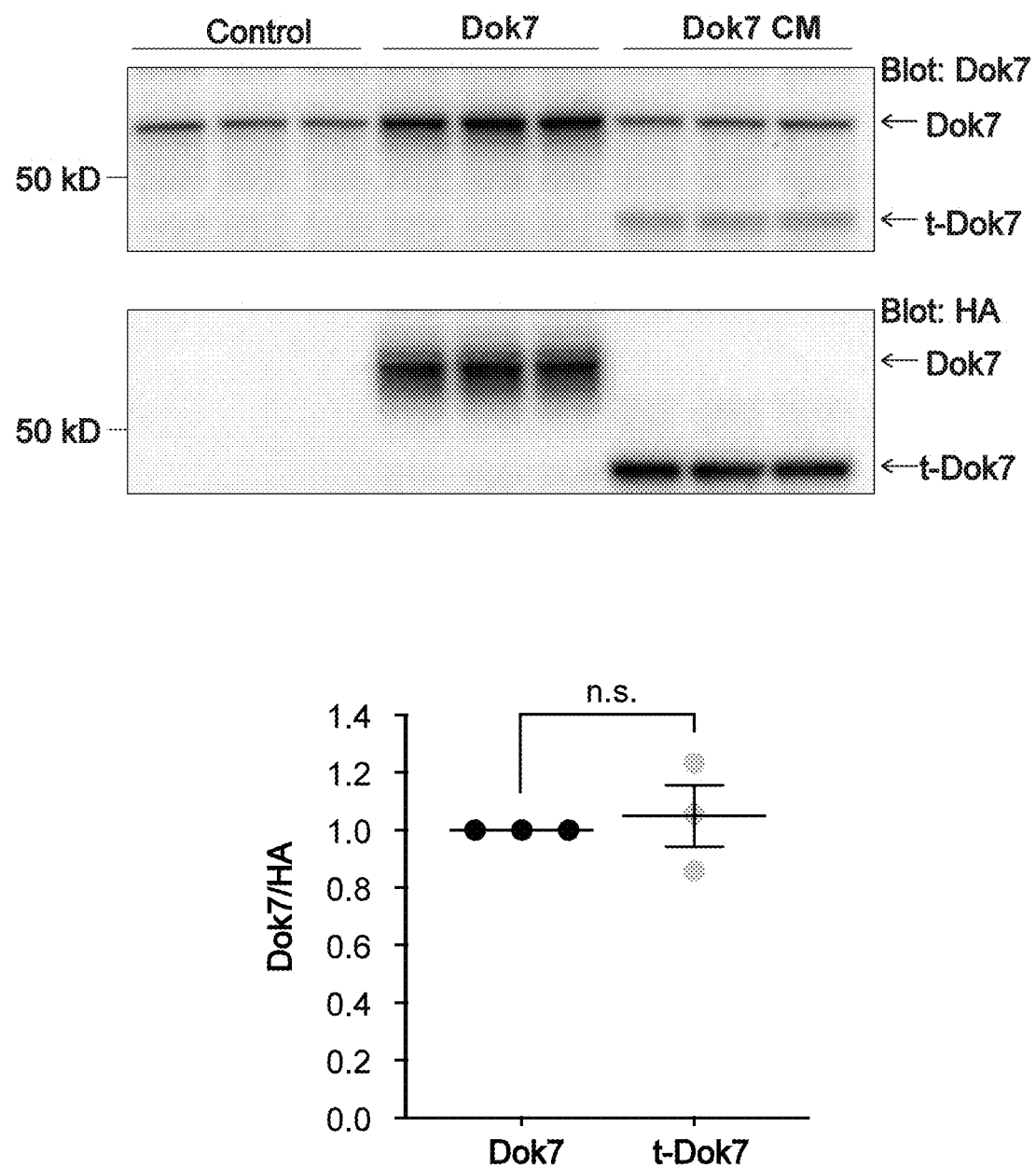
FIG. 9A shows that truncated Dok7 (t-Dok7), encoded by Dok7$^{CM}$, migrates at the predicted size, but is expressed at 3-fold lower levels than wildtype Dok7. Quantitation and comparison of the wildtype and mutant proteins were simplified as the two proteins are co-immunoprecipitated from the same lysate; similar results were obtained by comparing expression in wildtype and Dok7$^{CM/CM}$ mice (FIGS. 10A-
Figure 9B:
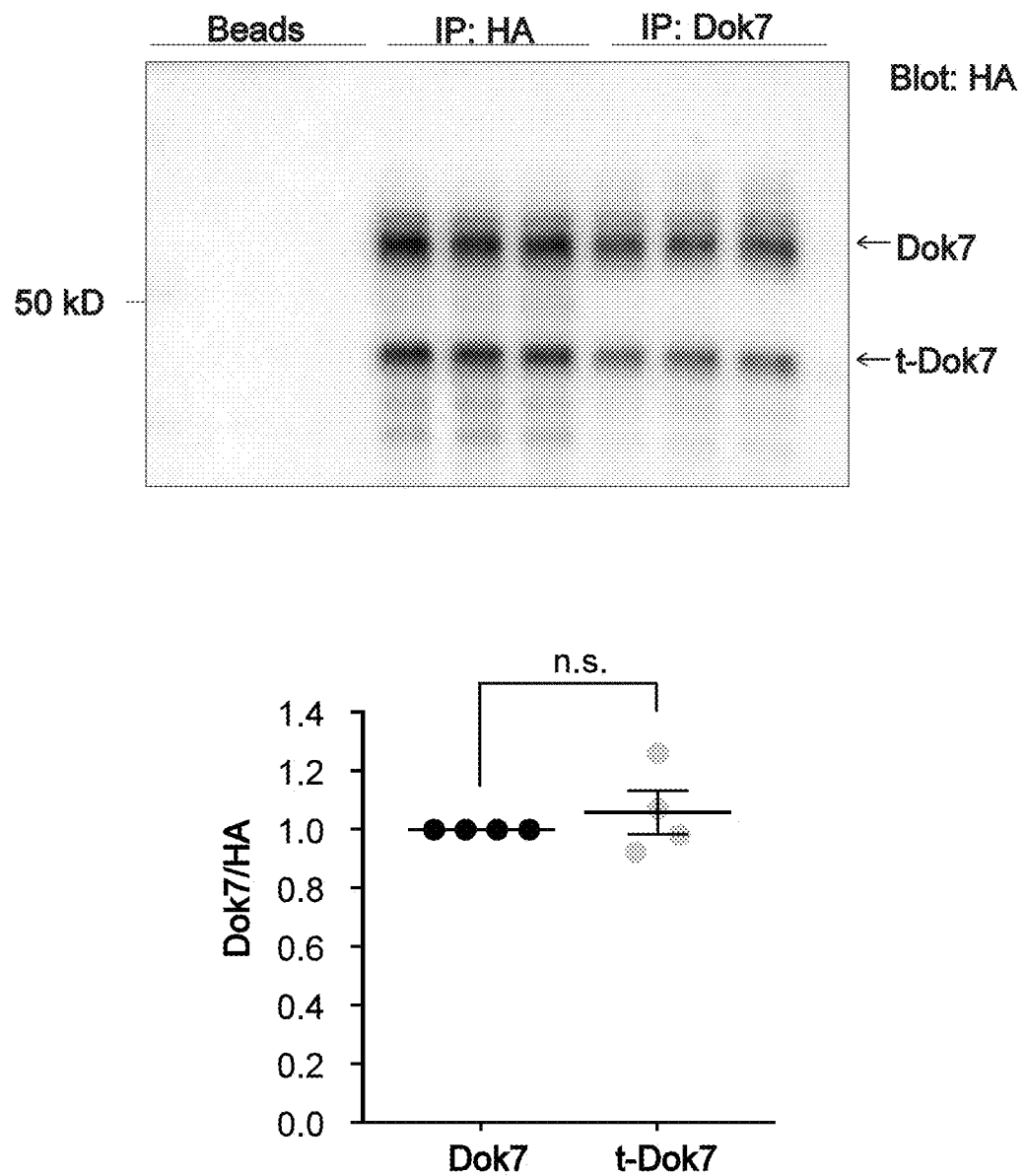

FIGS. 9A-9B demonstrate that wildtype and truncated Dok7 are detected with similar efficiency with antibodies to the PH/PTB domains in Dok7. FIG. 9A shows the results of an experiment in which HEK 293 cells were transiently transfected with a plasmid expressing either HA-tagged Dok7 or HA-tagged truncated Dok7 encoded by Dok7 1124_1127 TGCC dup. Proteins in cell lysates (triplicates) were separated by SDS-PAGE, and Western blots were probed either with a rabbit antibody to the PTB domain in Dok7 or a monoclonal antibody to HA. The grey levels of the bands for wildtype and truncated Dok7 proteins were measured and the level detected by Western blotting was normalized with the rabbit antibody to Dok7 with the level detected by Western blotting with the antibody to HA. The ratio for wildtype Dok7 was equivalent to the ratio for truncated Dok7, indicating that the rabbit antibody to Dok7 detected wildtype and truncated Dok7 proteins with similar efficiency by Western blotting. FIG. 9B shows the results of an experiment in which wildtype and truncated Dok7 were immunoprecipitated with similar efficiency by a goat antibody to the PTB domain in Dok7. HEK 293 cells were transiently co-transfected with plasmids expressing HA-tagged Dok7 and HA-tagged truncated Dok7 encoded by Dok7 1124_1127 TGCC dup. Dok7 proteins were immunoprecipitated from cell lysates (triplicates) either with a monoclonal antibody to HA or a goat antibody to the PTB domain in Dok7, and Western blots were probed with the monoclonal antibody to HA. Grey levels were measured; the level for the background band in the control, non-transfected samples was subtracted; and the value for each protein immunoprecipitated with the goat-antibody to Dok7 was normalized to the value for the same protein immunoprecipitated with the antibody to HA. This ratio was equivalent for wildtype and truncated Dok7 proteins, indicating that the goat antibody to Dok7 immunoprecipitated wildtype and truncated proteins with similar efficiency. The scatter plots in FIGS. 9A-9B show the values from 3 experiments and the mean±SEM (n.s., not significant).

Figure 10A:
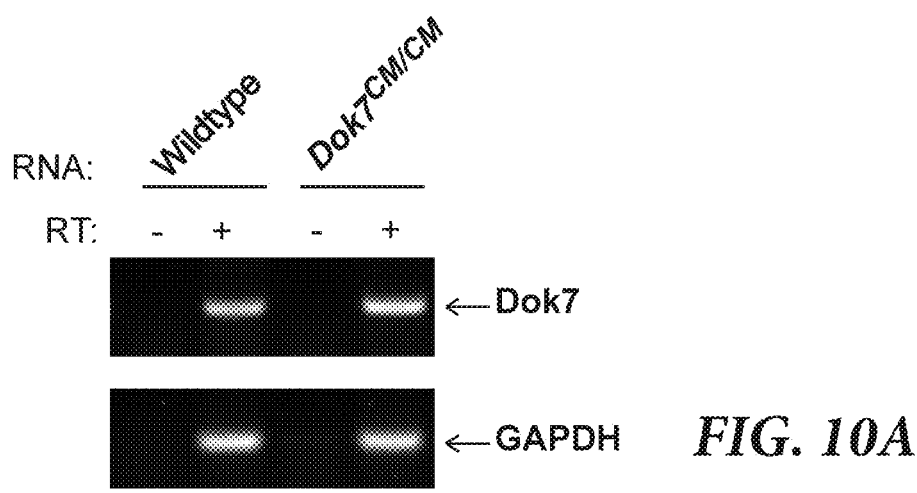
Figure 10B:
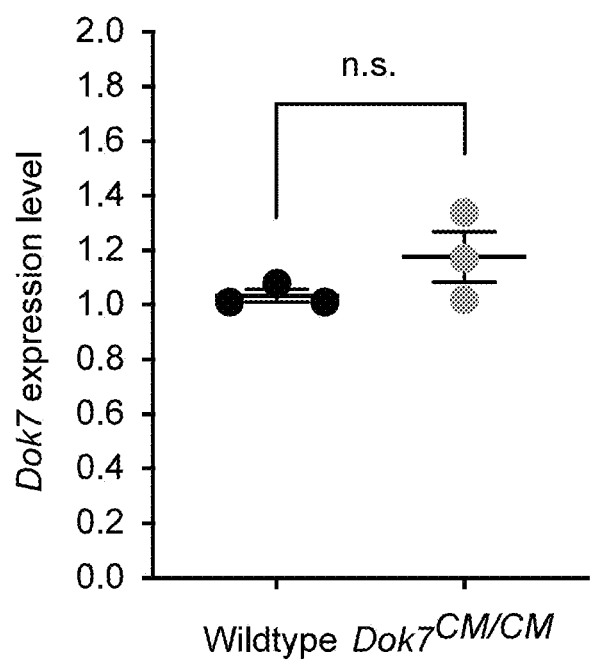

FIGS. 10A-10C demonstrate that Dok7 RNA expression is normal in Dok7$^{CM/CM}$ mice. FIG. 10A shows that RT-PCR amplification of Dok7 RNA showed that Dok7 mRNA levels are similar in muscle from E18.5 wildtype and Dok7$^{CM/CM}$ mice. GAPDH was used as a loading control. FIG. 10B shows the results of an experiment in which Dok7 mRNA levels were quantitated by qPCR, which showed that Dok7 mRNA levels are normal in Dok7$^{CM/CM}$ mice. The scatter plot shows the values and mean±SEM values from 3 mice (n.s., not significant). FIG. 10C shows the results of an experiment in which Dok7 was immunoprecipitated from muscles of E18.5 wildtype and Dok7$^{CM/CM}$ mice, and the blots were probed with antibodies to Dok7. Truncated Dok7 (t-Dok7), encoded by Dok7CM/CM, migrates at the predicted size, but is expressed at 3-fold lower levels than wildtype Dok7. The scatter plot shows the values for ten mice from each genotype and the mean±SEM values (p, ****<0.00005).

Figure 11:
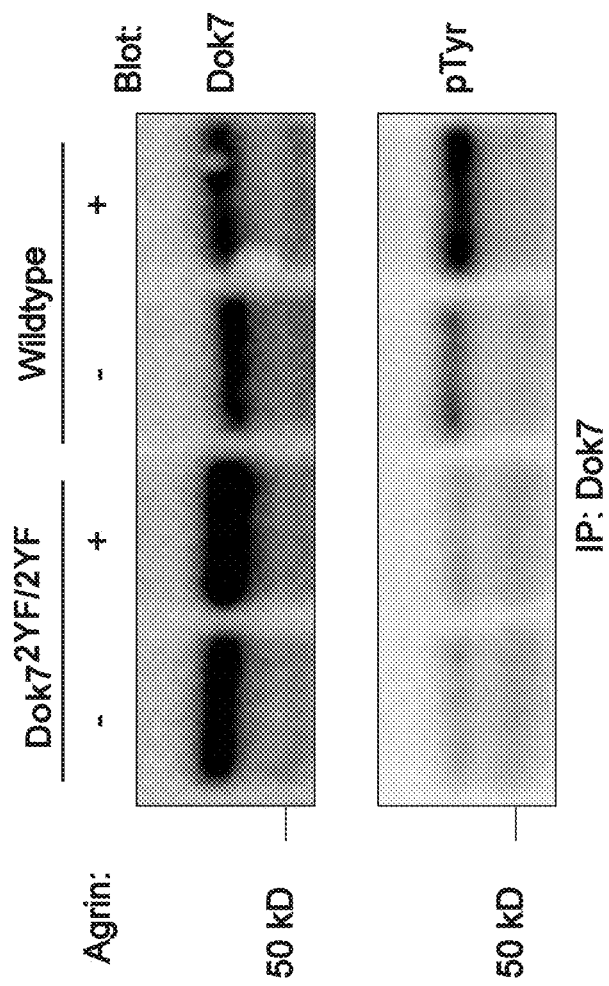

FIG. 11 demonstrates that Y396 and Y406 are the major if not sole tyrosine residues in Dok7 that are phosphorylated by Agrin stimulation. Muscle cell lines were generated from wildtype and Dok7$^{2YF/2YF}$ mice and treated the cultured myotubes with Agrin for 30 minutes. MuSK was immunoprecipitated, and Western blots were probed with antibodies to MuSK or phosphotyrosine (pTyr). Agrin stimulates Dok7 tyrosine phosphorylation in wildtype but not Dok72YF/2YF myotubes.

Figure 12A:
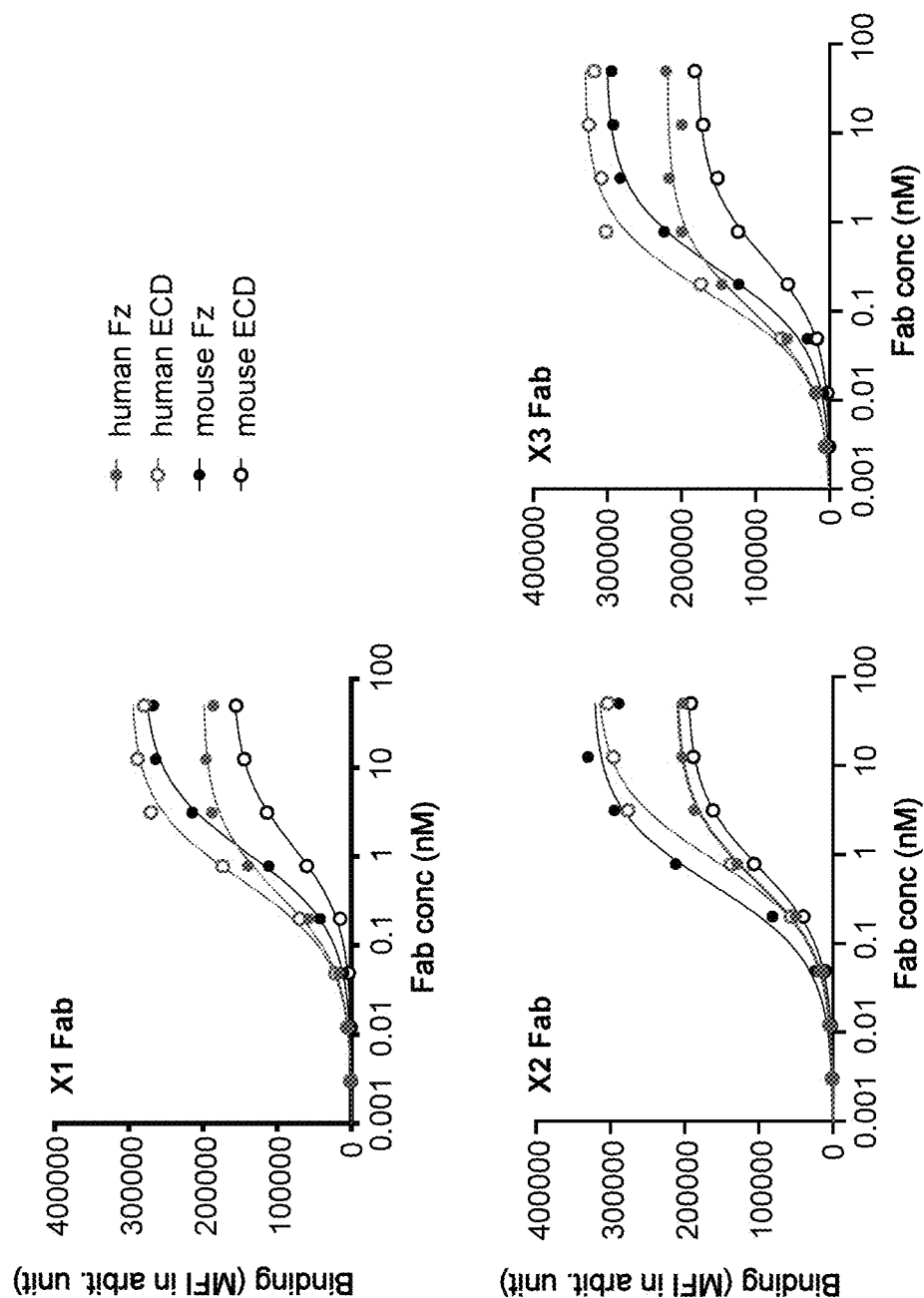
Figure 12B:
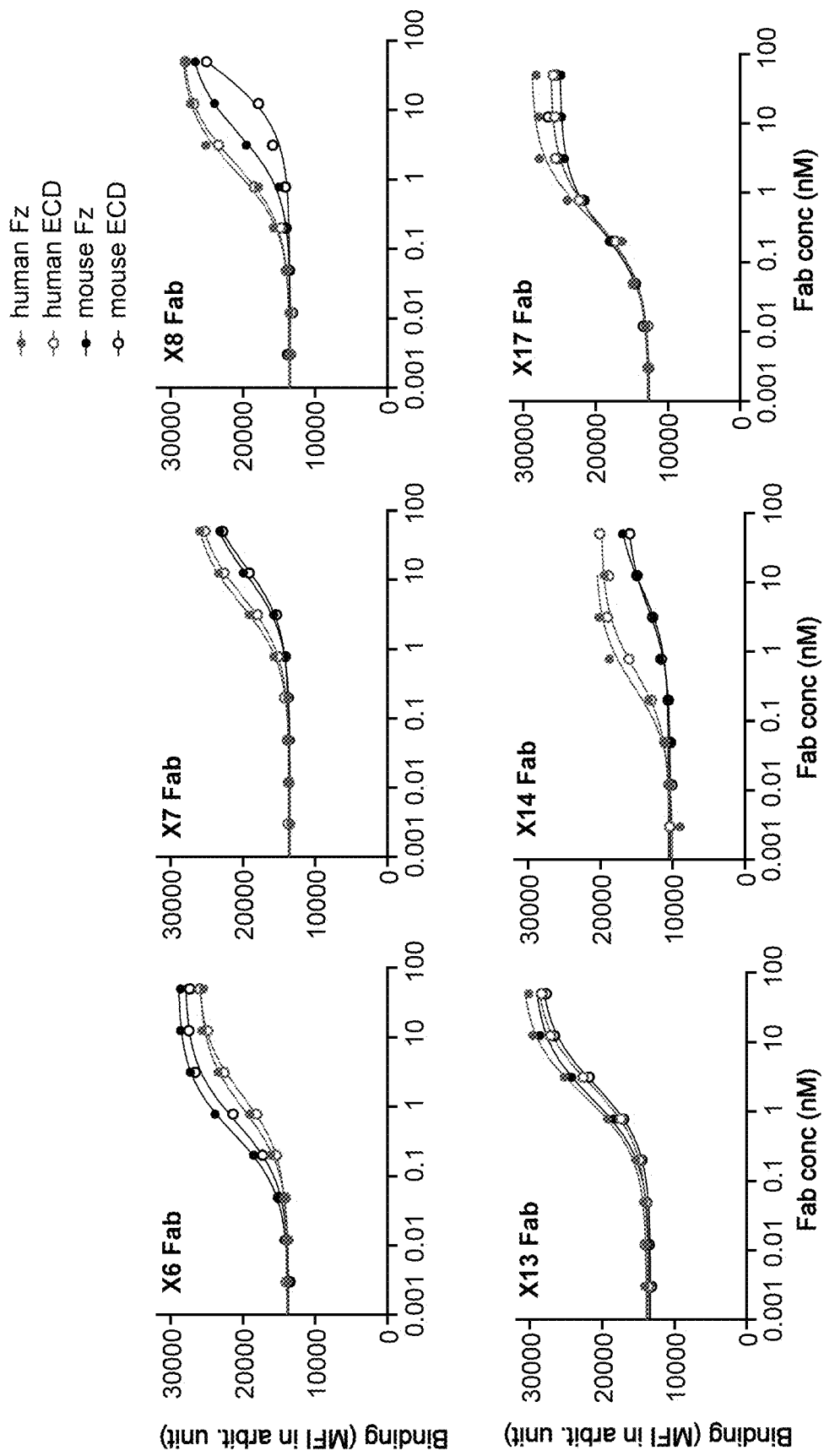
Figure 12C:
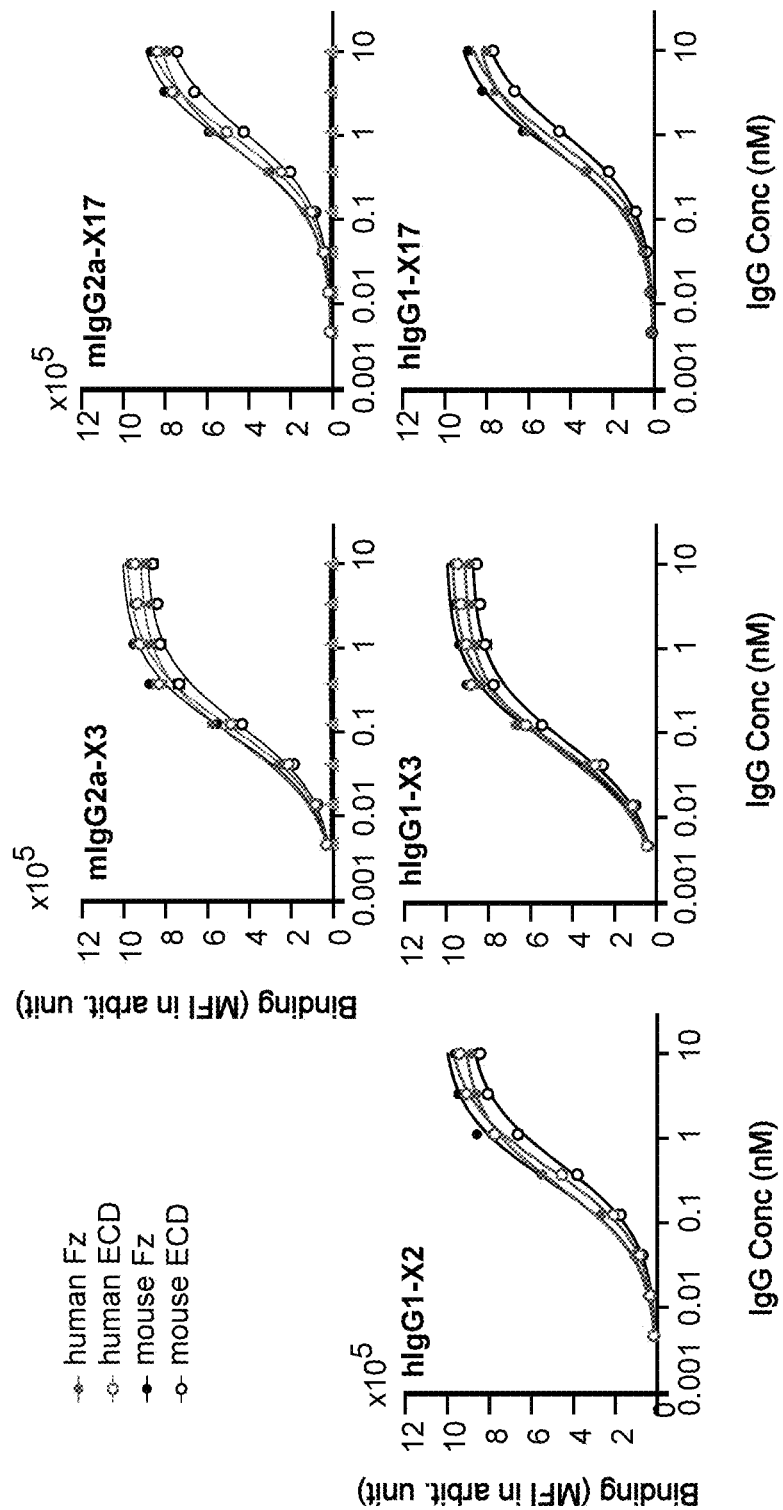

FIGS. 12A-12C show binding characteristics of MuSK antibody clones. FIG. 12A-12C show binding titration of antibodies to MuSK in the Fab format to immobilized hFz, hECD, mFz, and mECD, as tested using a bead-based binding assay. Curves show the best fit of the 1:1 binding model. The $K_D$ values are listed in FIG. 5A. The datasets in FIG. 12A and FIG. 12B were taken on different instruments, which resulted in different signal ranges. FIG. 12C shows the binding titration of antibodies to MuSK in the IgG format, as performed in the same manner as in FIG. 12A.

Figure 13A:
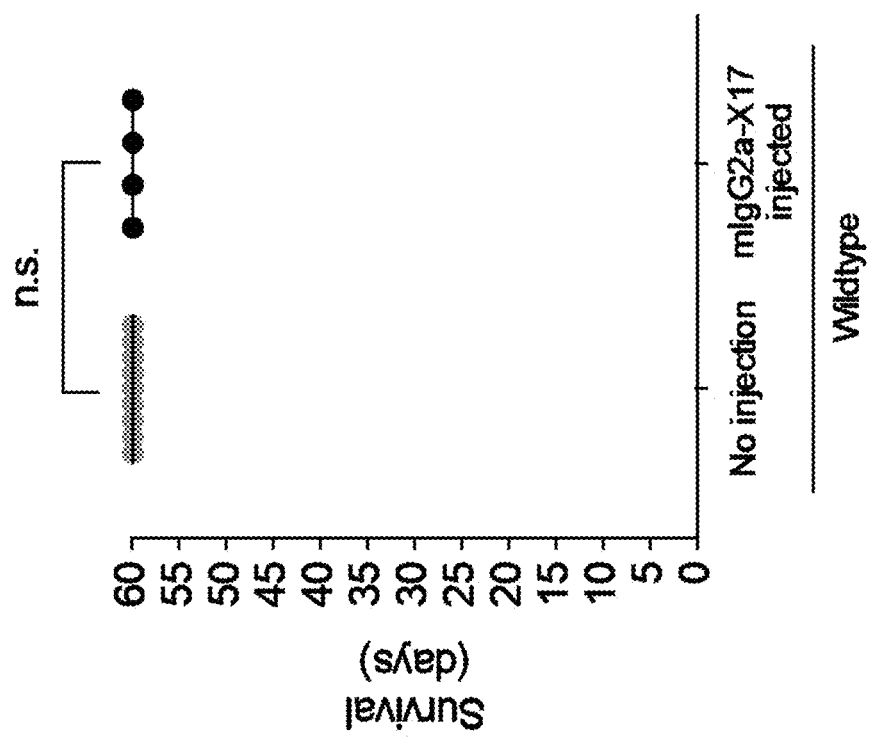
Figure 13B:
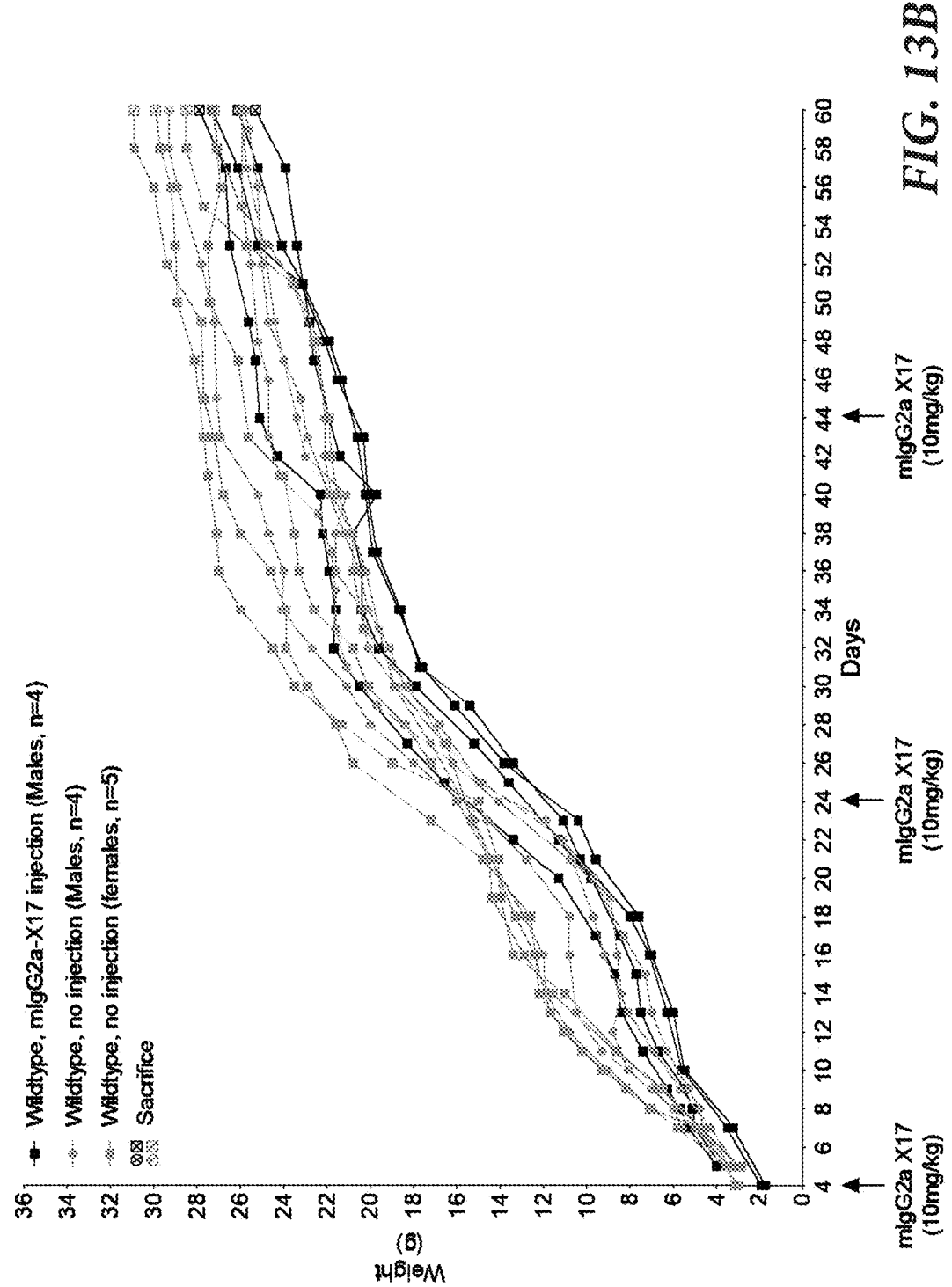
Figure 13C:
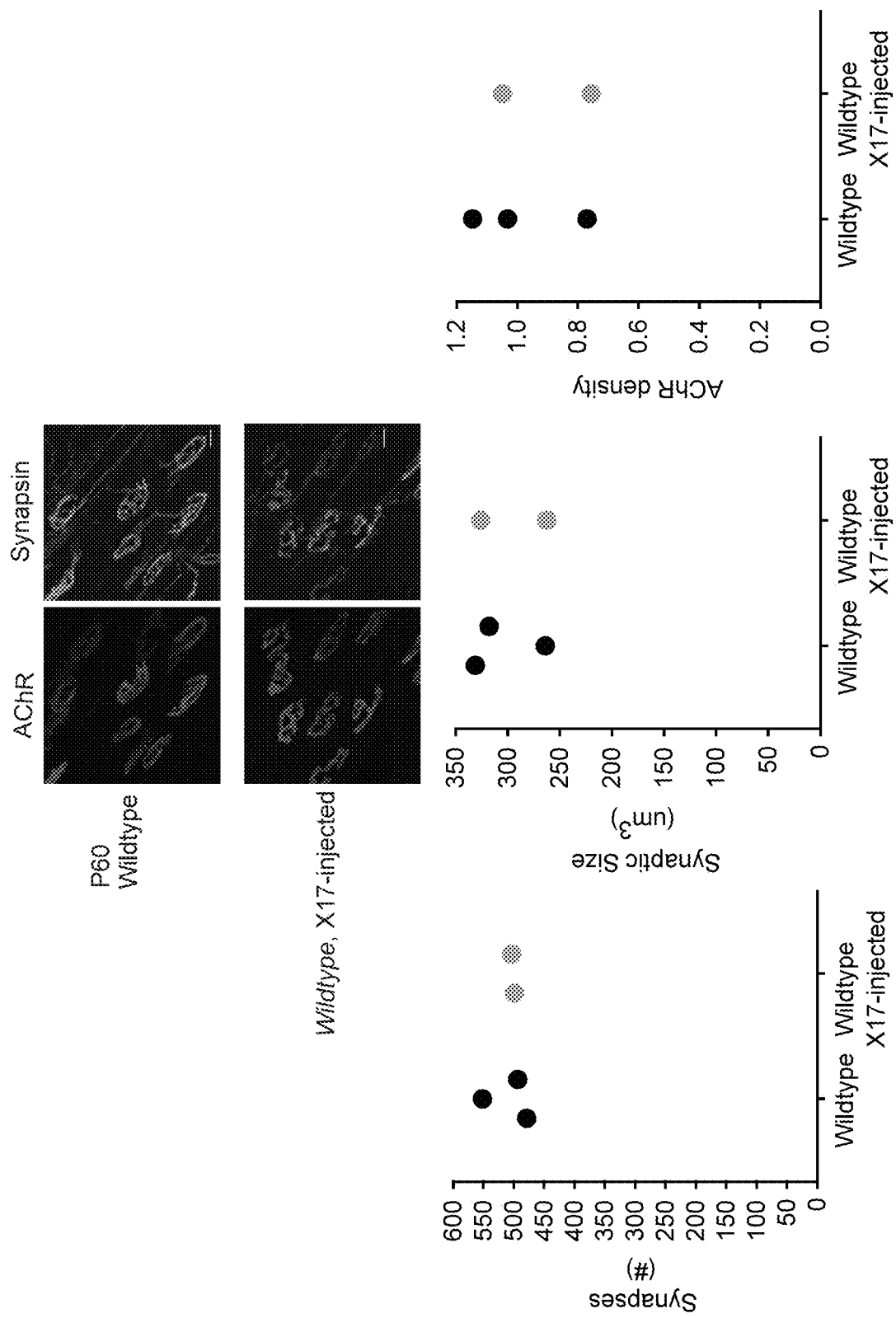
Figure 13D:
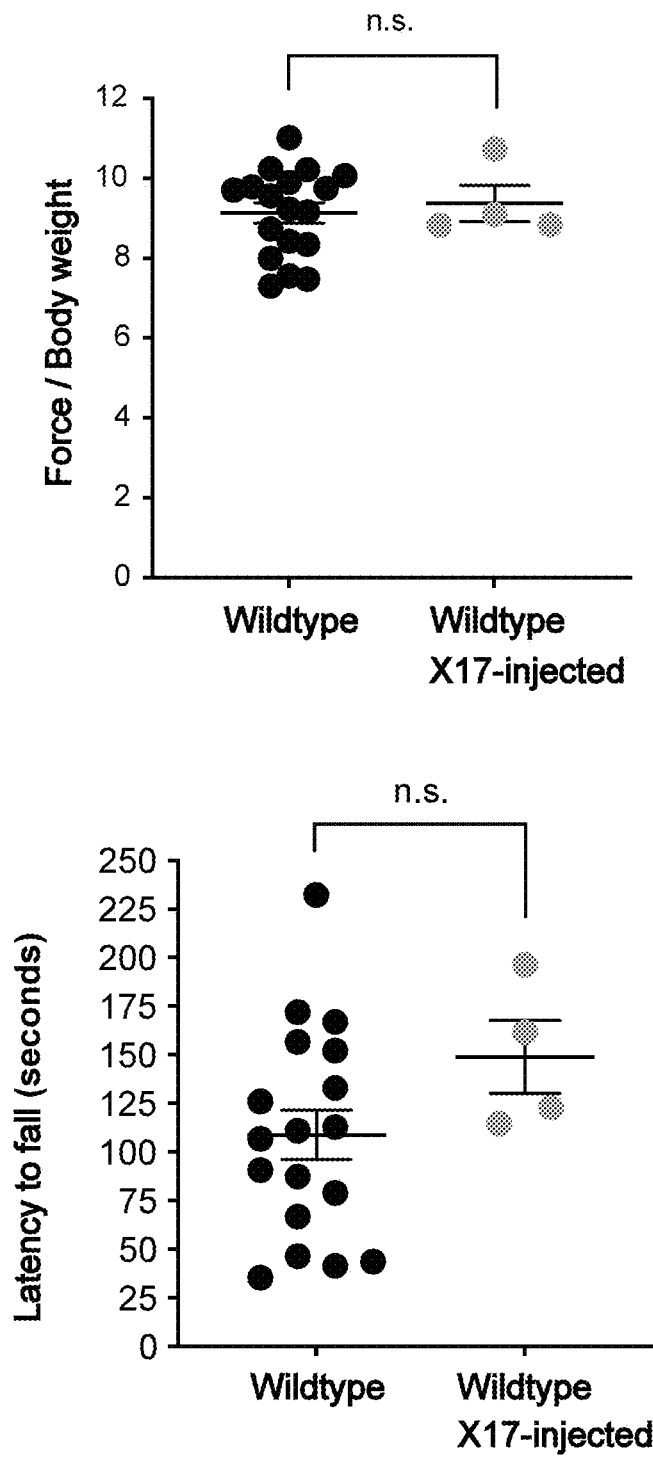

FIGS. 13A-13D demonstrate that chronic injection of MuSK agonist antibody mIgG2a-X17 in wildtype mice has no effect on survival, organization of neuromuscular synapses, weight gain or motor behavior. FIG. 13A is a scatter plot showing the results of an experiment in which wildtype mice in a C57BL/6-CBA mixed background, injected at P4, P24, and P44 with mIgG2a-X17 (n=4), survived until P60, when they were sacrificed. The scatter plot shows the survival time for 9 non-injected wildtype mice and 4 wildtype mice injected with mIgG2a-X17 and the mean±SEM values (n.s., not significant). FIG. 13B is a plot showing the results of an experiment in which wildtype mice, injected with mIgG2a-X17 (n=4), gained weight like wildtype mice (n=9). FIG. 13C shows that chronic injection of mIgG2a-X17 wildtype mice has no effect on the organization of neuromuscular synapses. Diaphragm muscles from P60 wildtype and wildtype mice injected with mIgG2a-X17 were stained with Alexa 488-α-BGT to label Acetylcholine Receptors (AChRs) and antibodies to βIII-Tubulin/Synapsin to label motor axons/nerve terminals. In wildtype mice treated with mIgG2a-X17, synapses matured from a simple, plaque-like shape to a complex, pretzel-like shape, characteristic of mature murine neuromuscular synapses. Scale bar=10 mm. Injection of mIgG2a-X17 in wildtype mice has no effect on synapses number, synaptic size, and AChR density. 100 synapses from 2 mice in each category were analyzed. FIG. 13D are scatter plots showing that chronic injection of mIgG2a-X17 in wildtype mice has no effect on motor behavior. The motor performance of wildtype mice injected with mIgG2a-X17, as assessed by grip strength and the latency to fall from a rotating rotarod, were similar to non-injected wildtype mice. The scatter plots show the values for 18 wildtype mice and 4 wildtype mice injected with mIgG2a-X17 and the mean±SEM values (n.s, not significant).

FIGS. 14A-14B are tables showing that Dok7$^{CM/CM}$ mice in a mixed genetic background survive approximately two weeks postnatally. A mixed genetic background of mice was used to analyze the survival of Dok7$^{CM/CM}$ mice. Dok7$^{CM/+}$ mice in a C57BL/6 background were crossed to wildtype CBA, 129sv1, FVB, or BALB/c mice. Heterozygous F1 progeny were then intercrossed to produce Dok7$^{CM/CM}$ mice in a mixed background. The genotype of the progeny at P5-P10 or post-mortem was determined. FIG. 14A is a table showing $x^2$-square analysis of F2 mice shows that the occurrence of genotypes is unlikely to occur by chance, indicating that homozygous Dok7$^{CM/CM}$ mice in each mixed genetic background survive postnatally. FIG. 14B is a table showing the average and maximum survival time (days) a of homozygous Dok7$^{CM/CM}$ mice in a mixed genetic background.

Figure 15A:
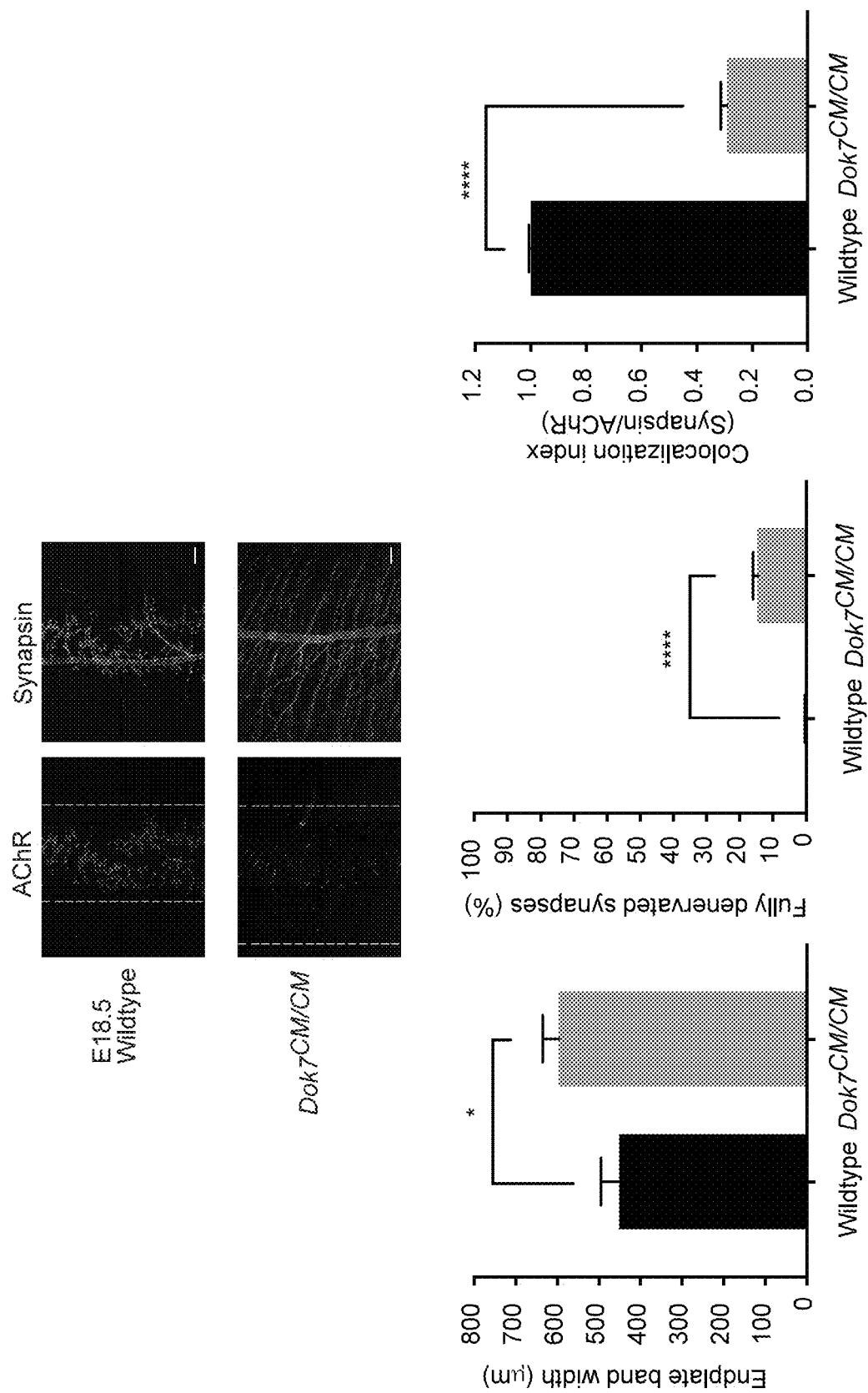
Figure 15B:
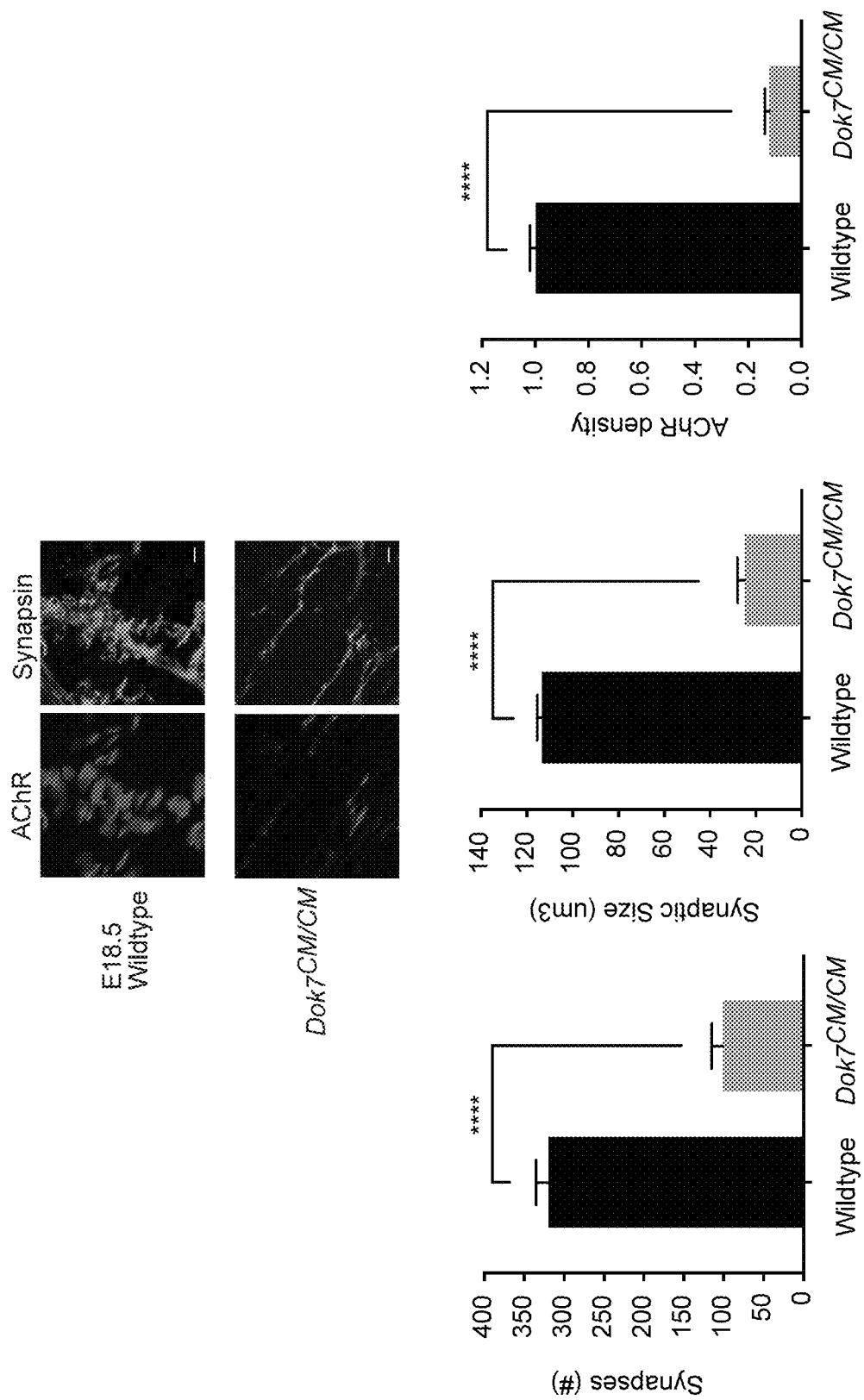
Figure 15C:
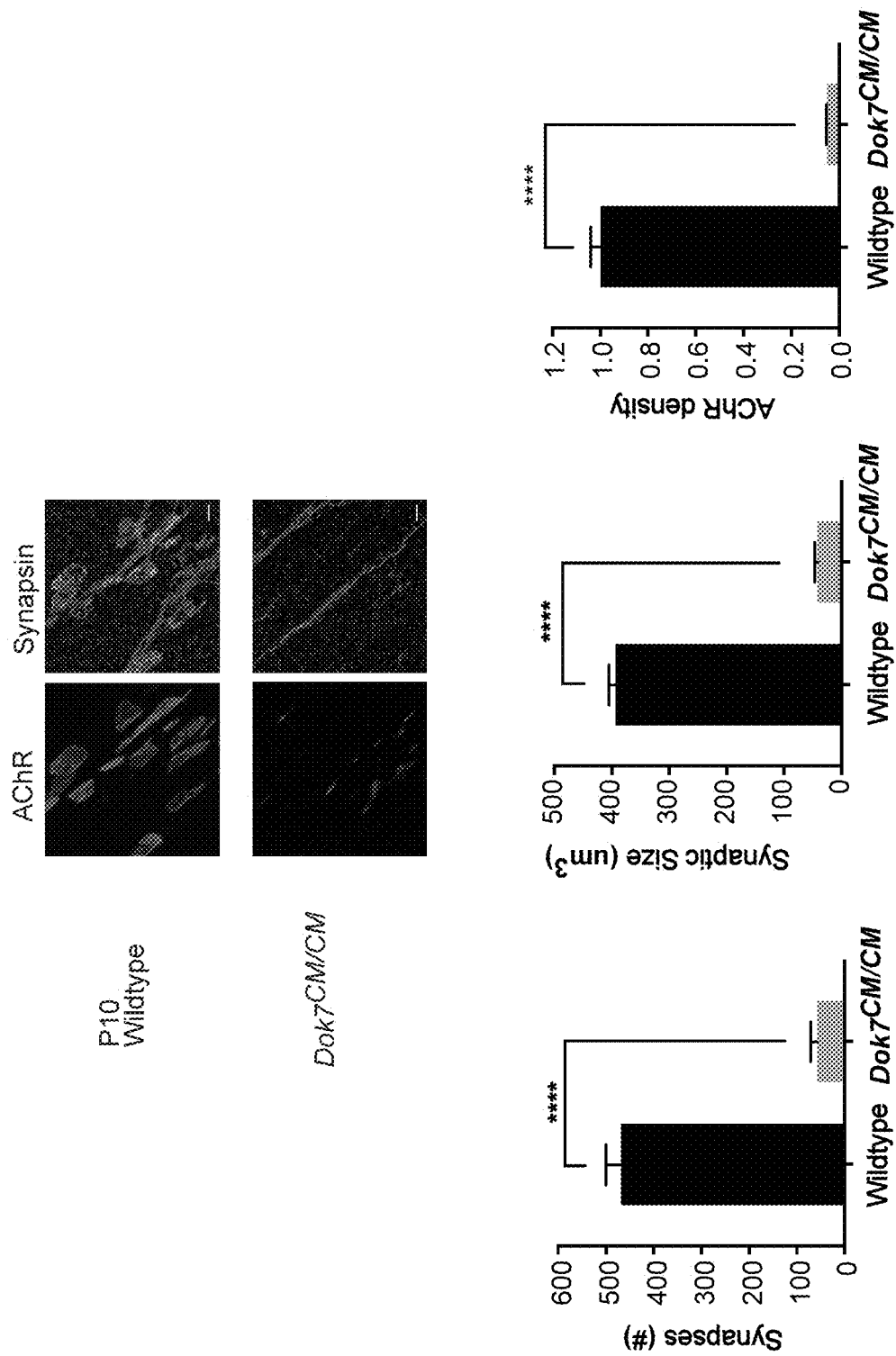
Figure 15C:
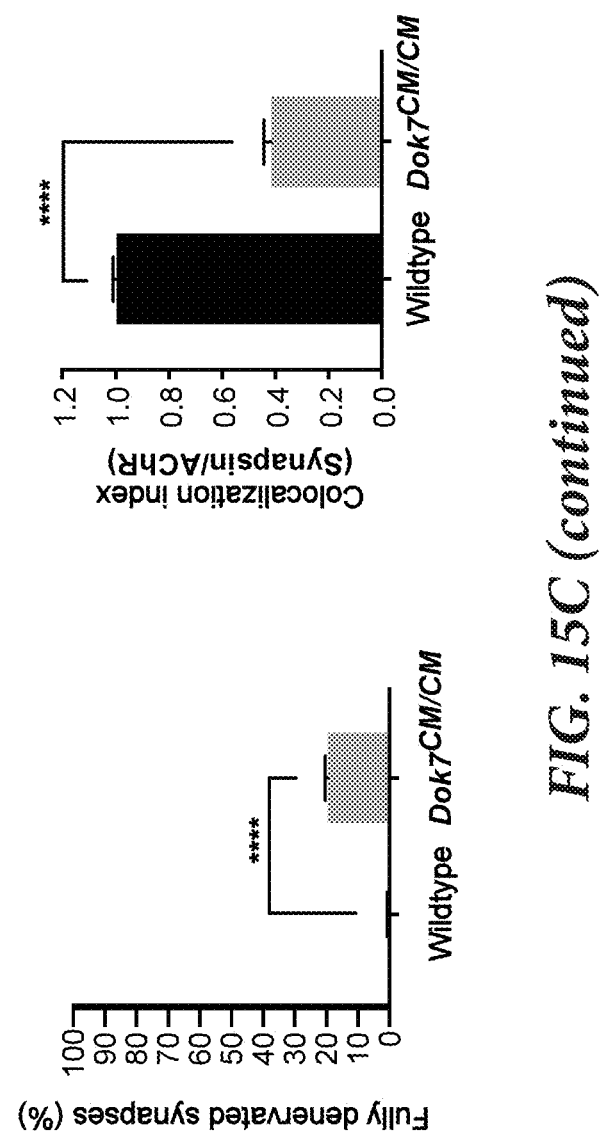
Figures 15D, 15E:
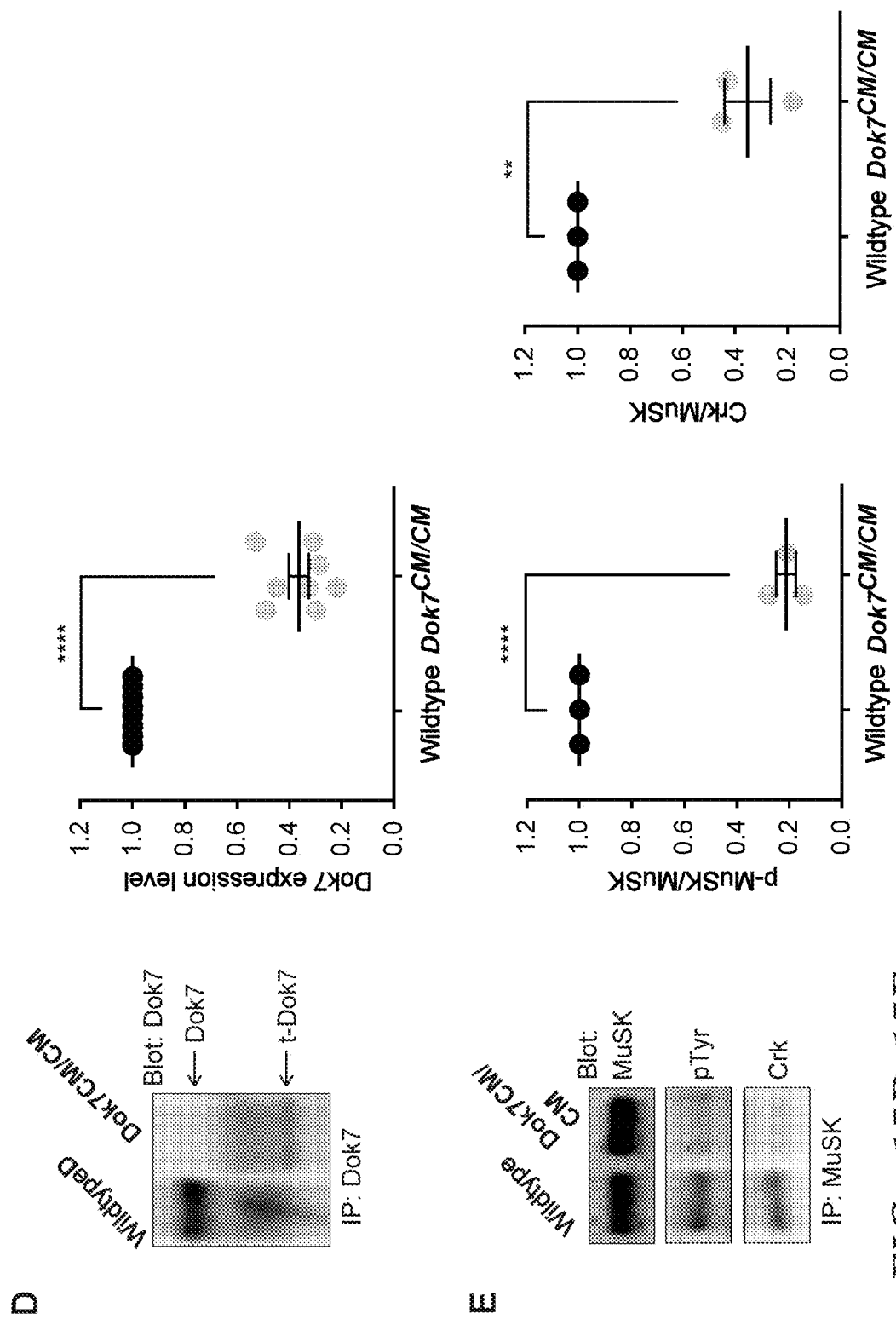

FIGS. 15A-15E demonstrate that the C-terminal region of Dok7 is essential for complete differentiation and maturation of the neuromuscular synapse in Dok7$^{CM/CM}$ mice in a mixed genetic background. In FIGS. 15A-15C, diaphragm muscles from wildtype and Dok7$^{CM/CM}$ mice in a C57BL/6-CBA mixed background at E18.5 and P10 were stained with Alexa 488-a-BGT to label AChRs (red) and antibodies to Neurofilament/Synapsin to label motor axons/nerve terminals (green). FIG. 15A shows that, at E18.5, the endplate band (dashed white lines) is 30% wider in Dok7CM/CM than wildtype mice. Moreover, nerve terminals were absent from 15% of the AChR clusters and the colocalization index (Synapsin/AChR) was reduced by 3.5-fold in Dok7$^{CM/CM}$ mice. Scale bar=50 μm. The mean±SEM values from 3 mice are shown (p, *<0.05; p, **<0.00005). FIG. 15B shows that the number of synapses, synaptic size and density of synaptic AChRs were reduced by 3.2-fold, 4.5-fold, and 8-fold, respectively, in E18.5 Dok7$^{CM/CM}$ mice. The mean±SEM values from 3 mice (100 synapses per mouse) are shown (p, <0.00005). Scale bar=10 μm. FIG. 15C shows that, at P10, the number of synapses, synaptic size and density of synaptic AChRs were reduced by over 10-fold in Dok7$^{CM/CM}$ mice. In addition, nerve terminals are absent from 20% of the AChR clusters in Dok7$^{CM/CM}$ mice. The mean±SEM values from 3 mice (100 synapses per mouse) are shown (p, <0.00005). FIG. 15D shows that Dok7 was immunoprecipitated from muscles of E18.5 wildtype and Dok7$^{CM/CM}$ mice, and the blots were probed with antibodies to Dok7. Truncated Dok7 (t-Dok7), encoded by Dok7$^{CM/CM}$, migrates at the predicted size, but is expressed at 3-fold lower levels than wildtype Dok7. Because Dok7 expression and MuSK phosphorylation were diminished to the same extent in the C57BL/6-CBA mixed breed and C57BL/6 inbred mice, other factors presumably led to increased survival in the mixed genetic background. The scatter plot shows the values for eight mice from each genotype and the mean±SEM values (p, <0.00005). FIG. 15E shows that MuSK was immunoprecipitated from muscles of E18.5 wildtype, Dok7$^{CM/CM}$, and the blots were probed with antibodies to MuSK, phosphotyrosine, and Crk. The level of phosphotyrosine and Crk that co-isolated with the MuSK complex was normalized to MuSK expression. Crk association with the MuSK complex was 2.8-fold lower in Dok7$^{CM/CM}$ mice than wildtype mice. MuSK tyrosine phosphorylation is lower in Dok7$^{CM/CM}$ mice than wildtype mice by 5-fold. The scatter plots show the values for 3 mice of each genotype and the mean±SEM values (p, <0.005, ****<0.00005). Scale bar=10 μm.

FIGS. 16A-16B are tables showing sequence analysis of potential off-target sites failed to identify mutations in these genes. The top-ranked potential off-target gene sequences 1-5 in Dok7 CM (FIG. 16A; SEQ ID NOs: 280-284) and off-target gene sequences 1-5 in Dok7 2YF (FIG. 16B; SEQ ID NOs: 285-289) mice are indicated.

Figure 17A:
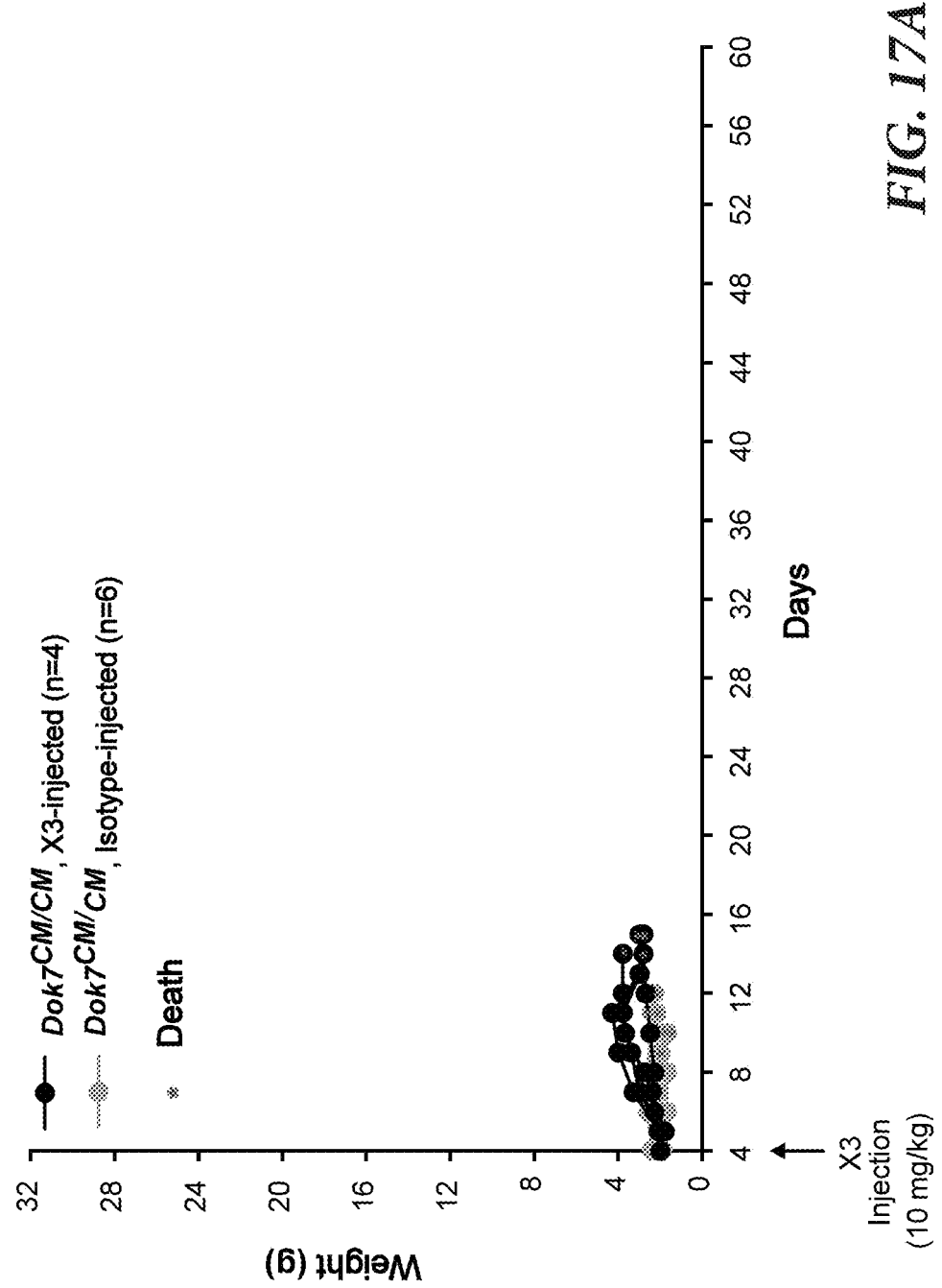
Figure 17B:
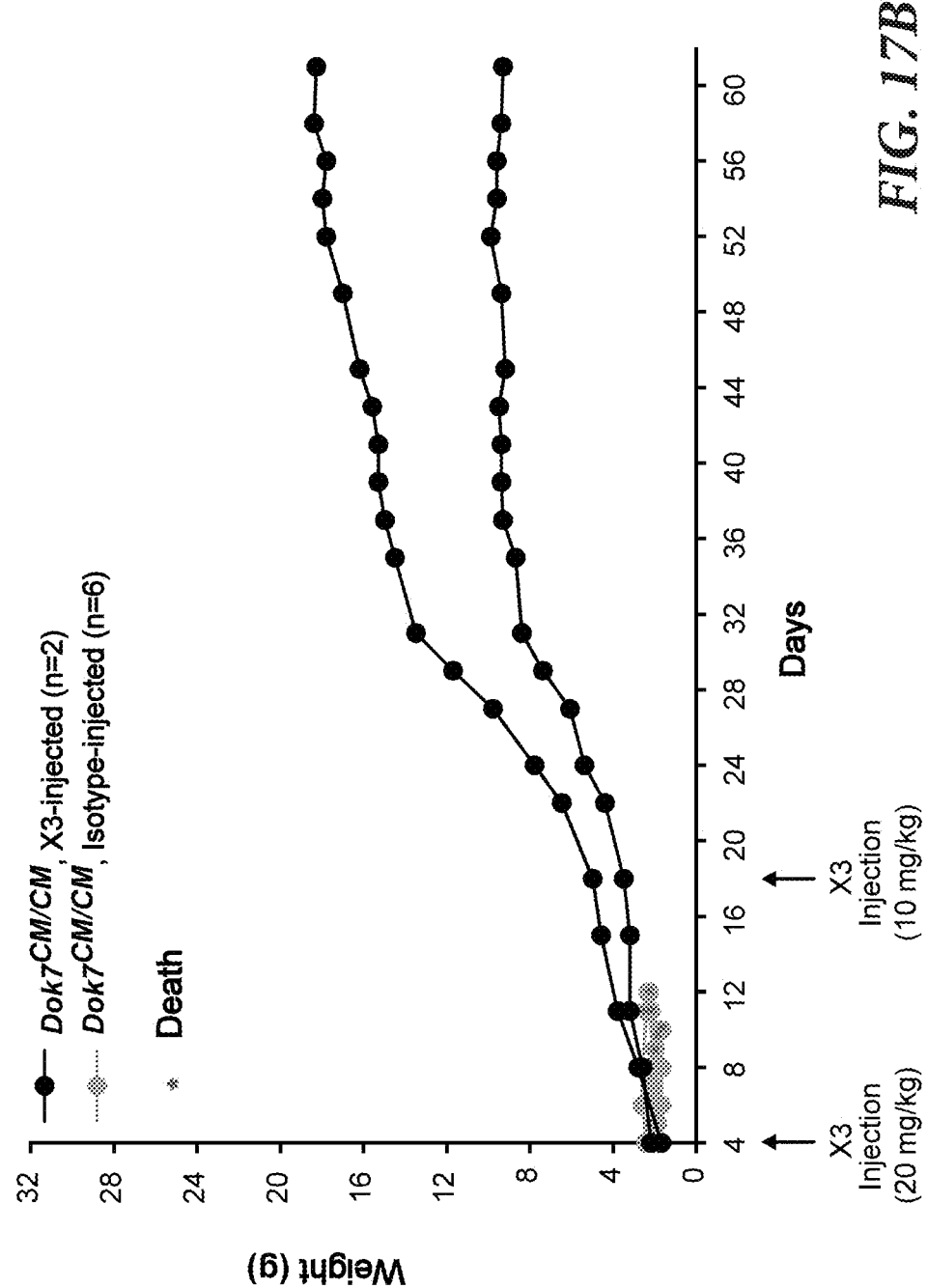
Figure 17C:
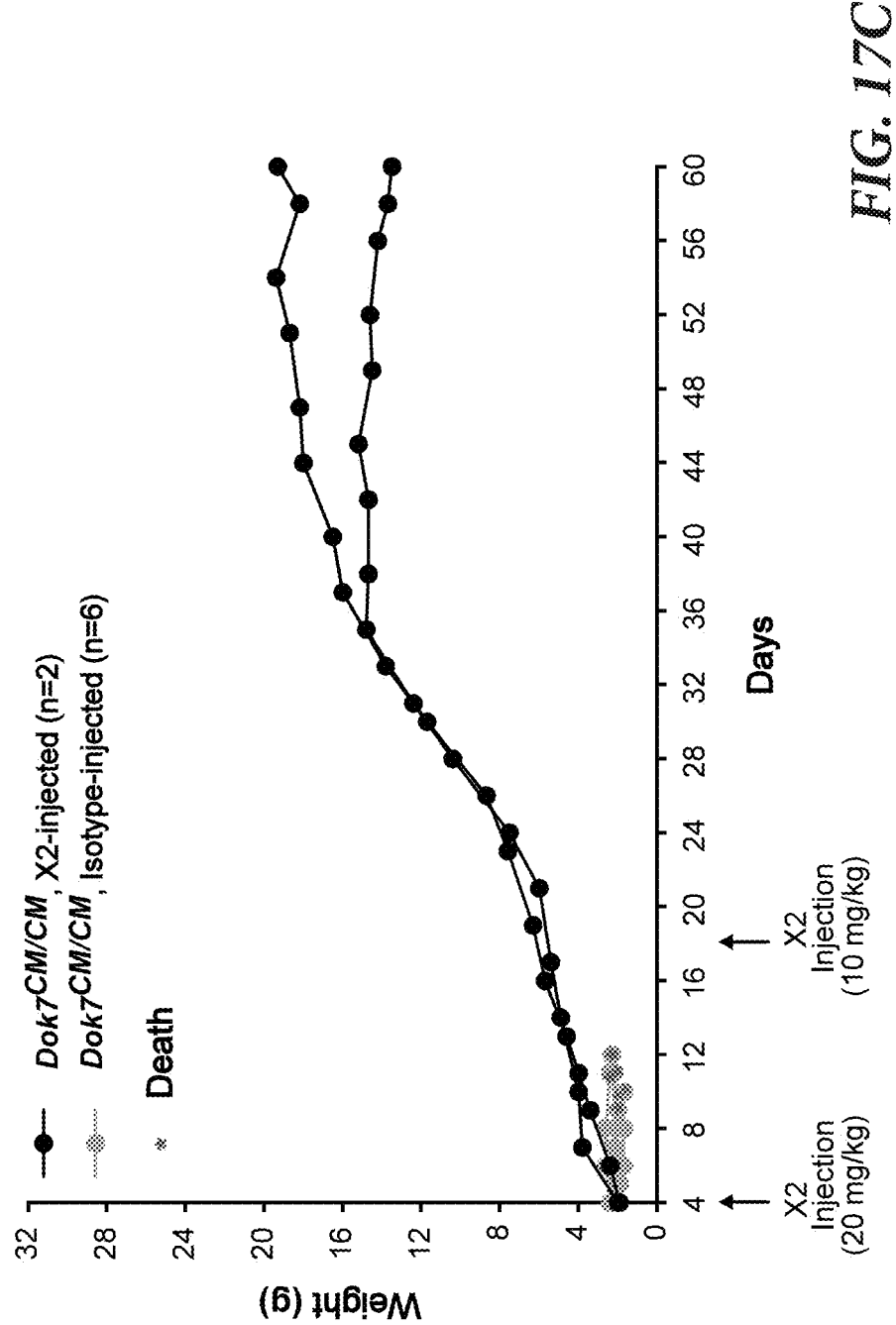

FIGS. 17A-17C are graphs showing that antibodies X2 and X3, like X17, rescue Dok7$^{CM/CM}$ mice from early lethality. FIG. 17A shows the results of an experiment in which Dok7$^{CM/CM}$ mice in a C57BL/6-CBA mixed background were injected at P4 with 10 mg/kg mIgG2a-X3 (see also FIG. 46B). At this dose, X3 failed to rescue the mice from lethality. In contrast, dosing with 20 mg/kg mIgG2a-X3 at P4 rescued the mice from early lethality (FIG. 17B (see also FIG. 47B)). These mice were subsequently injected with 10 mg/kg mIgG2a-X3 at P18, which led to survival until P60, when the mice were sacrificed. FIG. 17C shows that dosing Dok7$^{CM/CM}$ mice with 20 mg/kg hIgG1-X2 at P4 likewise rescued Dok7$^{CM/CM}$ mice from early lethality; subsequent injection of 10 mg/kg hIgG1-X2 at P18 led to survival of Dok7CM/CM mice until P60, when the mice were sacrificed.

Figure 18:
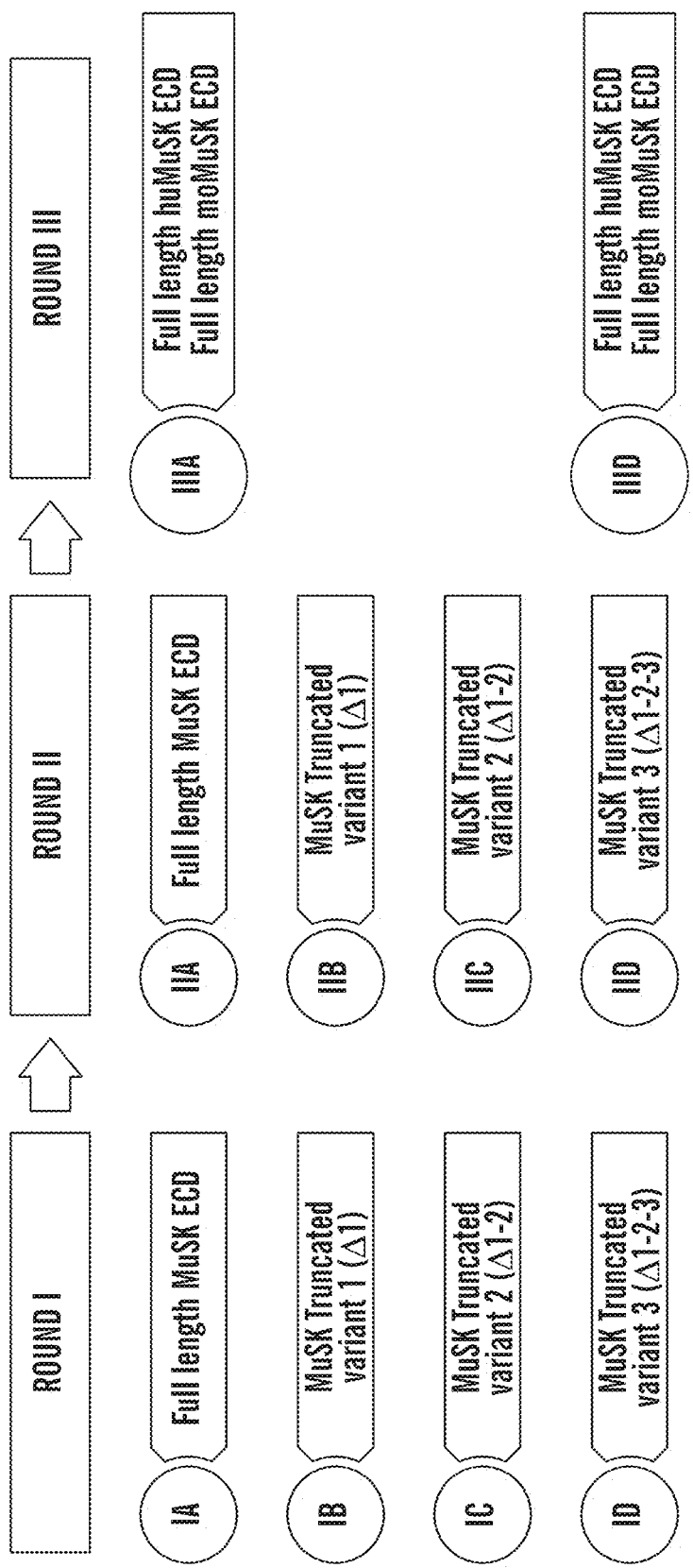

FIG. 18 is a schematic showing the strategy overview of phage display selections for llama immune Fab libraries.

Figure 19:
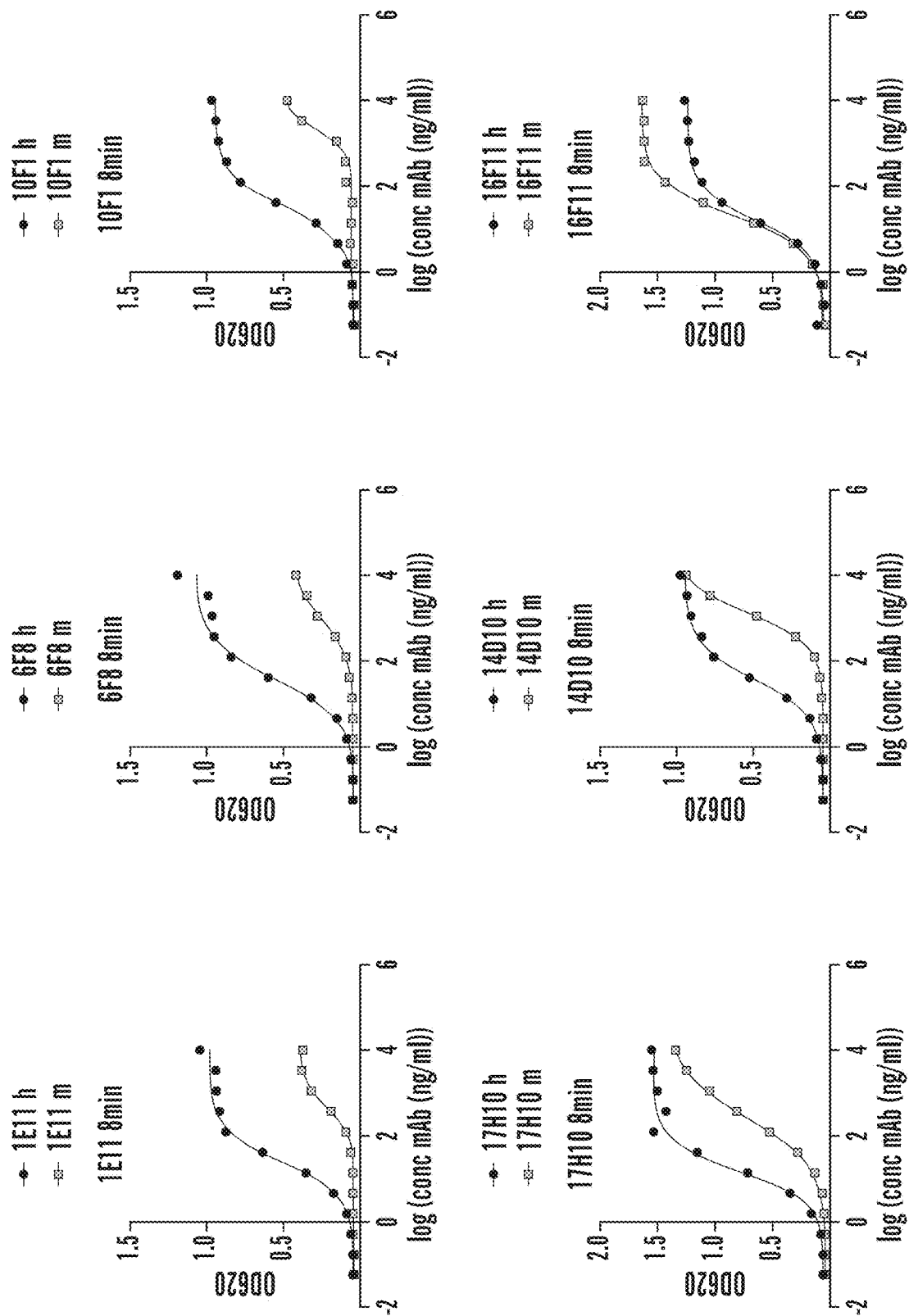

FIG. 19 shows the results of ELISA experiments which reveal poor binding of antibodies to human or mouse MuSK.

Figure 20:
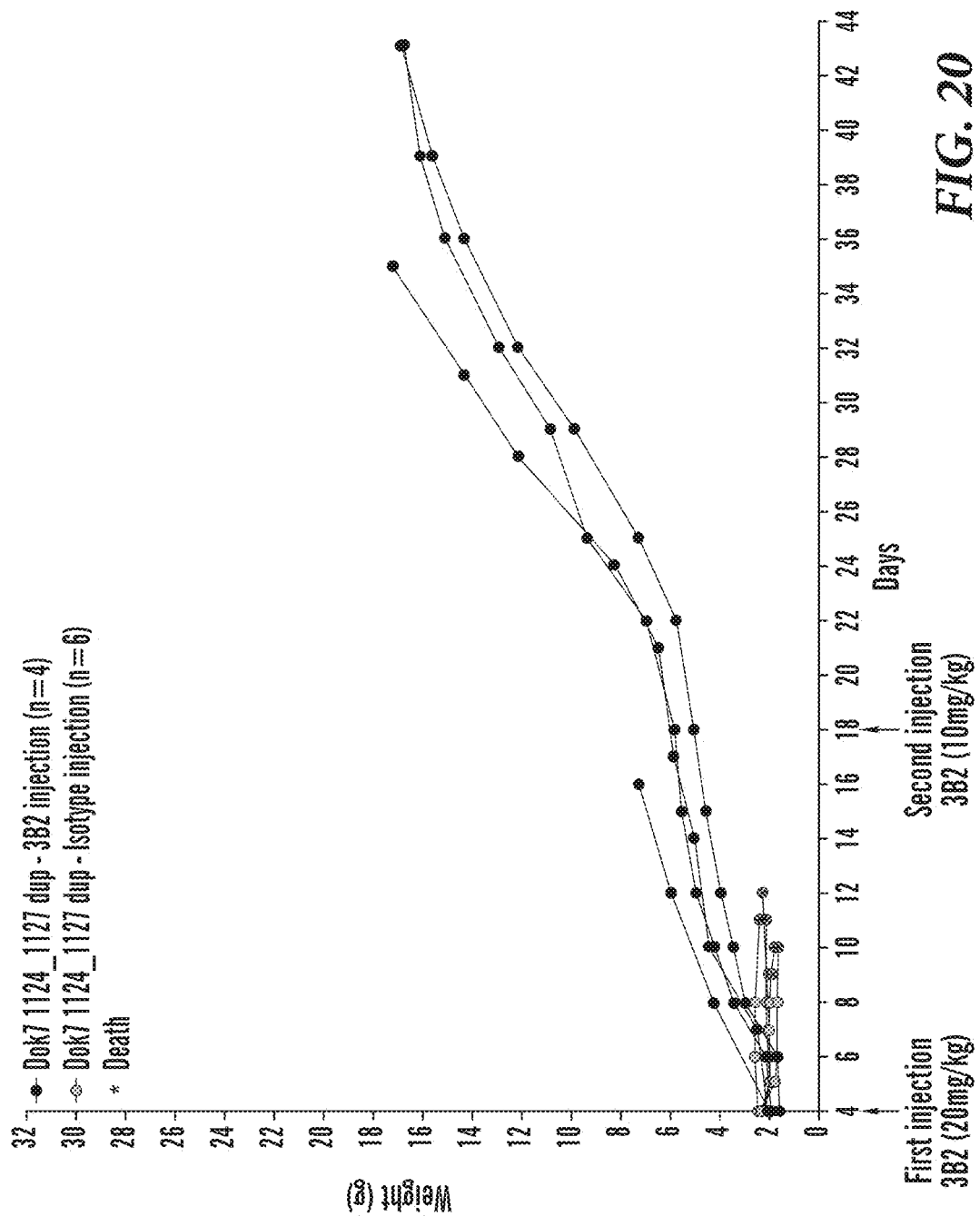

FIG. 20 is a plot demonstrating that 3B2 rescues early postnatal lethality of Dok7 1124_1127 dup mice.

Figure 21:
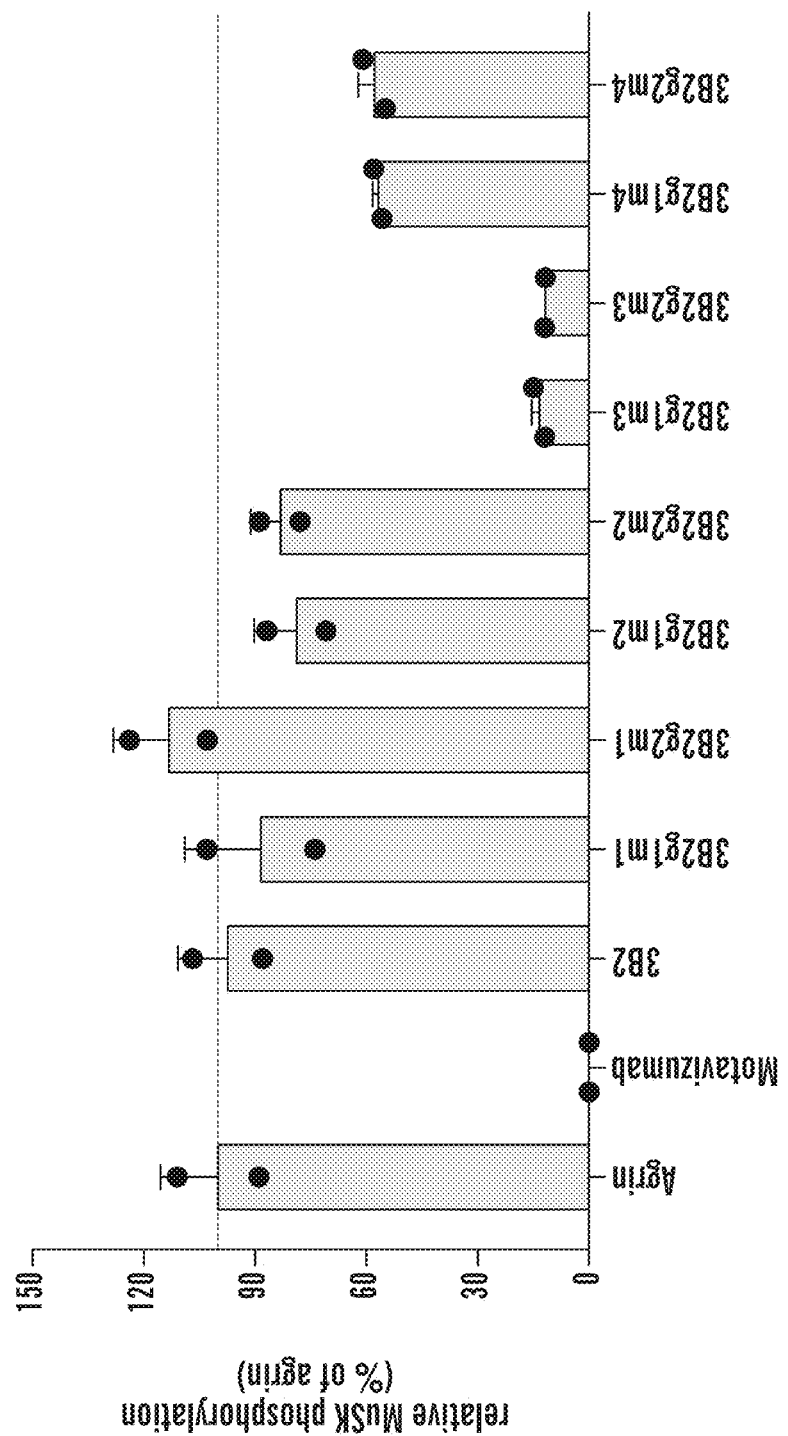

FIG. 21 is a graph showing the percent phosphorylation induced by MuSK antibodies of the present invention in a C2C12 phosphorylation assay.

Figure 22:
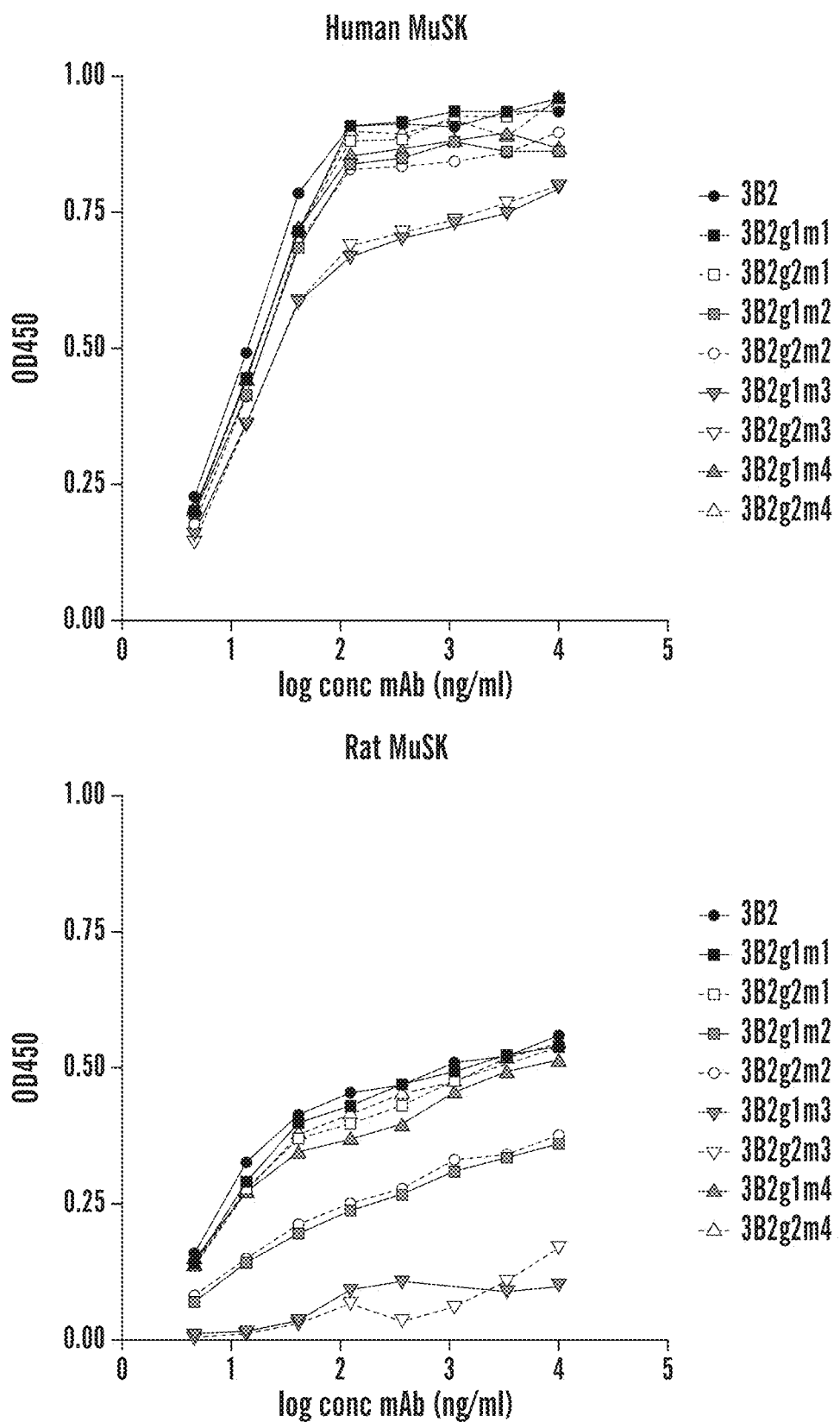
Figure 22:
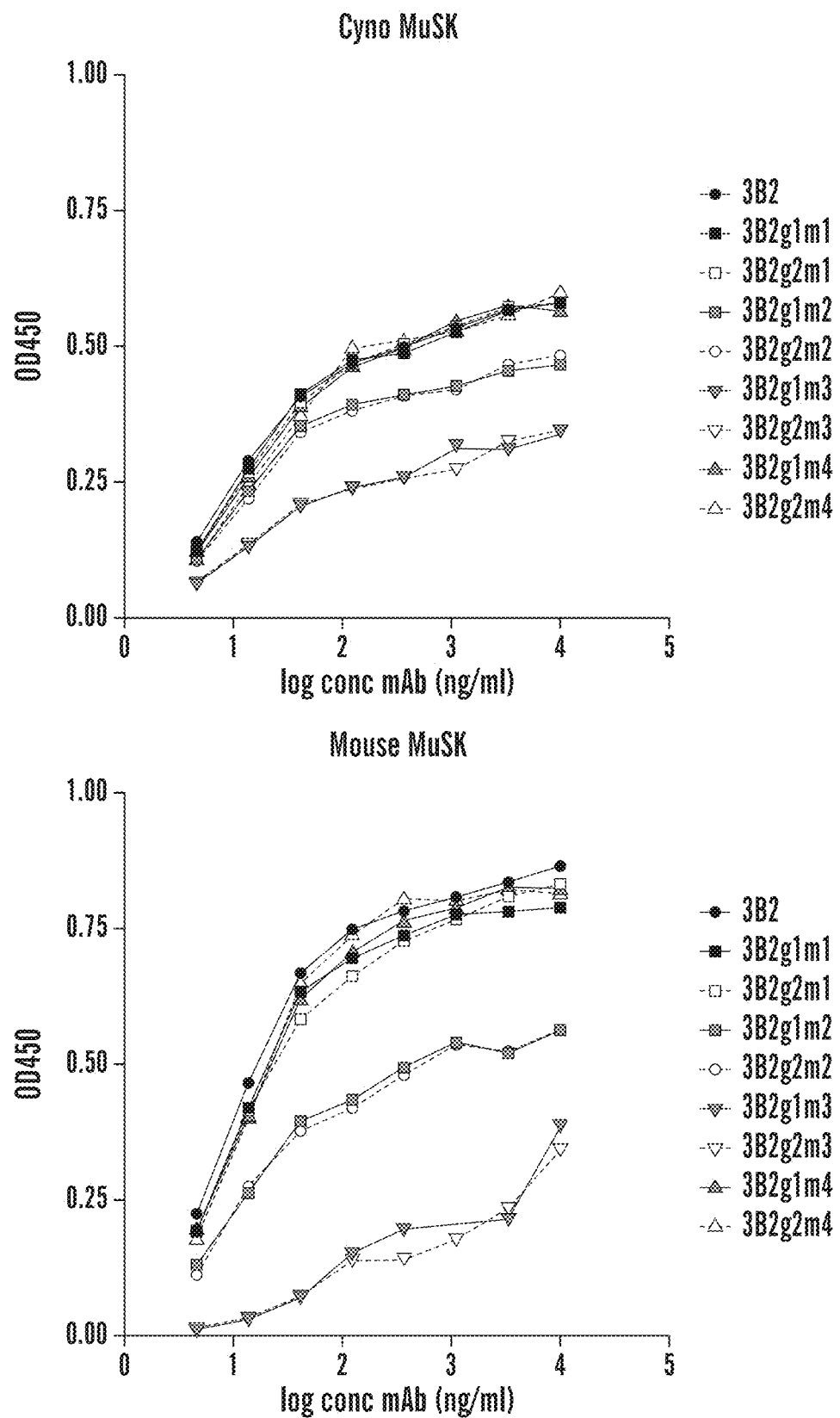

FIG. 22 are graphs showing binding affinity of 3B2 antibody and 3B2 antibody variants to human, cyno, rat, or mouse MuSK measured via ELISA.

Figure 23:
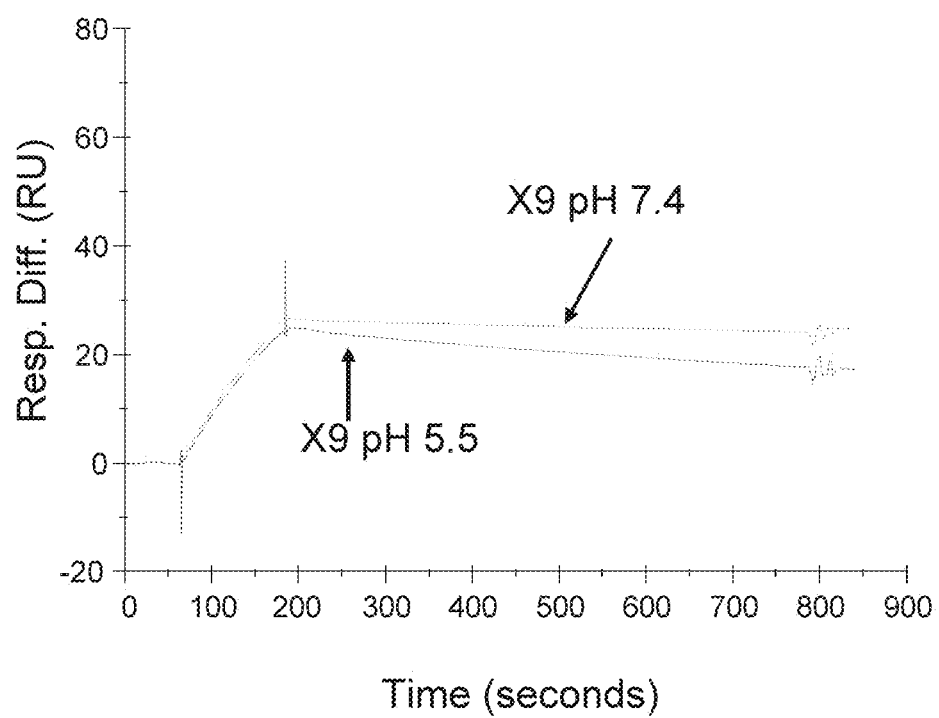

FIG. 23 are graphical representations of binding of MuSK agonist Fabs (Fabs X17, X2, X2m4, X3, 3B2, 3B2g2m1, X9) for mouse MuSK in Biacore at pH 7.4 and pH 5.5.

Figure 24:
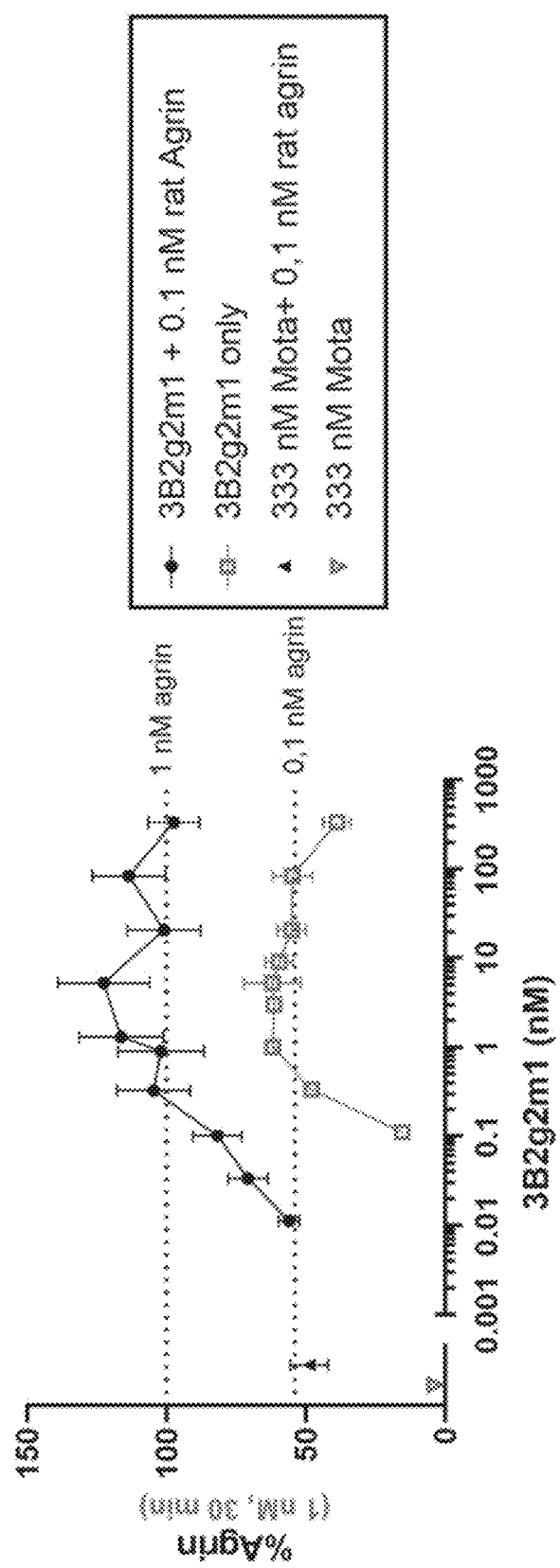

FIG. 24 is a scatter plot showing that MuSK phosphorylation can be co-stimulated by it natural ligand, agrin, and the agonist MuSK-mAb 3B2g2m1, targeting the Fz domain of MuSK.

Figure 25A:
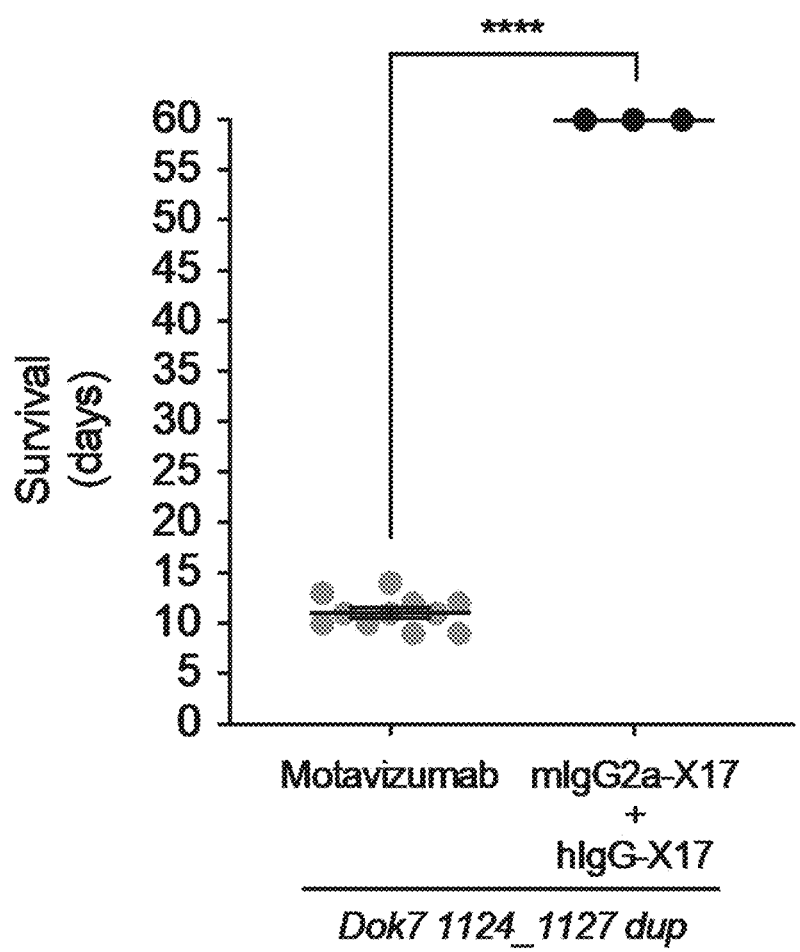
Figure 25B:
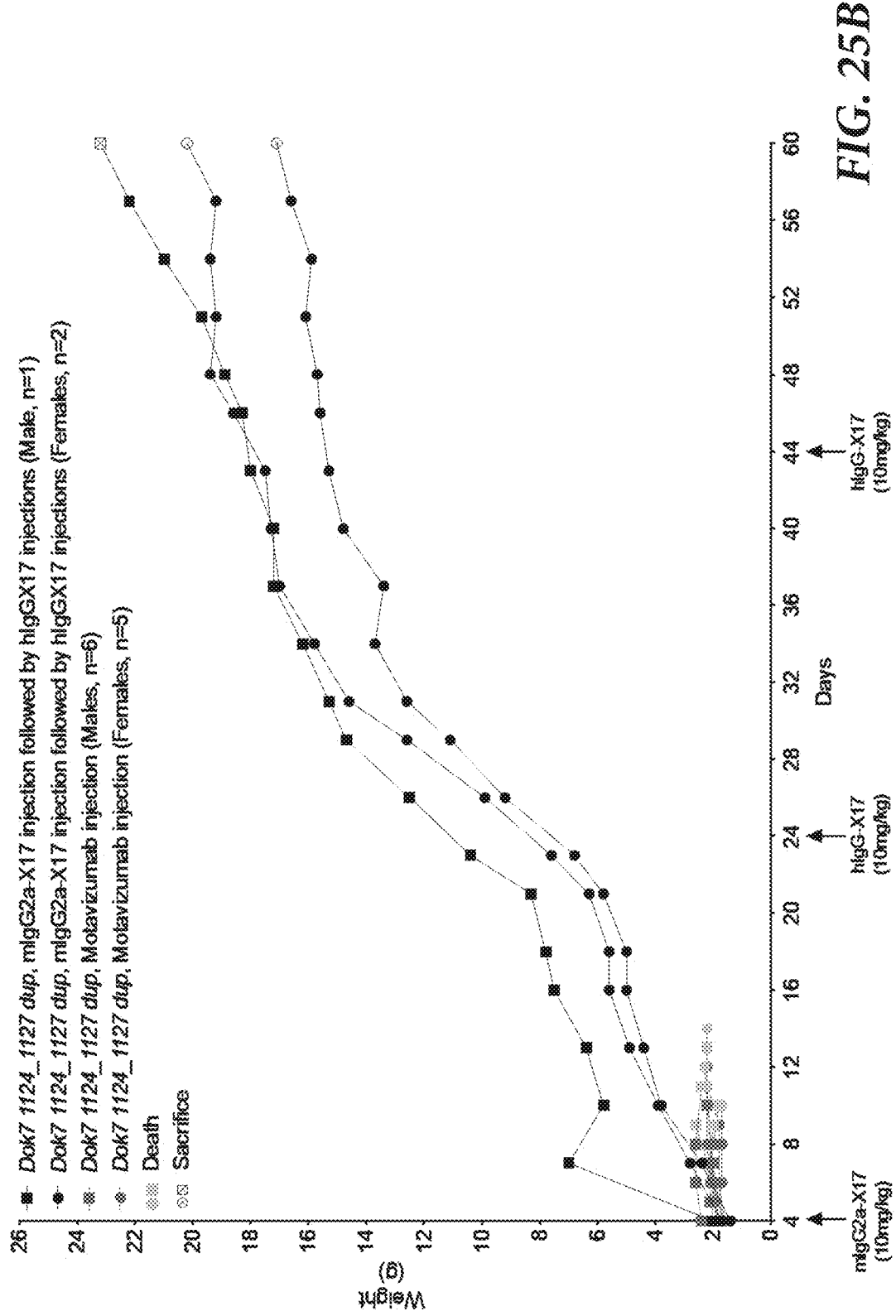

FIGS. 25A-25B demonstrate that agonist antibodies to MuSK, mIgG2a-X17 combined with hIgG-X17, rescue lethality in young Dok7 1124_1127 dup mice. FIG. 25A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody X17 or an isotype equivalent negative control, Motavizumab. Dok7 1124_1127 dup mice injected with the isotype control (n=11), like untreated mice, died one to two weeks after birth, whereas Dok7 1124_1127 dup mice injected with mIgG2a-X17 (n=3) at P4, and hIgG-X17 at P24 and P44 survived as adults. Mutant mice injected with mIgG2a-X17 and then hIgG-X17 were sacrificed at P60. The scatter plot shows the survival time for each mouse and the mean±SEM values (p, ****<0.00005). FIG. 25B is a plot showing that Dok7 1124_1127 dup mice, injected with mIgG2a-X17 and then hIgG-X17 gained weight, unlike Dok7 1124_1127 dup mice treated with the isotype control antibody. Dok7 1124_1127 dup mice were injected with mIgG2a-X17 (10 mg/kg) at P4, and hIgG-X17 (10 mg/kg) at P24 and P44.

Figure 26:
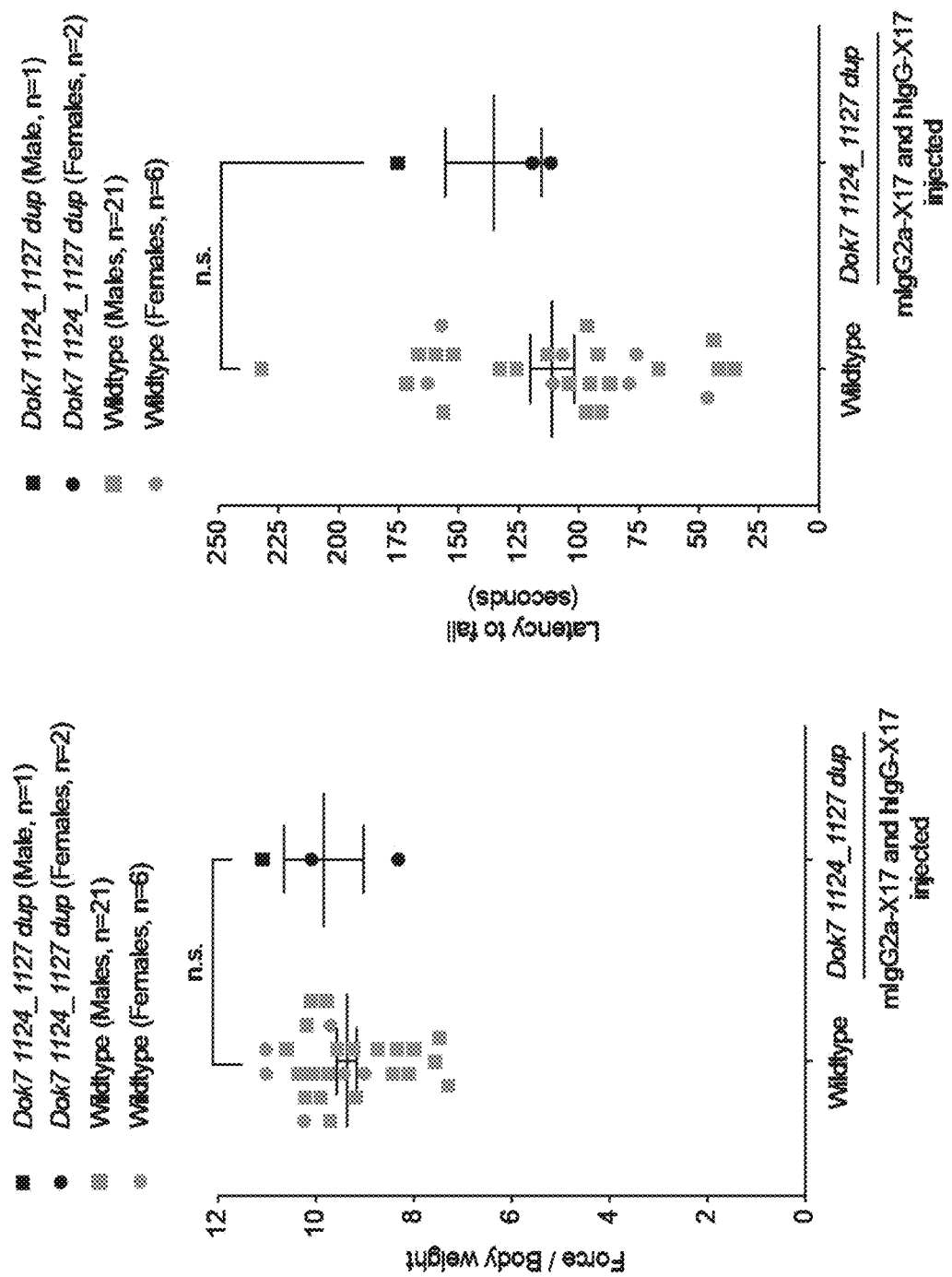

FIG. 26 demonstrates that mIgG2a-X17 combined with hIgG-X17 rescues motor performance of Dok7 1124_1127 dup mice. Motor performance of Dok7 1124_1127 dup mice, as assessed by grip strength (left panel) and the latency to fall from a rotating rotarod (right panel), were fully restored by treatment with mIgG2a-X17 combined with hIgG-X17. The scatter plots show the values for 27 wildtype mice and 3 Dok7 1124_1127 dup mice rescued with mIgG2a-X17 combined with hIgG-X17 and the mean±SEM values (n.s., not significant).

Figure 27:
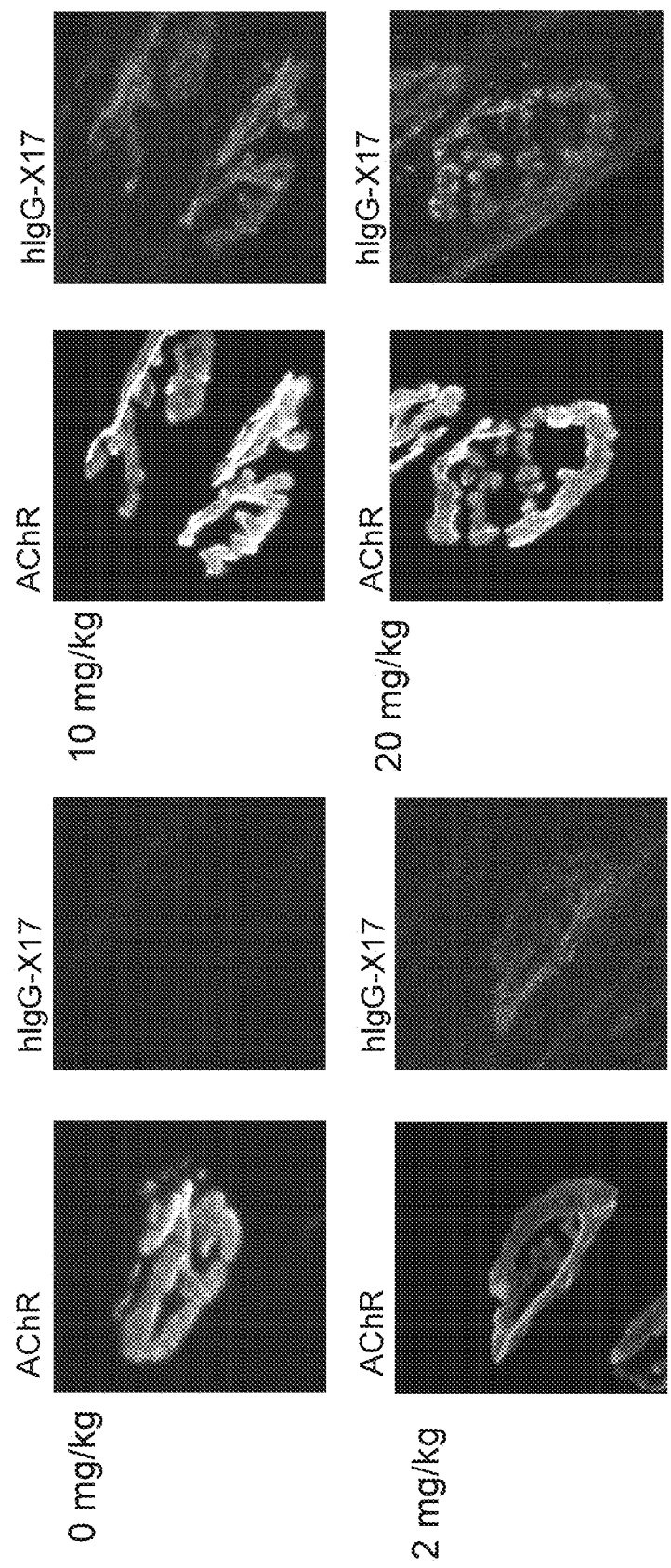
Figure 27:
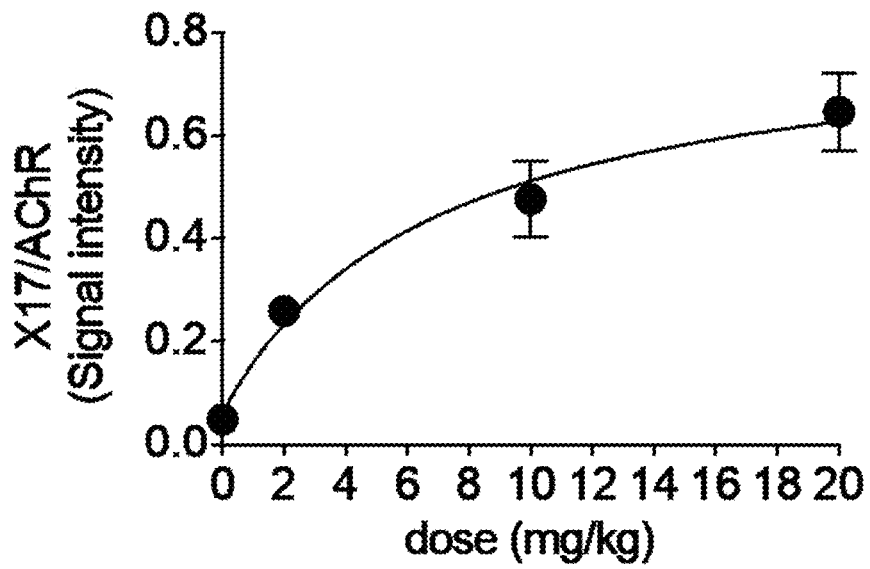

FIG. 27 demonstrates that MuSK agonist antibody hIgG-X17 engages MuSK at the synapse and saturates MuSK at 20 mg/kg. P40 wildtype mice were injected intraperitoneally with MuSK agonist antibody hIgG-X17 (0, 2, 10, 20 mg/kg). Two days later, mice were sacrificed and diaphragm muscles were stained with Alexa 488-α-BGT to label AChRs and Alexa 647 Goat Anti-Human IgG, F(ab)$_2$ fragment specific to label X17. Levels of saturation of X17 at the synapse were measured by the ratio of X17 to AChR signal intensity. The mean±SEM values from 3 mice at each concentration are shown.

Figure 28A:
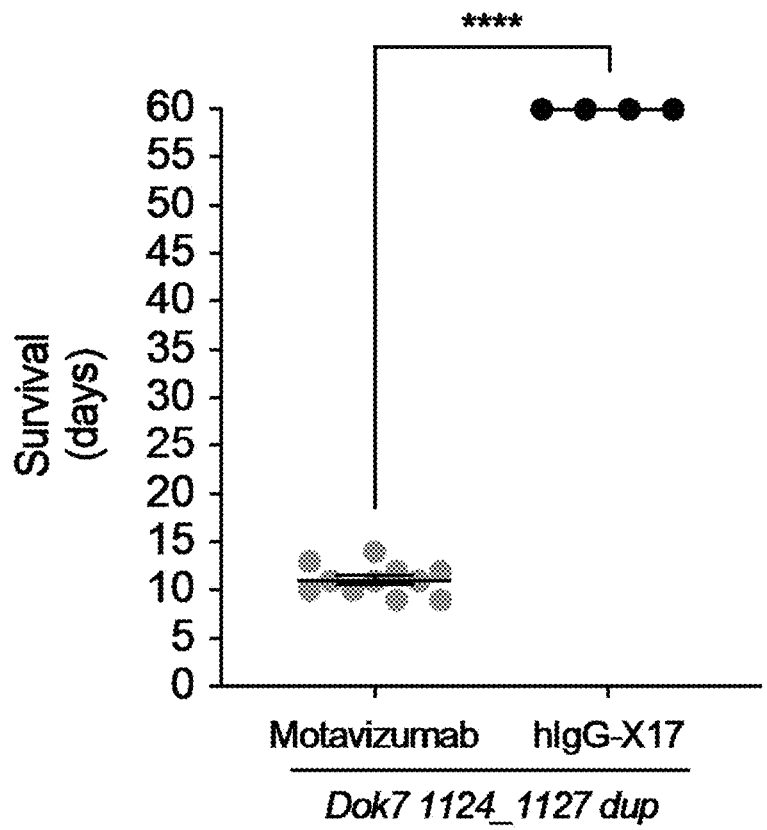
Figure 28B:
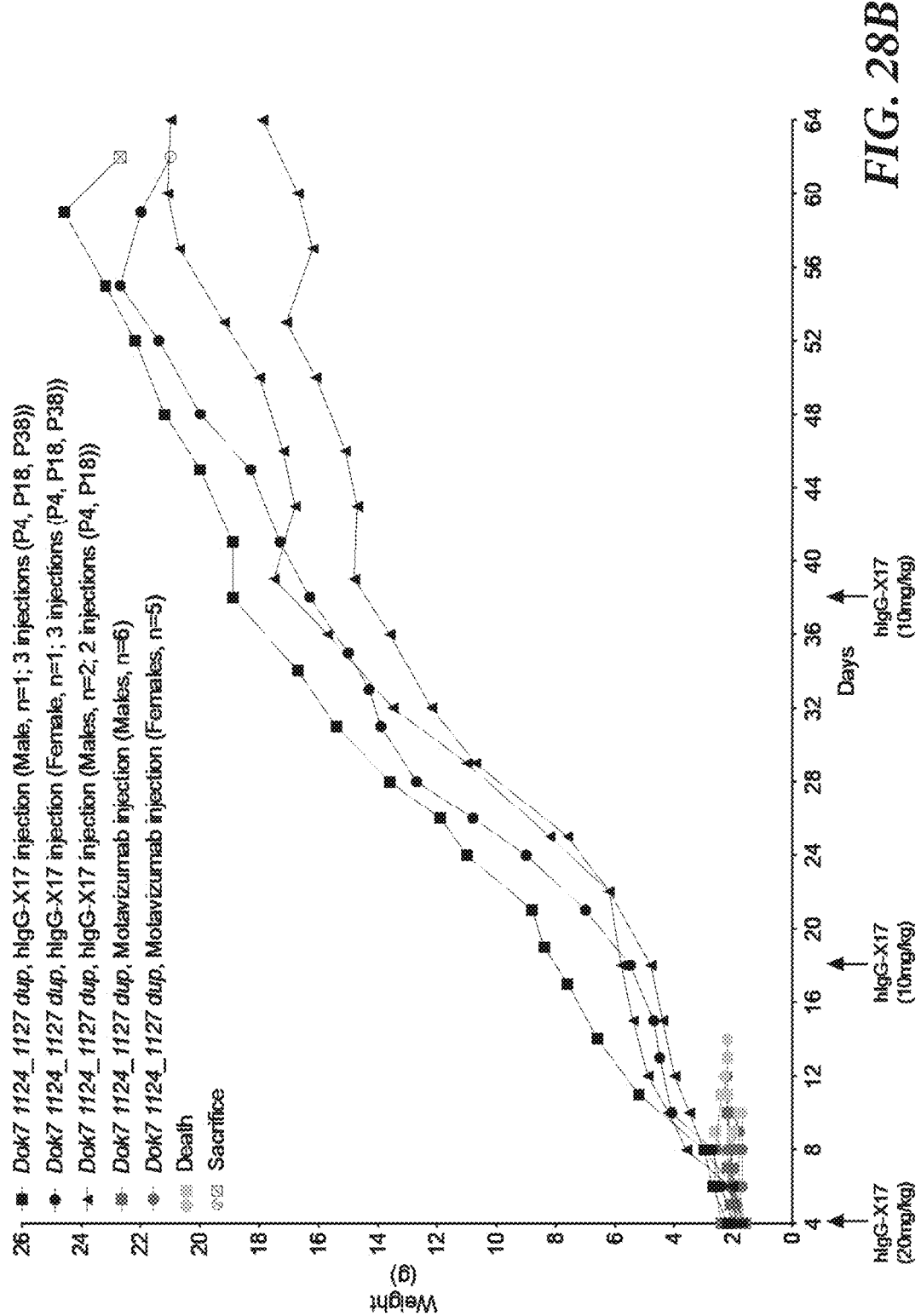

FIGS. 28A-28B demonstrate that agonist antibody to MuSK, hIgG-X17, rescues lethality in young Dok7 1124_1127 dup mice. FIG. 28A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody hIgG-X17 or an isotype equivalent negative control, Motavizumab. Dok7 1124_1127 dup mice (n=11) injected with the isotype control, like untreated mice, died one to two weeks after birth, whereas Dok7 1124_1127 dup mice injected with hIgG-X17 (n=4) at P4, P18, and P38 or P4 and P18 survived as adults. 2 of 4 mutant mice injected with hIgG-X17 were sacrificed at P60; 2 mutant mice were aged for disease relapse experiments. The scatter plot shows the survival time for each mouse and the mean±SEM values (p, ****<0.00005). FIG. 28B is a plot showing that Dok7 1124_1127 dup mice, injected with hIgG-X17 gained weight, unlike Dok7 1124_1127 dup mice treated with the isotype control antibody. Dok7 1124_1127 dup mice were injected with hIgG-X17 at P4 (20 mg/kg), P18, and P38 (10 mg/kg) or P4 (20 mg/kg and P18 (10 mg/kg).

Figure 29:
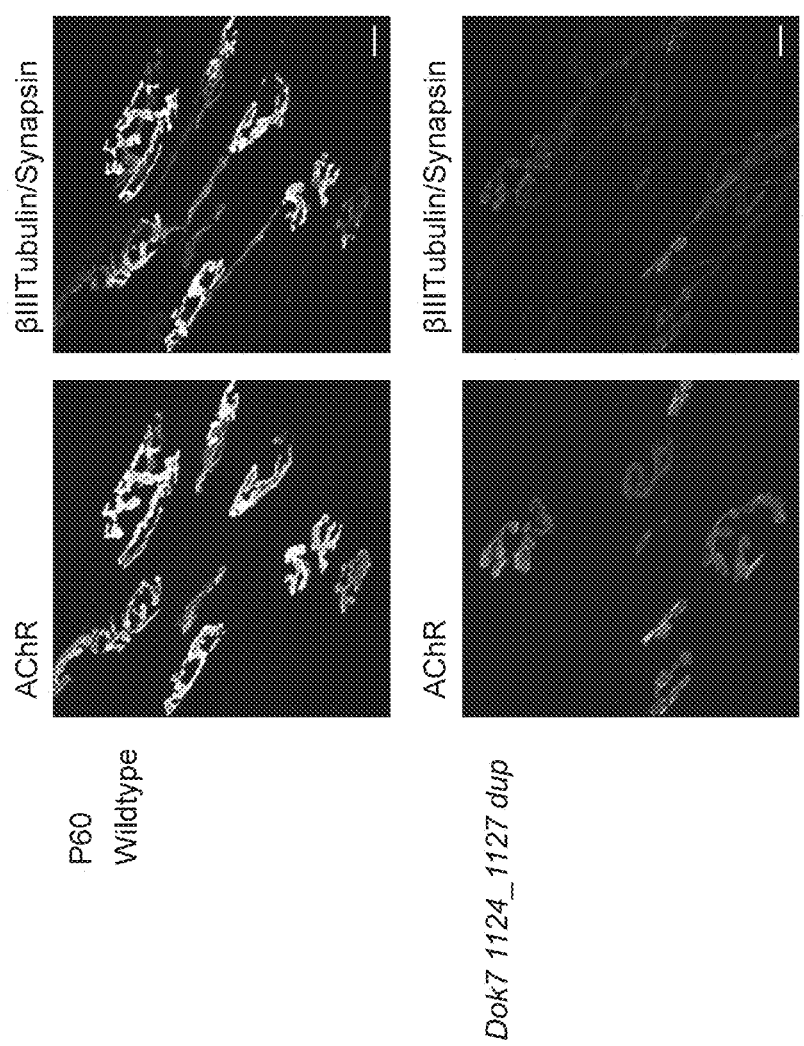
Figure 29:
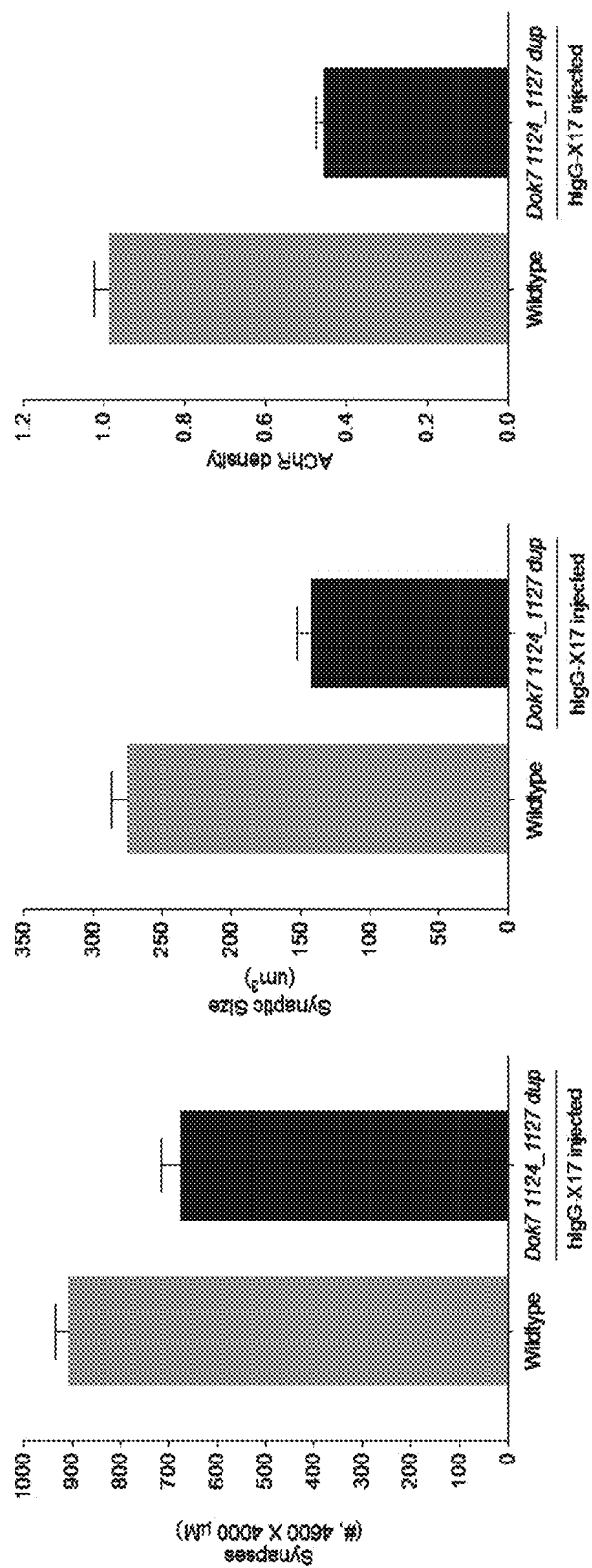

FIG. 29 demonstrates that hIgG-X17 restores synapse development in young Dok7 1124_1127 dup mice. Diaphragm muscles from P60 wildtype and Dok7 1124_1127 dup mice were stained with Alexa 488-α-BGT to label AChRs and antibodies to βIIITubulin/Synapsin to label motor axons/nerve terminals. In Dok7 1124_1127 dup mice treated with hIgG-X17, synapses matured from a simple, plaque-like shape to a complex, pretzel-like shape, characteristic of mature murine neuromuscular synapses. Scale bar=10 mm. In Dok7 1124_1127 dup mice treated with hIgG-X17, the number of synapses, synaptic size, and density of synaptic AChRs were restored to 70%, 50%, and 40%, respectively, of normal levels. The mean±SEM values from 2 mice (>50 synapses per mouse) are shown.

Figure 30:
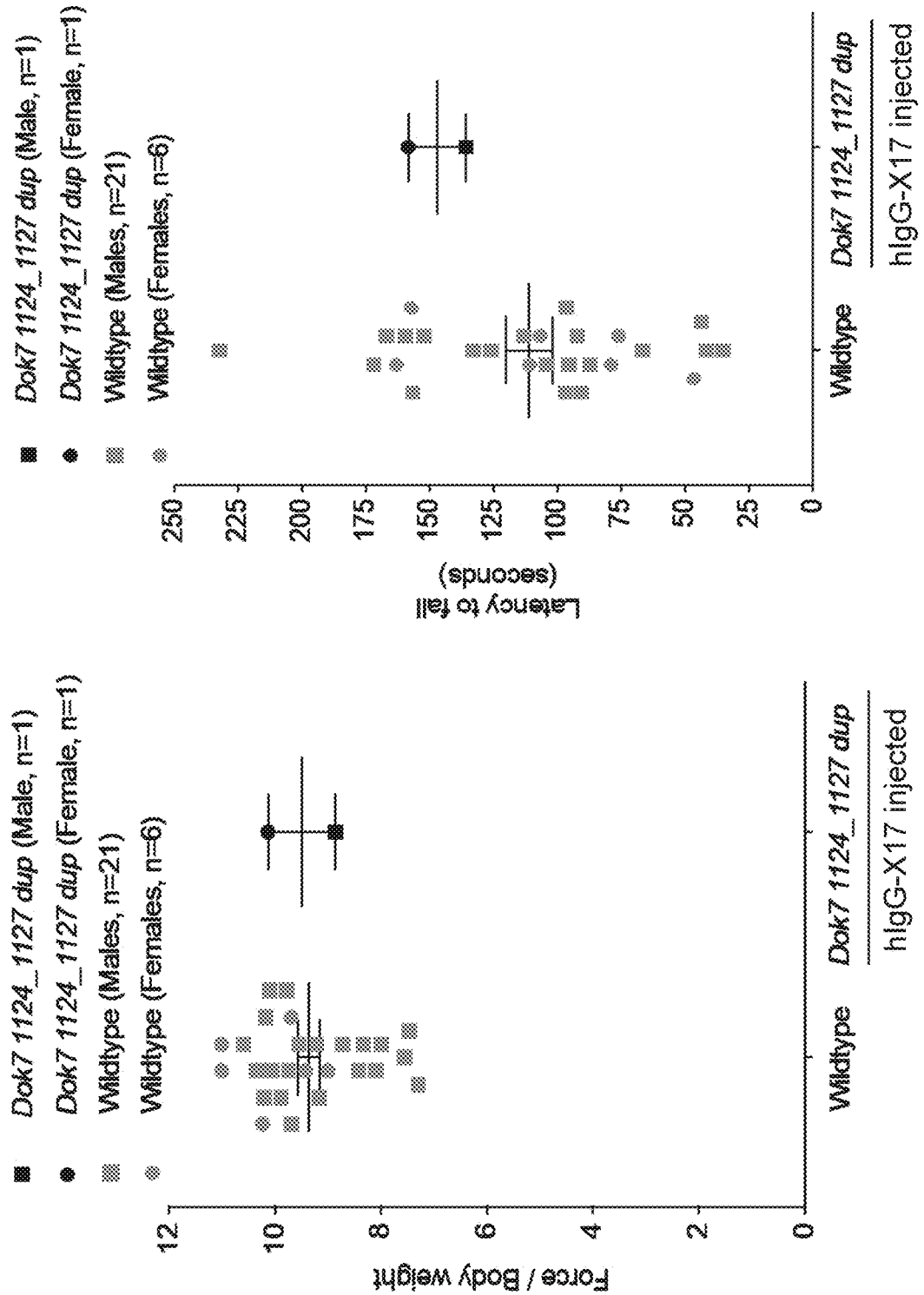

FIG. 30 demonstrates that hIgG-X17 rescues motor performance of Dok7 1124_1127 dup mice. Motor performance of Dok7 1124_1127 dup mice, as assessed by grip strength (left panel) and the latency to fall from a rotating rotarod (right panel), were fully restored by treatment with hIgG-X17. The scatter plots show the values for 27 wildtype mice and 2 Dok7 1124_1127 dup mice rescued with hIgG-X17 and the mean±SEM values.

Figure 31A:
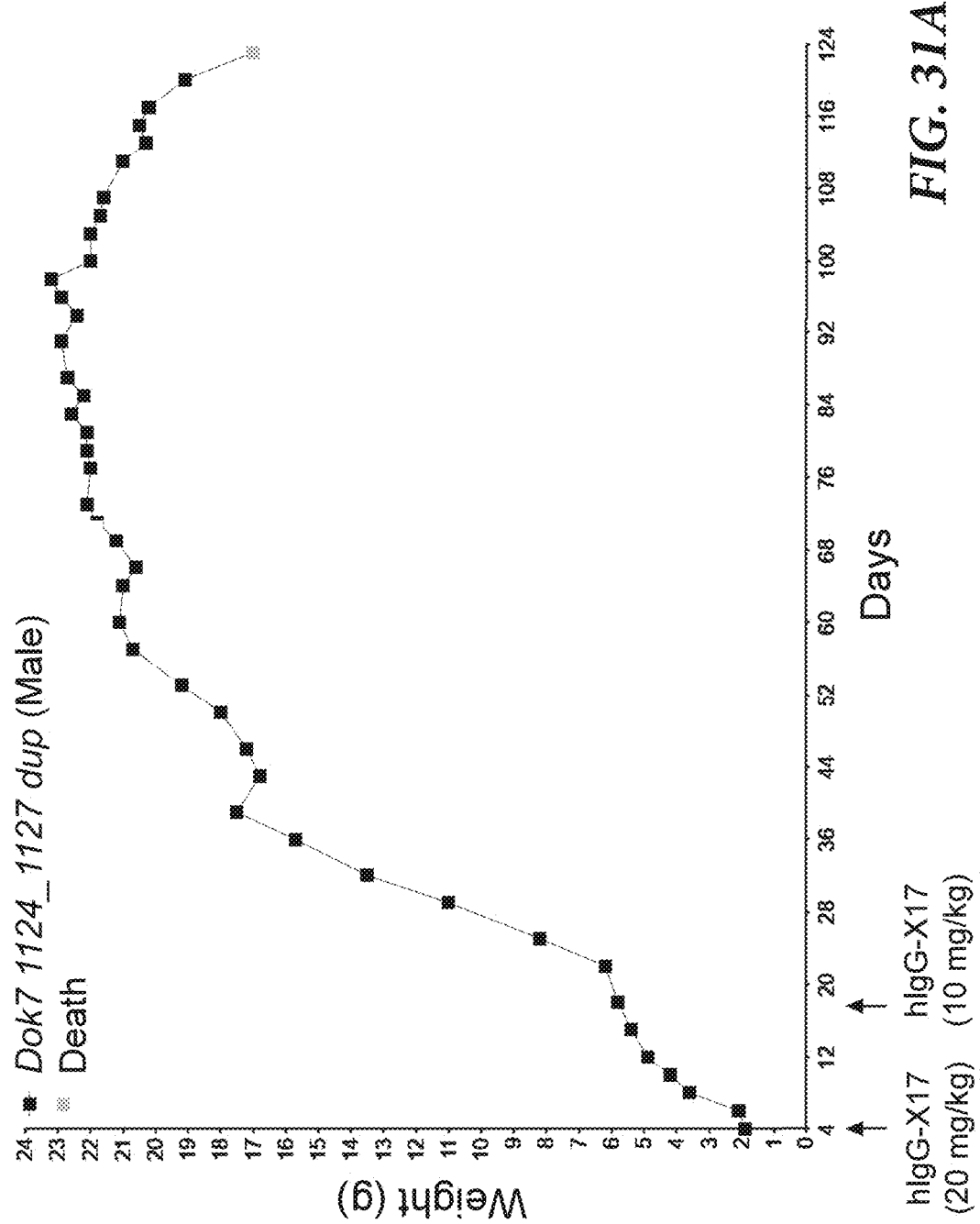
Figure 31B:
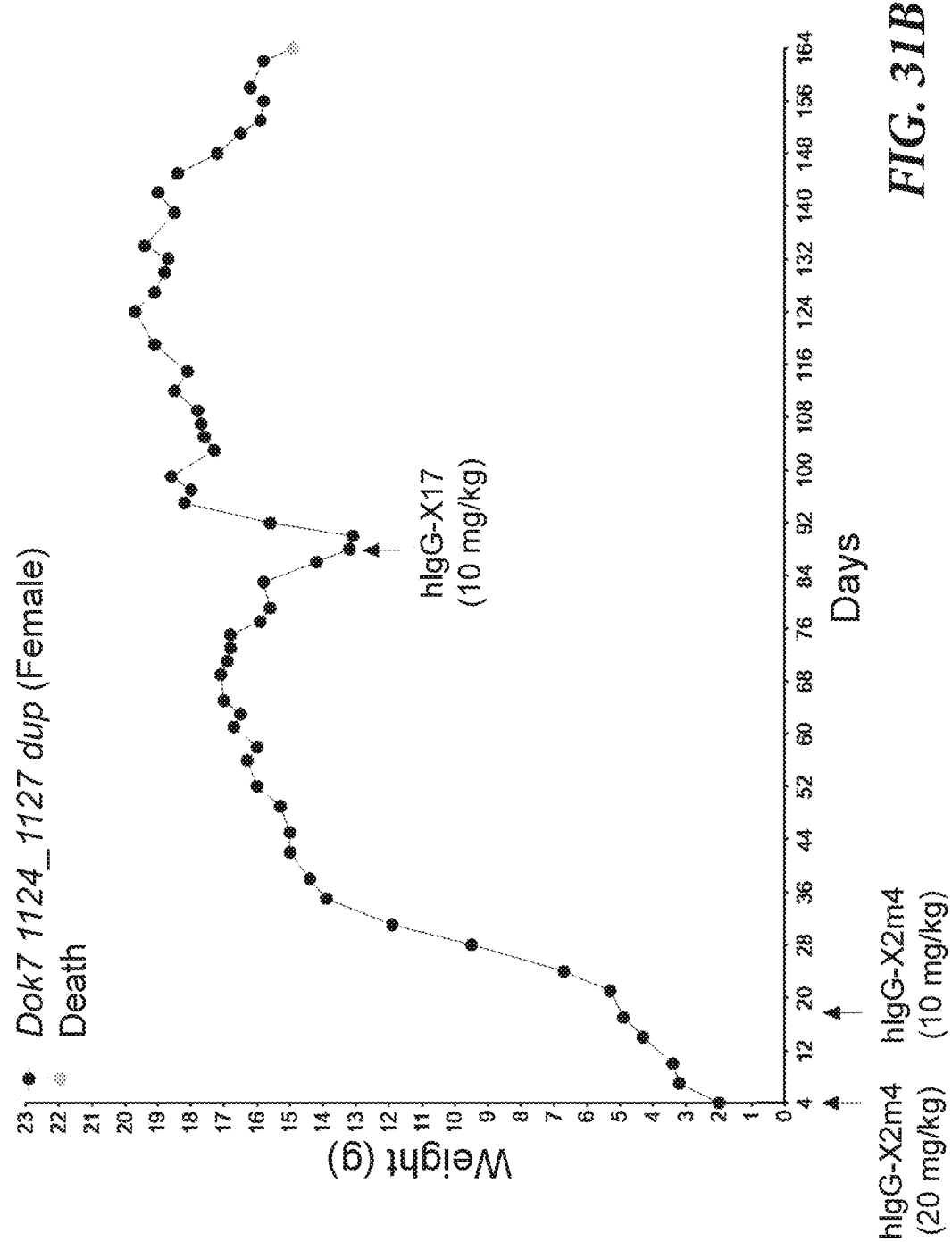
Figure 31B:
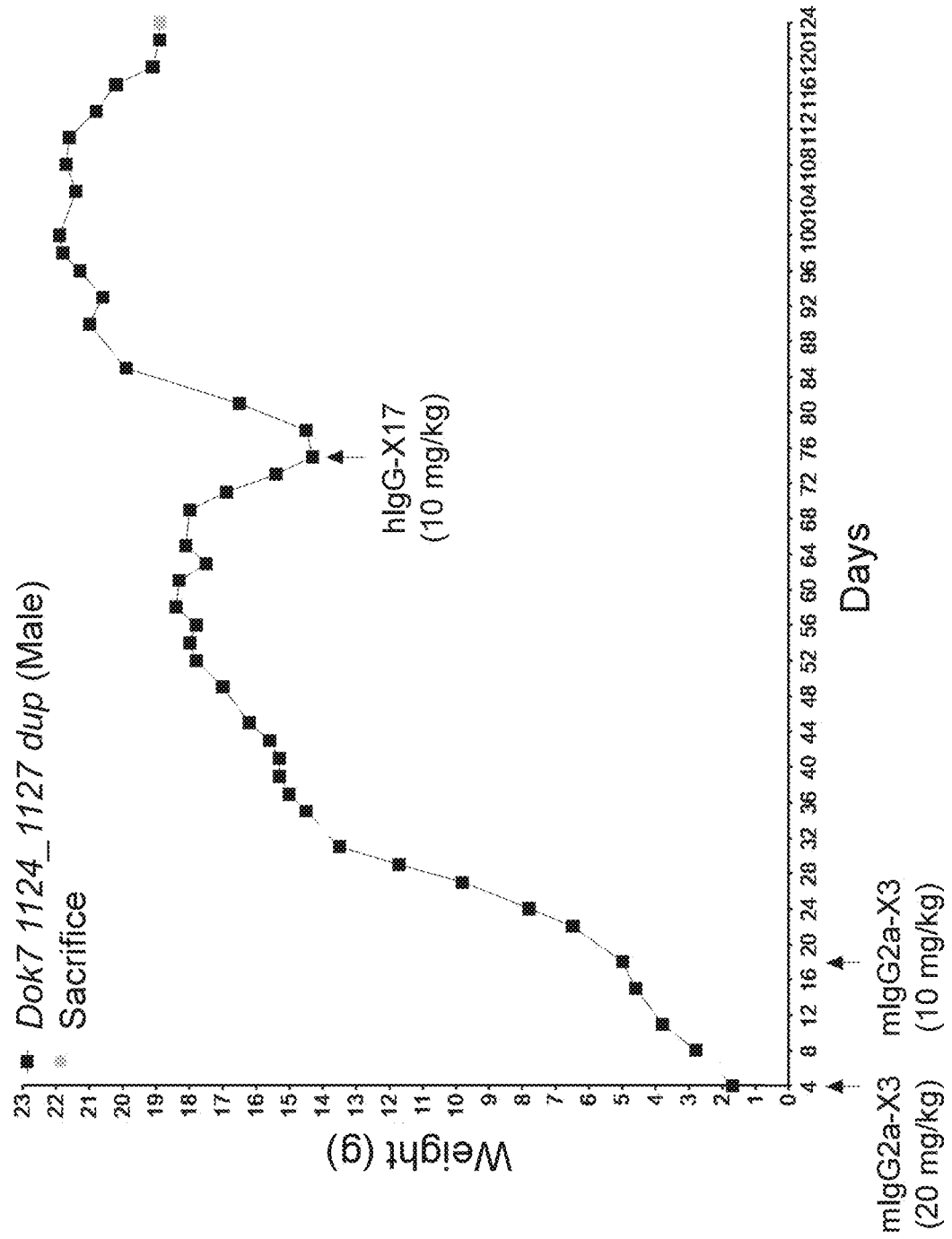
Figure 31B:
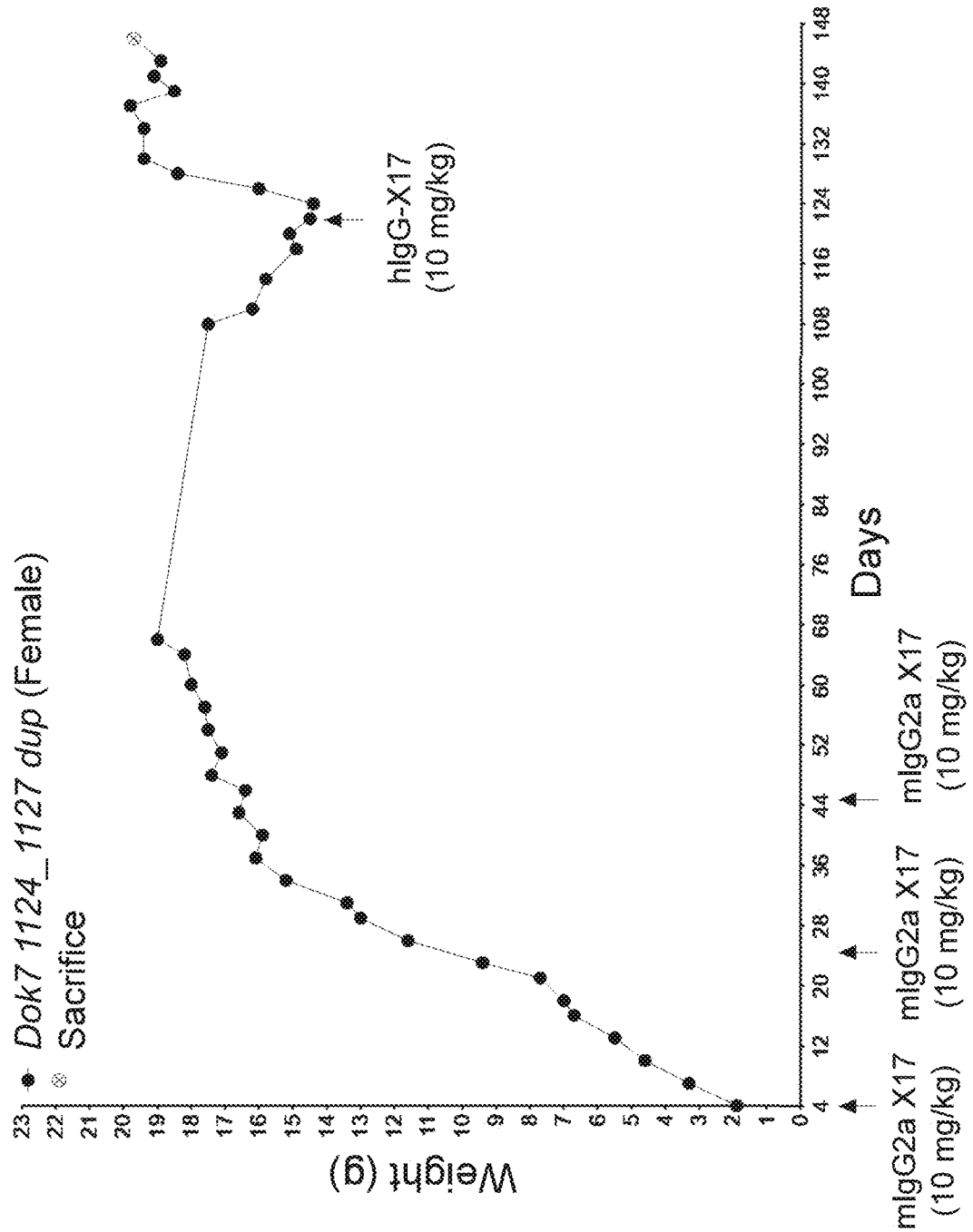
Figure 31B:
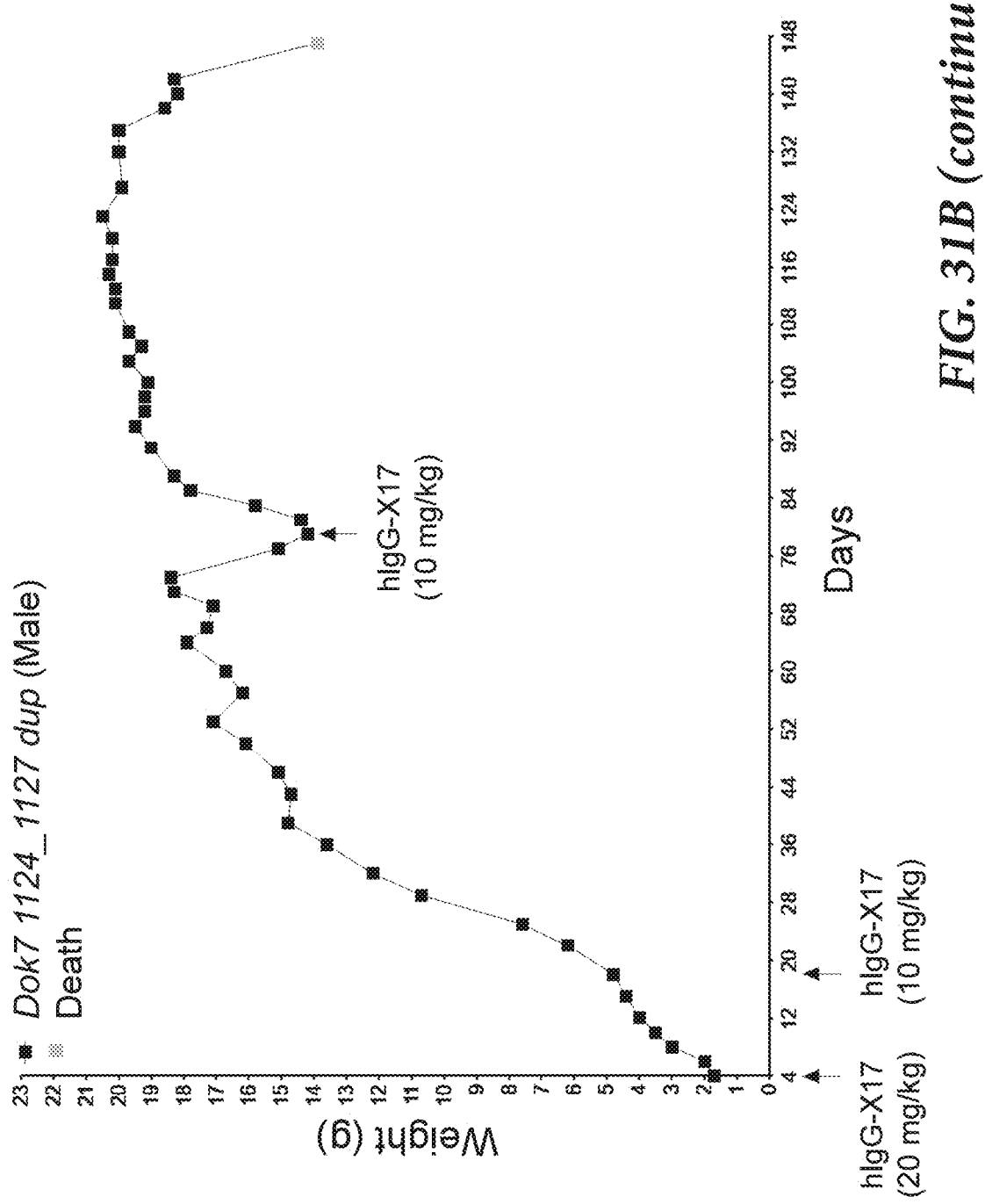
Figure 31B:
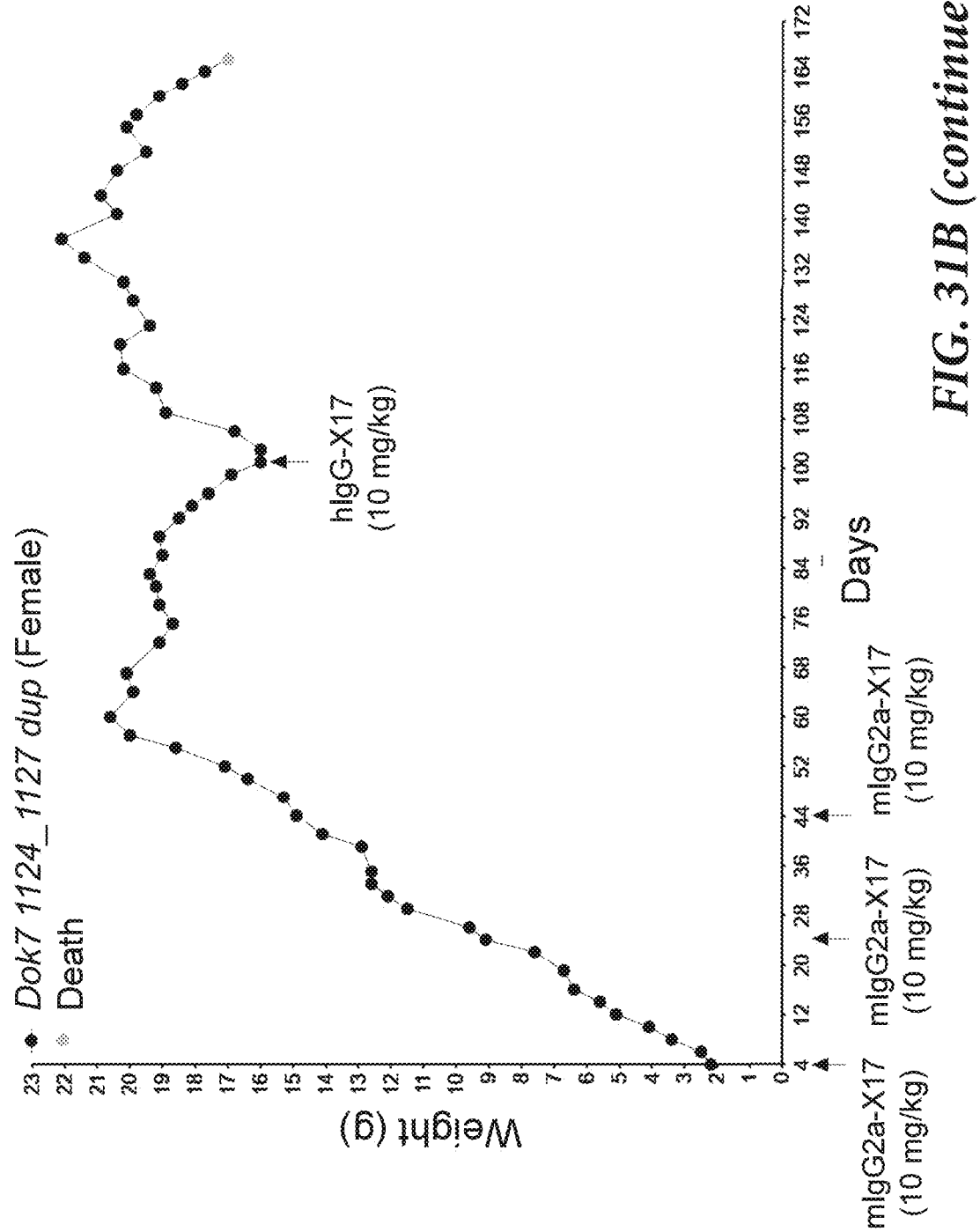
Figure 31C:
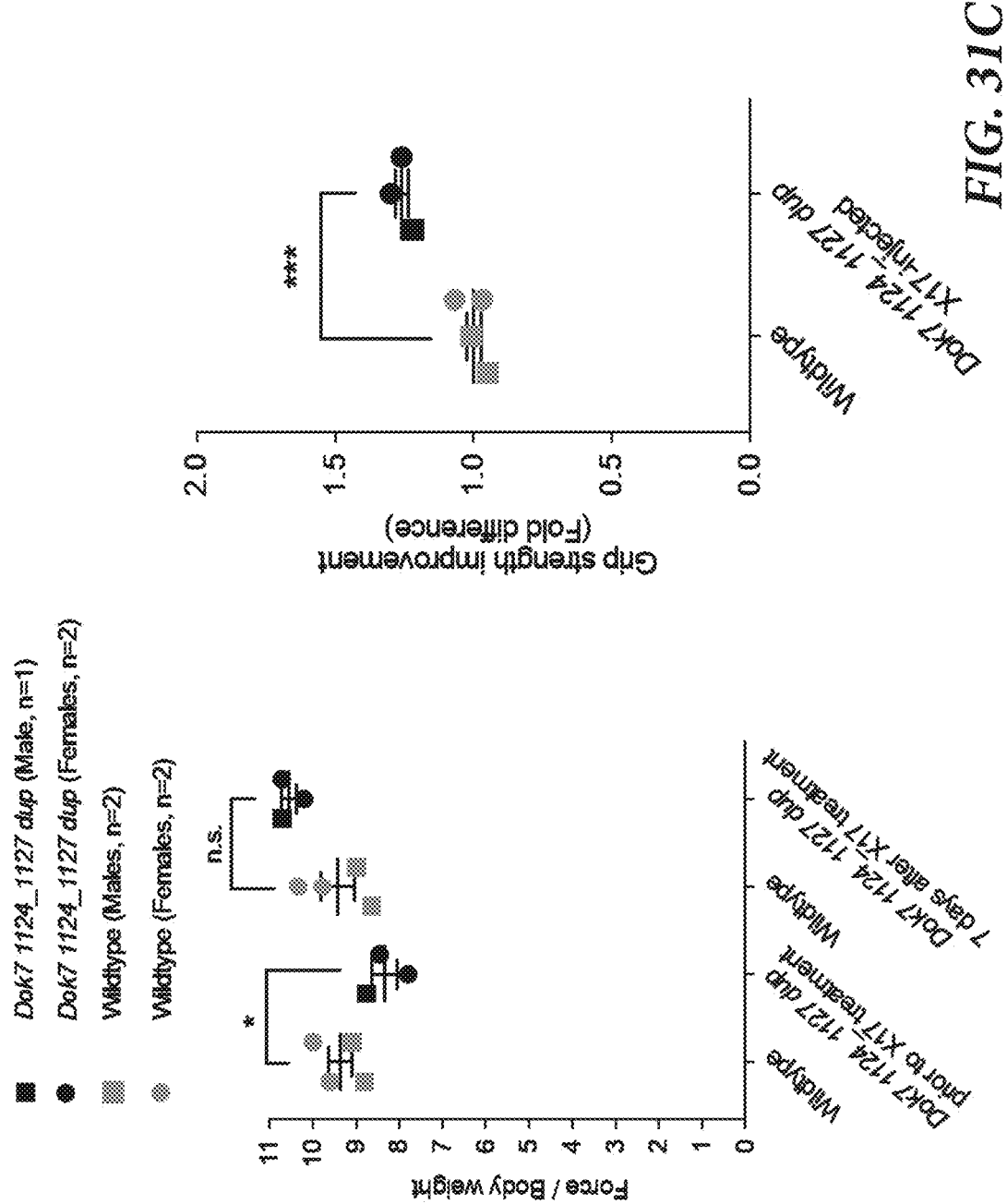
Figure 31C:
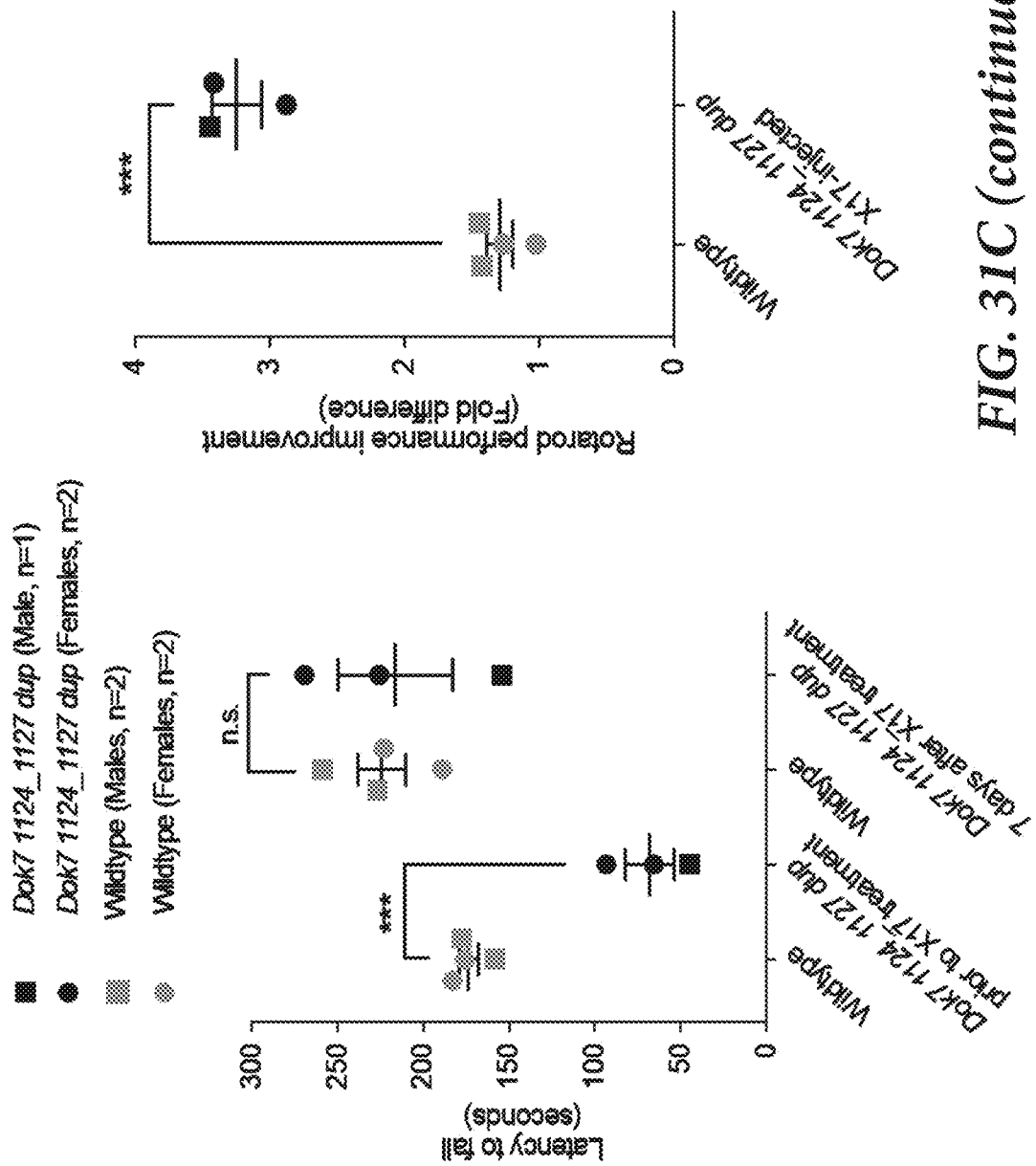

FIGS. 31A-31C demonstrate that hIgG-X17 reverses disease relapse in adult Dok7 1124_1127 dup mice. Dok7 1124_1127 dup mice were injected with MuSK agonist antibodies either at P4, P24, and P44, or P4, P18, and then discontinued antibody treatment. These Dok7 1124_1127 dup mice gained weight and maintained their mobility for several months but ultimately began to lose weight (FIG. 31A, FIG. 31B) and to display motor deficits, as assessed by grip strength and the latency to fall from a rotating rotarod (FIG. 31C). At this time, mice were, either not re-injected (FIG. 31A), or re-injected with hIgG-X17 (FIG. 31B). Non re-injected mice die within a few days (FIG. 31A), while after restarting X17 treatment, the Dok7 1124_1127 dup mice began to gain weight (FIG. 3B), and by one week after restarting treatment their motor deficits were reversed (FIG. 31C, left panels). Dok7 1124_1127 dup mice improved their performance on the rotarod by 3.25-fold, whereas the performance of wildtype mice improved by 1.30-fold (p, *<0.0005). Dok7 1124_1127 dup mice improved their grip strength by 1.30-fold, whereas the performance of wildtype mice did not improve (p, *<0.0005) (FIG. 31C).

Figure 32A:
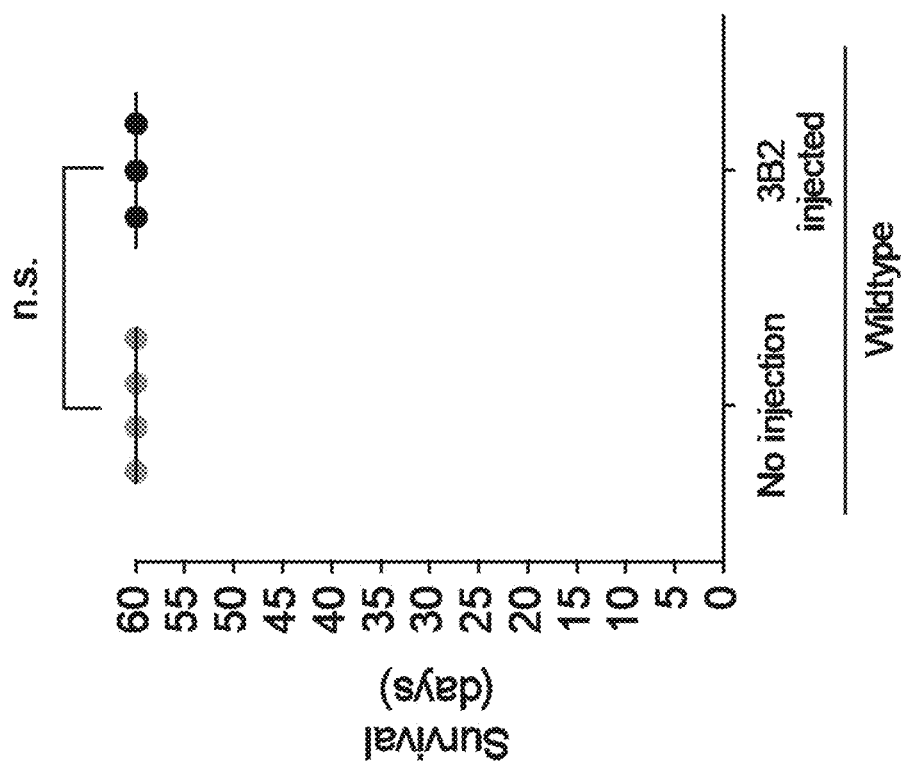
Figure 32B:
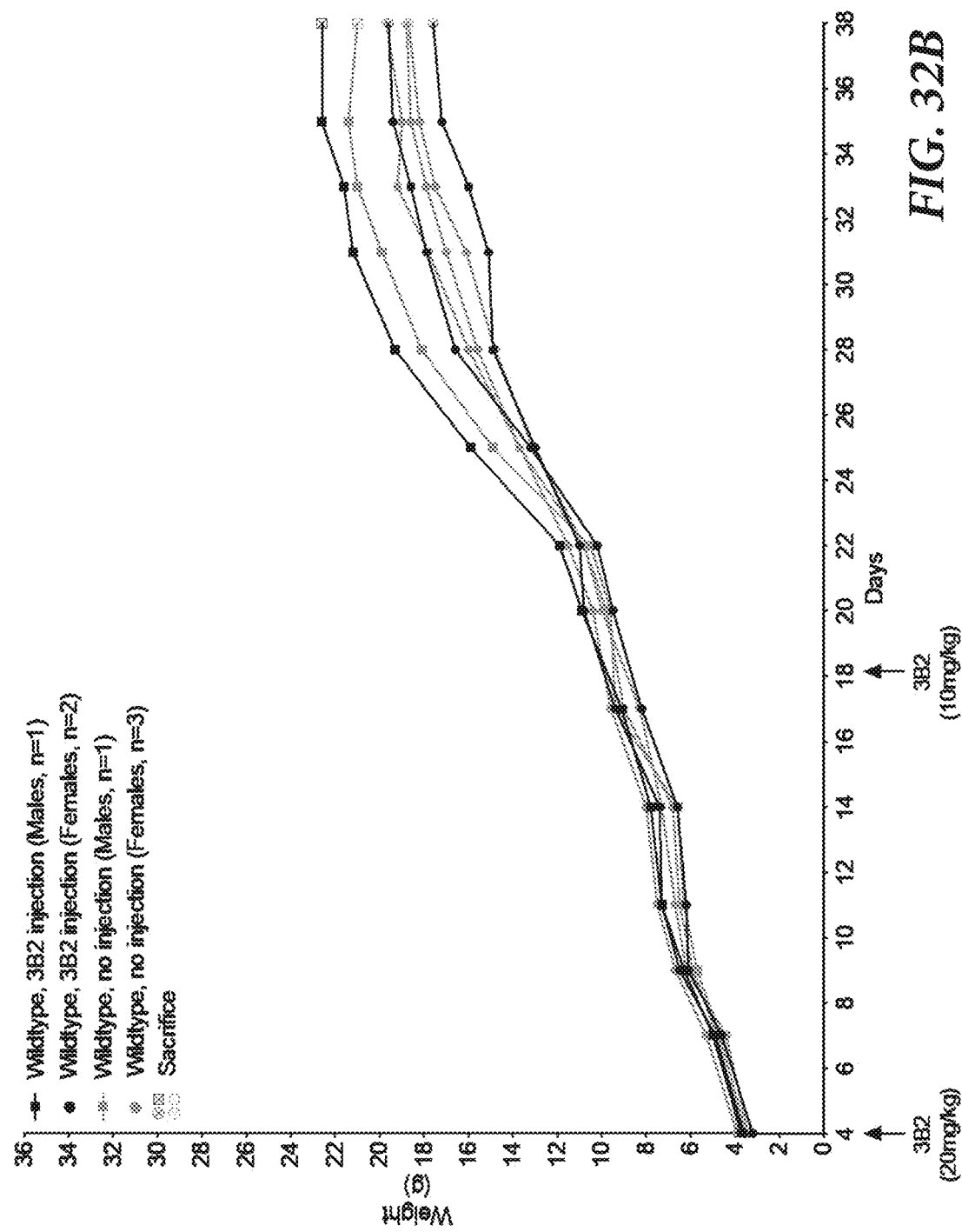

FIGS. 32A-32B demonstrate that chronic injection of 3B2 in wildtype mice has no effect on survival or weight gain. FIG. 32A is a scatter plot showing that wildtype mice in a C57BL/6-CBA mixed background, injected at P4, and P18 with 3B2 (n=3), survived until P38, when they were sacrificed. The scatter plot shows the survival time for 4 non-injected wildtype mice and 3 wildtype mice injected with 3B2 and the mean±SEM values (n.s., not significant). FIG. 32B is a scatter plot showing that wildtype mice, injected with 3B2 (n=3), gained weight like wildtype mice (n=4).

Figure 33A:
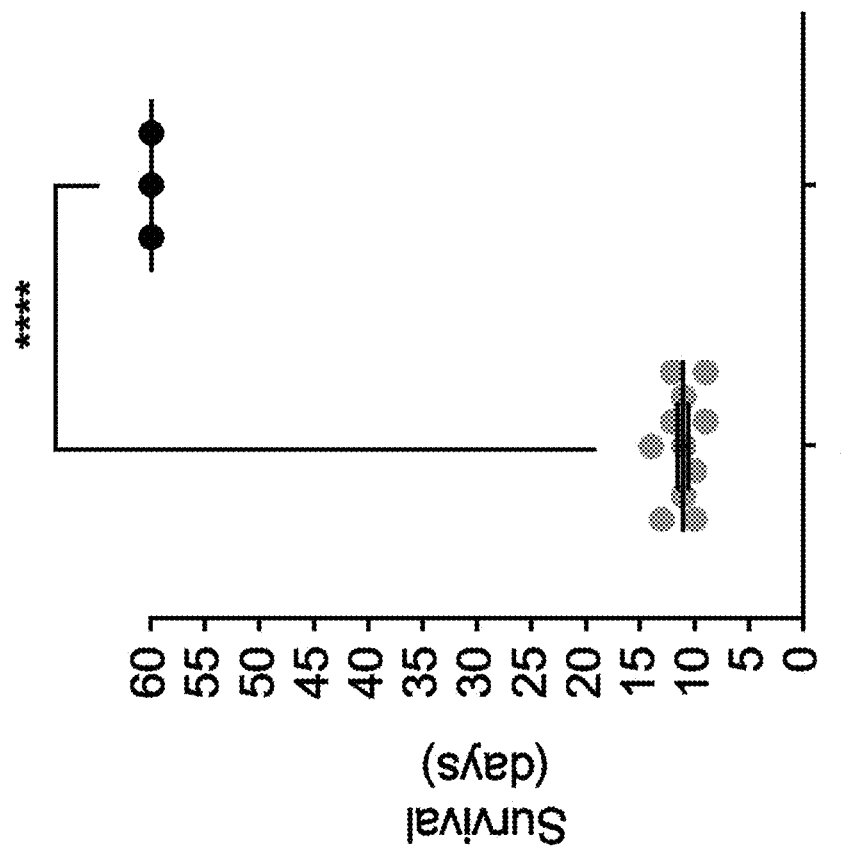
Figure 33B:
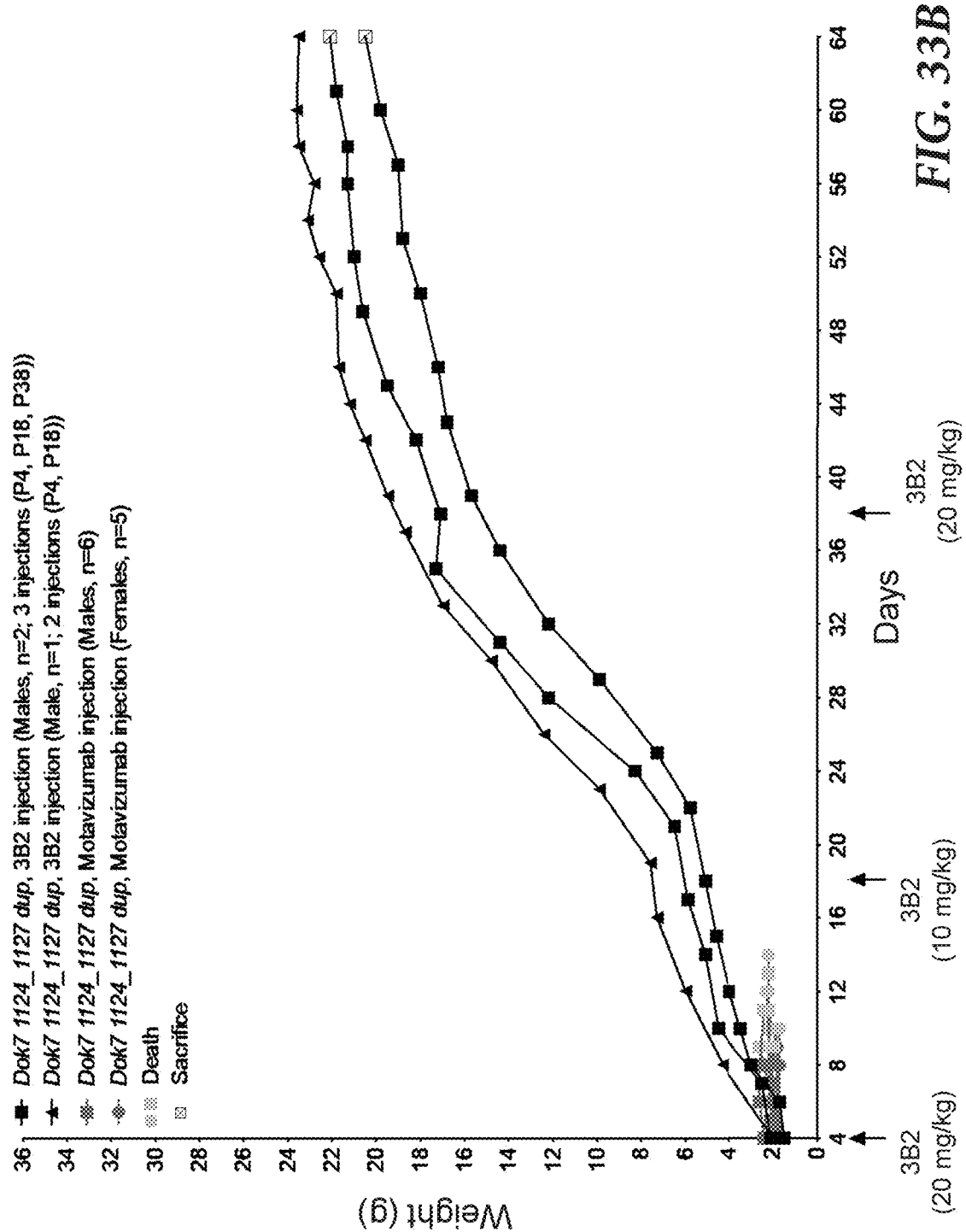

FIGS. 33A-33B demonstrate that 3B2 agonist antibody to MuSK rescues lethality in young Dok7 1124_1127 dup mice. FIG. 33A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody 3B2 or an isotype equivalent negative control, Motavizumab. Dok7 1124_1127 dup mice (n=11) injected with the isotype control, like untreated mice, died one to two weeks after birth, whereas Dok7 1124_1127 dup mice injected with 3B2 (n=3) at P4, P18, and P38 or P4 and P18 survived as adults. 2 of 3 mutant mice injected with 3B2 were sacrificed at P60; 1 mutant mouse was aged for disease relapse experiments. The scatter plot shows the survival time for each mouse and the mean±SEM values (p, ****<0.00005).

FIG. 33B is a scatter plot showing that Dok7 1124_1127 dup mice, injected with 3B2 gained weight, unlike Dok7 1124_1127 dup mice treated with the isotype control antibody. Dok7 1124_1127 dup mice were injected with 3B2 at P4 (20 mg/kg), P18, and P38 (10 mg/kg).

Figure 34:
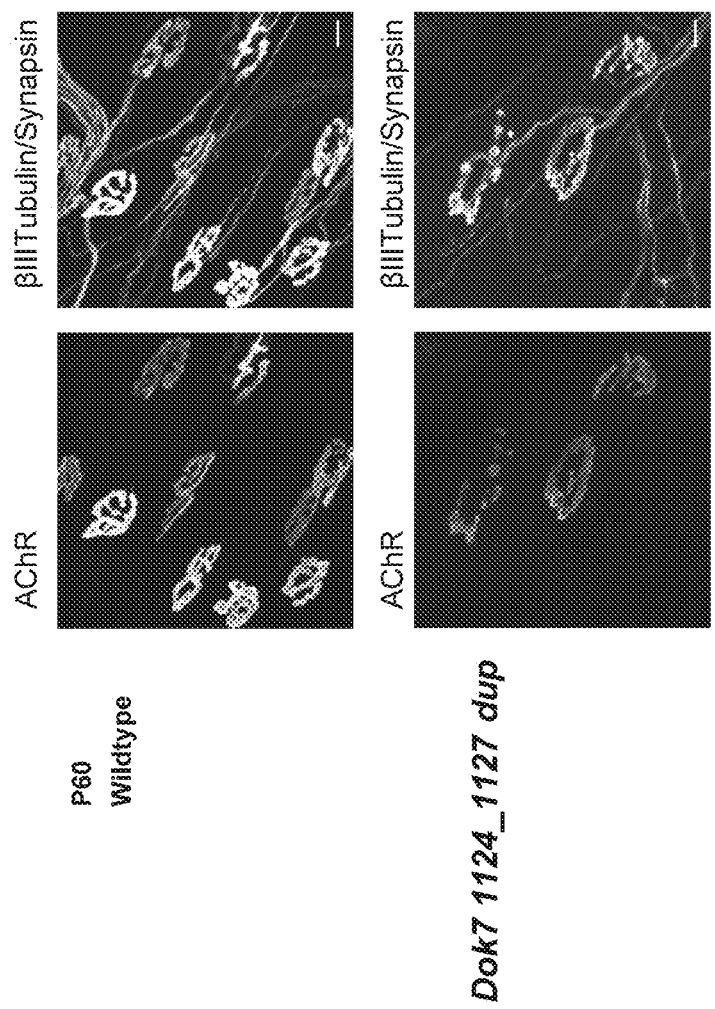
Figure 34:
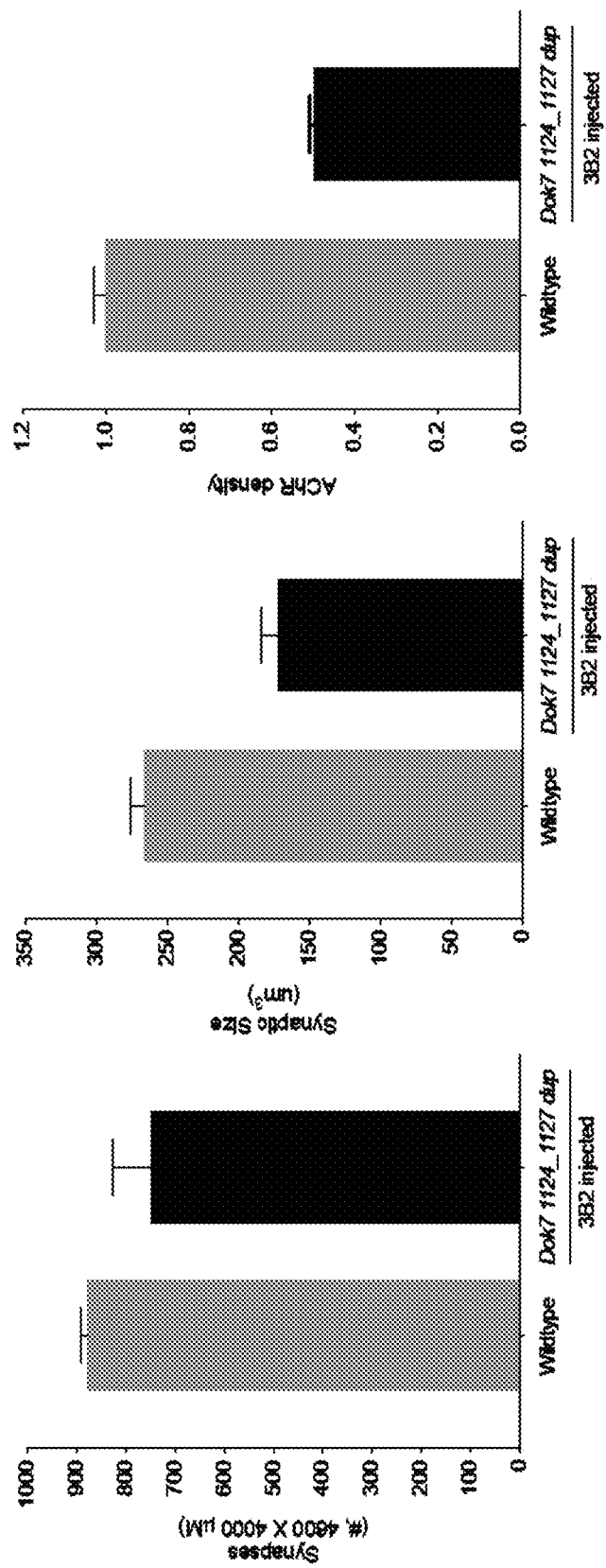

FIG. 34 demonstrate that 3B2 restores synapse development in young Dok7 1124_1127 dup mice. Diaphragm muscles from P60 wildtype and Dok7 1124_1127 dup mice were stained with Alexa 488-α-BGT to label AChRs and antibodies to βIIITubulin/Synapsin to label motor axons/nerve terminals. In Dok7 1124_1127 dup mice treated with 3B2, synapses matured from a simple, plaque-like shape to a complex, pretzel-like shape, characteristic of mature murine neuromuscular synapses. Scale bar=10 mm. In Dok7 1124_1127 dup mice treated with 3B2, the number of synapses, synaptic size and density of synaptic AChRs and were restored to 80%, 75%, and 40%, respectively, of normal levels. The mean±SEM values from 2 mice (>50 synapses per mouse) are shown.

Figure 35:
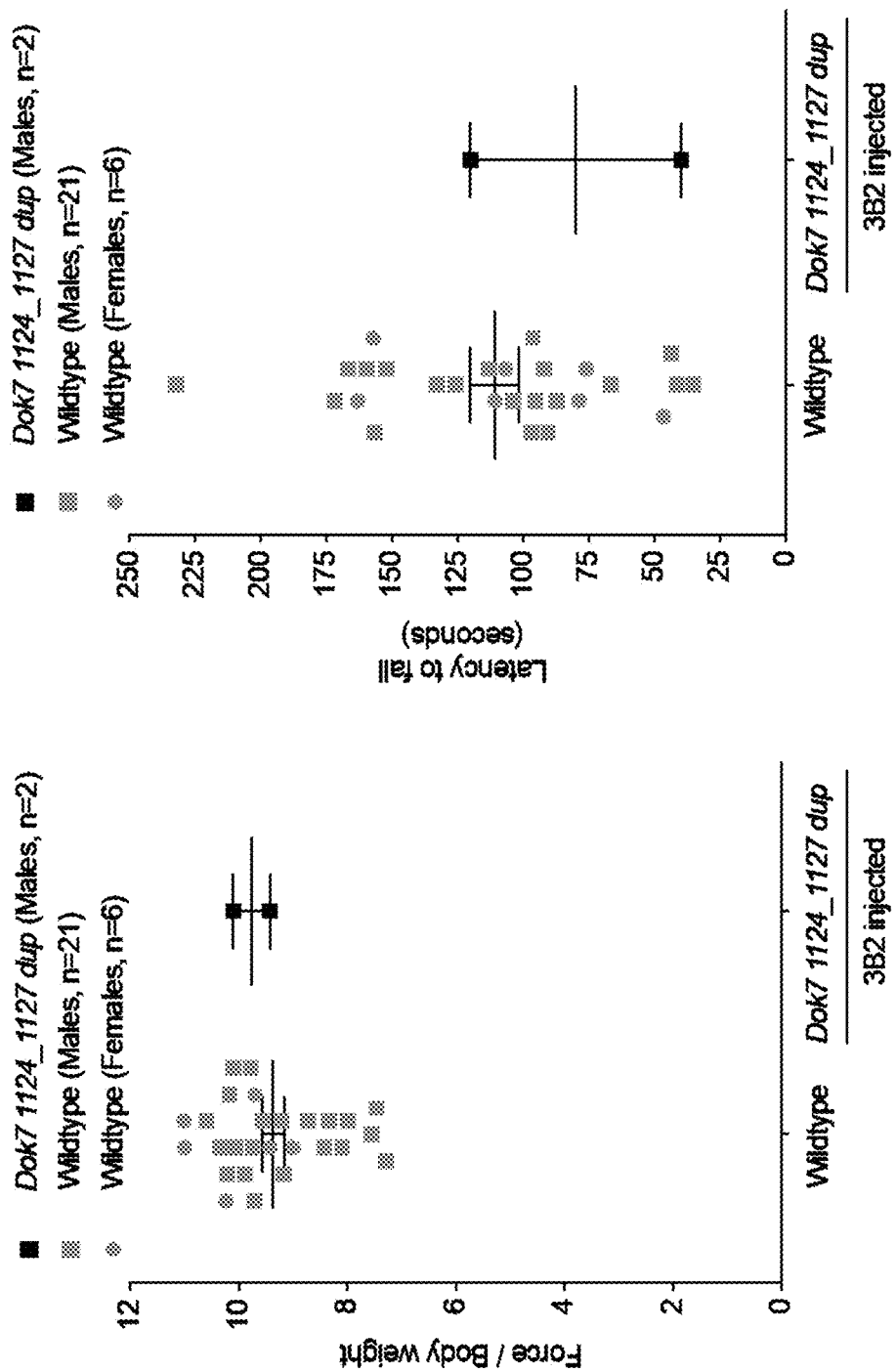

FIG. 35 demonstrates that 3B2 rescues motor performance of Dok7 1124_1127 dup mice. Motor performance of Dok7 1124_1127 dup mice, as assessed by grip strength (left panel) and the latency to fall from a rotating rotarod (right panel), were fully restored by treatment with 3B2. The scatter plots show the values for 27 wildtype mice and 2 Dok7 1124_1127 dup mice rescued with 3B2 and the mean±SEM values.

Figure 36:
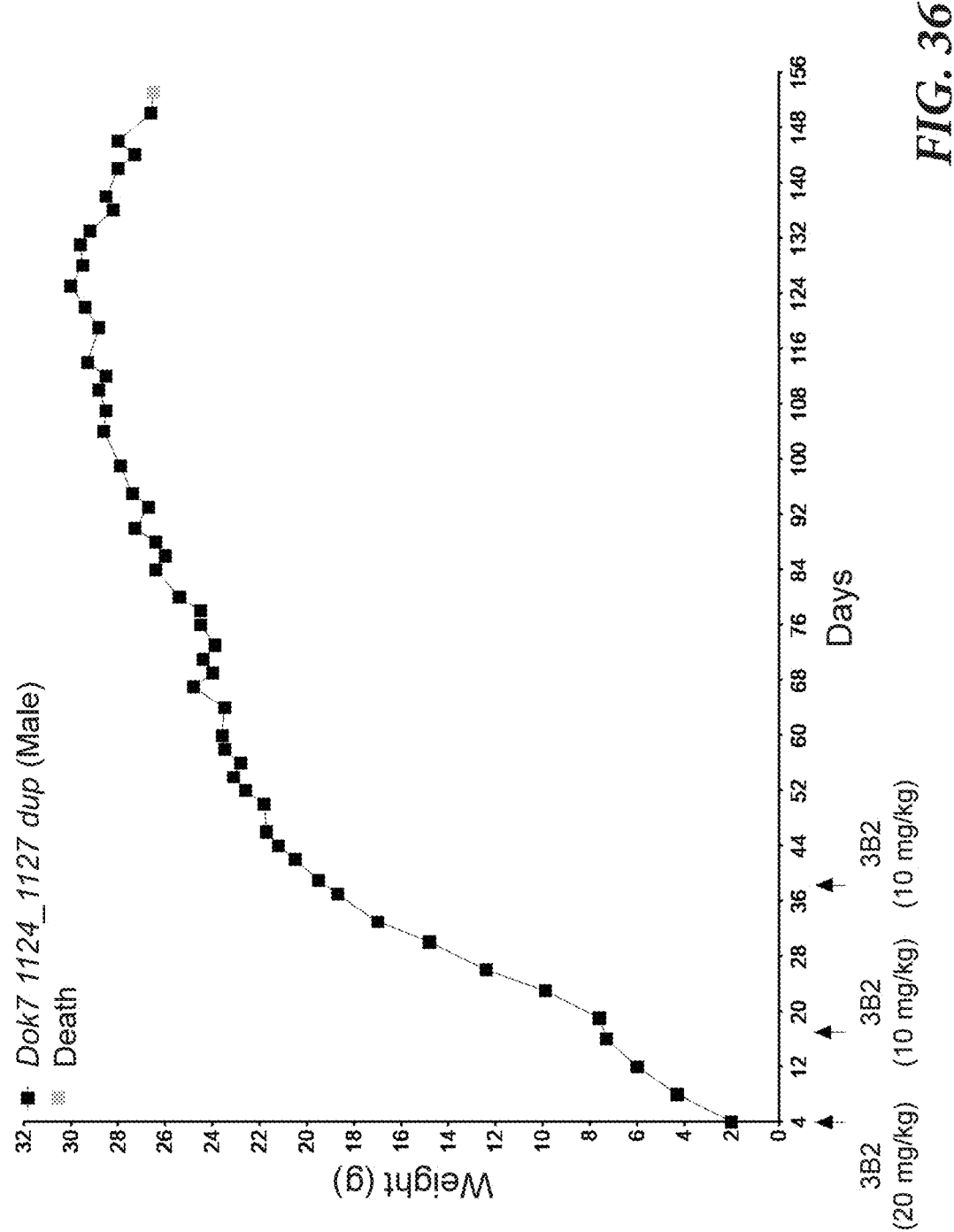

FIG. 36 demonstrates that 3B2 maintains Dok7 1124_1127 dup mice healthy for at least two months. A Dok7 1124_1127 dup mouse was injected with 3B2 at P4, P18, and P38 and then discontinued antibody treatment. This Dok7 1124_1127 dup mouse gained weight and maintained its mobility for several months but ultimately began to lose weight and die within a few days.

Figure 37:
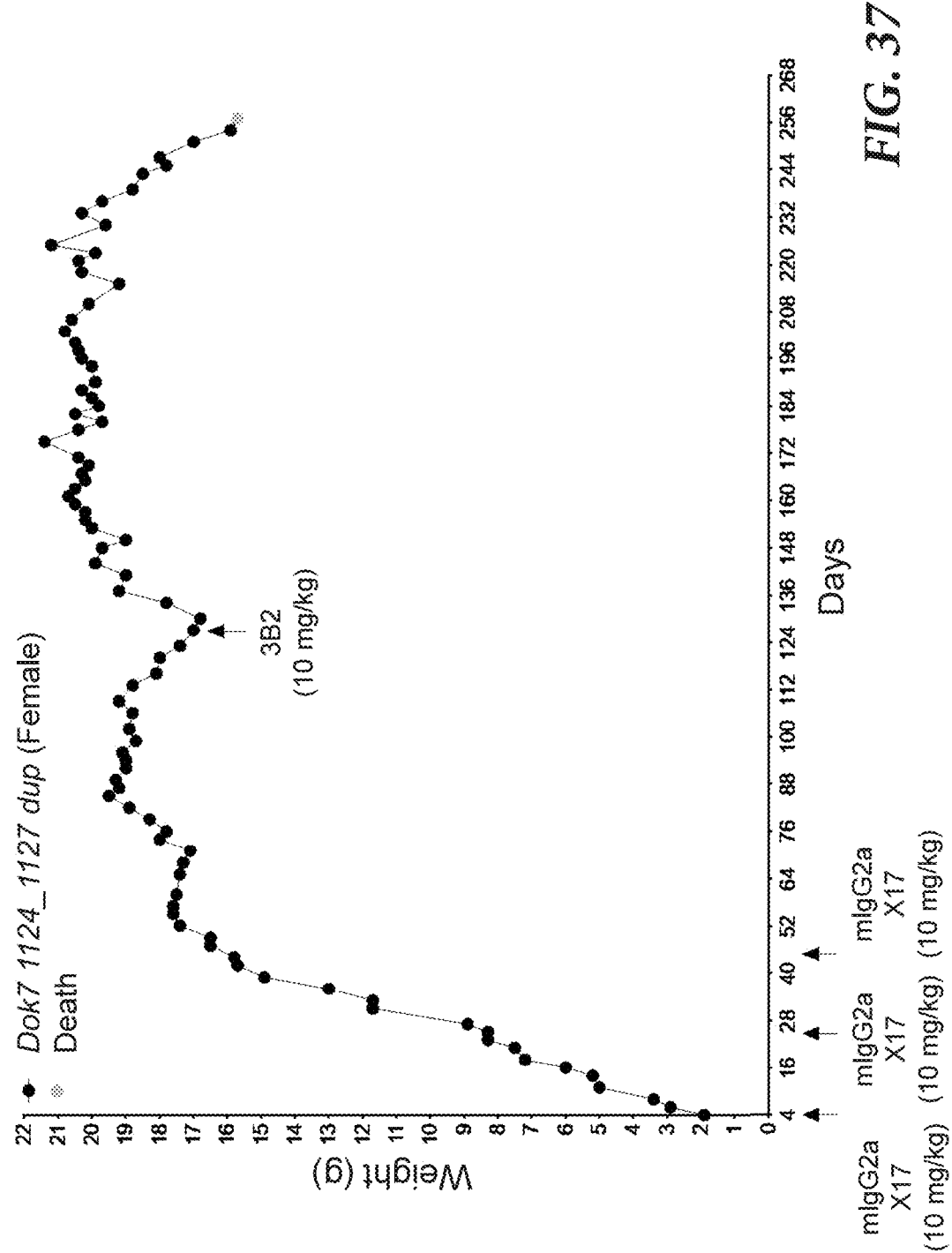

FIG. 37 demonstrates that 3B2 reverses disease relapse in adult Dok7 1124_1127 dup mice. A Dok7 1124_1127 dup mouse was injected with mIgG2a-X17 at P4, P24, and P44, and then antibody treatment was discontinued. These Dok7 1124_1127 dup mice gained weight and maintained its mobility for several months, but ultimately began to lose weight. At this time, the mouse was re-injected with 3B2. After restarting treatment with 3B2, this Dok7 1124_1127 dup mouse began to gain weight.

Figure 38A:
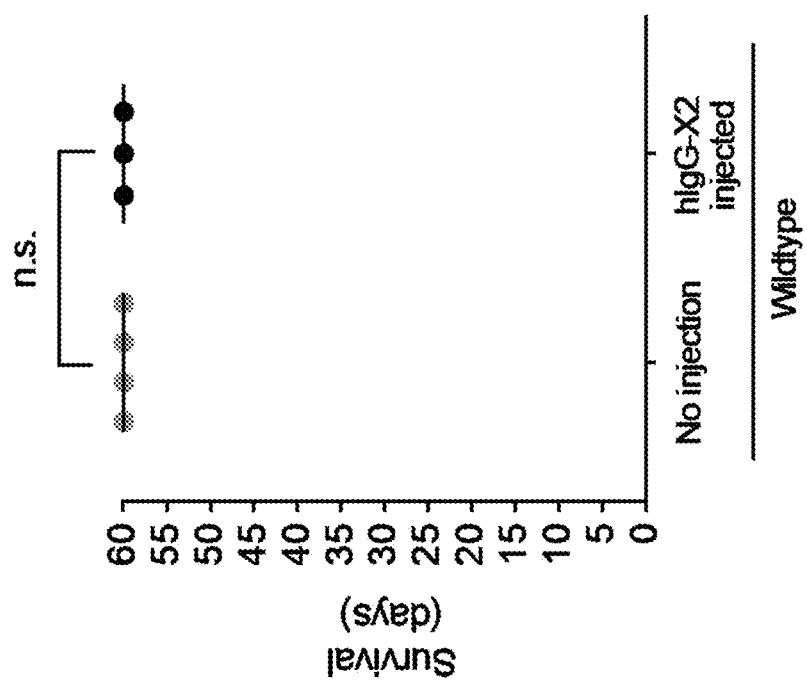
Figure 38B:
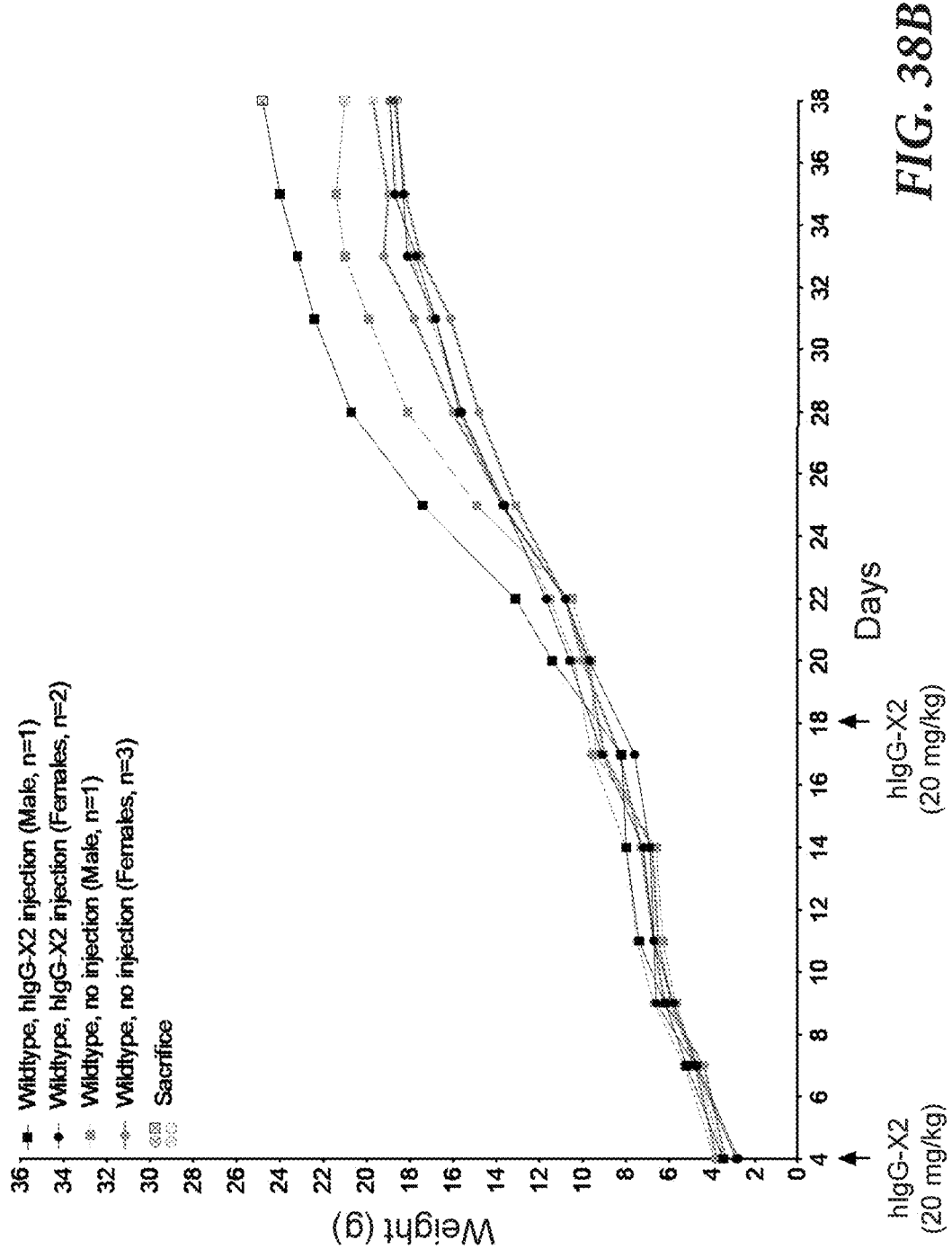

FIGS. 38A-38B demonstrate that chronic injection of hIgG-X2 in wildtype mice has no effect on survival or weight gain. FIG. 38A is a scatter plot showing that wildtype mice in a C57BL/6-CBA mixed background, injected at P4, and P18 with hIgG-X2 (n=3), survived until P38, when they were sacrificed. The scatter plot shows the survival time for 4 non-injected wildtype mice and 3 wildtype mice injected with hIgG-X2 and the mean±SEM values (n.s., not significant). FIG. 38B is a scatter plot showing that wildtype mice, injected with hIgG-X2 (n=3), gained weight like wildtype mice (n=4).

Figure 39A:
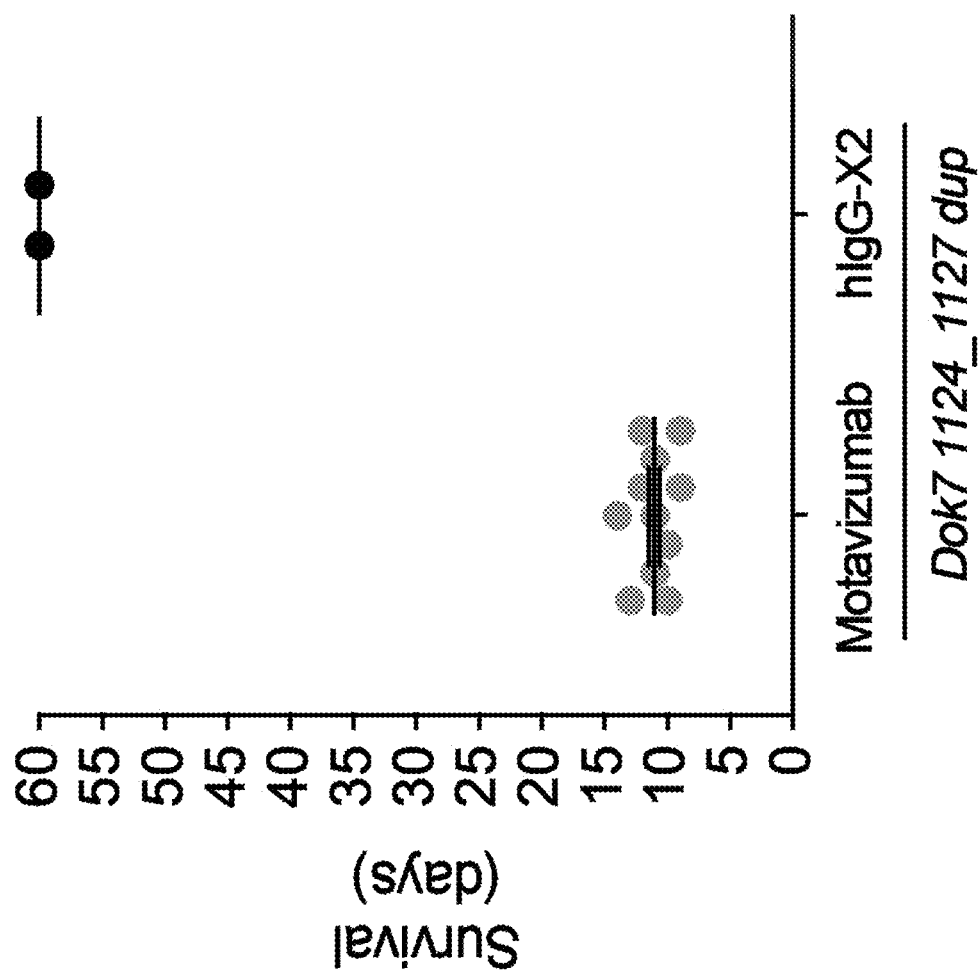
Figure 39B:
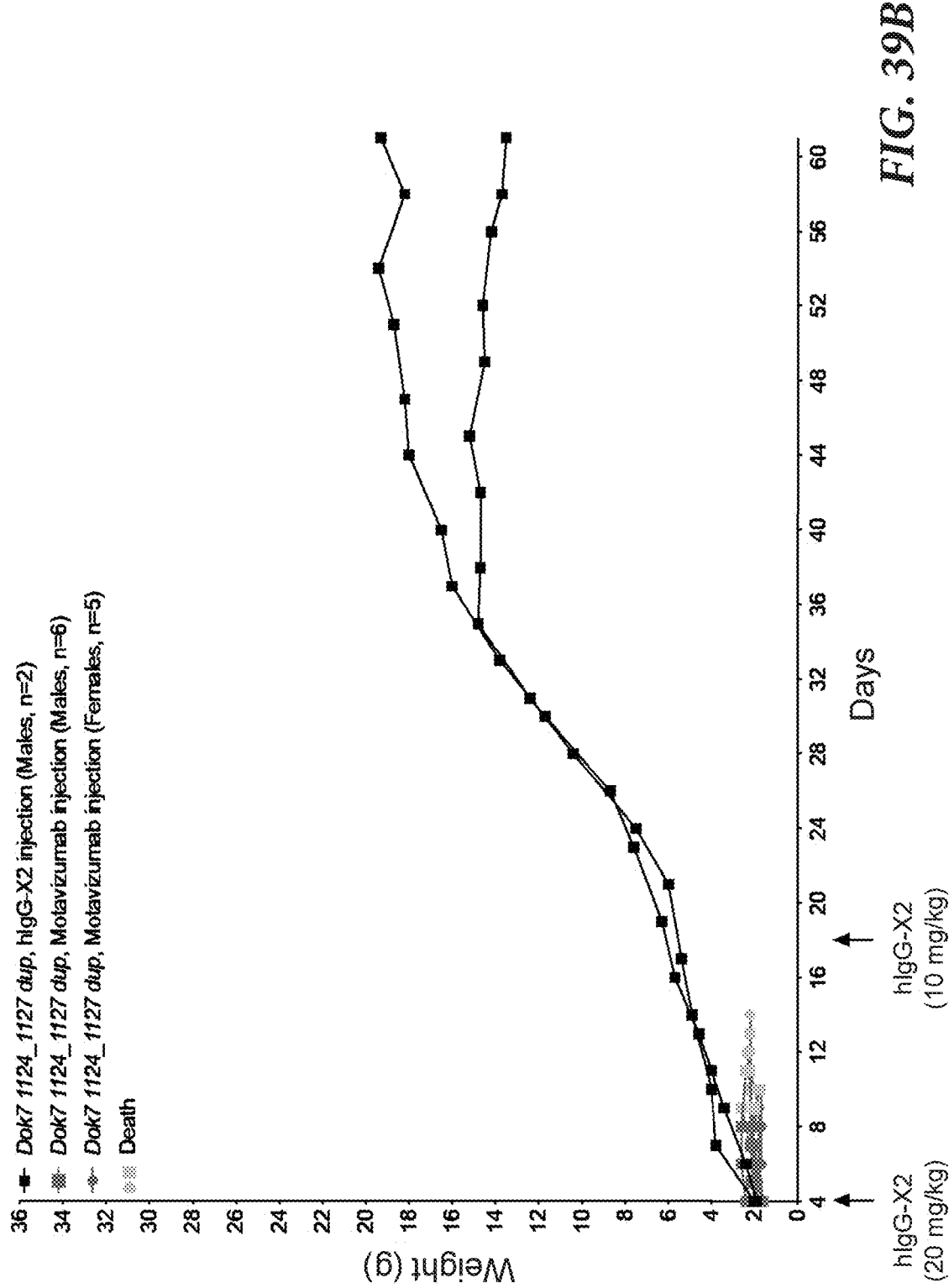

FIGS. 39A-39B demonstrate that agonist antibody to MuSK, hIgG-X2, rescues lethality in young Dok7 1124_1127 dup mice. FIG. 39A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody hIgG-X2 or an isotype equivalent negative control, Motavizumab. Dok7 1124_1127 dup mice (n=11) injected with the isotype control, like untreated mice, died one to two weeks after birth, whereas Dok7 1124_1127 dup mice injected with hIgG-X2 (n=2) at P4 and P18 survived as adults. Mutant mice injected with hIgG-X2 were aged for disease relapse experiments. The scatter plot shows the survival time for each mouse and the mean±SEM values (p, ****<0.00005). FIG. 39B is a scatter plot showing that Dok7 1124_1127 dup mice, injected with hIgG-X2 gained weight, unlike Dok7 1124_1127 dup mice treated with the isotype control antibody. Dok7 1124_1127 dup mice were injected with hIgG-X2 at P4 (20 mg/kg) and P18 (10 mg/kg).

Figure 40A:
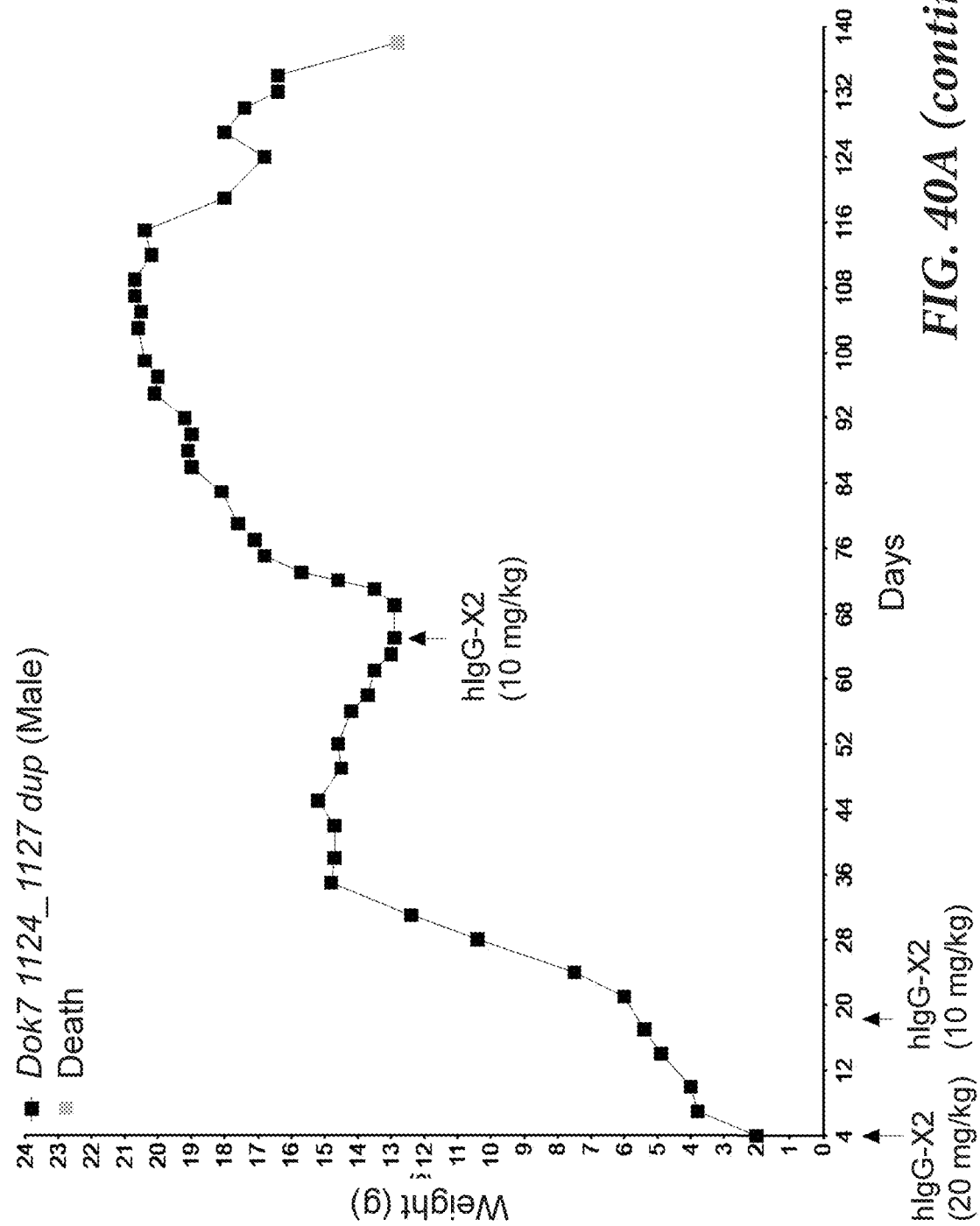
Figure 40B:
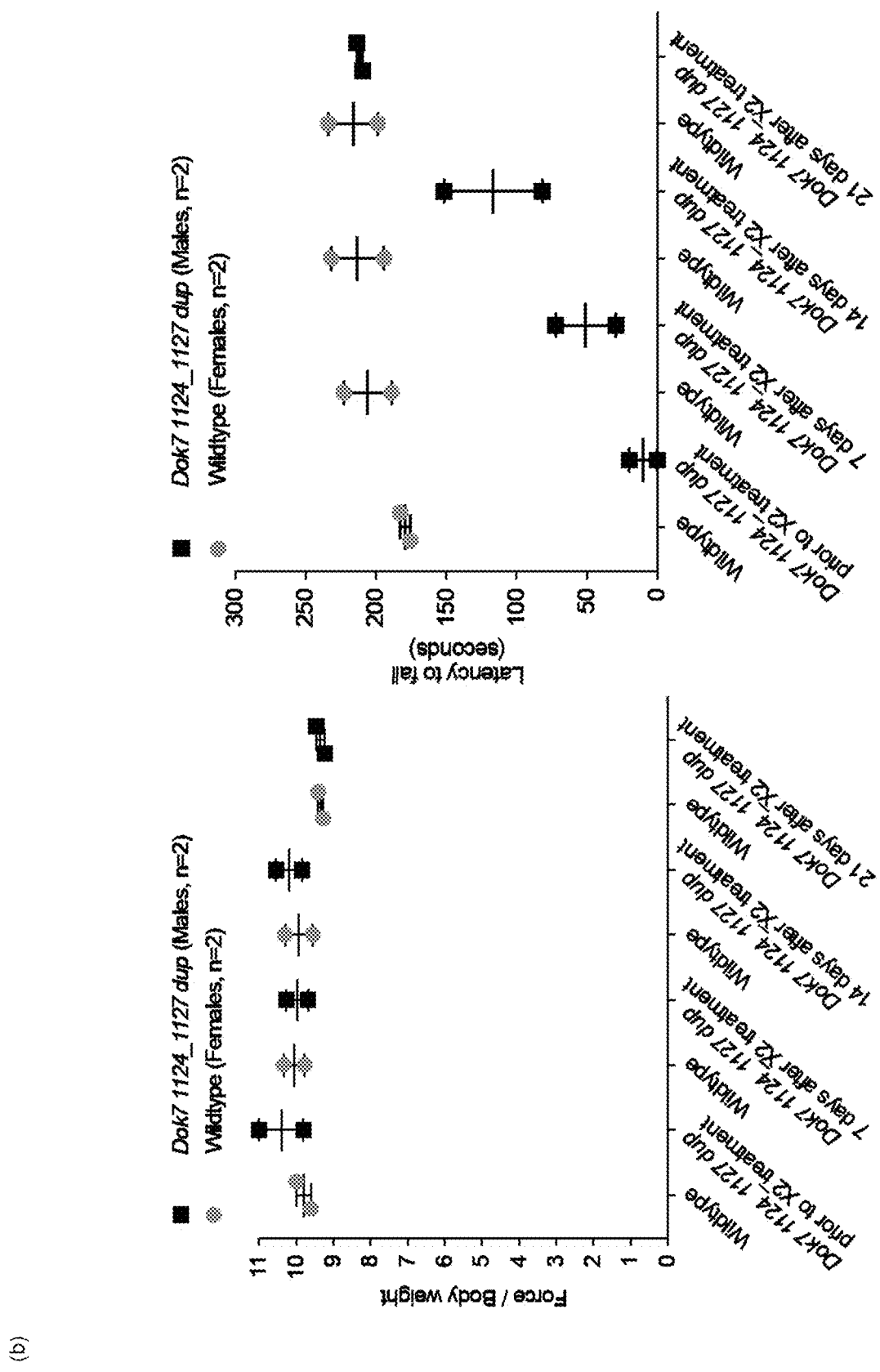

FIGS. 40A-40B demonstrate that hIgG-X2 reverses disease relapse in adult Dok7 1124_1127 dup mice. Dok7 1124_1127 dup mice were injected with hIgG-X2 at P4 and P18 and then discontinued antibody treatment. These Dok7 1124_1127 dup mice gained weight and maintained their mobility for several weeks but ultimately began to lose weight (FIG. 40A) and to display motor deficits, as assessed by grip strength and the latency to fall from a rotating rotarod (FIG. 40B). At this time, mice were re-injected with hIgG-X2. After restarting X2 treatment, the Dok7 1124_1127 dup mice began to gain weight (FIG. 40A), and by three weeks after restarting treatment their motor deficits were completely reversed (FIG. 40B).

Figure 41A:
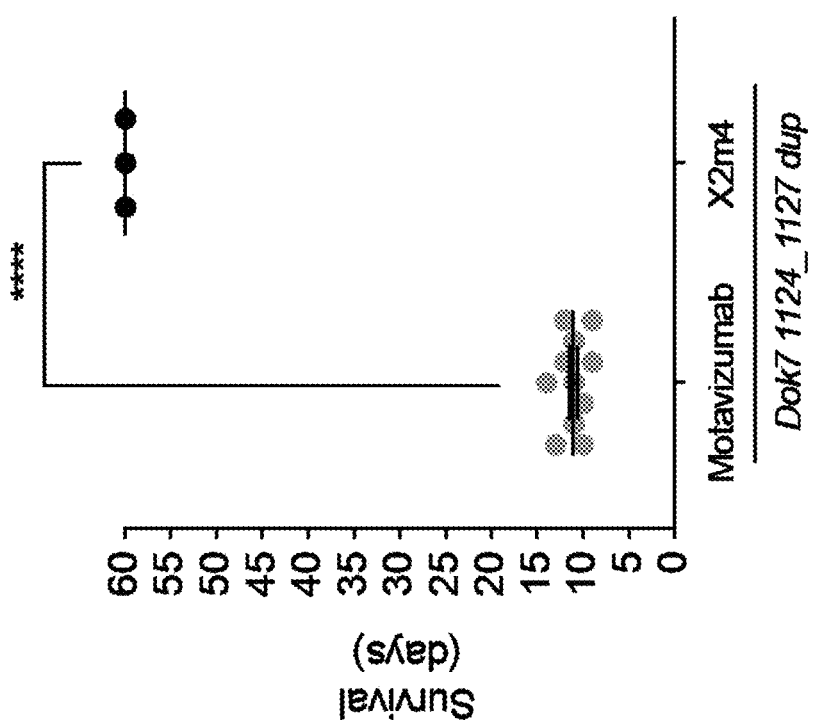
Figure 41B:
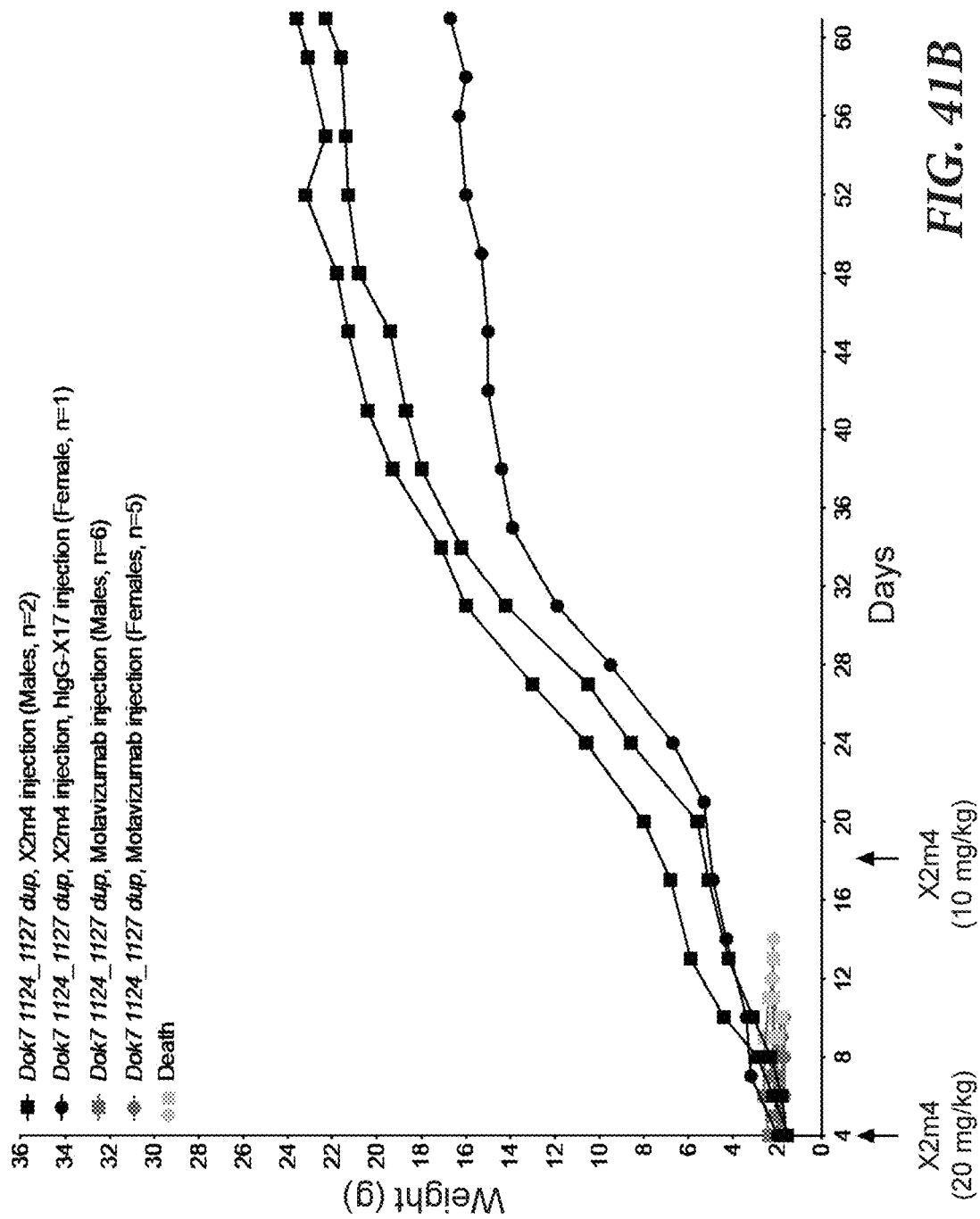

FIGS. 41A-41B demonstrate that an agonist antibody to MuSK, hIgG-X2m4, rescues lethality in young Dok7 1124_1127 dup mice. FIG. 41A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody hIgG-X2m4 or an isotype equivalent negative control, Motavizumab. Dok7 1124_1127 dup mice (n=11) injected with the isotype control, like untreated mice, died one to two weeks after birth, whereas Dok7 1124_1127 dup mice injected with hIgG-X2m4 (n=3) at P4 and P18 survived as adults. Mutant mice injected with hIgG-X2m4 were monitored for survival or aged for disease relapse experiments with hIgG-X17. The scatter plot shows the survival time for each mouse and the mean±SEM values (p, ****<0.00005). FIG. 41B is a scatter plot showing that Dok7 1124_1127 dup mice, injected with hIgG-X2m4 gained weight, unlike Dok7 1124_1127 dup mice treated with the isotype control antibody. Dok7 1124_1127 dup mice were injected with hIgG-X2m4 at P4 (20 mg/kg) and P18 (10 mg/kg). One mouse was used for disease relapse experiments with hIgG-X17, others were monitored for survival.

Figure 42:
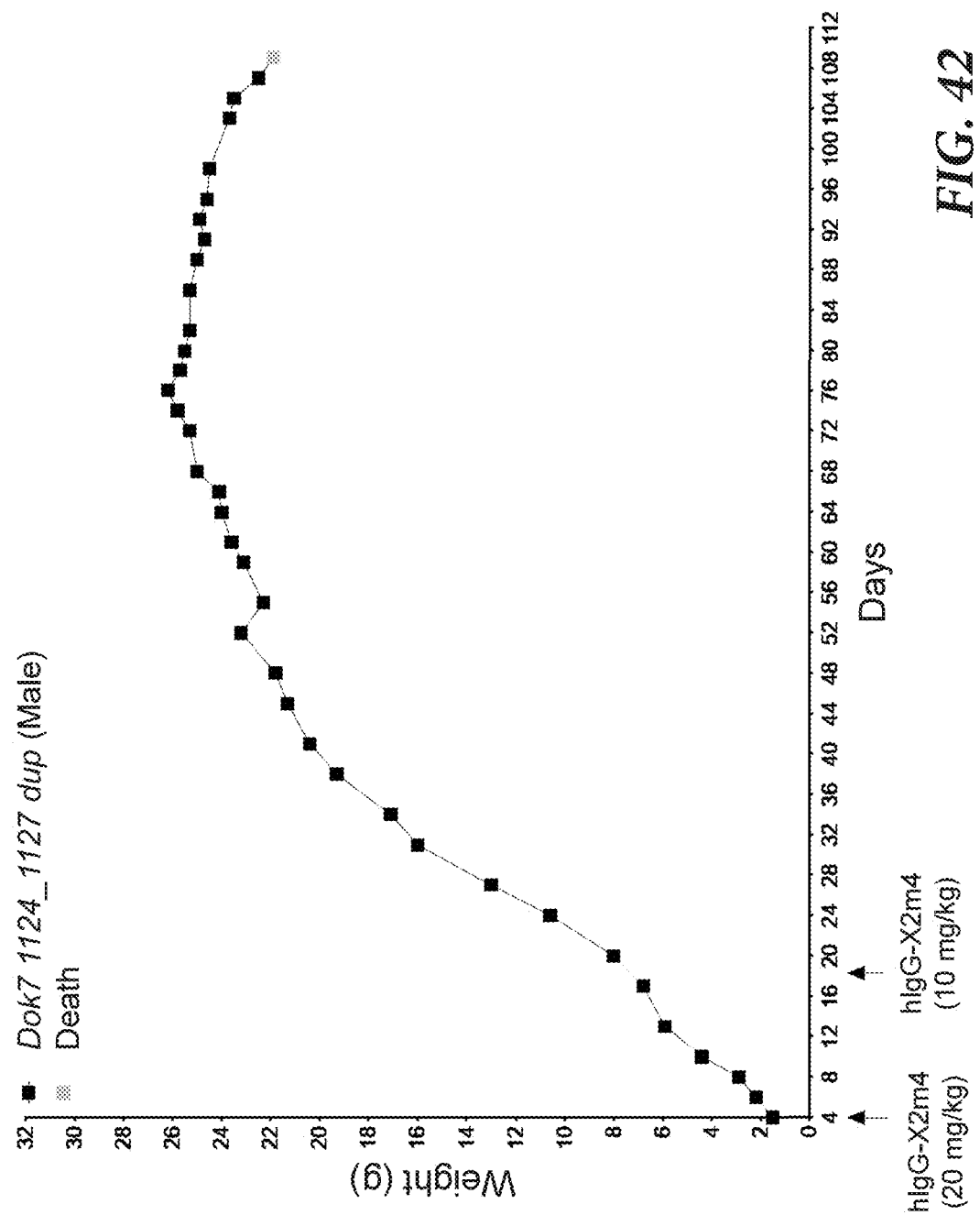
Figure 42:
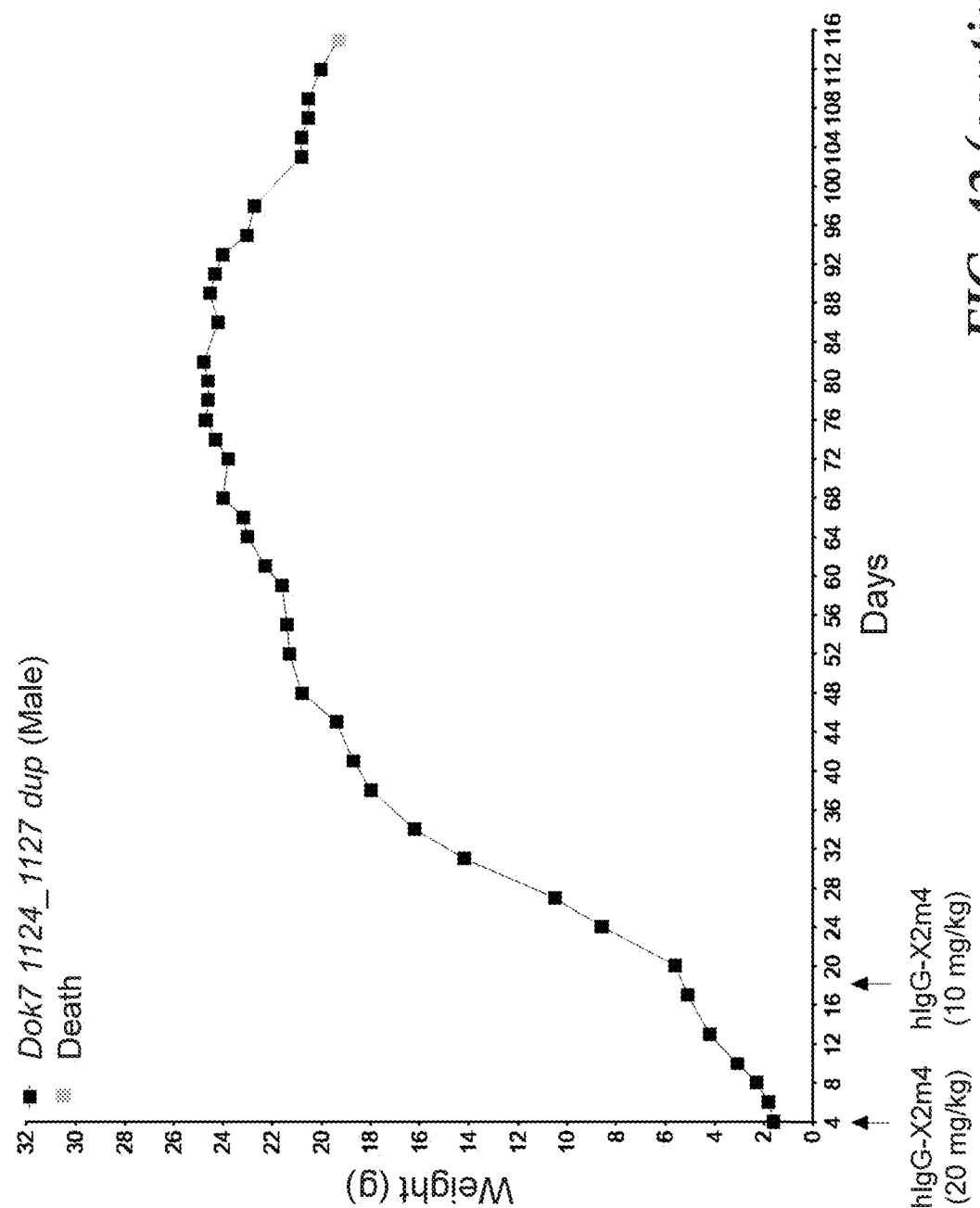

FIG. 42 are scatter plots showing that hIgG-X2m4 maintains Dok7 1124_1127 dup mice healthy for at least two months. Dok7 1124_1127 dup mice were injected with X2m4 at P4 and P18, and then antibody treatment was discontinued. These Dok7 1124_1127 dup mice gained weight and maintained their mobility for several months but ultimately began to lose weight and die within a few days.

Figure 43A:
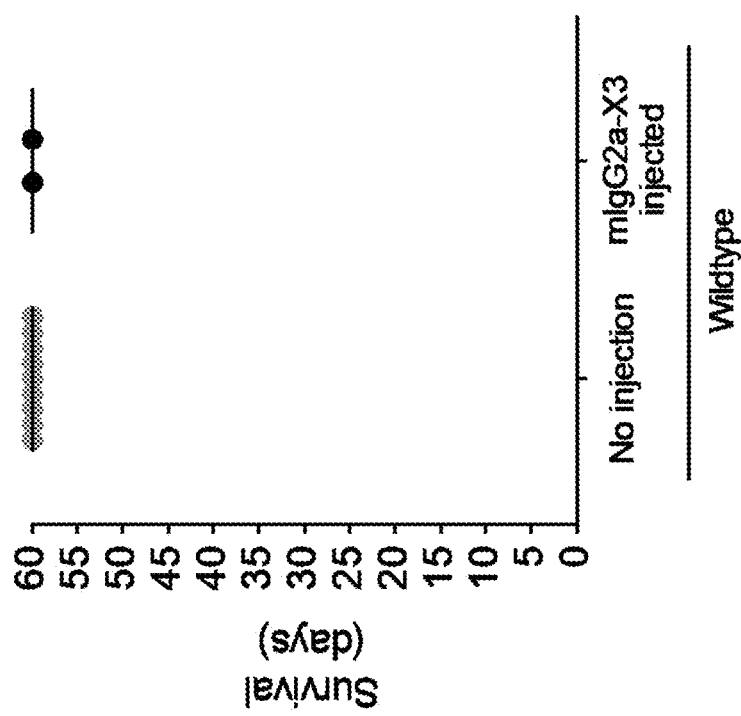
Figure 43B:
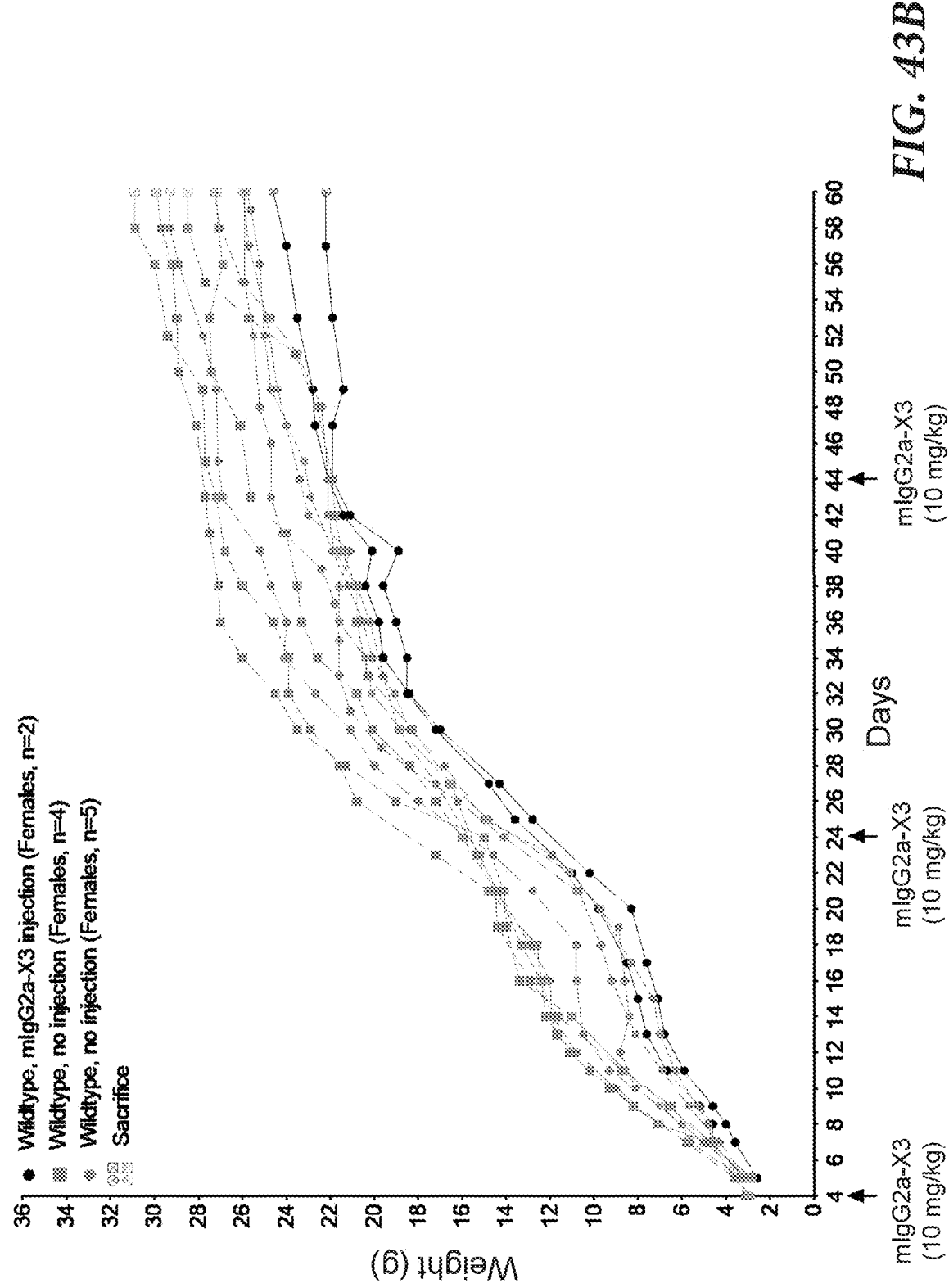

FIGS. 43A-43B demonstrate that chronic injection of mIgG2a-X3 in wildtype mice has no effect on survival or weight gain. FIG. 43A is a scatter plot showing that wildtype mice in a C57BL/6-CBA mixed background, injected at P4, P24, and P44 with mIgG2a-X3 (n=2), survived until P60, when they were sacrificed. The scatter plot shows the survival time for 9 non-injected wildtype mice and 2 wildtype mice injected with mIgG2a-X3 and the mean±SEM values. FIG. 43B is a scatter plot showing that wildtype mice, injected with mIgG2a-X3 (n=2), gained weight like wildtype mice without injection (n=9).

Figure 44:
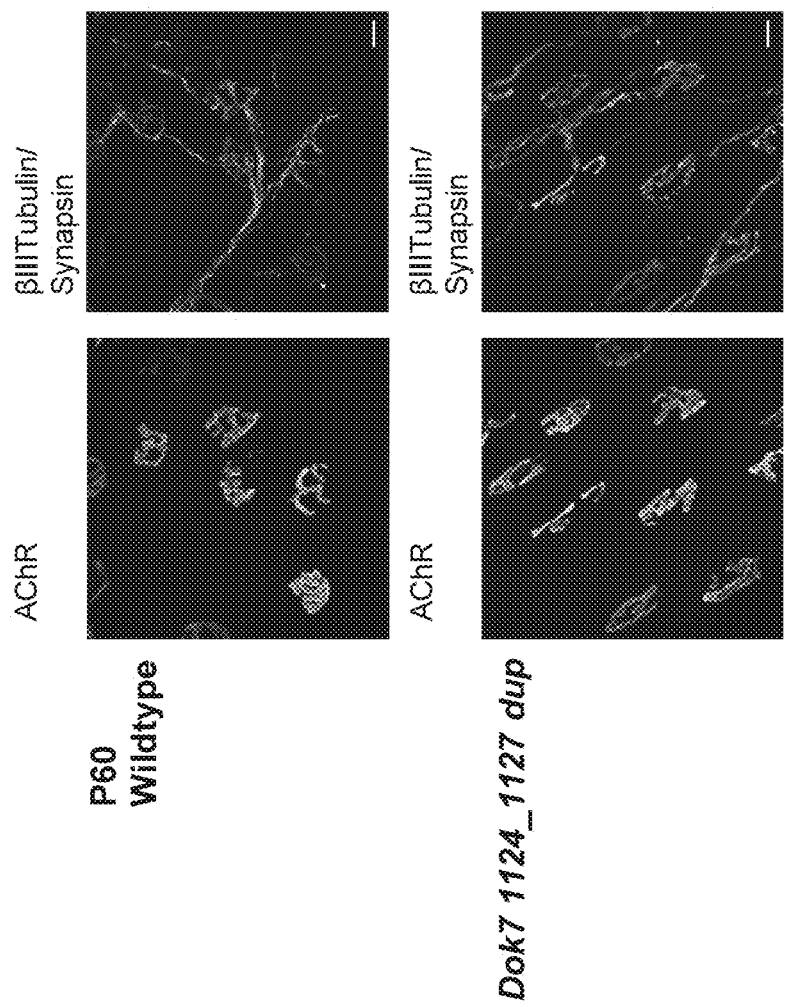
Figure 44:
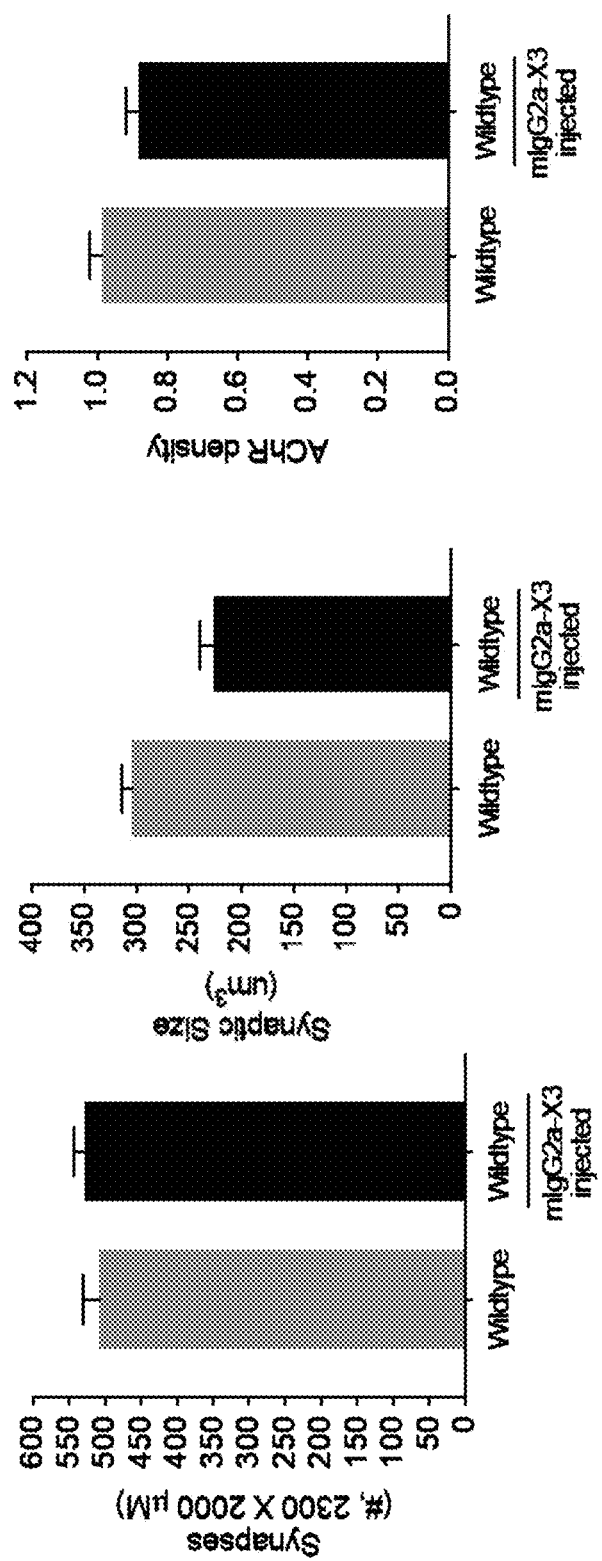

FIG. 44 demonstrates that chronic injection of mIgG2a-X3 in wildtype mice has no effect on the organization of neuromuscular synapses. Diaphragm muscles from P60 wildtype and wildtype mice injected with mIgG2a-X3 were stained with Alexa 488-α-BGT to label Acetylcholine Receptors and antibodies to βIII-Tubulin/Synapsin to label motor axons/nerve terminals. In wildtype mice treated with mIgG2a-X3, synapses matured from a simple, plaque-like shape to a complex, pretzel-like shape, characteristic of mature murine neuromuscular synapses. Scale bar=10 mm. Injection of mIgG2a-X3 in wildtype mice has no effect on synapses number, synaptic size, and AChR density. 100 synapses from 2 mice in each category were analyzed.

Figure 45:
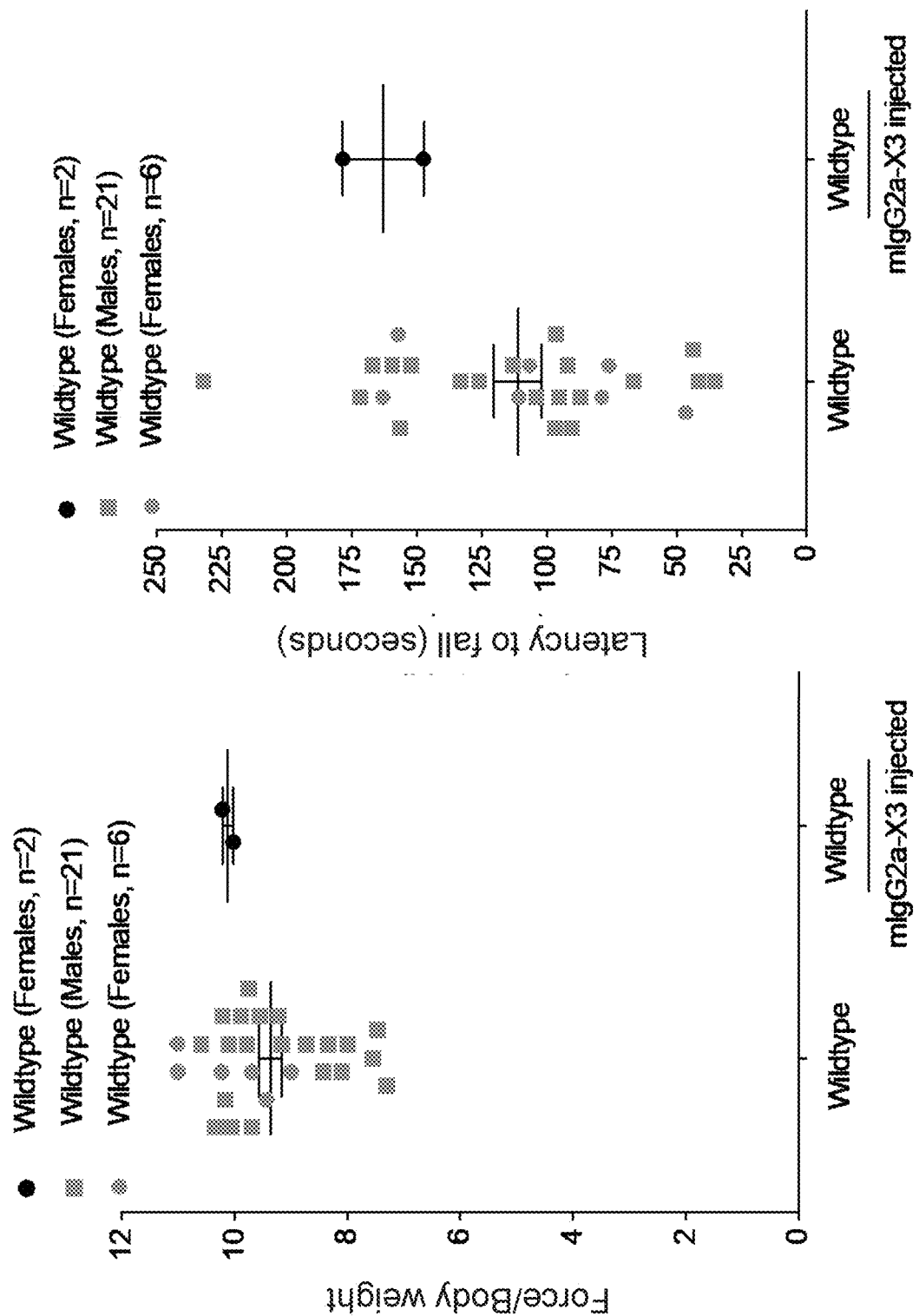

FIG. 45 demonstrates that chronic injection of mIgG2a-X3 in wildtype mice has no effect on motor behavior. Motor performance of wildtype mice injected with mIgG2a-X3, as assessed by grip strength (left panel) and the latency to fall from a rotating rotarod (right panel), were similar to non-injected wildtype mice. The scatter plots show the values for 27 wildtype mice and 2 wildtype mice injected with mIgG2a-X3 and the mean±SEM values.

Figure 46A:
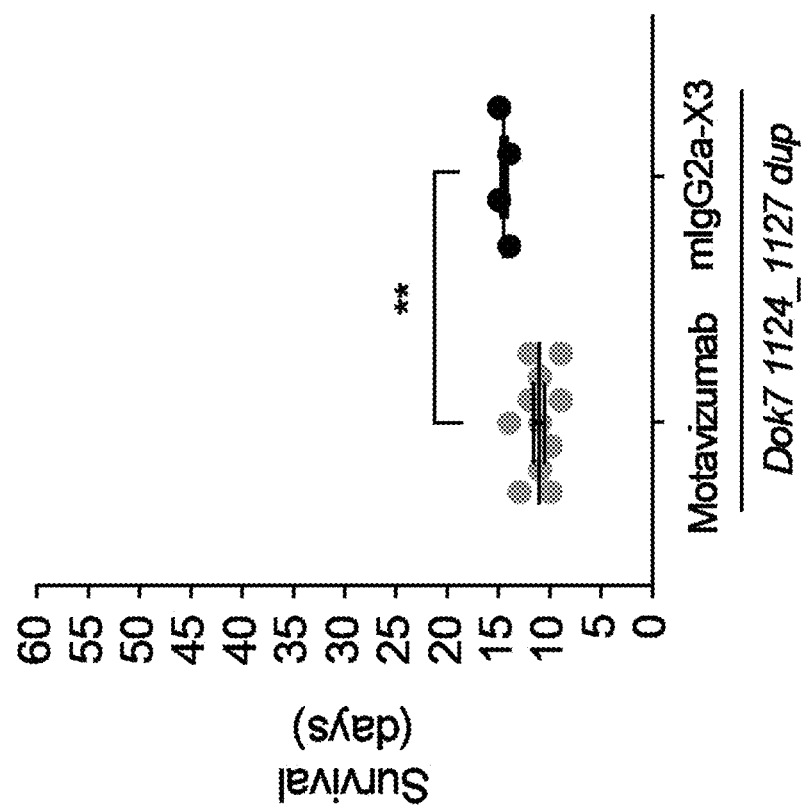
Figure 46B:
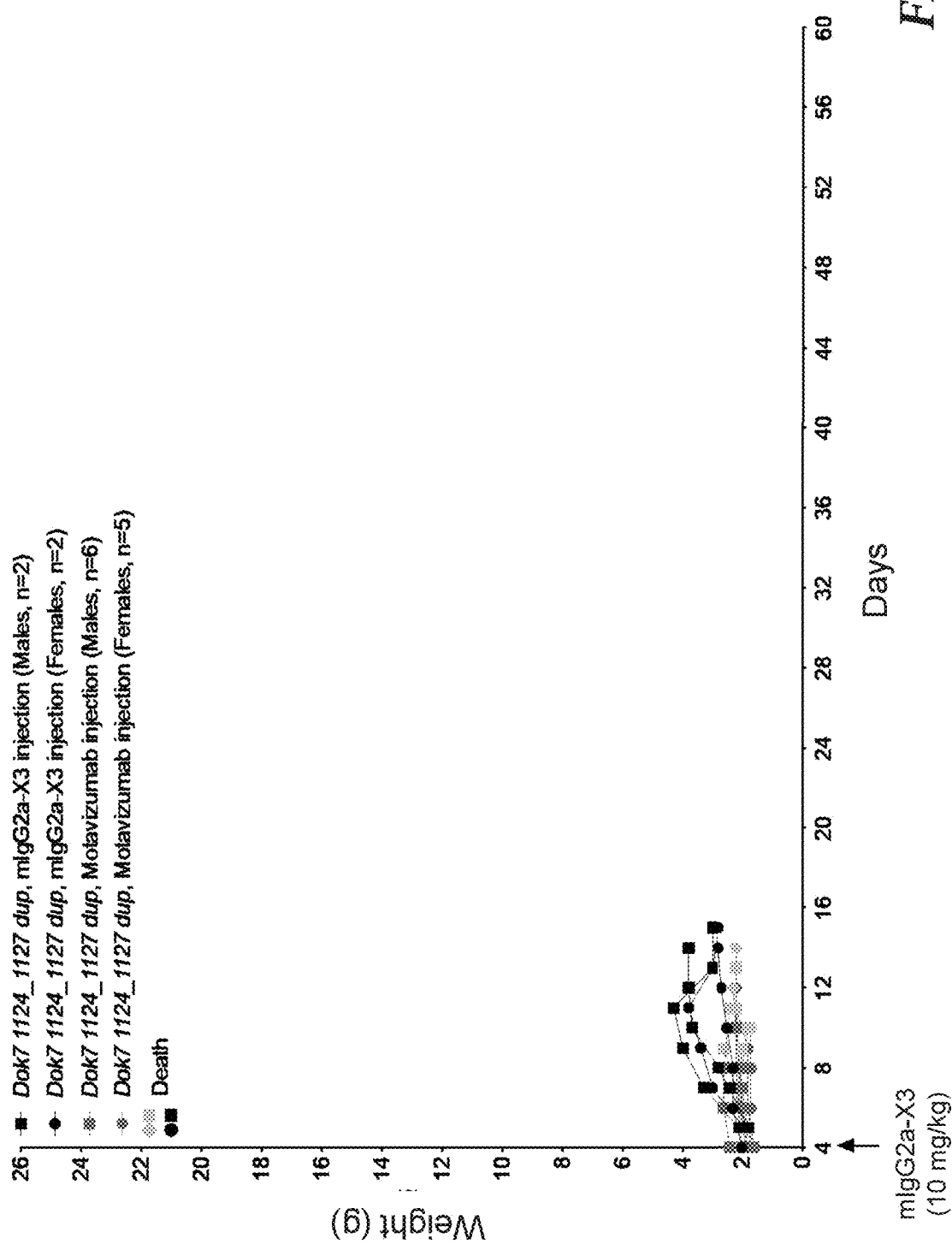

FIGS. 46A-46B demonstrate that agonist antibody to MuSK, mIgG2a-X3, at 10 mg/kg at P4, rescues lethality in young Dok7 1124_1127 dup mice for a few days. FIG. 46A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody mIgG2a-X3 or an isotype equivalent negative control, Motavizumab. Dok7 1124_1127 dup mice (n=11) injected with the isotype control, and Dok7 1124_1127 dup mice (n=4) injected with mIgG2a-X3, like untreated mice, died one to two weeks after birth. The scatter plot shows the survival time for each mouse and the mean±SEM values (p, **<0.05). FIG. 46B is a scatter plot showing that Dok7 1124_1127 dup mice, injected with mIgG2a-X3 did not gain weight, like Dok7 1124_1127 dup mice treated with the isotype control antibody. Dok7 1124_1127 dup mice were injected with mIgG2a-X3 (10 mg/kg) at P4.

Figure 47A:
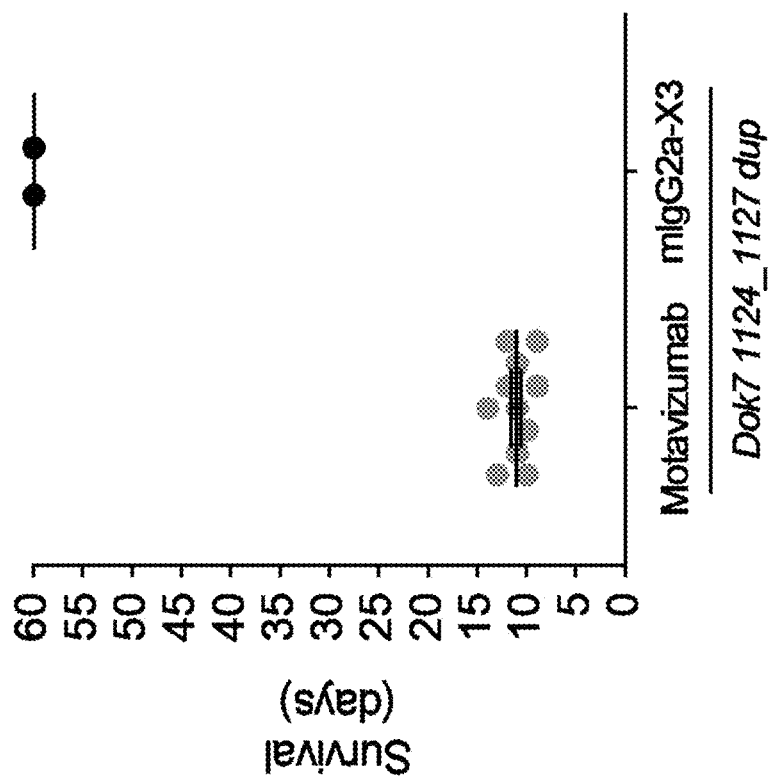
Figure 47B:
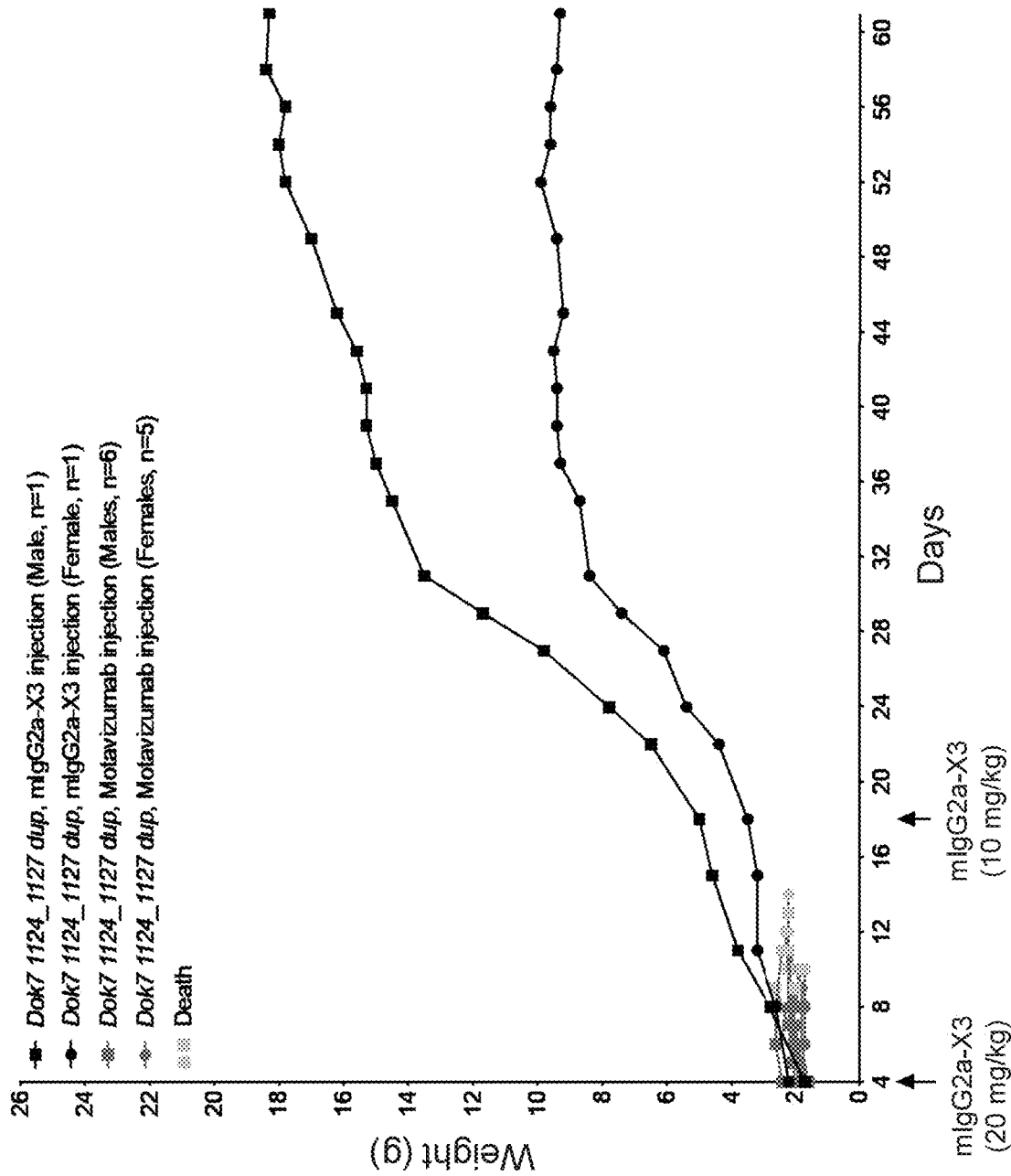

FIGS. 47A-47B demonstrate that agonist antibody to MuSK, mIgG2a-X3, at 20 mg/kg at P4, rescues lethality in young Dok7 1124_1127 dup mice. FIG. 47A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody mIgG2a-X3 (20 mg/kg) or an isotype equivalent negative control, Motavizumab. Dok7 1124_1127 dup mice (n=11) injected with the isotype control, like untreated mice, died one to two weeks after birth. Dok7 1124_1127 dup mice (n=2) injected with mIgG2a-X3 at P4 (20 mg/kg) and P18 (10 mg/kg), survived as adults. Mutant mice injected with mIgG2a-X3 were aged for disease relapse experiments. The scatter plot shows the survival time for each mouse and the mean±SEM values. FIG. 47B is a scatter plot showing that Dok7 1124_1127 dup mice, injected with mIgG2a-X3 gained weight, unlike Dok7 1124_1127 dup mice treated with the isotype control antibody. Dok7 1124_1127 dup mice were injected with mIgG2a-X3 at P4 (20 mg/kg) and at P18 (10 mg/kg).

Figure 48:
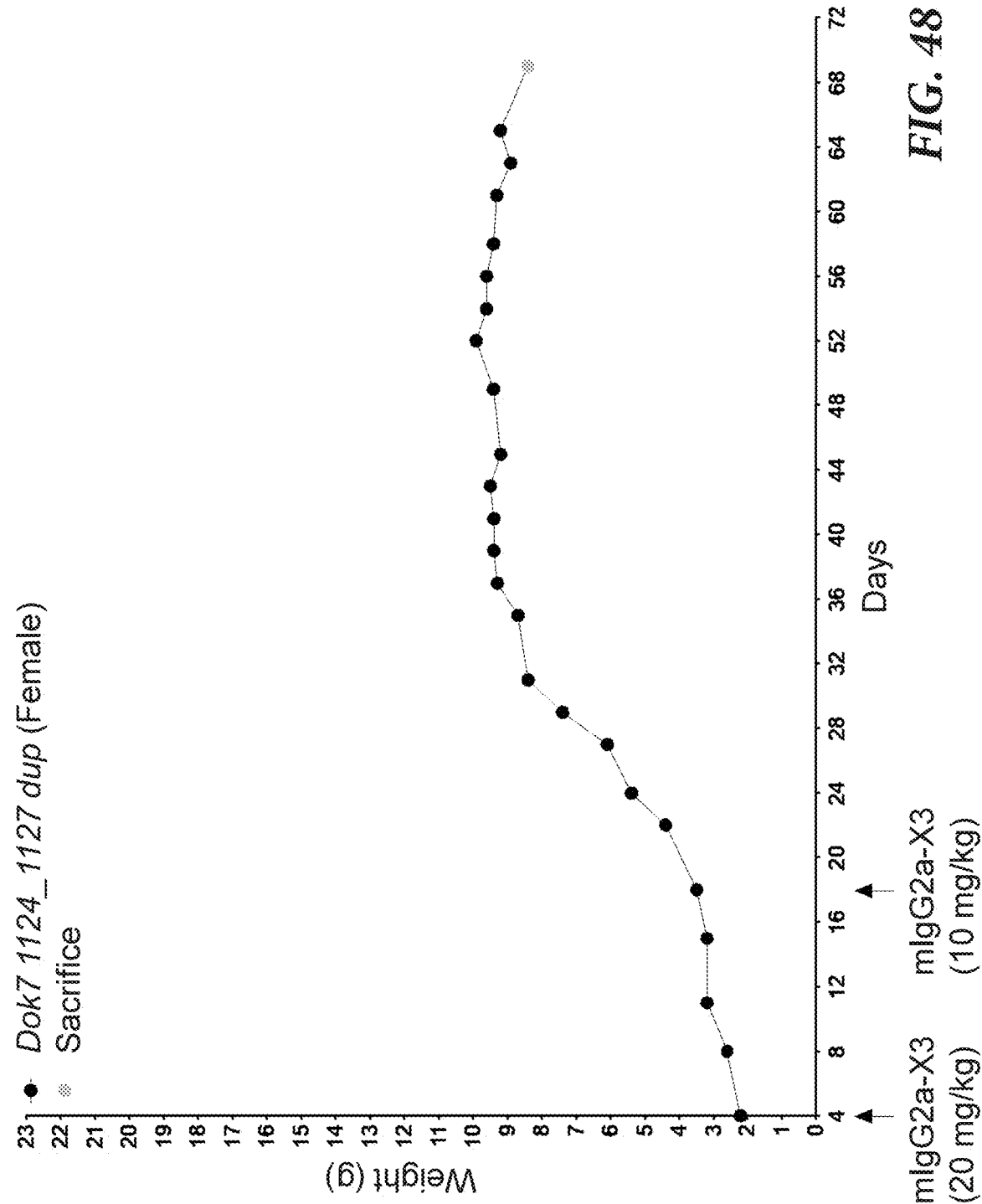

FIG. 48 demonstrates that mIgG2a-X3 maintains Dok7 1124_1127 dup mice healthy for at least two months. Dok7 1124_1127 dup mice were injected with mIgG2a-X3 at P4 and P18, and then discontinued antibody treatment. These Dok7 1124_1127 dup mice gained weight and maintained their mobility for two months but ultimately began to lose weight and die within a few days.

Figure 49A:
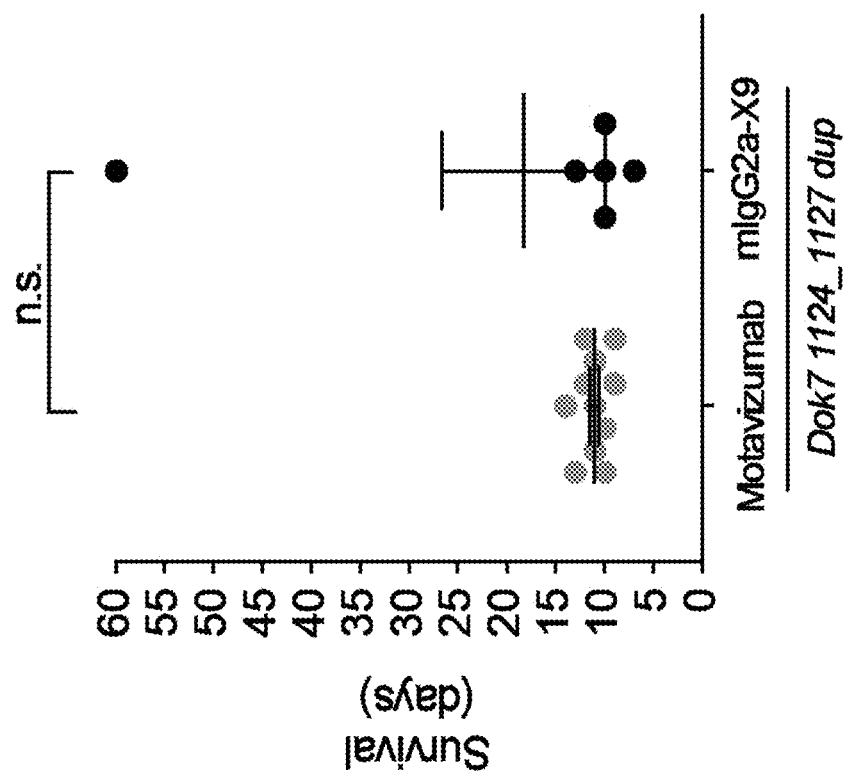
Figure 49B:
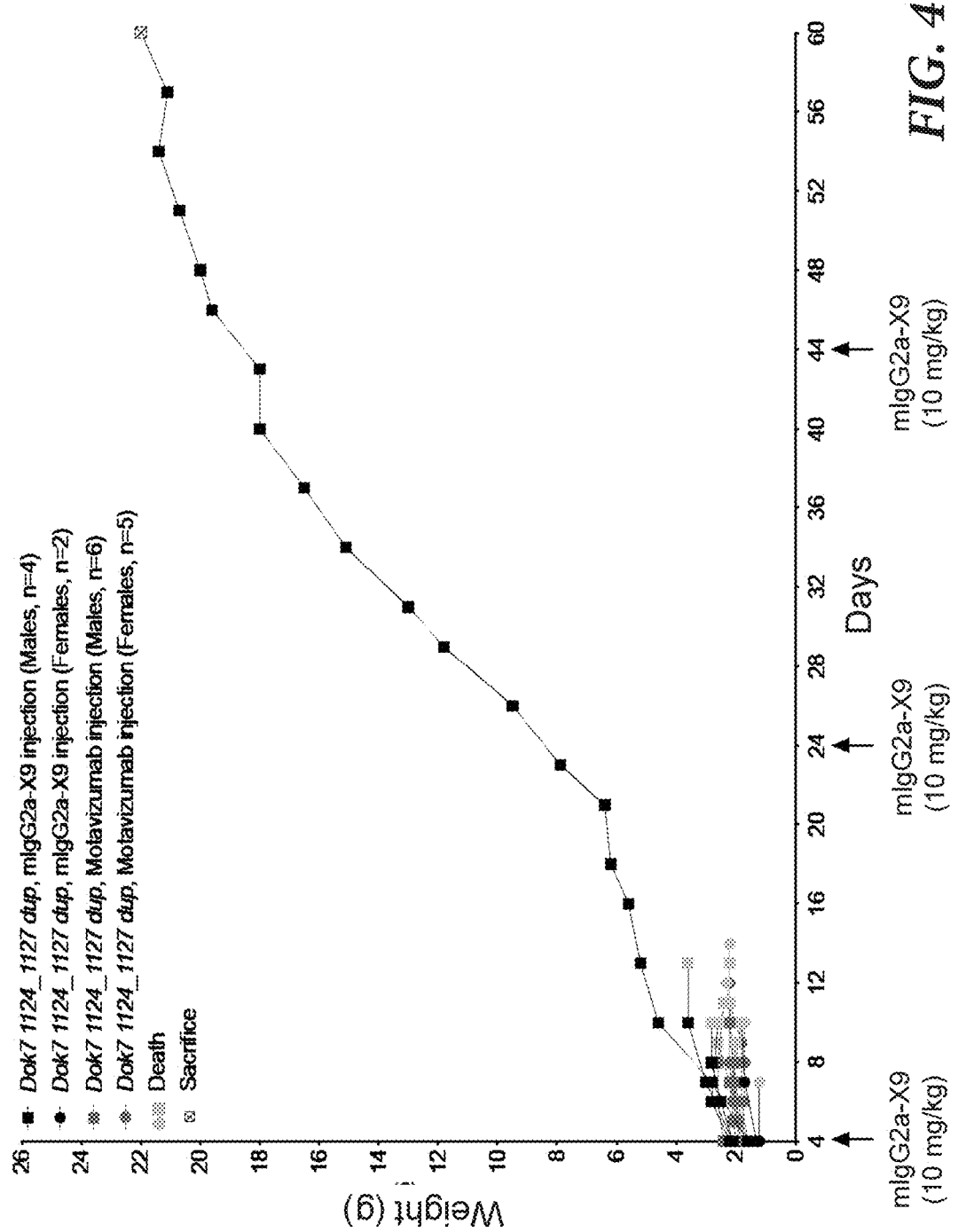

FIGS. 49A-49B demonstrate that agonist antibody to MuSK, mIgG2a-X9, may rescue lethality in young Dok7 1124_1127 dup mice. FIG. 49A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody mIgG2a-X9 or an isotype equivalent negative control, Motavizumab. Dok7 1124_1127 dup mice (n=11) injected with the isotype control, and Dok7 1124_1127 dup mice (n=6) injected with mIgG2a-X9, like untreated mice, died one to two weeks after birth. Only one Dok7 1124_1127 dup mouse injected with mIgG2a-X9 (10 mg/kg) at P4, P24, and P44, survived until P60. The scatter plot shows the survival time for each mouse and the mean±SEM values (n.s., not significant). FIG. 49B is a scatter plot showing that Dok7 1124_1127 dup mice, injected with mIgG2a-X9 did not gain weight, like Dok7 1124_1127 dup mice treated with the isotype control antibody. Only one Dok7 1124_1127 dup mouse injected with mIgG2a-X9 gained weight overtime. Dok7 1124_1127 dup mice were injected with mIgG2a-X9 (10 mg/kg) at P4, P24, and P44.

Figure 50:
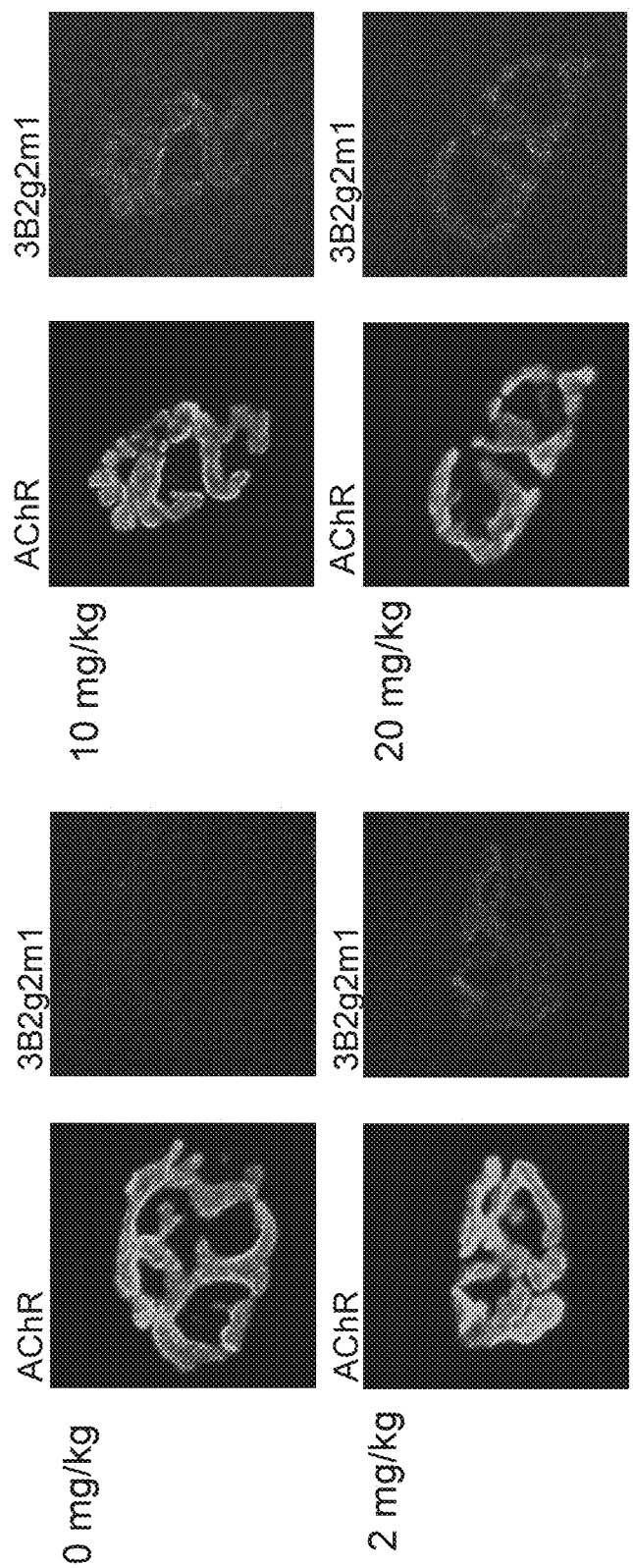
Figure 50:
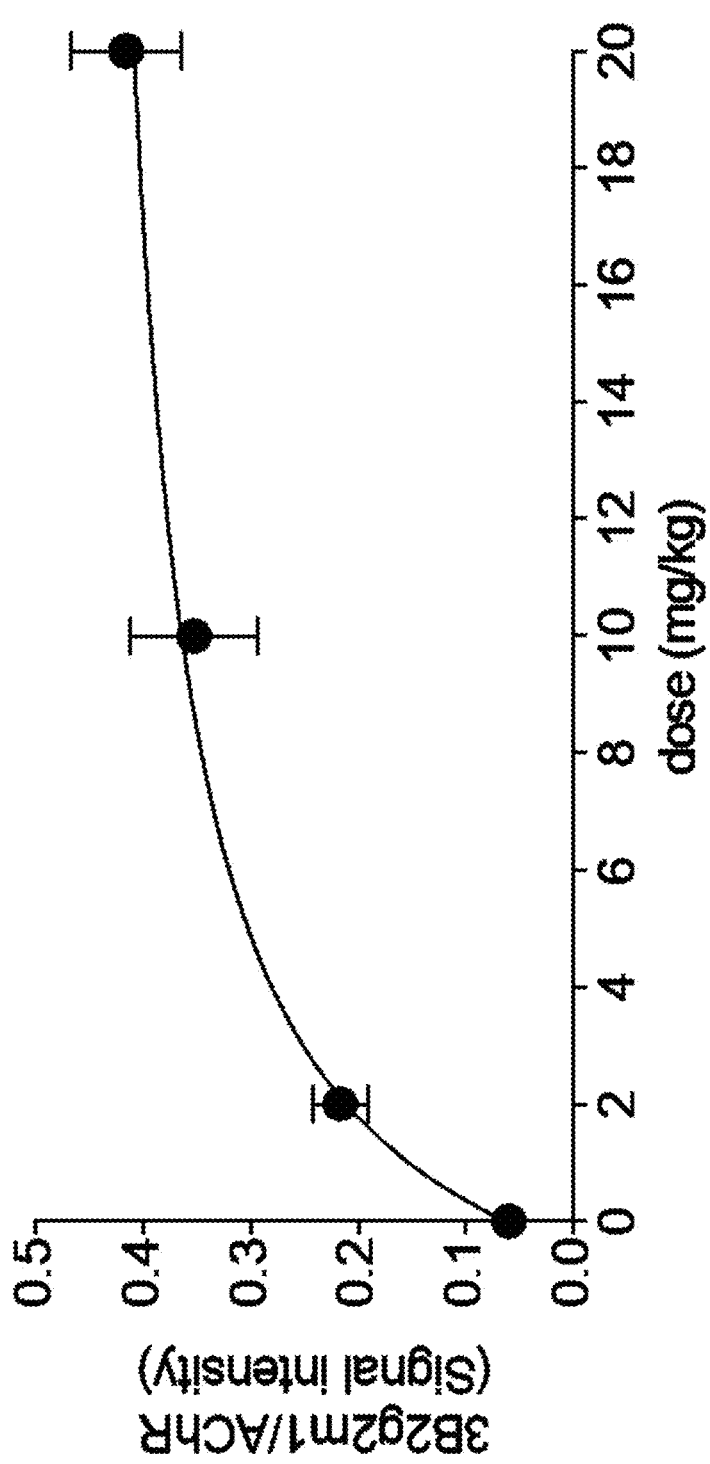

FIG. 50 demonstrates that MuSK agonist antibody 3B2g2m1 engages MuSK at the synapse and saturates MuSK at 20 mg/kg. P30 wildtype mice were injected intraperitoneally with MuSK agonist antibody 3B2g2m1 (0, 2, 10, 20 mg/kg). Two days later, mice were sacrificed and diaphragm muscles were stained with Alexa 488-α-BGT to label AChRs and Alexa 647 Goat Anti-Human IgG, F(ab)₂ fragment specific to label 3B2g2m1. Levels of saturation of 3B2g2m1 at the synapse were measured by the ratio of 3B2g2m1 to AChR signal intensity. The mean±SEM values from 3 mice at each concentration are shown.

Figure 51A:
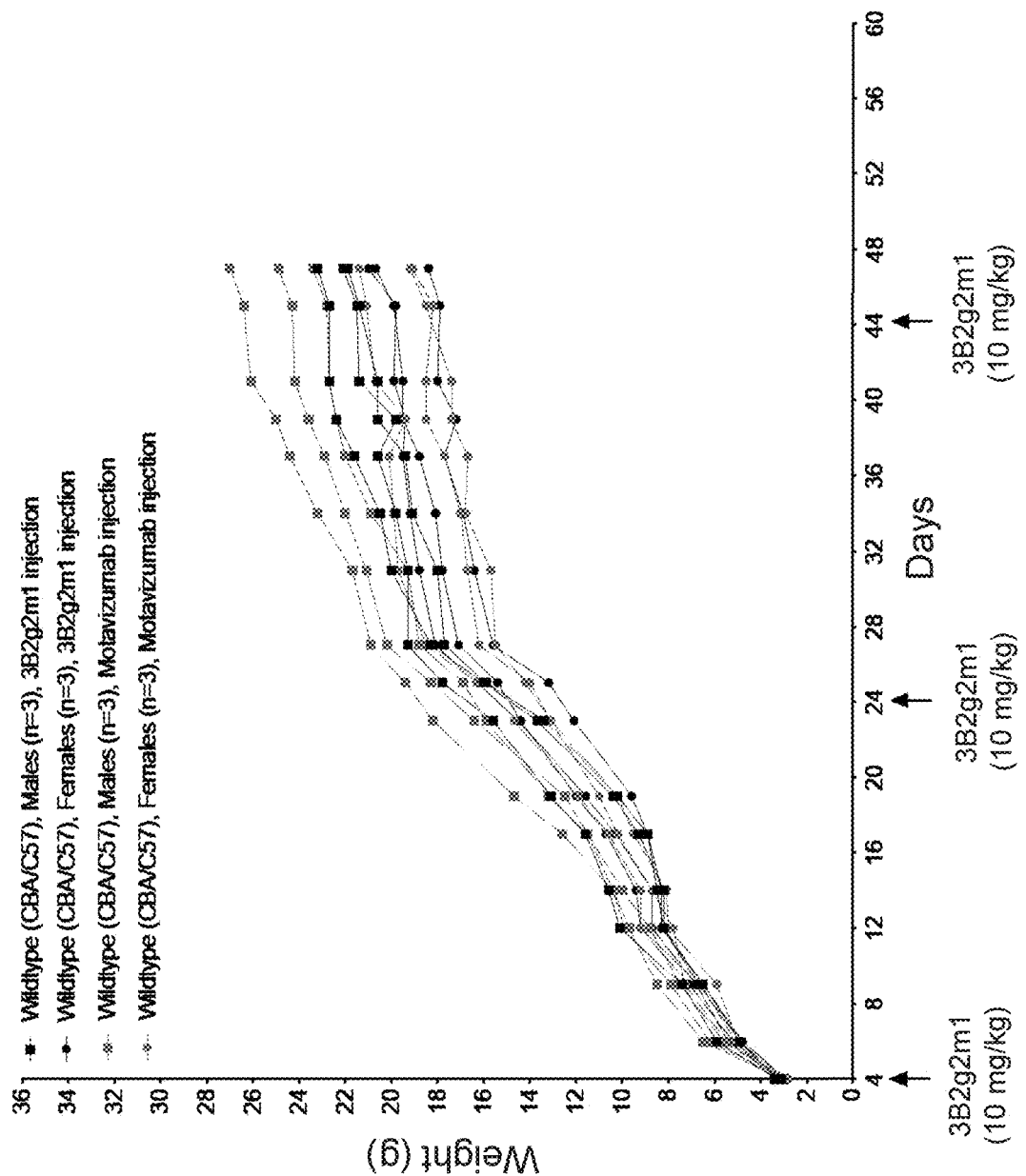
Figure 51B:
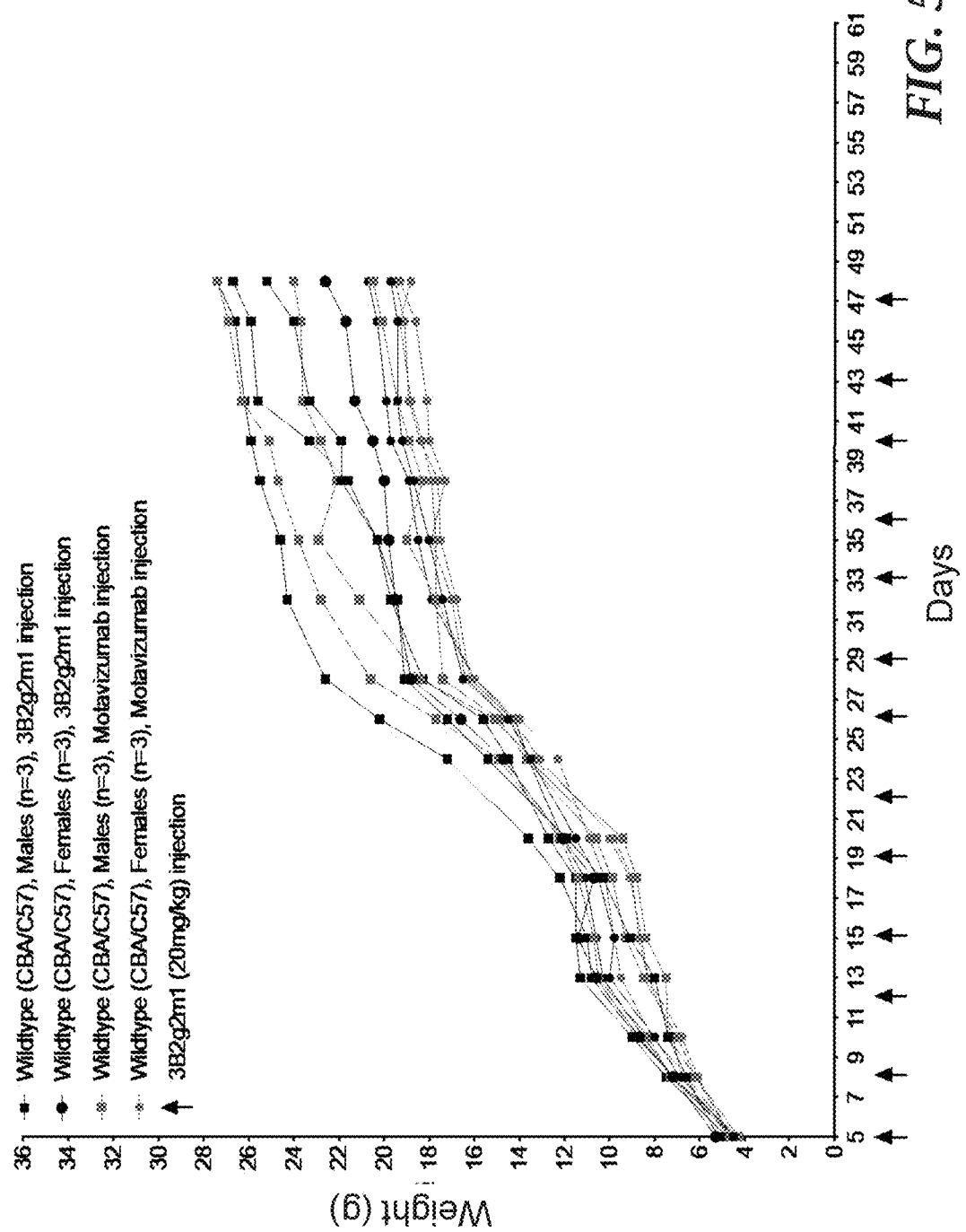

FIGS. 51A-51B demonstrate that chronic injection of 3B2g2m1 in wildtype mice has no effect on survival or weight gain. FIG. 51A is a scatter plot showing that wildtype mice in a C57BL/6-CBA mixed background, injected at P4, P24, and P44 with 10 mg/kg 3B2g2m1 (n=6) survived and gained weight like wildtype mice injected at P4, P24, and P44 with 10 mg/kg of an isotype equivalent negative control, Motavizumab (n=6). FIG. 51B is a scatter plot showing that wildtype mice in a C57BL/6-CBA mixed background, injected two times a week starting at P4 with 20 mg/kg 3B2g2m1 (n=6), survived and gained weight like wildtype mice, injected two times a week starting at P4 with 20 mg/kg of an isotype equivalent negative control, Motavizumab (n=6).

Figure 52A:
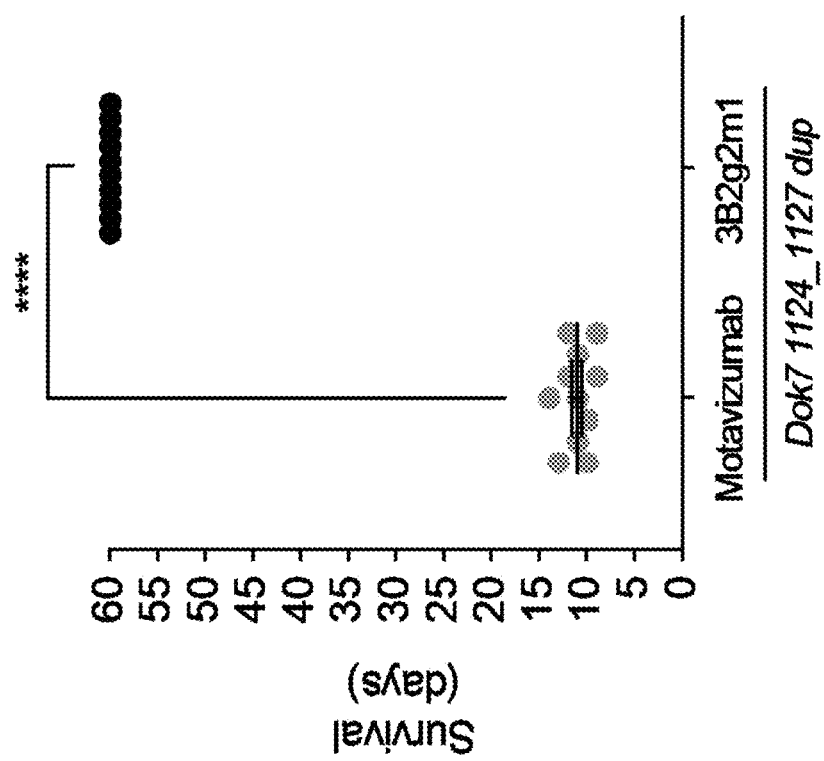
Figure 52B:
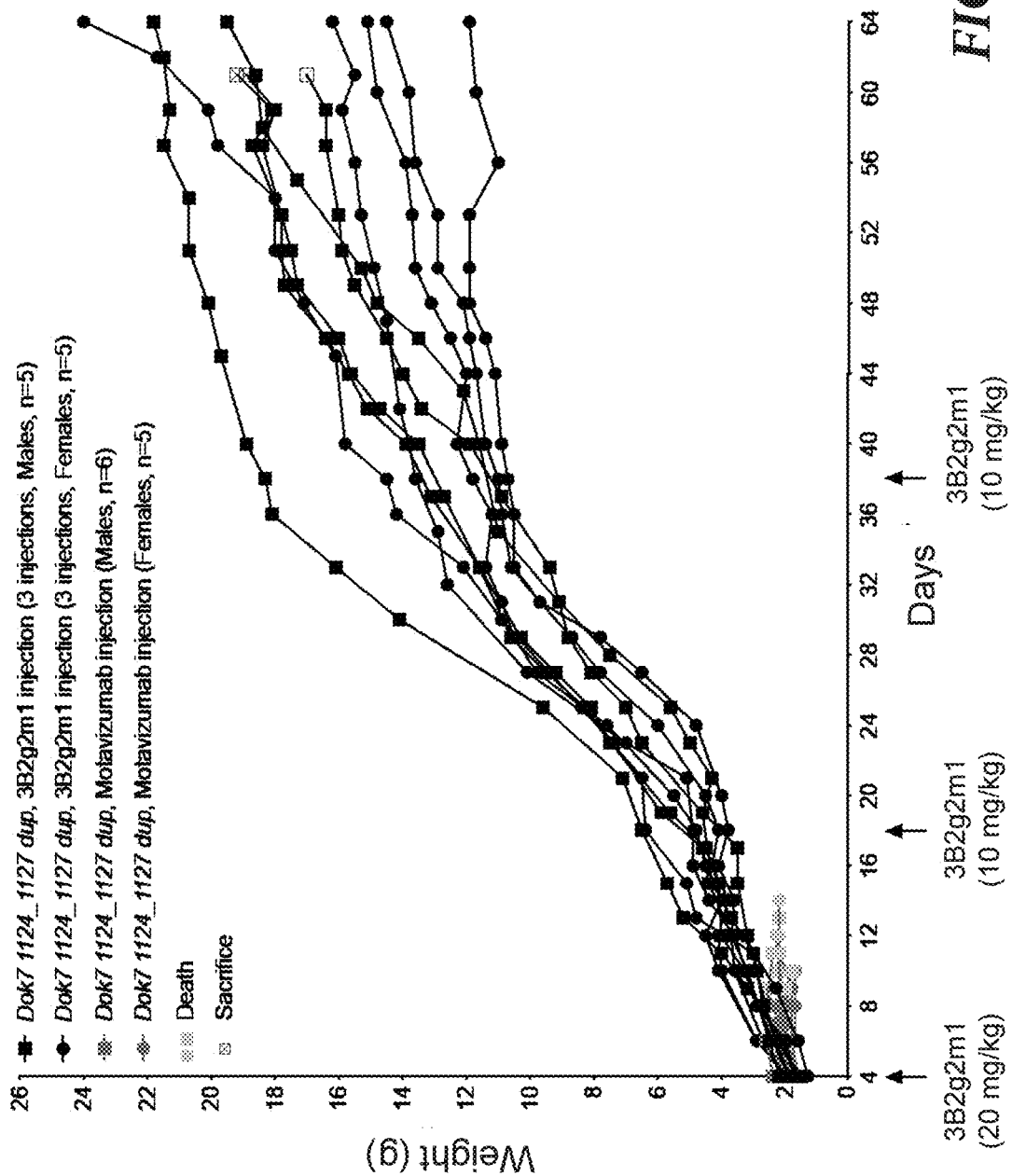

FIGS. 52A-52B demonstrate that agonist antibody to MuSK, 3B2g2m1, rescues lethality in young Dok7 1124_1127 dup mice. FIG. 52A is a scatter plot showing that Dok7 1124_1127 dup mice in a C57BL/6-CBA mixed background survive for one to two weeks postnatally. Dok7 1124_1127 dup mice in the mixed background were treated at P4 with agonist antibody 3B2g2m1 or an isotype equivalent negative control, Motavizumab. Dok7 1124_1127 dup mice (n=11) injected with the isotype control, like untreated mice, died one to two weeks after birth, whereas Dok7 1124_1127 dup mice injected with 3B2g2m1 (n=10) at P4 (20 mg/kg), P18 (10 mg/kg), and P38 (10 mg/kg) survived as adults. 3 of 10 mutant mice injected with 3B2g2m1 were sacrificed at P60; 7 mutant mice were aged for disease relapse experiments. The scatter plot shows the survival time for each mouse and the mean±SEM values (p, ****<0.00005). FIG. 52B is a scatter plot showing that Dok7 1124_1127 dup mice, injected with 3B2g2m1 gained weight, unlike Dok7 1124_1127 dup mice treated with the isotype control antibody. Dok7 1124_1127 dup mice were injected with 3B2g2m1 at P4 (20 mg/kg), P18 (10 mg/kg) and P44 (10 mg/kg).

Figure 53:
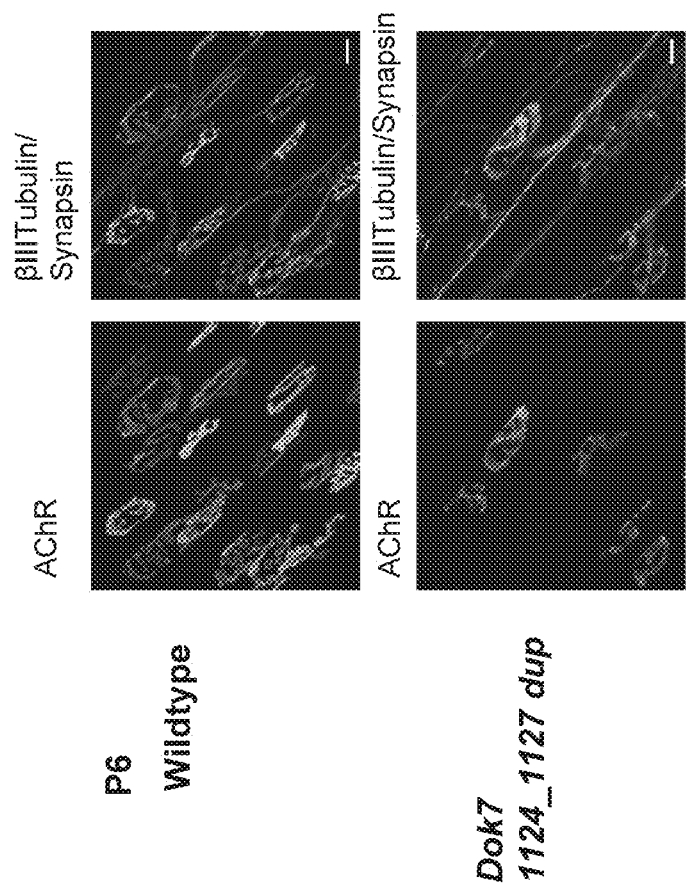
Figure 53:
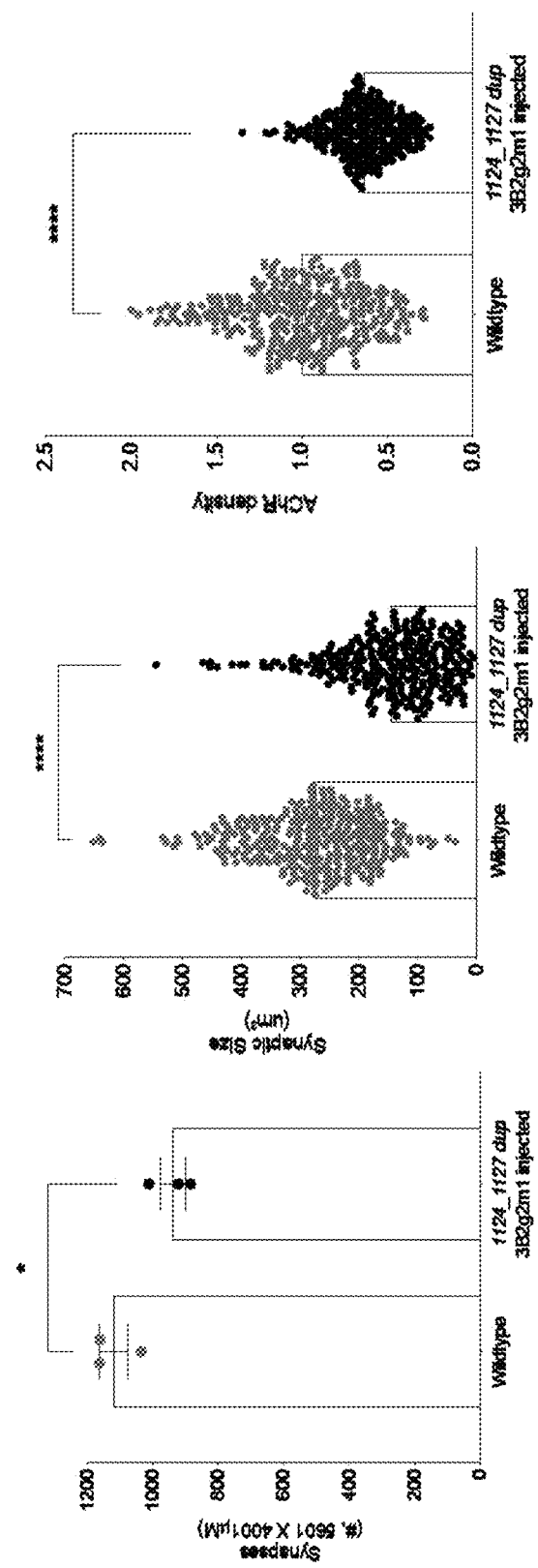

FIG. 53 demonstrates that 3B2g2m1 restores synapse development in young Dok7 1124_1127 dup mice. Diaphragm muscles from P60 wildtype and Dok7 1124_1127 dup mice were stained with Alexa 488-α-BGT to label AChRs and antibodies to βIIITubulin/Synapsin to label motor axons/nerve terminals. In Dok7 1124_1127 dup mice treated with 3B2g2m1, synapses matured from a simple, plaque-like shape to a complex, pretzel-like shape, characteristic of mature murine neuromuscular synapses. Scale bar=10 mm. In Dok7 1124_1127 dup mice treated with 3B2g2m1, the number of synapses, synaptic size and density of synaptic AChRs and were restored to 80%, 50%, and 60%, respectively, of normal levels. The mean±SEM values from 3 mice (>50 synapses per mouse) are shown (p, *<0.05, ****<0.00005).

Figure 54:
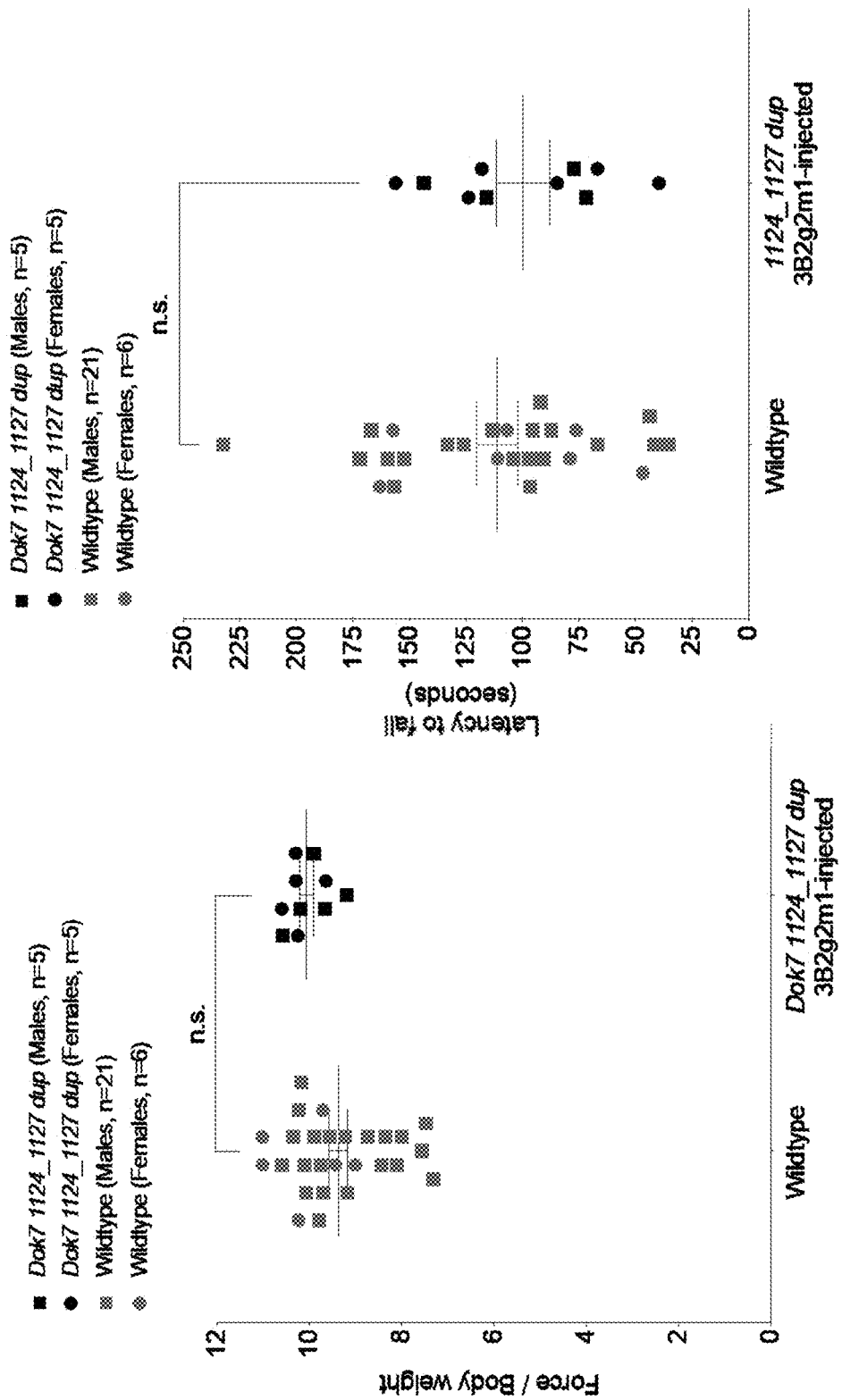

FIG. 54 demonstrates that 3B2g2m1 rescues motor performance of Dok7 1124_1127 dup mice. Motor performance of Dok7 1124_1127 dup mice, as assessed by grip strength (left panel) and the latency to fall from a rotating rotarod (right panel), were fully restored by treatment with 3B2g2m1. The scatter plots show the values for 27 wildtype mice and 10 Dok7 1124_1127 dup mice rescued with 3B2g2m1 and the mean±SEM values (n.s., not significant).

Figure 55:
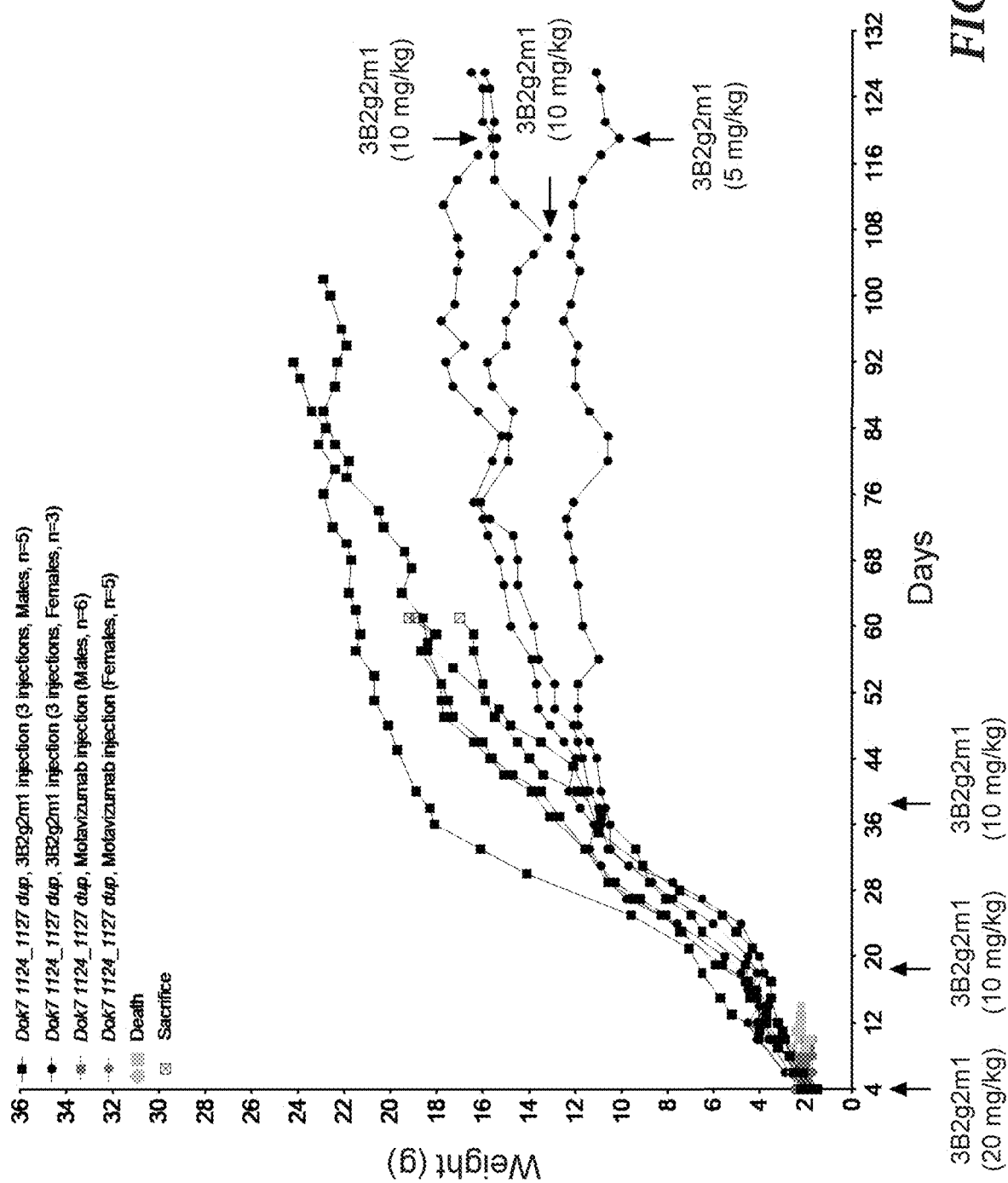

FIG. 55 demonstrates that 3B2g2m1 maintains Dok7 1124_1127 dup mice healthy for at least two months. Dok7 1124_1127 dup mice were injected with 3B2g2m1 at P4, P18, and P38 and then discontinued antibody treatment. These Dok7 1124_1127 dup mice gained weight and maintained their mobility for several months but ultimately began to lose weight. At this time, the mice were re-injected with either 5 mg/kg, or 10 mg/kg of 3B2g2m1. After restarting 3B2g2m1 treatment, the Dok7 1124_1127 dup mouse began to gain weight.

Figure 56A:
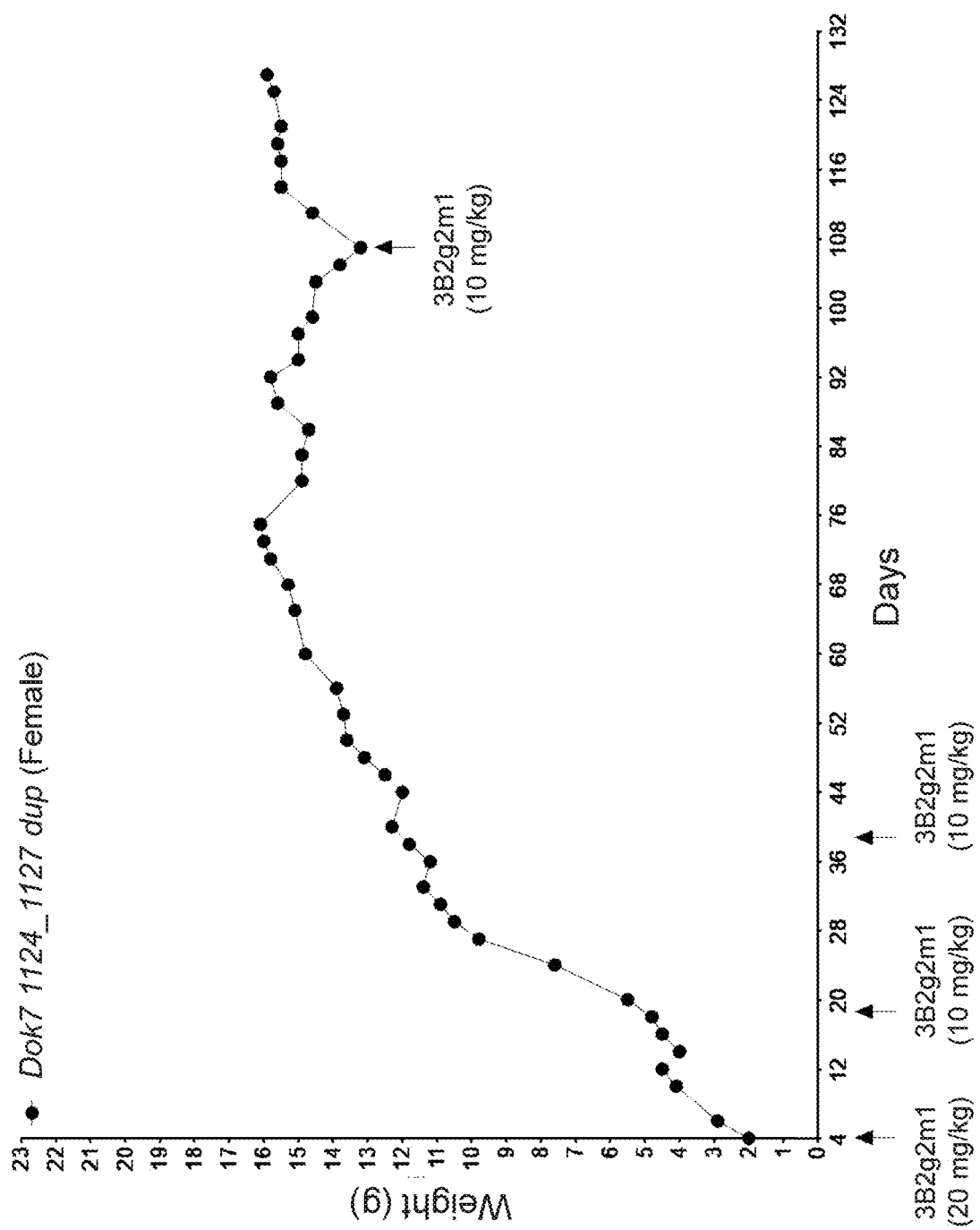
Figure 56B:
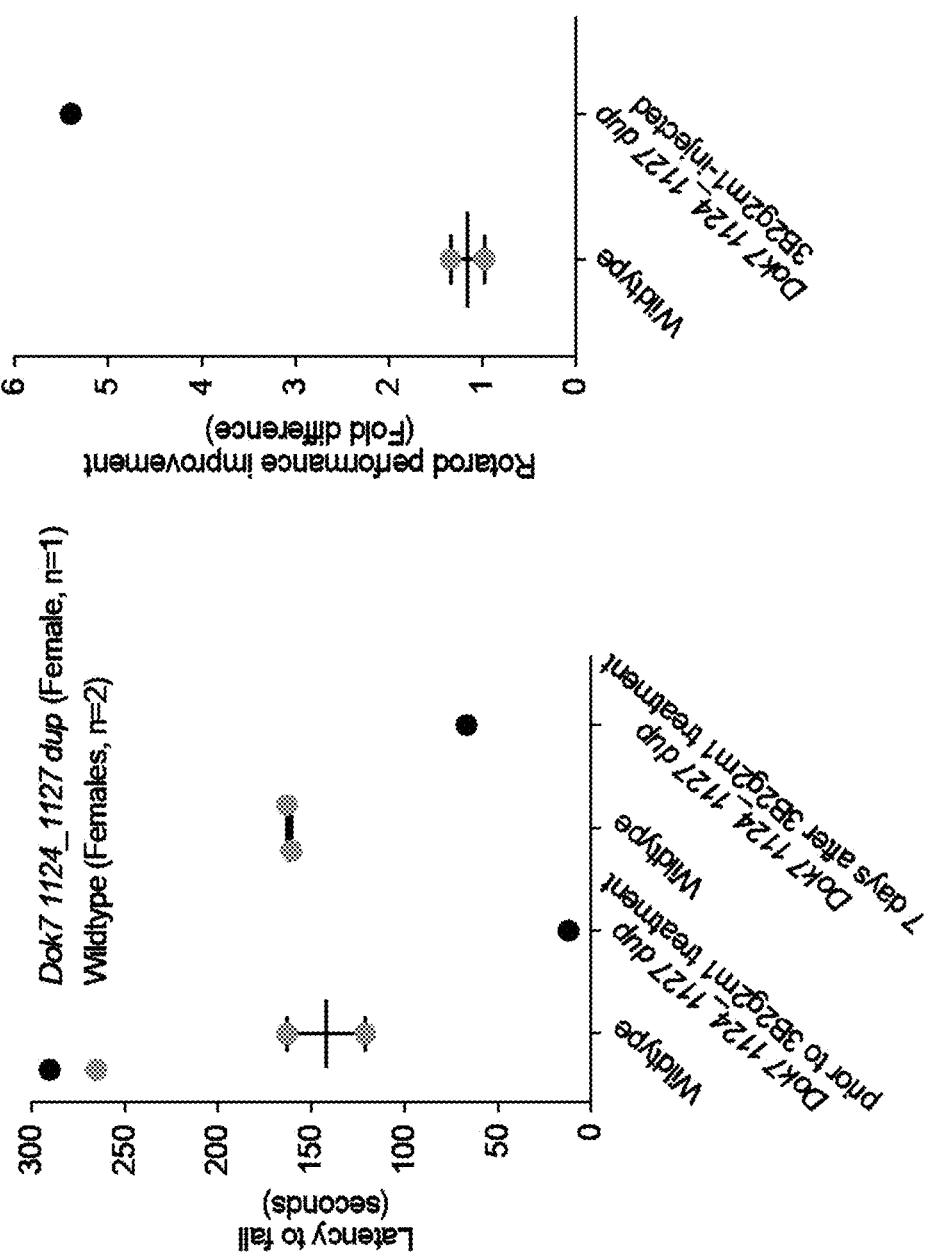
Figure 56C:
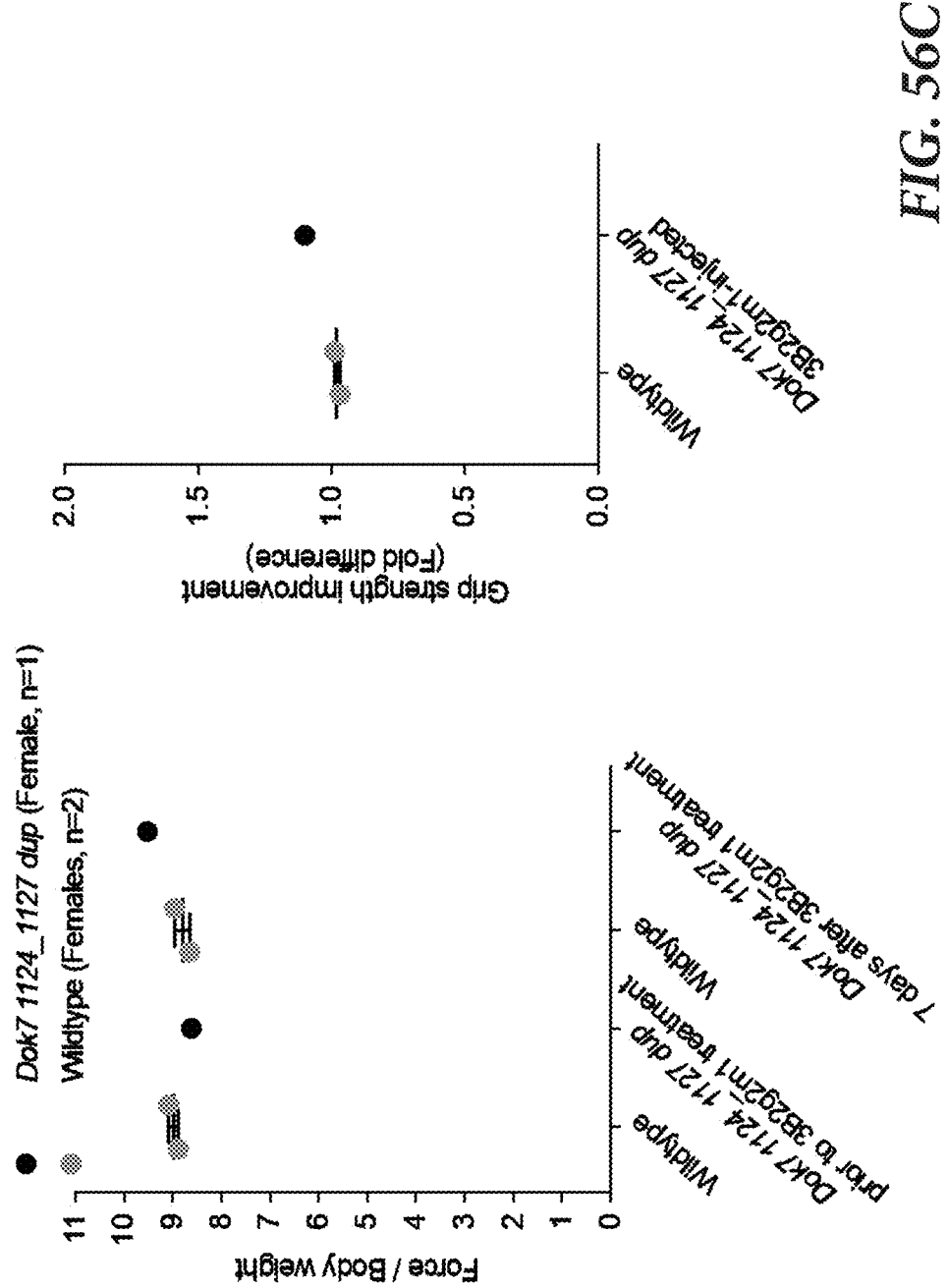

FIGS. 56A-56C demonstrate that 3B2g2m1 reverses disease relapse in adult Dok7 1124_1127 dup mice. A Dok7 1124_1127 dup mouse was injected with 3B2g2m1 at P4, P18, and P38, and then discontinued antibody treatment. This Dok7 1124_1127 dup mouse gained weight and maintained its mobility for several months but ultimately began to lose weight (FIG. 56A) and to display motor deficits, as assessed by grip strength and the latency to fall from a rotating rotarod (FIG. 56B). At this time, the mouse was re-injected with 3B2g2m1 (FIG. 56A). After restarting 3B2g2m1 treatment, the Dok7 1124_1127 dup mouse began to gain weight (FIG. 56A), and by a week after restarting treatment its motor deficits were reversed (FIG. 56B-56C). Dok7 1124_1127 dup mice improved their performance on the rotarod by 5.5-fold (FIG. 56B), and their grip strength by 1.1-fold (FIG. 56C).

Figure 57:
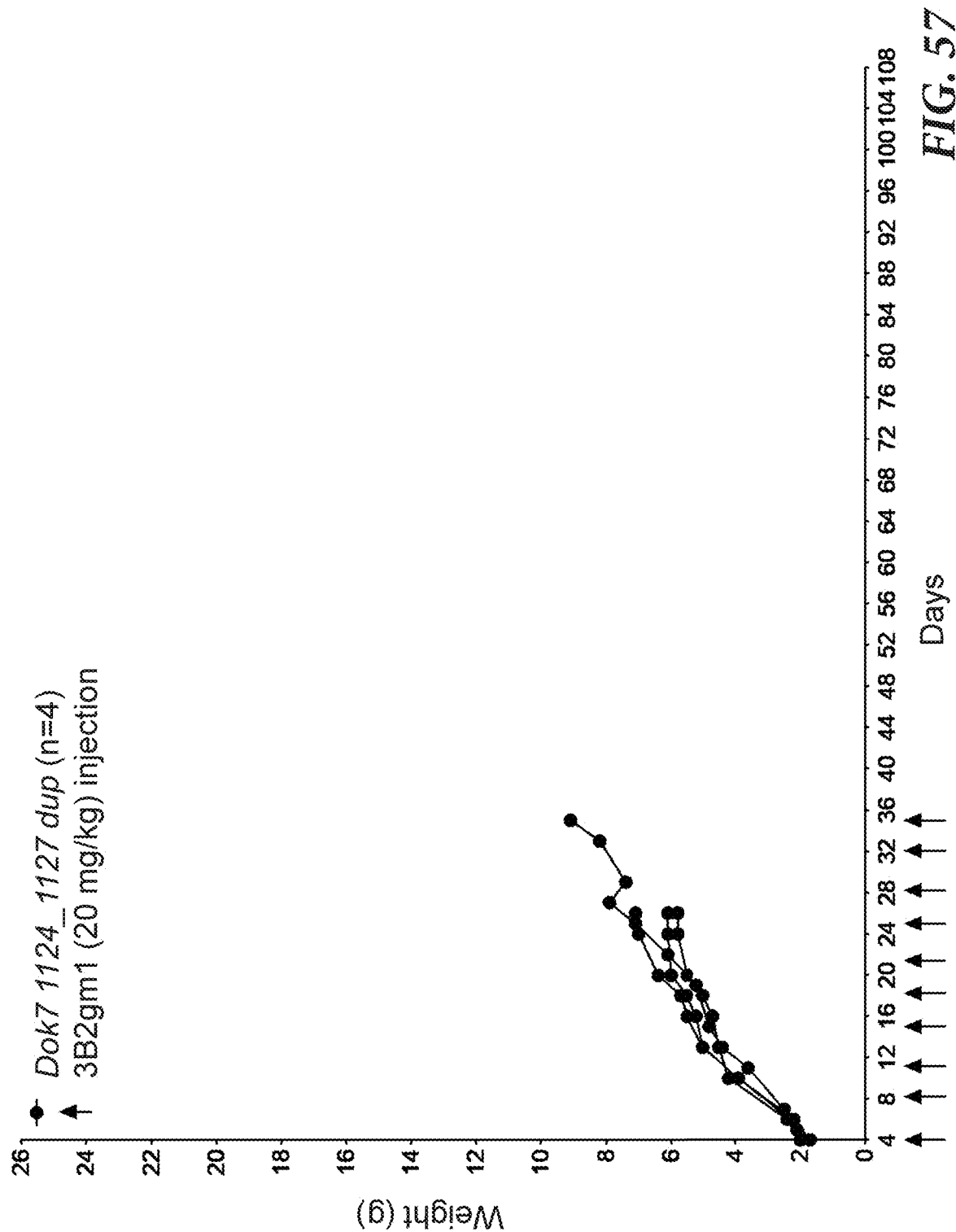

FIG. 57 demonstrates that agonist antibody to MuSK, 3B2g2m1, rescues lethality in young Dok7 1124_1127 dup mice (chronic dose 2 times a week). FIG. 57 demonstrates that Dok7 1124_1127 dup mice in a C57BL/6-CBA mixed background survive for one to two weeks postnatally. Dok7 1124_1127 dup mice in the mixed background were treated twice a week starting at P4 with agonist antibody 3B2g2m1 (20 mg/kg). Dok7 1124_1127 dup mice injected with 3B2g2m1 (n=4) survived as adults and gained weight.

Figure 58A:
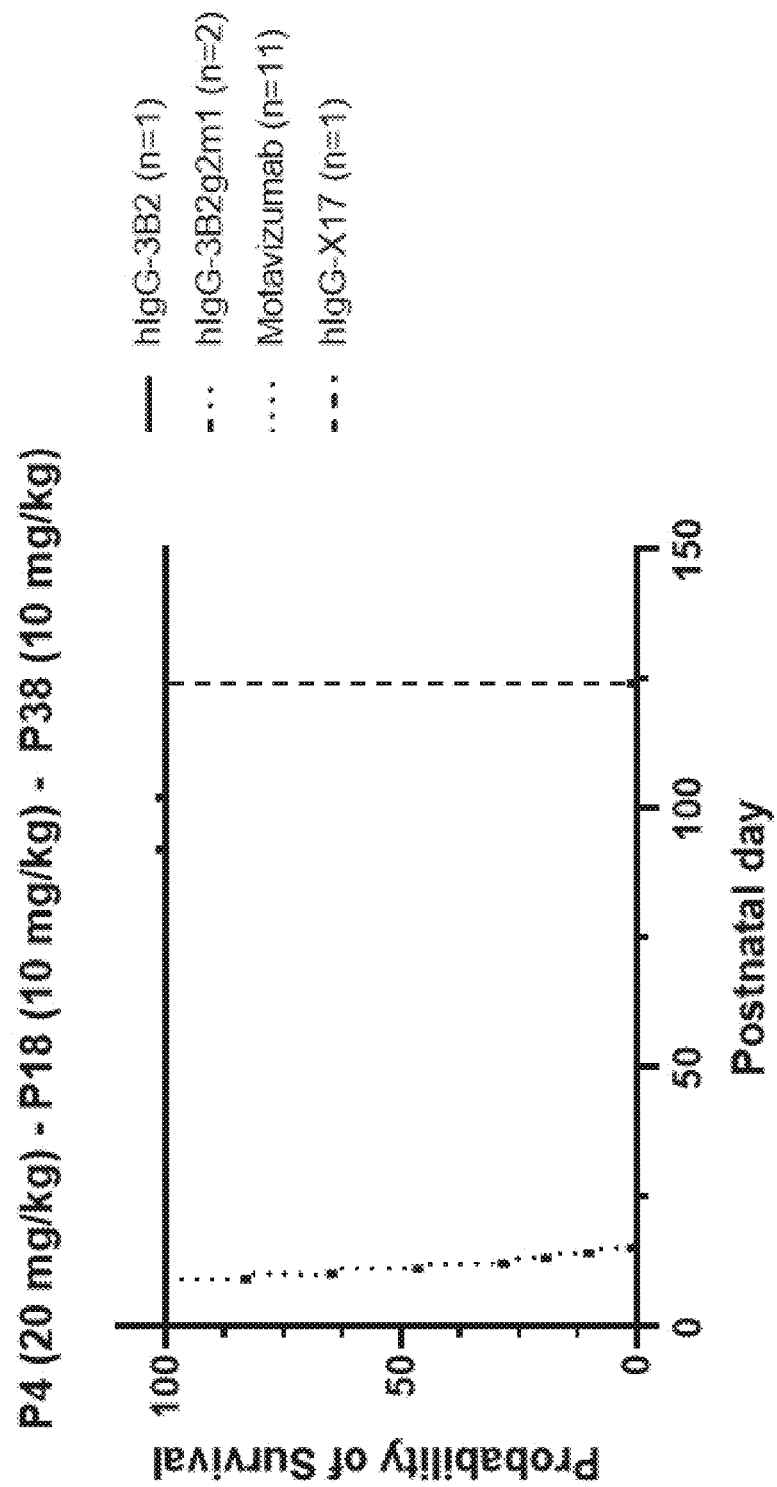
Figure 58B:
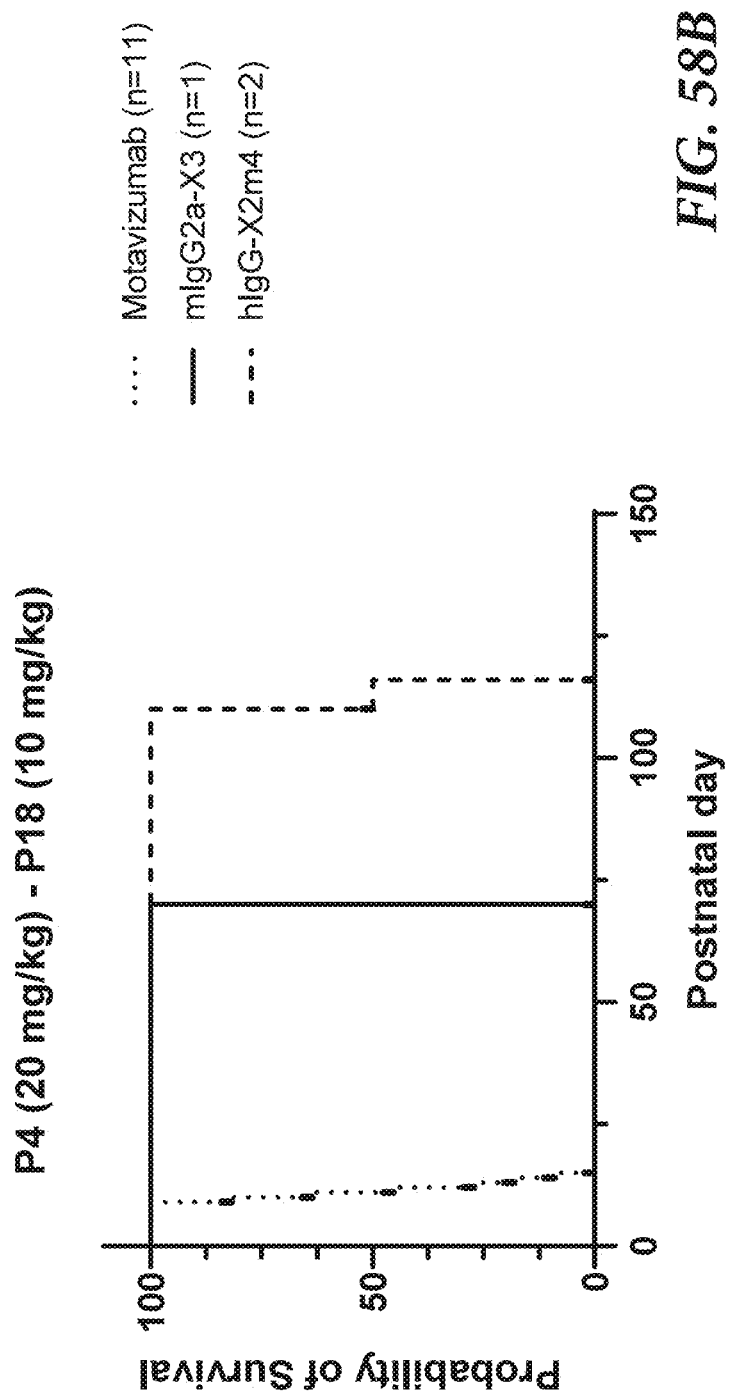
Figure 58C:
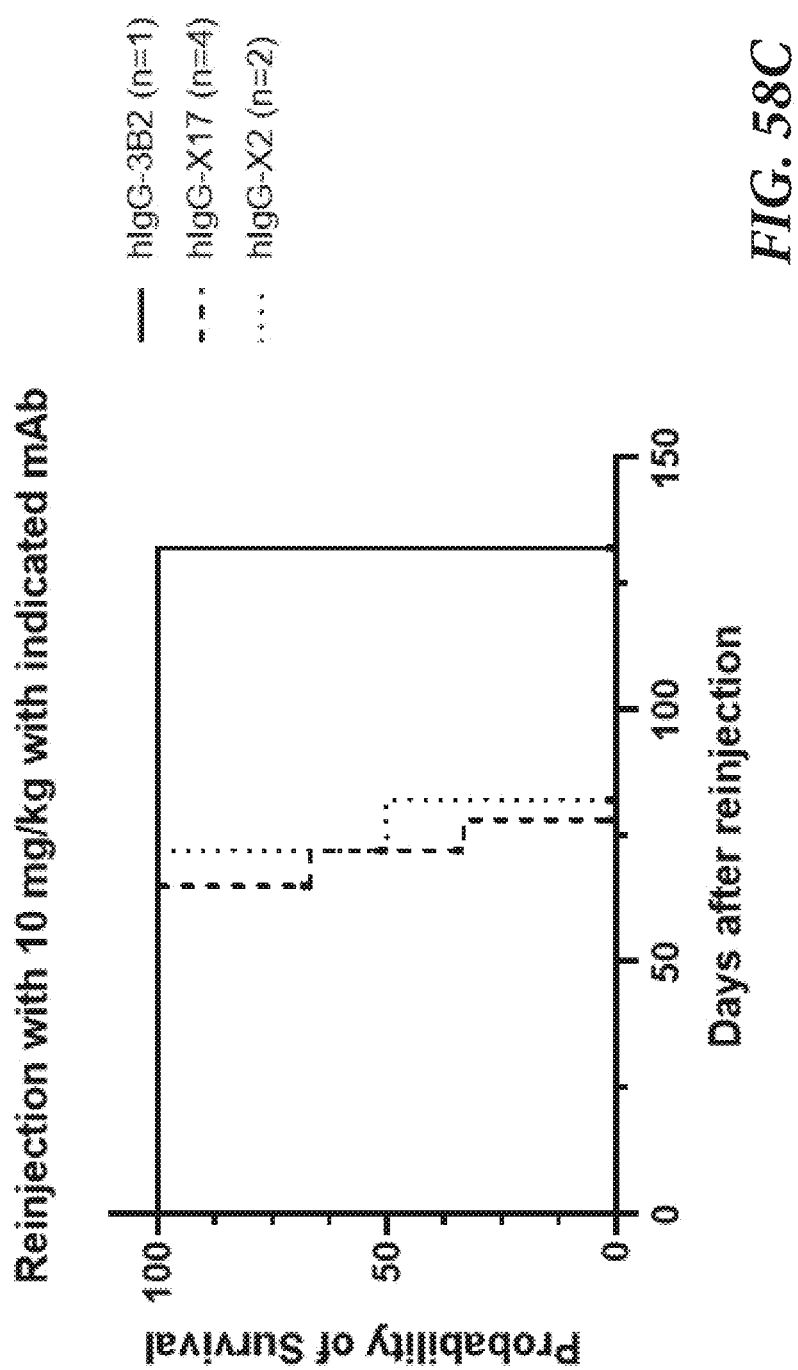

FIGS. 58A-58C show MuSK antibody treatment extends survival of Dok7 1124_1127 dup mice. FIG. 58A shows survival plots for Dok7 1124_1127 dup mice injected with the indicated MuSK agonist antibodies or isotype control (Motavizumab) at P4 (20 mg/kg), P18 (10 mg/kg), and P38 (10 mg/kg). FIG. 58B shows survival plots for Dok7 1124_1127 dup mice injected with MuSK agonist antibodies or isotype control (Motavizumab) at P4 (20 mg/kg), P18 (10 mg/kg). FIG. 58C shows survival plots for Dok7 1124_1127 dup mice reinjected (restarted treatment) with the indicated MuSK agonist antibodies (10 mg/kg) upon several days of body weight loss (FIG. 58C) were generated. These results demonstrate that injection of a MuSK agonist antibody extends survival of Dok7 1124_1127 dup mice.

DETAILED DESCRIPTION

General Definitions

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the singular forms "a", "an", and "the" include both singular and plural referents unless the context clearly dictates otherwise.

The terms "comprising", "comprises" and "comprised of" as used herein are synonymous with 'including', 'includes' or 'containing', 'contains', and are inclusive or open-ended and do not exclude additional, non-recited members, compounds, products, elements or method steps. The expression "essentially consists of" used in the context of a product or a composition ("a product essentially consisting of" or "a composition essentially consisting of") means that additional molecules may be present but that such molecule does not change/alter the characteristic/activity/functionality of said product or composition. For example, a composition may essentially consist of an antibody or an antibody fragment if the composition as such would exhibit similar characteristic/activity/functionality as one of the antibody or as the one of the antibody fragments.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, amino acid residues will be indicated either by their full name or according to the standard three-letter or one-letter amino acid code.

As used herein, the terms "polypeptide" or "protein" are used interchangeably, and refer to a polymeric form of amino acids of any length, which can include coded and non-coded amino acids, chemically or biochemically modified or derivatized amino acids, and polypeptides having modified peptide backbones. A "peptide" is also a polymer of amino acids with a length which is usually of up to 50 amino acids. A polypeptide or peptide is represented by an amino acid sequence.

As used herein, the terms "nucleic acid molecule", "polynucleotide", "polynucleic acid", "nucleic acid" are used interchangeably and refer to polymeric form of nucleotides of any length, either deoxyribonucleotides or ribonucleotides, or analogs thereof. A nucleic acid molecule is represented by a nucleic acid sequence, which is primarily characterized by its base sequence. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "homology" denotes at least secondary structural identity or similarity between two macromolecules, particularly between two polypeptides or polynucleotides, from same or different taxons, wherein said similarity is due to shared ancestry. Hence, the term 'homologues' denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence similarity between two amino acid sequences, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions have been already exemplified herein. Amino acid sequences and nucleic acid sequences are said to be 'exactly the same' if they have 100% sequence identity over their entire length.

Throughout this application, each time one refers to a specific amino acid sequence SEQ ID NO (take SEQ ID NO: Y as example), one may replace it by: a polypeptide comprising an amino acid sequence that has at least 80% sequence identity or similarity with amino acid sequence SEQ ID NO: Y. Throughout this application, the wording "a sequence is at least X % identical with another sequence" may be replaced by "a sequence has at least X % sequence identity with another sequence".

Each amino acid sequence described herein by virtue of its identity percentage (at least 80%) with a given amino acid sequence respectively has in a further preferred embodiment an identity of at least 80%, 81%, 82%, 83%, 84%, 85%, 86%, 87%, 88%, 89%, 90%, 91%, 92%, 93%, 94%, 95%, 96%, 97%, 98%, 99% or more identity with the given amino acid sequence respectively. In a preferred embodiment, sequence identity is determined by comparing the whole length of the sequences as identified herein. Each amino acid sequence described herein by virtue of its similarity percentage (at least 80%) with a given amino acid sequence respectively has in a further preferred embodiment a similarity of at least 80%, 81%, 82%, 83%, 84%, 85%, 86%, 87%, 88%, 89%, 90%, 91%, 92%, 93%, 94%, 95%, 96%, 97%, 98%, 99% or more similarity with the given amino acid sequence respectively. In a preferred embodiment, sequence similarity is determined by comparing the whole length of the sequences as identified herein. Unless otherwise indicated herein, identity or similarity with a given SEQ ID NO means identity or similarity based on the full length of said sequence (i.e. over its whole length or as a whole).

"Sequence identity" is herein defined as a relationship between two or more amino acid (polypeptide or protein) sequences or two or more nucleic acid (polynucleotide) sequences, as determined by comparing the sequences. The identity between two amino acid sequences is preferably defined by assessing their identity within a whole SEQ ID NO as identified herein or part thereof. Part thereof may mean at least 50% of the length of the SEQ ID NO, or at least 60%, or at least 70%, or at least 80%, or at least 90%.

In the art, "identity" also means the degree of sequence relatedness between amino acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., *Nucleic Acids Research* 12 (1): 387 (1984)), BestFit, FASTA, BLASTN, and BLASTP (Altschul, S. F. et al., J. Mol. Biol. 215:403-410 (1990)), EMBOSS Needle (Madeira, F., et al., *Nucleic Acids Research* 47(W1): W636-W641 (2019)). The BLAST program is publicly available from NCBI and other sources (BLAST Manual, Altschul, S., et al., NCBI NLM NIH Bethesda, Md. 20894; Altschul, S., et al., *J. Mol. Biol.* 215:403-410 (1990)). The EMBOSS program is publicly available from EMBL-EBI. The well-known Smith Waterman algorithm may also be used to determine identity. The EMBOSS Needle program is the preferred program used.

Preferred parameters for polypeptide sequence comparison include the following: Algorithm: Needleman and Wunsch, *J. Mol. Biol.* 48 (3):443-453 (1970); Comparison matrix: BLOSUM62 from Henikoff and Henikoff, *Proc. Natl. Acad. Sci. USA.* 89:10915-10919 (1992); Gap Open Penalty: 10; and Gap Extend Penalty: 0.5. A program useful with these parameters is publicly available as the EMBOSS Needle program from EMBL-EBI. The aforementioned parameters are the default parameters for a Global Pairwise Sequence alignment of proteins (along with no penalty for end gaps).

Preferred parameters for nucleic acid comparison include the following: Algorithm: Needleman and Wunsch, *J. Mol. Biol.* 48:443-453 (1970); Comparison matrix: DNAfull; Gap Open Penalty: 10; Gap Extend Penalty: 0.5. A program useful with these parameters is publicly available as the EMBOSS Needle program from EMBL-EBI. The aforementioned parameters are the default parameters for a Global Pairwise Sequence alignment of nucleotide sequences (along with no penalty for end gaps).

Also provided herein are embodiments wherein any embodiment described herein may be combined with any one or more other embodiments, provided the combination is not mutually exclusive.

MuSK Antibody-Based Molecules

The present invention relates to antibody-based molecules, including antibodies, epitope-binding domains thereof, and antibody derivatives as described herein, that are capable of binding and activating the signaling and/or phosphorylation of muscle-specific tyrosine protein kinase (MuSK). Such antibody-based molecules are useful for the treatment of conditions where a subject is in need of increased MuSK signaling or MuSK phosphorylation, such as neuromuscular conditions.

A first aspect of the present invention is directed to an antibody-based molecule that binds an epitope of MuSK. MuSK is a receptor tyrosine kinase that is expressed in skeletal muscle and has a crucial, master role in forming and maintaining neuromuscular synapses (Burden et al., "The Role of MuSK in Synapse Formation and Neuromuscular Disease," *Cold Spring Harb. Perspect. Biol.* 5:a009167 (2013), which is hereby incorporated by reference in its entirety). MuSK is a single pass, 120 kDa transmembrane protein, composed of an extracellular region containing three Ig-like domains and a Frizzled (Fz)-like domain, and an intracellular region containing a juxtamembrane region, a kinase domain and a short cytoplasmic tail (Jennings et al., "Muscle-Specific trk-Related Receptor with a Kringle Domain Defines a Distinct Class of Receptor Tyrosine Kinases," *Proc. Natl. Acad. Sci. USA* 90:2895-2899 (1993) and Valenzuela et al., "Receptor Tyrosine Kinase Specific for the Skeletal Muscle Lineage: Expression in Embryonicmuscle, at the Neuromuscular Junction, and After Injury," *Neuron* 15: 573-584 (1995), which are hereby incorporated by reference in their entirety). MuSK phosphorylation is stimulated by agrin, a signal provided by motor neurons. Once activated, MuSK stimulates pathways that (1) cluster and anchor AChRs and additional muscle proteins critical for synaptic transmission, (2) enhance transcription of genes encoding synaptic proteins in muscle 'synaptic nuclei' and (3) promote the production of retrograde signals that promote presynaptic differentiation and attachment of motor nerve terminals to muscle. In the absence of MuSK, neuromuscular synapses fail to form (Burden et al., "The Role of MuSK in Synapse Formation and Neuromuscular Disease," *Cold Spring Harb. Perspect. Biol.* 5:a009167 (2013), which is hereby incorporated by reference in its entirety). In addition to its role during synapse formation, MuSK is also required to maintain adult synapses, as inhibition of MuSK expression in adult muscle leads to profound defects in presynaptic and postsynaptic differentiation (Kong et al., "Inhibition of Synapse Assembly in Mammalian Muscle in vivo by RNA Interference," *EMBO Rep* 5:183-188 (2004) and Hesser et al., "Synapse Disassembly and Formation of New Synapses in Postnatal Muscle Upon Conditional Inactivation of MuSK," *Mol. Cell. Neurosci.* 31:470-480 (2006), which are hereby incorporated by reference in their entirety). Consistent with these findings in mice, mutations that impair MuSK kinase activity or inhibit signaling steps downstream from MuSK cause myasthenia (CM), characterized by structurally and functionally defective synapses, leading to muscle weakness and fatigue (Beeson et al., "Dok-7 Mutations Underlie a Neuromuscular Junction Synaptopathy," *Science* 313:1975-1978 (2006); Muller et al., "Phenotypical Spectrum of DOK7 Mutations in Congenital Myasthenic Syndromes," *Brain* 130:1497-1506 (2007); and Selcen et al., "A Compensatory Subpopulation of Motor Neurons in a Mouse Model of Amyotrophic Lateral Sclerosis," *J. Comp. Neurol.* 490:209-219 (2008), which are hereby incorporated by reference in their entirely).

The amino acid sequence of human MuSK has the amino acid sequence of SEQ ID NO: 129 below.

(SEQ ID NO: 129)
MRELVNIPLVHILTLVAFSGTEKLPKAPVITTPLETVDALVEEVATFMCA

VESYPQPEISWTRNKILIKLFDTRYSIRENGQLLTILSVEDSDDGIYCCT

ANNGVGGAVESCGALQVKMKPKITRPPINVKIIEGLKAVLPCTTMGNPKP

SVSWIKGDSPLRENSRIAVLESGSLRIHNVQKEDAGQYRCVAKNSLGTAY

SKVVKLEVEVFARILRAPESHNVTFGSFVTLHCTATGIPVPTITWIENGN

AVSSGSIQESVKDRVIDSRLQLFITKPGLYTCIATNKHGEKFSTAKAAAT

ISIAEWSKPQKDNKGYCAQYRGEVCNAVLAKDALVFLNTSYADPEEAQEL

LVHTAWNELKVVSPVCRPAAEALLCNHIFQECSPGVVPTPIPICREYCLA

VKELFCAKEWLVMEEKTHRGLYRSEMHLLSVPECSKLPSMHWDPTACARL

PHLDYNKENLKTFPPMTSSKPSVDIPNLPSSSSSSFSVSPTYSMTVIISI

MSSFAIFVLLTITTLYCCRRRKQWKNKKRESAAVTLTTLPSELLLDRLHP

NPMYQRMPLLLNPKLLSLEYPRNNIEYVRDIGEGAFGRVFQARAPGLLPY

EPFTMVAVKMLKEEASADMQADFQREAALMAEFDNPNIVKLLGVCAVGKP

MCLLFEYMAYGDLNEFLRSMSPHTVCSLSHSDLSMRAQVSSPGPPPLSCA

EQLCIARQVAAGMAYLSERKFVHRDLATRNCLVGENMVVKIADFGLSRNI

YSADYYKANENDAIPIRWMPPESIFYNRYTTESDVWAYGVVLWEIFSYGL

QPYYGMAHEEVIYYVRDGNILSCPENCPVELYNLMRLCWSKLPADRPSFT

SIHRILERMCERAEGTVSV

In accordance with the present invention, the MuSK antibody-based molecules described herein bind to an epitope within the Frizzled (Fz)-like domain of the MuSK protein. The Fz-like domain of MuSK has the amino acid sequence of SEQ ID NO: 130 as shown below.

(SEQ ID NO: 130)
DNKGYCAQYRGEVCNAVLAKDALVFLNTSYADPEEAQELLVHTAWNELKV

VSPVCRPAAEALLCNHIFQECSPGVVPTPIPICREYCLAVKELFCAKEWL

VMEEKTHRGLYRSEMHLLSVPECSKLPSMHWDPTACARL

The term "epitope" as used herein refers to an antigenic determinant capable of being bound to an antibody. Epitopes usually comprise surface groupings of molecules such as amino acids or sugar side chains and usually have specific three dimensional structural characteristics, as well as specific charge characteristics. Conformational and non-conformational epitopes are distinguished in that the binding to the former, but not the latter, is lost in the presence of denaturing solvents. An epitope may comprise amino acid residues directly involved in the binding (also called the immunodominant component of the epitope) and other amino acid residues, which are not directly involved in the binding, such as amino acid residues that are effectively blocked by the specific antigen-binding peptide (in other words, the amino acid residue is within the footprint of the specific antigen-binding peptide). An epitope typically includes at least 3, and more usually, at least 5, 6, 7, 8, 9, 10, 11, 12, 13, 14, 15, 16, 17, 18, 19, 20 or more amino acids in a unique spatial conformation.

The MuSK antibody-based molecules of the present invention immunospecifically bind an epitope within the MuSK Fz-like domain sequence of SEQ ID NO: 130 more frequently, more rapidly, with greater duration and/or with greater affinity or avidity than an alternative epitope. In an embodiment, the MuSK antibody-based molecules described herein bind immunospecifically to any 2, 3, 4, 5, 6, 7, 8, 9, 10 or more amino acid residues of SEQ ID NO: 130. The term "affinity", "specific binding", "binding", "immunospecific binding", "binding activity" or "specific binding activity", as used herein, refers to the degree to which an antibody or an antibody fragment as defined herein binds to an epitope within the MuSK-Fz-like domain sequence of SEQ ID NO:130.

In an embodiment, the MuSK antibody-based molecules as disclosed herein bind to the MuSK Fz-like domain with an affinity corresponding to a $K_D$ of about $10^{-7}$ M or less. For example, the MuSK antibody-based molecules disclosed herein bind to the MuSK Fz-like domain with an affinity corresponding to a $K_D$ of about $10^{-8}$ M, of about $10^{-9}$ M, of about $10^{-10}$ M, of about $10^{-11}$ M, of about $10^{-12}$ M or less when determined by, for instance, surface plasmon resonance (SPR) technology in a Biacore 3000 instrument (preferably using the antibody as the ligand and MuSK as the analyte). The MuSK antibody-based molecules as disclosed herein bind to the MuSK Fz-like domain with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., bovine serum albumin, casein, etc.). The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$k_d$" ($sec^{-1}$ or 1/s), as used herein, refers to the dissociation rate constant of a particular antibody-antigen interaction. The value is also referred to as the $k_{off}$ value. The term "$k_a$" ($M^{-1} \times sec^{-1}$ or 1/M), as used herein, refers to the association rate constant of a particular antibody-antigen interaction. The term "$K_D$" (M), as used herein, refers to the dissociation equilibrium constant of a particular antibody-antigen interaction and is obtained by dividing the kd by the ka. The term "$K_A$" ($M^{-1}$ or 1/M), as used herein, refers to the association equilibrium constant of a particular antibody-antigen interaction and is obtained by dividing the $k_a$ by the $k_d$.

In an embodiment, the MuSK antibody-based molecules described herein have a pH-dependent binding affinity for MuSK that allows for antibody recycling to enhance antigen binding. For example, in an embodiment, the association rate constant or dissociation rate constant may differ under acidic vs. neutral vs. basic pH conditions. In one embodiment, the MuSK antibody-based molecules described herein have a higher dissociation rate constant under acidic pH conditions, e.g., pH of <7.0, compared to neutral pH conditions, e.g., pH of ~7.0-7.9. In some embodiments, the MuSK antibody-based molecules described herein have a 2-fold to 3-fold higher dissociation rate constant (i.e., decreased binding affinity) at an acidic pH (e.g., pH ~5.5) as compared to a neutral pH. (pH ~7.4). In an embodiment, the MuSK antibody-based molecules bind the MuSK Fz-like domain with a higher affinity at neutral pH conditions than at acidic pH conditions. In other words, in an embodiment, the MuSK antibody-based molecules binds the MuSK Fz-like domain with a higher dissociation rate at acidic pH conditions than under neutral pH conditions. Neutral pH conditions may be defined as being a pH comprised from 7.0 to 7.9. Acidic pH conditions may be defined as being a pH being less than 7.0. Higher may mean at least 10%, 20%, 30%, 40%, 50%, 60%, 70%, 80%, 90%, 100%, 150%, 200%, 250%, 300% higher. Antibodies having this pH dependent dissociation characteristic dissociate from the antigen after binding and activation but before lysosomal degradation. Once dissociated, the antibody is transported via the neonatal Fc receptor back into circulation and is released to bind more antigen.

Binding of the MuSK antibodies of the present invention to their respective epitopes within the Fz-like domain activates MuSK signaling. In particular, when the MuSK antibodies of the present invention bind their respective epitope of the MuSK Fz-like domain, this binding induces MuSK phosphorylation and activation as described supra. The MuSK antibodies of the present invention induce MuSK phosphorylation by about 50% to about 100% relative to MuSK phosphorylation induced by agrin activation (as measured, e.g., in a C2C12 phosphorylation assay as described herein). In an embodiment, the MuSK antibodies of the present invention induce about 55%, 60%, 65%, 70%, 75%, 80%, 85%, 90%, 95% or 100% 95% MuSK phosphorylation (relative to MuSK phosphorylation induced by agrin activation). In an embodiment, the MuSK antibody-based molecules of the present invention induce about 90% to about 100% MuSK phosphorylation (relative to MuSK phosphorylation induced by agrin activation), upon MuSK binding. Phosphorylation of MuSK may be assessed using techniques known to the skilled person such as western blotting. The phosphorylation assay described in the Examples herein (i.e., the C2C12 myotube phosphorylation assay) can also be used to assess phosphorylation.

In some embodiments, the MuSK antibodies of the present invention, i.e., MuSK antibodies that bind to the Fz-domain of MuSK, do not interfere (i.e., do not block, impede, inhibit, or reduce) with natural ligand binding and stimulation of MuSK. In some embodiments, the MuSK antibodies co-stimulate MuSK activation with its natural ligand, i.e., agrin, to produce an additive effect of activation, e.g., MuSK phosphorylation. Thus, in some embodiments, the MuSK antibodies of the present invention potentiate natural MuSK activation, i.e., phosphorylation, induced by natural ligand binding. In some embodiments, the antibodies of the invention, in combination with the natural ligand, activate MuSK (i.e., MuSK phosphorylation) to >100% of endogenous activation levels such as at least 110%, 130%, 150%, 200% of endogenous activation levels. Phosphorylation of MuSK may be assessed as indicated earlier.

Accordingly, in an embodiment, activities of the MuSK antibody-based molecules of the invention include: (i) binding to an epitope of human muscle-specific tyrosine-protein kinase (MuSK), said epitope present in the MuSK Frizzled (Fz)-like domain sequence of SEQ ID NO: 130, wherein said antibody-based molecule induces MuSK phosphorylation upon binding to its epitope, and/or (ii) binding to the MuSK Fz-like domain does not block, impede, or inhibit natural or endogenous MuSK ligand induced phosphorylation, and may potentiate said natural or endogenous MuSK ligand induced phosphorylation, and (iii) binding to the MuSK Fz-like domain occurs with a higher affinity at neutral pH conditions than at acidic pH conditions.

All these features have been further defined herein.

Antibody-based molecules include, without limitation full antibodies, epitope binding fragments of whole antibodies, and antibody derivatives. An epitope binding fragment of an antibody can be obtained through the actual fragmenting of a parental antibody (for example, a Fab or (Fab)$_2$ fragment). Alternatively, the epitope binding fragment is an amino acid sequence that comprises a portion of the amino acid sequence of such parental antibody. As used herein, a molecule is said to be a "derivative" of an antibody (or relevant portion thereof) if it is obtained through the actual chemical modification of a parent antibody or portion thereof, or if it comprises an amino acid sequence that is substantially similar to the amino acid sequence of such parental antibody or relevant portion thereof (for example, differing by less than 30%, less than 20%, less than 10%, or less than 5% from such parental molecule or such relevant portion thereof, or by 10 amino acid residues, or by fewer than 10, 9, 8, 7, 6, 5, 4, 3 or 2 amino acid residues from such parental molecule or relevant portion thereof).

In an embodiment, an antibody-based molecule of the present invention is an intact immunoglobulin or a molecule having an epitope-binding fragment thereof. As used herein, the terms "fragment", "region", "portion", and "domain" are generally intended to be synonymous, unless the context of their use indicates otherwise. Naturally occurring antibodies typically comprise a tetramer, which is usually composed of at least two heavy (H) chains and at least two light (L) chains. Each heavy chain is comprised of a heavy chain variable ($V_H$) region and a heavy chain constant (CH) region, usually comprised of three domains ($C_H1$, $C_H2$ and $C_H3$ domains). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable ($V_L$) region and a light chain constant (CO region. Light chains include kappa chains and lambda chains. The heavy and light chain variable regions are typically responsible for antigen recognition, while the heavy and light chain constant regions may mediate the binding of the immunoglobulin to host tissues or factors, including various cells of the immune system (e.g., effector cells) and the first component (Clq) of the classical complement system. The $V_H$ and $V_L$ regions can be further subdivided into regions of hypervariability, termed "complementarity determining regions," or "CDRs," that are interspersed with regions of more conserved sequence, termed "framework regions" (FR). Each $V_H$ and $V_L$ region is composed of three CDR domains and four FR domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally-occurring antibody in amino acid sequence.

Fragments of antibodies (including Fab and (Fab)$_2$ fragments) that exhibit epitope-binding ability can be obtained, for example, by protease cleavage of intact antibodies. Single domain antibody fragments possess only one variable domain (e.g., $V_L$ or $V_H$). Examples of the epitope-binding fragments encompassed within the present invention include (i) Fab' or Fab fragments, which are monovalent fragments containing the $V_L$, $V_H$, $C_L$ and $C_H1$ domains; (ii) F(ab')2 fragments, which are bivalent fragments comprising two Fab fragments linked by a disulfide bridge at the hinge region; (iii) Fd fragments consisting essentially of the $V_H$ and $C_H1$ domains; (iv) Fv fragments consisting essentially of a $V_L$ and $V_H$ domain, (v) dAb fragments (Ward et al. "Binding Activities Of A Repertoire Of Single Immunoglobulin Variable Domains Secreted From *Escherichia coli*," Nature 341:544-546 (1989), which is hereby incorporated by reference in its entirety), which consist essentially of a $V_H$ or $V_L$ domain and also called domain antibodies (Holt et al. "Domain Antibodies: Proteins For Therapy," Trends Biotechnol. 21(11):484-490 (2003), which is hereby incorporated by reference in its entirety); (vi) nanobodies (Revets et al. "Nanobodies As Novel Agents For Cancer Therapy," Expert Opin. Biol. Ther. 5(1):111-124 (2005), which is hereby incorporated by reference in its entirety), and (vii) isolated complementarity determining regions (CDR). An epitope-binding fragment may contain 1, 2, 3, 4, 5 or all 6 of the CDR domains of such antibody. In an embodiment, a fragment (or region or portion or domain) of an antibody comprises, essentially consists of, or consists of 30 to 100 amino acids or 50 to 150 amino acids or 70 to 200 amino acids. In an embodiment, the length of a fragment (or region or portion or domain) of an antibody is at least 40%, 50%, 60%, 70%, 80%, 90% or 95% of the length of the antibody (full length antibody). In an embodiment, a fragment is an epitope binding fragment or a functional fragment of said antibody meaning it is expected it will elicit an activity of the antibody at least to some extent. "At least to some extent" may mean at least 20%, 30%, 40%, 50%, 60%, 70%, 80%, 90%, 95%, 100%, 150%, 200% or more. In an embodiment, the fragment of the antibody or the antibody should elicit a detectable activity of the antibody. An activity of the antibody has been earlier defined herein.

Such antibody fragments may be obtained using conventional techniques known to those of skill in the art. For example, F(ab')2 fragments may be generated by treating a full-length antibody with pepsin. The resulting F(ab')2 fragment may be treated to reduce disulfide bridges to produce Fab' fragments. Fab fragments may be obtained by treating an IgG antibody with papain and Fab' fragments may be obtained with pepsin digestion of IgG antibody. A Fab' fragment may be obtained by treating an F(ab')2 fragment with a reducing agent, such as dithiothreitol. Antibody fragments may also be generated by expression of nucleic acids encoding such fragments in recombinant cells (see e.g., Evans et al. "Rapid Expression Of An Anti-Human C5 Chimeric Fab Utilizing A Vector That Replicates In COS And 293 Cells," J. Immunol. Meth. 184:123-38 (1995), which is hereby incorporated by reference in its entirety). For example, a chimeric gene encoding a portion of a F(ab')2 fragment could include DNA sequences encoding the CH1 domain and hinge region of the heavy chain, followed by a translational stop codon to yield such a truncated antibody fragment molecule. Suitable fragments capable of binding to a desired epitope may be readily screened for utility in the same manner as an intact antibody.

Antibody derivatives include those molecules that contain at least one epitope-binding domain of an antibody, and are typically formed using recombinant techniques. One exemplary antibody derivative includes a single chain Fv (scFv). A scFv is formed from the two domains of the Fv fragment, the $V_L$ region and the $V_H$ region, which may be encoded by separate genes. Such gene sequences or their encoding cDNA are joined, using recombinant methods, by a flexible linker (typically of about 10, 12, 15 or more amino acid residues) that enables them to be made as a single protein chain in which the $V_L$ and $V_H$ regions associate to form monovalent epitope-binding molecules (see e.g., Bird et al. "Single-Chain Antigen-Binding Proteins," Science 242:423-426 (1988); and Huston et al. "Protein Engineering Of Antibody Binding Sites: Recovery Of Specific Activity In An Anti-Digoxin Single-Chain Fv Analogue Produced In *Escherichia coli,*" *Proc. Natl. Acad. Sci. (U.S.A.)* 85:5879-5883 (1988), which are hereby incorporated by reference in their entirety). Alternatively, by employing a flexible linker that is not too short (e.g., not less than about 9 residues) to enable the $V_L$ and $V_H$ regions of a different single polypeptide chains to associate together, one can form a bispecific antibody, having binding specificity for two different epitopes.

In another embodiment, the antibody derivative is a divalent or bivalent single-chain variable fragment, engineered by linking two scFvs together either in tandem (i.e., tandem scFv), or such that they dimerize to form a diabody (Holliger et al. "Diabodies': Small Bivalent And Bispecific Antibody Fragments," *Proc. Natl. Acad. Sci. (U.S.A.)* 90(14), 6444-8 (1993), which is hereby incorporated by reference in its entirety). In yet another embodiment, the antibody is a triabody, i.e., a trivalent single chain variable fragment, engineered by linking three scFvs together, either in tandem or in a trimer formation to form a triabody. In another embodiment, the antibody is a tetrabody of four single chain variable fragments. In another embodiment, the antibody is a "linear antibody" which is an antibody comprising a pair of tandem Fd segments ($V_H$-$C_H$1-$V_H$-$C_H$1) that form a pair of antigen binding regions (see Zapata et al. *Protein Eng.* 8(10):1057-1062 (1995), which is hereby incorporated by reference in its entirety). In another embodiment, the antibody derivative is a minibody, consisting of the single-chain Fv regions coupled to the $C_H$3 region (i.e., scFv-$C_H$3).

These and other useful antibody fragments and derivatives in the context of the present invention are discussed further herein. It also should be understood that the term antibody-based molecule, unless specified otherwise, also includes antibody-like polypeptides, such as chimeric antibodies and humanized antibodies, and antibody fragments retaining the ability to specifically bind to the antigen (epitope-binding fragments or functional fragment) provided by any known technique, such as enzymatic cleavage, peptide synthesis, and recombinant techniques. In an embodiment, the wording "antibody-based molecule" may be replaced by the word "antibody" or by the expression "antibody or a functional fragment thereof".

An antibody as generated herein may be of any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as antibody-dependent cellular cytotoxicity (ADCC) induction. Exemplary isotypes are IgG1, IgG2, IgG3, and IgG4. Particularly useful isotypes of the MuSK antibodies disclosed herein include IgG1 and IgG2.

Either of the human light chain constant regions, kappa or lambda, may be used. If desired, the class of a MuSK antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses.

In an embodiment, the antibody-based molecules of the present invention are "humanized," particularly if they are to be employed for therapeutic purposes. The term "humanized" refers to a chimeric molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild-type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. "Mouse/Human Chimeric Monoclonal Antibody In Man: Kinetics And Immune Response," *Proc. Natl. Acad. Sci. USA* 86:4220-4224 (1989), which is hereby incorporated by reference in its entirety). Another approach focuses not only on providing human-derived constant regions, but modifying the variable regions so as to reshape them as closely as possible to human form. The variable regions of both heavy and light chains contain three complementarity-determining regions (CDRs) which vary in response to the antigens in question and determine binding capability. The CDRs are flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody onto the FRs present in the human antibody to be modified. Suitable methods for humanizing the non-human antibody described herein are known in the art see e.g., Sato, K. et al., *Cancer Res* 53:851-856 (1993); Riechmann, L. et al., "Reshaping Human Antibodies for Therapy," *Nature* 332:323-327 (1988); Verhoeyen, M. et al., "Reshaping Human Antibodies: Grafting An Antilysozyme Activity," *Science* 239:1534-1536 (1988); Kettleborough, C. A. et al., "Humanization Of A Mouse Monoclonal Antibody By CDR-Grafting: The Importance Of Framework Residues On Loop Conformation," *Protein Engineering* 4:773-3783 (1991); Maeda, H. et al., "Construction Of Reshaped Human Antibodies With HIV-Neutralizing Activity," *Human Antibodies Hybridoma* 2:124-134 (1991); Gorman, S. D. et al., "Reshaping A Therapeutic CD4 Antibody," *Proc. Natl.*

Acad. Sci. USA 88:4181-4185 (1991); Tempest, P. R. et al., "Reshaping A Human Monoclonal Antibody To Inhibit Human Respiratory Syncytial Virus Infection In Vivo," *Bio/Technology* 9:266-271 (1991); Co, M. S. et al., "Humanized Antibodies For Antiviral Therapy," *Proc. Natl. Acad. Sci. USA* 88:2869-2873 (1991); Carter, P. et al., "Humanization Of An Anti-p185her2 Antibody For Human Cancer Therapy," *Proc. Natl. Acad. Sci. USA* 89:4285-4289 (1992); and Co, M. S. et al., "Chimeric And Humanized Antibodies With Specificity For The CD33 Antigen,"*J. Immunol.* 148: 1149-1154 (1992), which are hereby incorporated by reference in their entirety. In some embodiments, humanized MuSK antibodies of the present invention preserve all CDR sequences (for example, a humanized antibody containing all six CDRs from the llama or mouse antibody). In other embodiments, humanized MuSK antibodies of the present invention have one or more CDRs (one, two, three, four, five, six) which are altered with respect to the original antibody. Methods of humanizing an antibody are well-known in the art and suitable for humanizing the antibodies disclosed herein (see, e.g., U.S. Pat. No. 5,225,539 to Winter; U.S. Pat. Nos. 5,530,101 and 5,585,089 to Queen and Selick; U.S. Pat. No. 5,859,205 to Robert et al.; U.S. Pat. No. 6,407,213 to Carter; and U.S. Pat. No. 6,881,557 to Foote, which are hereby incorporated by reference in their entirety).

In some antibodies only part of a CDR, namely the subset of CDR residues required for binding termed the "specificity determining residues" ("SDRs"), are needed to retain binding of the antibody. CDR residues not contacting antigen and not in the SDRs can be identified based on previous studies from regions of Kabat CDRs lying outside Chothia hypervariable loops (see, Kabat et al., SEQUENCES OF PROTEINS OF IMMUNOLOGICAL INTEREST, National Institutes of Health Publication No. 91-3242 (1992); Chothia, C. et al., "Canonical Structures For The Hypervariable Regions Of Immunoglobulins," *J. Mol. Biol.* 196:901-917 (1987), which are hereby incorporated by reference in their entirety), by molecular modeling and/or empirically, or as described in Gonzales, N. R. et al., "SDR Grafting Of A Murine Antibody Using Multiple Human Germline Templates To Minimize Its Immunogenicity,"*Mol. Immunol.* 41:863-872 (2004), which is hereby incorporated by reference in its entirety. In such humanized antibodies, at positions in which one or more donor CDR residues is absent or in which an entire donor CDR is omitted, the amino acid residue occupying the position can be an amino acid residue occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of non-human amino acids in a humanized antibody and consequently decreasing potential immunogenicity. However, substitutions can also cause changes of affinity, and significant reductions in affinity are preferably avoided. Substitutions may also cause changes of activity. Such substitutions causing a significant reduction in activity are also preferably avoided. In this context, the antibody or antibody fragment should still exhibit a detectable activity of the antibody as earlier defined herein or an activity of the antibody at least to some extent. Positions for substitution within CDRs and amino acids to substitute can also be selected empirically.

Phage display technology can alternatively be used to increase (or decrease) CDR affinity of the antibody-based molecules of the present invention. This technology, referred to as affinity maturation, employs mutagenesis or "CDR walking" and re-selection using the target antigen or an antigenic fragment thereof to identify antibodies having CDRs that bind with higher (or lower) affinity to the antigen when compared with the initial or parental antibody (see, e.g. Glaser et al., "Antibody Engineering By Codon-Based Mutagenesis In A Filamentous Phage Vector System," *J. Immunology* 149:3903-3913 (1992), which is hereby incorporated by reference in its entirety). Mutagenizing entire codons rather than single nucleotides results in a semi-randomized repertoire of amino acid mutations. Libraries can be constructed consisting of a pool of variant clones each of which differs by a single amino acid alteration in a single CDR from another member of such library and which contain variants potentially representing each possible amino acid substitution for each CDR residue. Mutants with increased (or decreased) binding affinity for the antigen can be screened by contacting the immobilized mutants with labeled antigen. Any screening method known in the art can be used to identify variant antibody-based binding molecules with increased or decreased affinity to the antigen (e.g., ELISA) (See Wu, H. et al., "Stepwise In Vitro Affinity Maturation Of Vitaxin, An Alphav Beta3-Specific Humanized mAb," *Proc. Natl. Acad. Sci. USA* 95:6037-6042 (1998); Yelton et al., "Affinity Maturation Of The BR96 Anti-Carcinoma Antibody By Codon-Based Mutagenesis," *J. Immunology* 155:1994 (1995), which are hereby incorporated by reference in their entirety). CDR walking, which randomizes the light chain may be used (see, Schier, R. et al., "Isolation Of Picomolar Affinity Anti-c-erbB-2 Single-Chain Fv By Molecular Evolution Of The Complementarity Determining Regions In The Center Of The Antibody Binding Site," *J. Mol. Biol.* 263:551-567 (1996), which is hereby incorporated by reference in its entirety).

Methods for affinity maturation of the MuSK antibody molecule are described herein and disclosed for example, in Krause, J. C. et al., "An Insertion Mutation That Distorts Antibody Binding Site Architecture Enhances Function of a Human Antibody,"*MBio.* 2(1): e00345-10 (2011); Kuan, C. T. et al., "Affinity-Matured Anti-Glycoprotein NMB Recombinant Immunotoxins Targeting Malignant Gliomas And Melanomas," *Int. J. Cancer* 10.1002/ijc.25645 (2010); Hackel, B. J. et al., "Stability And CDR Composition Biases Enrich Binder Functionality Landscapes," *J. Mol. Biol.* 401(1):84-96 (2010); Montgomery, D. L. et al., "Affinity Maturation And Characterization Of A Human Monoclonal Antibody Against HIV-1 gp41," *MAbs* 1(5):462-474 (2009); Gustchina, E. et al., "Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth," *Virology* 393(1):112-119 (2009); Finlay, W. J. et al., "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," *J. Mol. Biol.* 388(3):541-558 (2009); Bostrom, J. et al., "Improving Antibody Binding Affinity And Specificity For Therapeutic Development," *Methods Mol. Biol.* 525:353-376 (2009); Steidl, S. et al., "In Vitro Affinity Maturation Of Human GM-CSF Antibodies By Targeted CDR-Diversification," *Mol. Immunol.* 46(1): 135-144 (2008); and Barderas, R. et al., "Affinity Maturation Of Antibodies Assisted By In Silico Modeling," *Proc. Natl. Acad. Sci. USA* 105(26):9029-9034 (2008), which are hereby incorporated by reference in their entirety.

In an aspect of the present invention, the MuSK-antibody based molecule as described herein comprises the amino acid sequence of any one, any two, any three, any four, any five, or any six CDRs as provided in Tables 1 and 2 herein.

In one aspect, the antibody-based molecule that binds to human muscle-specific tyrosine-protein kinase (MuSK) comprises a heavy chain variable region, where the heavy chain variable region comprises: (i) a complementarity-determining region 1 (CDR-H1) comprising an amino acid sequence of any one of SEQ ID NOs: 1-16, 135, 136, 147-149 or a modified amino acid sequence of any one of SEQ ID NOs: 1-16, 135, 136, or 147-149 said modified sequence having at least 80% sequence identity to any one of SEQ ID NOs: 1-16, 135, 136 or 147-149; (ii) a complementarity-determining region 2 (CDR-H2) comprising an amino acid sequence of any one of SEQ ID NOs: 17-32, 137, 138, 150-155 or a modified amino acid sequence of any one of SEQ ID NOs: 17-32, 137, 138, or 150-155 said modified sequences having at least 80% sequence identity to any one of SEQ ID NOs: 17-32, 137, 138, or 150-155; and (iii) a complementarity-determining region 3 (CDR-H3) comprising an amino acid sequence of any one of SEQ ID NOs: 33-48, 139, 140, 156-158, 240-251, or a modified amino acid sequence of any one of SEQ ID NO: 33-48, 139, 140, 156-158, or 240-251, said modified sequence having at least 80% sequence identity to any one of SEQ ID NOs: 33-48, 139, 140, 156-158, or 240-251.

In an embodiment, the antibody-based molecule that binds to human muscle-specific tyrosine-protein kinase (MuSK) comprises: (i) a heavy chain variable region comprising the CDR-H1 of SEQ ID NO: 1, the CDR-H2 of SEQ ID NO: 17, and the CDR-H3 of SEQ ID NO: 33; (ii) a heavy chain variable region comprising the CDR-H1 of SEQ ID NO: 2, the CDR-H2 of SEQ ID NO: 18, and the CDR-H3 of SEQ ID NO: 34; (iii) a heavy chain variable region comprising the CDR-H1 of SEQ ID NO: 3, the CDR-H2 of SEQ ID NO: 19, and the CDR-H3 of SEQ ID NO: 35; (iv) a heavy chain variable region comprising the CDR-H1 of SEQ ID NO: 4, the CDR-H2 of SEQ ID NO: 20, and the CDR-H3 of SEQ ID NO: 36; (v) a heavy chain variable region comprising the CDR-H1 of SEQ ID NO: 5, the CDR-H2 of SEQ ID NO: 21, and the CDR-H3 of SEQ ID NO: 37; (vi) a heavy chain variable region comprising the CDR-H1 of SEQ ID NO: 6, the CDR-H2 of SEQ ID NO: 22, and the CDR-H3 of SEQ ID NO: 38; (vii) a heavy chain variable region comprising the CDR-H1 of SEQ ID NO: 7, the CDR-H2 of SEQ ID NO: 23, and the CDR-H3 of SEQ ID NO: 39; (viii) a heavy chain variable region comprising the CDR-H1 of SEQ ID NO: 8, the CDR-H2 of SEQ ID NO: 24, and the CDR-H3 of SEQ ID NO: 40; (ix) a heavy chain variable region comprising the CDR-H1 of SEQ ID NO: 9, the CDR-H2 of SEQ ID NO: 25, and the CDR-H3 of SEQ ID NO: 41; (x) a heavy chain variable region comprising the CDR-H1 of SEQ ID NO: 10, the CDR-H2 of SEQ ID NO: 26, and the CDR-H3 of SEQ ID NO: 42; (xi) a heavy chain variable region comprising the CDR-H1 of SEQ ID NO: 11, the CDR-H2 of SEQ ID NO: 27, and the CDR-H3 of SEQ ID NO: 43; (xii) a heavy chain variable region comprising the CDR-H1 of SEQ ID NO: 12, the CDR-H2 of SEQ ID NO: 28, and the CDR-H3 of SEQ ID NO: 44; (xiii) a heavy chain variable region comprising the CDR-H1 of SEQ ID NO: 13, the CDR-H2 of SEQ ID NO: 29, and the CDR-H3 of SEQ ID NO: 45; (xiv) a heavy chain variable region comprising the CDR-H1 of SEQ ID NO: 14, the CDR-H2 of SEQ ID NO: 30, and the CDR-H3 of SEQ ID NO: 46; (xv) a heavy chain variable region comprising the CDR-H1 of SEQ ID NO: 15, the CDR-H2 of SEQ ID NO: 31, and the CDR-H3 of SEQ ID NO: 47; (xvi) a heavy chain variable region comprising the CDR-H1 of SEQ ID NO: 16, the CDR-H2 of SEQ ID NO: 32, and the CDR-H3 of SEQ ID NO: 48; (xvii) a heavy chain variable region comprising the CDR-H1 of SEQ ID NO: 135, the CDR-H2 of SEQ ID NO: 137, and the CDR-H3 of SEQ ID NO: 139; and (xviii) a heavy chain variable region comprising the CDR-H1 of SEQ ID NO: 136, the CDR-H2 of SEQ ID NO: 138, and the CDR-H3 of SEQ ID NO: 140. The sequences of the heavy chain CDR sequences are provided in Table 1 below.

In an embodiment, the antibody-based molecule that binds to human muscle-specific tyrosine-protein kinase (MuSK) comprises: (ii.a) a heavy chain variable region comprising the CDR-H1 of SEQ ID NO: 2, the CDR-H2 of SEQ ID NO: 18, and the CDR-H3 of SEQ ID NO: 240 (X2m1); (ii.b) a heavy chain variable region comprising the CDR-H1 of SEQ ID NO: 2, the CDR-H2 of SEQ ID NO: 18, and the CDR-H3 of SEQ ID NO: 241 (X2m2); (ii.c) a heavy chain variable region comprising the CDR-H1 of SEQ ID NO: 2, the CDR-H2 of SEQ ID NO: 18, and the CDR-H3 of SEQ ID NO: 242 (X2m3); (ii.d) a heavy chain variable region comprising the CDR-H1 of SEQ ID NO: 2, the CDR-H2 of SEQ ID NO: 18, and the CDR-H3 of SEQ ID NO: 243 (X2m4); (ii.e) a heavy chain variable region comprising the CDR-H1 of SEQ ID NO: 2, the CDR-H2 of SEQ ID NO: 18, and the CDR-H3 of SEQ ID NO: 244 (X2m5); (ii.f) a heavy chain variable region comprising the CDR-H1 of SEQ ID NO: 2, the CDR-H2 of SEQ ID NO: 18, and the CDR-H3 of SEQ ID NO: 245 (X2m6); (ii.g) a heavy chain variable region comprising the CDR-H1 of SEQ ID NO: 2, the CDR-H2 of SEQ ID NO: 18, and the CDR-H3 of SEQ ID NO: 246 (X2m7); (ii.h) a heavy chain variable region comprising the CDR-H1 of SEQ ID NO: 2, the CDR-H2 of SEQ ID NO: 18, and the CDR-H3 of SEQ ID NO: 247 (X2m8).

In an embodiment, the antibody-based molecule that binds to human muscle-specific tyrosine-protein kinase (MuSK) comprises: (xvii.a) a heavy chain variable region comprising the CDR-H1 of SEQ ID NO: 135, the CDR-H2 of SEQ ID NO: 137, and the CDR-H3 of SEQ ID NO: 248 (X17m1); (xvii.b) a heavy chain variable region comprising the CDR-H1 of SEQ ID NO: 135, the CDR-H2 of SEQ ID NO: 137, and the CDR-H3 of SEQ ID NO: 249 (X17m2); (xvii.c) a heavy chain variable region comprising the CDR-H1 of SEQ ID NO: 135, the CDR-H2 of SEQ ID NO: 137, and the CDR-H3 of SEQ ID NO: 250 (X17m3); (xvii.d) a heavy chain variable region comprising the CDR-H1 of SEQ ID NO: 135, the CDR-H2 of SEQ ID NO: 137, and the CDR-H3 of SEQ ID NO: 251 (X17m6).

In an embodiment, the antibody-based molecule that binds to human muscle-specific tyrosine-protein kinase (MuSK) comprises a heavy chain variable region, where the heavy chain variable region comprises: (xix) a heavy chain variable region comprising the CDR-H1 of SEQ ID NO: 147, the CDR-H2 of SEQ ID NO: 150, and the CDR-H3 of SEQ ID NO: 156; (xx) a heavy chain variable region comprising the CDR-H1 of SEQ ID NO: 148, the CDR-H2 of SEQ ID NO: 151, and the CDR-H3 of SEQ ID NO: 157; (xxi) a heavy chain variable region comprising the CDR-H1 of SEQ ID NO: 149, the CDR-H2 of SEQ ID NO: 152, and the CDR-H3 of SEQ ID NO: 158;

In an embodiment, the antibody-based molecule that binds to human muscle-specific tyrosine-protein kinase (MuSK) comprises a heavy chain variable region, where the heavy chain variable region comprises (xxii) a heavy chain variable region comprising the CDR-H1 of SEQ ID NO: 147, the CDR-H2 of SEQ ID NO: 153, and the CDR-H3 of SEQ ID NO:156 (3B2g1m1/3B2g2m1); (xxiii) a heavy chain variable region comprising the CDR-H1 of SEQ ID NO: 147, the CDR-H2 of SEQ ID NO: 154, and the CDR-H3 of SEQ ID NO: 156 (3B2g1m2/3B2g2m2); (xxiv) a heavy chain variable region comprising the CDR-H1 of SEQ ID NO: 147, the CDR-H2 of SEQ ID NO: 155, and the CDR-H3 of SEQ ID NO: 156 (3B2g1m4/3B2g2m4). The sequences of the heavy chain CDR sequences are provided in Table 1 below.

In an embodiment, the antibody-based molecule that binds to human muscle-specific tyrosine-protein kinase (MuSK) comprises a heavy chain variable region, where the heavy chain variable region comprises the CDR-H1 of SEQ ID NO: 147, CDR-H2 of SEQ ID NO: 153 or a CDR-H2 amino acid sequence having at least 80% sequence identity to SEQ ID NO: 153, and the CDR-H3 of SEQ ID NO:156 (3B2g2m1). In accordance with this embodiment, the CDR-H2 amino acid sequence having at least 80% sequence identity to SEQ ID NO: 153 comprises one or more amino acid substitutions relative to the amino acid sequence of SEQ ID NO: 153, wherein said substitutions are present at residues 1, 2, 6, 7, 8, 9, 10, 11, 12, 13, 14, 15, 16, 17, or any combination thereof. In an embodiment, the CDR-H2 amino acid sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 153. In an embodiment, the CDR-H2 of the antibody comprises a proline (P) at position 3, a tryptophan (W) at position 4, and a serine (S) or asparagine (N) at position 5.

In an embodiment, the antibody-based molecule that binds to human muscle-specific tyrosine-protein kinase (MuSK) comprises a heavy chain variable region, where the heavy chain variable region comprises the CDR-H1 of SEQ ID NO: 147, the CDR-H2 of SEQ ID NO: 153, and the CDR-H3 of SEQ ID NO:156.

The sequences of the heavy chain CDR sequences are provided in Table 1 below.

TABLE 1

Heavy Chain CDR Sequences of MuSK Antibodies

| mAb/Fab name | HCDR1 Sequence | SEQ ID NO: | HCDR2 Sequence | SEQ ID NO: | HCDR3 Sequence | SEQ ID NO: |
|---|---|---|---|---|---|---|
| X1 | SSSIH | 1 | SISSSSGSTSYADSVKG | 17 | KYWSQYYWAHYYGGLDY | 33 |
| X2 | SSSIH | 2 | SISSSYGSTSYADSVKG | 18 | SEGDRYVSGYMGMDY | 34 |
| X2m1 | SSSIH | 2 | SISSSYGSTSYADSVKG | 18 | SEGDRYVSGYFGFDY | 240 |
| X2m2 | SSSIH | 2 | SISSSYGSTSYADSVKG | 18 | SEGDRYVSGYFGLDY | 241 |
| X2m3 | SSSIH | 2 | SISSSYGSTSYADSVKG | 18 | SEGDRYVSGYSGFDY | 242 |
| X2m4 | SSSIH | 2 | SISSSYGSTSYADSVKG | 18 | SEGDRYVSGYSGLDY | 243 |
| X2m5 | SSSIH | 2 | SISSSYGSTSYADSVKG | 18 | SEGDRYVSGYFGMDY | 244 |
| X2m6 | SSSIH | 2 | SISSSYGSTSYADSVKG | 18 | SEGDRYVSGYSGMDY | 245 |
| X2m7 | SSSIH | 2 | SISSSYGSTSYADSVKG | 18 | SEGDRYVSGYMGFDY | 246 |
| X2m8 | SSSIH | 2 | SISSSYGSTSYADSVKG | 18 | SEGDRYVSGYMGLDY | 247 |
| X3 | SSSIH | 3 | SISSSSGYTYYADSVKG | 19 | SWYEMWMSGYFGFDY | 35 |
| X4 | SSSIH | 4 | SISSSSGSTYYADSVKG | 20 | GEHDYYVFGYLGMDY | 36 |
| X5 | SSSIH | 5 | SISSSSGSTYYADSVKG | 21 | SYTMFYYGGWYGSGYFGMDY | 37 |
| X6 | SSSIH | 6 | SISSYSGYTYYADSVKG | 22 | TYGSYYVSSYTGMDY | 38 |
| X7 | SSSIH | 7 | SISSSYSSTYYADSVKG | 23 | LAGLYHPGYLGLDY | 39 |
| X8 | SSSIH | 8 | SISSSSGSTSYADSVKG | 24 | SWSYHPWYYHVGWYTGLDY | 40 |

TABLE 1-continued

Heavy Chain CDR Sequences of MuSK Antibodies

| mAb/Fab name | HCDR1 Sequence | SEQ ID NO: | HCDR2 Sequence | SEQ ID NO: | HCDR3 Sequence | SEQ ID NO: |
|---|---|---|---|---|---|---|
| X9 | SSSIH | 9 | SIYSSSGSTYYADSVKG | 25 | SGGEFYITSYYGMDY | 41 |
| X10 | SSSIH | 10 | SISSSYSSTSYADSVKG | 26 | KYYRWRHNKYQGFDY | 42 |
| X11 | SSSIH | 11 | SISSYSGSTYYADSVKG | 27 | SWGSYYVSGFVGFDY | 43 |
| X12 | SSSIH | 12 | YISPSSGYTSYADSVKG | 28 | QYWVPQWWITQYFGMDY | 44 |
| X13 | SSSIH | 13 | SISSSSGSTSYADSVKG | 29 | SSEHWYTIGYYGIDY | 45 |
| X14 | SSSIH | 14 | SISSSSGYTYYADSVKG | 30 | GSHHWFLWIYSGLDY | 46 |
| X15 | SSSIH | 15 | SISSYSGSTSYADSVKG | 31 | SEGDRYVSGYMGMDY | 47 |
| X16 | SSSIH | 16 | SIYSSYGYTSYADSVKG | 32 | NWGYYMYWGWYYALDY | 48 |
| X17 | YSSIH | 135 | SIYSSSGSTYYADSVKG | 137 | GDHGYYVFGYLGMDY | 139 |
| X17m1 | YSSIH | 135 | SIYSSSGSTYYADSVKG | 137 | GDHGYYVSGYLGMDY | 248 |
| X17m2 | YSSIH | 135 | SIYSSSGSTYYADSVKG | 137 | GDHGYYVYGYLGMDY | 249 |
| X17m3 | YSSIH | 135 | SIYSSSGSTYYADSVKG | 137 | GDHGYYVSGYLGFDY | 250 |
| X17m6 | YSSIH | 135 | SIYSSSGSTYYADSVKG | 137 | GEHGYYVSGYLGFDY | 251 |
| X18 | SSSIH | 136 | SISSSSGYTSYADSVKG | 138 | KYSKRAYPDYYWRGLDY | 140 |
| 14D10 | DYGMS | 147 | AIPWNGGSTYYKESVKG | 150 | RSGRIAFGALDA | 156 |
| 7G4 | DYGMS | 147 | AIPWNGGSTYYKESVKG | 150 | RSGRIAFGALDA | 156 |
| 3C4 | DYGMS | 147 | AIPWNGGSTYYKESVKG | 150 | RSGRIAFGALDA | 156 |
| 3B2 | DYGMS | 147 | AIPWNGGSTYYKESVKG | 150 | RSGRIAFGALDA | 156 |
| 3G3 | DYGMS | 147 | AIPWNGGSTYYKESVKG | 150 | RSGRIAFGALDA | 156 |
| 31G2 | DYGMS | 147 | AIPWNGGSTYYKESVKG | 150 | RSGRIAFGALDA | 156 |
| 31B7 | DYGMS | 147 | AIPWNGGSTYYKESVKG | 150 | RSGRIAFGALDA | 156 |
| 17H10 | ARYYSWS | 148 | VIAYDGSTYYSPSLKS | 151 | GSSRVAAAFDS | 157 |
| 23B6 | ARYYSWS | 148 | VIAYDGSTYYSPSLKS | 151 | GSSRVAAAFDS | 157 |
| 30E1 | ARYYSWS | 148 | VIAYDGSTYYSPSLKS | 151 | GSSRVAAAFDS | 157 |

TABLE 1-continued

Heavy Chain CDR Sequences of MuSK Antibodies

| mAb/Fab name | HCDR1 Sequence | SEQ ID NO: | HCDR2 Sequence | SEQ ID NO: | HCDR3 Sequence | SEQ ID NO: |
|---|---|---|---|---|---|---|
| 30A11 | ARYYSWS | 148 | VIAYDGSTYYSPSLKS | 151 | GSSRVAAAFDS | 157 |
| 16F11 | LYYMN | 149 | VIDTHSIAYYADSVKG | 152 | GRTALVR | 158 |
| 4C11 | LYYMN | 149 | VIDTHSIAYYADSVKG | 152 | GRTALVR | 158 |
| 7A12 | LYYMN | 149 | VIDTHSIAYYADSVKG | 152 | GRTALVR | 158 |
| 7G12 | LYYMN | 149 | VIDTHSIAYYADSVKG | 152 | GRTALVR | 158 |
| 7B8 | LYYMN | 149 | VIDTHSIAYYADSVKG | 152 | GRTALVR | 158 |
| 3B2g1m1 | DYGMS | 147 | AIPWSGGSTYYKESVKG | 153 | RSGRIAFGALDA | 156 |
| 3B2g1m2 | DYGMS | 147 | AIPGSGGSTYYKESVKG | 154 | RSGRIAFGALDA | 156 |
| 3B2g1m4 | DYGMS | 147 | AIPWQGGSTYYKESVKG | 155 | RSGRIAFGALDA | 156 |
| 3B2g2m1 | DYGMS | 147 | AIPWSGGSTYYKESVKG | 153 | RSGRIAFGALDA | 156 |
| 3B2g2m2 | DYGMS | 147 | AIPGSGGSTYYKESVKG | 154 | RSGRIAFGALDA | 156 |
| 3B2g2m4 | DYGMS | 147 | AIPWQGGSTYYKESVKG | 155 | RSGRIAFGALDA | 156 |

In some embodiments, the MuSK antibody-based molecules as disclosed herein further comprise a light chain variable region. The light chain variable region comprises (i) a complementarity-determining region 1 (CDR-L1) having an amino acid sequence of any one of SEQ ID NOs: 49-64, 141, 142, 159-169, or a modified amino acid sequence of any one of SEQ ID NO: 49-64, 141, 142, or 159-169, said modified sequence having at least 80% sequence identity to any one of SEQ ID NO: 49-64, 141, 142, or 159-169; (ii) a complementarity-determining region 2 (CDR-L2) having an amino acid sequence of any one of SEQ ID NOs: 65-80, 143, 144, 170-179, or a modified amino acid sequence of any one of SEQ ID NO: 65-80, 143, 144 or 170-179, said modified sequence having at least 80% sequence identity to any one of SEQ ID NO: 65-80, 143, 144 or 170-179; and (iii) a complementarity-determining region 3 (CDR-L3) having an amino acid sequence of any one of SEQ ID NOs: 81-96, 145, 146, 180-195, or a modified amino acid sequence of any one of SEQ ID NO: 81-96, 145, 146, or 180-195, said modified sequence having at least 80% sequence identity to any one of SEQ ID NO: 81-96, 145, 146 or 180-195.

In an embodiment, the light chain variable region of the MuSK antibody based molecule disclosed herein comprises (i) a light chain variable region comprising the CDR-L1 of SEQ ID NO: 49, the CDR-L2 of SEQ ID NO: 65, and the CDR-L3 of SEQ ID NO: 81; (ii) a light chain variable region comprising the CDR-L1 of SEQ ID NO: 50, the CDR-L2 of SEQ ID NO: 66, and the CDR-L3 of SEQ ID NO: 82; (iii) a light chain variable region comprising the CDR-L1 of SEQ ID NO: 51, the CDR-L2 of SEQ ID NO: 67, and the CDR-L3 of SEQ ID NO: 83; (iv) a light chain variable region comprising the CDR-L1 of SEQ ID NO: 52, the CDR-L2 of SEQ ID NO: 68, and the CDR-L3 of SEQ ID NO: 84; (v) a light chain variable region comprising the CDR-L1 of SEQ ID NO: 53, the CDR-L2 of SEQ ID NO: 69, and the CDR-L3 of SEQ ID NO: 85; (vi) a light chain variable region comprising the CDR-L1 of SEQ ID NO: 54, the CDR-L2 of SEQ ID NO: 70, and the CDR-L3 of SEQ ID NO: 86; (vii) a light chain variable region comprising the CDR-L1 of SEQ ID NO: 55, the CDR-L2 of SEQ ID NO:71, and the CDR-L3 of SEQ ID NO: 87; (viii) a light chain variable region comprising the CDR-L1 of SEQ ID NO: 56, the CDR-L2 of SEQ ID NO: 72, and the CDR-L3 of SEQ ID NO: 88; (ix) a light chain variable region comprising the CDR-L1 of SEQ ID NO: 57, the CDR-L2 of SEQ ID NO: 73, and the CDR-L3 of SEQ ID NO: 89; (x) a light chain variable region comprising the CDR-L1 of SEQ ID NO: 58, the CDR-L2 of SEQ ID NO: 74, and the CDR-L3 of SEQ ID NO: 90; (xi) a light chain variable region comprising the CDR-L1 of SEQ ID NO: 59, the CDR-L2 of SEQ ID NO: 75, and the CDR-L3 of SEQ ID NO: 91; (xii) a light chain variable region comprising the CDR-L1 of SEQ ID NO: 60, the CDR-L2 of SEQ ID NO: 76, and the CDR-L3 of SEQ ID NO: 92; (xiii) a light chain variable region comprising the CDR-L1 of SEQ ID NO: 61, the CDR-L2 of SEQ ID NO: 77, and the CDR-L3 of SEQ ID NO: 93; (xiv) a light chain variable region comprising the CDR-L1 of SEQ ID NO: 62, the CDR-L2 of SEQ ID NO: 78, and the CDR-L3 of SEQ ID NO: 94; (xv) a light chain variable region comprising the CDR-L1 of SEQ ID NO: 63, the CDR-L2 of SEQ ID NO: 79, and the CDR-L3 of SEQ ID NO: 95; (xvi) a light chain variable region comprising the CDR-L1 of SEQ ID NO: 64, the CDR-L2 of SEQ ID NO: 80, and the CDR-L3 of SEQ ID NO: 96; (xvii) a light chain variable region comprising the CDR-L1 of SEQ ID NO: 141, the CDR-L2 of SEQ ID NO: 143, and the CDR-L3 of SEQ ID NO: 145; (xviii) a light chain variable region comprising the CDR-L1 of SEQ ID NO: 142, the CDR-L2 of SEQ ID NO: 144, and the CDR-L3 of SEQ ID NO: 146. The sequences of the light chain CDR sequences are provided in Table 2 below.

In an embodiment, the light chain variable region of the MuSK antibody based molecule disclosed herein comprises (xix) a light chain variable region comprising the CDR-L1 of SEQ ID NO: 159, the CDR-L2 of SEQ ID NO: 170, and the CDR-L3 of SEQ ID NO: 180; (xx) a light chain variable region comprising the CDR-L1 of SEQ ID NO: 159, the CDR-L2 of SEQ ID NO: 171, and the CDR-L3 of SEQ ID NO: 181; (xxi) a light chain variable region comprising the CDR-L1 of SEQ ID NO: 160, the CDR-L2 of SEQ ID NO: 172, and the CDR-L3 of SEQ ID NO: 182; (xxii) a light chain variable region comprising the CDR-L1 of SEQ ID NO: 159, the CDR-L2 of SEQ ID NO: 172, and the CDR-L3 of SEQ ID NO: 183; (xxiii) a light chain variable region comprising the CDR-L1 of SEQ ID NO: 159, the CDR-L2 of SEQ ID NO: 171, and the CDR-L3 of SEQ ID NO: 184; (xxiv) a light chain variable region comprising the CDR-L1 of SEQ ID NO: 159, the CDR-L2 of SEQ ID NO: 173, and the CDR-L3 of SEQ ID NO: 185; (xxv) a light chain variable region comprising the CDR-L1 of SEQ ID NO: 159, the CDR-L2 of SEQ ID NO: 173, and the CDR-L3 of SEQ ID NO: 186; (xxvi) a light chain variable region comprising the CDR-L1 of SEQ ID NO: 161, the CDR-L2 of SEQ ID NO: 174, and the CDR-L3 of SEQ ID NO: 187; (xxvii) a light chain variable region comprising the CDR-L1 of SEQ ID NO: 162, the CDR-L2 of SEQ ID NO: 174, and the CDR-L3 of SEQ ID NO: 188; (xxviii) a light chain variable region comprising the CDR-L1 of SEQ ID NO: 163, the CDR-L2 of SEQ ID NO: 174, and the CDR-L3 of SEQ ID NO: 188; (xxix) a light chain variable region comprising the CDR-L1 of SEQ ID NO: 164, the CDR-L2 of SEQ ID NO: 174, and the CDR-L3 of SEQ ID NO: 189; (xxx) a light chain variable region comprising the CDR-L1 of SEQ ID NO: 165, the CDR-L2 of SEQ ID NO: 175, and the CDR-L3 of SEQ ID NO: 190; (xxxi) a light chain variable region comprising the CDR-L1 of SEQ ID NO: 166, the CDR-L2 of SEQ ID NO: 176, and the CDR-L3 of SEQ ID NO: 191; (xxxi) a light chain variable region comprising the CDR-L1 of SEQ ID NO: 167, the CDR-L2 of SEQ ID NO: 177, and the CDR-L3 of SEQ ID NO: 192; (xxxii) a light chain variable region comprising the CDR-L1 of SEQ ID NO: 168, the CDR-L2 of SEQ ID NO: 178, and the CDR-L3 of SEQ ID NO: 193; (xxxiii) a light chain variable region comprising the CDR-L1 of SEQ ID NO: 169, the CDR-L2 of SEQ ID NO: 179, and the CDR-L3 of SEQ ID NO: 194.

In an embodiment, the light chain variable region of the MuSK antibody based molecule disclosed herein comprises the CDR-L1 of SEQ ID NO: 159, the CDR-L2 of SEQ ID NO: 172, and the CDR-L3 of SEQ ID NO: 195 or a CDR-L3 having at least 80% sequence identity to SEQ ID NO: 195. In accordance with this embodiment, the CDR-L3 amino acid sequence having at least 80% sequence identity to SEQ ID NO: 195 comprises one or more amino acid substitutions relative to the amino acid sequence of SEQ ID NO: 195, wherein said substitution is present at residue 1, 2, 6, 7, 8, 9, 10, 11, 12, 13, 14, 15, 16, 17, or any combination thereof. In an embodiment, the CDR-L3 amino acid sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 195.

The sequences of the light chain CDR sequences are provided in Table 2 below.

TABLE 2

Light Chain CDR Sequences of MuSK Antibodies

| mAb/Fab name | LCDR1 Sequence | SEQ ID NO: | LCDR2 Sequence | SEQ ID NO: | LCDR3 Sequence | SEQ ID NO: |
| --- | --- | --- | --- | --- | --- | --- |
| X1 | RASQSVSSAVA | 49 | SASSLYS | 65 | QQSSSSLIT | 81 |
| X2 | RASQSVSSAVA | 50 | SASSLYS | 66 | QQSGVWLIT | 82 |
| X3 | RASQSVSSAVA | 51 | SASSLYS | 67 | QQSSSSLIT | 83 |
| X4 | RASQSVSSAVA | 52 | SASSLYS | 68 | QQSYKPGALIT | 84 |
| X5 | RASQSVSSAVA | 53 | SASSLYS | 69 | QQSSSSLIT | 85 |
| X6 | RASQSVSSAVA | 54 | SASSLYS | 70 | QQSSSSLIT | 86 |
| X7 | RASQSVSSAVA | 55 | SASSLYS | 71 | QQSSRSSLLT | 87 |
| X8 | RASQSVSSAVA | 56 | SASSLYS | 72 | QQSSSSLIT | 88 |
| X9 | RASQSVSSAVA | 57 | SASSLYS | 73 | QQSSSSLIT | 89 |
| X10 | RASQSVSSAVA | 58 | SASSLYS | 74 | QQSLWYPVT | 90 |
| X11 | RASQSVSSAVA | 59 | SASSLYS | 75 | QQNSYYLIT | 91 |
| X12 | RASQSVSSAVA | 60 | SASSLYS | 76 | QQSSSSLIT | 92 |
| X13 | RASQSVSSAVA | 61 | SASSLYS | 77 | QQSYGSFSLIT | 93 |
| X14 | RASQSVSSAVA | 62 | SASSLYS | 78 | QQGSYHLIT | 94 |

TABLE 2-continued

Light Chain CDR Sequences of MuSK Antibodies

| mAb/Fab name | LCDR1 Sequence | SEQ ID NO: | LCDR2 Sequence | SEQ ID NO: | LCDR3 Sequence | SEQ ID NO: |
|---|---|---|---|---|---|---|
| X15 | RASQSVSSAVA | 63 | SASSLYS | 79 | QQSGVWLIT | 95 |
| X16 | RASQSVSSAVA | 64 | SASSLYS | 80 | QQWSSAQALIT | 96 |
| X17 | RASQSVSSAVA | 141 | SASSLYS | 143 | QQSYKPGALIT | 145 |
| X18 | RASQSVSSAVA | 142 | SASSLYS | 144 | QQSYWWPIT | 146 |
| 14D10 | GLSSGSVTSSNYPD | 159 | TTNSRHS | 170 | ALYMGGGSNVYV | 180 |
| 7G4 | GLSSGSVTSSNYPD | 159 | STNSRHS | 171 | ALYMGRGSNKDYV | 181 |
| 3C4 | GLSSGSVTASNYPD | 160 | STDSRHS | 172 | ALYMYSDSKLYV | 182 |
| 3B2 | GLSSGSVTSSNYPD | 159 | STDSRHS | 172 | GLYMYSGSKNYV | 183 |
| 3G3 | GLSSGSVTSSNYPD | 159 | STNSRHS | 171 | ALYMGSDIRNYV | 184 |
| 31G2 | GLSSGSVTSSNYPD | 159 | STNSRLS | 173 | ALYMGSGSRNYV | 185 |
| 31B7 | GLSSGSVTSSNYPD | 159 | STNSRLS | 173 | ALYMGSESRNYV | 186 |
| 17H10 | GGNRIGGKSVQ | 161 | ADSRRPS | 174 | HVWGSTASAD | 187 |
| 23B6 | GGDNIGSKNAQ | 162 | ADSRRPS | 174 | HVWDSSTNAW | 188 |
| 30E1 | GGDNIGSKNTQ | 163 | ADSRRPS | 174 | HVWDSSTNAW | 188 |
| 30A11 | GGDNIASKNVQ | 164 | ADSRRPS | 174 | QVWDSSTNVAV | 189 |
| 16F11 | KSSQSVVFGSNQKSYLN | 165 | YASTQES | 175 | QQAYSAPT | 190 |
| 4C11 | RSSQSVLYSSNQKNYLN | 166 | WASARES | 176 | QQSYKPPYG | 191 |
| 7A12 | ESSQSVLYNQKNYLN | 167 | WASTRQS | 177 | QQAYNAPLT | 192 |
| 7G12 | KSSQRVQLGSNQKSYLN | 168 | YASTQQS | 178 | QQGYSAPFT | 193 |
| 7B8 | KSSQSVLYNQKNYLA | 169 | WASTRES | 179 | QQGYSVPYT | 194 |
| 3B2g1m1 | GLSSGSVTSSNYPD | 159 | STDSRHS | 172 | GLYMYSGSKNYV | 183 |
| 3B2g1m2 | GLSSGSVTSSNYPD | 159 | STDSRHS | 172 | GLYMYSGSKNYV | 183 |
| 3B2g1m4 | GLSSGSVTSSNYPD | 159 | STDSRHS | 172 | GLYMYSGSKNYV | 183 |
| 3B2g2m1 | GLSSGSVTSSNYPD | 159 | STDSRHS | 172 | GLYSYSGSKNYV | 195 |
| 3B2g2m2 | GLSSGSVTSSNYPD | 159 | STDSRHS | 172 | GLYSYSGSKNYV | 195 |

TABLE 2-continued

Light Chain CDR Sequences of MuSK Antibodies

| mAb/Fab name | LCDR1 Sequence | SEQ ID NO: | LCDR2 Sequence | SEQ ID NO: | LCDR3 Sequence | SEQ ID NO: |
|---|---|---|---|---|---|---|
| 3B2g2m4 | GLSSGSVTSSNYPD | 159 | STDSRHS | 172 | GLYSYSGSKNYV | 195 |

Suitable amino acid modifications to the heavy chain CDR sequences and/or the light chain CDR sequences of the MuSK antibody-based molecule disclosed herein include, for example, conservative substitutions or functionally equivalent amino acid residue substitutions that result in variant CDR sequences having similar or enhanced binding characteristics to those of the CDR sequences disclosed herein as described above. Encompassed by the present invention are CDRs of Tables 1 and 2 containing 1, 2, 3, 4, 5, or more amino acid substitutions (depending on the length of the CDR) that maintain or enhance MuSK binding of the antibody. The resulting modified CDRs are at least 70%, at least 75%, at least 80%, at least 85%, at least 90%, at least 95% similar in sequence to the CDRs of Tables 1 and 2. Suitable amino acid modifications to the heavy chain CDR sequences of Table 1 and/or the light chain CDR sequences of Tables 1 and 2 include, for example, conservative substitutions or functionally equivalent amino acid residue substitutions that result in variant CDR sequences having similar or enhanced binding characteristics to those of the CDR sequences of Table 1 and Table 2. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences of Table 1 and the light chain CDR sequences of Table 2. Non-conservative substitutions involve substituting one or more amino acid residues of the CDR with one or more amino acid residues from a different class of amino acids to improve or enhance the binding properties of CDR. The amino acid sequences of the heavy chain variable region CDRs of Table 1 and/or the light chain variable region CDRs of Table 2 may further comprise one or more internal neutral amino acid insertions or deletions that maintain or enhance MuSK binding.

In an embodiment, the MuSK antibody-based molecule comprises:

(i) a heavy chain variable region comprising the CDR-H1 of SEQ ID NO: 1, the CDR-H2 of SEQ ID NO: 17, and the CDR-H3 of SEQ ID NO: 33, and a light chain variable region comprising the CDR-L1 of SEQ ID NO: 49, the CDR-L2 of SEQ ID NO: 65, and the CDR-L3 of SEQ ID NO: 81;

(ii) a heavy chain variable region comprising the CDR-H1 of SEQ ID NO: 2, the CDR-H2 of SEQ ID NO: 18, and the CDR-H3 of SEQ ID NO: 34, and a light chain variable region comprising the CDR-L1 of SEQ ID NO: 50, the CDR-L2 of SEQ ID NO: 66, and the CDR-L3 of SEQ ID NO: 82;

(iii) a heavy chain variable region comprising the CDR-H1 of SEQ ID NO: 3, the CDR-H2 of SEQ ID NO: 19, and the CDR-H3 of SEQ ID NO: 35, and a light chain variable region comprising the CDR-L1 of SEQ ID NO: 51, the CDR-L2 of SEQ ID NO: 67, and the CDR-L3 of SEQ ID NO: 83;

(iv) a heavy chain variable region comprising the CDR-H1 of SEQ ID NO: 4, the CDR-H2 of SEQ ID NO: 20, and the CDR-H3 of SEQ ID NO: 36, and a light chain variable region comprising the CDR-L1 of SEQ ID NO: 52, the CDR-L2 of SEQ ID NO: 68, and the CDR-L3 of SEQ ID NO: 84;

(v) a heavy chain variable region comprising the CDR-H1 of SEQ ID NO: 5, the CDR-H2 of SEQ ID NO: 21, and the CDR-H3 of SEQ ID NO: 37, and a light chain variable region comprising the CDR-L1 of SEQ ID NO: 53, the CDR-L2 of SEQ ID NO: 69, and the CDR-L3 of SEQ ID NO: 85;

(vi) a heavy chain variable region comprising the CDR-H1 of SEQ ID NO: 6, the CDR-H2 of SEQ ID NO: 22, and the CDR-H3 of SEQ ID NO: 38, and a light chain variable region comprising the CDR-L1 of SEQ ID NO: 54, the CDR-L2 of SEQ ID NO: 70, and the CDR-L3 of SEQ ID NO: 86;

(vii) a heavy chain variable region comprising the CDR-H1 of SEQ ID NO: 7, the CDR-H2 of SEQ ID NO: 23, and the CDR-H3 of SEQ ID NO: 39, and a light chain variable region comprising the CDR-L1 of SEQ ID NO: 55, the CDR-L2 of SEQ ID NO:71, and the CDR-L3 of SEQ ID NO: 87;

(viii) a heavy chain variable region comprising the CDR-H1 of SEQ ID NO: 8, the CDR-H2 of SEQ ID NO: 24, and the CDR-H3 of SEQ ID NO: 40, and a light chain variable region comprising the CDR-L1 of SEQ ID NO: 56, the CDR-L2 of SEQ ID NO: 72, and the CDR-L3 of SEQ ID NO: 88;

(ix) a heavy chain variable region comprising the CDR-H1 of SEQ ID NO: 9, the CDR-H2 of SEQ ID NO: 25, and the CDR-H3 of SEQ ID NO: 41, and a light chain variable region comprising the CDR-L1 of SEQ ID NO: 57, the CDR-L2 of SEQ ID NO: 73, and the CDR-L3 of SEQ ID NO: 89;

(x) a heavy chain variable region comprising the CDR-H1 of SEQ ID NO: 10, the CDR-H2 of SEQ ID NO: 26, and the CDR-H3 of SEQ ID NO: 42, and a light chain variable region comprising the CDR-L1 of SEQ ID NO: 58, the CDR-L2 of SEQ ID NO: 74, and the CDR-L3 of SEQ ID NO: 90;

(xi) a heavy chain variable region comprising the CDR-H1 of SEQ ID NO: 11, the CDR-H2 of SEQ ID NO: 27, and the CDR-H3 of SEQ ID NO: 43, and a light chain variable region comprising the CDR-L1 of SEQ ID NO: 59, the CDR-L2 of SEQ ID NO: 75, and the CDR-L3 of SEQ ID NO: 91;

(xii) a heavy chain variable region comprising the CDR-H1 of SEQ ID NO: 12, the CDR-H2 of SEQ ID NO: 28, and the CDR-H3 of SEQ ID NO: 44, and a light chain variable region comprising the CDR-L1 of SEQ ID NO: 60, the CDR-L2 of SEQ ID NO: 76, and the CDR-L3 of SEQ ID NO: 92;

(xiii) a heavy chain variable region comprising the CDR-H1 of SEQ ID NO: 13, the CDR-H2 of SEQ ID NO: 29, and the CDR-H3 of SEQ ID NO: 45, and a light chain variable region comprising the CDR-L1 of SEQ ID NO: 61, the CDR-L2 of SEQ ID NO: 77, and the CDR-L3 of SEQ ID NO: 93;

(xiv) a heavy chain variable region comprising the CDR-H1 of SEQ ID NO: 14, the CDR-H2 of SEQ ID NO: 30, and the CDR-H3 of SEQ ID NO: 46, and a light chain variable region comprising the CDR-L1 of SEQ ID NO: 62, the CDR-L2 of SEQ ID NO: 78, and the CDR-L3 of SEQ ID NO: 94;

(xv) a heavy chain variable region comprising the CDR-H1 of SEQ ID NO: 15, the CDR-H2 of SEQ ID NO: 31, and the CDR-H3 of SEQ ID NO: 47, and a light chain variable region comprising the CDR-L1 of SEQ ID NO: 63, the CDR-L2 of SEQ ID NO: 79, and the CDR-L3 of SEQ ID NO: 95;

(xvi) a heavy chain variable region comprising the CDR-H1 of SEQ ID NO: 16, the CDR-H2 of SEQ ID NO: 32, and the CDR-H3 of SEQ ID NO: 48, and a light chain variable region comprising the CDR-L1 of SEQ ID NO: 64, the CDR-L2 of SEQ ID NO: 80, and the CDR-L3 of SEQ ID NO: 96;

(xvii) a heavy chain variable region comprising the CDR-H1 of SEQ ID NO: 135, the CDR-H2 of SEQ ID NO: 137, and the CDR-H3 of SEQ ID NO: 139, and a light chain variable region comprising the CDR-L1 of SEQ ID NO: 141, the CDR-L2 of SEQ ID NO: 143, and the CDR-L3 of SEQ ID NO: 145; and (xviii) a heavy chain variable region comprising the CDR-H1 of SEQ ID NO: 136, the CDR-H2 of SEQ ID NO: 138, and the CDR-H3 of SEQ ID NO: 140, and a light chain variable region comprising the CDR-L1 of SEQ ID NO: 142, the CDR-L2 of SEQ ID NO: 144, and the CDR-L3 of SEQ ID NO: 146.

In an embodiment, the MuSK antibody-based molecule comprises:

(ii.a) a heavy chain variable region comprising the CDR-H1 of SEQ ID NO: 2, the CDR-H2 of SEQ ID NO: 18, and the CDR-H3 of SEQ ID NO: 240, and a light chain variable region comprising the CDR-L1 of SEQ ID NO: 50, the CDR-L2 of SEQ ID NO: 66, and the CDR-L3 of SEQ ID NO: 82 (X2m1);

(ii.b) a heavy chain variable region comprising the CDR-H1 of SEQ ID NO: 2, the CDR-H2 of SEQ ID NO: 18, and the CDR-H3 of SEQ ID NO: 241, and a light chain variable region comprising the CDR-L1 of SEQ ID NO: 50, the CDR-L2 of SEQ ID NO: 66, and the CDR-L3 of SEQ ID NO: 82 (X2m2);

(ii.c) a heavy chain variable region comprising the CDR-H1 of SEQ ID NO: 2, the CDR-H2 of SEQ ID NO: 18, and the CDR-H3 of SEQ ID NO: 242, and a light chain variable region comprising the CDR-L1 of SEQ ID NO: 50, the CDR-L2 of SEQ ID NO: 66, and the CDR-L3 of SEQ ID NO: 82 (X2m3);

(ii.d) a heavy chain variable region comprising the CDR-H1 of SEQ ID NO: 2, the CDR-H2 of SEQ ID NO: 18, and the CDR-H3 of SEQ ID NO: 243, and a light chain variable region comprising the CDR-L1 of SEQ ID NO: 50, the CDR-L2 of SEQ ID NO: 66, and the CDR-L3 of SEQ ID NO: 82 (X2m4);

(ii.e) a heavy chain variable region comprising the CDR-H1 of SEQ ID NO: 2, the CDR-H2 of SEQ ID NO: 18, and the CDR-H3 of SEQ ID NO: 244, and a light chain variable region comprising the CDR-L1 of SEQ ID NO: 50, the CDR-L2 of SEQ ID NO: 66, and the CDR-L3 of SEQ ID NO: 82 (X2m5);

(ii.f) a heavy chain variable region comprising the CDR-H1 of SEQ ID NO: 2, the CDR-H2 of SEQ ID NO: 18, and the CDR-H3 of SEQ ID NO: 245, and a light chain variable region comprising the CDR-L1 of SEQ ID NO: 50, the CDR-L2 of SEQ ID NO: 66, and the CDR-L3 of SEQ ID NO: 82 (X2m6);

(ii.g) a heavy chain variable region comprising the CDR-H1 of SEQ ID NO: 2, the CDR-H2 of SEQ ID NO: 18, and the CDR-H3 of SEQ ID NO: 246, and a light chain variable region comprising the CDR-L1 of SEQ ID NO: 50, the CDR-L2 of SEQ ID NO: 66, and the CDR-L3 of SEQ ID NO: 82 (X2m7);

(ii.f) a heavy chain variable region comprising the CDR-H1 of SEQ ID NO: 2, the CDR-H2 of SEQ ID NO: 18, and the CDR-H3 of SEQ ID NO: 247, and a light chain variable region comprising the CDR-L1 of SEQ ID NO: 50, the CDR-L2 of SEQ ID NO: 66, and the CDR-L3 of SEQ ID NO: 82 (X2m8).

In an embodiment, the MuSK antibody-based molecule comprises:

(xvii.a) a heavy chain variable region comprising the CDR-H1 of SEQ ID NO: 135, the CDR-H2 of SEQ ID NO: 137, and the CDR-H3 of SEQ ID NO: 248, and a light chain variable region comprising the CDR-L1 of SEQ ID NO: 141, the CDR-L2 of SEQ ID NO: 143, and the CDR-L3 of SEQ ID NO: 145 (X17m1);

(xvii.b) a heavy chain variable region comprising the CDR-H1 of SEQ ID NO: 135, the CDR-H2 of SEQ ID NO: 137, and the CDR-H3 of SEQ ID NO: 249, and a light chain variable region comprising the CDR-L1 of SEQ ID NO: 141, the CDR-L2 of SEQ ID NO: 143, and the CDR-L3 of SEQ ID NO: 145 (X17m2);

(xvii.c) a heavy chain variable region comprising the CDR-H1 of SEQ ID NO: 135, the CDR-H2 of SEQ ID NO: 137, and the CDR-H3 of SEQ ID NO: 250, and a light chain variable region comprising the CDR-L1 of SEQ ID NO: 141, the CDR-L2 of SEQ ID NO: 143, and the CDR-L3 of SEQ ID NO: 145 (X17m3);

(xvii.d) a heavy chain variable region comprising the CDR-H1 of SEQ ID NO: 135, the CDR-H2 of SEQ ID NO: 137, and the CDR-H3 of SEQ ID NO: 251, and a light chain variable region comprising the CDR-L1 of SEQ ID NO: 141, the CDR-L2 of SEQ ID NO: 143, and the CDR-L3 of SEQ ID NO: 145 (X17m6).

In an embodiment, the MuSK antibody-based molecule comprises:

(i) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 170, and the CDR-L3 of SEQ ID NO: 180 (14D10);

(ii) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 171, and the CDR-L3 of SEQ ID NO: 181 (7G4);

(iii) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 160, the CDR-L2 of SEQ ID NO: 172, and the CDR-L3 of SEQ ID NO: 182 (3C4);

(iv) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2);

(v) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 171, and the CDR-L3 of SEQ ID NO: 184 (3G3);

(vi) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 173, and the CDR-L3 of SEQ ID NO: 185 (31G2);

(vii) a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 173, and the CDR-L3 of SEQ ID NO: 186 (31B7);

(viii) a heavy chain variable region comprising the CDR-H1 of SEQ ID NO: 148, the CDR-H2 of SEQ ID NO: 151, and the CDR-H3 of SEQ ID NO: 157, and the light chain variable region comprising the CDR-L1 of SEQ ID NO: 161, the CDR-L2 of SEQ ID NO: 174, and the CDR-L3 of SEQ ID NO: 187 (17H10);

(ix) a heavy chain variable region comprising the CDR-H1 of SEQ ID NO: 148, the CDR-H2 of SEQ ID NO: 151, and the CDR-H3 of SEQ ID NO: 157, and the light chain variable region comprising the CDR-L1 of SEQ ID NO: 162, the CDR-L2 of SEQ ID NO: 174, and the CDR-L3 of SEQ ID NO: 188 (23B6);

(x) a heavy chain variable region comprising the CDR-H1 of SEQ ID NO: 148, the CDR-H2 of SEQ ID NO: 151, and the CDR-H3 of SEQ ID NO: 157, and the light chain variable region comprising the CDR-L1 of SEQ ID NO: 163, the CDR-L2 of SEQ ID NO: 174, and the CDR-L3 of SEQ ID NO: 188 (30E1);

(xi) a heavy chain variable region comprising the CDR-H1 of SEQ ID NO: 148, the CDR-H2 of SEQ ID NO: 151, and the CDR-H3 of SEQ ID NO: 157, and the light chain variable region comprising the CDR-L1 of SEQ ID NO: 164, the CDR-L2 of SEQ ID NO: 174, and the CDR-L3 of SEQ ID NO: 189 (30A11);

(xii) a heavy chain variable region comprising the CDR-H1 of SEQ ID NO: 149, the CDR-H2 of SEQ ID NO: 152, and the CDR-H3 of SEQ ID NO: 158, and the light chain variable region comprising the CDR-L1 of SEQ ID NO: 165, the CDR-L2 of SEQ ID NO: 175, and the CDR-L3 of SEQ ID NO: 190 (16F11);

(xiii) a heavy chain variable region comprising the CDR-H1 of SEQ ID NO: 149, the CDR-H2 of SEQ ID NO: 152, and the CDR-H3 of SEQ ID NO: 158, and the light chain variable region comprising the CDR-L1 of SEQ ID NO: 166, the CDR-L2 of SEQ ID NO: 176, and the CDR-L3 of SEQ ID NO: 191 (4C11);

(xiv) a heavy chain variable region comprising the CDR-H1 of SEQ ID NO: 149, the CDR-H2 of SEQ ID NO: 152, and the CDR-H3 of SEQ ID NO: 158, and the light chain variable region comprising the CDR-L1 of SEQ ID NO: 167, the CDR-L2 of SEQ ID NO: 177, and the CDR-L3 of SEQ ID NO: 192 (7A12);

(xv) a heavy chain variable region comprising the CDR-H1 of SEQ ID NO: 149, the CDR-H2 of SEQ ID NO: 152, and the CDR-H3 of SEQ ID NO: 158, and the light chain variable region comprising the CDR-L1 of SEQ ID NO: 168, the CDR-L2 of SEQ ID NO: 178, and the CDR-L3 of SEQ ID NO: 193 (7G12);

(xvi) a heavy chain variable region comprising the CDR-H1 of SEQ ID NO: 149, the CDR-H2 of SEQ ID NO: 152, and the CDR-H3 of SEQ ID NO: 158, and the light chain variable region comprising the CDR-L1 of SEQ ID NO: 169, the CDR-L2 of SEQ ID NO: 179, and the CDR-L3 of SEQ ID NO: 194 (7B8);

(xvii) a heavy chain variable region comprising the CDR-H1 of SEQ ID NO: 147, the CDR-H2 of SEQ ID NO: 153, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2g1m1);

(xviii) a heavy chain variable region comprising the CDR-H1 of SEQ ID NO: 147, the CDR-H2 of SEQ ID NO: 154, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2g1m2);

(xvix) a heavy chain variable region comprising the CDR-H1 of SEQ ID NO: 147, the CDR-H2 of SEQ ID NO: 155, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2g1m4);

(xx) a heavy chain variable region comprising the CDR-H1 of SEQ ID NO: 147, the CDR-H2 of SEQ ID NO: 153, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 195 (3B2g2m1);

(xxi) a heavy chain variable region comprising the CDR-H1 of SEQ ID NO: 147, the CDR-H2 of SEQ ID NO: 154, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 195 (3B2g2m2); and (xxii) a heavy chain variable region comprising the CDR-H1 of SEQ ID NO: 147, the CDR-H2 of SEQ ID NO: 155, and the CDR-H3 of SEQ ID NO: 156, and the light chain variable region comprising the CDR-L1 of SEQ ID NO:

159, the CDR-L2 of SEQ ID NO: 172, and the CDR-L3 of SEQ ID NO: 195 (3B2g2m4)

In a preferred embodiment, the MuSK antibody-based molecule comprises a heavy chain variable region comprising the CDR-H1 of SEQ ID NO: 147, the CDR-H2 of SEQ ID NO: 153, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 195 (3B2g2m1).

The MuSK antibody-based molecule as described herein may comprise a variable light (VL) chain, a variable heavy (VH) chain, or a combination of VL and VH chains. In some embodiments, the VH chain of the MuSK antibody-based molecule comprises any one of the VH amino acid sequences provided in Table 3 below, or an amino acid sequence that is at least 60%, at least 65%, at least 70%, at least 75%, at least 80%, at least 85%, at least 90%, at least 95% identical to any one of the VH amino acid sequences listed in Table 3. In some embodiments, the VL chain of the MuSK antibody-based molecule comprises any one of the VL amino acid sequences provided in Table 3 below, or an amino acid sequence that is at least 60%, at least 65%, at least 70%, at least 75%, at least 80%, at least 85%, at least 90%, at least 95% identical to any one of the VL amino acid sequences listed in Table 3.

TABLE 3

MuSK Antibody Variable Heavy (VH) and Variable Light (VL) Antibody Sequences

| mAb/Fab name | Region | Sequence | SEQ ID NO: |
|---|---|---|---|
| X1 | VH | EVQLVESGGGLVQPGGSLRLSCAASGFTFSSSSIHWVRQAPGKG LEWVASISSSSGSTSYADSVKGRFTISADTSKNTAYLQMNSLRA EDTAVYYCARKYWSQYYWAHYYGGLDYWGQGTLVTVSS | 97 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQSSSSLITFGQGTKVEIK | 98 |
| X2 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYMGMDYWGQGTLVTVSS | 99 |
| X2m1 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYFGFDYWGQGTLVTVSS | 252 |
| X2m2 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYFGLDYWGQGTLVTVSS | 253 |
| X2m3 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYSGFDYWGQGTLVTVSS | 254 |
| X2m4 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYSGLDYWGQGTLVTVSS | 255 |
| X2m5 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYFGMDYWGQGTLVTVSS | 256 |
| X2m6 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYSGMDYWGQGTLVTVSS | 257 |
| X2m7 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYMGFDYWGQGTLVTVSS | 258 |
| X2m8 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYMGLDYWGQGTLVTVSS | 259 |
| X2 | VL | DIQMTQSPSSLSASVGDRVTITCRASQSVSSAVAWYQQKPGKAP KLLIYSASSLYSGVPSRFSGSRSGTDFTLTISSLQPEDFATYYC QQSGVWLITFGQGTKVEIK | 100 |
| X3 | VH | EVQLVESGGGLVQPGGSLRLSCAASGFTISSSSIHWVRQAPGKG LEWVASISSSSGYTYYADSVKGRFTISADTSKNTAYLQMNSLRA EDTAVYYCARSWYEMWMSGYFGFDYWGQGTLVTVSS | 101 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQSSSSLITFGQGTKVEIK | 102 |

TABLE 3-continued

MuSK Antibody Variable Heavy (VH) and
Variable Light (VL) Antibody Sequences

| mAb/Fab name | Region | Sequence | SEQ ID NO: |
|---|---|---|---|
| X4 | VH | EVQLVESGGGLVQPGGSLRLSCAASGFTVSSSSIHWVRQAPGKGLEWVASISSSSGSTYYADSVKGRFTISADTSKNTAYLQMNSLRAEDTAVYYCARGEHDYYVFGYLGMDYWGQGTLVTVSS | 103 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSYKPGALITFGQGTKVEIK | 104 |
| X5 | VH | EVQLVESGGGLVQPGGSLRLSCAASGFTFYSSSIHWVRQAPGKGLEWVASISSSSGSTSYADSVKGRFTISADTSKNTAYLQMNSLRAEDTAVYYCARSYTMFYYGGWYGSGYFGMDYWGQGTLVTVSS | 105 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITFGQGTKVEIK | 106 |
| X6 | VH | EVQLVESGGGLVQPGGSLRLSCAASGFTFSSSSIHWVRQAPGKGLEWVASISSYSGYTYYADSVKGRFTISADTSKNTAYLQMNSLRAEDTAVYYCARTYGSYYVSSYTGMDYWGQGTLVTVSS | 107 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITFGQGTKVEIK | 108 |
| X7 | VH | EVQLVESGGGLVQPGGSLRLSCAASGFTLYSSSIHWVRQAPGKGLEWVASISSSYSSTYYADSVKGRFTISADTSKNTAYLQMNSLRAEDTAVYYCARLAGLYHYPGYLGLDYWGQGTLVTVSS | 109 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSRSSLLTFGQGTKVEIK | 110 |
| X8 | VH | EVQLVESGGGLVQPGGSLRLSCAASGFTVSSSSIHWVRQAPGKGLEWVASISSSSGSTSYADSVKGRFTISADTSKNTAYLQMNSLRAEDTAVYYCARSWSYHPWYYHVGWYTGLDYWGQGTLVTVSS | 111 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITFGQGTKVEIK | 112 |
| X9 | VH | EVQLVESGGGLVQPGGSLRLSCAASGFTFSSSSIHWVRQAPGKGLEWVASIYSSSGSTYYADSVKGRFTISADTSKNTAYLQMNSLRAEDTAVYYCARSGGEFYITSYYGMDYWGQGTLVTVSS | 113 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITFGQGTKVEIK | 114 |
| X10 | VH | EVQLVESGGGLVQPGGSLRLSCAASGFTFSSSSIHWVRQAPGKGLEWVASISSSYSSTSYADSVKGRFTISADTSKNTAYLQMNSLRAEDTAVYYCARKYYRWRHNKYQGFDYWGQGTLVTVSS | 115 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSLWYPVTFGQGTKVEIK | 116 |
| X11 | VH | EVQLVESGGGLVQPGGSLRLSCAASGFTISSSSIHWVRQAPGKGLEWVASISSYSGSTYYADSVKGRFTISADTSKNTAYLQMNSLRAEDTAVYYCARSWGSYYVSGFVGFDYWGQGTLVTVSS | 117 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQNSYYLITFGQGTKVEIK | 118 |
| X12 | VH | EVQLVESGGGLVQPGGSLRLSCAASGFTISSSSIHWVRQAPGKGLEWVAYISPSSGYTSYADSVKGRFTISADTSKNTAYLQMNSLRAEDTAVYYCARQYWVPQWWITQYFGMDYWGQGTLVTVSS | 119 |
| | VL | DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITFGQGTKVEIK | 120 |

TABLE 3-continued

MuSK Antibody Variable Heavy (VH) and
Variable Light (VL) Antibody Sequences

| mAb/Fab name | Region | Sequence | SEQ ID NO: |
|---|---|---|---|
| X13 | VH | EVQLVESGGGLVQPGGSLRLSCAASGFTISSSSIHWVRQAPGKG LEWVASISSSGSTSYADSVKGRFTISADTSKNTAYLQMNSLRA EDTAVYYCARSSEHWYTIGYYGIDYWGQGTLVTVSS | 121 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQSYGSFSLITFGQGTKVEIK | 122 |
| X14 | VH | EVQLVESGGGLVQPGGSLRLSCAASGFTFSSSSIHWVRQAPGKG LEWVASISSSSGYTYYADSVKGRFTISADTSKNTAYLQMNSLRA EDTAVYYCARGSHHWFLWIYSGLDYWGQGTLVTVSS | 123 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQGSYHLITFGQGTKVEIK | 124 |
| X15 | VH | EVQLVESGGGLVQPGGSLRLSCAASGFTVSSSSIHWVRQAPGKG LEWVASISSSYGSTSYADSVKGRFTISADTSKNTAYLQMNSLRA EDTAVYYCARSEGDRYVSGYMGMDYWGQGTLVTVSS | 125 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQSGVWLITFGQGTKVEIK | 126 |
| X16 | VH | EVQLVESGGGLVQPGGSLRLSCAASGFTFSSSSIHWVRQAPGKG LEWVASIYSSYGYTSYADSVKGRFTISADTSKNTAYLQMNSLRA EDTAVYYCARNWGYYMYWGWYYALDYWGQGTLVTVSS | 127 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQWSSAQALITFGQGTKVEIK | 128 |
| X17 | VH | EVQLVESGGGLVQPGGSLRLSCAASGFTISYSSIHWVRQAPGKG LEWVASIYSSSGSTYYADSVKGRFTISADTSKNTAYLQMNSLRA EDTAVYYCARGDHGYYVFGYLGMDYWGQGTLVTVSS | 131 |
| X17m1 | VH | EVQLVESGGGLVQPGGSLRLSCAASGFTISYSSIHWVRQAPGKG LEWVASIYSSSGSTYYADSVKGRFTISADTSKNTAYLQMNSLRA EDTAVYYCARGDHGYYVSGYLGMDYWGQGTLVTVSS | 260 |
| X17m2 | VH | EVQLVESGGGLVQPGGSLRLSCAASGFTISYSSIHWVRQAPGKG LEWVASIYSSSGSTYYADSVKGRFTISADTSKNTAYLQMNSLRA EDTAVYYCARGDHGYYVYGYLGMDYWGQGTLVTVSS | 261 |
| X17m3 | VH | EVQLVESGGGLVQPGGSLRLSCAASGFTISYSSIHWVRQAPGKG LEWVASIYSSSGSTYYADSVKGRFTISADTSKNTAYLQMNSLRA EDTAVYYCARGDHGYYVSGYLGFDYWGQGTLVTVSS | 262 |
| X17m6 | VH | EVQLVESGGGLVQPGGSLRLSCAASGFTISYSSIHWVRQAPGKG LEWVASIYSSSGSTYYADSVKGRFTISADTSKNTAYLQMNSLRA EDTAVYYCARGEHGYYVSGYLGFDYWGQGTLVTVSS | 263 |
| X17 | VL | DIQMTQSPSSLSASVGDRVTITCRASQSVSSAVAWYQQKPGKAP KLLIYSASSLYSGVPSRFSGSRSGTDFTLTISSLQPEDFATYYC QQSYKPGALITFGQGTKVEIK | 132 |
| X18 | VH | EVQLVESGGGLVQPGGSLRLSCAASGFTISSSSIHWVRQAPGKG LEWVASISSSSGYTSYADSVKGRFTISADTSKNTAYLQMNSLRA EDTAVYYCARKYSKRAYPDYYWRGLDYWGQGTLVTVSS | 133 |
| | VL | DIQMTQSPSSLSASVGDRVTITCRASQSVSSAVAWYQQKPGKAP KLLIYSASSLYSGVPSRFSGSRSGTDFTLTISSLQPEDFATYYC QQSYWWPITFGQGTKVEIK | 134 |
| 14D10 | VH | ELQLVESGGGLVQPGGSLRLSCAASGFTFDDYGMSWVRQAPGKG LEWVSAIPWNGGSTYYKESVKGRFTISRDNAKKTLYLQMNSLKS EDTAVYYCAKRSGRIAFGALDAWGQGTLVTVSS | 196 |
| | VL | QAVVTQEPSLSVSPGGTVTLTCGLSSGSVTSSNYPDWYQQTPGQ APRTLIYTTNSRHSGVPSRFSGSISGNKAALTITGAQPEDEADY YCALYMGGGSNVYVFGGGTKLTVL | 197 |

TABLE 3-continued

MuSK Antibody Variable Heavy (VH) and Variable Light (VL) Antibody Sequences

| mAb/Fab name | Region | Sequence | SEQ ID NO: |
|---|---|---|---|
| 7G4 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 198 |
| | VL | QAVVTQEPSLSVSPGGTVTLTCGLSSGSVTSSNYPDWYQQTPGQAPRALIYSTNSRHSGVPSRFSGSISGNKAALTITGAQPEDEADYYCALYMGRGSNKDYVFGGGTKLTVL | 199 |
| 3C4 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 200 |
| | VL | QAVVTQEPSLSVSPGGTVTLTCGLSSGSVTASNYPDWYQQTPGQAPRGLIYSTDSRHSGVPSRFSGSISGNKAALTITGAQPEDEADYYCALYMYSDSKLYVFGGGTKLTVL | 201 |
| 3B2 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 202 |
| | VL | QAVVTQEPSLSVSPGGTVTLTCGLSSGSVTSSNYPDWYQQTPGQAPRGLIYSTDSRHSGVPSRFSGSISGNKAALTITGAQSEDEADYYCGLYMYSGSKNYVFGGGTKLTVL | 203 |
| 3G3 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 204 |
| | VL | QTVVTQEPSLSVSPGGTVTLTCGLSSGSVTSSNYPDWYQQTPGQAPRALIYSTNSRHSGVPSRFSGSTSGNKAALTITGAQPEDEADYYCALYMGSDIRNYVFGGGTKLTVL | 205 |
| 31G2 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 206 |
| | VL | QAVVTQEPSLSVSPGGTVTLTCGLSSGSVTSSNYPDWYQQTPGQAPRALIYSTNSRLSGVPSRFSGSFSGNKAALTITGAQPEDEADYYCALYMGSGSRNYVFGGGTKLTVL | 207 |
| 31B7 | VH | ELQLVESGGGLVQPGGSLRLSCAASGFTFDDYGMSWVRQAPGKGLEWVSAIPWNGGSTYYKESVKGRFTISRDNAKKTLYLQMNSLKSEDTAVYYCAKRSGRIAFGALDAWGQGTLVTSS | 208 |
| | VL | QAVVTQEPSLSVSPGGTVTLTCGLSSGSVTSSNYPDWYQQTPGQAPRALIYSTNSRLSGVPSRFSGSFSGNKAALTITGAQPEDEADYYCALYMGSESRNYVFGGGTKLTVL | 209 |
| 17H10 | VH | QVQVQESGPGLVKPSQTLSLTCTVSGGSITARYYSWSWIRQPPGKGLEWMGVIAYDGSTYYSPSLKSRTSISRDTSKNQFSLHLSSVTPDDTAVYYCARGSSRVAAAFDSWGQGTQVTVSS | 210 |
| | VL | SYELTQSPSVSVALRQTAKITCGGNRIGGKSVQWYQQKPGQAPMLVIYADSRRPSGIPERFTGSNSGNTATLTITGAQAEDEADYYCHVWGSTASADFGGGTHLTVL | 211 |
| 23B6 | VH | QVQVQESGPGLVKPSQTLSLTCTVSGGSITARYYSWSWIRQPPGKGLEWMGVIAYDGSTYYSPSLKSRTSISRDTSKNQFSLHLSSVTPDDTAVYYCARGSSRVAAAFDSWGQGTQVTVSS | 212 |
| | VL | SYELTQSPSVSVALRQTAKITCGGDNIGSKNAQWYQQKPGQAPVMVLYADSRRPSGIPERFSGSNSGNTATLTISGAQAEDEADYYCHVWDSSTNAWFGGGTHLTVL | 213 |
| 30E1 | VH | QVQVQESGPGLVKPSQTLSLTCTVSGGSITARYYSWSWIRQPPGKGLEWMGVIAYDGSTYYSPSLKSRTSISRDTSKNQFSLHLSSVTPDDTAVYYCARGSSRVAAAFDSWGQGTQVTVSS | 214 |
| | VL | SYELTQSPSVSVALRRTAKITCGGDNIGSKNTQWYQQKPGQAPVLVIYADSRRPSGIPERFSGSNSGNTATLTISGAQAEDEADYYCHVWDSSTNAWFGGGTHLTVL | 215 |

TABLE 3-continued

MuSK Antibody Variable Heavy (VH) and Variable Light (VL) Antibody Sequences

| mAb/Fab name | Region | Sequence | SEQ ID NO: |
|---|---|---|---|
| 30A11 | VH | QVQVQESGPGLVKPSQTLSLTCTVSGGSITARYYSWSWIRQPPG KGLEWMGVIAYDGSTYYSPSLKSRTSISRDTSKNQFSLHLSSVT PDDTAVYYCARGSSRVAAAFDSWGQGTQVTVSS | 216 |
| | VL | SYELTQSPSVTVALRQTAKITCGGDNIASKNVQWYQQKPGQAPS LVIWADSRRPSGIPVRFSGSNFGNTATLTISGAQAEDEADYYCQ VWDSSTNVAVFGGGTHLTVL | 217 |
| 16F11 | VH | EVQLVESGGGLVQPGGSLSLSCVASGFTFSLYYMNWVRQAPGKG LEWLSVIDTHSIAYYADSVKGRFTISRDNVKNTLYLQLNNLKPE DTALYYCVLGRTALVRWGQGTQVTVSS | 218 |
| | VL | DIVMTQSPSSVTASVGEKVTINCKSSQSVVFGSNQKSYLNWYQQ RPGQSPRLLIYYASTQESGIPDRFSGSGSTTDFTLTISSVQPED AAVYYCQQAYSAPTFGSGTRLEIK | 219 |
| 4C11 | VH | EVQLVESGGGLVQPGGSLSLSCVASGFTFSLYYMNWVRQAPGKG LEWLSVIDTHSIAYYADSVKGRFTISRDNVKNTLYLQLNNLKPE DTALYYCVLGRTALVRWGQGTQVTVSS | 220 |
| | VL | DIVMTQSPSSVTASAGERVTINCRSSQSVLYSSNQKNYLNWYQQ RLGQSPRLLIYWASARESGVPDRFSGSGSTTNFTLTISSFQPED AAVYYCQQSYKPPYGFGSGTRLEIK | 221 |
| 7A12 | VH | EVQLVESGGGLVQPGGSLSLSCVASGFTFSLYYMNWVRQAPGKG LEWLSVIDTHSIAYYADSVKGRFTISRDNVKNTLYLQLNNLKPE DTALYYCVLGRTALVRWGQGTQVTVSS | 222 |
| | VL | EIVLTQSPSSVTASIGEKVTINCESSQSVLYNQKNYLNWYQQRP GQSPRLLIYWASTRQSGVPDRFSGSGSGSTTDFTLTISSFQPED VAVYYCQQAYNAPLTFGPGTKVELK | 223 |
| 7G12 | VH | EVQLVESGGGLVQPGGSLSLSCVASGFTFSLYYMNWVRQAPGKG LEWLSVIDTHSIAYYADSVKGRFTISRDNVKNTLYLQLNNLKPE DTALYYCVLGRTALVRWGQGTQVTVSS | 224 |
| | VL | EIVLTQSPNSVTASVGEKVTINCKSSQRVQLGSNQKSYLNWYQQ RPGQSPRLLIYYASTQQSGIPDRFSGSGSATDFTLTINSVQPED AAVYYCQQGYSAPFTFGQGTKVELK | 225 |
| 7B8 | VH | EVQLVESGGGLVQPGGSLSLSCVASGFTFSLYYMNWVRQAPGKG LEWLSVIDTHSIAYYADSVKGRFTISRDNVKNTLYLQLNNLKPE DTALYYCVLGRTALVRWGQGTQVTVSS | 226 |
| | VL | EIVLTQSPSSVTASAGEKVTINCKSSQSVLYNQKNYLAWYQQRP GQSPRLLIYWASTRESGVPDRFSGSGSTTDFTLTISSFQPEDVA VYYCQQGYSVPYTFGSGTRLEIK | 227 |
| 3B2g1m1 | VH | EVQLLESGGGLVQPGGSLRLSCAASGFTFSDYGMSWVRQAPGKG LEWVSAIPWSGGSTYYKESVKGRFTISRDNSKNTLYLQMNSLRA EDTAVYYCAKRSGRIAFGALDAWGQGTLVTVSS | 228 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYMYSGSKNYVFGGGTKLTVL | 229 |
| 3B2g1m2 | VH | EVQLLESGGGLVQPGGSLRLSCAASGFTFSDYGMSWVRQAPGKG LEWVSAIPGSGGSTYYKESVKGRFTISRDNSKNTLYLQMNSLRA EDTAVYYCAKRSGRIAFGALDAWGQGTLVTVSS | 230 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYMYSGSKNYVFGGGTKLTVL | 231 |
| 3B2g1m4 | VH | EVQLLESGGGLVQPGGSLRLSCAASGFTFSDYGMSWVRQAPGKG LEWVSAIPWQGGSTYYKESVKGRFTISRDNSKNTLYLQMNSLRA EDTAVYYCAKRSGRIAFGALDAWGQGTLVTVSS | 232 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYMYSGSKNYVFGGGTKLTVL | 233 |

TABLE 3-continued

MuSK Antibody Variable Heavy (VH) and
Variable Light (VL) Antibody Sequences

| mAb/Fab name | Region | Sequence | SEQ ID NO: |
|---|---|---|---|
| 3B2g2m1 | VH | EVQLLESGGGLVQPGGSLRLSCAASGFTFSDYGMSWVRQAPGKG LEWVSAIPWSGGSTYYKESVKGRFTISRDNSKNTLYLQMNSLRA EDTAVYYCAKRSGRIAFGALDAWGQGTLVTVSS | 234 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYSYSGSKNYVFGGGTKLTVL | 235 |
| 3B2g2m2 | VH | EVQLLESGGGLVQPGGSLRLSCAASGFTFSDYGMSWVRQAPGKG LEWVSAIPGSGGSTYYKESVKGRFTISRDNSKNTLYLQMNSLRA EDTAVYYCAKRSGRIAFGALDAWGQGTLVTVSS | 236 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYSYSGSKNYVFGGGTKLTVL | 237 |
| 3B2g2m4 | VH | EVQLLESGGGLVQPGGSLRLSCAASGFTFSDYGMSWVRQAPGKG LEWVSAIPWQGGSTYYKESVKGRFTISRDNSKNTLYLQMNSLRA EDTAVYYCAKRSGRIAFGALDAWGQGTLVTVSS | 238 |
| | VL | QTVVTQEPSFSVSPGGTVTLTCGLSSGSVTSSNYPDWYQQTPGQ APRTLIYSTDSRHSGVPDRFSGSILGNKAALTITGAQADDESDY YCGLYSYSGSKNYVFGGGTKLTVL | 239 |

In an embodiment, the MuSK antibody-based molecule disclosed herein comprises: (i) a heavy chain variable region comprising an amino acid sequence that is at least 80% identical to SEQ ID NO: 97 and a light chain variable region comprising an amino acid sequence that is at least 80% identical to SEQ ID NO: 98; (ii) a heavy chain variable region comprising an amino acid sequence that is at least 80% identical to any one of SEQ ID NOs: 99 and 252-259 and a light chain variable region comprising an amino acid sequence that is at least 80% identical to SEQ ID NO: 100; (iii) a heavy chain variable region comprising an amino acid sequence that is at least 80% identical to SEQ ID NO: 101 and a light chain variable region comprising an amino acid sequence that is at least 80% identical to SEQ ID NO: 102; (iv) a heavy chain variable region comprising an amino acid sequence that is at least 80% identical to SEQ ID NO: 103 and a light chain variable region comprising an amino acid sequence that is at least 80% identical to SEQ ID NO: 104; (v) a heavy chain variable region comprising an amino acid sequence that is at least 80% identical to SEQ ID NO: 105 and a light chain variable region comprising an amino acid sequence that is at least 80% identical to SEQ ID NO: 106; (vi) a heavy chain variable region comprising an amino acid sequence that is at least 80% identical to SEQ ID NO: 107 and a light chain variable region comprising an amino acid sequence that is at least 80% identical to SEQ ID NO: 108; or (vii) a heavy chain variable region comprising an amino acid sequence that is at least 80% identical to SEQ ID NO: 109 and a light chain variable region comprising an amino acid sequence that is at least 80% identical to SEQ ID NO: 110; (viii) a heavy chain variable region comprising an amino acid sequence that is at least 80% identical to SEQ ID NO: 111 and a light chain variable region comprising an amino acid sequence that is at least 80% identical to SEQ ID NO: 112; (ix) a heavy chain variable region comprising an amino acid sequence that is at least 80% identical to SEQ ID NO: 113 and a light chain variable region comprising an amino acid sequence that is at least 80% identical to SEQ ID NO: 114; (x) a heavy chain variable region comprising an amino acid sequence that is at least 80% identical to SEQ ID NO: 115 and a light chain variable region comprising an amino acid sequence that is at least 80% identical to SEQ ID NO: 116; (xi) a heavy chain variable region comprising an amino acid sequence that is at least 80% identical to SEQ ID NO: 117 and a light chain variable region comprising an amino acid sequence that is at least 80% identical to SEQ ID NO: 118; (xii) a heavy chain variable region comprising an amino acid sequence that is at least 80% identical to SEQ ID NO: 119 and a light chain variable region comprising an amino acid sequence that is at least 80% identical to SEQ ID NO: 120; (xiii) a heavy chain variable region comprising an amino acid sequence that is at least 80% identical to SEQ ID NO: 121 and a light chain variable region comprising an amino acid sequence that is at least 80% identical to SEQ ID NO: 122; (xiv) a heavy chain variable region comprising an amino acid sequence that is at least 80% identical to SEQ ID NO: 123 and a light chain variable region comprising an amino acid sequence that is at least 80% identical to SEQ ID NO: 124; (xv) a heavy chain variable region comprising an amino acid sequence that is at least 80% identical to SEQ ID NO: 125 and a light chain variable region comprising an amino acid sequence that is at least 80% identical to SEQ ID NO: 126; (xvi) a heavy chain variable region comprising an amino acid sequence that is at least 80% identical to SEQ ID NO: 127 and a light chain variable region comprising an amino acid sequence that is at least 80% identical to SEQ ID NO: 128; (xvii) a heavy chain variable region comprising an amino acid sequence that is at least 80% identical to any one of SEQ ID NOs: 131 and 260-263 and a light chain variable region comprising an amino acid sequence that is at least 80% identical to SEQ ID NO: 132; and (xviii) a heavy chain variable region comprising an amino acid sequence that is at least 80% identical to SEQ ID NO: 133 and a light chain variable region comprising an amino acid sequence that is at least 80% identical to SEQ ID NO: 134.

In some embodiments, the MuSK antibody-based molecule disclosed herein comprises: (i) a heavy chain variable region comprising an amino acid sequence that is at least 80% identical to SEQ ID NO: 196 and a light chain variable region comprising an amino acid sequence that is at least 80% identical to SEQ ID NO: 197; (ii) a heavy chain variable region comprising an amino acid sequence that is at least 80% identical to SEQ ID NO: 198 and a light chain variable region comprising an amino acid sequence that is at least 80% identical to SEQ ID NO: 199; (iii) a heavy chain variable region comprising an amino acid sequence that is at least 80% identical to SEQ ID NO: 200 and a light chain variable region comprising an amino acid sequence that is at least 80% identical to SEQ ID NO: 201; (iv) a heavy chain variable region comprising an amino acid sequence that is at least 80% identical to SEQ ID NO: 202 and a light chain variable region comprising an amino acid sequence that is at least 80% identical to SEQ ID NO: 203; (v) a heavy chain variable region comprising an amino acid sequence that is at least 80% identical to SEQ ID NO: 204 and a light chain variable region comprising an amino acid sequence that is at least 80% identical to SEQ ID NO: 205; (vi) a heavy chain variable region comprising an amino acid sequence that is at least 80% identical to SEQ ID NO: 206 and a light chain variable region comprising an amino acid sequence that is at least 80% identical to SEQ ID NO: 207; (vii) a heavy chain variable region comprising an amino acid sequence that is at least 80% identical to SEQ ID NO: 208 and a light chain variable region comprising an amino acid sequence that is at least 80% identical to SEQ ID NO: 209; (viii) a heavy chain variable region comprising an amino acid sequence that is at least 80% identical to SEQ ID NO: 210 and a light chain variable region comprising an amino acid sequence that is at least 80% identical to SEQ ID NO: 211; (vix) a heavy chain variable region comprising an amino acid sequence that is at least 80% identical to SEQ ID NO: 212 and a light chain variable region comprising an amino acid sequence that is at least 80% identical to SEQ ID NO: 213; (x) a heavy chain variable region comprising an amino acid sequence that is at least 80% identical to SEQ ID NO: 214 and a light chain variable region comprising an amino acid sequence that is at least 80% identical to SEQ ID NO: 215; (xi) a heavy chain variable region comprising an amino acid sequence that is at least 80% identical to SEQ ID NO: 216 and a light chain variable region comprising an amino acid sequence that is at least 80% identical to SEQ ID NO: 217; (xii) a heavy chain variable region comprising an amino acid sequence that is at least 80% identical to SEQ ID NO: 218 and a light chain variable region comprising an amino acid sequence that is at least 80% identical to SEQ ID NO: 219; (xiii) a heavy chain variable region comprising an amino acid sequence that is at least 80% identical to SEQ ID NO: 220 and a light chain variable region comprising an amino acid sequence that is at least 80% identical to SEQ ID NO: 221; (xiv) a heavy chain variable region comprising an amino acid sequence that is at least 80% identical to SEQ ID NO: 222 and a light chain variable region comprising an amino acid sequence that is at least 80% identical to SEQ ID NO: 223; (xv) a heavy chain variable region comprising an amino acid sequence that is at least 80% identical to SEQ ID NO: 224 and a light chain variable region comprising an amino acid sequence that is at least 80% identical to SEQ ID NO: 225; (xvi) a heavy chain variable region comprising an amino acid sequence that is at least 80% identical to SEQ ID NO: 226 and a light chain variable region comprising an amino acid sequence that is at least 80% identical to SEQ ID NO: 227; (xvii) a heavy chain variable region comprising an amino acid sequence that is at least 80% identical to SEQ ID NO: 228 and a light chain variable region comprising an amino acid sequence that is at least 80% identical to SEQ ID NO: 229; (xviii) a heavy chain variable region comprising an amino acid sequence that is at least 80% identical to SEQ ID NO: 230 and a light chain variable region comprising an amino acid sequence that is at least 80% identical to SEQ ID NO: 231; (xix) a heavy chain variable region comprising an amino acid sequence that is at least 80% identical to SEQ ID NO: 232 and a light chain variable region comprising an amino acid sequence that is at least 80% identical to SEQ ID NO: 233; (xx) a heavy chain variable region comprising an amino acid sequence that is at least 80% identical to SEQ ID NO: 234 and a light chain variable region comprising an amino acid sequence that is at least 80% identical to SEQ ID NO: 235; (xxi) a heavy chain variable region comprising an amino acid sequence that is at least 80% identical to SEQ ID NO: 236 and a light chain variable region comprising an amino acid sequence that is at least 80% identical to SEQ ID NO: 237; (xxii) a heavy chain variable region comprising an amino acid sequence that is at least 80% identical to SEQ ID NO: 238 and a light chain variable region comprising an amino acid sequence that is at least 80% identical to SEQ ID NO: 239.

Another aspect of the present invention is directed to isolated polynucleotides encoding the MuSK antibody-based molecules described herein. In one embodiment, the polynucleotide encoding the MuSK antibody of the present invention comprises a sequence encoding any one, any two, any three, any four, any five, or any six of the CDRs described supra, including the heavy chain CDRs of SEQ ID NOs: 1-48, 135-140, 147-158, 240-251 and the light chain CDRs of SEQ ID NOs: 49-96, 141-146, and 159-195.

In an embodiment, the polynucleotide comprises a nucleotide sequence encoding a $V_H$ domain, where the $V_H$ domain comprises (i) a heavy chain variable region comprising the CDR-H1 of SEQ ID NO: 1, the CDR-H2 of SEQ ID NO: 17, and the CDR-H3 of SEQ ID NO: 33; (ii) a heavy chain variable region comprising the CDR-H1 of SEQ ID NO: 2, the CDR-H2 of SEQ ID NO: 18, and the CDR-H3 of SEQ ID NO: 34; (iii) a heavy chain variable region comprising the CDR-H1 of SEQ ID NO: 3, the CDR-H2 of SEQ ID NO: 19, and the CDR-H3 of SEQ ID NO: 35; (iv) a heavy chain variable region comprising the CDR-H1 of SEQ ID NO: 4, the CDR-H2 of SEQ ID NO: 20, and the CDR-H3 of SEQ ID NO: 36; (v) a heavy chain variable region comprising the CDR-H1 of SEQ ID NO: 5, the CDR-H2 of SEQ ID NO: 21, and the CDR-H3 of SEQ ID NO: 37; (vi) a heavy chain variable region comprising the CDR-H1 of SEQ ID NO: 6, the CDR-H2 of SEQ ID NO: 22, and the CDR-H3 of SEQ ID NO: 38; (vii) a heavy chain variable region comprising the CDR-H1 of SEQ ID NO: 7, the CDR-H2 of SEQ ID NO: 23, and the CDR-H3 of SEQ ID NO: 39; (viii) a heavy chain variable region comprising the CDR-H1 of SEQ ID NO: 8, the CDR-H2 of SEQ ID NO: 24, and the CDR-H3 of SEQ ID NO: 40; (ix) a heavy chain variable region comprising the CDR-H1 of SEQ ID NO: 9, the CDR-H2 of SEQ ID NO: 25, and the CDR-H3 of SEQ ID NO: 41; (x) a heavy chain variable region comprising the CDR-H1 of SEQ ID NO: 10, the CDR-H2 of SEQ ID NO: 26, and the CDR-H3 of SEQ ID NO: 42; (xi) a heavy chain variable region comprising the CDR-H1 of SEQ ID NO: 11, the CDR-H2 of SEQ ID NO: 27, and the CDR-H3 of SEQ ID NO: 43; (xii) a heavy chain variable region comprising the CDR-H1 of SEQ ID NO: 12, the CDR-H2 of SEQ ID NO: 28, and the CDR-H3 of SEQ ID NO: 44; (xiii) a heavy chain variable region comprising the CDR-H1 of SEQ ID NO: 13, the CDR-H2 of SEQ ID NO: 29, and the CDR-H3 of SEQ ID NO: 45; (xiv) a heavy chain variable region comprising the CDR-H1 of SEQ ID NO: 14, the CDR-H2 of SEQ ID NO: 30, and the CDR-H3 of SEQ ID NO: 46; (xv) a heavy chain variable region comprising the CDR-H1 of SEQ ID NO: 15, the CDR-H2 of SEQ ID NO: 31, and the CDR-H3 of SEQ ID NO: 47; (xvi) a heavy chain variable region comprising the CDR-H1 of SEQ ID NO: 16, the CDR-H2 of SEQ ID NO: 32, and the CDR-H3 of SEQ ID NO: 48; (xvii) a heavy chain variable region comprising the CDR-H1 of SEQ ID NO: 135, the CDR-H2 of SEQ ID NO: 137, and the CDR-H3 of SEQ ID NO: 139; and (xviii) a heavy chain variable region comprising the CDR-H1 of SEQ ID NO: 136, the CDR-H2 of SEQ ID NO: 138, and the CDR-H3 of SEQ ID NO: 140.

In some embodiments, the polynucleotide comprises a nucleotide sequence encoding a $V_H$ domain, where the $V_H$ domain comprises (ii.a) a heavy chain variable region comprising the CDR-H1 of SEQ ID NO: 2, the CDR-H2 of SEQ ID NO: 18, and the CDR-H3 of SEQ ID NO: 240 (X2m1); (ii.b) a heavy chain variable region comprising the CDR-H1 of SEQ ID NO: 2, the CDR-H2 of SEQ ID NO: 18, and the CDR-H3 of SEQ ID NO: 241 (X2m2); (ii.c) a heavy chain variable region comprising the CDR-H1 of SEQ ID NO: 2, the CDR-H2 of SEQ ID NO: 18, and the CDR-H3 of SEQ ID NO: 242 (X2m3); (ii.d) a heavy chain variable region comprising the CDR-H1 of SEQ ID NO: 2, the CDR-H2 of SEQ ID NO: 18, and the CDR-H3 of SEQ ID NO: 243 (X2m4); (ii.e) a heavy chain variable region comprising the CDR-H1 of SEQ ID NO: 2, the CDR-H2 of SEQ ID NO: 18, and the CDR-H3 of SEQ ID NO: 244 (X2m5); (ii.f) a heavy chain variable region comprising the CDR-H1 of SEQ ID NO: 2, the CDR-H2 of SEQ ID NO: 18, and the CDR-H3 of SEQ ID NO: 245 (X2m6); (ii.g) a heavy chain variable region comprising the CDR-H1 of SEQ ID NO: 2, the CDR-H2 of SEQ ID NO: 18, and the CDR-H3 of SEQ ID NO: 246 (X2m7); (ii.h) a heavy chain variable region comprising the CDR-H1 of SEQ ID NO: 2, the CDR-H2 of SEQ ID NO: 18, and the CDR-H3 of SEQ ID NO: 247 (X2m8).

In some embodiments, the polynucleotide comprises a nucleotide sequence encoding a $V_H$ domain, where the $V_H$ domain comprises (xvii.a) a heavy chain variable region comprising the CDR-H1 of SEQ ID NO: 135, the CDR-H2 of SEQ ID NO: 137, and the CDR-H3 of SEQ ID NO: 248 (X17m1); (xvii.b) a heavy chain variable region comprising the CDR-H1 of SEQ ID NO: 135, the CDR-H2 of SEQ ID NO: 137, and the CDR-H3 of SEQ ID NO: 249 (X17m2); (xvii.c) a heavy chain variable region comprising the CDR-H1 of SEQ ID NO: 135, the CDR-H2 of SEQ ID NO: 137, and the CDR-H3 of SEQ ID NO: 250 (X17m3); (xvii.d) a heavy chain variable region comprising the CDR-H1 of SEQ ID NO: 135, the CDR-H2 of SEQ ID NO: 137, and the CDR-H3 of SEQ ID NO: 251 (X17m6).

In an embodiment, the polynucleotide comprises a nucleotide sequence encoding a $V_H$ domain, where the $V_H$ domain comprises: (xix) a heavy chain variable region comprising the CDR-H1 of SEQ ID NO: 147, the CDR-H2 of SEQ ID NO: 150, and the CDR-H3 of SEQ ID NO: 156; (xx) a heavy chain variable region comprising the CDR-H1 of SEQ ID NO: 148, the CDR-H2 of SEQ ID NO: 151, and the CDR-H3 of SEQ ID NO: 157; (xxi) a heavy chain variable region comprising the CDR-H1 of SEQ ID NO: 149, the CDR-H2 of SEQ ID NO: 152, and the CDR-H3 of SEQ ID NO: 158.

In an embodiment, the polynucleotide comprises a nucleotide sequence encoding a $V_H$ domain, where the $V_H$ domain comprises: (xxii) a heavy chain variable region comprising the CDR-H1 of SEQ ID NO: 147, the CDR-H2 of SEQ ID NO: 153, and the CDR-H3 of SEQ ID NO:156; (xxiii) a heavy chain variable region comprising the CDR-H1 of SEQ ID NO: 147, the CDR-H2 of SEQ ID NO: 154, and the CDR-H3 of SEQ ID NO: 156; (xxiv) a heavy chain variable region comprising the CDR-H1 of SEQ ID NO: 147, the CDR-H2 of SEQ ID NO: 155, and the CDR-H3 of SEQ ID NO: 156.

In an embodiment, the polynucleotide comprises a nucleotide sequence encoding a $V_L$ domain, where the $V_L$ domain comprises (i) a light chain variable region comprising the CDR-L1 of SEQ ID NO: 49, the CDR-L2 of SEQ ID NO: 65, and the CDR-L3 of SEQ ID NO: 81; (ii) a light chain variable region comprising the CDR-L1 of SEQ ID NO: 50, the CDR-L2 of SEQ ID NO: 66, and the CDR-L3 of SEQ ID NO: 82; (iii) a light chain variable region comprising the CDR-L1 of SEQ ID NO: 51, the CDR-L2 of SEQ ID NO: 67, and the CDR-L3 of SEQ ID NO: 83; (iv) a light chain variable region comprising the CDR-L1 of SEQ ID NO: 52, the CDR-L2 of SEQ ID NO: 68, and the CDR-L3 of SEQ ID NO: 84; (v) a light chain variable region comprising the CDR-L1 of SEQ ID NO: 53, the CDR-L2 of SEQ ID NO: 69, and the CDR-L3 of SEQ ID NO: 85; (vi) a light chain variable region comprising the CDR-L1 of SEQ ID NO: 54, the CDR-L2 of SEQ ID NO: 70, and the CDR-L3 of SEQ ID NO: 86; (vii) a light chain variable region comprising the CDR-L1 of SEQ ID NO: 55, the CDR-L2 of SEQ ID NO:71, and the CDR-L3 of SEQ ID NO: 87; (viii) a light chain variable region comprising the CDR-L1 of SEQ ID NO: 56, the CDR-L2 of SEQ ID NO: 72, and the CDR-L3 of SEQ ID NO: 88; (ix) a light chain variable region comprising the CDR-L1 of SEQ ID NO: 57, the CDR-L2 of SEQ ID NO: 73, and the CDR-L3 of SEQ ID NO: 89; (x) a light chain variable region comprising the CDR-L1 of SEQ ID NO: 58, the CDR-L2 of SEQ ID NO: 74, and the CDR-L3 of SEQ ID NO: 90; (xi) a light chain variable region comprising the CDR-L1 of SEQ ID NO: 59, the CDR-L2 of SEQ ID NO: 75, and the CDR-L3 of SEQ ID NO: 91; (xii) a light chain variable region comprising the CDR-L1 of SEQ ID NO: 60, the CDR-L2 of SEQ ID NO: 76, and the CDR-L3 of SEQ ID NO: 92; (xiii) a light chain variable region comprising the CDR-L1 of SEQ ID NO: 61, the CDR-L2 of SEQ ID NO: 77, and the CDR-L3 of SEQ ID NO: 93; (xiv) a light chain variable region comprising the CDR-L1 of SEQ ID NO: 62, the CDR-L2 of SEQ ID NO: 78, and the CDR-L3 of SEQ ID NO: 94; (xv) a light chain variable region comprising the CDR-L1 of SEQ ID NO: 63, the CDR-L2 of SEQ ID NO: 79, and the CDR-L3 of SEQ ID NO: 95; (xvi) a light chain variable region comprising the CDR-L1 of SEQ ID NO: 64, the CDR-L2 of SEQ ID NO: 80, and the CDR-L3 of SEQ ID NO: 96; (xvii) a light chain variable region comprising the CDR-L1 of SEQ ID NO: 141, the CDR-L2 of SEQ ID NO: 143, and the CDR-L3 of SEQ ID NO: 145; and (xviii) a light chain variable region comprising the CDR-L1 of SEQ ID NO: 142, the CDR-L2 of SEQ ID NO: 144, and the CDR-L3 of SEQ ID NO: 146.

In an embodiment, the polynucleotide comprises a nucleotide sequence encoding a $V_L$ domain, where the $V_L$ domain comprises (xix) a light chain variable region comprising the CDR-L1 of SEQ ID NO: 159, the CDR-L2 of SEQ ID NO: 170, and the CDR-L3 of SEQ ID NO: 180; (xx) a light chain variable region comprising the CDR-L1 of SEQ ID NO: 159, the CDR-L2 of SEQ ID NO: 171, and the CDR-L3 of SEQ ID NO: 181; (xxi) a light chain variable region comprising the CDR-L1 of SEQ ID NO: 160, the CDR-L2 of SEQ ID NO: 172, and the CDR-L3 of SEQ ID NO: 182; (xxii) a light chain variable region comprising the CDR-L1 of SEQ ID NO: 159, the CDR-L2 of SEQ ID NO: 172, and the CDR-L3 of SEQ ID NO: 183; (xxiii) a light chain variable region comprising the CDR-L1 of SEQ ID NO: 159, the CDR-L2 of SEQ ID NO: 171, and the CDR-L3 of SEQ ID NO: 184; (xxiv) a light chain variable region comprising the CDR-L1 of SEQ ID NO: 159, the CDR-L2 of SEQ ID NO: 173, and the CDR-L3 of SEQ ID NO: 185; (xxv) a light chain variable region comprising the CDR-L1 of SEQ ID NO: 159, the CDR-L2 of SEQ ID NO: 173, and the CDR-L3 of SEQ ID NO: 186; (xxvi) a light chain variable region comprising the CDR-L1 of SEQ ID NO: 161, the CDR-L2 of SEQ ID NO: 174, and the CDR-L3 of SEQ ID NO: 187; (xxvii) a light chain variable region comprising the CDR-L1 of SEQ ID NO: 162, the CDR-L2 of SEQ ID NO: 174, and the CDR-L3 of SEQ ID NO: 188; (xxviii) a light chain variable region comprising the CDR-L1 of SEQ ID NO: 163, the CDR-L2 of SEQ ID NO: 174, and the CDR-L3 of SEQ ID NO: 188; (xxix) a light chain variable region comprising the CDR-L1 of SEQ ID NO: 164, the CDR-L2 of SEQ ID NO: 174, and the CDR-L3 of SEQ ID NO: 189; (xxx) a light chain variable region comprising the CDR-L1 of SEQ ID NO: 165, the CDR-L2 of SEQ ID NO: 175, and the CDR-L3 of SEQ ID NO: 190; (xxxi) a light chain variable region comprising the CDR-L1 of SEQ ID NO: 166, the CDR-L2 of SEQ ID NO: 176, and the CDR-L3 of SEQ ID NO: 191; (xxxi) a light chain variable region comprising the CDR-L1 of SEQ ID NO: 167, the CDR-L2 of SEQ ID NO: 177, and the CDR-L3 of SEQ ID NO: 192; (xxxii) a light chain variable region comprising the CDR-L1 of SEQ ID NO: 168, the CDR-L2 of SEQ ID NO: 178, and the CDR-L3 of SEQ ID NO: 193; (xxxiii) a light chain variable region comprising the CDR-L1 of SEQ ID NO: 169, the CDR-L2 of SEQ ID NO: 179, and the CDR-L3 of SEQ ID NO: 194.

In an embodiment, the polynucleotide comprises a nucleotide sequence encoding a $V_L$ domain, where the $V_L$ domain comprises (xxxiv) a light chain variable region comprising the CDR-L1 of SEQ ID NO: 159, the CDR-L2 of SEQ ID NO: 172, and the CDR-L3 of SEQ ID NO: 183; (xxxv) a light chain variable region comprising the CDR-L1 of SEQ ID NO: 159, the CDR-L2 of SEQ ID NO: 172, and the CDR-L3 of SEQ ID NO: 195.

In one embodiment, the isolated polynucleotide encoding the MuSK antibody based molecule encodes any one of the $V_H$ and/or $V_L$ domain sequences as provided in Table 3 infra. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding for example a linker sequence, a marker or a tag sequence, such as a histidine tag or an HA tag to facilitate purification or detection of the protein, a signal sequence, a fusion protein partner such as RepA, Fc portion, or bacteriophage coat protein such as pIX or pIII.

Another embodiment of the invention is directed to a vector comprising at least one polynucleotide encoding the MuSK antibody-based molecule as described herein. Such vectors include, without limitation, plasmid vectors, viral vectors, including without limitation, vaccina vector, lentiviral vector, adenoviral vector, adeno-associated viral vector, vectors for baculovirus expression, transposon based vectors or any other vector suitable for introduction of the polynucleotides described herein into a given organism or genetic background by any means to facilitate expression of the encoded antibody polypeptide. In one embodiment, the polynucleotide sequence encoding the heavy chain variable domain, alone or together with the polynucleotide sequence encoding the light chain variable domain as described herein, are combined with sequences of a promoter, a translation initiation segment (e.g., a ribosomal binding sequence and start codon), a 3' untranslated region, polyadenylation signal, a termination codon, and transcription termination to form one or more expression vector constructs.

In one embodiment, the vector is an adenoviral-associated viral (AAV) vector. A number of therapeutic AAV vectors suitable for delivery of the polynucleotides encoding antibodies described herein to the central nervous system are known in the art. See e.g., Deverman et al., "Gene Therapy for Neurological Disorders: Progress and Prospects," Nature Rev. 17:641-659 (2018), which in hereby incorporated by reference in its entirety. Suitable AAV vectors include serotypes AAV1, AAV2, AAV3, AAV4, AAV5, AAV6, AAV7, AAV8, AAV9, AAV10, or AAV11 in their native form or engineered for enhanced tropism. AAV vectors known to have tropism for the CNS that are particularly suited for therapeutic expression of the MuSK antibodies described herein include, AAV1, AAV2, AAV4, AAV5, AAV8 and AAV9 in their native form or engineered for enhanced tropism. In one embodiment, the AAV vector is an AAV2 vector. In another embodiment, the AAV vector is an AAV5 vector (Vitale et al., "Anti-tau Conformational scFv MCI Antibody Efficiently Reduces Pathological Tau Species in Adult JNPL3 Mice," *Acta Neuropathol. Commun.* 6:82 (2018), which is hereby incorporate by reference in its entirety). In another embodiment, the AAV vector is an AAV9 vector (Haiyan et al., "Targeting Root Cause by Systemic scAAV9-hIDS Gene Delivery: Functional Correction and Reversal of Severe MPSII in Mice,"*Mol. Ther. Methods Clin. Dev.* 10:327-340 (2018), which is hereby incorporated by reference in its entirety). In another embodiment, the AAV vector is an AAVrh10 vector (Liu et al., "Vectored Intracerebral Immunizations with the Anti-Tau Monoclonal Antibody PHF1 Markedly Reduces Tau Pathology in Mutant Transgenic Mice," *J. Neurosci.* 36(49): 12425-35 (2016), which is hereby incorporated by reference in its entirety).

In another embodiment the AAV vector is a hybrid vector comprising the genome of one serotype, e.g., AAV2, and the capsid protein of another serotype, e.g., AAV1 or AAV3-9 to control tropism. See e.g., Broekman et al., "Adeno-associated Virus Vectors Serotyped with AAV8 Capsid are More Efficient than AAV-1 or -2 Serotypes for Widespread Gene Delivery to the Neonatal Mouse Brain," *Neuroscience* 138: 501-510 (2006), which is hereby incorporated by reference in its entirety. In one embodiment, the AAV vector is an AAV2/8 hybrid vector (Ising et al., "AAV-mediated Expression of Anti-Tau ScFv Decreases Tau Accumulation in a Mouse Model of Tauopathy," *J. Exp. Med.* 214(5):1227 (2017), which is hereby incorporated by reference in its entirety). In another embodiment the AAV vector is an AAV2/9 hybrid vector (Simon et al., "A Rapid Gene Delivery-Based Mouse Model for Early-Stage Alzheimer Disease-Type Tauopathy," *J. Neuropath. Exp. Neurol.* 72(11): 1062-71 (2013), which is hereby incorporated by reference in its entirety).

In another embodiment, the AAV vector is one that has been engineered or selected for its enhanced CNS transduction after intraparenchymal administration, e.g., AAV-DJ (Grimm et al., *J. Viol.* 82:5887-5911 (2008), which is hereby incorporated by reference in its entirety); increased transduction of neural stem and progenitor cells, e.g., SCH9 and AAV4.18 (Murlidharan et al., *J. Virol.* 89: 3976-3987 (2015) and Ojala et al., *Mol. Ther.* 26:304-319 (2018), which are hereby incorporated by reference in their entirety); enhanced retrograde transduction, e.g., rAAV2-retro (Muller et al., *Nat. Biotechnol.* 21:1040-1046 (2003), which is hereby incorporated by reference in its entirety); selective transduction into brain endothelial cells, e.g., AAV-BRI (Korbelin et al., *EMBO Mol. Med.* 8: 609-625 (2016), which is hereby incorporated by reference in its entirety); or enhanced transduction of the adult CNS after IV administration, e.g., AAV-PHP.B and AAVPHP.eB (Deverman et al., Nat. Biotechnol. 34: 204-209 (2016) and Chan et al., *Nat. Neurosci.* 20: 1172-1179 (2017), which are hereby incorporated by reference in their entirety.

In accordance with this embodiment, the expression vector construct encoding the MuSK antibody-based molecule includes the polynucleotide sequence encoding the heavy chain polypeptide, a functional fragment thereof, a variant thereof, or combinations thereof. The expression construct can alternatively include a nucleic acid sequence encoding the light chain polypeptide, a functional fragment thereof, a variant thereof, or combinations thereof. In an embodiment, the expression vector construct includes a nucleic acid sequence encoding the heavy chain polypeptide, a functional fragment thereof, or a variant thereof, and the light chain polypeptide, a functional fragment thereof, or a variant thereof.

In an embodiment, the expression construct further comprises a promoter sequence suitable for driving expression of the MuSK antibody-based molecule. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein.

In an embodiment, the expression construct further encodes a linker sequence. The linker sequence can encode an amino acid sequence that spatially separates and/or links the one or more components of the expression construct (heavy chain and light chain components of the encoded antibody).

Another aspect of the present invention is a host cell comprising one or more vector encoding the MuSK antibodies and producing said MuSK antibodies as described herein. The MuSK antibody-based molecules described herein can optionally be produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

In some embodiments, the host cell chosen for expression may be of mammalian origin. Suitable mammalian host cells include, without limitation, COS-1 cells, COS-7 cells, HEK293 cells, BHK21 cells, CHO cells, BSC-1 cells, HeG2 cells, SP2/0 cells, HeLa cells, mammalian myeloma cells, mammalian lymphoma cells, or any derivative, immortalized or transformed cell thereof. Other suitable host cells include, without limitation, yeast cells, insect cells, and plant cells. Alternatively, the host cell may be selected from a species or organism incapable of glycosylating polypeptides, e.g., a prokaryotic cell or organism, such as BL21, BL21(DE3), BL21-GOLD(DE3), XL1-Blue, JM109, HMS174, HMS174(DE3), and any of the natural or engineered *E. coli* spp, *Klebsiella* spp., or *Pseudomonas* spp strains.

The MuSK antibody-based molecules described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. In an embodiment, the MuSK antibody-based molecule described herein is a monoclonal antibody or functional binding fragment thereof. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells, in particular mammalian cells is sometimes preferable, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA,* 77: 4216-4220 (1980), which is hereby incorporated by reference in its entirety). Other suitable mammalian host cells include, without limitation, NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibody fragments, such as Fab fragments or scFv molecules. It is understood that variations on the above procedure are within the scope of the present invention. For example, it may be desirable to transfect a host cell with DNA encoding functional fragments of either the light chain and/or the heavy chain of an antibody described herein. Recombinant DNA technology may also be used to remove some or all of the DNA encoding either or both of the light and heavy chains that is not necessary for binding to the antigens of interest. The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Pharmaceutical Compositions Comprising MuSK Antibody-Based Molecules

The MuSK antibody-based molecules or polynucleotide encoding the MuSK antibody-based molecules of the present invention are advantageously administered as compositions. In an embodiment, such compositions are pharmaceutical compositions comprising an active therapeutic agent (i.e., the MuSK antibody) and one or more of a variety of other pharmaceutically acceptable components. See REMINGTON: THE SCIENCE AND PRACTICE OF PHARMACY ($21^{st}$ Edition) (2005) (Troy, D. B. et al. (Eds.) Lippincott Williams & Wilkins (Publs.), Baltimore Md.), which is hereby incorporated by reference in its entirety. The preferred form depends on the intended mode of administration and therapeutic application. The compositions can also include, depending on the formulation desired, pharmaceutically acceptable, non-toxic carriers, excipients, diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition, and which are vehicles commonly used to formulate pharmaceutical compositions for animal or human administration. The diluent is selected to not affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well-known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Suitability for carriers and other components of pharmaceutical compositions is determined based on the lack of significant negative impact on the desired biological properties of the active antibody-based molecule of the present invention (e.g., less than a substantial impact (e.g., 10% or less relative inhibition, 5% or less relative inhibition, etc.) on antigen binding).

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The antibodies of the present invention may be prepared with carriers that will protect the antibodies against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well-known in the art. Methods for the preparation of such formulations are generally known to those skilled in the art. See, e.g., SUSTAINED AND CONTROLLED RELEASE DRUG DELIVERY SYSTEMS, J. R. Robinson, ed., Marcel Dekker, Inc., New York, 1978.

In one embodiment, the antibodies of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art.

Pharmaceutical compositions for injection must typically be sterile and stable under the conditions of manufacture and storage. The composition may be formulated as a solution, microemulsion, liposome, or other ordered structure suitable to achieve high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

For parenteral administration, agents of the present invention are typically formulated as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention can be administered in the form of a depot injection or implant preparation which can be formulated in such a manner as to permit a sustained release of the active ingredient. An exemplary composition comprises an scFv at about 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety). Additional formulations suitable for other modes of administration include oral, intranasal, and pulmonary formulations, suppositories, and transdermal applications.

Administration of the Pharmaceutical Compositions Comprising MuSK Antibody Based Molecules The MuSK antibody based molecules of the present invention can be administered by parenteral, topical, oral or intranasal means for therapeutic treatment. Intramuscular injection (for example, into the arm or leg muscles) and intravenous infusion are preferred methods of administration of the molecules of the present invention. In some methods, such molecules are administered as a sustained release composition or device, such as a Medipad™ device (Elan Pharm. Technologies, Dublin, Ireland). In some methods, the antibodies disclosed herein are injected directly into a particular tissue, for example intracranial injection.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion.

In therapeutic applications (i.e., in applications involving a patient who has been diagnosed with a neuromuscular disorder such as amyotrophic lateral sclerosis (ALS), myasthenia gravis, or congenital myasthenia) the MuSK antibody based molecules of the present invention are administered to such patient in an amount sufficient to cure, treat, or at least partially arrest the symptoms of the disease (as adduced by biochemical, histologic and/or behavioral assessment), including its complications and intermediate pathological phenotypes in development of the disease. In some embodiments, the administration of the therapeutic molecules of the present invention reduces or eliminates the neuromuscular disorder.

Effective doses of the provided therapeutic molecules of the present invention, for the treatment of the above-described conditions may vary depending upon many different factors, including means of administration, target site, physiological state of the patient, other medications administered. Treatment dosages are typically titrated to optimize their safety and efficacy. On any given day that a dosage is given, the dosage of the MuSK antibody based molecules as described herein may range from about 0.0001 to about 100 mg/kg, and more usually from about 0.01 to about 20 mg/kg, of the patient's body weight. For example, dosages can be 1 mg/kg body weight or 10 mg/kg body weight or within the range of 1-10 mg/kg body weight. Exemplary dosages thus include: from about 0.1 to about 10 mg/kg body weight, from about 0.1 to about 5 mg/kg body weight, from about 0.1 to about 2 mg/kg body weight, from about 0.1 to about 1 mg/kg body weight, for instance about 0.15 mg/kg body weight, about 0.2 mg/kg body weight, about 0.5 mg/kg body weight, about 1 mg/kg body weight, about 1.5 mg/kg body weight, about 2 mg/kg body weight, about 5 mg/kg body weight, or about 10 mg/kg body weight A physician or veterinarian having ordinary skill in the art may readily determine and prescribe the effective amount of the pharmaceutical composition required. For example, the physician or veterinarian could start doses of antibody-based molecule in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible the antibody-based molecule of the present invention to be administered alone, it is preferable to administer the antibody-based molecule as a pharmaceutical composition as described above.

For therapeutic purposes, the MuSK antibody-based molecules of the present invention are usually administered on multiple occasions. Intervals between single dosages (e.g., a bolus or infusion) can be weekly, monthly, or yearly. In some methods, dosage is adjusted to achieve a plasma concentration of 1-1000 µg/mL and in some methods 25-300 µg/mL. Alternatively, the therapeutic molecules of the present invention can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and non-human antibodies. scFv molecules generally have short serum half-lives.

In another embodiment, a pharmaceutical composition comprising a recombinant nucleic acid sequence encoding the MuSK antibody-based molecule as described herein, is administered to a subject to facilitate in vivo expression and formation of the antibody-based molecule for the treatment of conditions mediated by reduced signaling and/or phosphorylation of MuSK. Expression vector constructs suitable for use in this embodiment of the invention are described supra.

The polynucleotide compositions can result in the generation of the MuSK antibody-based molecule in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the antibody-based molecule in the subject within at least about 1 day, 2 days, 3 days, 4 days, 5 days, 6 days, 7 days, 8 days, 9 days, or 10 days of administration of the composition to the subject. The composition can result in generation of the antibody-based molecule in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody-based molecule in the subject. The composition can result in the generation of the antibody-based molecule in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Therapeutic Utility of the MuSK-Binding Antibody-Based Molecules

One aspect of the present invention relates to a method of increasing muscle-specific tyrosine-protein kinase (MuSK) signaling in a subject in need thereof. This method involves administering to the subject MuSK antibody based molecule as described herein, or a pharmaceutical composition comprising a MuSK antibody based molecule as described herein or a polynucleotide encoding a MuSK antibody based molecule as described herein. In accordance with this method, the composition is administered in an amount effective to increase MuSK signaling in the subject relative to MuSK signaling in the subject prior to said administering. Such administration may be provided to a subject having a neuromuscular disorder, such as amyotrophic lateral sclerosis (ALS), myasthenia gravis (MG), congenital myasthenia, MuSK-MG, spinal muscular atrophy (SMA), Spinal and bulbar muscular atrophy (SBMA), charcot marie tooth disease (CMT), Distal hereditary motor neuronopathies (dHMN), Duchenne muscular dystrophy (DMD), Limb-girdle muscular dystrophies (LGMD), congenital muscular dystrophy (CMD), sarcopenia (SP), emery dreifuss muscular dystrophy. In an embodiment, the subject to be treated is a subject having congenital myasthenia. In an embodiment, the subject to be treated is a subject having Dok7 mediated congenital myasthenia. In accordance with this aspect of the invention, such administration treats the neuromuscular condition.

In an embodiment, the MuSK antibody-based molecule administered to the subject in need thereof is a MuSK antibody-based molecule comprising a heavy chain variable region comprising the CDR-H1 of SEQ ID NO: 147, the CDR-H2 of SEQ ID NO: 153, and the CDR-H3 of SEQ ID NO: 156, and a light chain variable region comprising the CDR-L1 of SEQ ID NO: 159, the CDR-L2 of SEQ ID NO: 172, and the CDR-L3 of SEQ ID NO: 195 (3B2g2m1).

In an embodiment, the MuSK antibody-based molecule administered to the subject in need thereof is a MuSK antibody-based molecule comprising a heavy chain variable region comprising the CDR-H1 of SEQ ID NO: 147, the CDR-H2 of SEQ ID NO: 153, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2g1m1).

In an embodiment, the MuSK antibody-based molecule administered to the subject in need thereof is a MuSK antibody-based molecule comprising a heavy chain variable region comprising the CDR-H1 of SEQ ID NO: 147, the CDR-H2 of SEQ ID NO: 154, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2g1m2).

In an embodiment, the MuSK antibody-based molecule administered to the subject in need thereof is a MuSK antibody-based molecule comprising a heavy chain variable region comprising the CDR-H1 of SEQ ID NO: 147, the CDR-H2 of SEQ ID NO: 154, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 195 (3B2g2m2).

In an embodiment, the MuSK antibody-based molecule administered to the subject in need thereof is a MuSK antibody-based molecule comprising a heavy chain variable region comprising the CDR-H1 of SEQ ID NO: 147, the CDR-H2 of SEQ ID NO: 150, and the CDR-H3 of SEQ ID NO: 156, and the light chain variable region comprising the CDR-L1 of SEQ ID NO: 159, the CDR-L2 of SEQ ID NO: 172, and the CDR-L3 of SEQ ID NO: 183 (3B2).

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," of the antibody-based molecule refers to an amount sufficient, at dosages and for periods of time necessary, to achieve an intended biological effect or a desired therapeutic result including, without limitation, clinical results. The phrase "therapeutically effective amount" when applied to an antibody-based molecule of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody-based molecule in combinations with other compounds. In such instances, the "effective amount" is the amount of the combination sufficient to cause the intended biological effect.

Another aspect of the present invention relates to a method of treating congenital myasthenia in a subject. This method involves administering, to a subject having congenital myasthenia, a muscle-specific tyrosine-protein kinase (MuSK) agonist in an amount effect to increase MuSK phosphorylation, thereby treating congenital myasthenia in the subject.

In some embodiments, MuSK agonist is a MuSK agonist antibody as described herein. A MuSK agonist antibody is one that binds to MuSK and enhances MuSK signaling or phosphorylation. In one embodiment, the MuSK agonist antibody binds the Frizzled-like domain of human MuSK. In one embodiment, the MuSK agonist antibody binds to an epitope with the amino acid sequence of SEQ ID NO: 130 (Fz-like domain). Suitable MuSK agonist antibodies include those disclosed herein. In some embodiments, the congenital myasthenia is a DOK7 mediated congenital myasthenia.

EXAMPLES

The present description is further illustrated by the following examples, which should not be construed as limiting in any way.

Materials and Methods for Example 1 and Examples 5-12

Mice—In order to generate Dok7 CM mice (also referred to herein as Dok7 1124_1127 dup mice), in vitro-transcribed sgRNA (5'-CTGCTCAGTCTGCCCCC-3' (SEQ ID NO:264)) (5 ng/μl) and in vitro-transcribed Cas9 RNA (10 ng/μl), were microinjected together with a DNA repair template (5'-ATGCCGGCAATCTG GACGTCTGGCGGGCCGGTGAGGAAT-TCGGTTCTCTGCTCAGTCTGCCTGCCCCT GGAGCCAGCGCACCTGAGCCCA-GACTGTGTGCCTGCCCACCTGGGGCGGCCGAG TA-3' (SEQ ID NO:265)) (10 ng/μl) containing the TGCC duplication, into the pronuclei of C57BL/6 zygotes (Price et al., "Specific Disruption of Abca1 Targeting Largely Mimics the Effects of miR-33 Knockout on Macrophage Cholesterol Efflux and Atherosclerotic Plaque Development," Circ. Res. 124:874-880 (2019), which is hereby incorporated by reference in its entirety). 14 mice that were born from injected zygotes were analyzed by sequencing tail DNA (primer: 5'-GCAGTTACAG GAGGTTGG-3' (SEQ ID NO:266)). One mouse carried aDok7 allele with the desired TGCC duplication. The founder mouse was crossed with wildtype C57BL/6 mice to generate the Dok7 CM line. DNA sequencing confirmed the sequence of the Dok7 mutation. Mice were subsequently genotyped using primers (forward: 5'-GCGGCCTCGGCAGTTACAG-3' (SEQ ID NO:267); reverse: 5'-GCTTTACCTTG AGTCCGCCACAGA-3'(SEQ ID NO:268)). Five genomic loci that scored the highest probability for off-target recognition were analyzed. No evidence for mutations in these genes was found (FIGS. 16A-16B).

To generate Dok7 2YF mice, a sgRNA (5'-TTCGAGGTGTGTCATAG-3'(SEQ ID NO:269)) (15 ng/μl) was injected and Cas9 RNA (30 ng/μl) was in vitro-transcribed, together with the DNA repair template (5'-ATGCCGGCAGCAACCTGGACGTGTGGCGGGCCGG TGAGGAAT-TCGGTTCTCTGCTCAGTCTGCCTGCCCCTG-GAGCCAGCGCACCTGA GCCCA-GACTGTGTGCCTGCCCACCTGGGGCGGCCGAGTA-3'(SEQ ID NO:270)) (30 ng/μl) to convert tyrosine 396 and tyrosine 406 to phenylalanine, into the cytoplasm of C57BL/6 zygotes. 33 mice that were born from injected zygotes were analyzed by sequencing tail DNA (primer: 5'-TGGCATTGCC ACAGGCAG-3'(SEQ ID NO:271)). One mouse carried aDok7 allele with the desired tyrosine to phenylalanine substitutions. The founder mouse was crossed with wildtype C57BL/6 mice to generate the Dok7 2YF line. DNA sequencing from these lines confirmed the sequence of the Dok7 mutation. Mice were housed and maintained according to Institutional Animal Use and Care Committee (IACUC) guidelines.

Growth of Cultured Skeletal Muscle Cells—C2C12 mouse muscle cells (ATCC Cat #CRL-1772) were grown at 37° C. in growth medium (GM): Dulbecco's Modified Eagle's Medium (DMEM) containing 4.5 g/L glucose, L-glutamine and sodium pyruvate (Corning cellgro), supplemented with 10% fetal bovine serum (FBS; GemCell™). Myoblast fusion and myotube differentiation were induced when myoblasts were 70% confluent by switching to differentiation medium (DM): DMEM with 4.5 g/L glucose and 1 mM L-glutamine, supplemented with 2% heat-inactivated horse serum. Immortalized myoblasts were isolated from wildtype and Dok7 2YF embryos and grown as described previously (Smith et al., "Src, Fyn, and Yes are not Required for Neuromuscular Synapse Formation but are Necessary for Stabilization of Agrin-Induced Clusters of Acetylcholine Receptors," *J Neurosci.* 21:3151-3160 (2001), which is hereby incorporated by reference in its entirety).

Agrin and Antibody Treatment of C2 Myotubes—Three days after C2C12 myotubes had formed, the cultures were treated for 30 minutes with 10 nM biotinylated Fabs in complex with 2.5 nM streptavidin, 10 nM IgGs, or 0.5 nM recombinant neural Agrin-B8 (R&D Systems). Myotubes were homogenized at 4° C. in lysis buffer (50 mM sodium chloride, 30 mM triethanolamine, pH 7.5, 50 mM sodium fluoride, 5 mM EDTA, 5 mM EGTA, 2 mM sodium orthovanadate, 1 mM N-ethylmaleimide, 1 mM sodium tetrathionate, 10 µM pepstatin, plus complete protease inhibitor mix) (Roche). NP-40 was added to a final concentration of 1%, and the extract was incubated with rocking for 30 minutes at 4° C. Insoluble proteins were removed by centrifugation at 12,000 rpm for 20 minutes at 4° C. The supernatant was precleared for 1 hour at 4° C. with Protein G-agarose beads (Sigma-Aldrich) before incubation overnight at 4° C. with antibodies to MuSK (MuSK 1A) (Takata, K. et al., "Characterization of Pathogenic Monoclonal Autoantibodies Derived from Muscle-Specific Kinase Myasthenia Gravis Patients," *JCI Insight* 4(12):e127167 (2019) and Fichtner et al., "Affinity Maturation is Required for Pathogenic Monovalent IgG4 Autoantibody Development in Myasthenia Gravis," *J Exp. Med.* 217(12):e20200513 (2020), which are hereby incorporated by reference in their entirety). Complexes were incubated for 4 hours with Protein G-agarose beads. The beads were subsequently washed (three times for 9 minutes) in lysis buffer containing 1% NP-40. Proteins were eluted from the beads with 1% SDS in lysis buffer.

Isolation of MuSK and DOk7 from Muscle Tissue—Whole leg muscles or cultured muscle cells were homogenized at 4° C. in lysis buffer (50 mM sodium chloride, 30 mM triethanolamine pH 7.5, 50 mM sodium fluoride, 5 mM EDTA, 5 mM EGTA, 2 mM sodium orthovanadate, 1 mM N-ethylmaleimide, 1 mM sodium tetrathionate, 10 µM pepstatin, plus complete protease inhibitor mix (Roche)). NP-40 was added to a final concentration of 1%, and the extract was incubated with rocking for 30 minutes at 4° C. Insoluble proteins were removed by centrifugation at 12,000 rpm for 20 minutes at 4° C. The supernatant was pre-cleared for 1 hour at 4° C. with Protein G-agarose beads (Sigma-Aldrich) before overnight incubation at 4° C. with antibodies to MuSK (MuSK 1A) (Takata, K. et al., "Characterization of Pathogenic Monoclonal Autoantibodies Derived from Muscle-Specific Kinase Myasthenia Gravis Patients," *JCI Insight* 4(12):e127167 (2019) and Fichtner et al., "Affinity Maturation is Required for Pathogenic Monovalent IgG4 Autoantibody Development in Myasthenia Gravis," *J. Exp. Med.* 217(12):e20200513 (2020), which are hereby incorporated by reference in their entirety) or goat anti-Dok7 (R&D Systems, AF 6398), followed by incubation for 4 hours with Protein G-agarose beads. The beads were subsequently washed (three times for 9 minutes) in lysis buffer containing 1% NP-40. Proteins were eluted from the beads with 1% SDS in lysis buffer.

Western Blotting Proteins were fractionated by SDS-PAGE and transferred to PVDF membranes. Blots were probed with antibodies to MuSK (R&D Systems, AF562), phosphotyrosine (Millipore, 05-321) or Dok7 (#1916), as described previously (Herbst & Burden, "The Juxtamembrane Region of MuSK has a Critical Role in Agrin-Mediated Signaling," *EMBO J.* 19:67-77 (2000); Bergamin et al., "The Cytoplasmic Adaptor Protein Dok7 Activates the Receptor Tyrosine Kinase MuSK via Dimerization,"*Mol. Cell* 39:100-109 (2010); Hallock et al., "Dok-7 Regulates Neuromuscular Synapse Formation by Recruiting Crk and Crk-L," *Genes Dev.* 24:2451-2461 (2010); Remedio et al., "Diverging Roles for Lrp4 and Wnt Signaling in Neuromuscular Synapse Development During Evolution," *Genes Dev.* 30:1058-1069 (2016); and Jaworski & Burden, "Neuromuscular Synapse Formation in Mice Lacking Motor Neuron- and Skeletal Muscle-Derived Neuregulin-1," *J. Neurosci.* 26:655-661 (2006), which are hereby incorporated by reference in their entirety). Antibodies to Crk (BD Bioscience, 610035) and Crk-L (Santa Cruz Biotechnology, sc-365092) have been described previously (Hallock et al., "Dok-7 Regulates Neuromuscular Synapse Formation by Recruiting Crk and Crk-L," *Genes Dev.* 24:2451-2461 (2010), which is hereby incorporated by reference in its entirety). Band intensities were quantitated with a ChemiDoc imaging system (BioRad), as described previously (Remedio et al., "Diverging Roles for Lrp4 and Wnt Signaling in Neuromuscular Synapse Development During Evolution," *Genes Dev.* 30:1058-1069 (2016), which is hereby incorporated by reference in its entirety). The graphs show the mean values from at least three separate experiments. The Wilcoxon-Mann-Whitney test was used to determine statistical significance and was conducted using GraphPad Prism 6.0 software.

Whole Mount Muscle Immunohistochemistry. Diaphragm muscles were dissected from E18.5 embryos and postnatal mice in oxygenated L-15 medium. The muscles were pinned onto Sylgard-coated dissection dishes, fixed for 1.5 hours in 1% PFA and blocked for 1 hour in PBS with 3% BSA (Sigma IgG free) and 0.5% Triton X-100 (PBT). Diaphragm muscles were stained with Alexa 488-conjugated a-BGT (Invitrogen) to label AChRs and with antibodies to Neurofilament-L (Synaptic Systems, 171002), b-TUBIII (Synaptic Systems 302302), or Synapsin 1/2 (Synaptic Systems, 106002) to label motor axons and nerve terminals, respectively (Kim & Burden, "MuSK Controls where Motor Axons Grow and Form Synapses," *Nat. Neurosci.* 11:19-27 (2008), which is hereby incorporated by reference in its entirety). The antibodies were force-pipetted into the muscle, and the muscles were incubated overnight at 4° C. on an orbital shaker in a humidified chamber. Diaphragm muscles were washed 10 times over the course of 5 hours with PT at room temperature and rinsed in PBS before the muscle was whole-mounted in 50% glycerol. Muscles from at least 3 mice of each genotype were analyzed for each experiment. Images were acquired with a Zeiss LSM 800 confocal microscope. Adjustments to detector gain and laser intensity were made to avoid saturation. The number and size of synapses, the density of synaptic AChRs, the width of the endplate zone, the extent of denervation and the co-localization index (Synapsin/AChRs) were quantitated using FIJI/ImageJ software, as described previously (Jaworski & Burden, "Neuromuscular Synapse Formation in Mice Lacking Motor Neuron- and Skeletal Muscle-Derived Neuregulin-1," *J. Neurosci.* 26:655-661 (2006), which is hereby incorporated by reference in its entirety). The Wilcoxon-Mann-Whitney test was used to determine statistical significance and was conducted using GraphPad Prism 9.0 software.

Isolation and Staining Single Muscle Fibers Tibialis anterior muscles were dissected in oxygenated L-15 medium and pinned to a Sylgard-coated dish and fixed in 2% PFA (in PBS) for 2 hours. After several rinses in PBS, one to three myofibers were manually teased with fine forceps (Ralston et al., "The Organization of the Golgi Complex and Microtubules in Skeletal Muscle is Fiber Type-Dependent," *J. Neurosci.* 19:10694-10705 (1999), which is hereby incorporated by reference in its entirety). Fixed myofibers were blocked for 2 hours at room temperature in PBS containing 5% BSA, 1% normal goat serum, and 0.04% saponin. Fibers were then incubated with primary antibodies overnight at 4° C., washed three times for 5 minutes with PBS containing 0.04% saponin, incubated with secondary antibodies for 2 hours at room temperature, washed again, and mounted in VectaShield (Vector Laboratories). Antibodies to Crk-L (Santa Cruz Biotechnology, sc-365092) were used and the postsynaptic membrane was visualized by staining with Alexa Fluor 488-α-BGT (Invitrogen).

Cryosection Immunohistochemistry Limb muscles were embedded in OCT media and frozen on a dry-ice platform. 10 µm sections, collected onto poly-L-lysine coated glass slides, were fixed in 1-4% PFA for 10 minutes, washed in PBS with 3% BSA (PB) 3 times for 5 minutes, permeabilized with PB+0.5% X-Triton (PBT) for 10 minutes, washed in PB and incubated overnight at 4° C. with primary antibodies to Crk-L (Santa Cruz Biotechnology, sc-365092) in PBT in a humidified chamber. Sections were washed in PB 3 times for 5 minutes before overnight incubation at 4° C. with secondary antibodies and Alexa Fluor 488-α-BGT (Invitrogen), diluted in PBS, in a humidified chamber. Sections were washed 3 times for 5 minutes in PB, then PBS, before mounting in VECTASHIELD anti-fade mounting medium.

Behavior Grip strength was measured using a grip strength apparatus (Bioseb), which measures both forelimb and all-limb grip strength. To measure forelimb grip strength, the mouse was positioned in the center of a metal grid and held gently at the base of its tail so that only its front paws were able to grip the grid. The mouse was pulled back steadily, until the forelimb grip was released from the grid. The grip strength meter digitally displayed the maximum force applied (in grams) as the grasp was released. For the all-limb measurements, the mouse was allowed to grip the grid with both forelimbs and hind limbs, and the mouse was pulled back steadily, until the mouse lost grip with the grid. The means of six consecutive trials of both forelimb and all-limb measurements were taken as an index of forelimb or all-limb grip strength. Mice were given an interval of 10-15 seconds between trials and 1-3 hours between forelimb and all-limb testing. Body weight was determined after all grip strength measurements to analyze for potential co-variability. To enhance the robustness and reliability of the grip strength assessment, all measurements were taken by the same experimenter (Mandillo et al., "Reliability, Robustness, and Reproducibility in Mouse Behavioral Phenotyping: A Cross-Laboratory Study,"*Physiol. Genomics* 34:243-255 (2008) and Oury et al., "MACF1 Links Rapsyn to Microtubule- and Actin-Binding Proteins to Maintain Neuromuscular Synapses," *J. Cell Biol.* 218:1686-1705 (2019), which are hereby incorporated by reference in their entirety).

Motor function of male and female mice at P60 was assessed on a rotarod (AccuRotor four-channel, Omnitech Electronics, Inc.). Mice were placed on the rotarod (3.0-cm rotating cylinder) rotating at 2.5 rpm, and the speed of rotation was increased linearly to 40 rpm over the course of 5 minutes. The time to fall from the rod was measured. Each mouse was subjected to three trials in 5 minute intervals, and the longest latency to fall from the three trials was recorded. The Wilcoxon-Mann-Whitney test was used to determine statistical significance and was conducted using GraphPad Prism 9.0 software.

Development of Human Synthetic Antibodies The full-length extracellular region (E22 to T494 of mouse MuSK and E22 to T495 of human MuSK), including the Fz domain and the C-terminal flanking sequence (D307 to T494 of mouse MuSK and K314-T495 of human MuSK) were expressed as a C-terminal fusion with the Avi- and His6-tags using the secretion signal sequence of mouse IgkVIII in EXPI293 cells using the ExpiFectamine 293 Transfection kit (Thermo Fisher Scientific) using standard procedures provided by the vendor. The proteins were purified from the filtered culture supernatant using a HiTrap Nickel column (GE Healthcare) and biotinylated in vitro using the BirA enzyme in the presence of 0.5 mM Biotin and 10 mM ATP. The biotinylated proteins were further purified using a Superdex S75 10/300 column (GE Healthcare).

Sorting of an antibody phage-display library was performed as described previously (Miller et al., "T Cell Receptor-Like Recognition of Tumor in vivo by Synthetic Antibody Fragment," *PLoS One* 7:e43746 (2012), which is hereby incorporated by reference in its entirety). Briefly, a phage-display library was first sorted with all four antigens at 100 nM in the first round, followed by sorting with a single antigen at 100, 50, and 20 nM in the second, third and fourth rounds, respectively. In order to enrich for clones that bind to both human and mouse Fz domains, multiple sorting strategies were employed in which alternate antigens were used in successive rounds (e.g., human Fz—mouse ECD—human ECD). Individual clones were screened using phage ELISA with the four antigens 45, and the DNA sequences of clones that exhibited binding to all the antigens were determined.

The Fab proteins with the Avi-tag at the C terminus of the heavy chain of selected clones were produced from *E. coli* and biotinylated as described previously (Miller et al., "T Cell Receptor-Like Recognition of Tumor in vivo by Synthetic Antibody Fragment," *PLoS One* 7:e43746 (2012), which is hereby incorporated by reference in its entirety). The mouse IgG2a-LALAPG sample of clone X17 was produced using a modified version of the pFUSE-mIgG2a-Fc vector (InvivoGen) containing the LALAPG mutations in the Fc region (Lo et al., "Effector-Attenuating Substitutions That Maintain Antibody Stability and Reduce Toxicity in Mice," *J. Biol. Chem.* 292:3900-3908 (2017), which is hereby incorporated by reference in its entirety). and human CH1 domain and the pFUSE-CLIg vector (InvivoGen). This chimeric antibody consisted of a human Fab and mouse Fc sequences. In addition, the mouse Fc sequences were exchanged with those from human IgG1, containing LALA mutations, to generate hIgG1-X17, hIgG1-X2, and hIgG1-X3 antibodies.

Affinity Measurements Affinity of antibody clones in the Fab and IgG formats were measured using a bead-binding assay (Nishikori et al., "Broad Ranges of Affinity and Specificity of Anti-Histone Antibodies Revealed by a Quantitative Peptide Immunoprecipitation Assay," *J. Mol. Biol.* 424:391-399 (2012); Nady et al., "ETO Family Protein Mtgr1 Mediates Prdm14 Functions in Stem Cell Maintenance and Primordial Germ Cell Formation," *Elife* 4:e10150 (2015); and Hattori et al., "Multiplex Bead Binding Assays Using Off-the-Shelf Components and Common Flow Cytometers," *J. Immunol. Methods* 490:112952 (2020), which are hereby incorporated by reference in their entirety). A biotinylated human antigen protein was immobilized on Dynabeads M280 streptavidin beads (Thermo Fisher Scientific) by rapidly mixing 100 µl of 10-fold diluted beads in PBSB (PBS containing 0.5% bovine serum albumin (BSA, GeminiBio)) and 100 µl of 50 nM Fz protein. The beads were then blocked with 2 µM biotin, washed twice with PBSB and resuspended in 1 ml of PBSB. This reaction was appropriately scaled for the number of measurements when necessary. Five microliters of the diluted beads and 20 µl of an antibody sample were mixed in a well of a 96-well polypropylene plate (Greiner Bio-One, catalog number 650261) and incubated at room temperature for 30 minutes with gentle shaking. Samples were transferred to the wells of a 96-well filter plate (Millipore MultiScreen HTS HV, 0.45 mm, Thermo Fisher); the liquid was removed using a vacuum manifold and the wells were washed three times with 200 µl of ice-cold PBSB using the vacuum manifold.

The beads were stained with anti-human Fab antibody labeled with Alexa Fluor 647 (Jackson Immuno Research, Alexa Fluor® 647 AffiniPure Goat Anti-Human IgG, F(ab)$_2$ fragment specific, 109-605-097). Following washing, the beads were suspended in 70 µl PBSB and analyzed using an iQue screener (Sartorius) or an Intellicyt HTFC system. The resulting titration curves were analyzed by nonlinear least squared fitting of a 1:1 binding model using the GraphPad Prizm software.

Blood Half-Life Measurement Mouse blood samples were centrifuged, and supernatants were diluted 2000-fold in the PBSB. Antibody levels were quantitated using the bead assay described above except that the binding reaction was performed at 4° C. The half-life was determined by nonlinear least squares fitting of the median fluorescence intensities with a single exponential curve.

Phosphopeptide Pull-Down Assay 293T cells were transfected with plasmids encoding HA-tagged Dok-7 and HA-tagged CrkI at 37° C. for 48 hours (Lipofectamine 3000, Thermofisher Scientific). After 48 hours, the transfected cells were homogenized at 4° C. in lysis buffer; NP-40 was added to a final concentration of 1%, and the extract was incubated with rocking for 30 utes min at 4° C. Insoluble proteins were removed by centrifugation at 12,000 rpm for 20 minutes at 4° C. The supernatants were precleared for 1 hour at 4° C. with streptavidin-agarose beads (Sigma-Aldrich).

Four biotinylated phosphopeptides, (1) ELLL-DRLHPNPMYQRMPLLLN (SEQ ID NO:272), (2) ELLL-DRLHPNPMp(Y)QRMPLLLN (SEQ ID NO:273), (3) ELLLDRLHPAPMp(Y)QRMPLLLN (SEQ ID NO:274), and (4) ELLLDRLHPNPMp(Y)AAAPLLLN (SEQ ID NO:275) (Thermofisher Scientific) were immobilized on streptavidin agarose beads and incubated overnight at 4° C. in lysis buffer (50 mM sodium chloride, 30 mM triethanolamine, pH 7.5, 50 mM sodium fluoride, 5 mM EDTA, 5 mM EGTA, 2 mM sodium orthovanadate, 1 mM N-ethylmaleimide, 1 mM sodium tetrathionate, and 10 µM pepstatin, plus complete protease inhibitor mix) (Roche), containing 1% NP-40. The cell extracts, pre-cleared on streptavidin-agarose beads, were incubated overnight at 4° C. with biotinylated phosphopeptides immobilized on streptavidin-agarose beads. The beads were subsequently washed (three times for 9 minutes) in lysis buffer containing 1% NP-40. Proteins were eluted from the beads with 1% SDS in lysis buffer. Western blotting was performed using antibodies to HA tag (Abcam, ab49969).

RT-qPCR Total RNA was isolated from muscles of E18.5 wildtype and Dok-7 CM embryos using TRIZOL reagent (Invitrogen) and reverse transcribed with Superscript-III First strand kit (Invitrogen). Real-time quantitative PCR was performed on a LightCycler 480 (Roche) using SYBR Green Master kit (Roche). PCRs were performed using primers pairs, 5'-CTGGTGAA AAGGACCTCTCGAAG-3' (SEQ ID NO:276) and 5'-CCAGTTTCACTAATGACACAAA CG-3' (SEQ ID NO:277) for Hprt, 5'-TCAGCCTCAGAAGAGCGTGTTG-3' (SEQ ID NO:278) and 5'-GCCTCAGAAGAGGAACTGGATAG-3' (SEQ ID NO:279) for Dok7. Samples were run in triplicates and Dok7 expression level was normalized to Hprt expression.

Example 1—Mechanism of Disease and Therapeutic Rescue of Dok7 Congenital Myasthenia Congenital myasthenia (CM) is a group of diseases caused by mutations in genes that play key roles in the formation, function, and maintenance of neuromuscular synapses (see, e.g., Muller et al., "Congenital Myasthenic Syndromes: Spotlight on Genetic Defects of Neuromuscular Transmission," *Expert Rev. Mol. Med.* 9:1-20 (2007); Engel, A. G., "Current Status of the Congenital Myasthenic Syndromes," *Neuromuscul. Disord.* 22:99-111 (2012); and Engel et al., "Congenital Myasthenic Syndromes: Pathogenesis, Diagnosis, and Treatment," *Lancet Neurol.* 14:420-434 (2015), which are hereby incorporated by reference in their entirety). For the most part, mutations in these genes are recessive and diminish gene activity, causing synaptic deficits that lead to early onset of structural and functional deficits in the neuromuscular synapse, which are responsible for fluctuating and fatigable or persistent muscle weakness throughout life.

Mutations in Dok7, the gene encoding an adapter protein crucial for forming and maintaining neuromuscular synapses (Okada et al., "The Muscle Protein Dok-7 is Essential for Neuromuscular Synaptogenesis," *Science* 312:1802-1805 (2006), which is hereby incorporated by reference in its entirety), constitute a substantial portion (10-20%) of all CM cases (Beeson et al., "Dok-7 Mutations Underlie a Neuromuscular Junction Synaptopathy," *Science* 313:1975-1978 (2006); Muller et al., "Phenotypical Spectrum of DOK7 Mutations in Congenital Myasthenic Syndromes," *Brain* 130:1497-1506 (2007); and Hamuro et al., "Mutations Causing DOK7 Congenital Myasthenia Ablate Functional Motifs in Dok-7," *J. Biol. Chem.* 283:5518-5524 (2008), which are hereby incorporated by reference in their entirety). The disease is debilitating, causing weakness in limb, neck and facial muscles, and one quarter of Dok7 CM patients require non-invasive ventilation at some point during their lifetime. Few treatments abate the clinical symptoms, although albuterol/salbutamol, which activates adrenergic receptors, can provide benefit for a subset of Dok7 CM patients through poorly understood mechanisms (Liewluck et al., "Beneficial Effects of Albuterol in Congenital Endplate Acetylcholinesterase Deficiency and Dok-7 Myasthenia,"*Muscle Nerve* 44:789-794 (2011) and Burke et al., "Salbutamol Benefits Children with Congenital Myasthenic Syndrome due to DOK7 mutations," *Neuromuscul. Disord.* 23:170-175 (2013), which are hereby incorporated by reference in their entirety).

The formation and maintenance of neuromuscular synapses requires the assembly of highly specialized presynaptic and postsynaptic membranes, requiring the coordinated action of several key molecules (Burden, S. J, "The Formation of Neuromuscular Synapses," *Genes Dev.* 12:133-148 (1998); Sanes & Lichtman, "Induction, Assembly, Maturation and Maintenance of a Postsynaptic Apparatus," *Nat. Rev. Neurosci.* 2:791-805 (2001); Burden, S. J., "SnapShot: Neuromuscular Junction," *Cell* 144:826-826(2011); Burden et al., "The Role of MuSK in Synapse Formation and Neuromuscular Disease," *Cold Spring Harb. Perspect. Biol.* 5:a009167 (2013); and Tintignac et al., "Mechanisms Regulating Neuromuscular Junction Development and Function and Causes of Muscle Wasting," *Physiol. Rev.* 95:809-852 (2015), which are hereby incorporated by reference in their entirety). Agrin, released from motor nerve terminals, binds to the lipoprotein receptor-related protein 4 (Lrp4) in muscle, stimulating formation of a complex between Lrp4 and muscle-specific kinase (MuSK), a receptor tyrosine kinase that acts as a master regulator of synaptic differentiation (Burden et al., "The Role of MuSK in Synapse Formation and Neuromuscular Disease," *Cold Spring Harb. Perspect. Biol.* 5:a009167 (2013); Tintignac et al., "Mechanisms Regulating Neuromuscular Junction Development and Function and Causes of Muscle Wasting," *Physiol. Rev.* 95:809-852 (2015); McMahan, U. J., "The Agrin Hypothesis," *Cold Spring Harb. Symp. Quant. Biol.* 55:407-418 (1990); Jennings et al., "Muscle-Specific trk-Related Receptor with a Kringle Domain Defines a Distinct Class of Receptor Tyrosine Kinases," *Proc. Natl. Acad. Sci. USA* 90:2895-2899 (1993); DeChiara et al., "The Receptor Tyrosine Kinase MuSK is Required for Neuromuscular Junction Formation in vivo," *Cell* 85:501-512 (1996); Glass et al., "Agrin Acts via a MuSK Receptor Complex," *Cell* 85:513-523 (1996); Kim et al., "Lrp4 is a Receptor for Agrin and Forms a Complex with MuSK," *Cell* 135:334-342 (2008); and Zhang et al., "LRP4 Serves as a Coreceptor of Agrin," *Neuron.* 60:285-297 (2008), which are hereby incorporated by reference in their entirety). Lrp4, clustered in the postsynaptic membrane as a consequence of MuSK activation, signals in a retrograde manner to motor axons to stimulate presynaptic differentiation (Yumoto et al., "Lrp4 is a Retrograde Signal for Presynaptic Differentiation at Neuromuscular Synapses," *Nature* 489:438-442 (2012), which is hereby incorporated by reference in its entirety). Mutations in Agrin, Lrp4, and MuSK, as well as acetylcholine receptor (AChR) subunit genes, also cause CM (Engel et al., "Congenital Myasthenic Syndromes: Pathogenesis, Diagnosis, and Treatment," *Lancet Neurol.* 14:420-434 (2015) and McMacken et al., "The Increasing Genetic and Phenotypical Diversity of Congenital Myasthenic Syndromes," *Neuropediatrics* 48:294-308 (2017), which are hereby incorporated by reference in their entirety).

MuSK activation also depends upon Dok7. The amino terminal region of Dok7 contains pleckstrin homology (PH) and phosphotyrosine-binding (PTB) domains (FIG. 1A), which function to dimerize Dok7 and bind a phosphorylated tyrosine motif in the MuSK juxtamembrane (JM) region (Yamanashi et al., "Activation of Receptor Protein-Tyrosine Kinases from the Cytoplasmic Compartment," *J. Biochem.* 151:353-359 (2012), which is hereby incorporated by reference in its entirety). A failure of Dok7 to bind MuSK, due to an absence of Dok7 or mutations in the MuSK JM region that preclude Dok7-binding, lead to a failure of Agrin to stimulate MuSK phosphorylation (Okada et al., "The Muscle Protein Dok-7 is Essential for Neuromuscular Synaptogenesis," *Science* 312:1802-1805 (2006); Herbst & Burden, "The Juxtamembrane Region of MuSK has a Critical Role in Agrin-Mediated Signaling," *EMBO J.* 19:67-77 (2000); and Zhou et al., "Distinct Domains of MuSK Mediate its Abilities to Induce and to Associate with Postsynaptic Specializations," *J. Cell Biol.* 146:1133-1146 (1999), which are hereby incorporated by reference in their entirety), demonstrating that binding of Dok7 to MuSK is essential to stabilize MuSK phosphorylation, likely by promoting MuSK dimerization (Bergamin et al., The Cytoplasmic Adaptor Protein Dok7 Activates the Receptor Tyrosine Kinase MuSK via Dimerization," *Mol. Cell* 39:100-109 (2010), which is hereby incorporated by reference in its entirety). In addition, Agrin-stimulated MuSK phosphorylation leads to phosphorylation of two tyrosine residues in the carboxy-terminal region of Dok7, triggering recruitment of Crk and Crk-L proteins that participate in clustering of acetylcholine receptors (AChRs) (Hallock et al., "Dok-7 Regulates Neuromuscular Synapse Formation by Recruiting Crk and Crk-L," *Genes Dev.* 24:2451-2461 (2010) and Hamuro et al., "Mutations Causing DOK7 Congenital Myasthenia Ablate Functional Motifs in Dok-7," *J. Biol. Chem.* 283:5518-5524 (2008), which are hereby incorporated by reference in their entirety).

The most common cause of Dok7 CM is a four base pair duplication (1124_1127 dup TGCC), which is nearly always present as one or two mutant alleles in Dok7 CM, leads to a frameshift and premature termination of Dok7 (Beeson et al., "Dok-7 Mutations Underlie a Neuromuscular Junction Synaptopathy," *Science* 313:1975-1978 (2006) and Cossins et al., "The Spectrum of Mutations that Underlie the Neuromuscular Junction Synaptopathy in DOK7 Congenital Myasthenic Syndrome," *Hum. Mol. Genet.* 21:3765-3775 (2012), which is hereby incorporated by reference in its entirety). The truncated form of Dok7 retains the PH and PTB domains and binds to the tyrosine phosphorylated JM region of MuSK (Beeson et al., "Dok-7 Mutations Underlie a Neuromuscular Junction Synaptopathy," *Science* 313: 1975-1978 (2006), which is hereby incorporated by reference in its entirety), but lacks the two tyrosine residues that are phosphorylated and recruit Crk proteins. These and other findings suggested that the absence of these two tyrosine residues in truncated Dok7 were responsible for the synaptic deficits in this common form of Dok7 CM (Engel et al., "Congenital Myasthenic Syndromes: Pathogenesis, Diagnosis, and Treatment," *Lancet Neurol.* 14:420-434 (2015); Hallock et al., "Dok-7 Regulates Neuromuscular Synapse Formation by Recruiting Crk and Crk-L," *Genes Dev.* 24:2451-2461 (2010); and Hamuro et al., "Mutations Causing DOK7 Congenital Myasthenia Ablate Functional Motifs in Dok-7," *J. Biol. Chem.* 283:5518-5524 (2008), which are hereby incorporated by reference in their entirety). However, the mechanism of Dok7 1124_1127 dup TGCC CM has not been elucidated.

The C-Terminal Region of Dok7 is Essential for Synapse Formation

Figures 1A, 1B:
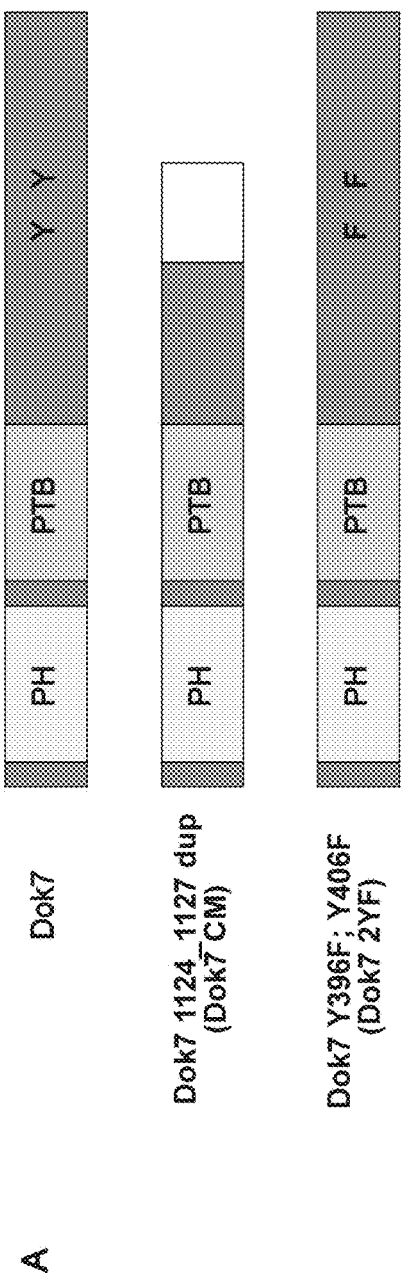
FIGS. 1A-1D demonstrate that the C-terminal region of Dok7 is essential for synaptic differentiation.

In order to study how loss of the carboxy-terminal region of Dok7 leads to defects in the structure and function of neuromuscular synapses a mouse model of the most common form of Dok7 CM (Dok7 1124_1127 dup) was generated (FIG. 1A). A second mouse mutant (Dok7 Y396F; Y406F), in which the two tyrosine residues in the carboxy-terminal region were mutated to phenylalanine (FIG. 1A) was also generated.

Figure 1C:
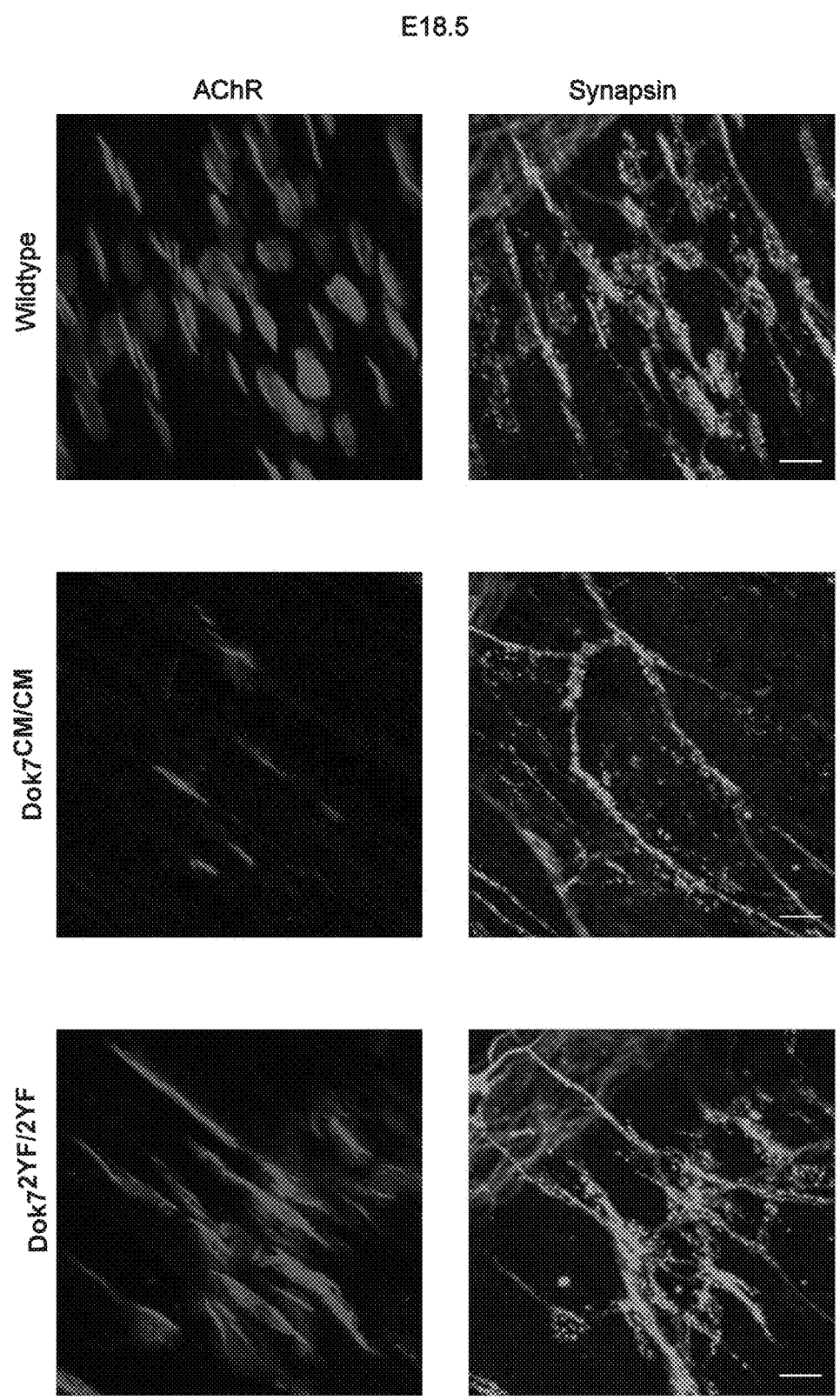
Figure 1D:
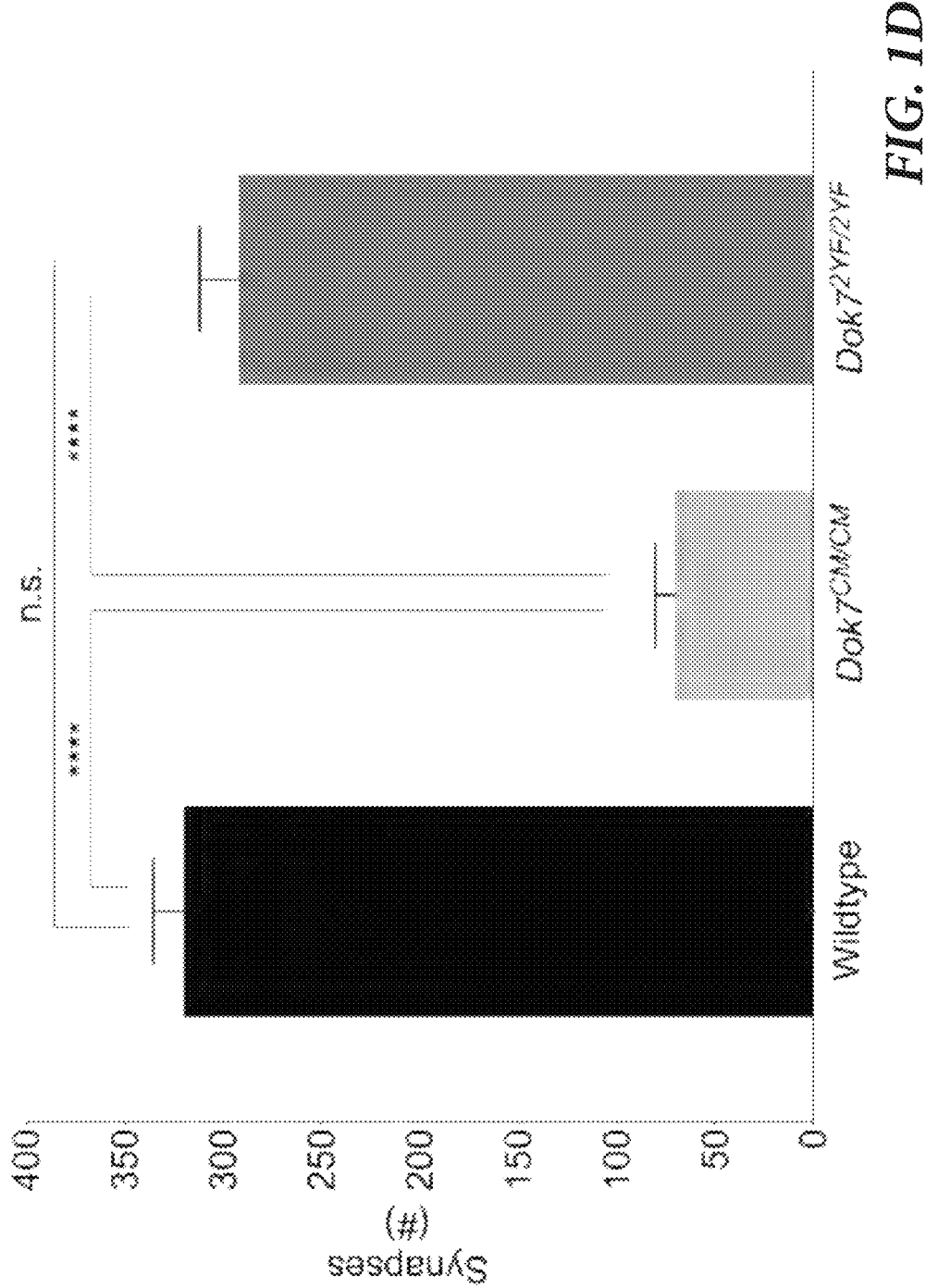
Figure 1D:
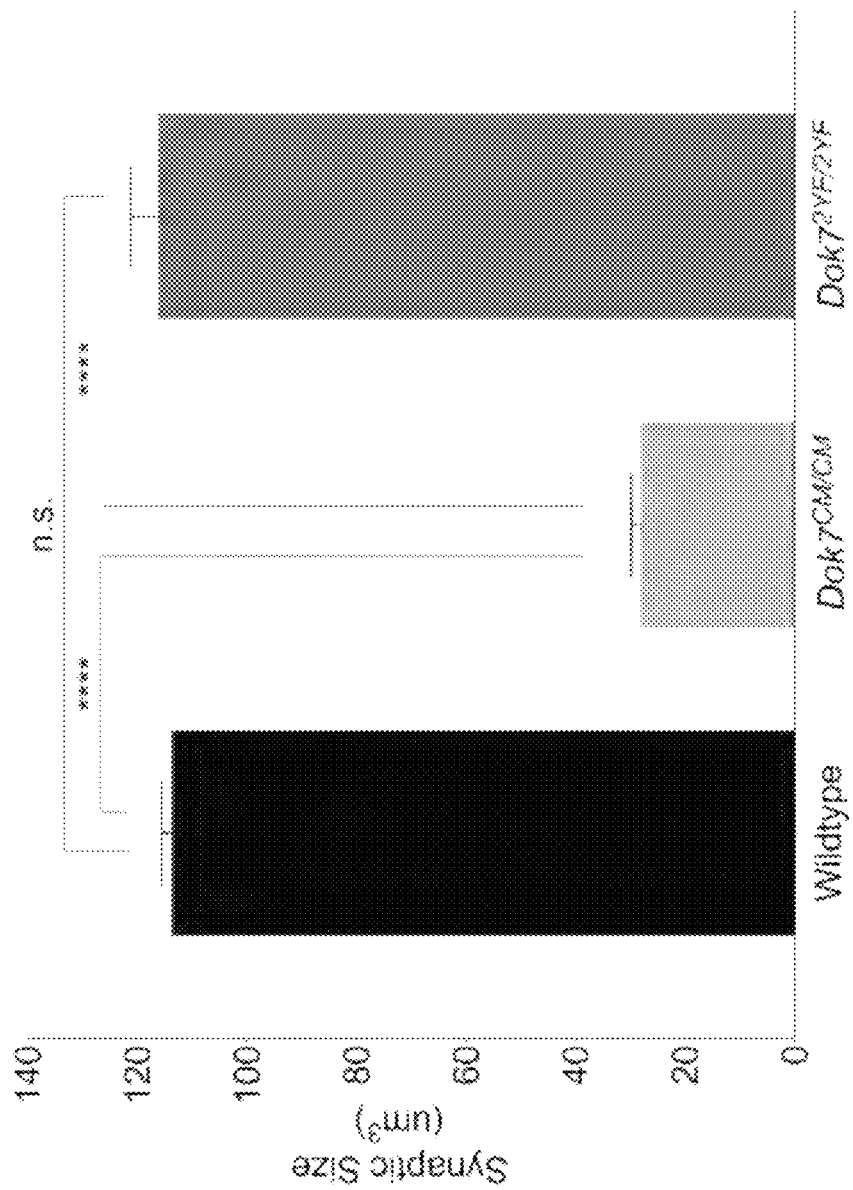
Figure 1D:
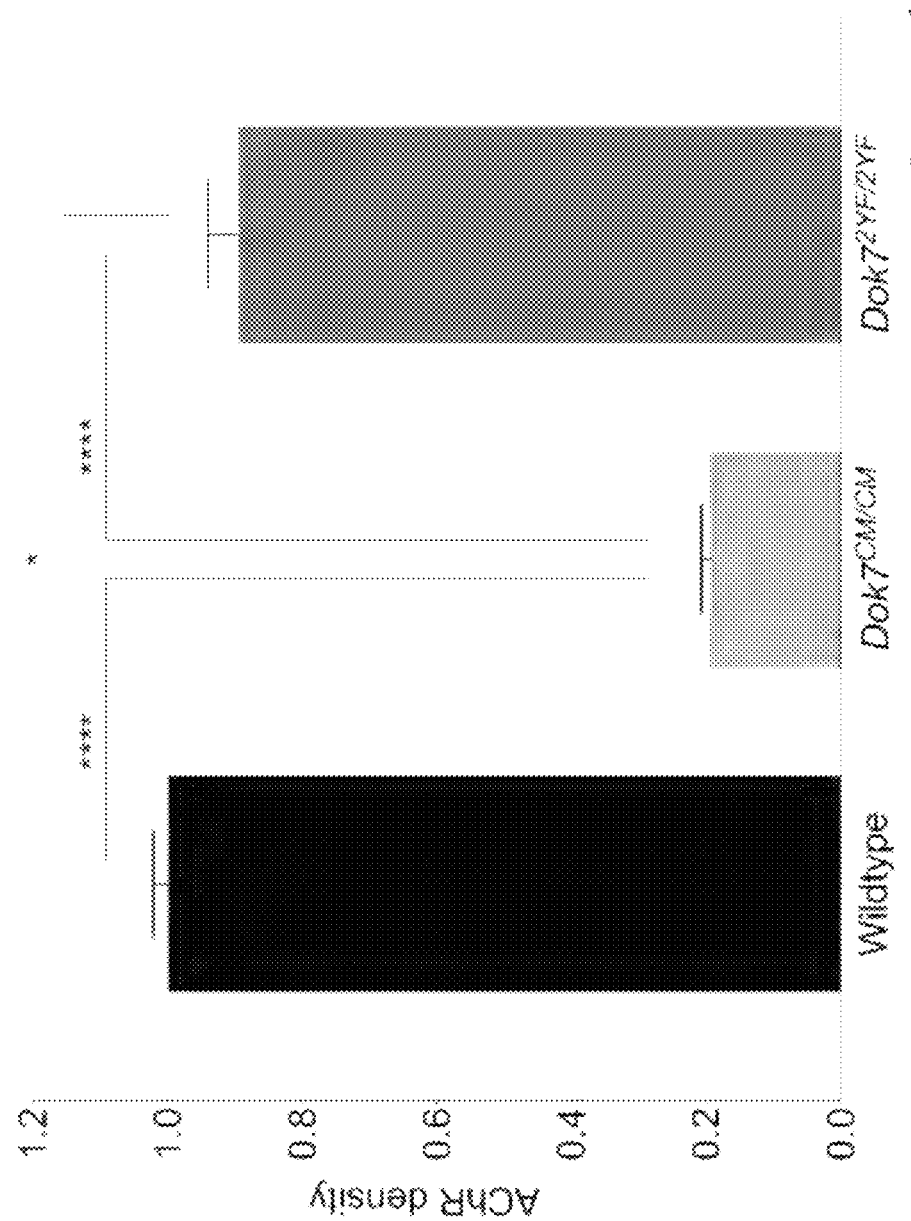

Homozygous Dok7 1124_1127 dup mice, which were termed Dok7 CM mice, were present at expected numbers at E18.5 but rarely found alive a day later, at birth, when neuromuscular synapses are essential for respiration and survival (FIG. 1B). Diaphragm muscles from E18.5 embryos were stained with probes that allowed visualization of presynaptic and postsynaptic differentiation. 5-fold fewer synapses were found in Dok7 CM than in wildtype mice (FIG. 1C). Moreover, the synapses that formed were immature, as synaptic size and the density of synaptic AChRs were each reduced by 5-fold (FIG. 1C; FIG. 7). In contrast, homozygous Dok7 Y396F; Y406F mice, which were termed Dok7 2YF mice, were born at the expected frequency (FIG. 1B), and their neuromuscular synapses appeared largely normal (FIG. 1C; FIG. 8). Moreover, Dok7 2YF mice thrived as fertile adult mice. Together, these findings indicate that loss of the two tyrosine residues in the carboxy-terminal region of Dok7, surprisingly, is not the cause for lethality and the severe deficits in synapse formation in Dok7 CM mice.

Dok7 Protein Levels and MuSK Tyrosine Phosphorylation are Reduced in Dok7 CM Mice To determine how the loss of the carboxy-terminal region caused the synaptic defects, the expression of Dok7 mRNA and truncated Dok7 protein in Dok7 CM mice was measured using antibodies to the Dok7 PTB domain that equally detected the truncated and wildtype proteins (FIGS. 9A-9B).

Dok7 mRNA levels were found to be normal in muscle from Dok7 CM mice (FIGS. 10A-10C), whereas the truncated Dok7 protein was expressed at 3-fold lower levels than wildtype Dok7 protein (FIG. 2A; FIGS. 10A-10C).

Because Dok7 functions as a dimer to dimerize MuSK, stabilizing MuSK tyrosine phosphorylation (Bergamin et al., "The Cytoplasmic Adaptor Protein Dok7 Activates the Receptor Tyrosine Kinase MuSK via Dimerization," Mol. Cell 39:100-109 (2010), which is hereby incorporated by reference in its entirety), whether the reduction in Dok7 protein levels in Dok7 CM mice may lead to diminished MuSK tyrosine phosphorylation was considered. MuSK was immunoprecipitated, MuSK phosphorylation was measured, and it was found that MuSK phosphorylation was reduced by 7-fold in Dok7 CM mice but normal in Dok7 2YF mice (FIGS. 2C-2D).

Crk Proteins are Recruited Directly to MuSK as Well as Dok7

It was anticipated that Crk recruitment to the synapse would be absent or severely reduced in both Dok7 CM and Dok7 2YF mutant mice. Indeed, Crk recruitment to the synapse and to the MuSK complex was substantially diminished (2.8-fold) in Dok7 CM mice (FIGS. 3A-3B), but surprisingly, only modestly reduced (28%) in Dok7 2YF mice (FIGS. 3A-3B). These findings suggested that Crk was recruited to a tyrosine phosphorylated synaptic protein(s) in addition to Dok7.

The three activation loop tyrosines and Y553 become phosphorylated in MuSK following Agrin stimulation (Okada et al., "The Muscle Protein Dok-7 is Essential for Neuromuscular Synaptogenesis," Science 312:1802-1805 (2006); Herbst & Burden, "The Juxtamembrane Region of MuSK has a Critical Role in Agrin-Mediated Signaling," EMBO J. 19:67-77 (2000); Watty et al., "The in vitro and in vivo Phosphotyrosine Map of Activated MuSK," Proc. Natl. Acad. Sci. USA 97:4585-4590 (2000); and Till et al., "Crystal Structure of the MuSK Tyrosine Kinase: Insights into Receptor Autoregulation," Structure 10:1187-1196 (2002), which are hereby incorporated by reference in their entirety). It was found that Y553 in the MuSK JM region is not only within a PTB-binding site that recruits Dok7 but also a potential SH2-binding motif for Crk proteins (FIG. 3C). FIG. 3D shows that CrkI, as well as Dok7, bound the MuSK JM site in a phosphorylation-dependent manner. Mutation of amino acids that compose the SH2-binding motif but not the PTB-binding site impaired CrkI-binding (FIG. 3D). Thus, Crk can bind not only to the phosphorylated carboxyterminal region of Dok7 but also directly to the tyrosine phosphorylated JM region of MuSK. This redundancy for recruiting Crk to the synapse and MuSK complex likely explains the near normal association of Crk with the MuSK complex in Dok7 2YF mice and may underlie the different phenotypes of Dok7 CM and Dok7 2YF mice.

Thus, the MuSK JM region harbors overlapping binding sites for a PTB- and a SH2-domain containing protein, an arrangement that offers flexibility and modulation in the mode of signaling downstream of receptor tyrosine kinases, which may be more common than currently understood.

Development of Agonist Antibodies to Human and Mouse MuSK

If diminished MuSK phosphorylation were crucial for disease in Dok7 CM, it was reasoned that stimulating MuSK may rescue the synaptic defects and overcome lethality. The idea that reduced MuSK phosphorylation was central to disease was explored by generating and treating Dok7 CM mice with agonist antibodies targeting MuSK.

A phage-display library expressing synthetic human antibodies in the Fab format was screened for antibodies that bound the Fz-like domain in the extracellular region of both mouse and human MuSK. The Fz-like domain was targeted because this domain is not essential for MuSK function and previous studies showed that antibodies to the Fz-like domain cause no obvious harm in mice (Remedio et al., "Diverging Roles for Lrp4 and Wnt Signaling in Neuromuscular Synapse Development During Evolution," Genes Dev. 30:1058-1069 (2016) and Cantor et al., "Preserving Neuromuscular Synapses in ALS by Stimulating MuSK with a Therapeutic Agonist Antibody," Elife 7:e34375 (2018), which are hereby incorporated by reference in their entirety).

High-affinity antibodies that bound the Fz-like domain in human and mouse MuSK were identified (FIG. 4A; FIGS. 12A-12C). A tetramerized version of each Fab, with the exception of X1, stimulated MuSK phosphorylation in mouse C2 myotubes (FIG. 4B). Antibodies X3 and X17 in both mouse IgG2a and human IgG1 formats, as well as X2 in the human IgG1 format, bound human and mouse MuSK with sub-nM affinity and likewise stimulated MuSK tyrosine phosphorylation, independent of Agrin (FIGS. 4C-4D). Because the antibodies had similar activities, X17 was chosen for further analysis in vivo.

Antibody X17 was injected in a mouse IgG2a format with the so-called LALAPG mutations that reduce Fc domain effector function (Lo et al., "Effector-Attenuating Substitutions That Maintain Antibody Stability and Reduce Toxicity in Mice," J. Biol. Chem. 292:3900-3908 (2017), which is hereby incorporated by reference in its entirety), interperitoneally into wildtype mice. It was found that X17 had a half-life of 5 days in blood (FIG. 4E). By staining for X17 to quantitate target engagement at neuromuscular synapses, it was found that 10 mg/kg of X17 was sufficient to saturate synaptic MuSK (FIG. 4F). Chronic injection of mIgG2a-X17 (10 mg/kg at P4, P24 and P44) in wildtype mice over two months had no effect on the organization of neuromuscular synapses, weight gain or motor behavior (FIGS. 13A-13D).

Agonist Antibody X17 Rescues Synapse Formation and Lethality of Dok7 CM Mice

Although Dok7 CM mice in a C57BL/6 background died at birth, it was found that Dok7 CM mice in a mixed genetic background survived for one to two weeks postnatally (FIGS. 14A-14B), facilitating experiments to study therapeutic efficacy. Dok7 CM mice in a C57BL/6-CBA mixed background showed signs of disease shortly after birth, as they were runted and had deficits in synapse formation (FIGS. 15A-15E). Despite surviving for a few weeks after birth, Dok7 expression, MuSK phosphorylation, and the organization of nerve terminals and AChRs were similar in E18.5 inbred C57BL/6 and mixed breed C57BL/6-CBA mice carrying the same Dok7 mutation.

Dok7 CM mice were injected at P4 with 10 mg/kg of antibody X17, or an isotype-matched negative control antibody. Untreated Dok7 CM mice, or Dok7 CM mice injected with the isotype-control antibody continued to lose weight and died within a week at P10-12 (FIGS. 5A-5B). Injection of antibody X17 reversed the weight loss and rescued the Dok7 CM mice from this early lethality (FIGS. 5A-5B). Over the next three weeks, the weight gain was continuous in nine of the twelve Dok7 CM mice injected with antibody X17; the weight gain slowed in three of the X17-injected mice, and they died at P23-P24. Another antibody, X3, rescued Dok7 CM mice from early postnatal lethality when dosed at 20 mg/kg but not at 10 mg/kg (FIGS. 17A-17C), suggesting that a higher initial dose of a MuSK agonist antibody may be more effective during early postnatal development, when synapses are undergoing critical steps in maturation.

Injection of antibody X17 was repeated in the nine surviving Dok7 CM mice at P24 and P44 in order to determine whether chronic dosing could lead to long-term survival. Chronic dosing of antibody X17 in the nine surviving Dok7 CM mice rescued these Dok7 CM mice for at least two months (FIGS. 5A-5B), when their motor performance was assessed and mice were sacrificed to examine their synapses.

Antibody X17 rescued synapse formation and maturation, as neuromuscular synapses developed the complex pretzel-like shape characteristic of fully mature murine neuromuscular synapses (FIG. 5C). Moreover, X17 rescued the recruitment of Crk proteins to the neuromuscular synapse (FIG. 5D).

Antibody X17 rescued motor function of Dok7 CM mice, as assessed by forelimb grip strength and rotarod assays (FIG. 5E). Moreover, Dok7 CM mice, injected with antibody X17, were fertile and produced offspring at the expected frequency. Together, these findings support the idea that reduced MuSK tyrosine phosphorylation is central to disease in Dok7 CM mice. Even if the carboxy-terminal region of Dok7 has an additional role in synapse formation, such function can be overridden by stimulating MuSK.

Therapeutic Reversal in Adult Dok7 CM Mice

Next, whether X17 could reverse neuromuscular deficits that develop during adulthood, a question particularly relevant to developing a human therapy as Dok7 CM in humans would likely be treated during adult life, was investigated. Dok7 CM mice were treated with X17 either at P4, P24, and P44 or at P4 and P18, but then discontinued antibody treatment. These Dok7 CM mice continued to maintain their weight and mobility for 2-3 months (FIG. 6A), indicating that rescue was more durable than the lifetime of the antibody in the blood. However, these Dok7 CM mice ultimately began to lose weight and display motor deficits (FIGS. 6A-6B). When the mice were losing weight at a rate of ~0.4 g/day, X17 was injected once again and the weight and mobility of the Dok7 CM mice was monitored. Two days after resuming X17 treatment, the Dok7 CM mice began to regain weight, increasing by ~0.4 g/day over the next week (FIG. 6A). Within one week after reinitiating antibody treatment, the motor performance of the Dok7 CM mice was restored (FIG. 6B). The rescued mice continued to gain weight and improve their motor performance for at least one additional week after antibody treatment, when the mice were sacrificed (FIGS. 6A-6B).

Discussion of Example 1

Stimulating MuSK with an agonist antibody rescued synapse formation and motor function, preventing lethality and allowing Dok7 CM mice to thrive postnatally as fertile adults. Moreover, following withdrawal of antibody treatment, Dok7 CM adult mice ultimately displayed motor deficits, which were readily reversed after reinitiating antibody treatment, suggesting that this therapeutic strategy may provide benefit for Dok7 CM as well as other neuromuscular diseases in humans.

Most previous studies of Dok7 have relied upon analysis of transfected muscle and non-muscle cells that overexpress Dok7 (Okada et al., "The Muscle Protein Dok-7 is Essential for Neuromuscular Synaptogenesis," Science 312:1802-1805 (2006); Hamuro et al., "Mutations Causing DOK7 Congenital Myasthenia Ablate Functional Motifs in Dok-7," J. Biol. Chem. 283:5518-5524 (2008); and Hallock et al., "Dok-7 Regulates Neuromuscular Synapse Formation by Recruiting Crk and Crk-L," Genes Dev. 24:2451-2461 (2010), which are hereby incorporated by reference in their entirety). In this context, which by-passes the normal requirement for Agrin and Lrp4 to stimulate MuSK, the in vivo consequences of Dok7 mutations may have been masked due to Dok7 overexpression.

An earlier study described a similar mouse model, generated using classic ES cell gene targeting, for this common form of Dok7 CM (Arimura et al., "Neuromuscular Disease. DOK7 Gene Therapy Benefits Mouse Models of Diseases Characterized by Defects in the Neuromuscular Junction," Science 345:1505-1508 (2014), which is hereby incorporated by reference in its entirety). Although the lethality of these mutant mice could be rescued by an adenoviral-associated vector expressing wildtype Dok7, establishing a therapeutic approach to treat Dok7 CM (Arimura et al., "Neuromuscular Disease. DOK7 Gene Therapy Benefits Mouse Models of Diseases Characterized by Defects in the Neuromuscular Junction," *Science* 345:1505-1508 (2014), which is hereby incorporated by reference in its entirety), this study did not examine the cause for disease in the Dok7 1124_1127 dup mouse model.

Inbred C57BL/6 mice harboring the Dok7 1124_1127 dup mutation displayed more severe functional deficits than humans with the same mutation. It was found that the mutant phenotype was less severe in mice with a mixed genetic background, as outbred mice survived for several weeks postnatally, whereas inbred mutant mice died at birth. Modifiers in the hybrid strains may lessen disease severity, or C57BL/6 mice may harbor genes that worsen the phenotype. In either case, the modestly prolonged lifespan of Dok7 CM mice in the mixed background offers a mouse model that presents a longer temporal window to better assess therapeutics.

These experiments demonstrate full rescue from congenital lethality by targeted therapy. These findings point to an unforeseen therapeutic approach to treat disease, as this strategy does not directly target the mutant protein but rather targets a wildtype protein with diminished activity, caused by mutation of an upstream gene, in this case Dok7. Such epistatic rescue may provide therapy for CM caused by mutations in Agrin, Lrp4, or MuSK, in addition to Dok7, as well as additional neuromuscular diseases. Moreover, this strategy has the potential for widespread use to treat recessive genetic disorders in humans for which the disease mechanism is understood and suitable targets have been identified.

Example 2—MuSK Antibodies

Selection of SIMPLE Antibodies Targeting the Frizzle Domain of MuSK

Two llamas were immunized with recombinant human MuSK (R&D systems, cat. 9810-MK). PBLs isolated from the immunized llamas were used for RNA extraction, RT-PCR and PCR-cloning of Fab in a phagemid using the strategy described by de Haard et al., "A Large Non-Immunized Human Fab Fragment Phage Library that Permits Rapid Isolation and Kinetic Analysis of High Affinity Antibodies," *J. Biol. Chem.* 274:18218-18230 (1999), which is hereby incorporated by reference in its entirety). Panning phage display selections were performed for up to three rounds using either full length human MuSK, full length mouse MuSK, or human MuSK lacking the Ig1-like and/or Ig2-like and/or Ig3-like domain (FIG. 18).

For each selection with enrichment, individual clones were grown in a 96-deep well plate and periplasmic fractions were prepared. These periplasmic extracts (containing Fabs), were tested for binding in ELISA to full length human MuSK, full length mouse MuSK, or human MuSK lacking the Ig1-like and/or Ig2-like and/or Ig3-like domain. Fabs that demonstrate clear binding in ELISA were then tested for off-rate in Biacore on a CM5 chip coated with full length human MuSK, full length mouse MuSK, or human MuSK lacking the Ig1-like and/or Ig2-like and/or Ig3-like domain. Binders with good affinity for human and mouse MuSK and specific for the Frizzle domain of MuSK were sequenced. Six distinct families of binders were obtained: 1E11, 6F8, 10F1, 17H10, 14D10, 16F11. These were cloned into a vector containing the sequence of the human IgG1 with the LALA mutations (L234A, L235A) to knock out effector functions. Antibodies were produced in HEK293 cells and purified on a protein-A column.

Binding of Antibodies to Human and Mouse MuSK in ELISA

An ELISA plate was coated with human MuSK (R&D Systems, cat. 10189-MK) or mouse MuSK (in house produced in HEK293 cells) at 0.2 µg/ml. After washing and blocking the plate, a dilution series of the anti-MuSK antibodies was applied and allowed to bind for 2 hours at room temperature. Binding was detected with goat anti human Fc-HRP (Jackson Immunoresearch, cat. #109-035-008) and TMB (Merck Millipore #CL07). OD at 620 nm was measured with a 96 well ELISA plate reader.

All 6 antibodies (1E11, 6F8, 10F1, 17H10, 14D10 and 16F11) showed binding to human MuSK. However binding to mouse MuSK was poor, except for 16F11. 16F11 had an increased binding to mouse MuSK at higher 16F11 concentrations than for human MuSK (FIG. 19). In conclusion, this assay revealed poor human mouse cross reactive binding of 5 of the 6 antibodies tested.

Light Chain Shuffling to Improve Mouse Cross Reactivity

Upon repeated exposures to the same antigen, such as during an immunization of llamas, the immune response is optimized by increasing the affinity of the antibody for the target. A secondary response can elicit antibodies with several log-fold greater affinity than in a primary response. As a consequence, B cells produce different antibodies and variants therefore of different affinities for the antigen. Five out of the six antibodies selected above were poorly mouse cross reactive. Therefore, chain shuffling was applied to mAbs. In this process, the VH of the Fab molecule is cloned into the full respective llama repertoire of the VL. The resulting library will contain the Fab-phage with VH chains specific for the Fab and random VL chains. Using phage display and different variants of MuSK (similar to what is described above), higher affinity variants were selected naturally occurring in the immunized animals. For each selection with enrichment, individual clones were grown in a 96-deep well plate and periplasmic fractions were prepared. These periplasmic extracts (containing Fabs), were tested for binding in Biacore on a CM5 chip coated with full length human MuSK and full length mouse MuSK. Binders with good affinity for human and mouse MuSK were sequenced. The campaign was successful for 14D10, 16F11, 6F8 and 17H10. For 10F1 and 1E11 no improvement in mouse cross reactivity was obtained.

For 14D10, 6 distinct sequences of cross reactive binders were obtained: 31G2, 31B7, 3C4, 7G4, 3G3 and 3B2. For 17H10, 3 distinct sequences of cross reactive binders were obtained: 23B6, 30E1 and 30A11. For 16F11, 4 distinct sequences of cross reactive binders were obtained: 4C11, 7G12, 7B8 and 7A12.

These were all cloned into a vector containing the sequence of the human IgG1 with the LALA mutations (L234A, L235A) to knock out effector functions. Antibodies were produced in HEK293 cells and purified on a protein-A column.

Binding of Antibodies to Human and Mouse MuSK in ELISA

An ELISA plate was coated with human MuSK (R&D Systems, cat. 10189-MK), rhesus monkey MuSK (in house produced in HEK293 cells), or mouse MuSK (in house produced in HEK293 cells) at 0.2 µg/ml. After washing and blocking the plate, a dilution series of the anti-MuSK antibodies was applied and allowed to bind for 2 hours at room temperature. Binding was detected with goat anti-human Fc-HRP (Jackson Immunoresearch, cat. #109-035-008) and TMB (Merck Millipore #CL07). After stopping the reaction with 0.5N H2SO4 (ChemLab #CL052615), the OD at 450 nm was measured with a 96 well ELISA plate reader. The $EC_{50}$ values are summarized in the Table 4. The improved affinity for Mouse MuSK was confirmed for all clones tested.

TABLE 4

Light Chain Shuffled Clone Characterization, $EC_{50}$ Values per mAb Resulting from a Binding ELISA to Human, Mouse, and Rhesus Monkey MuSK

| Clone* | Human homology (%) | Human identity (%) | Parental clone | Human MuSK | Mouse MuSK | Rhesus monkey MuSK | Potential liabilities (#) |
|---|---|---|---|---|---|---|---|
| 14D10 | 97.7 | 92.4 | NA | 23.6 | 467 | 20.9 | 2 |
| 7G4 | 97.7 | 91.1 | 14D10 | 19.1 | 20.8 | 17.8 | 2 |
| 3C4 | 97.7 | 91.1 | 14D10 | 18.6 | 17.7 | 20.0 | 2 |
| 3B2 | 97.7 | 91.1 | 14D10 | 19.7 | 19.3 | 17.1 | 2 |
| 3G3 | 97.7 | 89.9 | 14D10 | 25.9 | 26.5 | 23.2 | 2 |
| 31G2 | 97.7 | 89.9 | 14D10 | 8.2 | 6.9 | 7.4 | 2 |
| 31B7 | 97.7 | 89.9 | 14D10 | 8.6 | 8.0 | 8.5 | 2 |
| 17H10 | 93.7 | 89.7 | NA | 10.8 | 2493 | 12.3 | 4 |
| 23B6 | 93.7 | 89.7 | 17H10 | 10.5 | 17.9 | 8.6 | 4 |
| 30E1 | 94.9 | 89.7 | 17H10 | 10.0 | 24.1 | 8.6 | 4 |
| 30A11 | 89.9 | 89.7 | 17H10 | 12.8 | 18.4 | 11.3 | 4 |
| 16F11 | 90.8 | 80.0 | NA | 43.4 | 50.3 | 33.9 | 1 |
| 4C11 | 90.8 | 80.0 | 16F11 | 33.1 | 43.7 | 34.1 | 1 |
| 7A12 | 90.8 | 78.8 | 16F11 | 26.4 | 27.5 | 21.3 | 1 |

TABLE 4-continued

Light Chain Shuffled Clone Characterization, $EC_{50}$ Values per mAb Resulting from a Binding ELISA to Human, Mouse, and Rhesus Monkey MuSK

| Clone* | Human homology (%) | Human identity (%) | Parental clone | Human MuSK | Mouse MuSK | Rhesus monkey MuSK | Potential liabilities (#) |
|---|---|---|---|---|---|---|---|
| 7G12 | 90.8 | 78.8 | 16F11 | 38.3 | 31.3 | 28.6 | 1 |
| 7B8 | 90.8 | 82.5 | 16F11 | 28.2 | 34.9 | 35.6 | 1 |

*Sequences in bold were selected for large scale antibody production in HEK293 cells and in depth characterization.

The following criteria were used to select the best clones: (i) highest affinity for human, rhesus monkey and mouse MuSK; (ii) minimal difference in affinity between human, rhesus monkey and mouse MuSK; (iii) maximally 10-fold difference in affinity between human, rhesus monkey and mouse MuSK; (iv) low risk for manufacturability issues based on sequence analysis of the CDRs; and (v) highest human identity/homology.

Clones 3B2, 30A11 and 30E1 were selected for large scale antibody production in HEK293 cells and in depth characterization.

Binding Affinity for Human Versus Mouse MuSK in Biacore

Monovalent binding to MuSK can inhibit agrin-induced MuSK phosphorylation and AChR clustering as described in Huijbers et al., "MuSK Myasthenia Gravis Monoclonal Antibodies: Valency Dictates Pathogenicity," *Neurol. Neuroimmunol. Neuroinflamm.* 6(3):e547 (2019), which is hereby incorporated by reference in its entirety. Assessing affinity of the 3B2, 30E1, and 30A11 Fab for MuSK is therefore important. Indeed, a less affine Fab could reduce monovalent binding of the mAb and therefore have a potential safety advantage. Therefore, Fab affinity to human and mouse MuSK was compared to mAb affinity in Biacore.

For affinity determination, a CM5 chip was coated with either human or mouse MuSK (200RU) and a dilution series of the antibodies (mAbs and Fabs) was applied in order to be able to calculate the affinity.

Using this assay, 3B2 mAb affinity to both human and mouse MuSK was 0.1 nM. Fab 3B2 revealed an affinity of 3 nM for human and 1.5 nM for mouse MuSK which is 15-30 times lower than the affinity of the mAb.

30E1 showed a 10 fold difference in affinity for binding to human (0.01 nM) versus mouse MuSK (0.1 nM). 30A11 showed even a 100 fold difference in affinity for binding to human (0.001 nM) versus mouse MuSK (0.1 nM). So both antibodies are not sufficiently mouse cross reactive. Moreover, 30E1 Fab and 30A11 Fab showed a high affinity to human MuSK, respectively 0.07 nM and 0.8 nM. The lack of mouse cross reactivity for both antibodies was also observed for the Fabs. These results suggest a 10 to 100 fold difference for 30E1 and 30A11 mAb and at least a 1000 fold for 30E1 and 30A11 Fab when comparing its affinity for human versus mouse MuSK (Table 5). This difference in affinity of an antibody for its target is not recommended for further development of an antibody, since it will be difficult to assess in vivo mouse experiments and translate the data to human. In conclusion, 3B2 mAb and Fab show the desired affinity characteristics and cross species reactivity for further development.

TABLE 5

Affinity of mAbs and Fabs for human versus mouse MuSK in Biacore

| $K_D$ (pM) | mAb | | Fab | |
|---|---|---|---|---|
| | Human | Mouse | Human | Mouse |
| 3B2 | 145 | 134 | 3180 | 1520 |
| 30E1 | 11 | 153 | 70 | 5390 |
| 30A11 | 1 | 110 | 8 | 2420 |

Potency of Antibodies in C2C12 Phosphorylation Assay

In order to evaluate the extend of MuSK phosphorylation induced by 3B2, 30E1, 30A11, an in vitro MuSK phosphorylation assay using mouse C2C12 myotubes was used (91031101, Sigma Cell line service ECACC). Differentiated myotubes were stimulated with 10 nM of antibody. The positive control for MuSK phosphorylation was a stimulation condition applying 0.1 nM neural rat agrin (550-AG-100, R&D systems). Immunoprecipitation of MuSK was initiated immediately after exposure during an overnight incubation at 4° C. Bound antigen-antibody complexes were precipitated using streptavidin coated magnetic beads (V7820, Promega) for at least 1 hour at 4° C. and afterwards were extensively washed. Simultaneously, a streptavidin-coated MSD plate (L15SA-1, MSD) was blocked and coated with biotinylated hIgG4 anti-MuSK (clone 13-3B5—Evitria production 801457.1 PID 9860—biotinylation was performed at argenx). MuSK proteins were eluted from the beads applying acid conditions followed by a neutralization step and were incubated on the hIgG4 anti-MuSK coated MSD plate for at least 2.5 hours at room temperature. Sample incubation occurred in the presence of truncated MuSK (MuSK Δ1-2-3 Ig, argenx production in HEK) in solution to limit drug interference of co-eluted anti-MuSK hIgG1 antibodies. Samples were loaded in quadruplicate on the plate which allowed detection of total MuSK (mix of PA1-1741, Thermoscientific and MBS9205728, MyBioSource) and phosphorylated MuSK (mix of 05-321 Millipore Corp (clone 4G10) and ab10321, Abcam (clone PY20)) in the sample in duplicate. Final detection occurred applying SULFO-TAG conjugated antibodies, respectively anti-rabbit IgG for total MuSK detection (32AB-1, MSD) and anti-mouse IgG for Phosphorylated MuSK detection (R32AC-1, MSD). Bound antibodies were detected using the Quickplex SQ 120 (MSD).

Agrin (1 nM) addition to C2C12 myotubes induced MuSK phosphorylation and was set at a 100%. Three independent experiments were performed. Using this experimental setup, 3B2, 30E1 and 30A11 could induce MuSK phosphorylation in this assay, between 50 and 94% (Table 6).

TABLE 6

% Phosphorylation Induced in C2C12 Mouse Assay

| % versus agrin | Assay 1 | Assay 2 | Assay 3 | Average | STD |
|---|---|---|---|---|---|
| 1 nM agrin | 100 | 100 | 100 | 100 | 0 |
| 0.1 nM agrin | NA | 64 | 56 | 60 | 6 |
| motavizumab | 38 | 20 | 17 | 25 | 11 |
| 3B2 | 74 | 94 | 64 | 77 | 15 |
| 30E1 | 66 | 82 | 50 | 66 | 16 |
| 30A11 | 73 | 89 | 74 | 79 | 9 |

3B2 Rescues Early Postnatal Lethality of Dok7 1124_1127 Dup Mice

In a first experiment, intraperitoneal (IP) administration of 3B2 at 10 mg/kg both at P4 and P18 in wild type mice (C57BL/6//CBA) for at least 5 weeks revealed no difference versus isotype injected wild type mice with regards to body weight and overall health, suggesting no safety concerns or toxicity issues and revealing that the 3B2 antibody is safe for further in vivo experimental work.

Next, 3B2 was administered to Dok7 1124_1127 dup mice, a CMS mouse model. In Dok7 1124_1127 dup mice (hereafter called Dok7 mice), truncated Dok7 is poorly expressed, and MuSK tyrosine phosphorylation is severely reduced. The reduced level of MuSK phosphorylation in Dok7 mice plays a key role in disease. Stimulating MuSK phosphorylation with an agonist antibody to MuSK could rescues, lethality of Dok7 mice, allowing the mutant mice to survive as adults. Indeed, administration of 3B2 (20 mg/kg IP at P4 and 10 mg/kg IP at P18) could rescue early postnatal lethality of Dok7 mutant mice (FIG. 20).

3B2 Removal of Liabilities and CDR Grafting

3B2 antibody was diluted to 1 mg/mL in PBS-Tween and incubated at 37° C. for up to 6 weeks. Next, the sample was analyzed by mass spectrometry and screened for deamidation, glycosylation, isomerization and oxidation sites in the VH and VL. As predicted, two liabilities were identified: 1 deamidation site in the VH-CDR2 and 1 oxidation site in the VL-CDR3. Mutants were made to remove both liabilities. Moreover, 3B2 had already a high human identity/homology (94.2% and 97.7% resp) but this was further improved to 100% by CDR grafting on the closest human germline sequence.

Combining these two strategies, in total 8 variants were produced, summarized in Table 7. Antibodies were produced in HEK293 cells in the human IgG1-LALA backbone and purified on a protein-A column.

TABLE 7

Variants Produced to Remove Liabilities and to Obtain 100% Human Identity

| | VL | VH |
|---|---|---|
| 3B2g1m1 | VL3B2_g1 (M) | VH3B2m1_m1 (S) |
| 3B2g1m2 | | VH3B2m2_m2 (GS) |
| 3B2g1m3 | | VH3B2m3_m3 (SGS) |
| 3B2g1m4 | | VH3B2m4_m4 (Q) |
| 3B2g2m1 | VL3B2_g2 (S) | VH3B2m1_m1 (S) |
| 3B2g2m2 | | VH3B2m2_m2 (GS) |
| 3B2g2m3 | | VH3B2m3_m3 (SGS) |
| 3B2g2m4 | | VH3B2m4_m4 (Q) |

Affinity of Sequence Optimized Variants of 3B2 in Biacore

For affinity determination, a CM5 chip was coated with cynomolgus monkey, rat and mouse MuSK (200RU) and 66.7 nM of antibody was applied and kinetic parameters calculated (Table 8). The following conclusions could be drawn: (1) 3B2g1m3 and 3B2g2m3 (m3 variants) show significant drop in affinity for MuSK for all species tested; (2) 3B2g1m2 and 3B2g2m2 (m2 variants) show some drop in affinity for MuSK; (3) 3B2g1m1, 3B2g2m1, 3B2g1m4, 3B2g2m4 (m1 and m4 variants) show no drop in affinity for MuSK for all species tested; and (4) for all clones there is no difference between g1 and g2 variants (VL methionine versus serine in CDR3).

TABLE 8

Affinity of mAbs for Cynomolgus Versus Mouse Versus Rat MuSK in Biacore, Association, and Dissociation at pH7.4

| association and dissociation at pH7.4 mAb | cynomolgus MuSK | | | mouse MuSK | | | rat MuSK | | |
|---|---|---|---|---|---|---|---|---|---|
| | ka (1/Ms) (10E+4) | kd (1/s) (10E−3) | R0 (RU) | ka (1/Ms) (10E+4) | kd (1/s) (10E−3) | R0 (RU) | ka (1/Ms) (10E+4) | kd (1/s) (10E−3) | R0 (RU) |
| 3B2 | 79 | 0.97 | 143 | 113 | 0.61 | 195 | 114 | 1.86 | 162 |
| 3B2g1m1 | 84 | 1.17 | 143 | 125 | 1.10 | 193 | 132 | 1.92 | 157 |
| 3B2g1m2 | 85 | 1.83 | 133 | 161 | 2.53 | 155 | 145 | 3.14 | 125 |
| 3B2g1m3 | 141 | 3.24 | 104 | 275 | 9.82 | 104 | 272 | 15.30 | 60 |
| 3B2g1m4 | 73 | 0.86 | 140 | 108 | 0.65 | 192 | 112 | 1.92 | 155 |
| 3B2g2m1 | 89 | 1.09 | 144 | 132 | 1.04 | 195 | 140 | 1.93 | 160 |
| 3B2g2m2 | 89 | 1.79 | 136 | 171 | 2.31 | 158 | 156 | 2.81 | 130 |
| 3B2g2m3 | 139 | 3.06 | 108 | 248 | 8.52 | 115 | 235 | 14.50 | 69.6 |
| 3B2g2m4 | 79 | 0.88 | 142 | 115 | 0.64 | 193 | 119 | 1.96 | 158 |

Conventional antibodies are taken up into cells by non-specific endocytosis or pinocytosis or via receptor mediated internalization. A recycling antibody is engineered so that a single antibody molecule can bind to an antigen multiple times, in contrast to conventional antibodies, which can only bind antigen once. Indeed, once conventional antibodies bind to a membrane anchored antigen such as a receptor, the antibody-antigen complex is internalized and degraded within the lysosome. This results in a shorter half-life of the therapeutic antibody, necessitating frequent administration of the antibody drug or at higher doses to sustain efficacious plasma antibody concentration. Antibodies can be engineered such that the antibody dissociates from the antigen at acidic pH within the endosome. Once dissociated, the recycling antibody is free to bind to the FcRn (neonatal Fc Receptor) within the endosome, which transports the antibody back into circulation to bind to more antigen.

MuSK is expressed on the membrane of muscle cells and internalization of MuSK is described in Zhu et al., "Muscle-Specific Receptor Tyrosine Kinase Endocytosis in Acetylcholine Receptor Clustering in Response to Agrin," *J. Neurosci.* 28(7):1688-1696 (2008), which is hereby incorporated by reference in its entirety. Therefore, a recycling antibody against this target could be of interest.

Most of the pH-dependent antibodies reported so far have been obtained after heavy engineering of the CDRs but sometimes this property can be pre-existing. It was investigated in Biacore if 3B2 and the optimized sequence variants have the naturally existing pH dependency for binding to MuSK.

In order to study pH dependent binding of our antibodies to MuSK, the same Biacore was used as above, but now dissociation was done at pH 5.5 instead of pH 7.4. The results demonstrate that 3B2 binds with pH dependency to MuSK (cynomolgus monkey, rat or mouse), with a decreased affinity at pH 5.5 (Table 9). The following conclusions could be drawn for the different variants: (1) 3B2g1m3 and 3B2g2m3 (m3 variants) show significant drop in affinity for MuSK for all species tested; (2) 3B2g1m2 and 3B2g2m2 (m2 variants) show some drop in affinity for MuSK; (3) 3B2g1m1, 3B2g2m1, 3B2g1m4, 3B2g2m4 (m1 and m4 variants) show no drop in affinity for MuSK for all species tested; and (4) for all clones there is no difference between g1 and g2 variants (VL methionine versus serine in CDR3).

Binding Affinity of 3B2 Variants on Coated MuSK from Different Species in ELISA

In order to evaluate the binding affinity of the 3B2 variants to MuSK protein from different species, an ELISA was performed. A plate was coated with MuSK form human, cyno, rat, or mouse and binding of the different 3B2 variants compared to 3B2 was assessed as above. In this assay, 3B2g1m1, 3B2g2m1, 3B2g1m4, and 3B2g2m4 did not lose affinity compared to 3B2. Whereas 3B2g1m2, 3B2g2m2, 3B2g1m3, and 3B2g2m3 lost binding affinity to MuSK from different species (FIG. 22).

Example 3—Differences in pH Dependency of Agonistic MuSK Antibodies

Conventional antibodies are taken up into cells by non-specific endocytosis or pinocytosis or via receptor mediated internalization. As described supra, a recycling antibody is engineered so that a single antibody molecule can bind to an antigen multiple times, in contrast to conventional antibodies, which can only bind antigen once. Indeed, once conventional antibodies bind to a membrane anchored antigen such as a receptor, the antibody-antigen complex is internalized and degraded within the lysosome. This results in a shorter half-life of the therapeutic antibody, necessitating frequent administration of the antibody drug or at higher doses to sustain efficacious plasma antibody concentration.

TABLE 9

Affinity of mAbs for Cynomolgus Versus Mouse Versus Rat MuSK in Biacore, Association at pH7.4, Dissociation at pH5.5

| association at pH7.4, dissociation at pH5.5 mAb | cynomolgus MuSK | | | mouse MuSK | | | rat MuSK | | |
|---|---|---|---|---|---|---|---|---|---|
| | ka (1/Ms) (10E+4) | kd (1/s) (10E−3) | R0 (RU) | ka (1/Ms) (10E+4) | kd (1/s) (10E−3) | R0 (RU) | ka (1/Ms) (10E+4) | kd (1/s) (10E−3) | R0 (RU) |
| 3B2 | 74 | 3.17 | 149 | 105 | 2.96 | 194 | 98 | 6.20 | 174 |
| 3B2g1m1 | 81 | 2.90 | 147 | 119 | 3.39 | 192 | 116 | 5.95 | 166 |
| 3B2g1m2 | 80 | 3.40 | 148 | 7 | 9.15 | 152 | 4 | 86.50 | 136 |
| 3B2g1m3 | 122 | 9.17 | 131 | 6 | 491 | 85.5 | 3 | 527 | 83.2 |
| 3B2g1m4 | 68 | 2.61 | 146 | 98 | 3.04 | 191 | 95 | 5.58 | 171 |
| 3B2g2m1 | 85 | 2.88 | 151 | 118 | 3.39 | 193 | 115 | 5.55 | 174 |
| 3B2g2m2 | 86 | 3.26 | 146 | 21 | 88.20 | 153 | 4 | 97.30 | 145 |
| 3B2g2m3 | 131 | 8.10 | 133 | 4 | 411 | 88.3 | 2 | 444 | 85.3 |
| 3B2g2m4 | 75 | 2.56 | 148 | 104 | 3.00 | 191 | 102 | 5.38 | 172 |

In Vitro MuSK Phosphorylation Assay Evaluating 3B2 Variants

In order to evaluate the extend of MuSK phosphorylation induced by our agonistic 3B2 variant antibodies an in vitro MuSK phosphorylation assay using mouse C2C12 myotubes was used. Controls include agrin, the parental 3B2 and Motavizumab (non-MuSK binding Ab). Agrin addition to C2C12 myotubes induced MuSK phosphorylation and was set at a 100%, this includes subtracting the back ground MuSK phosphorylation analyzed by inducing MuSK Phosphorylation by the non-MuSK binder Motavizumab. The parental 3B2 Ab induced as much MuSK phosphorylation as 1 nM agrin. Moreover, 3B2 variants 3B2g1m1, and 3B2g2m1 performed equally well as the parental 3B2 Ab. 3B2g1m2 and 3B2g2m2 also induced strong MuSK phosphorylation (+/−80%). 3B2g1m3 and 3B2g2m3 lost the ability to induce MuSK, resulting in MuSK phosphorylation around 13%. Interestingly, 3B2g1m4 and 3B2g2m4 lost the ability to induce MuSK by almost half, resulting in MuSK phosphorylation around 58% (FIG. 21).

Antibodies can be engineered such that the antibody dissociates from the antigen at acidic pH within the endosome. Once dissociated, the recycling antibody is free to bind to the FcRn (neonatal Fc Receptor) within the endosome, which transports the antibody back into circulation to bind to more antigen.

MuSK is expressed on the membrane of muscle cells and internalization of MuSK is described in Zhu et al., "Muscle-Specific Receptor Tyrosine Kinase Endocytosis in Acetylcholine Receptor Clustering in Response to Agrin," *J. Neurosci.* 28(7):1688-1696 (2008), which is hereby incorporated by reference in its entirety. Therefore, a recycling antibody against this target could be of interest.

Most of the pH-dependent antibodies reported so far have been obtained after heavy engineering of the CDRs but sometimes this property can be pre-existing. Whether X2, X2m4, X3, X9, X17, 3B2 and 3B2g2m1 have the naturally existing pH dependency for binding to MuSK was investigated in Biacore.

In order to study pH dependent binding of the antibodies described herein to MuSK, a Biacore T200 was used. Briefly, a CM5 chip was coated with human and mouse MuSK (200RU) and 22.2 nM of Fab was applied and kinetic parameters calculated. Association was done at pH7.4, dissociation was done at pH 7.4 and also at pH 5.5. The following Fabs were tested, X2, X2m4, X3, X9, X17, 3B2 and 3B2g2m1 (Table 10 and FIG. 23). Interestingly, these results suggest that 3B2g2m1 has pH dependent properties for both human and mouse MuSK. Binding affinity at pH 5.5 is very low, resulting in a rapid dissociation at endosomal pH allowing 3B2g2m1 to recycle.

TABLE 10

Off Rate Analysis of MuSK Agonist Fabs for Human and Mouse MuSK in Biacore, Association at pH 7.4, Dissociation either at pH 7.4 or pH 5.5.

| Off rate analysis | Human MuSK | | | Mouse MuSK | | |
|---|---|---|---|---|---|---|
| Kd (1/s) (10E−4) | pH 7.4 | pH 5.5 | Ratio pH 5.5/7.4 | pH 7.4 | pH 5.5 | Ratio pH 5.5/7.4 |
| X17 Fab | 8.8 | 67.8 | 7.7 | 12.0 | 20.0 | 1.7 |
| X2 Fab | 5.7 | 3.4 | 0.6 | 5.3 | 5.1 | 1.0 |
| X2m4 Fab | 86.7 | 58.6 | 0.7 | 33.7 | 41.6 | 1.2 |
| X3 Fab | 6.3 | 22.5 | 3.5 | 55.8 | 246.4 | 4.4 |
| X9 Fab | 5.9 | 8.3 | 1.4 | 1.5 | 10.5 | 7.1 |
| 3B2 Fab | 38.8 | 224.0 | 5.8 | 34.7 | 1093.0 | 31.5 |
| 3B2g2m1 Fab | 47.2 | 288.4 | 6.1 | 76.6 | 679.2 | 8.9 |

Example 4—Agonistic MuSK Antibodies Targeting the Fz-Domain do not Interfere with MuSK Activation by its Natural Ligand Agrin Activation of MuSK requires motor neuron secreted agrin, muscle membrane located LRP4, and cytoplasmic DOK-7. LRP4 and MuSK are pre-assembled in the absence of agrin but activation of MuSK is induced only in the presence of agrin. Indeed, agrin bound LRP4 with MuSK initiates MuSK trans-phosphorylation and activation (Stiegler et al., "Crystal Structure of the Agrin-Responsive Immunoglobulin-Like Domains 1 and 2 of the Receptor Tyrosine Kinase MuSK," *J. Mol. Biol.* 364:424-433 (2006); Kim et al., "Lrp4 is a Receptor for Agrin and Forms a Complex with MuSK," *Cell* 135:334-342 (2008); and Zhang et al., "Agrin Binds to the N-Terminal Region of Lrp4 Protein and Stimulates Association between Lrp4 and the First Immunoglobulin-Like Domain in Muscle-Specific Kinase (MuSK)," *J. Biol. Chem.* 286:40624-40630 (2011); and Zong et al., "Structural Basis of Agrin-LRP4-MuSK Signaling," *Genes Dev.* 26:247-258 (2012), which are hereby incorporated by reference in their entirety).

MuSK agonistic antibodies targeting the Fz-domain of MuSK can potentially interfere with the activation of MuSK by agrin. In order to test if a Fz-binding MuSK agonist antibody can activate MuSK together with agrin, an in vitro co-stimulation experiment was performed.

An in vitro MuSK phosphorylation assay with mouse C2C12 myotubes was used, to evaluate the extend of MuSK phosphorylation induced by the agonistic MuSK antibody 3B2g2m1, with or without a non-saturating condition of agrin (0.1 nM agrin). Controls include agrin (at 1 nM and 0.1 nM), and Motavizumab (isotype control, non-MuSK binding mAb, 333 nM). All stimulations where performed for 30 minutes. 1 nM agrin addition to C2C12 myotubes induced MuSK phosphorylation and was set at 100%, this includes subtracting the background MuSK phosphorylation analyzed by the MuSK phosphorylation induction of the non-MuSK binder Motavizumab. Stimulating MuSK with 0.1 nM of agrin results in 53% induction of MuSK phosphorylation, suggesting a suboptimal concentration of agrin in this assay. Titrating 3B2g2m1 (without agrin) from 0.01-333 nM results in a dose dependent increase of MuSK phosphorylation. Importantly, co-stimulation of 3B2g2m1 with the suboptimal concentration of 0.1 nM agrin resulted in an increase of MuSK phosphorylation when comparing to stimulation with 3B2g2m1 or 0.1 nM agrin only. Remarkably, 0.3 nM of 3B2g2m1 in combination with 0.1 nM of agrin resulted in 100% MuSK phosphorylation, similar to stimulation with 1 nM of agrin only (FIG. 24). This data suggests that 3B2g2m1, binding to the Fz-domain of MuSK, can stimulation MuSK in parallel of agrin. Moreover, it can be suggested that 3B2g2m1 can activate MuSK on top of its natural ligand agrin, leading to increased MuSK phosphorylation. Indeed, agrin binds to LRP4, which in its turn bind the Ig-1-like domain of MuSK. Therefore, activating MuSK by targeting the Fz-domain with an agonistic MuSK antibody, does not interfere with MuSK activation by its natural ligand agrin.

Example 5—MuSK Agonist Antibodies mIgG2a-X17 And hIgG-X17

The therapeutic utility of the combination of mIgG2a-X17 and hIgG-X17 antibodies were tested in the Dok7 model. Although Dok7 1124_27 dup mice in a C57BL/6-CBA mixed background treated at P4 with an isotype equivalent negative control, Motavizumab, died one to two weeks after birth (as did untreated Dok7 1124_27 dup mice in the mixed genetic background), it was found that Dok7 1124_1127 dup mice injected with 10 mg/kg mIgG2a-X17 (n=3) at P4 and 10 mg/kg hIgG-X17 at P24 and P44 survived as adults (FIGS. 25A-25B).

Dok7 1124_1127 dup mice, injected with 10 mg/kg mIgG2a-X17 at P4 and 10 mg/kg hIgG-X17 at P24 and P44 gained weight, unlike Dok7 1124_1127 dup mice treated with the isotype control antibody (FIG. 25B). Moreover, the combination of mIgG2a-X1 and hIgG-X17 rescued motor function of Dok7 1124_27 dup mice, as assessed by grip strength and the latency to fall from a rotating rotarod (FIG. 26).

Together, these findings demonstrate that agonist antibodies to MuSK, mIgG2a-X17 combined with hIgG-X17 rescue young Dok7 1124_1127 dup mice.

Example 6—MuSK Agonist Antibody hIgG-X17

To determine whether MuSK agonist antibody hIgG-X17 engages MuSK at the synapse, P40 wildtype mice were injected intraperitoneally with MuSK agonist antibody hIgG-X17 (0, 2, 10, 20 mg/kg). Two days later, mice were sacrificed and diaphragm muscles were stained with Alexa 488-α-BGT to label AChRs and Alexa 647 Goat Anti-Human IgG, F(ab)$_2$ fragment specific to label X17. Levels of saturation of X17 at the synapse were measured by the ratio of X17 to AChR signal intensity. The graph of FIG. 27 demonstrates that MuSK agonist antibody hIgG-X17 engages MuSK at the synapse and saturates MuSK at 20 mg/kg.

Next, to investigate whether hIgG-X17 rescues lethality in young Dok7 1124_1127 dup mice, Dok7 1124_1127 dup mice in the mixed background were treated at P4 with agonist antibody hIgG-X17 or an isotype equivalent negative control, Motavizumab. Dok7 1124_1127 dup mice (n=11) injected with the isotype control, like untreated mice, died one to two weeks after birth, whereas Dok7 1124_1127 dup mice injected with hIgG-X17 (n=4) at P4, P18, and P38 survived as adults (FIG. 28A). Moreover, Dok7 1124_1127 dup mice, injected with 20 mg/kg hIgG-X17 at P4 and 10 mg/kg hIgG-X17 at P18 and P38 gained weight, unlike Dok7 1124_1127 dup mice treated with the isotype control antibody (FIG. 28B).

To evaluate whether hIgG-X17 restores synapse development in young Dok7 1124_1127 dup mice, diaphragm muscles from P60 wildtype and Dok7 1124_1127 dup mice were stained with Alexa 488-α-BGT to label AChRs and antibodies to βIIITubulin/Synapsin to label motor axons/nerve terminals (FIG. 29). In Dok7 1124_1127 dup mice treated with hIgG-X17, synapses matured from a simple, plaque-like shape to a complex, pretzel-like shape, characteristic of mature murine neuromuscular synapses (see immunohistochemical images of FIG. 29) and the number of synapses, synaptic size, and density of synaptic AChRs were restored to 70%, 50%, and 40%, respectively, of normal levels (see graphs of FIG. 29).

hIgG-X17 rescued motor function of Dok7 1124_27 dup mice, as assessed by grip strength and the latency to fall from a rotating rotarod (FIG. 30).

Next, whether hIgG-X17 could reverse neuromuscular deficits that develop during adulthood in Dok7 1124_1127 dup mice was evaluated. Briefly, Dok7 1124_1127 dup mice were injected with MuSK agonist antibodies either at P4, P24, and P44, or P4, P18, and then antibody treatment was discontinued. These Dok7 1124_1127 dup mice gained weight and maintained their mobility for several months but ultimately began to lose weight (FIG. 31A, FIG. 31B) and to display motor deficits, as assessed by grip strength and the latency to fall from a rotating rotarod (FIG. 31C). Mice were then, either not re-injected (FIG. 31A), or re-injected with hIgG-X17 (FIG. 31B). Mice that did not receive a further dose of antibody died within a few days (FIG. 31A), while in mice receiving another X17 treatment, the Dok7 1124_1127 dup mice began to gain weight (FIG. 31B), and by one week after restarting treatment their motor deficits were reversed (FIG. 31C). Dok7 1124_1127 dup mice improved their performance on the rotarod by 3.25-fold, whereas the performance of wildtype mice improved by 1.30-fold (FIG. 31C). Dok7 1124_1127 dup mice improved their grip strength by 1.30-fold, whereas the performance of wildtype mice did not improve (FIG. 31C).

Example 7—MuSK Agonist Antibody 3B2

To determine whether chronic injection of the MuSK agonist antibody 3B2 in wildtype mice has an effect on survival or weight gain, C57BL/6-CBA mixed background mice were injected at P4 and P18 with 3B2 (n=3) and compared to C57BL/6-CBA mixed background mice that were not injected (n=4). 3B2-injected wildtype mice, like non-injected wildtype mice, survived until sacrifice at P38 (FIG. 32A) and gained weight similar to non-injected wildtype mice (FIG. 32B).

Next, to investigate whether 3B2 rescues lethality in young Dok7 1124_1127 dup mice, Dok7 1124_1127 dup mice in a C57BL/6-CBA mixed background were treated at P4 with MuSK agonist antibody 3B2 or an isotype equivalent negative control, Motavizumab. Dok7 1124_1127 dup mice (n=11) injected with the isotype control, like untreated mice, died one to two weeks after birth, whereas Dok7 1124_1127 dup mice injected with 20 mg/kg 3B2 at P4, 10 mg/kg 3B2 at P18, and 10 mg/kg 3B2 at P38 survived as adults (n=3)(FIG. 33A). Moreover, Dok7 1124_1127 dup mice, injected with 20 mg/kg 3B2 at P4, 10 mg/kg 3B2 at P18, and 20 mg/kg 3B2 at P38 gained weight, unlike Dok7 1124_1127 dup mice treated with the isotype control antibody (FIG. 33B).

To evaluate whether 3B2 restores synapse development in young Dok7 1124_1127 dup mice, diaphragm muscles from P60 wildtype and Dok7 1124_1127 dup mice were stained with Alexa 488-α-BGT to label AChRs and antibodies to βIIITubulin/Synapsin to label motor axons/nerve terminals (FIG. 34). In Dok7 1124_1127 dup mice treated with 3B2, synapses matured from a simple, plaque-like shape to a complex, pretzel-like shape, characteristic of mature murine neuromuscular synapses (see immunohistochemical images of FIG. 34) and the number of synapses, synaptic size, and density of synaptic AChRs were restored to 80%, 75%, and 40%, respectively, of normal levels (see graphs of FIG. 34).

3B2 rescues motor performance of Dok7 1124_27 dup mice, as assessed by grip strength and the latency to fall from a rotating rotarod (FIG. 35). Moreover, injection with MuSK agonist antibody 3B2 at P4, P18, and P38 maintains Dok7 1124_1127 dup mice healthy for at least two months (FIG. 36).

Next, whether 3B2 could reverse disease relapse in adult Dok7 1124_1127 dup mice was evaluated. Briefly, a Dok7 1124_1127 dup mouse was injected with 10 mg/kg mIgG2a-X-17 at P4, P24, and P44. The Dok7 1124_1127 dup mice gained weight and maintained its mobility for several months but ultimately began to lose weight (FIG. 37). The mouse was then injected with 10 mg/kg 3B2 (FIG. 37). After restarting treatment with 3B2, this Dok7 1124_1127 dup mouse began to gain weight (FIG. 37).

Example 8—MuSK Agonist Antibody hIgG-X2

To determine whether chronic injection of the MuSK agonist antibody hIgG-X2 in wildtype mice has an effect on survival or weight gain, C57BL/6-CBA mixed background mice were injected at P4 and P18 with hIgG-X2 (n=3) and compared to C57BL/6-CBA mixed background mice that were not injected (n=4). hIgG-X2-injected wildtype mice, like non-injected wildtype mice, survived until sacrifice at P38 (FIG. 38A) and gained weight similar to non-injected wildtype mice (FIG. 38B).

Next, to investigate whether hIgG-X2 rescues lethality in young Dok7 1124_1127 dup mice, Dok7 1124_1127 dup mice in a C57BL/6-CBA mixed background were treated at P4 with MuSK agonist antibody hIgG-X2 or an isotype equivalent negative control, Motavizumab. Dok7 1124_1127 dup mice (n=11) injected with the isotype control, like untreated mice, died one to two weeks after birth, whereas Dok7 1124_1127 dup mice injected with 20 mg/kg hIgG-X2 at P4 and 10 mg/kg hIgG-X2 at P18 survived as adults (n=2) (FIG. 39A). Moreover, Dok7 1124_1127 dup mice, injected with 20 mg/kg hIgG-X2 at P4 and 10 mg/kg hIgG-X2 at P18 gained weight, unlike Dok7 1124_1127 dup mice treated with the isotype control antibody (FIG. 39B).

Next, whether hIgG-X2 could reverse disease relapse in adult Dok7 1124_1127 dup mice was evaluated. Briefly, Dok7 1124_1127 dup mice were injected with 20 mg/kg hIgG-X2 at P4 and 10 mg/kg hIgG-X2 at P18. The Dok7 1124_1127 dup mice gained weight and maintained its mobility for several months but ultimately began to lose weight (FIG. 40) and display motor defects, as assessed by grip strength and the latency to fall from a rotating rotarod (FIG. 40B). The mice were then injected with 10 mg/kg hIgG-X2 (FIG. 40A). After restarting treatment with hIgG- X2, Dok7 1124_1127 dup mouse began to gain weight (FIG. 40A) and their motor deficiency was completely reversed (FIG. 40B).

Example 9—MuSK Agonist Antibody hIgG-X2m4

To investigate whether hIgG-X2m4 rescues lethality in young Dok7 1124_1127 dup mice, Dok7 1124_1127 dup mice in a C57BL/6-CBA mixed background were treated at P4 with MuSK agonist antibody hIgG-X2m4 or an isotype equivalent negative control, Motavizumab. Dok7 1124_1127 dup mice (n=11) injected with the isotype control, like untreated mice, died one to two weeks after birth, whereas Dok7 1124_1127 dup mice injected with 20 mg/kg hIgG-X2m4 at P4 and 10 mg/kg hIgG-X2m4 at P18 survived as adults (n=3) (FIG. 41A). Moreover, Dok7 1124_1127 dup mice, injected with 20 mg/kg hIgG-X2m4 at P4 and 10 mg/kg hIgG-X2m4 at P18 gained weight, unlike Dok7 1124_1127 dup mice treated with the isotype control antibody (FIG. 41B). Moreover, injection with 20 mg/kg hIgG-X2m4 at P4 and 10 mg/kg hIgG-X2m4 at P18 maintains Dok7 1124_1127 dup mice healthy for at least two months (FIG. 42).

Example 10—MuSK Agonist Antibody mIgG2a-X3

To determine whether injection of the MuSK agonist antibody mIgG2a-X3 in wildtype mice has an effect on survival or weight gain, C57BL/6-CBA mixed background mice were injected with 10 mg/kg mIgG2a-X3 at P4, P24, and P44 (n=2) and compared to C57BL/6-CBA mixed background mice that were not injected (n=9). mIgG2a-X3 injected wildtype mice, like non-injected wildtype mice, survived until sacrifice at P60 (FIG. 43A) and gained weight similar to non-injected wildtype mice (FIG. 43B).

To evaluate whether injection of mIgG2a-X3 has an effect on the organization of neuromuscular synapses, diaphragm muscles from P60 wildtype and wildtype mice injected with mIgG2a-X3 were stained with Alexa 488-α-BGT to label AChRs and antibodies to βIIITubulin/Synapsin to label motor axons/nerve terminals (FIG. 44). In wildtype mice treated with mIgG2a-X3, synapses matured from a simple, plaque-like shape to a complex, pretzel-like shape, characteristic of mature murine neuromuscular synapses (see immunohistochemical images of FIG. 44). Injection of mIgG2a-X3 in wildtype mice had no effect on the number of synapses, synaptic size, and density of synaptic AChRs (see graphs of FIG. 44). Moreover, chronic injection of mIgG2a-X3 in wildtype mice has no effect on motor behavior, as assessed by grip strength and the latency to fall from a rotating rotarod (FIG. 45).

To investigate whether mIgG2a-X3 rescues lethality in young Dok7 1124_1127 dup mice, Dok7 1124_1127 dup mice in a C57BL/6-CBA mixed background were treated at P4 with 10 mg/kg mIgG2a-X3 or an isotype equivalent negative control, Motavizumab. Dok7 1124_1127 dup mice (n=11) injected with the isotype control and Dok7 1124_1127 dup mice (n=4) injected with mIgG2a-X3, like untreated mice, died one to two weeks after birth (FIGS. 46A-46B). The results in FIGS. 46A-46B demonstrate that the MuSK agonist antibody mIgG2a-X3 administered at 10 mg/kg at P4 rescues lethality in young Dok7 1124_1127 dup mice for a few days, as compared to Motavizumab.

Next, Dok7 1124_1127 dup mice in a C57BL/6-CBA mixed background were treated at P4 with 20 mg/kg mIgG2a-X3 or an isotype negative control at P18 with 10 mg/kg mIgG2a-X3 or an isotype equivalent negative control, Motavizumab. Dok7 1124_1127 dup mice (n=11) injected with the isotype control, like untreated mice, died one to two weeks after birth, whereas and Dok7 1124_1127 dup mice (n=2) injected with mIgG2a-X3 survived until sacrifice (FIG. 47A). Dok7 1124_1127 dup mice, injected with mIgG2a-X3 gained weight, unlike Dok7 1124_1127 dup mice treated with the isotype control antibody (FIG. 47B). Moreover, injection with 20 mg/kg mIgG2a-X3 at P4 and 10 mg/kg mIgG2a-X3 at P18 maintains Dok7 1124_1127 dup mice healthy for at least two months (FIG. 47B; FIG. 48).

Example 11—MuSK Agonist Antibody mIgG2a-X9

To investigate whether mIgG2a-X9 rescues lethality in young Dok7 1124_1127 dup mice, Dok7 1124_1127 dup mice in a C57BL/6-CBA mixed background were treated at P4, P24, and P44 with 10 mg/kg of the MuSK agonist antibody mIgG2a-X9 or an isotype equivalent negative control, Motavizumab. Dok7 1124_1127 dup mice (n=11) injected with the isotype control and most of the Dok7 1124_1127 dup mice (n=5) injected with mIgG2a-X9, like untreated mice, died one to two weeks after birth (FIG. 49A). One Dok7 1124_1127 dup mouse injected with mIgG2a-X9 survived until P60 (FIG. 49A). Likewise, most Dok7 1124_1127 dup mice injected with mIgG2a-X9 did not gain weight, like Dok7 1124_1127 dup mice treated with the isotype control antibody (FIG. 49B). However, FIG. 49B demonstrates that a single Dok7 1124_1127 dup mouse injected with mIgG2a-X9 gained weight overtime.

Example 12—MuSK Agonist Antibody 3B2g2m1

To determine whether MuSK agonist antibody 3B2g2m1 engages MuSK at the synapse, P30 wildtype mice were injected intraperitoneally with MuSK agonist 3B2g2m1 (0, 2, 10, 20 mg/kg). Two days later, mice were sacrificed and diaphragm muscles were stained with Alexa 488-α-BGT to label AChRs and Alexa 647 Goat Anti-Human IgG, F(ab)$_2$ fragment specific to label 3B2g2m1. Levels of saturation of 3B2g2m1 at the synapse were measured by the ratio of 3B2g2m1 to AChR signal intensity. The graph of FIG. 50 demonstrates that MuSK agonist antibody 3B2g2m1 engages MuSK at the synapse and saturates MuSK at 20 mg/kg.

To determine whether chronic injection of the MuSK agonist antibody 3B2g2m1 in wildtype mice has an effect on survival or weight gain, C57BL/6-CBA mixed background mice were injected at P4, P24, and P44 with 10 mg/kg 3B2g2m1 (n=6) and compared to C57BL/6-CBA mixed background mice that were injected at P4, P24, and P44 with 10 mg/kg of an isotype equivalent negative control, Motavizumab (n=6). 3B2g2m1 injected mice survived and gained weight like wildtype mice (FIG. 51A). FIG. 51B demonstrates that wildtype mice in a C57BL/6-CBA mixed background injected two times a week starting at P4 with 20 mg/kg 3B2g2m1 (n=6), survived and gained weight like wildtype mice, injected two times a week starting at P4 with 20 mg/kg of an isotype equivalent negative control, Motavizumab (n=6). These results indicate that chronic injection of 3B2g2m1 in wildtype mice has no effect on survival or weight gain.

To investigate whether 3B2g2m1 rescues lethality in young Dok7 1124_1127 dup mice, Dok7 1124_1127 dup mice in a C57BL/6-CBA mixed background were treated at P4 with MuSK agonist antibody 3B2g2m1 or an isotype equivalent negative control, Motavizumab. Dok7

1124_1127 dup mice (n=11) injected with the isotype control, like untreated mice, died one to two weeks after birth, whereas Dok7 1124_1127 dup mice injected with 3B2g2m1 (n=10) at P4, P18, and P38 survived as adults (FIG. 52A). Moreover, Dok7 1124_1127 dup mice, injected with 20 mg/kg 3B2g2m1 at P4 and 10 mg/kg 3B2g2m1 at P18 and P38 gained weight, unlike Dok7 1124_1127 dup mice treated with the isotype control antibody (FIG. 52B).

To evaluate whether 3B2g2m1 restores synapse development in young Dok7 1124_1127 dup mice, diaphragm muscles from P60 wildtype and Dok7 1124_1127 dup mice were stained with Alexa 488-α-BGT to label AChRs and antibodies to βIIITubulin/Synapsin to label motor axons/nerve terminals (FIG. 53). In Dok7 1124_1127 dup mice treated with 3B2g2m1, synapses matured from a simple, plaque-like shape to a complex, pretzel-like shape, characteristic of mature murine neuromuscular synapses (see immunohistochemical images of FIG. 53) and the number of synapses, synaptic size, and density of synaptic AChRs were restored to 80%, 50%, and 60%, respectively, of normal levels (see graphs of FIG. 53).

3B2g2m1 rescues motor performance of Dok7 1124_27 dup mice, as assessed by grip strength and the latency to fall from a rotating rotarod (FIG. 54). Moreover, injection with 3B2g2m1 at P4, P18, and P38 maintains Dok7 1124_1127 dup mice healthy for at least two months, but mice ultimately began to lose weight (FIG. 55). However, administration of either 5 mg/kg or 10 mg/kg of 3B2g2m1 after initial weight loss allowed the treated Dok7 1124_1127 dup mouse to gain weight (FIG. 55).

Next, whether 3B2g2m1 could reverse disease relapse in adult Dok7 1124_1127 dup mice was evaluated. Briefly, a Dok7 1124_1127 dup mice were injected with 3B2g2m1 at P4, P18, and P38. The Dok7 1124_1127 dup mouse gained weight and maintained its mobility for several months but ultimately began to lose weight (FIG. 56A) and to display motor deficits, as assessed by grip strength and the latency to fall from a rotating rotarod (FIG. 56B). At this time, the mouse was re-injected with 3B2g2m1 (FIG. 56B). After restarting 3B2g2m1 treatment, the Dok7 1124_1127 dup mouse began to gain weight (FIG. 56A), and by a week after restarting treatment its motor deficits were reversed (FIG. 56B). Dok7 1124_1127 dup mice improved their performance on the rotarod by 5.5-fold, and their grip strength by 1.1-fold (FIG. 56C). These results demonstrate that 3B2g2m1 reverses disease relapse in adult Dok7 1124_1127 dup mice.

To investigate whether chronic 3B2g2m1 rescues lethality in young Dok7 1124_1127 dup mice, Dok7 1124_1127 dup mice in a C57BL/6-CBA mixed background were treated twice a week starting at P4 with 20 mg/kg of the MuSK agonist antibody 3B2g2m1 or an isotype equivalent negative control, Motavizumab. Dok7 1124_1127 dup mice injected with 3B2g2m1 (n=4) survived as adults and gained weight (FIG. 57).

FIGS. 58A-58C demonstrate that injection of a indicated MuSK agonist antibody extends survival of Dok7 1124_1127 dup mice. FIG. 58A is a survival plot of Dok7 1124_1127 dup mice injected with MuSK agonist antibodies as shown or isotype control (Motavizumab) at P4 (20 mg/kg), P18 (10 mg/kg), P38 (10 mg/kg), and then discontinued antibody treatment. FIG. 58B is a survival plot of Dok7 1124_1127 dup mice injected with MuSK agonist antibodies or isotype control (Motavizumab) at P4 (20 mg/kg), P18 (10 mg/kg), and then discontinued antibody treatment. FIG. 58C is a survival plot of Dok7 1124_1127 dup mice reinjected (restarted treatment) with a MuSK agonist antibody (10 mg/kg) upon several days of body weight loss and then discontinued antibody treatment.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An antibody that specifically binds to human muscle-specific tyrosine-protein kinase (MuSK), wherein the antibody comprises:
   (a) a heavy chain variable region comprising the CDR-H1, CDR-H2, and CDR-H3 amino acid sequences of the heavy chain variable region amino acid sequence of SEQ ID NO: 234; and
   (b) a light chain variable region comprising the CDR-L1, CDR-L2, and CDR-L3 amino acid sequences of the light chain variable region amino acid sequence of SEQ ID NO: 235.

2. The antibody of claim 1, wherein the antibody comprises the CDR-H1, CDR-H2, CDR-H3, CDR-L1, CDR-L2, and CDR-L3 amino acid sequences of SEQ ID NOs: 147, 153, 156, 159, 172, and 195, respectively.

3. The antibody of claim 1, wherein the heavy chain variable region comprises the amino acid sequence of SEQ ID NO: 234.

4. The antibody of claim 1, wherein the light chain variable region comprises the amino acid sequence of SEQ ID NO: 235.

5. The antibody of claim 1, wherein the antibody comprises a human IgG$_1$ heavy chain constant region.

6. The antibody of claim 5, wherein the human IgG$_1$ heavy chain constant region comprises L234A and L235A mutations.

7. The antibody of claim 1, wherein the antibody comprises a human lambda light chain constant region.

8. An antibody that specifically binds to human muscle-specific tyrosine-protein kinase (MuSK), wherein the antibody comprises a heavy chain variable region comprising the amino acid sequence of SEQ ID NO: 234; and a light chain variable region comprising the amino acid sequence of SEQ ID NO: 235.

9. The antibody of claim 8, wherein the antibody comprises a human IgG$_1$ heavy chain constant region.

10. The antibody of claim 9, wherein the human IgG$_1$ heavy chain constant region comprises L234A and L235A mutations.

11. The antibody of claim 8, wherein the antibody comprises a human lambda light chain constant region.

12. An antibody that specifically binds to human muscle-specific tyrosine-protein kinase (MuSK), wherein the antibody comprises a heavy chain and a light chain, wherein:
   (a) the heavy chain comprises:
      (i) a heavy chain variable region comprising the amino acid sequence of SEQ ID NO: 234; and
      (ii) a human IgG$_1$ heavy chain constant region comprising L234A and L235A mutations; and
   (b) the light chain comprises:
      (i) a light chain variable region comprising the amino acid sequence of SEQ ID NO: 235; and
      (ii) a human lambda light chain constant region.

13. A pharmaceutical composition comprising the antibody of claim 1, and a pharmaceutically acceptable carrier.

14. A pharmaceutical composition comprising the antibody of claim 2, and a pharmaceutically acceptable carrier.

15. A pharmaceutical composition comprising the antibody of claim 3, and a pharmaceutically acceptable carrier.

16. A pharmaceutical composition comprising the antibody of claim 4, and a pharmaceutically acceptable carrier.

17. A pharmaceutical composition comprising the antibody of claim 5, and a pharmaceutically acceptable carrier.

18. A pharmaceutical composition comprising the antibody of claim 6, and a pharmaceutically acceptable carrier.

19. A pharmaceutical composition comprising the antibody of claim 7, and a pharmaceutically acceptable carrier.

20. A pharmaceutical composition comprising the antibody of claim 8, and a pharmaceutically acceptable carrier.

21. A pharmaceutical composition comprising the antibody of claim 9, and a pharmaceutically acceptable carrier.

22. A pharmaceutical composition comprising the antibody of claim 10, and a pharmaceutically acceptable carrier.

23. A pharmaceutical composition comprising the antibody of claim 11, and a pharmaceutically acceptable carrier.

24. A pharmaceutical composition comprising the antibody of claim 12, and a pharmaceutically acceptable carrier.

\* \* \* \* \*

UNITED STATES PATENT AND TRADEMARK OFFICE
CERTIFICATE OF CORRECTION

| | |
|---|---|
| PATENT NO. | : 11,492,401 B2 |
| APPLICATION NO. | : 17/565994 |
| DATED | : November 8, 2022 |
| INVENTOR(S) | : Steven J. Burden et al. |

It is certified that error appears in the above-identified patent and that said Letters Patent is hereby corrected as shown below:

On the Title Page

In Item (72), Inventors, add:
Christophe Steyaert, Ghent (BE);
Kathleen Moens, Ghent (BE);
Bernhardt Vankerckhoven, Ghent (BE);

In the Specification

Column 6, Line 61, replace "FIG." with "FIGS."

Column 10, Line 41, replace "die" with "died"

Column 10, Line 43, replace "FIG. 3B" with "FIG. 31B"

Column 11, Line 15, replace "demonstrate" with "demonstrates"

Column 11, Line 25, replace "AChRs and" with "AChRs"

Column 15, Line 50, replace "FIG." with "FIGS."

Column 22, Line 18, replace "binds" with "bind"

Column 23, Line 51, replace "(CO region." with "(CO region)."

Column 29, Line 24, replace "NO:" with "NOs:"

Column 30, Line 61, replace "158;" with "158."

Column 35, Lines 41, 43, 47, 49, 53 and 55, replace "NO:" with "NOs:"

Signed and Sealed this
Twenty-fifth Day of June, 2024

Katherine Kelly Vidal
*Director of the United States Patent and Trademark Office*

Column 46, Line 46, replace "(xvix)" with "(xix)"

Column 59, Line 34, replace "(vix)" with "(ix)"

Column 63, Line 27, replace "(xxxi)" with "(xxxii)"

Column 63, Line 30, replace "(xxxii)" with "(xxxiii)"

Column 63, Line 33, replace "(xxxiii)" with "(xxxiv)"

Column 66, Line 53, replace "is" with "are"

Column 70, Line 55, replace "body weight" with "body weight."

Column 74, Line 37, replace "aDok7" with "a Dok7"

Column 84, Line 30, replace "interperi-" with "intraperi-"

Column 91, Line 48, replace "rescues, lethality" with "rescue lethality"